(12) United States Patent
Bischoff et al.

(10) Patent No.: US 7,842,696 B2
(45) Date of Patent: Nov. 30, 2010

(54) PIPERAZINE DERIVATIVES AS INHIBITORS OF STEAROYL-COA DESATURASE

(75) Inventors: Alexander Bischoff, Smithtown, NY (US); Hosahalli Subramanya, Karnataka (IN); Kumar Sundaresan, Karnataka (IN); Srinivasa Raju Sammeta, Andhra Pradesh (IN); Anil Kumar Vaka, Andhra Pradesh (IN)

(73) Assignee: Forest Laboratories Holdings Limited (BM)

(*) Notice: Subject to any disclaimer, the term of this patent is extended or adjusted under 35 U.S.C. 154(b) by 225 days.

(21) Appl. No.: 12/144,604

(22) Filed: Jun. 23, 2008

(65) Prior Publication Data

US 2009/0221583 A1    Sep. 3, 2009

Related U.S. Application Data

(60) Provisional application No. 60/951,997, filed on Jul. 26, 2007.

(30) Foreign Application Priority Data

Jun. 21, 2007    (IN) .................... 1280/CHE/2007

(51) Int. Cl.
*A61K 31/4965* (2006.01)
*C07D 295/00* (2006.01)
(52) U.S. Cl. .................. 514/255.01; 544/387
(58) Field of Classification Search ............... 544/387; 514/255.01
See application file for complete search history.

(56) References Cited

U.S. PATENT DOCUMENTS

| | | | |
|---|---|---|---|
| 3,356,658 A | 12/1967 | Andersen et al. | |
| 4,167,567 A * | 9/1979 | McCall | 514/252.18 |
| 6,987,001 B2 | 1/2006 | Hayden et al. | |
| 7,390,813 B1 | 6/2008 | Gray-Keller et al. | |
| 2006/0009456 A1 | 1/2006 | Hutchinson et al. | |
| 2006/0009459 A1 | 1/2006 | Chakka et al. | |
| 2006/0199802 A1 | 9/2006 | Abreo et al. | |
| 2006/0205713 A1 | 9/2006 | Gschwend et al. | |
| 2006/0241121 A1 | 10/2006 | Greenlee et al. | |
| 2006/0252767 A1 | 11/2006 | Sviridov et al. | |
| 2008/0167321 A1 | 7/2008 | Kamboj et al. | |
| 2008/0182838 A1 | 7/2008 | Leblanc et al. | |
| 2008/0182851 A1 | 7/2008 | Thomas et al. | |
| 2008/0207587 A1 | 8/2008 | Kamboj et al. | |

FOREIGN PATENT DOCUMENTS

| WO | WO 01/62954 | 8/2001 |
|---|---|---|
| WO | WO 02/34940 | 5/2002 |
| WO | WO 03/075925 | 9/2003 |
| WO | WO 2005/011653 | 2/2005 |
| WO | WO 2005/011654 | 2/2005 |
| WO | WO 2005/011655 | 2/2005 |
| WO | WO 2005/011656 | 2/2005 |
| WO | WO 2005/016657 | 2/2005 |
| WO | WO 2006/034312 | 3/2006 |
| WO | WO 2006 034315 | 3/2006 |
| WO | WO 2006/034338 | 3/2006 |
| WO | WO 2006/034341 | 3/2006 |
| WO | WO 2006/034440 | 3/2006 |
| WO | WO 2006/034441 | 3/2006 |
| WO | WO 2006/034446 | 3/2006 |
| WO | WO 2006/086445 | 8/2006 |
| WO | WO 2006/086447 | 8/2006 |
| WO | WO 2006/014168 | 9/2006 |
| WO | WO 2006/101521 | 9/2006 |
| WO | WO 2006/125178 | 11/2006 |
| WO | WO 2006/125180 | 11/2006 |
| WO | WO 2006/125194 | 11/2006 |
| WO | WO 2006/130986 | 12/2006 |
| WO | WO 2007/009236 | 1/2007 |
| WO | WO 2007/056846 | 5/2007 |
| WO | WO 2007/071023 | 6/2007 |
| WO | WO 2007/134457 | 11/2007 |
| WO | WO 2008/017161 | 2/2008 |
| WO | WO 2008/029266 | 3/2008 |
| WO | WO 2008/046226 | 4/2008 |
| WO | WO 2008/062276 | 5/2008 |
| WO | WO 2008/064474 | 6/2008 |
| WO | WO 2008/089580 | 7/2008 |
| WO | WO 2008/120759 | 10/2008 |

OTHER PUBLICATIONS

U.S. Appl. No. 12/644,162, filed Dec. 2009, Bischoff, et al.*
International Search Report for PCT/US2008/067951, mailed Sep. 29, 2008.
Written Opinion of the International Searching Authority for PCT/US2008/067951, mailed Sep. 29, 2008.
Flowers, Matthew T., et al., Role of Stearoyl-coenzyme A Desaturase in Regulating Lipid Metabolism, Current Opinion in Lipidology, 19, 248-256, 2008.
Sampath, Harini, et al., Role of Stearoyl-CoA Desaturase in Human Metabolic Disease, Future Lipidol, 3(2), 163-173, 2008.

(Continued)

*Primary Examiner*—James O Wilson
*Assistant Examiner*—Erich A Leeser
(74) *Attorney, Agent, or Firm*—Charles Ryan; Michael Ciraolo; Hemant Khanna

(57) ABSTRACT

The present invention relates to piperazine derivatives that act as inhibitors of stearoyl-CoA desaturase. The invention also relates to methods of preparing the compounds, compositions containing the compounds, and to methods of treatment using the compounds.

53 Claims, No Drawings

OTHER PUBLICATIONS

Dobrzyn, Agnieszka, et al., Inhibition of Stearoyl-CoA Desaturase by Cyclic Amine Derivatives, Expert Opin. Ther. Patents, 18(4):457-460, 2008.

Xin, Zhili, et al., Discovery of Piperidine-aryl Urea-based Stearoyl-CoA Desaturase 1 Inhibitors, Bioorganic & Medicinal Chemistry Letters 18, 4298-4302, 2008.

Liu, Gang, et al., Discovery of Potent, Selective, Orally Biovailable Stearoyl-CoA Desaturase 1 Inhibitors, J. Med. Chem., 50, 3086-3100, 2007.

Kusunoki, Jun, et al., Modulation of Fatty Acid Metabolism as a Potential Approach to the Treatment of Obesity and the Metabolic Syndrome, Endocrine, vol. 29, No. 1, 91-100, 2006.

* cited by examiner

PIPERAZINE DERIVATIVES AS INHIBITORS OF STEAROYL-COA DESATURASE

This application claims the benefit of Indian Application No. 1280/CHE/2007, filed Jun. 21, 2007, and U.S. Provisional Application No. 60/951,997, filed Jul. 26, 2007, both of which are incorporated by reference in their entirety.

FIELD OF THE INVENTION

The present invention relates to piperazine derivatives that act as inhibitors of stearoyl-CoA desaturase. The invention also relates to methods of preparing the compounds, compositions containing the compounds, and to methods of treatment using the compounds.

BACKGROUND OF THE INVENTION

Metabolic syndrome has become one of the leading health problems in the world. As a component of metabolic syndrome, obesity also has causal roles in other components of the syndrome, including insulin resistance, dyslipidemia, and cardiovascular diseases. Effective treatments for metabolic syndrome in general and obesity in particular have been lacking. Effective therapies for the treatment of obesity, a key element of metabolic syndrome, are urgently needed.

A number of mammalian stearoyl-coenzyme A desaturase (SCD) genes have been cloned. For example, two genes have been cloned from rat (SCD1, SCD2) and four SCD genes have been isolated from mouse (SCD1, 2, 3, and 4). While the basic biochemical role of SCD has been known in rats and mice since the 1970's (see, e.g., Jeffcoat, R. et al., Elsevier Science, Vol. 4, pp. 85-112, 1984; de Antueno, R J, *Lipids*, Vol. 28, No. 4, pp. 285-290, 1993), it has only recently been directly implicated in human disease processes.

A single SCD gene, stearoyl-coenzyme A desaturase-1 (SCD1) has been characterized in humans. SCD1 is described in, e.g., International Publication No. application, WO 01/62954. A second human SCD isoform has recently been identified, and because it bears little sequence homology to alternate mouse or rat isoforms it has been named human SCD5 or hSCD5 (see, e.g., International Publication No. WO 02/26944).

SCD-1 catalyzes conversion of saturated fatty acids, stearoyl-CoA and palmitoyl-CoA, to monounsaturated fatty acids, oleoyl-CoA and pamitoleoyl-CoA, respectively. These fatty acids are components of membrane phospholipids, triglycerides, and cholesterol esters. Changes in SCD activity ultimately change membrane fluidity, lipoprotein metabolism, and adiposity. SCD-1 inhibition can lead to decreased adiposity and thus be a potential therapy for metabolic syndrome.

Since obesity is becoming increasingly prevalent worldwide, much effort is being devoted to understanding its pathogenesis and treatment. In recent years, several candidate genes have been proposed as therapeutic targets. However, stearoyl-CoA desaturase 1 is of special significance, because it is the major gene target of leptin—a central mediator of energy homeostasis. There is evidence that SCD1 deficiency activates metabolic pathways that promote b-oxidation and decrease lipogenesis in liver and skeletal muscles. One mechanism is via increased activation of AMP-activated protein kinase. SCD1 mutation results also in global changes in expression of genes involved in lipid metabolism. SCD1 deficient mice have increased energy expenditure, reduced body adiposity, and are resistant to diet-induced obesity.

Thus, SCD1 inhibition represents a new and important target for the treatment of various disorders such as obesity and related metabolic disorders. Accordingly, there is a need in the art for derivatives that act as inhibitors of stearoyl-CoA desaturase, such as SCD1.

SUMMARY OF THE INVENTION

The present invention relates to piperazine derivatives that act as inhibitors of stearoyl-CoA desaturase. The invention also relates to methods of preparing the compounds, compositions containing the compounds, and to methods of treatment using the compounds.

DETAILED DESCRIPTION OF THE INVENTION

In one aspect, the present invention includes compounds of formula I:

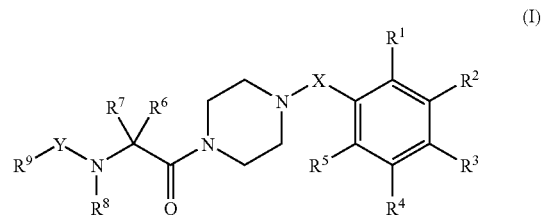

(I)

wherein $R^1$ is halogenated alkyl (e.g., $CF_3$);

$R^2$, $R^3$, $R^4$ and $R^5$ are each independently hydrogen, halogen, hydroxy, cyano, nitro, amino, alkylamino, dialkylamino, carboxyl, alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, cycloalkyloxy, cycloalkylalkyloxy, arylalkyloxy, heteroarylalkyloxy, alkylhio, arylthio, alkylsulfinyl, alkylsulfonyl, alkoxycarbonyl, aryloxycarbonyl or heteroaryloxycarbonyl;

$R^6$ and $R^7$ are each independently hydrogen, hydroxyl, cyano, alkyl, alkenyl, alkynyl, aryl, arylalkyl, heteroaryl, heteroarylalkyl, heterocycle or heterocyclealkyl;

$R^8$ is hydrogen, alkyl, alkenyl, alkynyl, aryl, arylalkyl, heteroaryl, heteroarylalkyl, heterocycle or heterocyclealkyl;

$R^9$ is hydrogen, alkyl, alkenyl, alkynyl, aryl, arylalkyl, heteroaryl, heteroarylalkyl, heterocycle or heterocyclealkyl;

X is —C(O)—, —C(O)—O—, —S(O)$_2$—, —S(O)—, or —C(O)NR$^{10}$—, where $R^{10}$ is hydrogen, alkyl, alkenyl, alkynyl, cycloalkyl, cycloalkylalkyl, aryl, arylalkyl, heteroaryl, heteroarylalkyl, heterocycle or heterocyclealkyl;

Y is —C(O)—, —S(O)$_2$—, or —S(O)—;

wherein, when present, any aryl, heteroaryl, or heterocycle group may optionally be substituted by halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylhio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl, arylalkyl-C(O)—, —C(O)O-alkyl, benzodioxol, benzo[d]oxazol-2(3H)-one, cycloalkyl-NH—C(O)—, and combinations thereof;

and pharmaceutically acceptable salts or solvates (e.g., hydrates) or N-oxides thereof, or solvates of pharmaceutically acceptable salts thereof, or pharmaceutically acceptable salts or solvates of N-oxides thereof; or prodrugs thereof;

with the proviso that said compound is not 4-chloro-N-[2-oxo-2-[4-[[2-(trifluoromethyl)phenyl]sulfonyl]-1-piperazinyl]ethyl]benzamide or a pharmaceutically acceptable salt thereof.

In certain embodiments, $R^1$ is $CF_3$. In additional embodiments, $R^1$ is $CF_3$ and $R^2$, $R^3$, $R^4$ and $R^5$ are each independently hydrogen or halogen. In additional embodiments, $R^1$ is $CF_3$ and $R^2$, $R^3$, $R^4$ and $R^5$ are hydrogen In a further embodiment, $R^1$ is $CF_3$ and one of $R^2$-$R^5$ is halogen (e.g., $R^1$ is $CF_3$, $R^4$ is halogen and $R^2$, $R^3$ and $R^5$ are hydrogen).

In further embodiments, $R^6$ and $R^7$ are not —CH(CH$_3$)CH$_2$CH$_3$. In further embodiments, $R^6$ and $R^7$ are not alkyl. In a further embodiment, $R^6$ and $R^7$ are hydrogen. In another embodiment, $R^8$ is hydrogen or alkyl, for example, $R^8$ is hydrogen.

In additional embodiments, $R^9$ is aryl (e.g., phenyl), heteroaryl (e.g., furanyl, isoxazolyl, pyridinyl, thienyl, indolyl, oxadiazolyl, pyrazolyl), heterocycle (e.g., piperidinyl) or arylalkyl (e.g., benzyl, phenethyl), each of which may be optionally substituted.

In additional embodiments, $R^9$ is aryl (e.g., phenyl), heteroaryl (e.g., furanyl, isoxazolyl, pyridinyl, thienyl, indolyl, oxadiazolyl, pyrazolyl), heterocycle (e.g., piperidinyl) or arylalkyl (e.g., benzyl), each of which may be optionally substituted by hydroxyl, halogen, nitro, cyano, amino, carboxyl, amido, optionally substituted alkyl (e.g., —CF$_3$), optionally substituted arylalkyloxy (e.g., OCH$_2$C$_6$H$_5$), optionally substituted heteroaryloxy (e.g., O—C$_5$H$_3$N(CN)), optionally substituted arylamino (e.g., —NHC$_6$H$_5$), optionally substituted arylsulfinyl (e.g., —S(O)—C$_6$H$_5$), optionally substituted arylsulfonyl (e.g., —S(O)$_2$—C$_6$H$_5$), optionally substituted aryloxy (e.g., —OC$_6$H$_5$, —OC$_6$H$_4$(OH), —OC$_6$H$_3$F$_2$), optionally substituted aryl (e.g., —C$_6$H$_5$, —C$_6$H$_4$(CF$_3$), —C$_6$H$_4$(OH), —C$_6$H$_4$—O—CH$_2$C$_6$H$_5$), optionally substituted acyl (e.g., —C(O)C$_6$H$_5$)), and combinations thereof.

In certain embodiments, $R^9$ is aryl (e.g., phenyl), heteroaryl (e.g., furanyl, isoxazolyl, pyridinyl, thienyl, indolyl, oxadiazolyl, pyrazolyl), heterocycle (e.g., piperidinyl) or arylalkyl (e.g., benzyl), each of which may be optionally substituted by hydroxyl, halogen, nitro, cyano, amino, carboxyl, amido, —CF$_3$, —OCH$_2$C$_6$H$_5$, —O—C$_5$H$_3$N(CN), —NHC$_6$H$_5$, —S(O)—C$_6$H$_5$, —S(O)$_2$—C$_6$H$_5$, —OC$_6$H$_5$, —OC$_6$H$_4$(OH), —OC$_6$H$_3$F$_2$, —C$_6$H$_5$, —C$_6$H$_4$(CF$_3$), —C$_6$H$_4$(OH), —C$_6$H$_4$—O—CH$_2$C$_6$H$_5$, —C(O)C$_6$H$_5$, 2-oxo-2,3-dihydrobenzooxazol, benzo[1,3]dioxol, cyclopentylamide, —C$_6$H$_3$(F)$_2$, —C$_6$H$_4$F, —C$_6$H$_4$—N(CH$_3$)$_2$, —C$_6$H(OCH$_3$), —C(O)CH$_2$CH$_2$C$_6$H$_5$, —CH$_2$CH$_2$CH$_2$C$_6$H$_5$, —OC(O)CH$_3$, —C(O)NHCH$_3$, N(C$_6$H$_4$)(CH$_3$), —C$_5$H$_3$N(OH), —C$_6$H$_4$(NH$_2$), —CCH, —C$_3$H$_4$N$_2$, —C$_7$H$_6$N$_2$, —C$_8$H$_7$N, —OCH$_3$, —CH$_3$, —C$_3$H$_2$NO(CH$_3$), —C$_2$HON$_2$(CH$_3$), —C$_4$H$_9$N$_2$(CH$_3$), —C$_3$H$_3$N$_2$(CH$_3$), —C$_4$H$_9$ON, —C$_{10}$H$_8$, —C$_2$H$_2$N$_2$O, —C$_6$H$_5$, —O(CH$_2$)$_2$C$_6$H$_5$, —(CH$_2$)$_3$C$_6$H$_5$, —C$_5$H$_{11}$N, —C$_5$H$_5$N, —C$_4$H$_4$N, —C$_3$H$_3$SN, —C$_4$H$_4$S, and combinations thereof.

For example, $R^9$ is (benzenesulfinyl)phenyl (e.g., 4-benzenesulfinylphenyl), (phenylamino)phenyl (e.g., (4-phenylamino)phenyl), (hydroxyphenoxy)phenyl (e.g., (4-hydroxyphenoxy)phenyl), (benzenesulfonyl)phenyl (e.g., 4-benzenesulfonylphenyl), biphenyl (e.g., 4-biphenyl), (trifluoromethylphenyl)furanyl (e.g., 5-(3-trifluoromethylphenyl)furan-2-yl), phenoxyphenyl (e.g., 3-phenoxyphenyl, 4-phenoxyphenyl), benzoylphenyl (e.g., 4-benzoylphenyl), fluorophenyl (e.g., 4-fluorophenyl), nitrophenyl (e.g., 4-nitrophenyl), benzyl, cyanophenyl (e.g., 4-cyanophenyl), trifluoromethylphenyl (e.g., 4-trifluoromethylphenyl), (benzyloxyphenyl)isoxazolyl (e.g., 5-(4-benzyloxyphenyl)isoxazol-3-yl), (hydroxyphenyl)isoxazolyl (e.g., 5-(4-hydroxyphenyl)isoxazol-3-yl), hydroxypyridinyl (e.g., 6-hydroxypyridin-3-yl), nitrofuranyl (e.g., 5-nitrofuran-2-yl), (difluorophenoxy)phenyl (e.g., 4-(2,6,-difluorophenoxy)phenyl), aminophenyl (e.g., 4-aminophenyl), phenylpyridinyl (e.g., 6-phenylpyridin-3-yl, 5-phenylpyridin-2-yl), phenylthienyl (e.g., 4-phenylthien-2-yl), phenylpiperidinyl (e.g., 4-phenylpiperidinyl), carboxylphenyl (e.g., 4-carboxylphenyl), amidophenyl (e.g., 4-amidophenyl), (cyanopyridinyloxy)phenyl (e.g., 4-(5-cyanopyridin-2-yloxy)phenyl), hydroxyphenyl (e.g., 4-hydroxyphenyl, 3-hydroxyphenyl, 2-hydroxyphenyl), phenylfuranyl (e.g., 5-phenylfuran-2-yl), (benzyloxy)phenyl (e.g., (4-benzyloxy)phenyl), hydroxybenzyl (e.g., 4-hydroxybenzyl), hydroxyphenethyl (e.g., 4-hydroxyphenethyl), indolyl (e.g., 1H-indol-5-yl), thienyl (e.g., thien-2-yl), furnayl (e.g., furan-2-yl), phenyl, (phenyl)oxadizolyl (e.g., 5-phenyl-[1,3,4]oxadizol-2-yl), (phenyl)isoxazolyl (e.g., 5-phenyl-isoxazol-3-yl) or (phenyl)pyroazlyl (e.g., (5-phenyl-1H-pyrazol-3-yl).

In certain embodiments, X is —C(O)—. In other embodiments, Y is —C(O)— or —S(O)$_2$—.

In additional embodiments, $R^1$ is halogenated alkyl (e.g., CF$_3$); $R^2$, $R^3$, $R^4$ and $R^5$ are each independently hydrogen or halogen (e.g., $R^2$-$R^5$ are hydrogen, $R^2$, $R^3$ and $R^5$ are hydrogen and $R^4$ is halogen); X is —C(O)—; Y is —(CO)— or —S(O)$_2$—; $R^6$, $R^7$ and $R^8$ are hydrogen and $R^9$ is aryl, arylalkyl, heteroaryl or heterocycle, each of which may be optionally substituted.

In certain embodiments, the compound of formula I is selected from:

4-Benzenesulfinyl-N-{2-oxo-2-[4-(2-trifluoromethyl-benzoyl)-piperazin-1-yl]-ethyl}-benzamide, N-{2-Oxo-2-[4-(2-trifluoromethyl-benzoyl)-piperazin-1-yl]-ethyl}-4-phenylamino-benzamide, 4-(4-Hydroxy-phenoxy)-N-{2-oxo-2-[4-(2-trifluoromethyl-benzoyl)-piperazin-1-yl]-ethyl}-benzamide, 4-Benzenesulfonyl-N-{2-oxo-2-[4-(2-trifluoromethyl-benzoyl)-piperazin-1-yl]-ethyl}-benzamide, Biphenyl-4-sulfonicacid {2-oxo-2-[4-(2-trifluoromethyl-benzoyl)-piperazin-1-yl]-ethyl}-amide, 5-(3-Trifluoromethyl-phenyl)-furan-2-carboxylic acid {2-oxo-2-[4-(2-trifluoromethyl-benzoyl)-piperazin-1-yl]-ethyl}-amide, N-{2-Oxo-2-[4-(2-trifluoromethyl-benzoyl)-piperazin-1-yl]-ethyl}-3-phenoxy-benzamide, 4-Benzoyl-N-{2-oxo-2-[4-(2-trifluoromethyl-benzoyl)-piperazin-1-yl]-ethyl}-benzamide, 4-Fluoro-N-{2-oxo-2-[4-(2-trifluoromethyl-benzoyl)-piperazin-1-yl]-ethyl}-benzamide, 4-Nitro-N-{2-oxo-2-[4-(2-trifluoromethyl-benzoyl)-piperazin-1-yl]-ethyl}-benzamide, N-{2-Oxo-2-[4-(2-trifluoromethyl-benzoyl)-piperazin-1-yl]-ethyl}-2-phenyl-acetamide, 4-Cyano-N-{2-oxo-2-[4-(2-trifluoromethyl-benzoyl)-piperazin-1-yl]-ethyl}-benzamide, N-{2-Oxo-2-[4-(2-trifluoromethyl-benzoyl)-piperazin-1-yl]-ethyl}-4-trifluoromethyl-benzamide, N-{2-Oxo-2-[4-(2-trifluoromethyl-benzoyl)-piperazin-1-yl]-ethyl}-4-phenoxy-benzamide, 5-(4-Benzyloxy-phenyl)-isoxazole-3-carboxylic acid {2-oxo-2-[4-(2-trifluoromethyl-benzoyl)-piperazin-1-yl]-ethyl}-amide, Biphenyl-4-carboxylic acid {2-oxo-2-[4-(2-trifluoromethyl-benzoyl)-piperazin-1-yl]-ethyl}-amide, 5-(4-Hydroxy-phenyl)-isoxazole-3-carboxylic acid {2-oxo-2-[4-(2-trifluoromethyl-benzoyl)-piperazin-1-yl]-ethyl}-amide,
6-Hydroxy-N-{2-oxo-2-[4-(2-trifluoromethyl-benzoyl)-piperazin-1-yl]-ethyl}-nicotinamide,
5-Nitro-furan-2-carboxylic acid {2-oxo-2-[4-(2-trifluoromethyl-benzoyl)-piperazin-1-yl]-ethyl}-amide,
4-(2,6-Difluoro-phenoxy)-N-{2-oxo-2-[4-(2-trifluoromethyl-benzoyl)-piperazin-1-yl]-ethyl}-benzamide,
4-Amino-N-{2-oxo-2-[4-(2-trifluoromethyl-benzoyl)-piperazin-1-yl]-ethyl}-benzamide,
N-{2-Oxo-2-[4-(2-trifluoromethyl-benzoyl)-piperazin-1-yl]-ethyl}-6-phenyl-nicotinamide,
Biphenyl-3-carboxylic acid {2-oxo-2-[4-(2-trifluoromethyl-benzoyl)-piperazin-1-yl]-ethyl}-amide,
4-Phenyl-thiophene-2-carboxylic acid {2-oxo-2-[4-(2-trifluoromethyl-benzoyl)-piperazin-1-yl]-ethyl}-amide,
5-Phenyl-pyridine-2-carboxylic acid {2-oxo-2-[4-(2-trifluoromethyl-benzoyl)-piperazin-1-yl]-ethyl}-amide,
1-Phenyl-piperidine-4-carboxylic acid {2-oxo-2-[4-(2-trifluoromethyl-benzoyl)-piperazin-1-yl]-ethyl}-amide,
N-{2-Oxo-2-[4-(2-trifluoromethyl-benzoyl)-piperazin-1-yl]-ethyl}-terephthalamic acid,
N-{2-Oxo-2-[4-(2-trifluoromethyl-benzoyl)-piperazin-1-yl]-ethyl}-terephthalamide,
4-(5-Cyano-pyridin-2-yloxy)-N-{2-oxo-2-[4-(2-trifluoromethyl-benzoyl)-piperazin-1-yl]-ethyl}-benzamide,
4-Hydroxy-N-{2-oxo-2-[4-(2-trifluoromethyl-benzoyl)-piperazin-1-yl]-ethyl}-benzamide,
3-Hydroxy-N-{2-oxo-2-[4-(2-trifluoromethyl-benzoyl)-piperazin-1-yl]-ethyl}-benzamide,
2-Hydroxy-N-{2-oxo-2-[4-(2-trifluoromethyl-benzoyl)-piperazin-1-yl]-ethyl}-benzamide,
5-Phenyl-furan-2-carboxylic acid {2-oxo-2-[4-(2-trifluoromethyl-benzoyl)-piperazin-1-yl]-ethyl}-amide,
5-(3-Trifluoromethyl-phenyl)-furan-2-carboxylic acid {2-oxo-2-[4-(2-trifluoromethyl-benzoyl)-piperazin-1-yl]-ethyl}-amide,
N-{2-Oxo-2-[4-(2-trifluoromethyl-benzoyl)-piperazin-1-yl]-ethyl}-3-phenoxy-benzamide,
4-Benzoyl-N-{2-oxo-2-[4-(2-trifluoromethyl-benzoyl)-piperazin-1-yl]-ethyl}-benzamide,
4-Fluoro-N-{2-oxo-2-[4-(2-trifluoromethyl-benzoyl)-piperazin-1-yl]-ethyl}-benzamide,
4-Nitro-N-{2-oxo-2-[4-(2-trifluoromethyl-benzoyl)-piperazin-1-yl]-ethyl}-benzamide,
5-Nitro-furan-2-carboxylic acid {2-oxo-2-[4-(2-trifluoromethyl-benzoyl)-piperazin-1-yl]-ethyl}-amide,
1-Phenyl-piperidine-4-carboxylic acid {2-oxo-2-[4-(2-trifluoromethyl-benzoyl)-piperazin-1-yl]-ethyl}-amide,
4-Benzyloxy-N-{2-oxo-2-[4-(2-trifluoromethyl-benzoyl)-piperazin-1-yl]-ethyl}-benzamide,
2-(4-Hydroxy-phenyl) N-{2-oxo-2-[4-(2-trifluoromethyl-benzoyl)-piperazin-1-yl]-ethyl}-acetamide,
3-(4-Hydroxy-phenyl) N-{2-oxo-2-[4-(2-trifluoromethyl-benzoyl)-piperazin-1-yl]-ethyl}-propionamide,
1H-Indole-5-carboxylic acid {2-oxo-2-[4-(2-trifluoromethyl-benzoyl)-piperazine-1-yl]-ethyl}-amide,
Thiophene-2-carboxylic acid {2-oxo-2-[4-(2-trifluoromethyl-benzoyl)-piperazine-1-yl]-ethyl}-amide,
Furan-2-carboxylic acid {2-oxo-2-[4-(2-trifluoromethyl-benzoyl)-piperazine-1-yl]-amide, and
N-{2-Oxo-2-[4-(2-trifluoromethyl-benzoyl)-piperazine-1-yl]-ethyl}Benzamide,
wherein free base forms listed above can also be in the form of a pharmaceutically acceptable salt,
wherein a compound listed above (in either a free base form or in the form of a pharmaceutically acceptable salt) can also be in the form of a solvate (such as a hydrate),
wherein a compound listed above (in either a free base form or in the form of a pharmaceutically acceptable salt) can also be in the form of an N-oxide,
wherein a compound listed above (in a free base form or solvate or N-oxide thereof, or in the form of a pharmaceutically acceptable salt or solvate thereof,) can also be in the form of a polymorph, and
wherein if the compound exhibits chirality it can be in the form of a mixture of enantiomers such as a racemate or a mixture of diastereomers, or can be in the form of a single enantiomer or a single diastereomer.

In additional embodiments, the compound of formula I is selected from:
5-Phenyl-[1,3,4]oxadiazole-2-carboxylic acid {2-oxo-2-[4-(2-trifluoromethyl-benzoyl)-piperazin-1-yl]-ethyl}-amide,
5-Phenyl-isoxazole-3-carboxylic acid {2-oxo-2-[4-(2-trifluoromethyl-benzoyl)-piperazin-1-yl]-ethyl}-amide,
5-Phenyl-isoxazole-3-carboxylic acid {2-[4-(5-fluoro-2-trifluoromethyl-benzoyl)-piperazin-1-yl]-2-oxo-ethyl}-amide,
5-Phenyl-1H-pyrazole-3-carboxylic acid {2-oxo-2-[4-(2-trifluoromethyl-benzoyl)-piperazin-1-yl]-ethyl}-amide, and
5-Phenyl-1H-pyrazole-3-carboxylic acid {2-[4-(5-fluoro-2-trifluoromethyl-benzoyl)-piperazin-1-yl]-2-oxo-ethyl}-amide,
wherein free base forms listed above can also be in the form of a pharmaceutically acceptable salt,
wherein a compound listed above (in either a free base form or in the form of a pharmaceutically acceptable salt) can also be in the form of a solvate (such as a hydrate),
wherein a compound listed above (in either a free base form or in the form of a pharmaceutically acceptable salt) can also be in the form of an N-oxide,
wherein a compound listed above (in a free base form or solvate or N-oxide thereof, or in the form of a pharmaceutically acceptable salt or solvate thereof,) can also be in the form of a polymorph, and
wherein if the compound exhibits chirality it can be in the form of a mixture of enantiomers such as a racemate or a mixture of diastereomers, or can be in the form of a single enantiomer or a single diastereomer.

In additional embodiments, the compound of formula I is selected from:
5-(3-Hydroxy-phenyl)-1H-pyrazole-3-carboxylic acid {2-oxo-2-[4-(2-trifluoromethyl-benzoyl)-piperazin-1-yl]-ethyl}-amide,
5-(2-Hydroxy-phenyl)-1H-pyrazole-3-carboxylic acid {2-[4-(5-fluoro-2-trifluoromethyl-benzoyl)-piperazin-1-yl]-2-oxo-ethyl}-amide,
5-(2-Amino-phenyl)-1H-pyrazole-3-carboxylic acid {2-oxo-2-[4-(2-trifluoromethyl-benzoyl)-piperazin-1-yl]-ethyl}-amide,
5-Phenyl-pyridine-2-carboxylic acid {2-[4-(5-fluoro-2-trifluoromethyl-benzoyl)-piperazin-1-yl]-2-oxo-ethyl}-amide,
1H-Indole-2-carboxylic acid {2-oxo-2-[4-(2-trifluoromethyl-benzoyl)-piperazin-1-yl]-ethyl}-amide,
4-Phenyl-pyrazole-1-carboxylic acid {2-oxo-2-[4-(2-trifluoromethyl-benzoyl)-piperazin-1-yl]-ethyl}-amide,
4-Phenyl-pyrazole-1-carboxylic acid {2-[4-(5-fluoro-2-trifluoromethyl-benzoyl)-piperazin-1-yl]-2-oxo-ethyl}-amide, 4-(2-Fluoro-phenyl)-pyrazole-1-carboxylic acid {2-[4-(5-fluoro-2-trifluoromethyl-benzoyl)-piperazin-1-yl]-2-oxo-ethyl}-amide, 5-Phenyl-1H-pyrrole-2-carboxylic acid {2-oxo-2-[4-(2-trifluoromethyl-benzoyl)-piperazin-1-yl]-ethyl}-amide, 4-Phenyl-1H-pyrrole-2-carboxylic acid {2-oxo-2-[4-(2-trifluoromethyl-benzoyl)-piperazin-1-yl]-ethyl}-amide, 1-Phenyl-1H-pyrazole-3-carboxylic acid {2-oxo-2-[4-(2-trifluoromethyl-benzoyl)-piperazin-1-yl]-ethyl}-amide, 3'-Dimethylamino-biphenyl-4-carboxylic acid {2-oxo-2-[4-(2-trifluoromethyl-benzoyl)-piperazin-1-yl]-ethyl}-amide, Biphenyl-4-carboxylic acid methyl-{2-oxo-2-[4-(2-trifluoromethyl-benzoyl)-piperazin-1-yl]-ethyl}-amide, 5-(3-Hydroxy-phenyl)-isoxazole-3-carboxylic acid {2-oxo-2-[4-(2-trifluoromethyl-benzoyl)-piperazin-1-yl]-ethyl}-amide, 5-(2-Hydroxy-phenyl)-isoxazole-3-carboxylic acid {2-oxo-2-[4-(2-trifluoromethyl-benzoyl)-piperazin-1-yl]-ethyl}-amide, 5-(2-Fluoro-phenyl)-isoxazole-3-carboxylic acid {2-[4-(5-fluoro-2-trifluoromethyl-benzoyl)-piperazin-1-yl]-2-oxo-ethyl}-amide, 5-(2-Hydroxy-phenyl)-1H-pyrazole-3-carboxylic acid {2-oxo-2-[4-(2-trifluoromethyl-benzoyl)-piperazin-1-yl]-ethyl}-amide, 5-Benzo[1,3]dioxol-5-yl-1H-pyrazole-3-carboxylic acid {2-oxo-2-[4-(2-trifluoromethyl-benzoyl)-piperazin-1-yl]-ethyl}-amide, 5-(2-Methoxy-phenyl)-1H-pyrazole-3-carboxylic acid {2-[4-(5-fluoro-2-trifluoromethyl-benzoyl)-piperazin-1-yl]-2-oxo-ethyl}-amide, 5-(2-Trifluoromethyl-phenyl)-1H-pyrazole-3-carboxylic acid {2-[4-(5-fluoro-2-trifluoromethyl-benzoyl)-piperazin-1-yl]-2-oxo-ethyl}-amide, 5-(2-Trifluoromethyl-phenyl)-1H-pyrazole-3-carboxylic acid {2-oxo-2-[4-(2-trifluoromethyl-benzoyl)-piperazin-1-yl]-ethyl}-amide, 5-(2-Methoxy-phenyl)-1H-pyrazole-3-carboxylic acid {2-oxo-2-[4-(2-trifluoromethyl-benzoyl)-piperazin-1-yl]-ethyl}-amide, 1-(3-Phenyl-propionyl)-piperidine-4-carboxylic acid {2-oxo-2-[4-(2-trifluoromethyl-benzoyl)-piperazin-1-yl]-ethyl}-amide, 1-(3-Phenyl-propyl)-piperidine-4-carboxylic acid {2-oxo-2-[4-(2-trifluoromethyl-benzoyl)-piperazin-1-yl]-ethyl}-amide, Pyrazine-2-carboxylic acid {2-oxo-2-[4-(2-trifluoromethyl-benzoyl)-piperazin-1-yl]-ethyl}-amide, N-{2-Oxo-2-[4-(2-trifluoromethyl-benzoyl)-piperazin-1-yl]-ethyl}-4-thiophen-3-yl-benzamide, Dibenzofuran-2-carboxylic acid {2-oxo-2-[4-(2-trifluoromethyl-benzoyl)-piperazin-1-yl]-ethyl}-amide, 4-(1-Methyl-1H-pyrazol-4-yl)-N-{2-oxo-2-[4-(2-trifluoromethyl-benzoyl)-piperazin-1-yl]-ethyl}-benzamide N-{2-Oxo-2-[4-(2-trifluoromethyl-benzoyl)-piperazin-1-yl]-ethyl}-4-pyrimidin-5-yl-benzamide, N-{2-Oxo-2-[4-(2-trifluoromethyl-benzoyl)-piperazin-1-yl]-ethyl}-4-pyrimidin-2-yl-benzamide, N-{2-Oxo-2-[4-(2-trifluoromethyl-benzoyl)-piperazin-1-yl]-ethyl}-4-pyrazin-2-yl-benzamide, 9H-Fluorene-2-carboxylic acid {2-oxo-2-[4-(2-trifluoromethyl-benzoyl)-piperazin-1-yl]-ethyl}-amide, 4-[1,2,4]Oxadiazol-3-yl-N-{2-oxo-2-[4-(2-trifluoromethyl-benzoyl)-piperazin-1-yl]-ethyl}-benzamide, 1-Oxy-5-phenyl-pyridine-2-carboxylic acid {2-oxo-2-[4-(2-trifluoromethyl-benzoyl)-piperazin-1-yl]-ethyl}-amide, 5-Hydroxy-pyrazine-2-carboxylic acid {2-oxo-2-[4-(2-trifluoromethyl-benzoyl)-piperazin-1-yl]-ethyl}-amide, N-{2-oxo-2-[4-(2-trifluoromethyl-benzoyl)-piperazin-1-yl]-ethyl}-4-pyridin-2-yl-benzamide, 2'-Fluoro-biphenyl-4-carboxylic acid {2-oxo-2-[4-(2-trifluoromethyl-benzoyl)-piperazin-1-yl]-ethyl}-amide, 5-Methyl-isoxazole-3-carboxylic acid {2-oxo-2-[4-(2-trifluoromethyl-benzoyl)-piperazin-1-yl]-ethyl}-amide, 2,4-Difluoro-biphenyl-4-carboxylic acid {2-oxo-2-[4-(2-trifluoromethyl-benzoyl)-piperazin-1-yl]-ethyl}-amide, 5-Phenyl-pyrazine-2-carboxylic acid {2-oxo-2-[4-(2-trifluoromethyl-benzoyl)-piperazin-1-yl]-ethyl}-amide, 6-Phenyl-pyridazine-3-carboxylic acid {2-oxo-2-[4-(2-trifluoromethyl-benzoyl)-piperazin-1-yl]-ethyl}-amide, 2-Phenyl-thiazole-5-carboxylic acid {2-oxo-2-[4-(2-trifluoromethyl-benzoyl)-piperazin-1-yl]-ethyl}-amide, 4-Methyl-N-{2-oxo-2-[4-(2-trifluoromethyl-benzoyl)-piperazin-1-yl]-ethyl}-benzamide, N-{2-Oxo-2-[4-(2-trifluoromethyl-benzoyl)-piperazin-1-yl]-ethyl}-isophthalamic acid methyl ester, 4-[1,3,4]Oxadiazol-2-yl-N-{2-oxo-2-[4-(2-trifluoromethyl-benzoyl)-piperazin-1-yl]-ethyl}-benzamide, N-Methyl-N'-{2-oxo-2-[4-(2-trifluoromethyl-benzoyl)-piperazin-1-yl]-ethyl}-terephthalamide, N-Methyl-N'-{2-oxo-2-[4-(2-trifluoromethyl-benzoyl)-piperazin-1-yl]-ethyl}-isophthalamide, 4-(5-Methyl-[1,3,4]oxadiazol-2-yl)-N-{2-oxo-2-[4-(2-trifluoromethyl-benzoyl)-piperazin-1-yl]-ethyl}-benzamide, 4-[1,3,4]Oxadiazol-2-yl-N-{2-oxo-2-[4-(2-trifluoromethyl-benzoyl)-piperazin-1-yl]-ethyl}-benzamide, 4-(2-Oxo-2H-pyridin-1-yl)-N-{2-oxo-2-[4-(2-trifluoromethyl-benzoyl)-piperazin-1-yl]-ethyl}-benzamide, 6-Benzyloxy-N-{2-oxo-2-[4-(2-trifluoromethyl-benzoyl)-piperazin-1-yl]-ethyl}-nicotinamide, 3-Hydroxy-biphenyl-4-carboxylic acid {2-oxo-2-[4-(2-trifluoromethyl-benzoyl)-piperazin-1-yl]-ethyl}-amide, 2',3'-Difluoro-biphenyl-4-carboxylic acid {2-oxo-2-[4-(2-trifluoromethyl-benzoyl)-piperazin-1-yl]-ethyl}-amide 6-Hydroxy-N-{2-oxo-2-[4-(2-trifluoromethyl-benzoyl)-piperazin-1-yl]-ethyl}-nicotinamide, 3'-Amino-biphenyl-4-carboxylic acid {2-oxo-2-[4-(2-trifluoromethyl-benzoyl)-piperazin-1-yl]-ethyl}-amide, 3-Methoxy-biphenyl-4-carboxylic acid {2-oxo-2-[4-(2-trifluoromethyl-benzoyl)-piperazin-1-yl]-ethyl}-amide, 2',6'-Difluoro-biphenyl-4-carboxylic acid {2-oxo-2-[4-(2-trifluoromethyl-benzoyl)-piperazin-1-yl]-ethyl}-amide, N-{2-Oxo-2-[4-(2-trifluoromethyl-benzoyl)-piperazin-1-yl]-ethyl}-4-thiazol-5-yl-benzamide, 2',5'-Difluoro-biphenyl-4-carboxylic acid {2-oxo-2-[4-(2-trifluoromethyl-benzoyl)-piperazin-1-yl]-ethyl}-amide, 2'-Methoxy-biphenyl-4-carboxylic acid {2-oxo-2-[4-(2-trifluoromethyl-benzoyl)-piperazin-1-yl]-ethyl}-amide, N-{2-Oxo-2-[4-(2-trifluoromethyl-benzoyl)-piperazin-1-yl]-ethyl}-4-piperidin-1-yl-benzamide, 4-Imidazol-1-yl-N-{2-oxo-2-[4-(2-trifluoromethyl-benzoyl)-piperazin-1-yl]-ethyl}-benzamide, 2'-Hydroxy-biphenyl-4-carboxylic acid {2-oxo-2-[4-(2-trifluoromethyl-benzoyl)-piperazin-1-yl]-ethyl}-amide, 5-Methyl-1-phenyl-1H-pyrazole-4-carboxylic acid {2-oxo-2-[4-(2-trifluoromethyl-benzoyl)-piperazin-1-yl]-ethyl}-amide, 1H-Indole-3-carboxylic acid {2-oxo-2-[4-(2-trifluoromethyl-benzoyl)-piperazin-1-yl]-ethyl}-amide, 1H-Indazole-3-carboxylic acid {2-[4-(5-fluoro-2-trifluoromethyl-benzoyl)-piperazin-1-yl]-2-oxo-ethyl}-amide, 1-phenyl-5-trifluoromethyl-1H-pyrazole-4-carboxylic acid {2-[4-(5-fluoro-2-trifluoromethyl-benzoyl)-piperazin-1-yl]-2-oxo-ethyl}-amide, 5-(2-Fluoro-phenyl)-1H-pyrazole-3-carboxylic acid {2-[4-(5-fluoro-2-trifluoromethyl-benzoyl)-piperazin-1-yl]-2-oxo-ethyl}-amide, 5-(2-Fluoro-phenyl)-1H-pyrazole-3-carboxylic acid {2-oxo-2-[4-(2-trifluoromethyl-benzoyl)-piperazin-1-yl]-ethyl}-amide, 1-Phenyl-1H-pyrazole-4-carboxylic acid {2-[4-(5-fluoro-2-trifluoromethyl-benzoyl)-piperazin-1-yl]-2-oxo-ethyl}-amide, Naphthalene-1-carboxylic acid {2-[4-(5-fluoro-2-trifluoromethyl-benzoyl)-piperazin-1-yl]-2-oxo-ethyl}-amide, 1-Phenyl-1H-pyrazole-4-carboxylic acid {2-oxo-2-[4-(2-trifluoromethyl-benzoyl)-piperazin-1-yl]-ethyl}-amide, 1-Phenyl-1H-[1,2,3]triazole-4-carboxylic acid {2-[4-(5-fluoro-2-trifluoromethyl-benzoyl)-piperazin-1-yl]-2-oxo-ethyl}-amide, 1-Pyridin-2-yl-1H-[1,2,3]triazole-4-carboxylic acid {2-[4-(5-fluoro-2-trifluoromethyl-benzoyl)-piperazin-1-yl]-2-oxo-ethyl}-amide, N-{2-[4-(5-Fluoro-2-trifluoromethyl-benzoyl)-piperazin-1-yl]-2-oxo-ethyl}-4-morpholin-4-yl-benzamide, N-{2-[4-(5-Fluoro-2-trifluoromethyl-benzoyl)-piperazin-1-yl]-2-oxo-ethyl}-4-(4-methyl-piperazin-1-yl)-benzamide, N-Cyclopentyl-N'-{2-oxo-2-[4-(2-trifluoromethyl-benzoyl)-piperazin-1-yl]-ethyl}-terephthalamide, 4-Ethynyl-N-{2-[4-(5-fluoro-2-trifluoromethyl-benzoyl)-piperazin-1-yl]-2-oxo-ethyl}-benzamide, 5-(2-Oxo-2,3-dihydro-benzooxazol-6-yl)-1H-pyrazole-3-carboxylic acid {2-[4-(5-fluoro-2-trifluoromethyl-benzoyl)-piperazin-1-yl]-2-oxo-ethyl}-amide, 4-Benzyloxy-N-{1,1-dimethyl-2-oxo-2-[4-(2-trifluoromethyl-benzoyl)-piperazin-1-yl]-ethyl}-benzamide, N-{1,1-Dimethyl-2-oxo-2-[4-(2-trifluoromethyl-benzoyl)-piperazin-1-yl]-ethyl}-4-hydroxy-benzamide, 4-Benzyloxy-N-{1-methyl-2-oxo-2-[4-(2-trifluoromethyl-benzoyl)-piperazin-1-yl]-ethyl}-benzamide, 4-Hydroxy-N-{1-methyl-2-oxo-2-[4-(2-trifluoromethyl-benzoyl)-piperazin-1-yl]-ethyl}-benzamide, N-{2-[4-(5-Fluoro-2-trifluoromethyl-benzoyl)-piperazin-1-yl]-2-oxo-ethyl}-4-phenylamino-benzamide, 4-(Methyl-phenyl-amino)-N-{2-oxo-2-[4-(2-trifluoromethyl-benzoyl)-piperazin-1-yl]-ethyl}-benzamide, 5-Phenylamino-pyridine-2-carboxylic acid {2-[4-(5-fluoro-2-trifluoromethyl-benzoyl)-piperazin-1-yl]-2-oxo-ethyl}-amide, 5-Phenylamino-pyridine-2-carboxylic acid {2-oxo-2-[4-(2-trifluoromethyl-benzoyl)-piperazin-1-yl]-ethyl}-amide, N-{2-Oxo-2-[4-(2-trifluoromethyl-benzoyl)-piperazin-1-yl]-ethyl}-6-phenylamino-nicotinamide, Biphenyl-4-carboxylic acid {2-[4-(2-fluoro-6-trifluoromethyl-benzoyl)-piperazin-1-yl]-2-oxo-ethyl}-amide.

wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof,) can also be in the form of a polymorph, and wherein if the compound exhibits chirality it can be in the form of a mixture of enantiomers such as a racemate or a mixture of diastereomers, or can be in the form of a single enantiomer or a single diastereomer.

According to another aspect, the present invention includes compounds of formula (II):

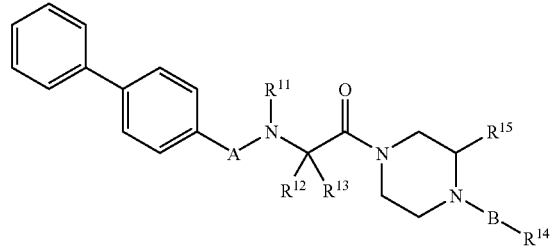

wherein $R^{11}$ is hydrogen, alkyl, alkenyl, alkynyl, aryl, arylalkyl, heteroaryl, heteroarylalkyl, heterocycle or heterocyclealkyl;

$R^{12}$ and $R^{13}$ are each independently hydrogen, hydroxyl, cyano, alkyl, alkenyl, alkynyl, aryl, arylalkyl, heteroaryl, heteroarylalkyl, heterocycle or heterocyclealkyl;

A is —CH$_2$—, —C(O)—, —S(O)$_2$—, or —S(O)—;

B is a bond, —C(O)—, —C(O)—O—, —S(O)$_2$—, —S(O)—, or —C(O)NR$^{15}$—, where $R^{15}$ is hydrogen, alkyl, alkenyl, alkynyl, cycloalkyl, cycloalkylalkyl, aryl, arylalkyl, heteroaryl, heteroarylalkyl, heterocycle or heterocyclealkyl;

$R^{14}$ is aryl, arylalkyl, heteroaryl, heteroarylalkyl, heterocycle or heterocyclealkyl;

$R^{15}$ is hydrogen or alkyl;

wherein, when present, any aryl, heteroaryl, or heterocycle group may optionally be substituted by halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylhio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl and combinations thereof;

and pharmaceutically acceptable salts or solvates (e.g., hydrates) or N-oxides thereof, or solvates of pharmaceutically acceptable salts thereof, or pharmaceutically acceptable salts or solvates of N-oxides thereof;

with the proviso that when B is a bond, $R^{14}$ is arylalkyl; and said compound is not N-[2-[4-(2-furanylcarbonyl)-1-piperazinyl]-2-oxoethyl]-[1,1'-biphenyl]-4-carboxamide, N-[2oxo-2-[4-(2-thienylcarbonyl)-1-piperazinyl]ethyl]-[1,1'-biphenyl]-4-carboxamide, or N-[1-methyl-2-oxo-2-[4-(phenylmethyl)-1-piperazinyl]ethyl]-[1,1'-biphenyl]-4-carboxamide, N-[2-[4-[(4-cyanophenyl)methyl]-1-piperazinyl]-2-oxoethyl]-[1,1'-biphenyl]-4-carboxamide, 2-[([1,1'-biphenyl]-4-ylmethyl)amino]3-phenyl-1-[4-(phenylmethyl)-1-piperazinyl]-1-propanone, or a pharmaceutically acceptable salt thereof.

When B is a bond, $R^{14}$ is directly attached to the piperazinyl ring.

In one embodiment, $R^{11}$ is hydrogen or alkyl, for example, $R^{11}$ is hydrogen. In another embodiment, $R^{12}$ and $R^{13}$ are independently hydrogen or alkyl, for example, $R^{12}$ and $R^{13}$ are hydrogen.

In one embodiment, $R^{15}$ is hydrogen or methyl. In another embodiment, $R^{15}$ is hydrogen.

In a further embodiment, B is a bond, —C(O)— or —S(O)$_2$—. For example, B is —C(O)— or —S(O)$_2$—. In certain embodiments, B is other than a bond In additional embodiments, A is —S(O)$_2$— or —C(O)—. For example, A is —C(O)—.

In additional embodiments, $R^{14}$ is aryl (e.g., phenyl), heteroaryl (e.g., thienyl, pyridinyl, pyrazinyl) or arylalkyl (e.g., benzyl), each of which may be optionally substituted.

In additional embodiments, $R^{14}$ is aryl (e.g., phenyl), heteroaryl (e.g., thienyl, pyridinyl, pyrazinyl) or arylalkyl (e.g., benzyl), each of which may be optionally substituted by halogen (e.g., F, Cl, Br), alkyl (e.g., methyl), halogenated alkyl (e.g., CF$_3$), alkoxy (e.g., methoxy, trifluoromethoxy), acyl (e.g., —C(O)CH$_3$), cycloalkylalkyloxy (e.g., cyclopropylmethyloxy), hydroxyl, carboxyl, alkoxycarbonyl (e.g., CO$_2$CH$_3$) and combinations thereof.

For example, $R^{14}$ is dichlorophenyl (e.g., 2,5-dichlorophenyl), fluorophenyl (e.g., 2-fluorophenyl, 4-fluorophenyl), bromophenyl (e.g., 2-bromophenyl), methylphenyl (e.g., 2-methylphenyl), dimethylphenyl (e.g., 2,4-dimethylphenyl), methylthienyl (e.g., 3-methyl-2-thienyl), bromo(methoxy)phenyl (e.g., 2-bromo-5-methoxyphenyl), trifluoromethylphenyl (e.g., 2-trifluoromethylphenyl), methoxyphenyl (e.g., 2-methoxyphenyl), fluoro(trifluoromethyl)phenyl (e.g., 2-fluoro-5-trifluoromethylphenyl), cyclopropylmethoxyphenyl (e.g., 2-cyclopropylmethoxyphenyl), acetylphenyl (e.g., 2-acetylphenyl), bistrifluoromethykphenyl (e.g., 2,5-bis-trifluoromethylphenyl), chloro(trifluoromethyl)phenyl (e.g., 2-chloro-5-trifluoromethylphenyl), fluoro(trifluoromethyl)phenyl (e.g., 2-fluoro-5-trifluoromethylphenyl), hydroxyphenyl (e.g., 2-hydroxyphenyl), trifluoromethylphenyl (e.g., 4-trifluoromethylphenyl), trifluoromethylpyridinyl (e.g., 4-trifluoromethylpyridin-3-yl), trifluorophenyl (e.g., 3,4,5-trifluorophenyl), trifluoromethoxyphenyl (e.g., 2-trifluoromethoxyphenyl), chlorofluorophenyl (e.g., 2-chloro-4-fluorophenyl), chlorophenyl (e.g., 2-chlorophenyl), chloropyridinyl (e.g., 2-chloropyridin-3-yl), chlorodifluorophenyl (e.g., 4-chloro-2,5-difluorophenyl), bromofluorophenyl (e.g., 2-bromo-5-fluorophenyl), difluorophenyl (e.g., 2,5-difluorophenyl), dichlorofluorophenyl (e.g., 2,4-dichloro-5-fluorophenyl), fluoro(trifluoromethyl)phenyl (e.g., 3-fluoro-5-trifluoromethylphenyl), trifluorophenyl (e.g., 2,3,6-trifluorophenyl), trifluoromethoxybenzyl (e.g., 2-trifluoromethoxybenzyl), 2-C$_6$H$_4$(C(O)OCH$_3$) or caroxylphenyl (e.g., 2-C$_6$H$_4$(CO$_2$H)).

In additional embodiments, A is —C(O)—; B is a bond, —C(O)— or —S(O)$_2$— (e.g., B is —C(O)— or —S(O)$_2$—); $R^{11}$, $R^{12}$ and $R^{13}$ are hydrogen; and $R^{14}$ is aryl, arylalkyl or heteroaryl, each of which may be optionally substituted.

In certain embodiments, the compound of formula II is selected from:

Biphenyl-4-carboxylicacid {2-[4-(2,5-dichloro-benzoyl)-piperazin-1-yl]-2-oxo-ethyl}-amide,
Biphenyl-4-carboxylicacid {2-[4-(2-fluoro-benzoyl)-piperazin-1-yl]-2-oxo-ethyl}-amide,
Biphenyl-4-carboxylicacid {2-[4-(2,4-dimethyl-benzoyl)-piperazin-1-yl]-2-oxo-ethyl}-amide,
Biphenyl-4-carboxylicacid {2-[4-(4-fluoro-benzoyl)-piperazin-1-yl]-2-oxo-ethyl}-amide,
Biphenyl-4-carboxylicacid {2-[4-benzoyl-piperazin-1-yl]-2-oxo-ethyl}-amide,
Biphenyl-4-carboxylicacid {2-[4-(2-trifluoromethyl-benzyl)-piperazin-1-yl]-2-oxo-ethyl}-amide,
Biphenyl-4-carboxylicacid {2-[4-(3-methyl-thiophene-2-carbonyl)-piperazin-1-yl]-2-oxo-ethyl}-amide,
Biphenyl-4-carboxylicacid {2-[4-(2-methyl-benzoyl)-piperazin-1-yl]-2-oxo-ethyl}-amide,
Biphenyl-4-carboxylic acid {2-[4-(2-bromo-5-methoxy-benzoyl)-piperazin-1-yl]-2-oxo-ethyl}-amide, and
Biphenyl-4-carboxylic acid {2-[4-(2-bromo-benzoyl)-piperazin-1-yl]-2-oxo-ethyl}-amide, wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof,) can also be in the form of a polymorph, and wherein if the compound exhibits chirality it can be in the form of a mixture of enantiomers such as a racemate or a mixture of diastereomers, or can be in the form of a single enantiomer or a single diastereomer.

In additional embodiments, the compound of Formula (II) is selected from:
Biphenyl-4-carboxylicacid {2-[4-(2-methoxy-benzoyl)-piperazin-1-yl]-2-oxo-ethyl}-amide,
Biphenyl-4-carboxylicacid {2-[4-(2-fluoro-5-trifluoromethyl-benzoyl)-piperazin-1-yl]-2-oxo-ethyl}-amide,
Biphenyl-4-carboxylic acid {2-[4-(2-cyclopropylmethoxy-benzoyl)-piperazin-1-yl]-2-oxo-ethyl}-amide,
Biphenyl-4-carboxylicacid {2-[4-(2-acetyl-benzoyl)-piperazin-1-yl]-2-oxo-ethyl}-amide,
Biphenyl-4-carboxylicacid {2-[4-benzene sulfonyl-piperazin-1-yl]-2-oxo-ethyl}-amide,
Biphenyl-4-carboxylicacid {2-[4-(2,5-bis-trifluoromethyl-benzoyl)-piperazin-1-yl]-2-oxo-ethyl}-amide,
Biphenyl-4-carboxylicacid {2-[4-(2-chloro-5-trifluoromethyl-benzoyl)-piperazin-1-yl]-2-oxo-ethyl}-amide,
Biphenyl-4-carboxylicacid {2-[4-(5-fluoro-2-trifluoromethyl-benzoyl)-piperazin-1-yl]-2-oxo-ethyl}-amide,
Biphenyl-4-carboxylicacid {2-[4-(2-hydroxy-benzoyl)-piperazin-1-yl]-2-oxo-ethyl}-amide,
Biphenyl-4-carboxylicacid {2-[4-(4-trifluoromethyl-benzoyl)-piperazin-1-yl]-2-oxo-ethyl}-amide,
Biphenyl-4-carboxylicacid {2-oxo-2-[4-(4-trifluoromethyl-pyridine-3-carbonyl)-piperazin-1-yl]-ethyl}-amide,
Biphenyl-4-carboxylicacid {2-oxo-2-[4-(pyrazine-2-carbonyl)-piperazin-1-yl]-ethyl}-amide,
Biphenyl-4-carboxylicacid {2-oxo-2-[4-(3,4,5-trifluoro-benzoyl)-piperazin-1-yl]-ethyl}-amide,
Biphenyl-4-carboxylicacid {2-oxo-2-[4-(2-trifluoromethoxy-benzoyl)-piperazin-1-yl]-ethyl}-amide,
Biphenyl-4-carboxylicacid {2-[4-(2-chloro-4-fluoro-benzoyl)-piperazin-1-yl]-2-oxo-ethyl}-amide,
Biphenyl-4-carboxylicacid {2-[4-(2-chloro-benzoyl)-piperazin-1-yl]-2-oxo-ethyl}-amide,
Biphenyl-4-carboxylicacid {2-[4-(2-chloro-pyridine-3-carbonyl)-piperazin-1-yl]-2-oxo-ethyl}-amide,
Biphenyl-4-carboxylicacid {2-[4-(4-chloro-2,5-difluoro-benzoyl)-piperazin-1-yl]-2-oxo-ethyl}-amide,
Biphenyl-4-carboxylicacid {2-[4-(2-bromo-5-fluoro-benzoyl)-piperazin-1-yl]-2-oxo-ethyl}-amide, Biphenyl-4-carboxylicacid {2-[4-(2,5-difluoro-benzoyl)-piperazin-1-yl]-2-oxo-ethyl}-amide,
Biphenyl-4-carboxylicacid {2-[4-(2,4-dichloro-5-fluoro-benzoyl)-piperazin-1-yl]-2-oxo-ethyl}-amide,
Biphenyl-4-carboxylicacid {2-[4-(3-fluoro-5-trifluoromethyl-benzoyl)-piperazin-1-yl]-2-oxo-ethyl}-amide,
Biphenyl-4-carboxylicacid {2-oxo-2-[4-(2,3,6-trifluoro-benzoyl)-piperazin-1-yl]-ethyl}-amide,
2-(4-{2-[(Biphenyl-4-carbonyl)-amino]-acetyl}-piperazine-1-carbonyl)-benzoic acid methylester, and
2-(4-{2-[(Biphenyl-4-carbonyl)-amino]-acetyl}-piperazine-1-carbonyl)-benzoic acid,
wherein free base forms listed above can also be in the form of a pharmaceutically acceptable salt,
wherein a compound listed above (in either a free base form or in the form of a pharmaceutically acceptable salt) can also be in the form of a solvate (such as a hydrate),
wherein a compound listed above (in either a free base form or in the form of a pharmaceutically acceptable salt) can also be in the form of an N-oxide,
wherein a compound listed above (in a free base form or solvate or N-oxide thereof, or in the form of a pharmaceutically acceptable salt or solvate thereof,) can also be in the form of a polymorph, and
wherein if the compound exhibits chirality it can be in the form of a mixture of enantiomers such as a racemate or a mixture of diastereomers, or can be in the form of a single enantiomer or a single diastereomer.

In additional embodiments, the compound of formula (II) is selected from:
Biphenyl-4-carboxylic acid {2-oxo-2-[4-(2,4,5-trifluoro-benzoyl)-piperazin-1-yl]-ethyl}-amide,
Biphenyl-4-carboxylic acid {2-[4-(6-bromo-pyridine-2-carbonyl)-piperazin-1-yl]-2-oxo-ethyl}-amide,
Biphenyl-4-carboxylic acid {2-[4-(2-chloro-5-fluoro-benzoyl)-piperazin-1-yl]-2-oxo-ethyl}-amide,
Biphenyl-4-carboxylic acid {2-[4-(3,5-dichloro-benzoyl)-piperazin-1-yl]-2-oxo-ethyl}-amide,
Biphenyl-4-carboxylic acid {2-[4-(2-amino-benzoyl)-piperazin-1-yl]-2-oxo-ethyl}-amide,
Biphenyl-4-carboxylic acid {2-[4-(2-bromo-5-nitro-benzoyl)-piperazin-1-yl]-2-oxo-ethyl}-amide,
Biphenyl-4-carboxylic acid {2-[4-(2,6-dichloro-benzoyl)-piperazin-1-yl]-2-oxo-ethyl}-amide,
Biphenyl-4-carboxylic acid {2-[4-(2,6-difluoro-benzoyl)-piperazin-1-yl]-2-oxo-ethyl}-amide,
Biphenyl-4-carboxylic acid {2-[4-(2-chloro-pyridine-4-carbonyl)-piperazin-1-yl]-2-oxo-ethyl}-amide,
Biphenyl-4-carboxylic acid {2-[4-(6-chloro-pyridine-3-carbonyl)-piperazin-1-yl]-2-oxo-ethyl}-amide,
Biphenyl-4-carboxylic acid {2-[4-(2-chloro-pyridine-3-carbonyl)-piperazin-1-yl]-2-oxo-ethyl}-amide,
Biphenyl-4-carboxylic acid {2-[4-(5-amino-2-bromo-benzoyl)-piperazin-1-yl]-2-oxo-ethyl}-amide,
Biphenyl-4-carboxylic acid {2-[4-(2-bromo-5-hydroxy-benzoyl)-piperazin-1-yl]-2-oxo-ethyl}-amide,
Biphenyl-4-carboxylic acid {2-[4-(2-bromo-5-methoxy-benzoyl)-3-methyl-piperazin-1-yl]-2-oxo-ethyl}-amide,
wherein free base forms listed above can also be in the form of a pharmaceutically acceptable salt,
wherein a compound listed above (in either a free base form or in the form of a pharmaceutically acceptable salt) can also be in the form of a solvate (such as a hydrate),
wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof,) can also be in the form of a polymorph, and
wherein if the compound exhibits chirality it can be in the form of a mixture of enantiomers such as a racemate or a mixture of diastereomers, or can be in the form of a single enantiomer or a single diastereomer.

According to another aspect, the present invention includes compounds of formula (III):

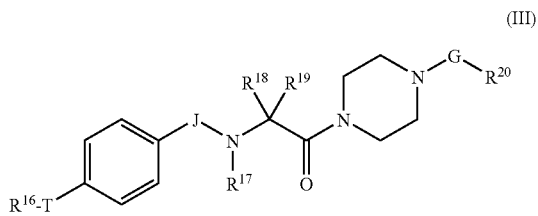

(III)

wherein
$R^{16}$ is hydrogen, aryl, arylalkyl, heteroaryl, heteroarylalkyl, heterocycle or heterocyclealkyl;
$R^{17}$ is hydrogen, alkyl, alkenyl, alkynyl, aryl, arylalkyl, heteroaryl, heteroarylalkyl, heterocycle or heterocyclealkyl;
$R^{18}$ and $R^{19}$ are each independently hydrogen, hydroxyl, cyano, alkyl, alkenyl, alkynyl, aryl, arylalkyl, heteroaryl, heteroarylalkyl, heterocycle or heterocyclealkyl;
$R^{20}$ is aryl, arylalkyl, heteroaryl, heteroarylalkyl, heterocycle or heterocyclealkyl;
J is —C(O)—, —S(O)$_2$—, or —S(O)—;
G is a bond, —C(O)—, —C(O)—O—, —S(O)$_2$—, —S(O)—, or —C(O)NR$^{21}$—, where $R^{21}$ is hydrogen, alkyl, alkenyl, alkynyl, cycloalkyl, cycloalkylalkyl, aryl, arylalkyl, heteroaryl, heteroarylalkyl, heterocycle or heterocyclealkyl;
T is —O—, —S—, —NH—, —C(O)—, —S(O)— or —S(O)$_2$—;
wherein, when present, any aryl, heteroaryl, or heterocycle group may optionally be substituted by halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl, and combinations thereof;
and pharmaceutically acceptable salts or solvates (e.g., hydrates) or N-oxides thereof, or solvates of pharmaceutically acceptable salts thereof, or pharmaceutically acceptable salts or solvates of N-oxides thereof;
with the proviso that when J is —C(O)—, $R^{17}$-$R^{19}$ are hydrogen and G is a bond, then $R^{20}$ is not thienylmethyl, thiazolylmethyl, pyridinyl, thiazolylmethyl, pyrrolidinylethyl or pyridinylmethyl;
and said compound is not
N-[2-[4-(2-furanylcarbonyl)-1-piperazinyl]2-oxoethyl]4-phenoxy-benzamide,
N-[2-[4-[(3,5-dimethyl-4-isoxazolyl)sulfonyl]-1-piperazinyl]-2-oxoethyl]4-phenoxy-benzamide,
N-[(3,5-dimethyl-4-isoxazolyl)methoxy]-N-methyl-N-[2-oxo-2-[4-(phenylmethyl)-1-piperazinyl]ethyl]-benzamide, N-2-oxo-2-[4-(2-thienylsulfonyl)-1-piperazinyl]ethyl]-4-phenoxy-benzamide, N-[2-oxo-2-[4-(2-thienylcarbonyl)-1-piperazinyl]ethyl]-4-phenoxy-benzamide, or N-methyl-N-[2-[4-[(3-methylphenyl)methyl]-1-piperazinyl]-2-oxoethyl]-4-(1-pyrrolidinylsulfonyl)-benzamide, N-[2-[4-(4-acetylphenyl)-1-piperazinyl]-2-oxoethyl]-4-phenoxy-benzamide, N-[2-[4-(4-methoxyphenyl)-1-piperazinyl]-2-oxoethyl]-4-phenoxy-benzamide, or a pharmaceutically acceptable salt thereof.

When G is a bond, $R^{21}$ is directly attached to the piperazinyl ring.

In one embodiment, $R^{17}$ is hydrogen or alkyl, for example, $R^{17}$ is hydrogen.

In further embodiments, $R^{18}$ and $R^{19}$ are independently hydrogen or alkyl, for example, $R^{18}$ and $R^{19}$ are hydrogen.

In additional embodiments, G is a bond, —S(O)$_2$—, —C(O)—NR$^{21}$— or —C(O)—. For example, G is —S(O)$_2$—, —C(O)—NR$^{21}$— or —C(O)—. In a further embodiment, G is other than a bond.

In other embodiments, J is —S(O)$_2$— or —C(O)—. For example, J is —C(O)—.

In further embodiments, T is —O—.

In additional embodiments, $R^{16}$ is hydrogen, arylalkyl (e.g., optionally substituted benzyl), aryl (e.g., phenyl), each of which may be optionally substituted. For example, $R^{16}$ is hydrogen, phenyl or benzyl.

In additional embodiments, $R^{20}$ is aryl (e.g., phenyl), arylalkyl (e.g., benzyl), or heteroaryl (e.g., thienyl, furanyl), each of which may be optionally substituted. In certain embodiments, $R^{20}$ is phenyl, benzyl, thienyl or furanyl, each of which may be optionally substituted by halogen (e.g., F, Cl, Br), alkyl (e.g., methyl), halogenated alkyl (e.g., trifluoromethyl), alkoxy (e.g., methoxy) and combinations thereof.

For example, $R^{20}$ is phenyl, benzyl, methylthienyl (e.g., 3-methyl-2-thienyl), methoxyphenyl (e.g., 3-methoxyphenyl), bromomethoxyphenyl (e.g., 2-bromo-5-methoxyphenyl), furanyl, methylphenyl (e.g., 2-methylphenyl), dimethylphenyl (e.g., 2,4-dimethylphenyl), fluorophenyl (e.g., 2-fluorophenyl, 4-fluorophenyl), dichlorophenyl (e.g., 2,4-dichlorophenyl, 2,5-dichlorophenyl) or trifluoromethylphenyl (e.g., 2-trifluoromethylphenyl).

In other embodiments, $R^{20}$ is aryl, arylalkyl, heteroaryl, heteroarylalkyl, heterocycle or heterocyclealkyl. In one embodiment, when G is a bond, $R^{20}$ is arylalkyl (e.g., benzyl).

In additional embodiments, $R^{16}$ is H or aryl, arylalkyl, both of which may be optionally substituted; $R^{17}$, $R^{18}$ and $R^{19}$ are hydrogen, $R^{20}$ is arylalkyl or heteroaryl, each of which may be optionally substituted, T is —O—, G is a bond, —C(O)—, —S(O)$_2$— or —C(O)NR$^{21}$— (e.g., G is —C(O)—, —S(O)$_2$— or —C(O)NR$^{21}$); J is —C(O)—; and $R^{21}$ is hydrogen.

In certain embodiments, the compound of formula III is selected from:

4-Benzyloxy-N-[2-oxo-2-(4-phenylacetyl-piperazin-1-yl)-ethyl]-benzamide,

4-Hydroxy-N-[2-oxo-2-(4-phenylacetyl-piperazin-1-yl)-ethyl]-benzamide,

4-Benzyloxy-N-{2-[4-(3-methyl-thiophene-2-carbonyl)-piperazin-1-yl]-2-oxo-ethyl}-benzamide, 4-Hydroxy-N-{2-[4-(3-methyl-thiophene-2-carbonyl)-piperazin-1-yl]-2-oxo-ethyl}-benzamide, 4-Benzyloxy-N-{2-[4-(2-bromo-5-methoxy-benzoyl)-piperazin-1-yl]-2-oxo-ethyl}-benzamide, 4-Hydroxy-N-{2-[4-(3-methoxy-benzoyl)-piperazin-1-yl]-2-oxo-ethyl}-benzamide, N-{2-[4-(2-Bromo-5-methoxy-benzoyl)-piperazin-1-yl]-2-oxo-ethyl}-4-phenoxy-benzamide, N-{2-[4-(3-Methyl-thiophene-2-carbonyl)-piperazin-1-yl]-2-oxo-ethyl}-4-phenoxy-benzamide, N-{2-[4-(Furan-2-carbonyl)-piperazin-1-yl]-2-oxo-ethyl}-4-phenoxy-benzamide, N-{2-[4-(2-Methyl-benzoyl)-piperazin-1-yl]-2-oxo-ethyl}-4-phenoxy-benzamide, N-{2-[4-(2-Fluoro-benzoyl)-piperazin-1-yl]-2-oxo-ethyl}-4-phenoxy-benzamide, N-[2-(4-Benzyl-piperazin-1-yl)-2-oxo-ethyl]-4-phenoxy-benzamide, N-{2-[4-(4-Fluoro-benzoyl)-piperazin-1-yl]-2-oxo-ethyl}-4-phenoxy-benzamide, N-{2-Oxo-2-[4-(2-trifluoromethyl-benzyl)-piperazin-1-yl]-ethyl}-4-phenoxy-benzamide, N-{2-[4-(2,4-Dimethyl-benzoyl)-piperazin-1-yl]-2-oxo-ethyl}-4-phenoxy-benzamide, N-[2-(4-Benzoyl-piperazin-1-yl)-2-oxo-ethyl]-4-phenoxy-benzamide, N-[2-(4-Benzenesulfonyl-piperazin-1-yl)-2-oxo-ethyl]-4-phenoxy-benzamide, N-{2-[4-(2,4-Dichloro-benzoyl)-piperazin-1-yl]-2-oxo-ethyl}-4-phenoxy-benzamide, N-{2-[4-(2,5-Dichloro-benzoyl)-piperazin-1-yl]-2-oxo-ethyl}-4-phenoxy-benzamide, 4-[2-(4-Benzyloxy-benzoylamino)-acetyl]-piperazine-1-carboxylic acid o-tolylamide, 4-[2-(4-Hydroxy-benzoylamino)-acetyl]-piperazine-1-carboxylic acid o-tolylamide, and 4-Benzyloxy-N-{2-oxo-2-[4-(2-trifluoromethyl-benzoyl)-piperazin-1-yl]-ethyl}-benzamide, wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof,) can also be in the form of a polymorph, and wherein if the compound exhibits chirality it can be in the form of a mixture of enantiomers such as a racemate or a mixture of diastereomers, or can be in the form of a single enantiomer or a single diastereomer.

In additional embodiments, the compound of formula III is selected from:

N-{2-[4-(2,4-Dichloro-benzoyl)-piperazin-1-yl]-2-oxo-ethyl}-4-phenylamino-benzamide, N-{2-[4-(2-Chloro-5-trifluoromethyl-benzoyl)-piperazin-1-yl]-2-oxo-ethyl}-4-phenylamino-benzamide, N-{2-[4-(3,5-Dichloro-benzoyl)-piperazin-1-yl]-2-oxo-ethyl}-4-phenylamino-benzamide, wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof,) can also be in the form of a polymorph, and wherein if the compound exhibits chirality it can be in the form of a mixture of enantiomers such as a racemate or a mixture of diastereomers, or can be in the form of a single enantiomer or a single diastereomer.

In a further aspect, the present invention includes compounds of formula (IV):

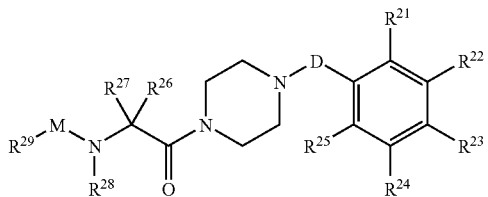

(IV)

wherein $R^{21}$ is halogen (e.g., Br, Cl);

$R^{24}$ is halogen (e.g., Cl, Br) or alkoxy (e.g., methoxy);

$R^{22}$, $R^{23}$ and $R^{25}$ are each independently hydrogen, halogen, hydroxy, cyano, nitro, amino, alkylamino, dialkylamino, carboxyl, alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, cycloalkyloxy, cycloalkylalkyloxy, arylalkyloxy, heteroarylalkyloxy, alkylthio, arylthio, alkylsulfinyl, alkylsulfonyl, alkoxycarbonyl, aryloxycarbonyl or heteroaryloxycarbonyl;

$R^{26}$ and $R^{27}$ are each independently hydrogen, hydroxyl, cyano, alkyl, alkenyl, alkynyl, aryl, arylalkyl, heteroaryl, heteroarylalkyl, heterocycle or heterocyclealkyl;

$R^{28}$ is hydrogen, alkyl, alkenyl, alkynyl, aryl, arylalkyl, heteroaryl, heteroarylalkyl, heterocycle or heterocyclealkyl;

$R^{29}$ is aryl, arylalkyl, heteroaryl, heteroarylalkyl, heterocycle or heterocyclealkyl;

D is —C(O)—, —C(O)—O—, —S(O)$_2$—, —S(O)—, or —C(O)NR$^{30}$—, where R$^{30}$ is hydrogen, alkyl, alkenyl, alkynyl, cycloalkyl, cycloalkylalkyl, aryl, arylalkyl, heteroaryl, heteroarylalkyl, heterocycle or heterocyclealkyl;

M is —C(O)—, —S(O)$_2$—, or —S(O)—;

wherein, when present, any aryl, heteroaryl, or heterocycle group may optionally be substituted by halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl (e.g., hydroxyaryl and in particular hydroxyphenyl), arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl, and combinations thereof;

and pharmaceutically acceptable salts or solvates (e.g., hydrates) or N-oxides thereof, or solvates of pharmaceutically acceptable salts thereof, or pharmaceutically acceptable salts or solvates of N-oxides thereof;

with the proviso that said compound is not

N-[2-[4-[(2,5-difluorophenyl)sulfonyl]1-piperazinyl]2-oxoethyl]-3-fluoro-benzamide, N-[2-[4-[(2,5-difluorophenyl)sulfonyl]1-piperazinyl]2-oxoethyl]-3,4-dimethoxy-benzamide, N-[2-[4-(2-bromo-5-methoxybenzoyl)-1-piperazinyl]-2-oxoethyl]-4-methoxy-2-quinolinecarboxamide, N-[2-[4-(2,5-dibromophenyl)sulfonyl)-1-piperazinyl]-2-oxoethyl]-4-methoxy-2-quinolinecarboxamide, or a pharmaceutically acceptable salt thereof.

In certain embodiments, $R^{21}$ is halogen and $R^{24}$ is halogen. For example, $R^{21}$ is Cl and $R^{24}$ is Cl. In additional embodiments, $R^{21}$ is halogen and $R^{24}$ is alkoxy. For example, $R^{21}$ is Br and $R^{24}$ is methoxy. In further embodiments, $R^{21}$ is halogen, $R^{24}$ is halogen or alkoxy and $R^{22}$, $R^{23}$ and $R^{25}$ are each hydrogen (e.g., $R^{21}$ is Br, $R^{24}$ is methoxy and $R^{22}$, $R^{23}$ and $R^{25}$ are each hydrogen; $R^{21}$ is Cl, $R^{24}$ is Cl and $R^{22}$, $R^{23}$ and $R^{25}$ are each hydrogen).

In further embodiments, $R^{26}$ and $R^{27}$ are hydrogen. In another embodiment, $R^{28}$ is hydrogen.

In additional embodiments, $R^{29}$ is heteroaryl (e.g., isoxazolyl, pyrazolyl), which may be optionally substituted. For example, $R^{29}$ is heteroaryl (e.g., isoxazolyl, pyrazolyl), optionally substituted by aryl (e.g., phenyl). For example, $R^{29}$ is (phenyl)isoxazolyl (e.g., 5-phenyl-isoxazol-3-yl) or (phenyl)pyrazolyl (e.g., 5-phenyl-1H-pyrazol-3-yl).

In certain embodiments, D is —C(O)— or —S(O)$_2$—, for example, D is —C(O)—.

In other embodiments, M is —C(O)— or —S(O)$_2$—, for example, M is —C(O)—.

In additional embodiments, $R^{21}$ is halogen (e.g., Br, Cl); $R^{24}$ is halogen (e.g., Cl) or alkoxy (e.g., methoxy), $R^{22}$, $R^{23}$, and $R^{25}$ are each hydrogen; D is —C(O)—; M is —(CO)— $R^{26}$, $R^{27}$ and $R^{28}$ are hydrogen and $R^{29}$ is optionally substituted heteroaryl.

In certain embodiments, the compound of formula IV is selected from:

5-Phenyl-isoxazole-3-carboxylic acid {2-[4-(2-bromo-5-methoxy-benzoyl)-piperazin-1-yl]-2-oxo-ethyl}-amide, 5-Phenyl-isoxazole-3-carboxylic acid {2-[4-(2,5-dichloro-benzoyl)-piperazin-1-yl]-2-oxo-ethyl}-amide, 5-Phenyl-1H-pyrazole-3-carboxylic acid {2-[4-(2-bromo-5-methoxy-benzoyl)-piperazin-1-yl]-2-oxo-ethyl}-amide, and 5-Phenyl-1H-pyrazole-3-carboxylic acid {2-[4-(2,5-dichloro-benzoyl)-piperazin-1-yl]-2-oxo-ethyl}-amide, wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof,) can also be in the form of a polymorph, and wherein if the compound exhibits chirality it can be in the form of a mixture of enantiomers such as a racemate or a mixture of diastereomers, or can be in the form of a single enantiomer or a single diastereomer.

In additional embodiments, the compound of formula IV is selected from:

5-(2-Hydroxy-phenyl)-1H-pyrazole-3-carboxylic acid {2-[4-(2-bromo-5-fluoro-benzoyl)-piperazin-1-yl]-2-oxo-ethyl}-amide, 5-(2-Hydroxy-phenyl)-1H-pyrazole-3-carboxylic acid {2-[4-(2,5-dichloro-benzoyl)-piperazin-1-yl]-2-oxo-ethyl}-amide, N-{2-[4-(2,5-Dichloro-benzoyl)-piperazin-1-yl]-2-oxo-ethyl}-4-phenylamino-benzamide, N-{2-[4-(2-Bromo-5-methoxy-benzoyl)-piperazin-1-yl]-2-oxo-ethyl}-4-phenylamino-benzamide, N-{2-[4-(2,5-Difluoro-benzoyl)-piperazin-1-yl]-2-oxo-ethyl}-4-phenylamino-benzamide, N-{2-[4-(2-Bromo-5-fluoro-benzoyl)-piperazin-1-yl]-2-oxo-ethyl}-4-phenylamino-benzamide, wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof,) can also be in the form of a polymorph, and wherein if the compound exhibits chirality it can be in the form of a mixture of enantiomers such as a racemate or a mixture of diastereomers, or can be in the form of a single enantiomer or a single diastereomer.

In another aspect, the present invention includes compounds of formula (V):

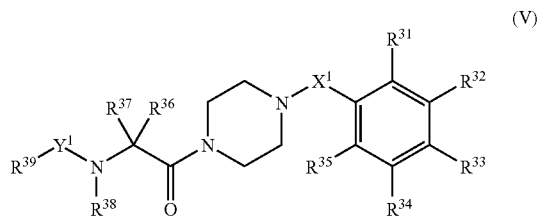

wherein
$R^{31}$ is halogenated alkyl (e.g., $CF_3$);
$R^{32}$, $R^{33}$, $R^{34}$ and $R^{35}$ are each independently hydrogen or halogen;
$R^{36}$ and $R^{37}$ are each independently hydrogen or alkyl;
$R^{38}$ is hydrogen or alkyl;
$R^{39}$ is aryl, arylalkyl, heteroaryl, heteroarylalkyl, heterocycle or heterocyclealkyl;
$X^1$ is —C(O)—, —S(O)$_2$—, or —S(O)—;
$Y^1$ is —C($R^{40}$)($R^{41}$)—, where $R^{40}$ and $R^{41}$ are each independently hydrogen or alkyl;

wherein, when present, any aryl, heteroaryl, or heterocycle group may optionally be substituted by halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl and combinations thereof;

and pharmaceutically acceptable salts or solvates (e.g., hydrates) or N-oxides thereof, or solvates of pharmaceutically acceptable salts thereof, or pharmaceutically acceptable salts or solvates of N-oxides thereof; or prodrugs thereof.

In certain embodiments, $R^{31}$ is $CF_3$. In additional embodiments, $R^{31}$ is $CF_3$ and $R^{32}$, $R^{33}$, $R^{34}$ and $R^{35}$ are each independently hydrogen or halogen. In additional embodiments, $R^{31}$ is $CF_3$ and $R^{32}$, $R^{33}$, $R^{34}$ and $R^{35}$ are hydrogen. In a further embodiment, $R^{31}$ is $CF_3$ and one of $R^{32}$-$R^{35}$ is halogen (e.g., $R^{31}$ is $CF_3$, $R^{34}$ is halogen (e.g., F) and $R^{32}$, $R^{33}$ and $R^{35}$ are hydrogen).

In a further embodiment, $R^{36}$ and $R^{37}$ are hydrogen or methyl. For example, $R^{36}$ and $R^{37}$ are hydrogen. In another embodiment, $R^{38}$ is hydrogen or methyl, for example, $R^{38}$ is hydrogen.

In further embodiments, $Y^1$ is —$CH_2$—, or —CH(alkyl)-. For example, $Y^1$ is —$CH_2$— or —CH($CH_3$)—

In additional embodiments, $R^{39}$ is aryl (e.g., phenyl), or heteroaryl (e.g., isoxazolyl, pyrazolyl) each of which may be optionally substituted.

In additional embodiments, $R^{39}$ is aryl (e.g., phenyl) or heteroaryl (e.g., isoxazolyl, pyrazolyl) each of which may be optionally substituted by aryl (e.g., phenyl), heteroaryl (e.g., thienyl) and combinations thereof.

For example, $R^{39}$ is phenyl(isoxazolyl) (e.g., 5-phenyl-isoxazol-3-yl), biphenyl (e.g., 4-biphenyl), thienyl)phenyl (e.g., 4-thien-3-ylphenyl) or (phenyl)pyrazolyl (e.g., 1-phenyl-1H-pyrazol-4-yl).

In certain embodiments, $X^1$ is —C(O)— or —S(O)$_2$—. For example, $X^1$ is —C(O)—.

In certain embodiments, the compound of formula V is selected from:

2-[(Biphenyl-4-ylmethyl)-amino]-1-[4-(5-fluoro-2-trifluoromethyl-benzoyl)-piperazin-1-yl]-ethanone, 1-[4-(5-Fluoro-2-trifluoromethyl-benzoyl)-piperazin-1-yl]-2-[(5-phenyl-isoxazol-3-ylmethyl)-amino]-ethanone, 2-[(5-Phenyl-isoxazol-3-ylmethyl)-amino]-1-[4-(2-trifluoromethyl-benzoyl)-piperazin-1-yl]-ethanone, 2-(1-Biphenyl-4-yl-ethylamino)-1-[4-(5-fluoro-2-trifluoromethyl-benzoyl)-piperazin-1-yl]-ethanone.hydrochloride, 2-[(Biphenyl-4-ylmethyl)-amino]-1-[4-(2-trifluoromethyl-benzoyl)-piperazin-1-yl]-ethanone, 1-[4-(5-Fluoro-2-trifluoromethyl-benzoyl)-piperazin-1-yl]-2-[(1-phenyl-1H-pyrazol-4-ylmethyl)-amino]-ethanone, 1-[4-(5-Fluoro-2-trifluoromethyl-benzoyl)-piperazin-1-yl]-2-(4-thiophen-3-yl-benzylamino)-ethanone, wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof,) can also be in the form of a polymorph, and wherein if the compound exhibits chirality it can be in the form of a mixture of enantiomers such as a racemate or a mixture of diastereomers, or can be in the form of a single enantiomer or a single diastereomer.

As used herein the term "halogen" means F, Cl, Br, and I.

The term "alkyl" means a substituted or unsubstituted saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "halogenated alkyl" means a saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms, that is substituted by one or more halogens, such as, but not limited to, —$CF_3$, $CF_2CF_3$, $CHF_2$, $CH_2F$, and the like. The use of the term "halogenated alkyl" should not be construed to mean that a "substituted alkyl" group may not be substituted by one or more halogens.

The term "alkenyl" means a substituted or unsubstituted hydrocarbon radical which may be straight-chain or branched-chain, which contains one or more carbon-carbon double bonds, and which may comprise about 1 to about 20 carbon atoms, such as 1 to 12 carbon atoms, for instance 1 to 6 carbon atoms. Suitable alkenyl groups include ethenyl, propenyl, butenyl, etc.

Substituted alkenyl groups are alkenyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

The term "alkynyl" means a substituted or unsubstituted aliphatic hydrocarbon radical which may be straight-chain or branched-chain and which contains one or more carbon-carbon triple bonds. Preferably the alkynyl group contains 2 to 15 carbon atoms, such as 2 to 12 carbon atoms, e.g., 2 to 8 carbon atoms. Suitable alkynyl groups include ethynyl, propynyl, butynyl, etc.

Substituted alkynyl groups are alkynyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "amino" means —$NH_2$.

The term "alkylamino" means —NH(alkyl), wherein alkyl is as described above.

The term "dialkylamino" means —N(alkyl)$_2$, wherein alkyl is as described above.

The term "aryl" means a substituted or unsubstituted aromatic mono-, bi-, or tri-cyclic ring system comprising about 5 to about 14 carbon atoms, e.g., about 6 to about 10 carbon atoms. Suitable aryl groups include, but are not limited to, phenyl, naphthyl, anthracenyl.

Substituted aryl groups include the above-described aryl groups which are substituted one or more times by, for example, but not limited to, halogen, hydroxyl, amino, carboxy, alkylamino, dialkylamino, aryl, heteroaryl, alkoxy, nitro and cyano, and combinations thereof.

The term "arylamino" means —NH(aryl) or —N($CH_3$)(aryl), wherein aryl is as described above.

The term "diarylamino" means —N(aryl)$_2$, wherein aryl is as described above.

The term "amido" means —$CONH_2$ or —C(O)$NHCH_3$.

The term "arylalkyl" refers to an -(alkylene)-aryl group in which the aryl and alkylene portions are in accordance with the previous descriptions. Suitable examples include, but are not limited to, benzyl, 1-phenethyl, 2-phenethyl, phenpropyl, phenbutyl, phenpentyl, and napthylmethyl.

The term "carboxyl" means —C(O)OH.

The term "cycloalkyl" means a monocyclic, bicyclic or tricyclic nonaromatic saturated hydrocarbon radical having 3 to 10 carbon atoms, such as 3 to 8 carbon atoms, for example, 3 to 6 carbon atoms. Suitable cycloalkyl groups include, but are not limited to, cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include, but are not limited to, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl. Preferred cycloalkyl groups include cyclopropyl, cyclobutyl, cyclopentyl and cyclohexyl. The cycloalkyl group can be substituted, for example, by one or more halogens and/or alkyl groups.

The term "cycloalkylalkyl" means a -(alkylene)-cycloalkyl in which the cycloalkyl group is as previously described; e.g., cyclopropylmethyl, cyclobutylmethyl, cyclopentylethyl, or cyclohexylmethyl, and the like.

The term "heteroaryl" means a substituted or unsubstituted aromatic monocyclic or multicyclic ring system comprising 5 to 14 ring atoms, preferably about 5 to about 10 ring atoms and most preferably 5 or 6 ring atoms, wherein at least one of the ring atoms is an N, O or S atom. Suitable heteroaryl groups include, but are not limited to furyl, thienyl, pyrrolyl, pyrazolyl, imidazolyl, pyridyl, pyridin-2(3H)-one, pyrimidinyl, benzimidazolyl, indazolyl, indolyl, quinolinyl, isoquinolinyl, naphthyridinyl and the like.

Substituted heteroaryl groups include the above-described heteroaryl groups which are substituted one or more times by, for example, but not limited to, halogen, hydroxyl, amino, carboxy, alkylamino, dialkylamino, aryl, heteroaryl, alkoxy, alkyl, nitro and combinations thereof.

The term "heteroarylalkyl" refers to a -(alkylene)-heteroaryl group wherein the heteroaryl and alkylene portions are in accordance with the previous discussions. Suitable examples include, but are not limited to, pyridylmethyl, thiazolylmethyl, thienylmethyl, pyrimidinylmethyl, pyrazinylmethyl, and isoquinolinylmethyl, and the like.

The term "heterocycle" means a substituted or unsubstituted non-aromatic mono- or multicyclic ring system comprising 3 to 10 atoms, preferably 5 or 6, wherein at least one of the ring atoms is an N, O or S atom. Suitable heterocyle groups include, but are not limited to tetrahydrofuranyl, tetrahydrothienyl, tetrahydropyranyl, dihydropyranyl, pyrrolidinyl, piperidinyl, piperazinyl, thiomorpholinyl, morpholinyl, isoxazolinyl, and the like Substituted heterocycle groups include the above-described heterocycle groups which are substituted one or more times by, for example, halogen, amino, alkyl, hydroxy, carboxy, and combinations thereof. Heterocycle groups may also be substituted by, e.g., aryl or heteroaryl.

The term "heterocyclealkyl" refers to a -(alkylene)-heterocycle group wherein the heterocycle and alkylene portions are in accordance with the previous discussions.

The term "aroyl" means an aryl-C(O)—, in which the aryl group is as previously described. Suitable aroyl groups include, but are not limited to, benzoyl and 1-naphthoyl.

The term "acyl" means an HC(O)—, alkyl-C(O)—, cycloalkyl-C(O)—, aryl-C(O)—, or heteroalkyl-C(O)—, in which the various groups are as previously described, e.g., acetyl, propionyl, benzoyl, pyridinylcarbonyl, and the like.

The term "alkoxy" means alkyl-O— groups in which the alkyl portion is in accordance with the previous discussion. Suitable alkoxy groups include, but are not limited to, methoxy, trifluoromethoxy, ethoxy, n-propoxy, iso-propoxy, n-butoxy, t-butoxy, pentoxy, hexoxy, heptoxy, octoxy, and the like. For example, the alkoxy can be trifluoromethoxy, methoxy or ethoxy.

The term "aryloxy" means an aryl-O— group, in which the aryl group is as previously described.

The term "heteroaryloxy" means an heteroaryl-O— group, in which the heteroaryl group is as previously described.

The term "cycloalkylalkyloxy" means a —O-(alkylene)-cycloalkyl group, in which the cycloalkyl and alkylene groups are as previously described.

The term "alkylthio" means an alkyl-S— group, in which the alkyl group is as previously described.

The term "arylthio" means an aryl-S— group, in which the aryl group is as previously described.

The term "alkylsulfinyl" means a —SOR radical where R is alkyl as defined above, e.g., methylsulfinyl, ethylsulfinyl, and the like.

The term "alkylsulfonyl" means a —SO$_2$R radical where R is alkyl as defined above, e.g., methylsulfonyl, ethylsulfonyl, and the like.

The term "arylsulfinyl" means a —SOR radical where R is aryl as defined above, e.g., phenylsulfinyl, and the like.

The term "arylsulfonyl" means a —SO$_2$R radical where R is aryl as defined above, e.g., phenylsulfonyl, and the like.

The term "heteroarylsulfinyl" means a —SOR radical where R is heteroaryl as defined above.

The term "heteroarylsulfonyl" means a —SO$_2$R radical where R is heteroaryl as defined above.

The term "alkoxycarbonyl" means an alkyl-O—C(O)— group, in which the alkyl group is as previously described.

The term "aryloxycarbonyl" means an aryl-O—C(O)— group, in which the aryl group is as previously described.

The term "heteroaryloxycarbonyl" means an heteroaryl-O—C(O)— group, in which the heteroaryl group is as previously described.

The term "cycloalkyloxy" means a —O-cycloalkyl group in which the cycloalkyl group is as previously described, e.g., cyclopropyloxy, cyclobutyloxy, cyclopentyloxy, cyclohexyloxy, and the like The term "arylalkyloxy" means —O-(alkylene)-aryl group, in which the aryl and alkylene groups are as previously described.

The term "heteroarylalkyloxy" means —O-(alkylene)-heteroaryl group, in which the heteroaryl and alkylene groups are as previously described.

One of ordinary skill in the art will recognize that compounds of formulas I-IV can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of formula I can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2$H, $^3$H, $^{11}$C, $^{13}$C and/or $^{14}$C. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as base free forms, and pharmaceutically acceptable salts or prodrugs of all the compounds of the present invention for which salts or prodrugs can be prepared. Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, aDIPEAtes, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, or a maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of formulas I-IV can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of formulas I-IV can exist in different solvate forms. Solvates of the compounds of the invention may also form when solvent molecules are incorporated into the crystalline lattice structure of the compound molecule during the crystallization process.

The present invention also includes prodrugs of compounds of formulas I-IV. The term prodrug is intended to represent covalently bonded carriers, which are capable of releasing the active ingredient of formulas I-IV when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of formulas I-IV include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of formulas I-IV), amides (e.g., trifluoroacetylamino, acetylamino, and the like), and the like. Prodrugs of compounds of formulas I-IV are also within the scope of this invention.

The present invention also provides processes for preparing the compounds of formulas I-IV. Suitable general reaction schemes are shown below.

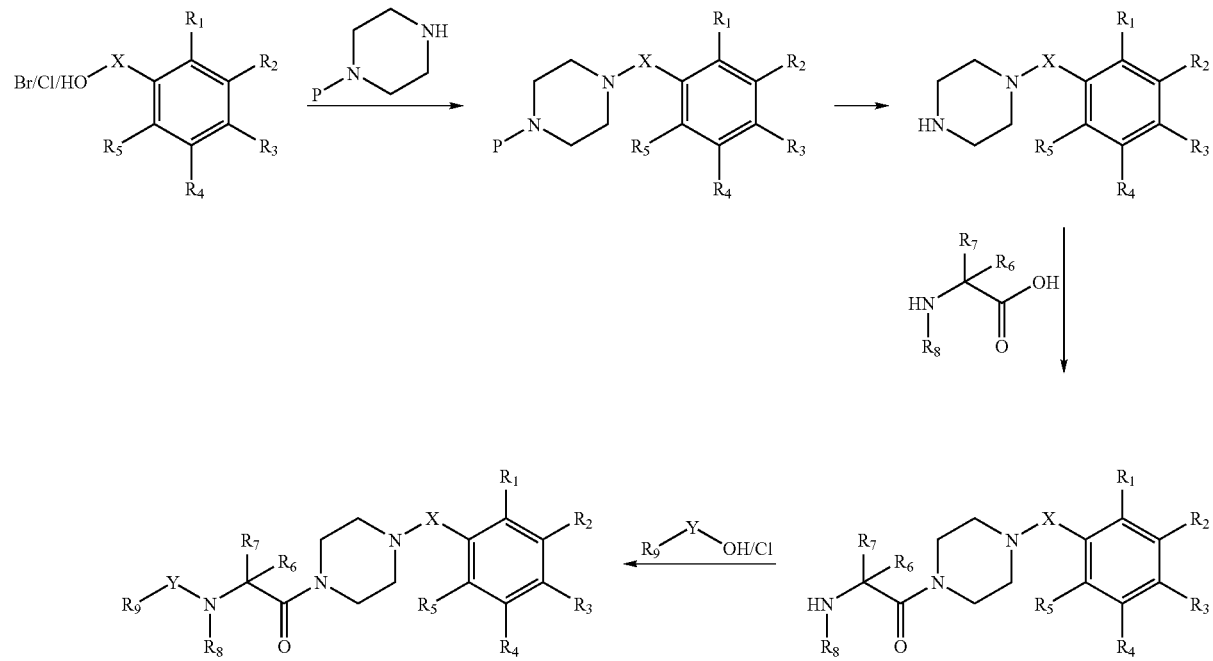

General Scheme I

A monoprotected piperazine is reacted with an appropriately substituted alkyl, aryl or heteroaryl acid or halide under coupling reaction conditions using a suitable solvent, such as DMF. The coupled product is then deprotected and coupled with an unsubstituted or substituted protected (for example Boc protected) glycine. Deprotection followed by a coupling reaction with a substituted, unsubstituted alkyl, aryl or heteroaryl acid or halide affords a compound of formula I.

General Scheme II

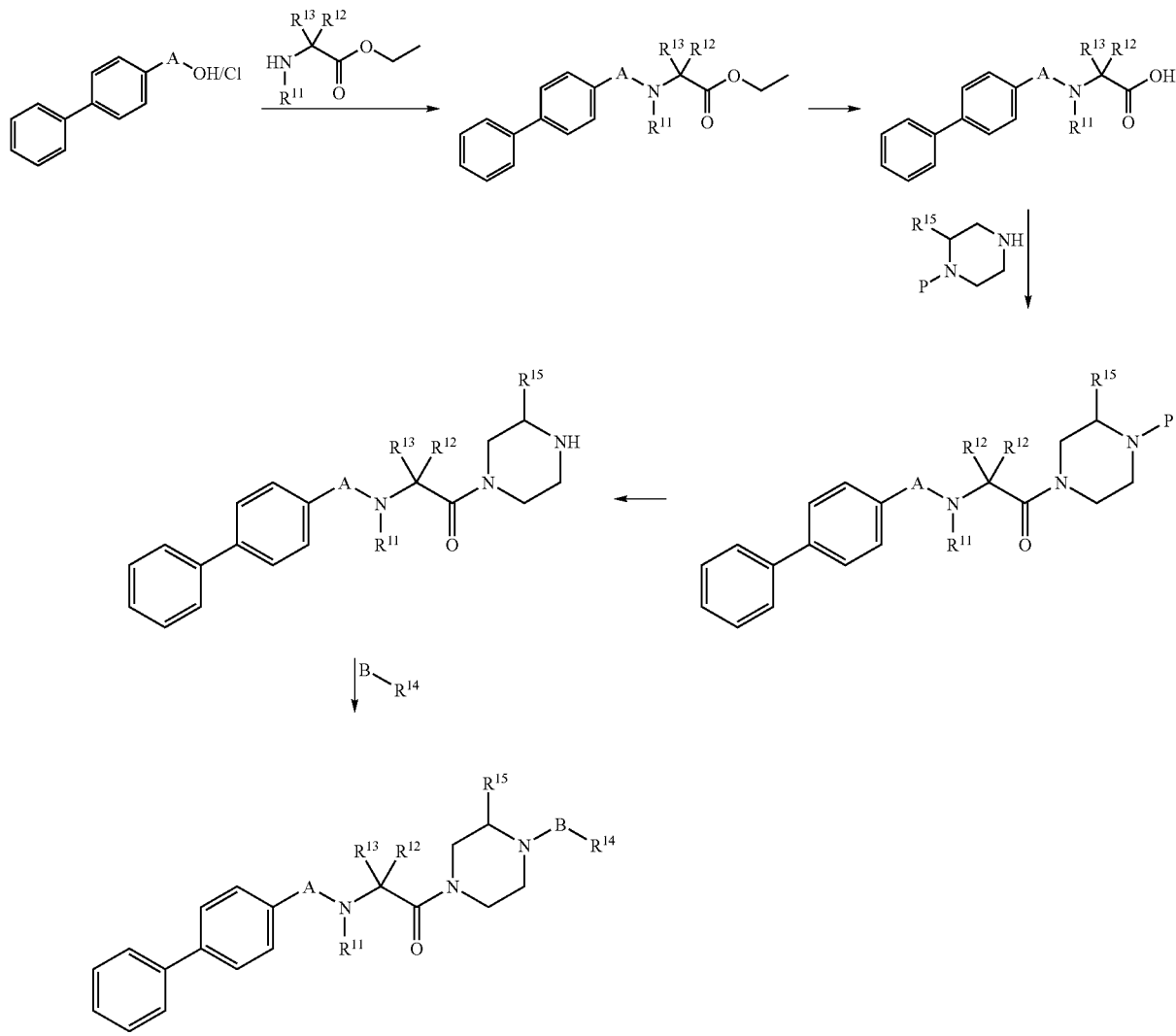

A substituted or unsubstituted glycine ester is reacted with a biphenyl carboxylic acid under coupling reaction conditions in a suitable solvent, such as DMF. The coupled product is then hydrolyzed and coupled with a mono protected piperazine or a suitably coupled piperazine. Deprotection, followed by a coupling reaction with a substituted, unsubstituted alkyl, aryl and heteroaryl acid affords a compound of formula II.

General Scheme III

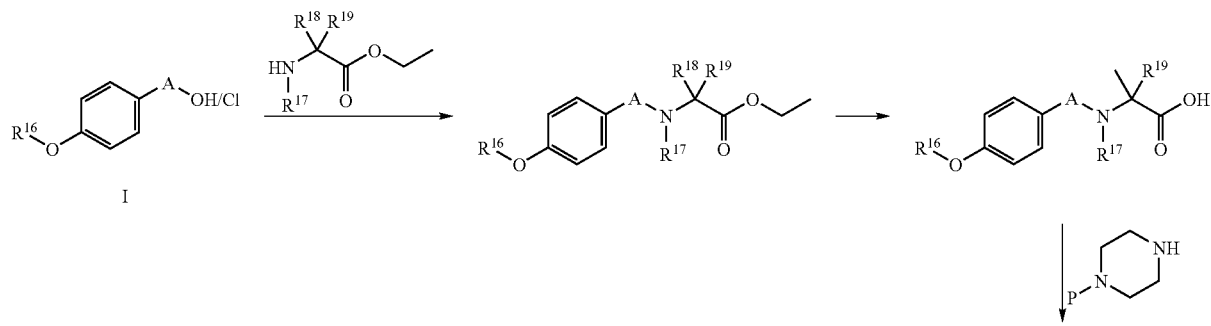

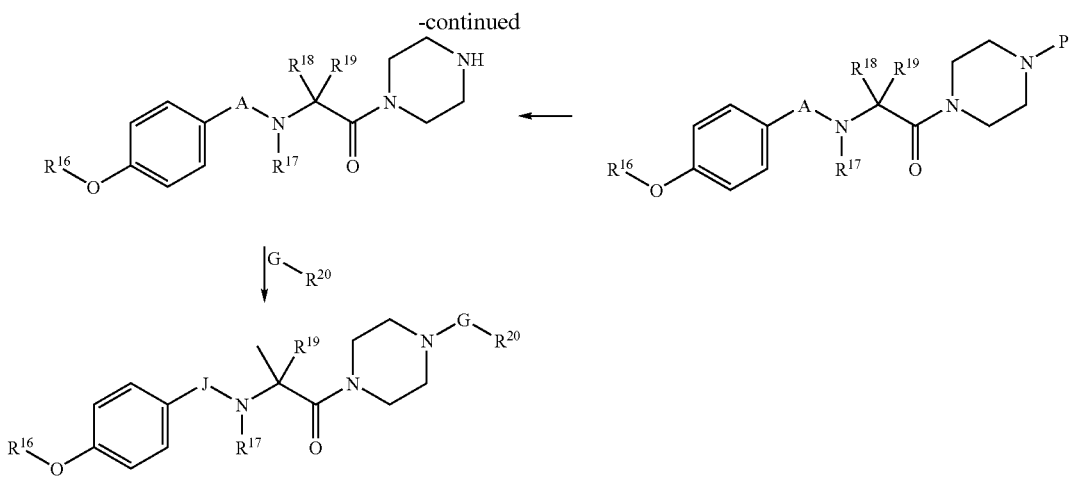

A substituted or unsubstituted glycine ester is reacted with compound I under coupling reaction conditions in a suitable solvent, such as DMF. The coupled product is then hydrolyzed and coupled with a mono protected piperazine or suitably coupled piperazine. Deprotection followed by a coupling reaction with a substituted or unsubstituted alkyl, aryl and heteroaryl acid affords the final compound of formula III.

The compounds of the invention can be administered alone or as an active ingredient of a formulation. Thus, the present invention also includes pharmaceutical compositions of compounds of formulas I-IV, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the compounds of the present invention may be accomplished according to patient needs, for example, orally, nasally, parenterally (subcutaneously, intraveneously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, the compounds of formulas I-IV can be administered by inhalation in the form of a powder (e.g., micronized) or in the form of atomized solutions or suspensions. The aerosol formulation can be placed into a pressurized acceptable propellant.

The compounds of the present invention may be useful as inhibitors of stearoyl-CoA desaturase (SCD) enzymes, for example, as inhibitors of SCD-1 enzyme. Therefore, the compounds are useful in the treatment of conditions mediated by stearoyl-CoA desaturase (SCD) enzymes, e.g., SCD-1 enzyme.

According to another embodiment, the present invention relates to a method of treating a disease or condition mediated by stearoyl-CoA desaturase (e.g., SCD-1) by administering to a patient in need thereof a therapeutically effective amount of a compound of formulas I-IV.

An SCD-mediated disease or condition includes but is not limited to a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids), cholesterol, and total cholesterol, hypercholesterolemia, as well as cholesterol disorders (including disorders characterized by defective reverse cholesterol transport), familial combined hyperlipidemia, coronary artery disease, atherosclerosis, heart disease, cerebrovascular disease (including, but not limited to stroke, ischemic stroke and transient ischemic attack (TIA)), peripheral vascular disease, and ischemic retinopathy. In an embodiment, compounds of the invention will, in a patient, increase HDL levels and/or decrease triglyceride levels and/or decrease LDL or non-HDL-cholesterol levels.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin related diseases. In an embodiment, the compounds of formulas I-IV are useful in the treatment of diabetes mellitus and obesity. In another embodiment, the compounds of formulas I-IV are useful in the treatment of obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes, but is not limited to, a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including, but not limited to, eczema, acne, psoriasis, keloid scar formation or prevention, diseases related to production or secretions from mucous membranes, such as monounsaturated fatty acids, wax esters, and the like.

An SCD-mediated disease or condition also includes inflammation, sinusitis, asthma, pancreatitis, osteoarthritis, rheumatoid arthritis, cystic fibrosis, and pre-menstrual syndrome.

An SCD-mediated disease or condition also includes but is not limited to a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition which is, or is related to, neurological diseases, psychiatric disorders, multiple sclerosis, eye diseases, and immune disorders.

An SCD-mediated disease or condition also includes a disease or condition which is, or is related to, viral diseases or infections including, but not limited, to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, Elheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POTYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

In one embodiment, the compounds of the inventions are useful in the treatment of elevated levels of lipids, cardiovascular diseases, diabetes, obesity, and metabolic syndrome. For example, the compounds of the present invention are useful in the treatment of obesity and diabetes (e.g., Type II diabetes)

The term "treating" means to relieve, alleviate, delay, reduce, reverse, improve or prevent at least one symptom of a condition in a subject. The term "treating" may also mean to arrest, delay the onset (i.e., the period prior to clinical manifestation of a disease) and/or reduce the risk of developing or worsening a condition.

An "effective amount" means the amount of a compound of formulas I-IV that, when administered to a patient (e.g., a mammal) for treating a disease, is sufficient to effect such treatment for the disease to achieve the objectives of the invention. The "effective amount" will vary depending on the compound, the disease and its severity and the age, weight, etc., of the patient to be treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In some embodiments, the compounds of the present invention are administered as a mono-therapy. In other embodiments, the compounds of the present invention are administered as part of a combination therapy. For example, a compound of formulas I-IV may be used in combination with other drugs or therapies that are used in the treatment/prevention/suppression or amelioration of the diseases or conditions for which compounds of formulas I-IV are useful.

Such other drug(s) may be administered, by a route and in an amount commonly used therefor, contemporaneously or sequentially with a compound of formulas I-IV. When a compound of formulas I-IV is used contemporaneously with one or more other drugs, a pharmaceutical unit dosage form containing such other drugs in addition to the compound of formulas I-IV may be employed. Accordingly, the pharmaceutical compositions of the present invention include those that also contain one or more other active ingredients, in addition to a compound of formulas I-IV.

EXAMPLES

The present invention will now be further described by way of the following non-limiting examples. In applying the disclosure of these examples, it should be kept clearly in mind that other and different embodiments of the methods and synthetic schemes disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The following abbreviations are used herein: Ac ($CH_3CO$), BINAP (2,2'-bis(diphenylphosphino)-1,1-binaphthyl), Bn (benzyl), DCM (dichloromethane), DMF (dimethylformamide), DIPEA (1-ethyl-3-[3-dimethylaminopropyl]carbodiimide hydrochloride), EDCI (1-ethyl-3-[3-dimethylaminopropyl]carbodiimide hydrochloride), Et (ethyl), HOBT (1-hydroxybenzotriazole), Me (methyl), TFA (trifluoroacetic acid), THF (tetrahydrofuran), EtOAc (ethyl acetate), MeOH (methanol), $Pd(OAc)_2$ (palladium acetate), $K_2CO_3$ (potassium carbonate), $HCOONH_4$ (ammonium formate), Pd/C (palladium on carbon), Boc (tert-butoxycarbonyl), $Na_2SO_4$ (sodium sulphate), $NaHCO_3$ (sodium bicarbonate) HCl (hydrochloric acid), HBr (hydrogen bromide), NaCl (sodium chloride), brine (saturated sodium chloride solution), $CHCl_3$ (chloroform), $Cs_2CO_3$ (caesium carbonate, cesium carbonate), $NaClO_2$ (sodium chlorite), $NH_3SO_3[NH_2.SO_3H]$ (Sulphamic acid), NaOH (sodium hydroxide), celite (diatomaceous earth), TLC (thin layer chromatography), NMR (nuclear magnetic resonance), DMSO-$d_6$ (deuterated dimethyl sulfoxide), $CDCl_3$ (deuterated chloroform), LC-MS (LC-MS liquid chromatography-mass spectrometry), HPLC (high pressure liquid chromatography or high performance liquid chromatography).

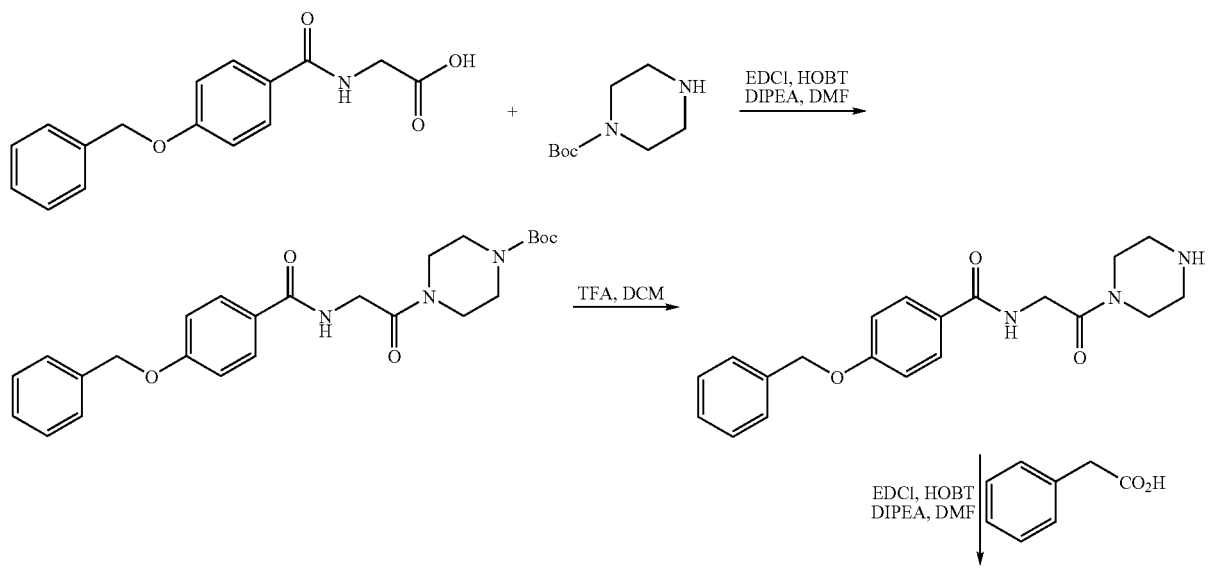

SCHEME-1

-continued

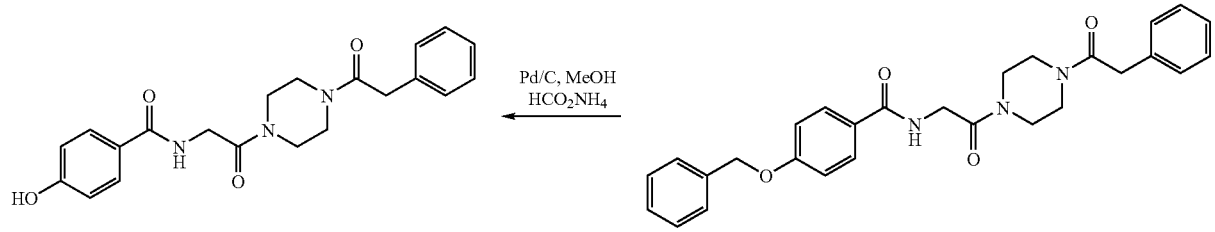

Step 1: Synthesis of 4-[2-(4-Benzyloxy-benzoylamino)-acetyl]-piperazine-1-carboxylic acid tert-butyl ester

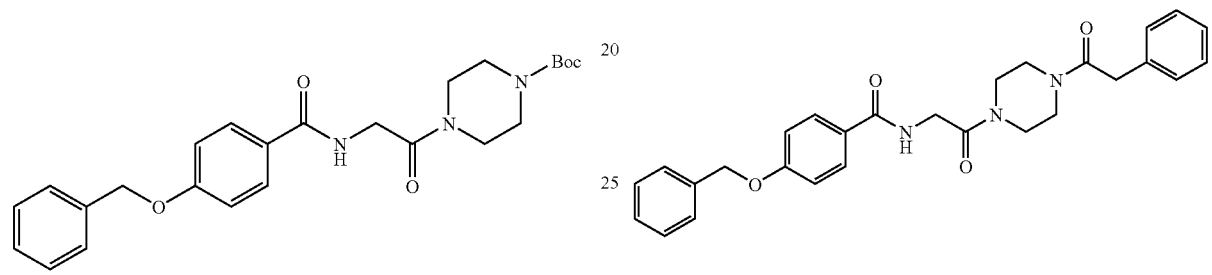

EDCI.HCl (618 mg, 3.26 mmol), 348 mg of HOBT (348 mg, 2.58 mmol) and DIPEA (1.116 mL, 6.4516 mmol) were added to a mixture of (4-Benzyloxy-benzoylamino)-acetic acid (735 mg, 2.58 mmol) in DMF (8 mL). The resulting mixture was allowed to stir at room temperature overnight. Water was then added, and the resulting solid was isolated by filtration under reduced pressure to afford 4-[2-(4-Benzyloxy-benzoylamino)-acetyl]-piperazine-1-carboxylic acid tert-butyl ester in 78% yield. LC-MS purity: 96%

Step 2: Synthesis of 4-Benzyloxy-N-(2-oxo-2-piperazin-1-yl-ethyl)-benzamide

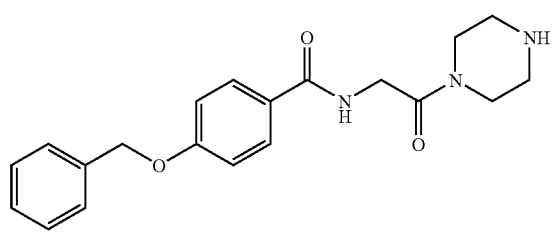

A mixture of 4-(2-trifluoromethyl-benzoylamino)-piperidine-1-carboxylic acid tert-butyl ester, (200 mg, 0.44 mmol) and DCM (3 mL) was cooled in an ice bath to 0° C. TFA (1 mL in 1 mL DCM) was then added drop wise with stirring while maintaining the temperature at 0° C. The resulting mixture was then allowed to stir for 4 hrs at room temperature. The mixture was then cooled and DIPEA (2 mL) added dropwise till fuming ceased. Concentration of the mixture under reduced pressure afforded 4-Benzyloxy-N-(2-oxo-2-piperazin-1-yl-ethyl)-benzamide in 99% yield.

1) Synthesis of 4-Benzyloxy-N-[2-oxo-2-(4-phenylacetyl-piperazin-1-yl)-ethyl]-benzamide EDCI.HCl (122 mg, 0.634 mmol), HOBT (68 mg, 0.51 mmol) and DIPEA (220 µL, 1.27 mmol) were added to a mixture of 4-benzyloxy-N-(2-oxo-2-piperazin-1-yl-ethyl)-benzamide (150 mg, 0.42 mmol), DMF (5 mL) and phenyl acetic acid (69 mg, 0.51 mmol). The resulting mixture was allowed to stir at room temperature overnight. Water was then added, and the product was extracted using EtOAc. The organic phase was washed with brine, dried over $Na_2SO_4$ and concentrated under reduced pressure to afford a crude product, which was purified twice by column chromatography (using silica gel with a mesh size of 60-120, and 80:20 EtOAc:hexane as the eluent) to afford 4-benzyloxy-N-[2-oxo-2-(4-phenylacetyl-piperazin-1-yl)-ethyl]-benzamide in 55% yield. LC-MS purity: 92% $^1$H NMR (DMSO-D6): δ 8.4 (t, 1H), 7.8 (d, 2H), 7.4 (m, 7H), 7.2 (d, 3H), 7.1 (d, 2H), 5.2 (s, 2H), 4.1 (d, 2H), 3.8 (d, 2H), 3.5 (m, 8H).

2) Synthesis of 4-Hydroxy-N-[2-oxo-2-(4-phenylacetyl-piperazin-1-yl)-ethyl]-benzamide

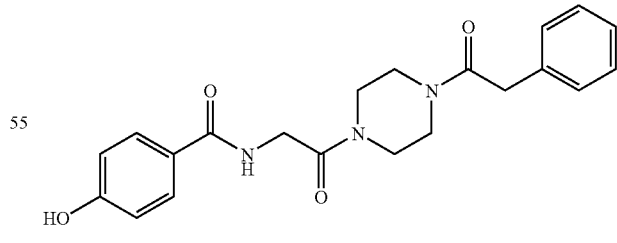

Ammonium formate (107 mg, 1.6985 mmoles) was added to a mixture of 4-benzyloxy-N-[2-oxo-2-(4-phenylacetyl-piperazin-1-yl)-ethyl]-benzamide (80 mg, 0.17 mmol) in MeOH (15 mL). Pd/C (30 mg in 3 drops of water) was then added and the resulting mixture was refluxed at 75° C. for three hours. The reaction mixture was then filtered through a bed of celite under reduced pressure. The methanol was removed and EtOAc and water were added. The organic layer was extracted, washed with brine, dried over sodium sulphate and concentrated to afford 4-hydroxy-N-[2-oxo-2-(4-phenylacetyl-piperazin-1-yl)-ethyl]-benzamide in 70% yield. LC-MS purity 94.82%. ¹H NMR (DMSO-D6): δ 10 (s, 1H), 8.3 (s, 1H), 7.7 (d, 2H), 7.3 (t, 2H), 7.2 (d, 2H), 6.8 (d, 2H), 4.1 (d, 2H), 3.8 (d, 2H), 3.5 (m, 8H).

tography purification (using neutral alumina 90:10 EtOAc:MeOH as the eluent) afforded 4-benzyloxy-N-{2-[4-(3-methyl-thiophene-2-carbonyl)-piperazin-1-yl]-2-oxo-ethyl}-benzamide in 46% yield. LC-MS purity: 87%. ¹H NMR (DMSO-D6): δ 8.4 (t, 1H), 7.8 (d, 2H), 7.6 (d, 1H), 7.4 (m, 5H), 7.1 (d, 2H), 6.9 (d, 1H), 5.2 (s, 2H), 4.2 (d, 2H), 3.5 (d, 8H), 2.3 (s, 3H).

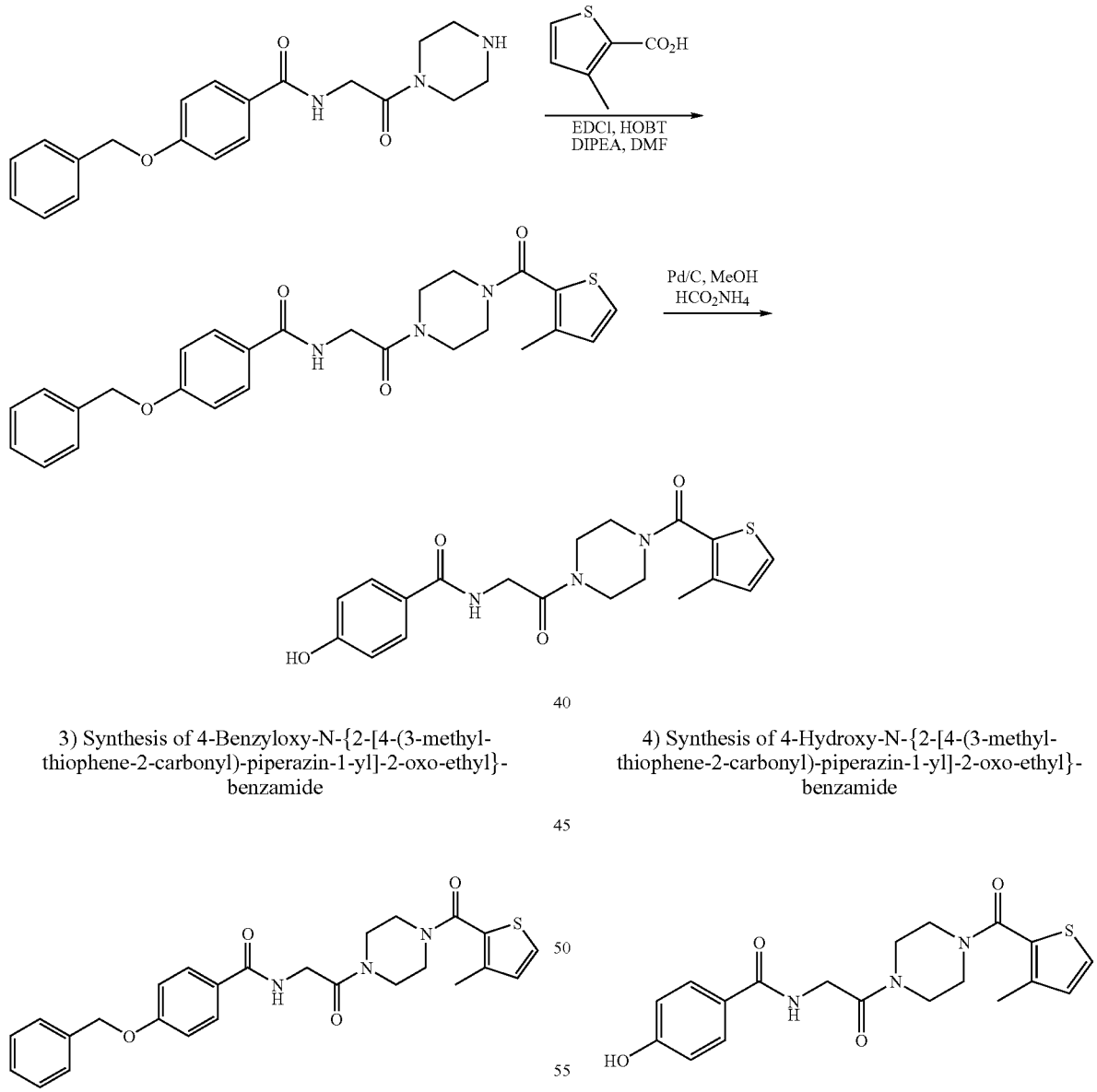

3) Synthesis of 4-Benzyloxy-N-{2-[4-(3-methyl-thiophene-2-carbonyl)-piperazin-1-yl]-2-oxo-ethyl}-benzamide 4) Synthesis of 4-Hydroxy-N-{2-[4-(3-methyl-thiophene-2-carbonyl)-piperazin-1-yl]-2-oxo-ethyl}-benzamide 3-Methyl-2-thiophene carboxylic acid (74 mg, 0.53 mmol) was added to 4-benzyloxy-N-(2-oxo-2-piperazin-1-yl-ethyl)-benzamide (155 mg, 0.44 mmol) in DMF (5 mL). EDCI.HCl (126 mg, 0.66 mmol), HOBT (71 mg, 0.53 mmol) and DIPEA (227 µL, 1.32 mmol) were then added and the resulting mixture was allowed to stir at room temperature overnight. Water was then added and the product was extracted with EtOAc and washed with brine. The organic phase was dried over $Na_2SO_4$ and concentrated under reduced pressure to afford a crude product. Column chroma- Ammonium formate (85 mg, 1.36 mmol) was added to a mixture of 4-benzyloxy-N-{2-[4-(3-methyl-thiophene-2-carbonyl)-piperazin-1-yl]-2-oxo-2-ethyl}-benzamide (65 mg, 0.14 mmol) in MeOH (15 mL). Pd/C (60 mg in 3 drops of water) was then added and the resulting mixture was refluxed at 75° C. for six hours. The reaction mixture was then filtered through a bed of celite bed under reduced pressure. The methanol was removed and EtOAc and water were added to the residue. The organic layer was extracted, washed with brine, dried over sodium sulphate and concentrated to afford 4-hydroxy-N-{2-[4-(3-methyl-thiophene-2-carbonyl)-piperazin-1-yl]-2-oxo-ethyl}-benzamide in 48% yield. LC-MS purity: 90.7%. ¹H NMR (CDCl₃): δ 7.7 (d, 2H), 7.3 (d, 1H), 7.1 (s, 1H), 6.8 (m, 3H), 6.5 (s, 1H), 4.3 (d, 2H), 3.7 (d, 6H), 3.5 (t, 2H), 2.3 (s, 3H).

as the eluent (1ˢᵗ purification) and (ii) neutral alumina and 65:35 EtOAc:Hexane as the eluent (2ⁿᵈ purification) to afford 4-benzyloxy-N-{2-[4-(2-bromo-5-methoxy-benzoyl)-piperazin-1-yl]-2-oxo-ethyl}-benzamide in 43% yield. LC-MS

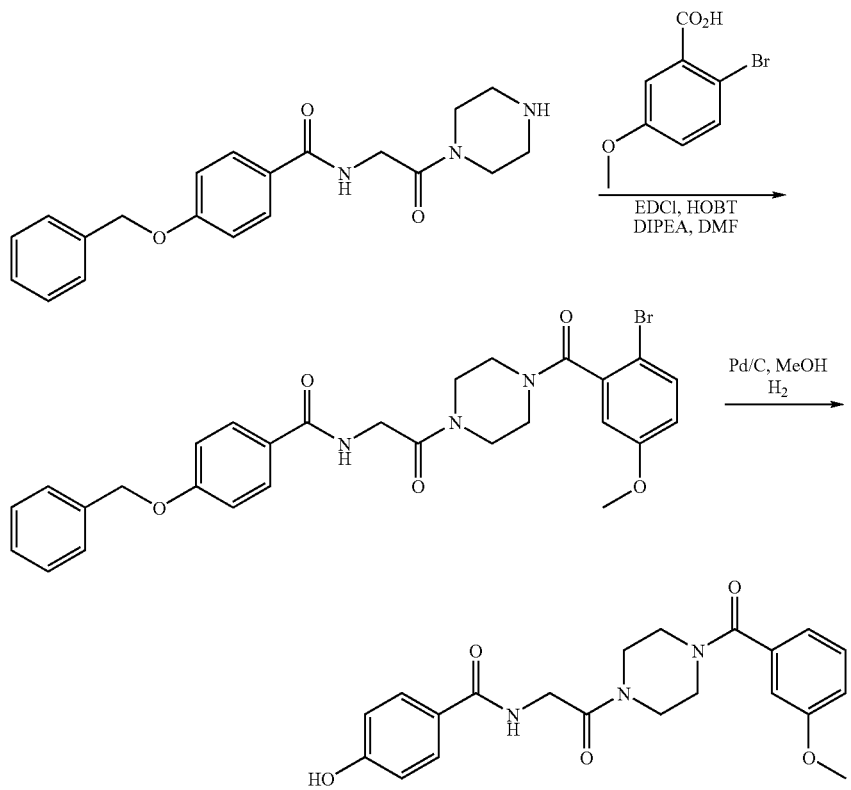

5) Synthesis of 4-Benzyloxy-N-{2-[4-(2-bromo-5-methoxy-benzoyl)-piperazin-1-yl]-2-oxo-ethyl}-benzamide purity: 99.6%. ¹H NMR (CDCl₃): δ 7.9 (d, 2H), 7.5 (m, 6H), 7.2 (s, 1H), 7 (d, 2H), 6.8 (d, 2H), 5.2 (s, 2H), 4.4 (d, 2H), 4 (m, 2H), 3.8 (s, 3H), 3.7 (t, 3H), 3.6 (t, 2H), 3.5 (m, 2H), 3.3 (m, 1H).

6) Synthesis of 4-Hydroxy-N-{2-[4-(3-methoxy-benzoyl)-piperazin-1-yl]-2-oxo-ethyl}-benzamide

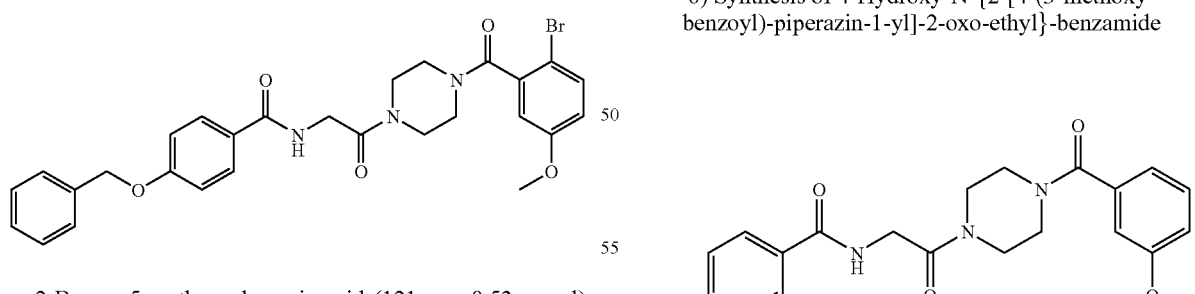

2-Bromo-5-methoxy benzoic acid (121 mg, 0.53 mmol) was added to 4-benzyloxy-N-(2-oxo-2-piperazin-1-yl-ethyl)-benzamide (155 mg, 0.44 mmol) in DMF (5 mL). EDCI.HCl (126 mg, 0.66 mmol), HOBT (71 mg, 0.53 mmol) and DIPEA (227 µL, 1.32 mmol) were added and the resulting mixture was stirred at room temperature for 4 hours. Water was then added and the product was extracted with EtOAc and washed with brine. The organic phase was dried over Na₂SO₄ and concentrated under reduced pressure. The crude product was purified twice by column chromatography using (i) silica gel of mesh size of 60-120 and 70:30 EtOAc:Hexane Pd/C (50 mg in 3 drops of water) was added to a mixture of 4-benzyloxy-N-{2-[4-(2-bromo-5-methoxy-benzoyl)-piperazin-1-yl]-2-oxo-2-ethyl}-benzamide (85 mg, 0.15 mmol) and MeOH (10 mL). The resulting mixture was stirred at room temperature under an atmosphere of hydrogen for 7 hours. The reaction mixture was then filtered through a bed of celite. The methanol was removed and EtOAc and water were added to the residue. The organic layer was extracted, washed with brine, dried over sodium sulphate and concentrated to afford 45 mg of crude compound which was recrystallised from hexane to afford 35 mg of 4-hydroxy-N-{2-[4-(3-methoxy-benzoyl)-piperazin-1-yl]-2-oxo-ethyl}-benzamide (59% yield). LC-MS purity: 92.1%. $^1$H NMR (DMSO-D6): δ 10 (s, 1H), 8.4 (t, 1H), 7.8 (d, 2H), 7.4 (t, 1H), 7 (m, 3H), 6.8 (d, 2H), 4.1 (s, 2H), 3.8 (s, 3H), 3.6 (s, 8H).

7) Synthesis of 4-Benzenesulfinyl-N-{2-oxo-2-[4-(2-trifluoromethyl-benzoyl)-piperazin-1-yl]-ethyl}-benzamide Step 1

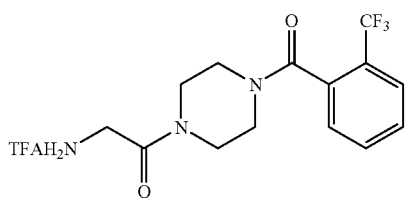

TFA (6 mL) was slowly added to a chilled (0° C.) solution of {2-oxo-2-[4-(2-trifluoromethyl-benzoyl)-piperazin-1-yl]-ethyl}-carbamic acid tert-butyl ester (3.0 g, 7.7 mmol) in DCM (30 mL). The reaction mixture was slowly allowed to warm to room temperature and maintained at this temperature for 1 hour. The solvent was removed under reduced pressure and the resulting residue was washed with ether to afford 2.8 g (84.8% yield) of 4-benzenesulfinyl-N-{2-oxo-2-[4-(2-trifluoromethyl-benzoyl)-piperazin-1-yl]-ethyl}-benzamide as a solid. $^1$H NMR (DMSO-d$_6$): δ 8.1 (bs, 2H), 7.9-7.8 (m, 2H), 7.7 (m, 1H), 7.6-7.5 (m, 1H), 4.0-3.8 (dd, 2H), 3.8-3.6 (m, 3H), 3.6-3.4 (m, 2H), 3.4-3.2 (m, 1H), 3.2-3.0 (m, 2H).

Step 2

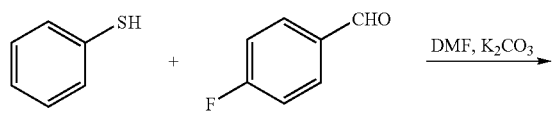

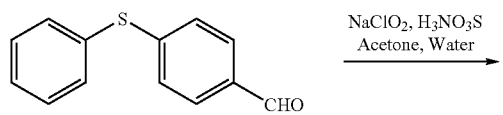

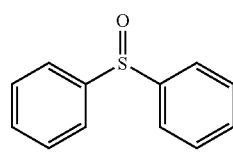

Step 2A: Synthesis of 4-Phenylsulfanyl-benzaldehyde

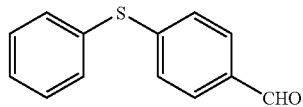

Benzenethiol (500 mg, 4.537 mmol) was dissolved in 6 mL of DMF. K$_2$CO$_3$ (940 mg, 6.81 mmol) was then added and the resulting mixture was allowed to stir at room temperature for 10 minutes. 4-Fluorobenzaldehyde (675 mg, 5.4 mmol) was then added and the resulting mixture was allowed to stir at 50° C. for 2 hours. The mixture was then stirred at 80° C. for 3 hours. Water was then added and the product was extracted with EtOAc and washed with brine. The organic phase was dried over Na$_2$SO$_4$ and concentrated under reduced pressure to afford a crude product. Purification by column chromatography (using 60-120 mesh silica gel and 5:95: EtOAc:Hexane as the eluent) afforded 940 mg (96% yield) of 4-phenylsulfanyl-benzaldehyde. LC-MS purity: 91.3

Step 2B: Synthesis of 4-Benzenesulfinyl-benzoic acid

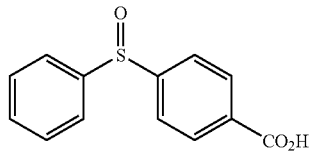

Sulphamic acid (0.68 gm, 7.00 mmol) in 2 mL water was added at 0° C. to a mixture of 4-phenylsulfanyl-benzaldehyde (0.5 g, 2.34 mmol) in 10 mL acetone. After 5 minutes sodium chlorite (0.845 g, 9.34 mmol) was added and the resulting mixture was stirred at 0° C. for 30 minutes. Water was added and the solid obtained was isolated by filtration to afford 0.49 g (85% yield) of 4-benzenesulfinyl-benzoic acid.

Step 3

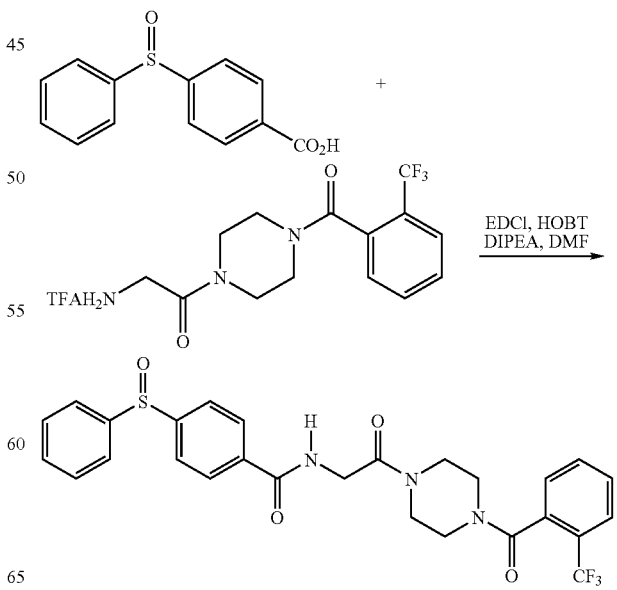

Synthesis of 4-Benzenesulfinyl-N-{2-oxo-2-[4-(2-trifluoromethyl-benzoyl)-piperazin-1-yl]-ethyl}-benzamide

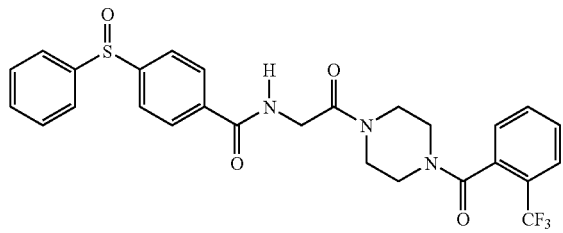

DIPEA (0.084 mL, 0.49 mmol) was added drop wise to 4-benzenesulfinyl-benzoic acid (48 mg, 0.19 mmol) in DMF (4 mL). EDCI (78 mg, 0.41 mmol) and HOBT 26 mg, 0.19 mmol) were added consecutively and 2-amino-1-[4-(2-trifluoromethyl-benzoyl)-piperazin-1-yl]-ethanone in its TFA salt form (70 mg, 0.16 mmol) was added after a further 10 mins. The resulting mixture was allowed to stir at room temperature overnight. Water was then added and the product was extracted with EtOAc and washed with brine. The organic phase was dried over $Na_2SO_4$ and concentrated under reduced pressure to afford a crude product. Purification by column chromatography (using silica gel with a mesh size of 60-120 and 100% EtOAc as eluent) afforded 45 mg (51% yield) of 4-benzenesulfinyl-N-{2-oxo-2-[4-(2-trifluoromethyl-benzoyl)-piperazin-1-yl]-ethyl}-benzamide. LC-MS purity: 91.93%. $^1$H NMR (DMSO-$D_6$): δ 8.7 (t, 1H), 8 (m, 3H), 7.8 (m, 6H), 7.5 (m, 3H), 7.2 (m, 1H), 4.2 (d, 2H), 3.6 (m, 6H), 3.1 (m, 2H).

8) Synthesis of N-{2-Oxo-2-[4-(2-trifluoromethyl-benzoyl)-piperazin-1-yl]-ethyl}-4-phenylamino-benzamide Step 1

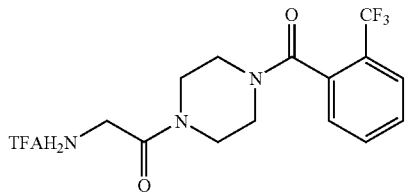

2-Amino-1-[4-(2-trifluoromethyl-benzoyl)-piperazin-1-yl]-ethanone in its TFA salt form was prepared as described above.

Step 2: Synthesis of 4-Phenylamino-benzoic acid

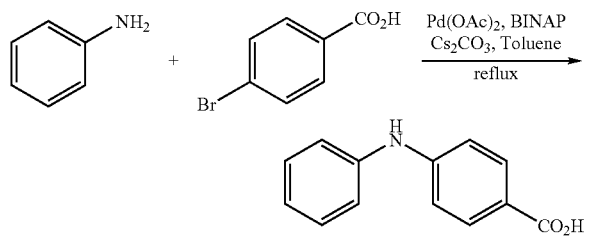

BINAP (0.1 g, 0.16 mmol) and Pd(OAc)$_2$ (0.014 g, 0.06 mmol) were mixed in toluene (10 mL) and this first solution was purged with argon for 15 minutes. Phenylamine (0.3 gm, 3.22 mmol), 4-bromo-benzoic acid (0.776 g, 3.89 mmol) and $Cs_2CO_3$ (3.14 gm, 9.66 mmol) were mixed in toluene (20 mL) and this second solution was purged with argon for 15 minutes. The first solution was added to the second solution, and the resulting mixture was heated to reflux overnight. Additional BINAP (0.1 g, 0.16 mmol) and Pd(OAc)$_2$ (0.014 g, 0.06 mmol) were then added and the mixture heated to reflux for a further 6 hours. The toluene was removed and the residue was acidified with 10% HCl. The product was extracted with EtOAc and washed with brine. The organic layer was dried over $Na_2SO_4$ and concentrated under reduced pressure to afford 950 mg crude product. Purification by column chromatography (using silica gel of mesh size of 60-120 and 30:70 EtOAc:Hexane as the eluent) afforded 300 mg (43% yield) of 4-Phenylamino-benzoic acid.

Step 3: Synthesis of N-{2-Oxo-2-[4-(2-trifluoromethyl-benzoyl)-piperazin-1-yl]-ethyl}-4-phenylamino-benzamide

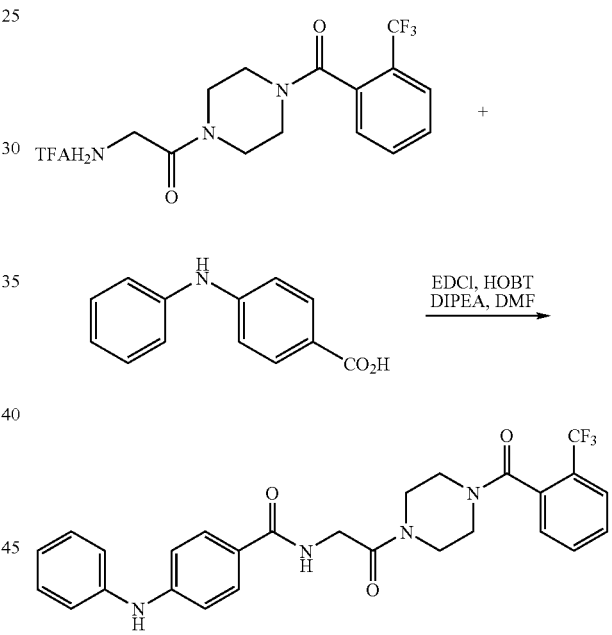

DIPEA (0.096 mL, 0.56 mmol) was added drop wise to 4-phenylamino-benzoic acid (47 mg, 0.22 mmol) in DMF (4 mL). EDCI (53 mg, 0.28 mmol) and HOBT (30 mg, 0.22 mmol) were added consecutively and, after 10 mins, 2-amino-1-[4-(2-trifluoromethyl-benzoyl)-piperazin-1-yl]-ethanone in its TFA salt form (80 mg, 0.19 mmol) was added. The resulting mixture was stirred at room temperature overnight. Water was then added the resulting solid filtered to afford 68 mg of crude product. Purification by column chromatography (using silica gel of mesh size of 60-120 and 80/20 EtOAc:Hexane as the eluent) afforded 45 mg (47% yield) of N-{2-Oxo-2-[4-(2-trifluoromethyl-benzoyl)-piperazin-1-yl]-ethyl}-4-phenylamino-benzamide. LC-MS purity: 96.8%. $^1$H-NMR (DMSO-D6): δ 8.6 (s, 1H), 8.3 (t, 1H), 7.8 (m, 5H), 7.6 (d, 1H), 7.3 (t, 2H), 7.2 (m, 1H), 7.1 (d, 2H), 6.9 (t, 1H), 4.1 (d, 2H), 3.6 (m, 4H), 3.4 (m, 2H), 3.1 (m, 2H).

9) Synthesis of 4-(4-Hydroxy-phenoxy)-N-{2-oxo-2-[4-(2-trifluoromethyl-benzoyl)-piperazin-1-yl]-ethyl}-benzamide

Step 1

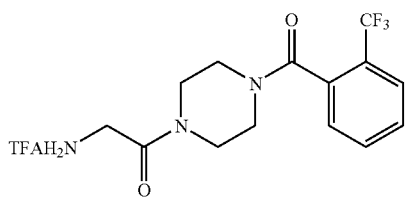

2-Amino-1-[4-(2-trifluoromethyl-benzoyl)-piperazin-1-yl]-ethanone in its TFA salt form was prepared as described above.

Step 2

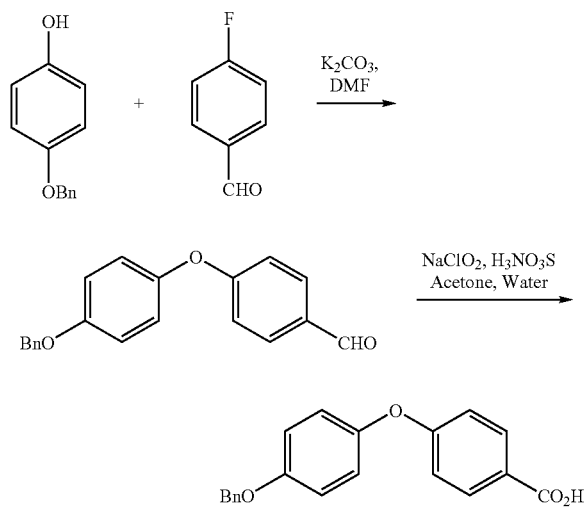

Step 2A: Synthesis of 4-(4-Benzyloxy-phenoxy)-benzaldehyde

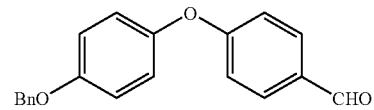

4-Benzyloxy-phenol (500 mg, 2.50 mmol) was dissolved in 7 mL of DMF. $K_2CO_3$ (414 mg 3.00 mmol) was added and the resulting mixture was stirred at room temperature for 10 mins. 4-Fluorobenzaldehyde (371 mg, 3.00 mmol) was added and the resulting mixture was stirred at 50° C. for 2 hours. The reaction mixture was then heated to 80° C. for 3 hours. Water was then added and the product was extracted with EtOAc and washed with brine. The organic phase was dried over $Na_2SO_4$ and concentrated under reduced pressure to afford 710 mg of crude product. Purification by column chromatography (using silica gel of mesh size of 60-120 and 3/97 EtOAc:Hexane as the eluent) afforded 550 mg (72% yield) of 4-(4-Benzyloxy-phenoxy)-benzaldehyde. LC-MS purity: 99.5%

Step 2B: Synthesis of 4-(4-Benzyloxy-phenoxy)-benzoic acid

Sulphamic acid (0.526 g, 5.43 mmol) in 2 mL water was added at 0° C. to 4-(4-benzyloxy-phenoxy)-benzaldehyde (0.55 g, 1.81 mmol) in acetone (8 mL). After 5 minutes, sodium chlorite (0.654 g, 7.24 mmol) was added and the mixture was stirred at 0° C. for three hours. Water was added and the resulting solid was isolated by filtration to afford 495 mg (85% yield) of 4-(4-benzyloxy-phenoxy)-benzoic acid.

Step 3: Synthesis of 4-(4-Benzyloxy-phenoxy)-N-{2-oxo-2-[4-(2-trifluoromethyl-benzoyl)-piperazin-1-yl]-ethyl}-benzamide

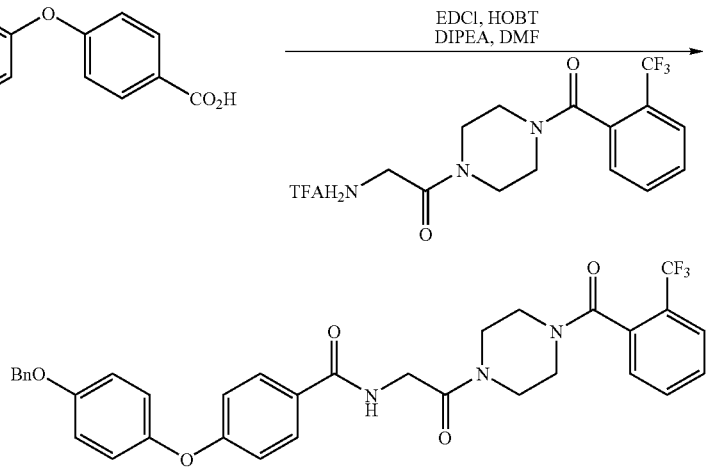

DIPEA (0.084 mL, 0.49 mmol) was added dropwise to 4-(4-benzyloxy-phenoxy)-benzoic acid (62 mg, 0.20 mmol) in DMF (4 mL). EDCI (78 mg, 0.41 mmol) and HOBT (26 mg, 0.20 mmol) were added consecutively and, after 10 mins, 2-amino-1-[4-(2-trifluoromethyl-benzoyl)-piperazin-1-yl]-ethanone in its TFA salt form (70 mg, 0.16 mmol) was added. The resulting mixture was stirred at room temperature overnight. Water was added and the resulting solid was isolated by filtration to afford 80 mg (80% yield) of 4-(4-benzyloxy-phenoxy)-N-{2-oxo-2-[4-(2-trifluoromethyl-benzoyl)-piperazin-1-yl]-ethyl}-benzamide.

Step 4: Synthesis of 4-(4-Hydroxy-phenoxy)-N-{2-oxo-2-[4-(2-trifluoromethyl-benzoyl)-piperazin-1-yl]-ethyl}-benzamide

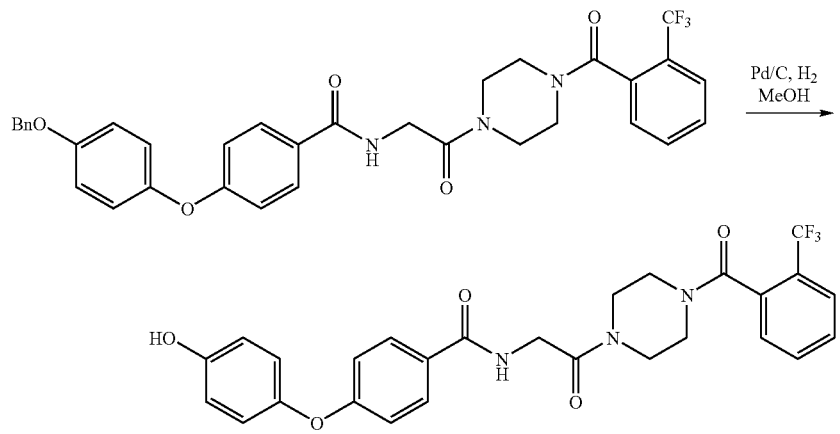

Pd/C (20 mg in 3 drops of water) was added to 4-(4-benzyloxy-phenoxy)-N-{2-oxo-2-[4-(2-trifluoromethyl-benzoyl)-piperazin-1-yl]-ethyl}-benzamide (80 mg, 0.13 mmol) in MeOH (10 mL). The resulting reaction mixture was stirred at room temperature under an atmosphere of hydrogen for 3 hours. The reaction mixture was then filtered through a bed of celite. The methanol was removed to afford 80 mg of crude product. Purification by column chromatography (using silica gel of mesh size of 60-120 and 80/20 EtOAc: Hexane as the eluent) afforded 33 mg (48% yield) of 4-(4-hydroxy-phenoxy)-N-{2-oxo-2-[4-(2-trifluoromethyl-benzoyl)-piperazin-1-yl]-ethyl}-benzamide LC-MS purity: 93%. $^1$H NMR (DMSO-D$_6$): δ 9.4 (s, 1H), 8.5 (t, 1H), 7.9-7.5 (m, 6H), 6.8-7 (m, 5H), 4.2 (d, 2H), 3.5 (m, 6H), 3.1 (m, 2H).

10) Synthesis of N-{2-[4-(2,4-Dichloro-benzoyl)-piperazin-1-yl]-2-oxo-ethyl}-4-phenylamino-benzamide

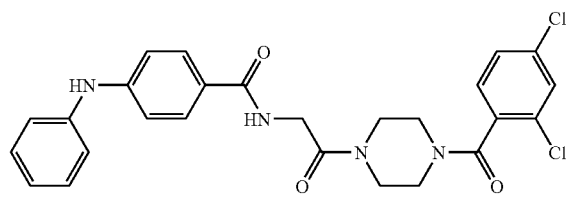

DIPEA (133 mg, 0.18 mL, 0.56 mmol) was added drop wise to 4-phenylamino-benzoic acid (preparation as described above) (75 mg, 0.35 mmol) in DMF (4 mL). EDCI (167 mg, 0.87 mmol) and HOBT (56 mg, 0.42 mmol) were added consecutively and, after 10 minutes, 2-amino-1-[4-(2,4-dichloro-benzoyl)-piperazin-1-yl]-ethanone in its TFA salt form (180 mg, 0.42 mmol) was added. The resulting mixture was stirred at room temperature overnight. Cold water was then added, filtered the solid precipitated. The solid was purified by column chromatography (using silica gel of 60-120 mesh and 70% EtOAc in Hexane as eluent) to afford 95 mg (53% yield) of N-{2-[4-(2,4-Dichloro-benzoyl)-piperazin-1-yl]-2-oxo-ethyl}-4-phenylamino-benzamide. LC-MS purity: 96.05%. $^1$H-NMR (DMSO-D6): δ 8.6 (s, 1H), 8.3 (t, 1H), 7.8 (d, 3H), 7.5 (m, 2H), 7.3 (t, 2H), 7.2 (d, 2H), 7.1 (d, 2H), 6.9 (t, 1H), 4.1 (dd, 2H), 3.6 (m, 4H), 3.5 (m, 2H), 3.2 (m, 2H).

11) Synthesis of N-{2-[4-(5-Fluoro-2-trifluoromethyl-benzoyl)-piperazin-1-yl]-2-oxo-ethyl}-4-phenylamino-benzamide

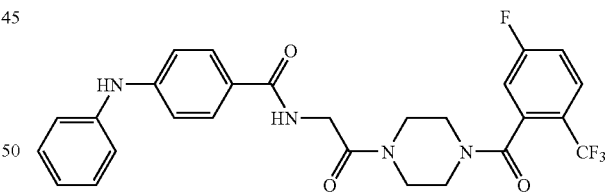

DIPEA (133 mg, 0.18 mL, 0.56 mmol) was added drop wise to 4-phenylamino-benzoic acid (preparation as described above) (75 mg, 0.35 mmol) in DMF (5 mL). EDCI (167 mg, 0.87 mmol) and HOBT (56 mg, 0.42 mmol) were added. After 10 minutes, 2-amino-1-[4-(5-fluoro-2-trifluoromethyl-benzoyl)-piperazin-1-yl]-ethanone in its TFA salt form (187 mg, 0.42 mmol) was added. The resulting mixture was stirred at room temperature overnight. Cold water was then added, filtered the solid precipitated to afford 87 mg (47% yield) of N-{2-[4-(5-Fluoro-2-trifluoromethyl-benzoyl)-piperazin-1-yl]-2-oxo-ethyl}-4-phenylamino-benzamide. LC-MS purity: 88.27%. $^1$H-NMR (DMSO-D6): δ 8.6 (s, 1H), 8.3 (t, 1H), 7.9 (m, 1H), 7.8 (d, 2H), 7.6 (m, 2H), 7.3 (t, 2H), 7.2 (d, 2H), 7.1 (d, 2H), 6.9 (t, 1H), 4.2 (d, 2H), 3.8 (m, 4H), 3.6 (m, 2H), 3.2 (m, 2H), 3.1 (m, 1H).

12) Synthesis of 4-(Methyl-phenyl-amino)-N-{2-oxo-2-[4-(2-trifluoromethyl-benzoyl)-piperazin-1-yl]-ethyl}-benzamide

Step 1: Synthesis of 4-(Methyl-phenyl-amino)-benzoic acid methyl ester

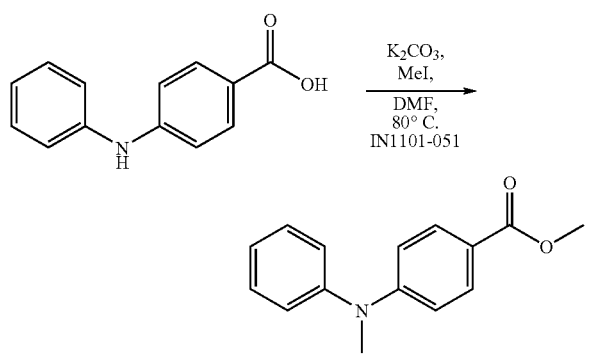

Methyl iodide (227 mg, 0.1 mL, 1.68 mmol) was added drop wise to a suspension of 4-(Methyl-phenyl-amino)-benzoic acid (120 mg, 0.56 mmol) and $K_2CO_3$ in DMF (5 mL). The resulting mixture was heated at 80° C. with stirring overnight. The mixture was filtered, cold water was then added, and the product was extracted with EtOAc. The organic layer was washed with saturated brine solution and dried over Na2SO4. The organic layer was then concentrated under reduced pressure to get the residue The obtained residue was purified by column chromatography (using silica gel of 60-120 mesh and 5% EtOAc in Hexane as eluent) to afford 85 mg (75% yield) of 4-(Methyl-phenyl-amino)-benzoic acid methyl ester. $^1$H-NMR (CDCl$_3$): δ 7.8 (d, 2H), 7.4 (T, 2H), 7.2 (m, 2H), 6.8 (d, 2H), 3.8 (s, 3H), 3.2 (s, 3H).

Step 2: Synthesis of 4-(Methyl-phenyl-amino)-benzoic acid 4-(Methyl-phenyl-amino)-benzoic acid was prepared by the method described above.

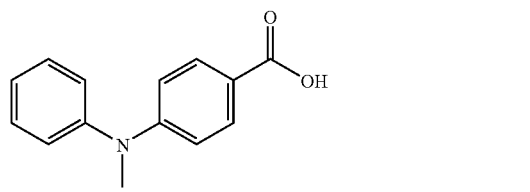

Step 3: Synthesis of 4-(Methyl-phenyl-amino)-N-{2-oxo-2-[4-(2-trifluoromethyl-benzoyl)-piperazin-1-yl]-ethyl}-benzamide

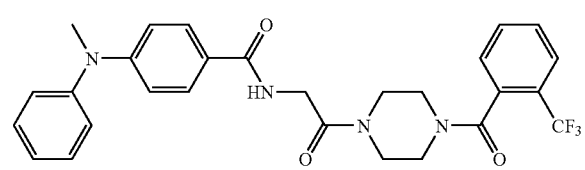

DIPEA (92 mg, 0.125 mL, 0.72 mmol) was added drop wise to 4-(Methyl-phenyl-amino)-benzoic acid (55 mg, 0.24 mmol) in DMF (5 mL). EDCI (115 mg, 0.6 mmol) and HOBT (39 mg, 0.28 mmol) were added consecutively and, after 10 minutes, 2-amino-1-[4-(2-trifluoromethyl-benzoyl)-piperazin-1-yl]-ethanone in its TFA salt form (124 mg, 0.289 mmol) was added. The resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by Preparative HPLC [(Column-Zorbax XDB $C_{18}$-21.2×150 mm, mobile phase-0.1% TFA in water (A)/acetonitrile (B), gradient: (Time): (% B)-0:20; 2:30; 8:70)]) to afford 34 mg (26% yield) of 4-(Methyl-phenyl-amino)-N-{2-oxo-2-[4-(2-trifluoromethyl-benzoyl)-piperazin-1-yl]-ethyl}-benzamide. LC-MS purity: 97.62%. $^1$H-NMR (CDCl$_3$): δ 7.7 (m, 3H), 7.6 (m, 2H), 7.4 (q, 3H), 7.2 (m, 2H), 7.1 (m, 1H), 6.8 (d, 2H), 4.3 (dd, 1H), 4.2 (dd, 1H), 4.0 (m, 1H), 3.9 (m, 1H), 3.7 (m, 3H), 3.4 (m, 1H), 3.3 (s, 3H), 3.2 (m, 2H).

13) Synthesis of N-{2-[4-(2,5-Dichloro-benzoyl)-piperazin-1-yl]-2-oxo-ethyl}-4-phenylamino-benzamide

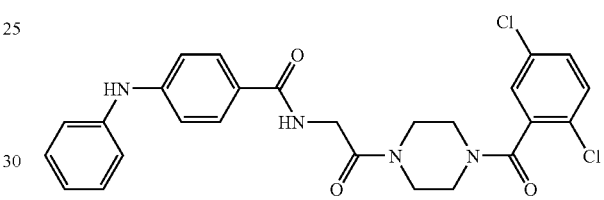

DIPEA (133 mg, 0.18 mL, 1.0 mmol) was added drop wise to 4-(-phenyl-amino)-benzoic acid (75 mg, 0.35 mmol) in DMF (5 mL). EDCI (167 mg, 0.87 mmol) and HOBT (56 mg, 0.42 mmol) were added consecutively and, after 10 minutes, 2-amino-1-[4-(2,5-dichloro-benzoyl)-piperazin-1-yl]-ethanone in its TFA salt form (148 mg, 0.42 mmol) was added. The resulting mixture was stirred at room temperature overnight. Cold water was then added and filtered the solid to afford 140 mg (78% yield) of N-{2-[4-(2,5-dichloro-benzoyl)-piperazin-1-yl]-2-oxo-ethyl}-4-phenylamino-benzamide. LC-MS purity: 95.65%. $^1$H-NMR (DMSO-d$_6$): δ 8.6 (s, 1H), 8.3 (t, 1H), 7.8 (m, 5H), 7.3 (t, 2H), 7.2 (m, 4H), 6.9 (t, 1H), 4.1 (d, 2H), 3.6 (m, 6H), 3.2 (d, 2H).

14) Synthesis of N-{2-[4-(2-Bromo-5-methoxy-benzoyl)-piperazin-1-yl]-2-oxo-ethyl}-4-phenylamino-benzamide

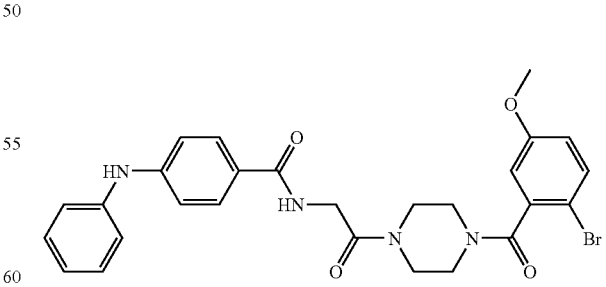

DIPEA (133 mg, 0.18 mL, 1.0 mmol) was added drop wise to 4-(-phenyl-amino)-benzoic acid (75 mg, 0.35 mmol) in DMF (5 mL). EDCI (167 mg, 0.87 mmol) and HOBT (56 mg, 0.42 mmol) were added consecutively and, after 10 minutes, 2-amino-1-[4-(2-bromo-5-methoxy-benzoyl)-piperazin-1-yl]-ethanone in its TFA salt form (164 mg, 0.42 mmol) was added. The resulting mixture was stirred at room temperature overnight. Cold water was then added and filtered the solid to afford 130 mg (67% yield) of N-{2-[4-(2-bromo-5-methoxy-benzoyl)-piperazin-1-yl]-2-oxo-ethyl}-4-phenylamino-benzamide. LC-MS purity: 96.77%. $^1$H-NMR (DMSO-$d_6$): δ 8.6 (s, 1H), 8.3 (t, 1H), 7.8 (d, 2H), 7.6 (d, 1H), 7.3 (d, 2H), 7.1 (d, 2H), 7.0 (m, 3H) 4.2 (dd, 2H), 3.8 (s, 3H), 3.6 (m, 6H), 3.2 (m, 2H).

15) Synthesis of N-{2-[4-(2-Chloro-5-trifluoromethyl-benzoyl)-piperazin-1-yl]-2-oxo-ethyl}-4-phenylamino-benzamide

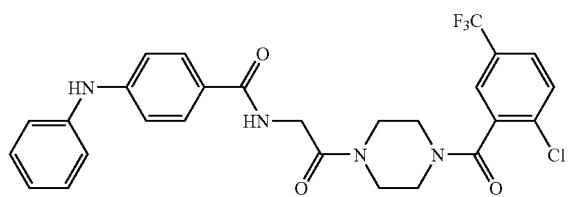

DIPEA (74 mg, 0.1 mL, 0.63 mmol) was added drop wise to 4-(phenyl-amino)-benzoic acid (45 mg, 0.21 mmol) in DMF (5 mL). EDCI (100 mg, 0.52 mmol) and HOBT (34 mg, 0.25 mmol) were added consecutively and, after 10 minutes, 2-amino-1-[4-(2-chloro-5-trifluoromethyl-benzoyl)-piperazin-1-yl]-ethanone in its HCl salt form (97 mg, 0.25 mmol) was added. The resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 70% EtOAc in Hexane as eluent) to afford 60 mg (52% yield) of N-{2-[4-(2-chloro-5-trifluoromethyl-benzoyl)-piperazin-1-yl]-2-oxo-ethyl}-4-phenylamino-benzamide. LC-MS purity: 98.43%. $^1$H-NMR (DMSO-$d_6$): δ 8.6 (s, 1H), 8.3 (t, 1H), 7.9 (d, 1H), 7.8 (m, 4H), 7.3 (t, 2H), 7.2 (d, 2H), 7.1 (d, 2H), 6.9 (t, 1H), 4.1 (dd, 2H), 3.6 (m, 6H), 3.2 (m, 2H).

16) Synthesis of 5-Phenylamino-pyridine-2-carboxylic acid {2-[4-(5-fluoro-2-trifluoromethyl-benzoyl)-piperazin-1-yl]-2-oxo-ethyl}-amide

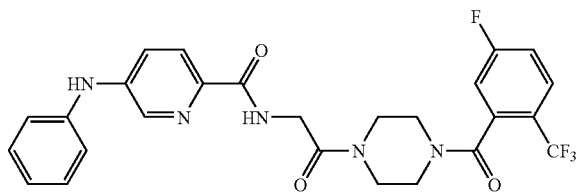

DIPEA (90 mg, 0.12 mL, 0.7 mmol) was added drop wise to 5-(phenyl-amino)-pyridine-2-carboxylic acid (50 mg, 0.23 mmol) in DMF (5 mL). EDCI (111 mg, 0.58 mmol) and HOBT (37 mg, 0.28 mmol) were added consecutively and, after 10 minutes, 2-amino-1-[4-(2-trifluoromethyl-5-fluoro-benzoyl)-piperazin-1-yl]-ethanone in its HCl salt form (125 mg, 0.28 mmol) was added. The resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 70% EtOAc in Hexane as eluent) to afford 55 mg (44% yield) of 5-phenylamino-pyridine-2-carboxylic acid {2-[4-(5-fluoro-2-trifluoromethyl-benzoyl)-piperazin-1-yl]-2-oxo-ethyl}-amide. LC-MS purity: 99.28%. $^1$H-NMR (DMSO-$d_6$): δ 8.9 (s, 1H), 8.5 (t, 1H), 7.9 (m, 2H), 7.6 (d, 3H), 7.4 (t, 2H), 7.2 (d, 2H), 7.0 (t, 1H), 4.2 (d, 2H), 3.6 (m, 5H), 3.2 (m, 3H).

17) Synthesis of 5-Phenylamino-pyridine-2-carboxylic acid {2-oxo-2-[4-(2-trifluoromethyl-benzoyl)-piperazin-1-yl]-ethyl}-amide

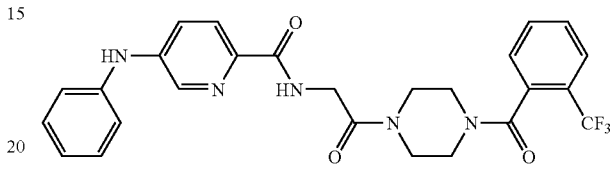

DIPEA (90 mg, 0.12 mL, 0.7 mmol) was added drop wise to 5-(phenyl-amino)-pyridine-2-carboxylic acid (50 mg, 0.23 mmol) in DMF (5 mL). EDCI (111 mg, 0.58 mmol) and HOBT (37 mg, 0.28 mmol) were added consecutively and, after 10 minutes, 2-amino-1-[4-(2-trifluoromethyl-benzoyl)-piperazin-1-yl]-ethanone in its HCl salt form (98 mg, 0.28 mmol) was added. The resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 50% EtOAc in Hexane as eluent) to afford 50 mg (42% yield) of 5-phenylamino-pyridine-2-carboxylic acid {2-[4-(2-trifluoromethyl-benzoyl)-piperazin-1-yl]-2-oxo-ethyl}-amide. LC-MS purity: 93.93%. $^1$H-NMR (DMSO-$d_6$): δ 8.9 (s, 1H), 8.5 (t, 1H), 8.3 (d, 1H), 7.8 (m, 5H), 7.6 (d, 2H), 7.4 (t, 2H), 7.2 (d, 2H), 7.0 (t, 1H), 4.2 (dd, 2H), 3.6 (m, 4H), 3.4 (m, 2H), 3.2 (m, 2H).

18) Synthesis of N-{2-[4-(2,5-Difluoro-benzoyl)-piperazin-1-yl]-2-oxo-ethyl}-4-phenylamino-benzamide

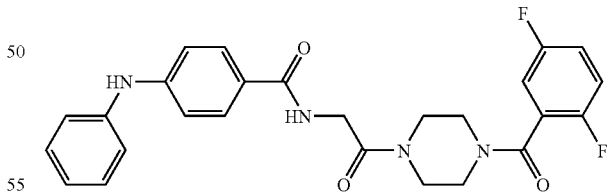

DIPEA (68 mg, 0.09 mL, 0.53 mmol) was added drop wise to 2,5-difluoro-benzoic acid (33 mg, 0.21 mmol) in DMF (5 mL). EDCI (40 mg, 0.21 mmol) and HOBT (28 mg, 0.21 mmol) were added consecutively and, after 10 minutes, N-(2-Oxo-2-piperazin-1-yl-ethyl)-4-phenylamino-benzamide in its HCl salt form (60 mg, 0.17 mmol) was added. The resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 60% EtOAc in Hexane as eluent) to afford 39 mg (46% yield) of N-{2-[4-(2,5-difluoro-benzoyl)-piperazin-1-yl]-2-oxo-ethyl}-4-phenylamino-benzamide. LC-MS purity: 96.62%. $^1$H-NMR (DMSO-$d_6$): δ 8.6 (s, 1H), 8.3 (t, 1H), 7.8 (d, 2H), 7.4 (t, 3H), 7.3 (t, 2H), 7.2 (d, 2H), 7.1 (d, 2H), 6.9 (t, 1H), 4.1 (dd, 2H), 3.6 (m, 4H), 3.5 (m, 2H), 3.2 (m, 2H).

19) Synthesis of N-{2-Oxo-2-[4-(2-trifluoromethyl-benzoyl)-piperazin-1-yl]-ethyl}-6-phenylamino-nicotinamide

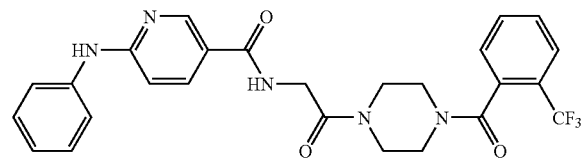

DIPEA (126 mg, 0.17 mL, 0.98 mmol) was added drop wise to 6-(phenyl-amino)-pyridine-3-carboxylic acid (70 mg, 0.32 mmol) in DMF (5 mL). EDCI (74 mg, 0.39 mmol) and HOBT (53 mg, 0.39 mmol) were added consecutively and, after 10 minutes, 2-amino-1-[4-(2-trifluoromethyl-benzoyl)-piperazin-1-yl]-ethanone in its HCl salt form (137 mg, 0.39 mmol) was added. The resulting mixture was stirred at room temperature overnight. Cold water was then added and filtered the solid precipitated to afford 110 mg (65% yield) of N-{2-oxo-2-[4-(2-trifluoromethyl-benzoyl)-piperazin-1-yl]-ethyl}-6-phenylamino-nicotinamide. LC-MS purity: 93.71%. $^1$H-NMR (DMSO-$d_6$): δ 9.4 (s, 1H), 8.7 (s, 1H), 8.5 (t, 1H), 8.0 (d, 1H), 7.8 (m, 2H), 7.7 (d, 3H), 7.6 (m, 1H), 6.9 (t, 1H), 6.8 (d, 1H), 4.2 (dd, 2H), 3.6 (m, 4H), 3.4 (m, 2H), 3.2 (m, 2H).

20) Synthesis of N-{2-[4-(2-Bromo-5-fluoro-benzoyl)-piperazin-1-yl]-2-oxo-ethyl}-4-phenylamino-benzamide

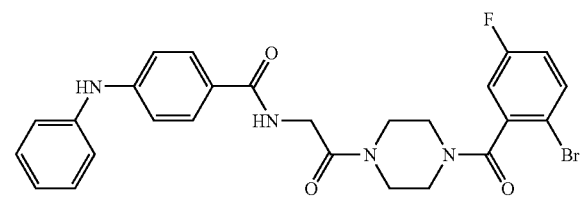

DIPEA (114 mg, 0.15 mL, 0.88 mmol) was added drop wise to 2-bromo-5-fluoro-benzoic acid (77 mg, 0.35 mmol) in DMF (5 mL). EDCI (114 mg, 0.88 mmol) and HOBT (47 mg, 0.35 mmol) were added consecutively and, after 10 minutes, N-(2-Oxo-2-piperazin-1-yl-ethyl)-4-phenylamino-benzamide in its HCl salt form (100 mg, 0.29 mmol) was added. The resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 70% EtOAc in Hexane as eluent) to afford 80 mg (50% yield) of N-{2-[4-(2-bromo-5-fluoro-benzoyl)-piperazin-1-yl]-2-oxo-ethyl}-4-phenylamino-benzamide. LC-MS purity: 94.48%. $^1$H-NMR (DMSO-$d_6$): δ 8.6 (s, 1H), 8.3 (t, 1H), 7.8 (d, 3H), 7.4 (m, 4H), 7.2 (d, 2H), 7.1 (d, 2H), 6.9 (t, 1H), 4.1 (dd, 2H), 3.6 (m, 6H), 3.2 (m, 2H).

21) Synthesis of N-{2-[4-(3,5-Dichloro-benzoyl)-piperazin-1-yl]-2-oxo-ethyl}-4-phenylamino-benzamide

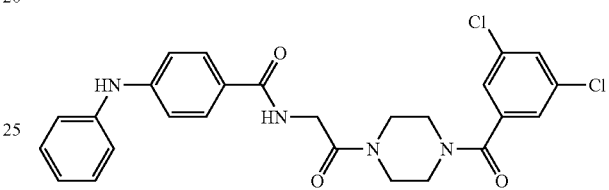

DIPEA (125 mg, 0.17 mL, 0.97 mmol) was added drop wise to 3,5-dichloro-benzoic acid (74 mg, 0.389 mmol) in DMF (5 mL). EDCI (74 mg, 0.389 mmol) and HOBT (52 mg, 0.389 mmol) were added consecutively and, after 10 minutes, N-(2-Oxo-2-piperazin-1-yl-ethyl)-4-phenylamino-benzamide in its HCl salt form (110 mg, 0.32 mmol) was added. The resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 50% EtOAc in Hexane as eluent) to afford 39 mg (15% yield) of N-{2-[4-(3,5-Dichloro-benzoyl)-piperazin-1-yl]-2-oxo-ethyl}-4-phenylamino-benzamide. LC-MS purity: 95.72%. $^1$H-NMR (DMSO-$d_6$): δ 8.6 (s, 1H), 8.3 (t, 1H), 7.8 (d, 3H), 7.5 (s, 2H), 7.3 (t, 2H), 7.2 (d, 2H), 7.1 (d, 2H), 6.9 (t, 1H), 4.1 (m, 2H), 3.6 (m, 2H).

22) Synthesis of 4-Benzenesulfonyl-N-{2-oxo-2-[4-(2-trifluoromethyl-benzoyl)-piperazin-1-yl]-ethyl}-benzamide Step 1

SCHEME-4

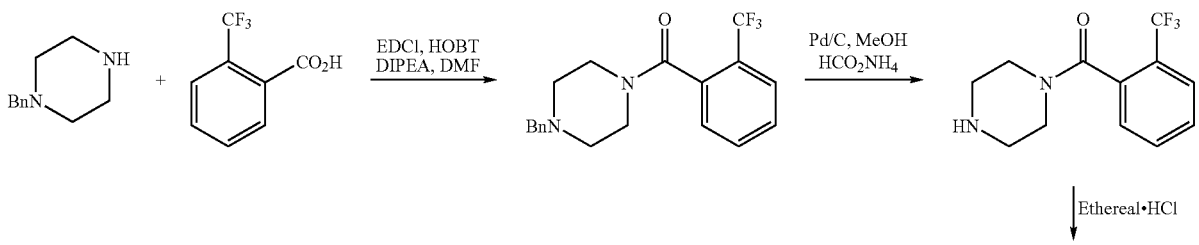

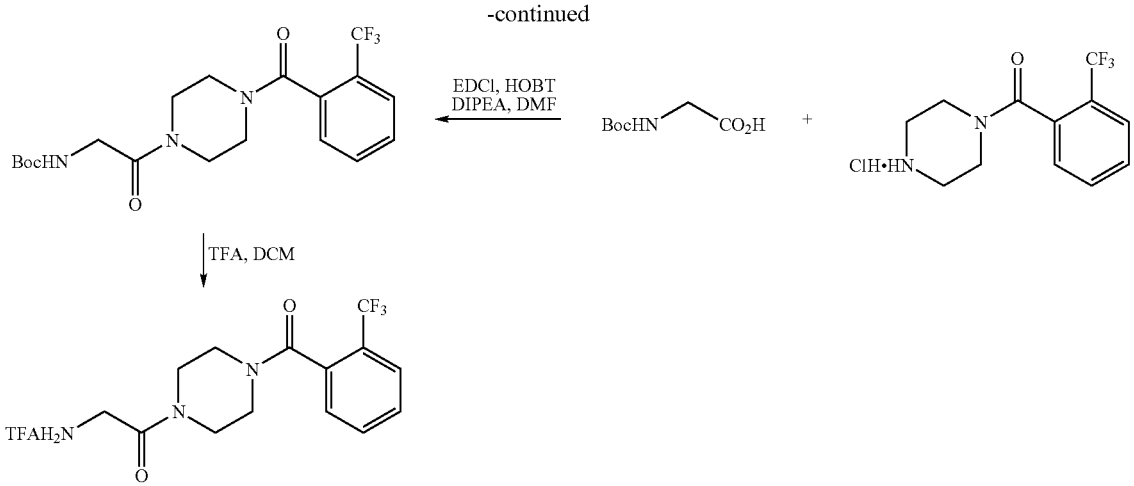

Step 1A: Synthesis of (4-Benzyl-piperazin-1-yl)-(2-trifluoromethyl-phenyl)-methanone

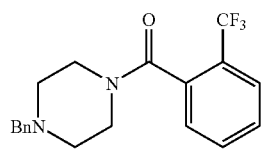

DIPEA (13.6 mL, 78.90 mmol) was added drop wise to 2-trifluoromethyl-benzoic acid (5 g, 26.30 mmol) in DMF (20 mL). EDCI (12.6 g, 65.75 mmol) and HOBT (4.26 g, 31.56 mmol) were added consecutively and after 10 mins, 1-benzyl-piperazine (5.56 g, 31.56 mmol) was added. The resulting mixture was stirred at room temperature overnight. Water was then added and the product was extracted with EtOAc and washed with brine. The organic phase was dried over Na₂SO₄ and concentrated under reduced pressure to afford 12.6 g of crude product. Purification by column chromatography (using silica gel of mesh size of 60-120 and 30/70 EtOAc:hexane as the eluent) afforded 8.6 g (93% yield) of (4-benzyl-piperazin-1-yl)-(2-trifluoromethyl-phenyl)-methanone.

Step 1B: Synthesis of piperazin-1-yl-(2-trifluoromethyl-phenyl)-methanone

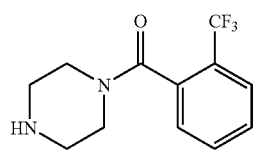

Ammonium formate (15.5 g, 247.126 mmol) was added to (4-benzyl-piperazin-1-yl)-(2-trifluoromethyl-phenyl)-methanone (8.6 g, 24.71 mmol) in MeOH (40 mL). Pd/C (1.8 g in 2 mL water) was then added and the resulting mixture was heated to reflux at 75° C. for 4 hours. The reaction mixture was then filtered through a bed of celite bed and the methanol was removed. EtOAc and water were then added to the residue and the organic layer was extracted, washed with 10% NaOH solution, brine, dried over sodium sulphate, and concentrated to afford 5.5 g (86% yield) of piperazin-1-yl-(2-trifluoromethyl-phenyl)-methanone.

Step 1C: Synthesis of piperazin-1-yl-(2-trifluoromethyl-phenyl)-methanone hydrochloride

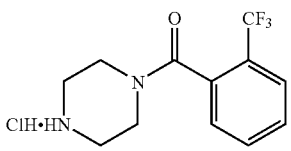

Ethereal HCl (30 mL) was added to piperazin-1-yl-(2-trifluoromethyl-phenyl)-methanone (5.5 g, 21.40 mmol) and the resulting mixture was stirred at 0° C. for 30 minutes. The ether was then evaporated to afford 5.7 g (91% yield) of piperazin-1-yl-(2-trifluoromethyl-phenyl)-methanone hydrochloride.

Step 1D: Synthesis of {2-Oxo-2-[4-(2-trifluoromethyl-benzoyl)-piperazin-1-yl]-ethyl}-carbamic acid tert-butyl ester DIPEA (3.5 mL, 20.41 mmol) was added dropwise to tert-butoxycarbonylamino-acetic acid (1.42 g, 8.16 mmol) in DMF (15 mL). EDCI (2.6 g, 13.61 mmol) and HOBT (1.1 g, 8.16 mmol) were added consecutively and, after 10 mins, piperazin-1-yl-(2-trifluoromethyl-phenyl)-methanone hydrochloride (2 g, 6.80 mmol) was added. The resulting mixture was stirred at room temperature overnight. Water was then added and the product was extracted with EtOAc and washed with brine. The organic phase was dried over Na₂SO₄ and concentrated under reduced pressure to afford 3.3 g of crude product. Purification by column chromatography (using silica gel of mesh size of 60-120 and 60/40 EtOAc:hexane as the eluent) afforded 2.6 g (96% yield) of {2-Oxo-2-[4-(2-trifluoromethyl-benzoyl)-piperazin-1-yl]-ethyl}-carbamic acid tert-butyl ester.

Step 1E: Synthesis of 2-Amino-1-[4-(2-trifluoromethyl-benzoyl)-piperazin-1-yl]-ethanone TFA salt

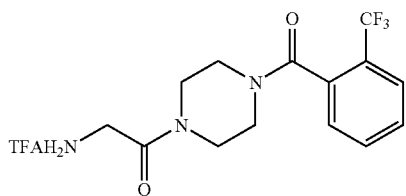

TFA (13 mL) was added drop wise to {2-Oxo-2-[4-(2-trifluoromethyl-benzoyl)-piperazin-1-yl]-ethyl}-carbamic acid tert-butyl ester (2.6 g, 6.27 mmol) in DCM (15 mL) at 0° C. The resulting mixture was stirred at room temperature for 2 hours. Concentrating the mixture afforded a crude product, which was recrystallized from hexane to afford 2.5 g (93% yield) of 2-amino-1-[4-(2-trifluoromethyl-benzoyl)-piperazin-1-yl]-ethanone as TFA salt.

Step 2

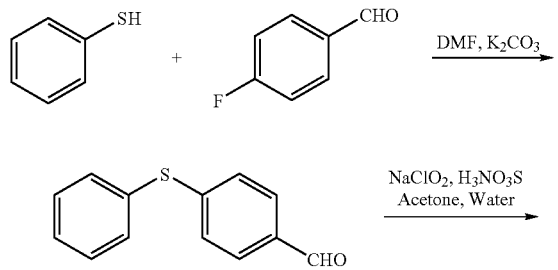

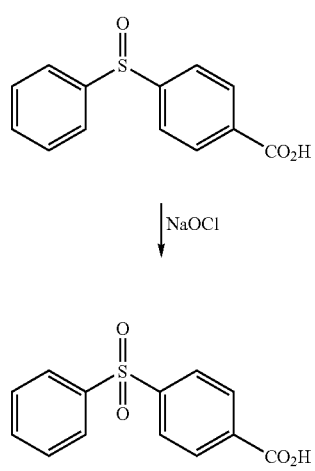

Step 2A: Synthesis of 4-Phenylsulfanyl-benzaldehyde

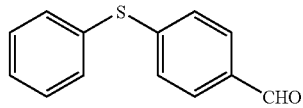

Benzenethiol (500 mg, 4.54 mmol) was dissolved in 6 mL of DMF. K₂CO₃ (940 mg, 6.81 mmol) was added and the resulting mixture was stirred at room temperature for 10 mins. 4-Fluoro-benzaldehyde (675 mg, 5.44 mmol) was then added and the resulting mixture was stirred at 50° C. for 2 hours. The mixture was then stirred at 80° C. for 3 hours. Water was added and the product was extracted with EtOAc and washed with brine. The organic phase was dried over Na₂SO₄ and concentrated under reduced pressure to afford crude product. Purification by column chromatography (using silica gel of mesh size of 60-120 and 5/95 EtOAc:hexane as the eluent) afforded 940 mg (96% yield) of 4-phenylsulfanyl-benzaldehyde. LC-MS purity: 91.3%

Step 2B: Synthesis of 4-Benzenesulfinyl-benzoic acid

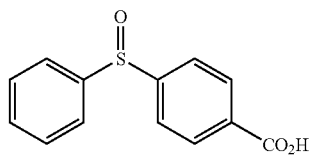

Sulphamic acid (0.272 g, 2.80 mmol) in 2 mL water was added to 4-phenylsulfanyl-benzaldehyde (0.2 g, 0.93 mmol) in 5 mL acetone at 0° C. After 5 minutes, sodium chlorite (0.338 g, 3.74 mmol) was added and the mixture stirred at 0° C. for 30 minutes. Sodium chlorite (0.676 g, 7.48 mmol) was then added and the resulting mixture was stirred at room temperature overnight. Water was then added and the resulting solid was filtered to afford 140 mg (60% yield) of 4-benzenesulfinyl-benzoic acid.

Step 2C: Synthesis of 4-Benzenesulfonyl-benzoic acid

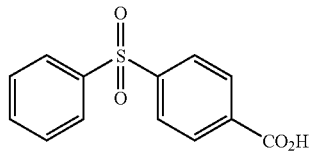

A mixture of 5 mL sodium hypochlorite and 4-benzenesulfinyl-benzoic acid (0.14 gm, 0.57 mmol) in DMF (5 mL) was stirred at room temperature overnight. A further 5 mL of sodium hypochlorite was then added and the mixture stirred at room temperature overnight. After acidification using 10% HCl, the resulting solid was filtered to afford 105 mg (70% yield) of 4-benzenesulfonyl-benzoic acid.

Step 3: Synthesis of 4-Benzenesulfonyl-N-{2-oxo-2-[4-(2-trifluoromethyl-benzoyl)-piperazin-1-yl]-ethyl}-benzamide

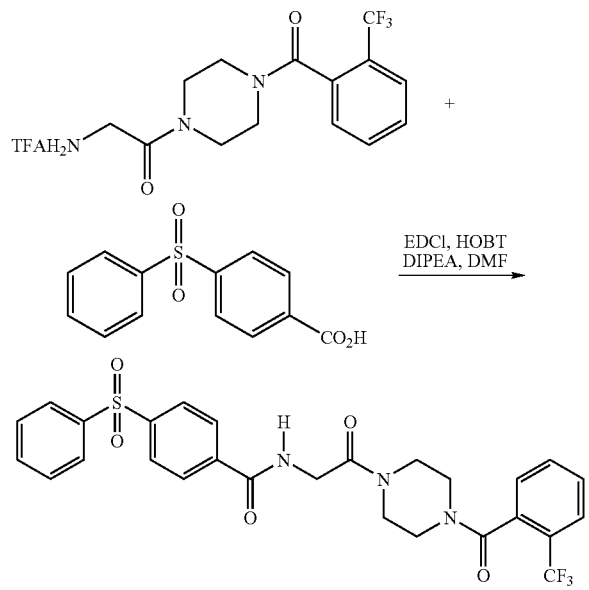

DIPEA (0.084 mL, 0.49 mmol) was added drop wise to 4-benzenesulfonyl-benzoic acid (51 mg, 0.20 mmol) in DMF (5 mL). EDCI (78 mg, 0.41 mmol) and HOBT (26 mg, 0.20 mmol) were added consecutively and, after 10 mins, 2-amino-1-[4-(2-trifluoromethyl-benzoyl)-piperazin-1-yl]-ethanone in its TFA salt form (70 mg, 0.16 mmol) was added. The resulting mixture was stirred at room temperature overnight. Water was then added and the resulting solid was filtered to afford 60 mg (65% yield) of 4-benzenesulfonyl-N-{2-oxo-2-[4-(2-trifluoromethyl-benzoyl)-piperazin-1-yl]-ethyl}-benzamide. LC-MS purity: 95.5%. $^1$H NMR (DMSO-D$_6$): δ 8.8 (t, 1H), 8.1 (m, 5H), 7.8 (m, 6H), 7.6 (m, 1H), 4.2 (d, 2H), 3.6 (m, 6H), 3.2 (m, 2H).

23) Synthesis of 1-(3-Phenyl-propionyl)-piperidine-4-carboxylic acid {2-oxo-2-[4-(2-trifluoromethyl-benzoyl)-piperazin-1-yl]-ethyl}-amide

Step 1: Synthesis of Piperidine-4-carboxylic acid benzyl ester

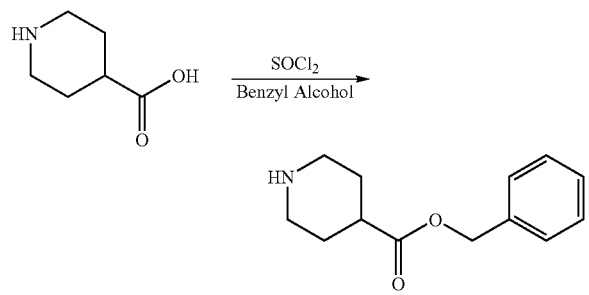

Thionyl chloride (5.42 g, 46 mmol) was added to a cold (0-4° C.) stirred solution piperidine-4-carboxylic acid (5 g, 38.7 mmol) in benzyl alcohol (150 mL) and stirring was continued overnight. Benzyl alcohol was removed by stirring with hexane, ether and decanting the solvent, dried to afford 8.26 g (97.25% yield) of piperidine-4-carboxylic acid benzyl ester. LCMS Purity: 94.8%.

Step 2: Synthesis of 1-(3-Phenyl-propionyl)-piperidine-4-carboxylic acid benzyl ester

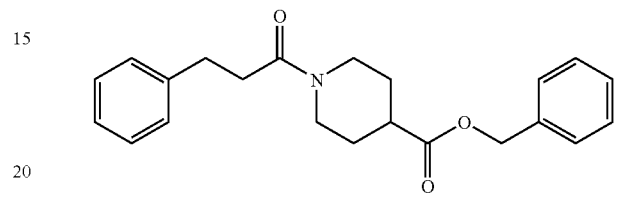

DIPEA (7 g, 9.44 mL, 54.6 mmol) was added to a stirred solution of 3-phenyl-propionic acid (3.27 g, 21.8 mmol) in DMF (15 mL). HOBT (2.94 g, 21.8 mmol) and EDCI (4.16 g, 21.8 mmol) were then added at room temperature. After 2 minutes, piperidine-4-carboxylic acid benzyl ester (4 g, 18.2 mmol) was added and the resulting mixture was stirred at room temperature overnight. Cold water was then added and the product was extracted with EtOAc and the organic layer was washed with brine. The organic phase was dried over Na$_2$SO$_4$ and concentrated under reduced pressure to get the residue. The obtained residue was purified by column chromatography (using 60-120 silica gel and EtOAc in hexane as eluent) to afford 2.64 g (41.25% yield) of 1-(3-phenyl-propionyl)-piperidine-4-carboxylic acid benzyl ester. LCMS Purity: 86.15%.

Step 3: Synthesis of 1-(3-Phenyl-propionyl)-piperidine-4-carboxylic acid

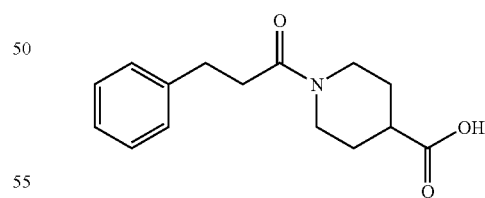

Pd/c (528 mg) was added to a stirred solution of 1-(3-phenyl-propionyl)-piperidine-4-carboxylic acid benzyl ester (2.64 gm, 7.5 mmol) in MeOH (52.8 mL) and continued the stirring under hydrogen atmosphere for 3 hrs. The mixture was filtered over a bed of celite. The celite was washed with MeOH and the filtrate was concentrated under reduced pressure to afford 1.17 g (59.6% yield) of 1-(3-phenyl-propionyl)-piperidine-4-carboxylic acid. LCMS Purity: 93.56%.

Step 4: Synthesis of 1-(3-Phenyl-propionyl)-piperidine-4-carboxylic acid {2-oxo-2-[4-(2-trifluoromethyl-benzoyl)-piperazin-1-yl]-ethyl}-amide

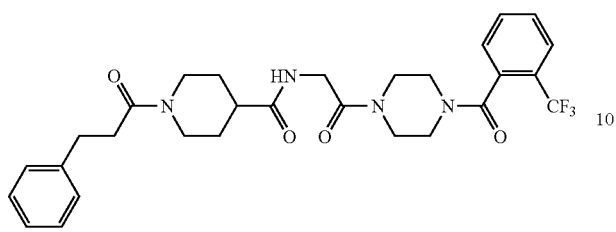

DIPEA (72.27 mg, 0.09 mL, 0.55 mmol) was added to a stirred solution of 1-(3-phenyl-propionyl)-piperidine-4-carboxylic acid (58.38 mg, 0.22 mmol) in DMF (1 mL). HOBT (30.2 mg, 0.22 mmol) and EDCI (42.76 mg, 0.22 mmol) were then added at room temperature. After 2 minutes, 2-amino-1-[4-(2-trifluoromethyl-benzoyl)-piperazin-1-yl]-ethanone trifluoroacetic acid salt (80 mg, 0.18 mmol) was added and the resulting mixture was stirred at room temperature for 16 hrs. Cold water was then added and the product was extracted with EtOAc and the organic layer was washed with brine. The organic phase was dried over $Na_2SO_4$ and concentrated under reduced pressure to afford 28 mg (26.89% yield) of 1-(3-phenyl-propionyl)-piperidine-4-carboxylic acid {2-oxo-2-[4-(2-trifluoromethyl-benzoyl)-piperazin-1-yl]-ethyl}-amide, LCMS Purity: 92.41%. $^1$H NMR ($CDCl_3$): δ 7.8-7.7 (d, 1H), 7.68-7.52 (m, 2H), 7.38-7.28 (m, 2H), 7.26-7.14 (m, 3H), 6.62-6.48 (s, 1H), 4.7-4.55 (d, 1H), 4.2-3.4 (m, 9H), 3.4-3.1 (d, 3H), 3.05-2.85 (t, 3H), 2.7-2.5 (t, 3H), 2.5-2.3 (t, 2H), 1.9-1.3 (t, 2H), 0.9 (d, 1H).

24) Synthesis of 1-(3-Phenyl-propyl)-piperidine-4-carboxylic acid {2-oxo-2-[4-(2-trifluoromethyl-benzoyl)-piperazin-1-yl]-ethyl}-amide

Step 1: Synthesis of 1-(3-Phenyl-propyl)-piperidine-4-carboxylic acid benzyl ester

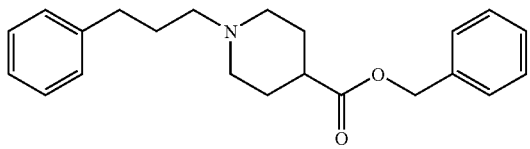

To a solution of piperidine-4-carboxylic acid benzyl ester (4 g, 18.2 mmol) (prepared by the method as described above) and potassium carbonate (10.04 g, 72.8 mmol) in DMF (10 ml) (3-Bromo-propyl)-benzene (3.04 g, 20 mmol) was added. The reaction mixture was then stirred at 60 c for 4 hrs. Cold water was then added and the product was extracted with EtOAc and the organic layer was washed with brine. The organic phase was dried over $Na_2SO_4$ and concentrated under reduced pressure to get the residue. The obtained residue was purified by column chromatography (using 60-120 silica gel and 20% EtOAc in hexane as eluent) to afford 1.86 gm (30.24% yield) of 1-(3-phenyl-propyl)-piperidine-4-carboxylic acid benzyl ester, LCMS Purity: 70.73%.

Step 2: Synthesis of 1-(3-Phenyl-propyl)-piperidine-4-carboxylic acid

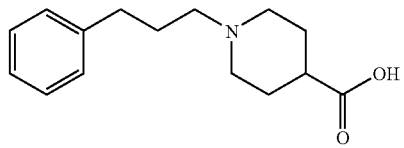

Pd/C (378 mg) was added to a stirred solution of 1-(3-phenyl-propyl)-piperidine-4-carboxylic acid benzyl ester (1.89 g, 5 mmol) in MeOH (38 mL) and stirring was continued under hydrogen atmosphere for 2 hrs. The mixture was filtered over a bed of celite. The celite was washed with MeOH and the filtrate was concentrated under reduced pressure to afford 1.502 mg (93.93% yield) of 1-(3-phenyl-propyl)-piperidine-4-carboxylic acid. LCMS Purity: 95.08%.

Step 3: Synthesis of 1-(3-Phenyl-propyl)-piperidine-4-carboxylic acid {2-oxo-2-[4-(2-trifluoromethyl-benzoyl)-piperazin-1-yl]-ethyl}-amide

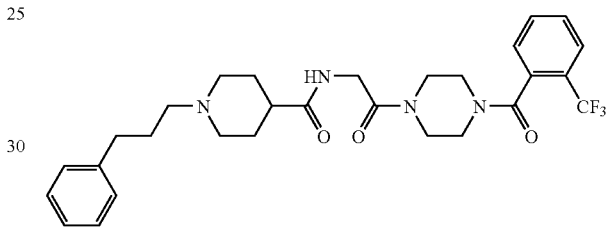

DIPEA (95.64 mg, 0.11 mL, 0.74 mmol) was added to a stirred solution of 1-(3-Phenyl-propyl)-piperidine-4-carboxylic acid (55.22 mg, 0.22 mmol) in DMF (1 mL). HOBT (30.19 mg, 0.22 mmol) and EDCI (42.74 mg, 0.22 mmol) were then added at room temperature. After 2 minutes, 2-amino-1-[4-(2-trifluoromethyl-benzoyl)-piperazin-1-yl]-ethanone trifluoroacetic acid salt (80 mg, 0.18 mmol) was added and the resulting mixture was stirred at room temperature for 16 hrs. Cold water was then added and the product was extracted with EtOAc and the organic layer was washed with brine. The organic phase was dried over $Na_2SO_4$ and concentrated under reduced pressure to afford 58 mg (57.16% yield) of 1-(3-Phenyl-propyl)-piperidine-4-carboxylic acid {2-oxo-2-[4-(2-trifluoromethyl-benzoyl)-piperazin-1-yl]-ethyl}-amide. LCMS Purity: 95.21%. $^1$H NMR ($CDCl_3$): δ 7.8-7.5 (d, 3H), 7.38-7.3 (s, 1H), 7.22-7.08 (s, 3H), 6.62-6.5 (s, 1H), 4.2-3.8 (m, 4H), 3.7-3.4 (m, 4H), 3.4-3.2 (m, 3H), 3.0 (s, 2H), 2.7-2.6 (s, 2H), 2.5-2.1 (m, 4H), 2.0-1.8 (m, 6H).

25) Synthesis of Pyrazine-2-carboxylic acid {2-oxo-2-[4-(2-trifluoromethyl-benzoyl)-piperazin-1-yl]-ethyl}-amide

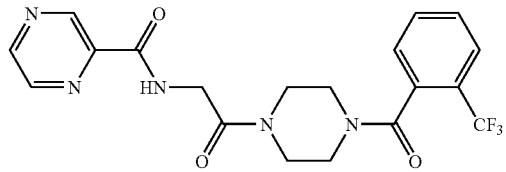

DIPEA (78 mg, 0.1 mL, 0.6 mmol) was added to a stirred solution of pyrazine-2-carboxylic acid (25 mg, 0.2 mmol) in DMF (0.5 mL). HOBT (32 mg, 0.24 mmol) and EDCI (46 mg, 0.24 mmol) were then added at room temperature. After 2 minutes, 2-amino-1-[4-(2-trifluoromethyl-benzoyl)-piperazin-1-yl]-ethanone trifluoroacetic acid salt (104 mg, 0.24 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to afford 28 mg (32.9% yield) of pyrazine-2-carboxylic acid {2-oxo-2-[4-(2-trifluoromethyl-benzoyl)-piperazin-1-yl]-ethyl}-amide. LCMS Purity: 94.8%. $^1$H NMR (DMSO-d6): δ 9.2 (m, 1H), 8.9 (d, 1H), 8.9-8.8 (bt, 1H), 8.8-8.7 (m, 1H), 7.9-7.8 (m, 1H), 7.8-7.7 (m, 1H), 7.7-7.6 (m, 1H), 7.6-7.5 (m, 1H), 4.3-4.1 (m, 2H), 3.8-3.5 (m, 4H), 3.5-3.4 (m, 2H), 3.2-3.0 (m, 2H).

26) Synthesis of N-{2-Oxo-2-[4-(2-trifluoromethyl-benzoyl)-piperazin-1-yl]-ethyl}-4-thiophen-3-yl-benzamide

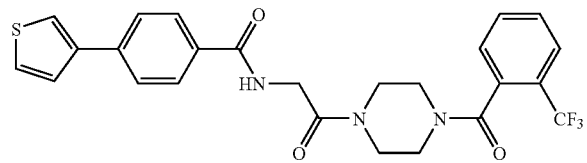

DIPEA (74.9 mg, 0.09 mL, 0.58 mmol) was added to a stirred solution of 4-thiophen-3-yl-benzoic acid (40 mg, 0.19 mmol) in DMF (1 mL). HOBT (32 mg, 0.23 mmol) and EDCI (45 mg, 0.23 mmol) were then added at room temperature. After 2 minutes, 2-amino-1-[4-(2-trifluoromethyl-benzoyl)-piperazin-1-yl]-ethanone trifluoroacetic acid salt (100 mg, 0.23 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to afford 46 mg (46.9% yield) of N-{2-oxo-2-[4-(2-trifluoromethyl-benzoyl)-piperazin-1-yl]-ethyl}-4-thiophen-3-yl-benzamide. LCMS Purity: 97.5%. $^1$H NMR (DMSO-d6): δ 8.7-8.6 (m, 1H), 8.1-8.0 (s, 1H), 7.96-7.9 (m, 2H), 7.88-7.8 (m, 3H), 7.8-7.74 (m, 1H), 7.72-7.62 (m, 3H), 7.6-7.5 (bt, 1H), 4.24-4.08 (m, 2H), 3.78-3.56 (m, 4H), 3.5-3.4 (m, 2H), 3.2-3.06 (m, 2H).

27) Synthesis of Dibenzofuran-2-carboxylic acid {2-oxo-2-[4-(2-trifluoromethyl-benzoyl)-piperazin-1-yl]-ethyl}-amide

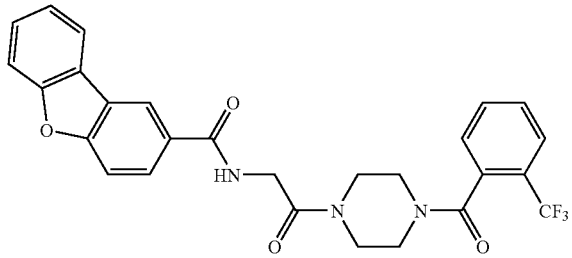

DIPEA (137 mg, 0.18 mL, 1.06 mmol) was added to a stirred solution of dibenzofuran-2-carboxylic acid (75 mg, 0.35 mmol) in DMF (3 mL). HOBT (47.8 mg, 0.35 mmol) and EDCI (81.3 mg, 0.42 mmol) were then added at room temperature. After 2 minutes 2-amino-1-[4-(2-trifluoromethyl-benzoyl)-piperazin-1-yl]-ethanone trifluoroacetic acid salt (166 mg, 0.38 mmol) was added and the resulting mixture was stirred at room temperature overnight. Cold water was then added, filtered the solid precipitated to afford 60 mg (33.3%) of dibenzofuran-2-carboxylic acid {2-oxo-2-[4-(2-trifluoromethyl-benzoyl)-piperazin-1-yl]-ethyl}-amide. LCMS Purity: 97.09%. $^1$H NMR (DMSO-d$_6$): δ 8.7 (bs, 2H), 8.2 (d, 1H), 8.06 (d, 1H), 7.9-7.55 (m, 7H), 7.55 (t, 1H), 4.41-4.3 (bs, 2H), 3.8-3.6 (bs, 4H), 3.5-3.4 (bs, 2H), 3.2-3.0 (bs, 2H).

28) Synthesis of 4-(1-Methyl-1H-pyrazol-4-yl)-N-{2-oxo-2-[4-(2-trifluoromethyl-benzoyl)-piperazin-1-yl]-ethyl}-benzamide

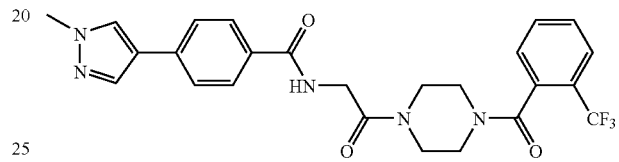

DIPEA (76.2 mg, 0.09 mL, 0.59 mmol) was added to a stirred solution of 4-(1-methyl-1H-pyrazol-4-yl)-benzoic acid (40 mg, 0.19 mmol) in DMF (1 mL). HOBT (32 mg, 0.23 mmol) and EDCI (46 mg, 0.23 mmol) were then added at room temperature. After 2 minutes, 2-amino-1-[4-(2-trifluoromethyl-benzoyl)-piperazin-1-yl]-ethanone trifluoroacetic acid salt (102 mg, 0.23 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to afford 50 mg (50.5% yield) of 4-(1-methyl-1H-pyrazol-4-yl)-N-{2-oxo-2-[4-(2-trifluoromethyl-benzoyl)-piperazin-1-yl]-ethyl}-benzamide. LCMS Purity: 90.78%. $^1$H NMR (DMSO-d6): δ 8.6-8.5 (bt, 1H), 8.3-8.2 (s, 1H), 8.0-7.8 (s, 1H), 7.9-7.84 (m, 3H), 7.8-7.74 (m, 1H), 7.74-7.6 (m, 3H), 7.6-7.5 (m, 1H), 4.2-4.1 (m, 2H), 3.9-3.88 (s, 3H), 3.84-3.68 (m, 2H), 3.68-3.54 (m, 2H), 3.54-3.4 (m, 2H), 3.22-3.0 (m, 2H).

29) Synthesis of N-{2-Oxo-2-[4-(2-trifluoromethyl-benzoyl)-piperazin-1-yl]-ethyl}-4-pyrimidin-5-yl-benzamide

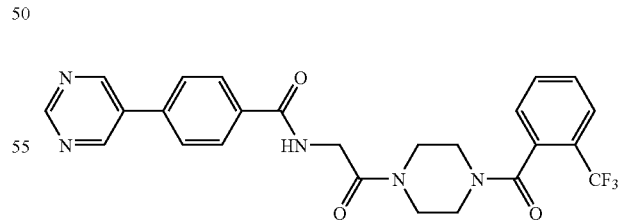

DIPEA (185 mg, 0.24 mL, 1.1 mmol) was added to a stirred solution of 4-pyrimidin-5-yl-benzoic acid (85 mg, 0.42 mmol) in DMF (2 mL). HOBT (75 mg, 0.46 mmol) and EDCI (98 mg, 0.46 mmol) were then added at room temperature. After 2 minutes, 2-amino-1-[4-(2-trifluoromethyl-benzoyl)-piperazin-1-yl]-ethanone hydrochloride salt (165 mg, 0.46 mmol) was added and the resulting mixture was stirred at room temperature overnight. Cold water was then added and filtered the residue. The obtained residue was purified by column chromatography (using silica gel of 60-120 mesh and 70% EtOAc in Hexane as eluent) to afford 65 mg (31% yield) of N-{2-Oxo-2-[4-(2-trifluoromethyl-benzoyl)-piperazin-1-yl]-ethyl}-4-pyrimidin-5-yl-benzamide. LCMS Purity: 97%. $^1$H NMR (CDCl$_3$): δ 9.2 (s, 1H), 9.0 (s, 2H), 8.0 (dd, 2H), 7.56 (d, 1H), 7.65 (m, 4H), 7.35 (m, 2H), 4.35 (m, 1H), 4.25 (m, 1H), 4.0 (m, 2H), 3.7 (m, 2H), 3.6 (m, 2H), 3.42 (m, 1H), 3.25 (m, 2H).

30) Synthesis of N-{2-Oxo-2-[4-(2-trifluoromethyl-benzoyl)-piperazin-1-yl]-ethyl}-4-pyrimidin-2-yl-benzamide

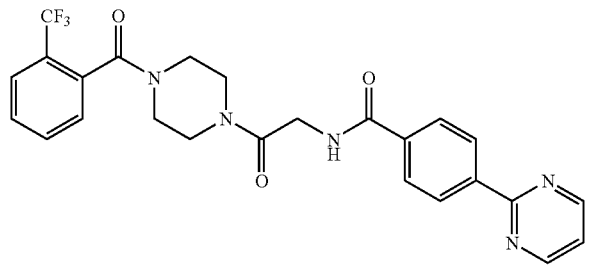

DIPEA (77 mg, 0.1 mL, 0.59 mmol) was added to a stirred solution of 4-pyrimidin-2-yl-benzoic acid (40 mg, 0.19 mmol) in DMF (2 mL). HOBT (32 mg, 0.23 mmol) and EDCI (46 mg, 0.23 mmol) were then added at room temperature. After 2 minutes 2-amino-1-[4-(2-trifluoromethyl-benzoyl)-piperazin-1-yl]-ethanone hydrochloride salt (84 mg, 0.23 mmol) was added and the resulting mixture was stirred at room temperature overnight. Cold water was then added and then extrated with ethyl acetate. The organic layer was washed with brine and dried over Na$_2$SO$_4$ and concentrated under reduced pressure to afford 30 mg (30.9%) of N-{2-oxo-2-[4-(2-trifluoromethyl-benzoyl)-piperazin-1-yl]-ethyl}-4-pyrimidin-2-yl-benzamide. LCMS Purity: 97.15%. $^1$H NMR (DMSO-d$_6$): δ 9-8.9 (d, 2H), 8.8-8.7 (m, 1H), 8.5 (d, 2H), 8.1-8.0 (d, 2H), 7.9-7.5 (m, 5H), 4.3-4.1 (m, 2H), 3.8-3.5 (m, 4H), 3.5-3.4 (m, 2H), 3.2-3.0 (m, 2H).

31) Synthesis of N-{2-Oxo-2-[4-(2-trifluoromethyl-benzoyl)-piperazin-1-yl]-ethyl}-4-pyrazin-2-yl-benzamide

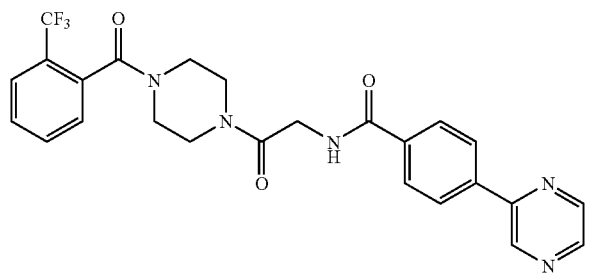

DIPEA (96 mg, 0.12 mL, 0.74 mmol) was added to a stirred solution of 4-pyrazin-2-yl-benzoic acid (50 mg, 0.24 mmol) in DMF (2 mL). HOBT (40 mg, 0.23 mmol) and EDCI (57 mg, 0.29 mmol) were then added at room temperature. After 2 minutes 2-amino-1-[4-(2-trifluoromethyl-benzoyl)-piper- azin-1-yl]-ethanone hydrochloride salt (105 mg, 0.29 mmol) was added and the resulting mixture was stirred at room temperature overnight. Cold water was then added and then extrated with ethyl acetate. The organic layer was washed with brine and dried over Na$_2$SO$_4$ and concentrated under reduced pressure to afford 78 mg (63.4%) of N-{2-oxo-2-[4-(2-trifluoromethyl-benzoyl)-piperazin-1-yl]-ethyl}-4-pyrazin-2-yl-benzamide. LCMS Purity: 96.69%. $^1$H NMR (DMSO-d$_6$): δ 9.4-9.3 (d, 1H), 8.8-8.7 (m, 2H), 8.7-8.6 (d, 1H), 8.3-8.2 (d, 1H), 8.1-8.0 (d, 2H), 7.9-7.6 (m, 3H), 7.6-7.5 (bt, 1H), 4.3-4.1 (m, 2H), 3.8-3.54 (m, 4H), 3.54-3.4 (m, 2H), 3.2-3.04 (m, 2H).

32) Synthesis of 9H-Fluorene-2-carboxylic acid {2-oxo-2-[4-(2-trifluoromethyl-benzoyl)-piperazin-1-yl]-ethyl}-amide

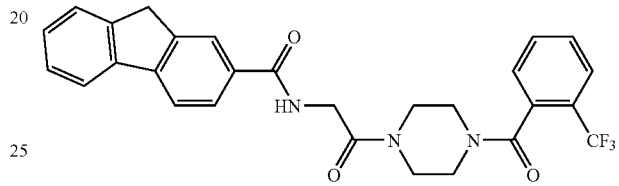

DIPEA (184 mg, 0.24 mL, 1.42 mmol) was added to a stirred solution of 9H-fluorene-2-carboxylic acid (100 mg, 0.47 mmol) in DMF (2 mL). HOBT (64 mg, 0.47 mmol) and EDCI (109 mg, 0.57 mmol) were then added at room temperature. After 2 minutes 2-amino-1-[4-(2-trifluoromethyl-benzoyl)-piperazin-1-yl]-ethanone hydrochloride salt (167 mg, 0.47 mmol) was added and the resulting mixture was stirred at room temperature overnight. Cold water was then added, filtered the solid precipitated. The solid obtained was recrystallized from a mixture of ethyl acetate and hexane afford 105 mg (43.4%) of 9H-fluorene-2-carboxylic acid {2-oxo-2-[4-(2-trifluoromethyl-benzoyl)-piperazin-1-yl]-ethyl}-amide. LCMS Purity: 98.25%. $^1$H NMR (DMSO-d$_6$): δ 8.6 (m, 1H), 8.1 (s, 1H), 8.0-7.4 (m, 10H), 4.2 (bs, 2H), 4.0 (s, 2H), 3.8-3.4 (m, 6H), 3.2 (b, 2H).

33) Synthesis of 4-[1,2,4]Oxadiazol-3-yl-N-{2-oxo-2-[4-(2-trifluoromethyl-benzoyl)-piperazin-1-yl]-ethyl}-benzamide

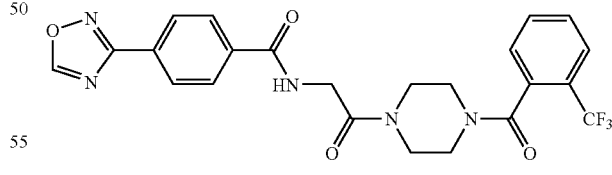

Triethyl ortho-formate (370 mg, 0.42 mL, 2.5 mmol) was added to a stirred solution of 4-(N-Hydroxycarbamimidoyl)-N-{2-oxo-2-[4-(2-trifluoromethyl-benzoyl)-piperazin-1-yl]-ethyl}-benzamide (400 mg, 0.84 mmol) in THF (10 ml) and cooled to 0-5° C. BF$_3$ metherate (1.14 g, 0.95 ml, 1.0 mmol) was then added and stirring was continued at room temperature overnight.

The reaction mixture was concentrated under reduced pressure to get the residue. The residue obtained was purified by preparative HPLC to afford 45 mg (11.48% yield) 4-[1,2, 4]Oxadiazol-3-yl-N-{2-oxo-2-[4-(2-trifluoromethyl-benzoyl)-piperazin-1-yl]-ethyl}-benzamide. LCMS Purity: 97.7%. $^1$H NMR (DMSO-d6): δ 9.8 (s, 1H), 8.8 (s, 1H), 8.16 (d, 2H), 8.06 (d, 2H), 7.74 (m, 3H), 7.56 (t, 1H), 4.2 (d, 2H), 3.5 (m, 5H), 3.15 (m, 3H).

34) Synthesis of 1-Oxy-5-phenyl-pyridine-2-carboxylic acid {2-oxo-2-[4-(2-trifluoromethyl-benzoyl)-piperazin-1-yl]-ethyl}-amide

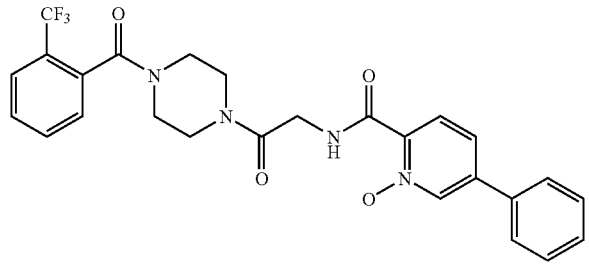

m-Chloroperbenzoic acid (111 mg, 0.64 mmol) was added to a stirred solution of 5-phenyl-pyridine-2-carboxylic acid {2-oxo-2-[4-(2-trifluoromethyl-benzoyl)-piperazin-1-yl]-ethyl}-amide (100 mg, 0.19) in DCM (2 ml) and the resulting mixture was stirred at room temperature overnight. DCM was then added and the organic layer was washed with water followed by brine. The organic phase was dried over $Na_2SO_4$ and concentrated under reduced pressure to get the residue. The obtained residue was purified by column chromatography (using silica gel of 60-120 mesh and 3% MeOH in $CHCl_3$ as eluent) to afford 29 mg (29.29%) of 1-oxy-5-phenyl-pyridine-2-carboxylic acid {2-oxo-2-[4-(2-trifluoromethyl-benzoyl)-piperazin-1-yl]-ethyl}-amide. LCMS Purity: 96.25%. $^1$H NMR (DMSO-d$_6$): δ 8.6-8.5 (m, 1H), 8.5-8.38 (m, 1H), 7.8-7.7 (d, 1H), 7.7-7.5 (m, 8H), 7.4-7.3 (d, 1H), 4.48-4.28 (m, 2H), 4.1-3.8 (m, 2H), 3.8-3.4 (m, 6H), 3.2 (m, 2H).

35) Synthesis of 5-Hydroxy-pyrazine-2-carboxylic acid {2-oxo-2-[4-(2-trifluoromethyl-benzoyl)-piperazin-1-yl]-ethyl}-amide

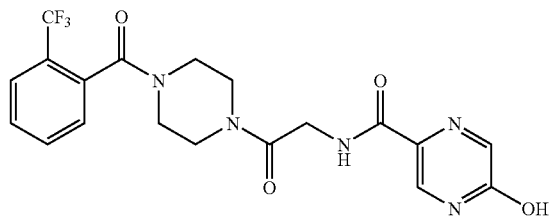

DIPEA (553 mg, 0.732 mL, 4.28 mmol) was added to a stirred solution of 5-hydroxy-pyrazine-2-carboxylic acid (200 mg, 1.42 mmol) in DMF (3 mL). HOBT (231 mg, 1.71 mmol) and EDCI (328 mg, 1.71 mmol) were then added at room temperature. After 2 minutes 2-amino-1-[4-(2-trifluoromethyl-benzoyl)-piperazin-1-yl]-ethanone hydrochloride salt (600 mg, 1.71 mmol) was added and the resulting mixture was stirred at room temperature overnight. The reaction mixture was concentrated, methanol was then added, filtered the solid precipitated. The solid obtained was purified by column chromatography (using silica gel of 60-120 mesh and 10% MeOH in $CHCl_3$ as eluent) to afford 205 mg (32.85%) of 5-hydroxy-pyrazine-2-carboxylic acid {2-oxo-2-[4-(2-trifluoromethyl-benzoyl)-piperazin-1-yl]-ethyl}-amide. LCMS Purity: 91.22%. $^1$H NMR (DMSO-d$_6$): δ 8.3 (bt, 1H), δ 8.0 (m, 2H), 7.9-7.76 (m, 2H), 7.7 (m, 1H), 7.6-7.5 (d, 2H), 4.26-4.1 (dd, 2H), 3.8-3.68 (m, 2H), 3.6-3.5 (m, 2H), 3.4 (m, 2H), δ 3.2-3.0 (m, 2H).

36) Synthesis of N-{2-oxo-2-[4-(2-trifluoromethyl-benzoyl)-piperazin-1-yl]-ethyl}-4-pyridin-2-yl-benzamide

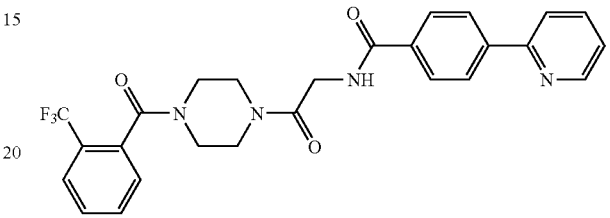

DIPEA (116.32 mg, 0.15 mL, 0.9 mmol) was added to a stirred solution of 4-pyridin-2-yl-benzoic acid (60 mg, 0.3 mmol) in DMF (1.5 mL). HOBT (48 mg, 0.36 mmol) and EDCI (70 mg, 0.36 mmol) were then added at room temperature. After 2 minutes 2-amino-1-[4-(2-trifluoromethyl-benzoyl)-piperazin-1-yl]-ethanone hydrochloride salt (127 mg, 0.36 mmol) was added and the resulting mixture was stirred at room temperature overnight. Cold water was then added and then extrated with ethyl acetate. The organic layer was washed with brine and dried over $Na_2SO_4$ and concentrated under reduced pressure to afford 29 mg (19.46%) of N-{2-oxo-2-[4-(2-trifluoromethyl-benzoyl)-piperazin-1-yl]-ethyl}-4-pyridin-2-yl-benzamide. LCMS Purity: 89.36%. $^1$H NMR (DMSO-d$_6$): δ 9-8.9 (d, 1H), 8.6 (d, 1H), 8.5 (m, 1H), 8.2-8.1 (dt, 1H), 8.0 (d, 2H), 7.9-7.6 (m, 5H), 7.6-7.5 (m, 2H), 4.2 (m, 2H), 3.8-3.6 (m, 4H), 3.2-3.4 (m, 2H), 3.2-3 (m, 2H).

37) Synthesis of 2'-Fluoro-biphenyl-4-carboxylic acid {2-oxo-2-[4-(2-trifluoromethyl-benzoyl)-piperazin-1-yl]-ethyl}-amide

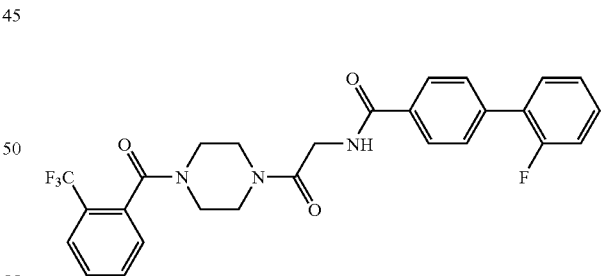

DIPEA (71 mg, 0.09 mL, 0.55 mmol) was added to a stirred solution of 2'-fluoro-biphenyl-4-carboxylic acid (40 mg, 0.18 mmol) in DMF (1 mL). HOBT (30 mg, 0.22 mmol) and EDCI (43 mg, 0.22 mmol) were then added at room temperature. After 2 minutes 2-amino-1-[4-(2-trifluoromethyl-benzoyl)-piperazin-1-yl]-ethanone hydrochloride salt (78 mg, 0.22 mmol) was added and the resulting mixture was stirred at room temperature overnight. Cold water was then added and then extrated with ethyl acetate. The organic layer was washed with brine and dried over $Na_2SO_4$ and concentrated under reduced pressure to afford 35 mg (36.8%) of 2'-fluorobiphenyl-4-carboxylic acid {2-oxo-2-[4-(2-trifluoromethyl-benzoyl)-piperazin-1-yl]-ethyl}-amide. LCMS Purity: 91.09%. ¹H NMR (DMSO-d₆): δ 8.02-7.94 (d, 2H), 7.9-7.72 (m, 2H), 7.72-7.64 (m, 3H), 7.64-7.54 (m, 2H), 7.54-7.42 (m, 1H), 7.4-7.3 (m, 2H), 4.2 (m, 2H), 3.8-3.4 (m, 2H), 3.2-3 (m, 2H).

38) Synthesis of 5-Methyl-isoxazole-3-carboxylic acid {2-oxo-2-[4-(2-trifluoromethyl-benzoyl)-piperazin-1-yl]-ethyl}-amide

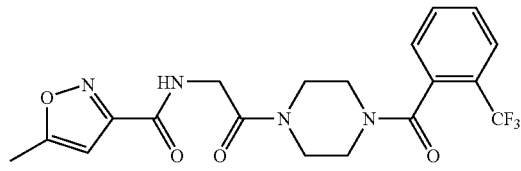

DIPEA (82.66 mg, 0.09 mL, 0.63 mmol) was added to a stirred solution of 5-methyl-isoxazole-3-carboxylic acid (32.52 mg, 0.25 mmol) in DMF (2 mL). HOBT (34.53 mg, 0.25 mmol) and EDCI (48.9 mg, 0.25 mol) were then added at room temperature. After 2 minutes, 2-amino-1-[4-(2-trifluoromethyl-benzoyl)-piperazin-1-yl]-ethanone hydrochloride salt (75 mg, 0.21 mmol) was added and the resulting mixture was stirred at room temperature overnight. Cold water was then added and the product was extracted with EtOAc and the organic layer was washed with brine. The organic phase was dried over Na₂SO₄ and concentrated under reduced pressure to get the residue. The obtained residue was purified by column chromatography (using 60-120 silica gel and 80% EtOAC in hexane as eluent) to afford 53 mg (58.62% yield) of 5-methyl-isoxazole-3-carboxylic acid {2-oxo-2-[4-(2-trifluoromethyl-benzoyl)-piperazin-1-yl]-ethyl}-amide. LCMS Purity: 88.47%. ¹H NMR (DMSO-d₆): δ 8.55 (s, 1H), 7.88-7.74 (m, 2H), 7.74-7.62 (m, 1H), 7.6-7.5 (s, 1H), 6.75 (s, 1H), 4.22-4.4 (dd, 2H), 3.8-3.64 (m, 2H), 3.64-3.52 (s, 3H), 3.5-3.36 (m, 3H), 3.22-3.0 (m, 3H), 2.48-2.44 (s, 3H).

39) Synthesis of 2,4-Difluoro-biphenyl-4-carboxylic acid {2-oxo-2-[4-(2-trifluoromethyl-benzoyl)-piperazin-1-yl]-ethyl}-amide

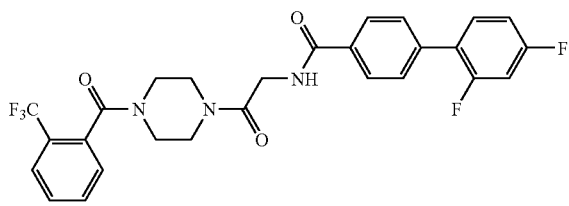

DIPEA (83 mg, 0.11 mL, 0.21 mmol) was added to a stirred solution of 2,4-difluoro-biphenyl-4-carboxylic acid (50 mg, 0.21 mmol) in DMF (1 mL). HOBT (35 mg, 0.25 mmol) and EDCI (50 mg, 0.25 mmol) were then added at room temperature. After 2 minutes 2-amino-1-[4-(2-trifluoromethyl-benzoyl)-piperazin-1-yl]-ethanone hydrochloride salt (90 mg, 0.25 mmol) was added and the resulting mixture was stirred at room temperature overnight. Cold water was then added and then extrated with ethyl acetate. The organic layer was washed with brine and dried over Na₂SO₄ and concentrated under reduced pressure to afford 56.9 mg (50.35%) of 2,4-difluoro-biphenyl-4-carboxylic acid {2-oxo-2-[4-(2-trifluoromethyl-benzoyl)-piperazin-1-yl]-ethyl}-amide. LCMS Purity: 95.42%. ¹H NMR (DMSO-d₆): δ 8.2-7.94 (d, 2H), 7.88-7.74 (m, 2H), 7.74-7.6 (m, 4H), 7.6-7.5 (m, 1H), 7.46-7.34 (m, 1H), 7.3-7.2 (m, 1H), 4.3-4.1 (m, 2H), 3.8-3.4 (m, 6H), 3.2-3.0 (m, 2H).

40) Synthesis of 5-Phenyl-pyrazine-2-carboxylic acid {2-oxo-2-[4-(2-trifluoromethyl-benzoyl)-piperazin-1-yl]-ethyl}-amide

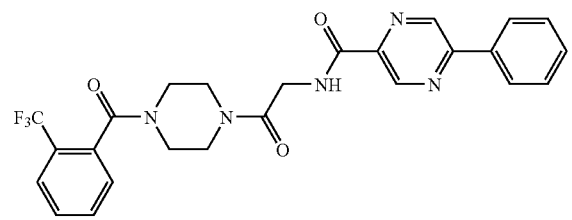

Na₂CO₃ (140 mg, 1.32 mmol) was added to a stirred solution of 5-chloro-pyrazine-2-carboxylic acid {2-oxo-2-[4-(2-trifluoromethyl-benzoyl)-piperazin-1-yl]-ethyl}-amide (200 mg, 0.44 mmol) in DMF (3 mL). PdCl₂ (dppf) (96 mg, 0.13 mmol) and phenyl boronic acid (64 mg, 0.52 mmol) were then added and the reaction mixture was heated at 90° C. overnight. The reaction mixture was filtered, filtrate was then diluted with water and the product was extracted with ethyl acetate. The organic layer was washed with saturated brine solution, dried over sodium sulphate and concentrated to afford 29 mg (13.3% yield) of 5-phenyl-pyrazine-2-carboxylic acid {2-oxo-2-[4-(2-trifluoromethyl-benzoyl)-piperazin-1-yl]-ethyl}-amide. LCMS Purity: 93.2%. ¹H NMR (CDCl₃): δ 9.4 (d, 1H), 9.0 (d, 1H), 8.7-8.6 (m, 1H), 8.1-8.0 (m, 2H), 7.8-7.7 (d, 1H), 7.7-7.5 (m, 5H), 7.4-7.3 (d, 1H), 4.46-4.18 (m, 2H), 4.46-4.18 (m, 2H), 4.1-3.86 (m, 2H), 3.8-3.5 (m, 4H), 3.5-3.4 (m, 1H), 3.3-3.2 (m, 2H).

41) Synthesis of 6-Phenyl-pyridazine-3-carboxylic acid {2-oxo-2-[4-(2-trifluoromethyl-benzoyl)-piperazin-1-yl]-ethyl}-amide

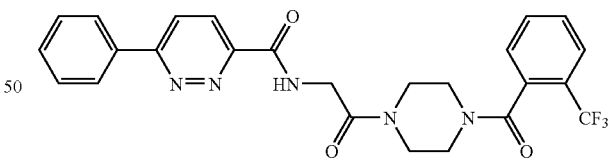

Na₂CO₃ (183 mg, 1.73 mmol) was added to a stirred solution of 6-chloro-pyridazine-3-carboxylic acid {2-oxo-2-[4-(2-trifluoromethyl-benzoyl)-piperazin-1-yl]-ethyl}-amide (263 mg, 0.57 mmol) in DMF (6 mL). PdCl₂ (dppf) (80.4 mg, 0.11 mmol) and phenyl boronic acid (89.9 mg, 0.69 mmol) were then added and the reaction mixture was heated at 80° C. for 2 hrs. The reaction mixture was diluted with water and the product was extracted with ethyl acetate. The organic layer was washed with saturated brine solution, dried over sodium sulphate and concentrated to get the residue. The residue obtained was purified by preparative HPLC afford 34 mg (11% yield) of 6-Phenyl-pyridazine-3-carboxylic acid {2-oxo-2-[4-(2-trifluoromethyl-benzoyl)-piperazin-1-yl]- ethyl}-amide. LCMS Purity: 93.2%. ¹H NMR (DMSO-d₆): δ 9.3 (t, 1H), 8.5 (d, 1H), 8.3 (t, 3H), 8.0-7.5 (m, 7H), 4.4 (d, 2H), 3.8 (d, 4H), 3.46 (bs, 2H), 3.2 (d, 2H).

42) Synthesis of 2-Phenyl-thiazole-5-carboxylic acid {2-oxo-2-[4-(2-trifluoromethyl-benzoyl)-piperazin-1-yl]-ethyl}-amide

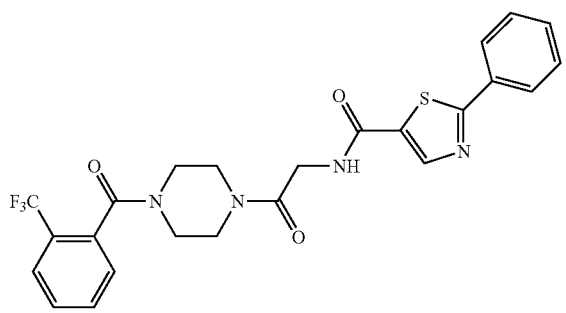

DIPEA (170 mg, 0.22 mL, 1.31 mmol) was added to a stirred solution of 2-phenyl-thiazole-5-carboxylic acid (90 mg, 0.43 mmol) in DMF (2 mL). HOBT (71 mg, 0.52 mmol) and EDCI (100 mg, 0.52 mmol) were then added at room temperature. After 2 minutes 2-amino-1-[4-(2-trifluoromethyl-benzoyl)-piperazin-1-yl]-ethanone hydrochloride salt (185 mg, 0.52 mmol) was added and the resulting mixture was stirred at room temperature overnight. Cold water was then added and then extrated with ethyl acetate. The organic layer was washed with brine and dried over Na₂SO₄ and concentrated under reduced pressure to afford 77.1 mg (35%) of 2-phenyl-thiazole-5-carboxylic acid {2-oxo-2-[4-(2-trifluoromethyl-benzoyl)-piperazin-1-yl]-ethyl}-amide. LCMS Purity: 95.1%. ¹H NMR (DMSO-d₆): δ 9.0-8.9 (m, 1H), 8.54-8.5 (s, 1H), 8.0 (m, 2H), 7.9-7.64 (m, 3H), 7.6-7.5 (m, 4H), 4.24-4.1 (m, 2H), 3.8-3.6 (m, 4H), 3.5-3.4 (m, 2H), 3.2-3.0 (m, 2H).

43) Synthesis of 4-Methyl-N-{2-oxo-2-[4-(2-trifluoromethyl-benzoyl)-piperazin-1-yl]-ethyl}-benzamide

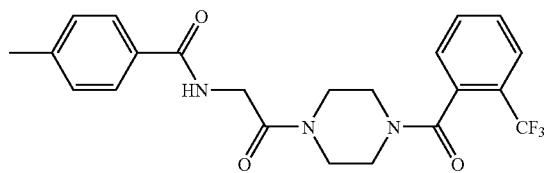

4-Methyl benzoyl chloride (44 mg, 0.03 ml, 1.8 mmol) was added to a stirred a cold (0° C.) solution of 2-amino-1-[4-(2-trifluoromethyl-benzoyl)-piperazin-1-yl]-ethanone hydrochloride salt (prepared by the method described above)(100 mg, 0.28 mmol) and triethylamine (72 mg, 0.1 ml, 0.71 mmol) in DCM (5 mL) and stirring continued at room temperature for 3 hrs. Cold water was then added and the product was extracted with EtOAc and the organic layer was washed with brine. The organic phase was dried over Na₂SO₄ and concentrated under reduced pressure to get the residue. The obtained residue was purified by column chromatography (using silica gel of 60-120 mesh and 50% EtOAc in Hexane as eluent) to afford 91 mg (73.98% yield 4-methyl-N-{2-oxo-2-

[4-(2-trifluoromethyl-benzoyl)-piperazin-1-yl]-ethyl}-benzamide. LCMS Purity: 98.52%. ¹H NMR (DMSO-d₆): δ 8.54-8.42 (bs, 1H), 7.88-7.62 (m, 5H), 7.58-7.5 (bs, 1H), 7.3-7.22 (d, 2H), 4.2-4.1 (d, 2H), 3.8-3.5 (m, 4H), 3.5-3.4 (bs, 2H), 3.3-3.0 (bd, 2H), 2.3 (s, 3H)

44) Synthesis of N-{2-Oxo-2-[4-(2-trifluoromethyl-benzoyl)-piperazin-1-yl]-ethyl}-isophthalamic acid methyl ester

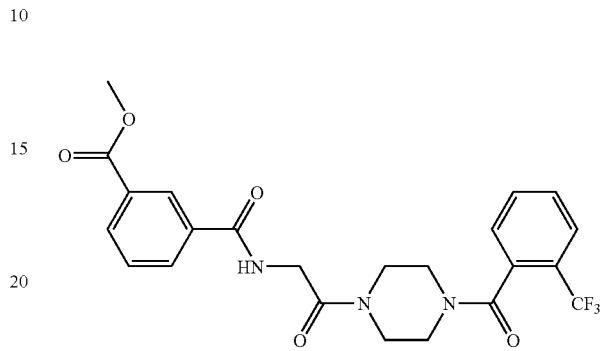

DIPEA (450 mg, 0.6 mL, 3.5 mmol) was added drop wise to 4-(2-trifluoromethyl)-benzoic acid (200 mg, 1.1 mmol) in DMF (2 mL). EDCI (250 mg, 1.3 mmol) and HOBT (180 mg, 1.3 mmol) were added consecutively and, after 10 minutes, 2-Amino-1-[4-(2-trifluoromethyl-benzoyl)-piperazin-1-yl]-ethanone in its HCl salt form (390 mg, 1.1 mmol) was added. The resulting mixture was stirred at room temperature overnight. Cold water was then added and the product was extracted with EtOAc and the organic layer was washed with brine. The organic phase was dried over Na₂SO₄ and concentrated under reduced pressure to get the residue. The obtained residue was purified by column chromatography (using silica gel of 60-120 mesh and 10% EtOAc in Hexane as eluent) to afford 30 mg (16.6% yield) of N-{2-oxo-2-[4-(2-trifluoromethyl-benzoyl)-piperazin-1-yl]-ethyl}-isophthalamic acid methyl ester. LCMS Purity: 98.6%. ¹H NMR (CDCl₃): δ 8.7 (s, 1H), 8.2 (d, 1H), 8.1 (m, 1H), 7.8 (m, 2H), 7.7 (m, 4H), 7.2 (m, 2H), 4.4 (m, 2H), 4.1 (m, 1H), 4.0 (s, 3H), 3.8 (m, 4H), 3.4 (m, 1H), 3.2 (m, 2H).

45) Synthesis of 4-[1,3,4]Oxadiazol-2-yl-N-{2-oxo-2-[4-(2-trifluoromethyl-benzoyl)-piperazin-1-yl]-ethyl}-benzamide

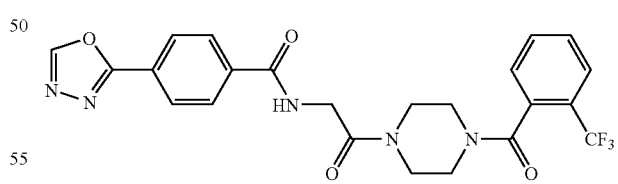

DIPEA (80 mg, 0.1 mL, 0.64 mmol) was added drop wise to 4-[1,3,4]Oxadiazol-2-yl-benzoic acid (40 mg, 0.2 mmol) in DMF (2 mL). EDCI (45 mg, 0.24 mmol) and HOBT (32 mg, 0.24 mmol) were added consecutively and, after 10 minutes, 2-Amino-1-[4-(2-trifluoromethyl-benzoyl)-piperazin-1-yl]-ethanone in its HCl salt form (70 mg, 0.2 mmol) was added. The resulting mixture was stirred at room temperature overnight. Cold water was then added and the product was extracted with EtOAc and the organic layer was washed with brine. The organic phase was dried over Na₂SO₄ and concentrated under reduced pressure to get the residue. The obtained residue was purified by column chromatography (using silica gel of 60-120 mesh and 10% EtOAc in Hexane as eluent) to afford 30 mg (33% yield) of 4-[1,3,4]oxadiazol-2-yl-N-{2-oxo-2-[4-(2-trifluoromethyl-benzoyl)-piperazin-1-yl]-ethyl}-benzamide. LCMS Purity: 93.4%. $^1$H NMR (CDCl$_3$): δ 8.5 (s, 1H), 8.2 (d, 2H), 8.0 (d, 2H), 7.8 (m, 3H), 7.3 (m, 2H), 4.2 (m, 2H), 3.8 (m, 5H), 3.4 (m, 1H), 3.2 (m, 3H).

46) Synthesis of N-Methyl-N'-{2-oxo-2-[4-(2-trifluoromethyl-benzoyl)-piperazin-1-yl]-ethyl}-terephthalamide

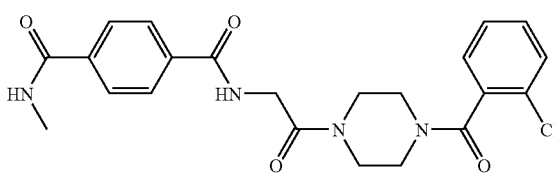

DIPEA (165 mg, 0.2 mL, 1.2 mmol) was added drop wise to N-methyl-terephthalamic acid (80 mg, 0.4 mmol) in DMF (5 mL). EDCI (100 mg, 0.5 mmol) and HOBT (67 mg, 0.5 mmol) were added consecutively and, after 10 minutes, 2-Amino-1-[4-(2-trifluoromethyl-benzoyl)-piperazin-1-yl]-ethanone in its HCl salt form (150 mg, 0.4 mmol) was added. The resulting mixture was stirred at room temperature overnight. Cold water was then added and the product was extracted with EtOAc and the organic layer was washed with brine. The organic phase was dried over Na$_2$SO$_4$ and concentrated under reduced pressure to get the residue. The obtained residue was purified by column chromatography (using basic alumina and 10% MeOH in CHCl$_3$ as eluent) to afford 30 mg (15.74% yield) of N-methyl-N'-{2-oxo-2-[4-(2-trifluoromethyl-benzoyl)-piperazin-1-yl]-ethyl}-terephthalamide. LCMS Purity: 97.3%. $^1$H NMR (CDCl$_3$): δ 8.7 (d, 2H), 8.2 (d, 2H), 7.8 (m, 1H), 7.7 (m, 3H), 7.2 (m, 2H), 4.4 (m, 2H), 4.1 (s, 1H), 3.8 (s, 3H), 3.4 (m, 4H).

47) Synthesis of N-Methyl-N'-{2-oxo-2-[4-(2-trifluoromethyl-benzoyl)-piperazin-1-yl]-ethyl}-isophthalamide

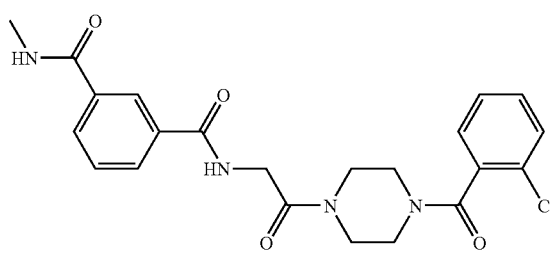

DIPEA (330 mg, 0.44 mL, 2.6 mmol) was added drop wise to N-methyl-isophthalamic acid (145 mg, 0.8 mmol) in DMF (3 mL). EDCI (180 mg, 0.96 mmol) and HOBT (130 mg, 0.96 mmol) were added consecutively and, after 10 minutes, 2-Amino-1-[4-(2-trifluoromethyl-benzoyl)-piperazin-1-yl]-ethanone in its HCl salt form (281 mg, 0.8 mmol) was added. The resulting mixture was stirred at room temperature overnight. Cold water was then added and the product was extracted with EtOAc and the organic layer was washed with brine. The organic phase was dried over Na$_2$SO$_4$ and concentrated under reduced pressure to get the residue. The obtained residue was purified by column chromatography (using basic alumina and 10% MeOH in CHCl$_3$ as eluent) to afford 35 mg (9.18% yield) of N-methyl-N'-{2-oxo-2-[4-(2-trifluoromethyl-benzoyl)-piperazin-1-yl]-ethyl}-isophthalamide. LCMS Purity: 97.7%. $^1$H NMR (CDCl$_3$): δ 8.1 (bs, 1H), 7.9 (m, 2H), 7.7 (m, 1H), 7.5 (m, 3H), 7.4 (m, 2H), 6.3 (bs, 1H), 4.2 (m, 2H), 4.0 (m, 2H), 3.6 (m, 5H), 3.4 (m, 1H), 3.2 (m, 2H), 3.0 (d, 3H).

48) Synthesis of 4-(5-Methyl-[1,3,4]oxadiazol-2-yl)-N-{2-oxo-2-[4-(2-trifluoromethyl-benzoyl)-piperazin-1-yl]-ethyl}-benzamide

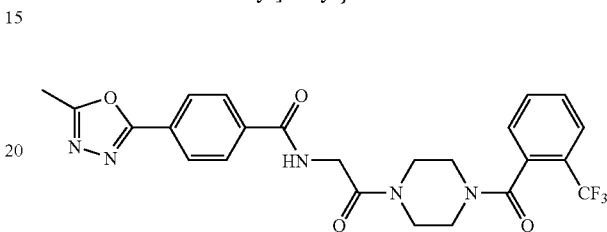

DIPEA (180 mg, 0.24 mL, 1.4 mmol) was added drop wise to 4-(5-methyl-[1,3,4]oxadiazol-2-yl)-benzoic acid (90 mg, 0.4 mmol) in DMF (3 mL). EDCI (92 mg, 0.48 mmol) and HOBT (65 mg, 0.48 mmol) were added consecutively and, after 10 minutes, 2-Amino-1-[4-(2-trifluoromethyl-benzoyl)-piperazin-1-yl]-ethanone in its HCl salt form (150 mg, 0.4 mmol) was added. The resulting mixture was stirred at room temperature overnight. Cold water was then added and the product was extracted with EtOAc and the organic layer was washed with brine. The organic phase was dried over Na$_2$SO$_4$ and concentrated under reduced pressure to get the residue purified by column chromatography (using silica gel of 60-120 mesh and 10% EtOAc in Hexane as eluent to afford 40 mg (19.9% yield) of 4-(5-Methyl-[1,3,4]oxadiazol-2-yl)-N-{2-oxo-2-[4-(2-trifluoromethyl-benzoyl)-piperazin-1-yl]-ethyl}-benzamide. LCMS Purity: 96.6%. $^1$H NMR (CDCl$_3$): δ 8.1 (d, 2H), 7.9 (m, 2H), 7.7 (m, 1H), 7.5 (m, 2H), 7.3 (m, 2H), 4.2 (m, 2H), 4.0 (m, 2H), 3.6 (m, 3H), 3.4 (m, 1H), 2.6 (s, 3H).

49) Synthesis of 4-[1,3,4]Oxadiazol-2-yl-N-{2-oxo-2-[4-(2-trifluoromethyl-benzoyl)-piperazin-1-yl]-ethyl}-benzamide

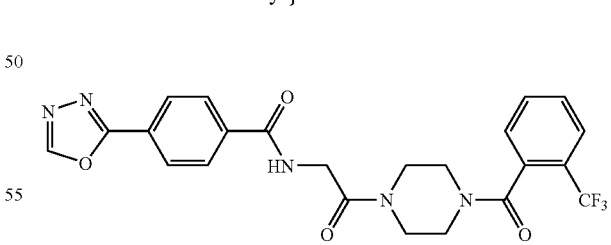

DIPEA (154 mg, 0.2 mL, 1.19 mmol) was added drop wise to 4-[1,3,4]oxadiazol-2-yl)-benzoic acid (65 mg, 0.34 mmol) in DMF (3 mL). EDCI (98.2 mg, 0.51 mmol) and HOBT (50 mg, 0.37 mmol) were then added. After 2 minutes, 2-Amino-1-[4-(2-trifluoromethyl-benzoyl)-piperazin-1-yl]-ethanone in its HCl salt form (150 mg, 0.4 mmol) was added. The resulting mixture was stirred at room temperature overnight. Cold water was then added and filtered the solid precipitated to afford 90 mg (54% yield) of 4-[1,3,4]oxadiazol-2-yl-N-{2- oxo-2-[4-(2-trifluoromethyl-benzoyl)-piperazin-1-yl]-ethyl}-benzamide. LCMS Purity: 94.4%. ¹H NMR (DMSO-d$_6$): δ 9.4 (s, 1H), 8.9 (bs, 1H), 8.5 (s, 1H), 8.15 (dd, 2H), 7.7 (m, 4H), 7.55 (t, 1H), 4.2 (dd, 2H), 3.7 (bs, 4H), 3.5 (s, 1H), 3.1 (d, 3H).

50) Synthesis of 4-(2-Oxo-2H-pyridin-1-yl)-N-{2-oxo-2-[4-(2-trifluoromethyl-benzoyl)-piperazin-1-yl]-ethyl}-benzamide

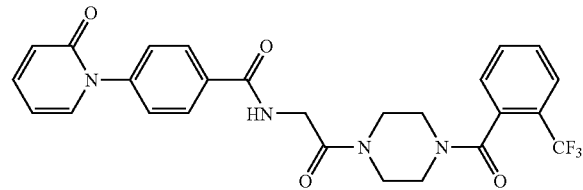

DIPEA (213 mg, 0.27 mL, 1.65 mmol) was added to a stirred solution of 4-(2-oxo-2H-pyridin-1-yl)-benzoic acid (120 mg, 0.55 mmol) in DMF (2 mL). HOBT (74.5 mg, 0.55 mmol) and EDCI (126.5 mg, 0.66 mmol) were then added at room temperature. After 2 minutes, 2-amino-1-[4-(2-trifluoromethyl-benzoyl)-piperazin-1-yl]-ethanone hydrochloride salt (196 mg, 0.55 mmol) was added and the resulting mixture was stirred at room temperature overnight. Cold water was then added and filtered the solid precipitated out to afford 42 mg (14.7% yield) of 4-(2-Oxo-2H-pyridin-1-yl)-N-{2-oxo-2-[4-(2-trifluoromethyl-benzoyl)-piperazin-1-yl]-ethyl}-benzamide. LCMS Purity: 94.83%. ¹H NMR (DMSO-d$_6$): δ 8.0 (m, 2H), 7.9 (m, 2H), 7.7 (m, 2H), 7.5 (m, 4H), 6.5 (m, 1H), 6.4 (t, 1H), 4.2 (m, 2H), δ 3.9-3.6 (m, 4H), 3.5-3.4 (m, 2H), 3.2-3 (s, 2H).

51) Synthesis of 6-Benzyloxy-N-{2-oxo-2-[4-(2-trifluoromethyl-benzoyl)-piperazin-1-yl]-ethyl}-nicotinamide

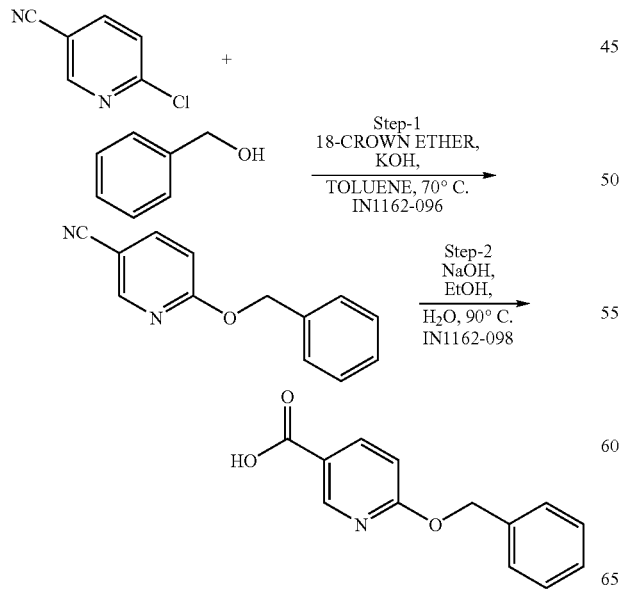

Step 1: Synthesis of 6-Benzyloxy-nicotinonitrile

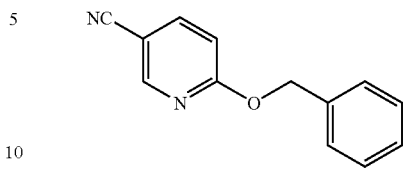

To a stirred solution of 6-chloronicotinonitrile (1 g, 7.2 mmol) and benzyl alcohol (780 mg, 7.2 mmol) in toluene (15 mL) was added KOH (729 mg, 12.99 mmol) and 18 crown ether (2.86 g, 10.8 mmol). The resulting mixture was stirred at 70° C. for 7 hrs. The mixture was diluted with cold water and the product was extracted with EtOAc. The organic layer was washed with saturated brine solution and dried over Na2SO4. The organic layer was then concentrated under reduced pressure. The obtained residue was purified by column chromatography (using neutral alumina and 5% MeOH: CHCl$_3$ as eluent) to afford 610 mg (40.1% yield) of 6-benzyloxy-nicotinonitrile. LCMS Purity: 77.69%.

Step 2: Synthesis of 6-Benzyloxy-nicotinic acid

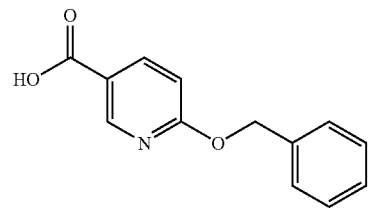

To a stirred solution of 6-benzyloxy-nicotinonitrile (100 mg, 0.47 mmol) in a mixture of EtOH (5 mL) and water (5 mL), was added NaOH (95.1 mg, 2.3 mmol) and the resulting mixture was stirred at 90° C. for 20 hrs. The mixture was evaporated under reduced pressure. The residue was diluted with cold water, adjusted the pH to 3 and extracted with EtOAc. The organic layer was washed with saturated brine solution and dried over Na2SO4. The organic layer was then concentrated under reduced pressure to afford 105 mg (96% yield) of 6-benzyloxy-nicotinic acid.

Step 3: Synthesis of 6-Benzyloxy-N-{2-oxo-2-[4-(2-trifluoromethyl-benzoyl)-piperazin-1-yl]-ethyl}-nicotinamide

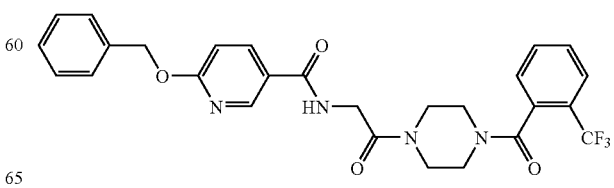

DIPEA (253 mg, 0.34 mL, 1.9 mmol) was added to a stirred solution of 2-amino-1-[4-(2-trifluoromethyl-benzoyl)-piperazin-1-yl]-ethanone hydrochloride salt (184 mg, 0.52 mmol) in DMF (4 mL). HOBT (64.8 mg, 0.479 mmol) and EDCI (167 mg, 0.87 mmol) were then added at room temperature. After 2 minutes, 6-benzyloxy-nicotinic acid (100 mg, 0.43 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 70% EtOAc in Hexane as eluent) to afford 102 mg (45.33% yield) 6-benzyloxy-N-{2-oxo-2-[4-(2-trifluoromethyl-benzoyl)-piperazin-1-yl]-ethyl}-nicotinamide. LCMS Purity: 98.91%. $^1$H NMR (DMSO-$d_6$): δ 8.7 (d, 2H), 8.2-8.1 (d, 1H), 7.9-7.64 (m, 5H), 7.62-7.5 (m, 1H), 7.5-7.3 (m, 3H), 7.0-6.9 (d, 1H), 5.4 (s, 2H), 4.24-4.06 (d, 2H), 3.8-3.56 (m, 4H), 3.54-3.4 (m, 2H), 3.2-3.02 (m, 2H).

52) Synthesis of 3-Hydroxy-biphenyl-4-carboxylic acid {2-oxo-2-[4-(2-trifluoromethyl-benzoyl)-piperazin-1-yl]-ethyl}-amide

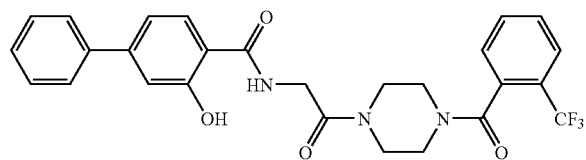

Ammonium formate (250 mg, 3.96 mmol) was added to a stirred solution of enzyloxy-biphenyl-4-carboxylic acid {2-oxo-2-[4-(2-trifluoromethyl-benzoyl)-piperazin-1-yl]-ethyl}-amide (prepared by the method as described above) (123 mg, 0.2 mmol) in MeOH (20 mL). 10% Pd/c (40 mg) was then added and the resulting mixture stirred at room temperature under an inert atmosphere. The reaction mixture was then stirred at reflux temperature for 3 hrs. The mixture was filtered over a bed of celite. The celite was washed with MeOH and the filtrate was concentrated. The residue was dissolved in EtOAc, washed with 5% aqueous NaOH solution, followed by saturated brine solution. The organic layer was dried over Na2SO4 and concentrated in vacuo to afford 80 mg (76.92% yield) of 3-Hydroxy-biphenyl-4-carboxylic acid {2-oxo-2-[4-(2-trifluoromethyl-benzoyl)-piperazin-1-yl]-ethyl}-amide. LCMS Purity: 91.28%. $^1$H NMR (DMSO-$d_6$): δ 10.8 (bs, 1H), 7.9-7.74 (m, 3H), 7.72-7.52 (m, 4H), 7.48-7.3 (m, 3H), 7.0 (bs, 1H), 6.86-6.76 (bs, 1H), 4.3-4.12 (bd, 2H), 3.8-3.54 (bd, 6H), 3.16-3.04 (bd, 2H).

53) Synthesis of 2',3'-Difluoro-biphenyl-4-carboxylic acid {2-oxo-2-[4-(2-trifluoromethyl-benzoyl)-piperazin-1-yl]-ethyl}-amide

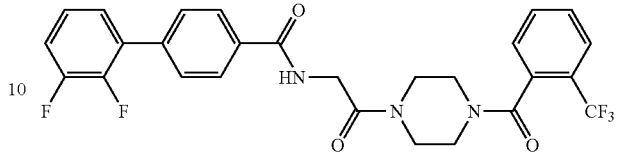

DIPEA (273 mg, 0.37 mL, 2.1 mmol) was added to a stirred solution of 2-amino-1-[4-(2-trifluoromethyl-benzoyl)-piperazin-1-yl]-ethanone hydrochloride salt (198.2 mg, 0.56 mmol) in DMF (3 mL). HOBT (69.7 mg, 0.51 mmol) and EDCI (225 mg, 1.1 mmol) were then added at room temperature. After 2 minutes, 2',3'-difluoro-biphenyl-4-carboxylic acid (110 mg, 0.46 mmol) (prepared by the method as described above) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 60% EtOAc in Hexane as eluent) to afford 120 mg (48.07% yield) of 2',3'-difluoro-biphenyl-4-carboxylic acid {2-oxo-2-[4-(2-trifluoromethyl-benzoyl)-piperazin-1-yl]-ethyl}-amide. LCMS Purity: 82.25%. $^1$H NMR (DMSO-$d_6$): δ 8.8 (s, 1H), 8.2-8.0 (d, 2H), 7.9-7.64 (m, 5H), 7.62-7.1 (m, 4H), 4.2 (d, 2H), 3.8-3.54 (m, 4H), 3.52-3.4 (m, 2H), 3.2-3.08 (m, 2H).

54) Synthesis of 6-Hydroxy-N-{2-oxo-2-[4-(2-trifluoromethyl-benzoyl)-piperazin-1-yl]-ethyl}-nicotinamide

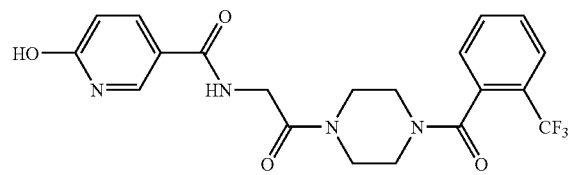

DIPEA (418 mg, 0.56 mL, 3.2 mmol) was added to a stirred solution of 2-amino-1-[4-(2-trifluoromethyl-benzoyl)-piperazin-1-yl]-ethanone hydrochloride salt (303.4 mg, 0.86 mmol) in DMF (4 mL). HOBT (106 mg, 0.79 mmol) and EDCI (344 mg, 1.7 mmol) were then added at room temperature. After 2 minutes, 6-hydroxy nicotinic acid (100 mg, 0.71 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by preparative HPLC to afford 77 mg (24.6% yield) of 6-hydroxy-N-{2-oxo-2-[4-(2-trifluoromethyl-benzoyl)-piperazin-1-yl]-ethyl}-nicotinamide. LCMS Purity: 95.26%. $^1$H NMR (DMSO-$d_6$): δ 12 (s, 1H), 8.4 (s, 1H), 7.9-7.74 (m, 3H), 7.72-7.62 (m, 1H), 7.6-7.5 (m, 1H), 4.2-4.0 (d, 2H), 3.9-3.52 (m, 5H), 3.24-3.0 (m, 3H).

55) Synthesis of 3'-Amino-biphenyl-4-carboxylic acid {2-oxo-2-[4-(2-trifluoromethyl-benzoyl)-piperazin-1-yl]-ethyl}-amide

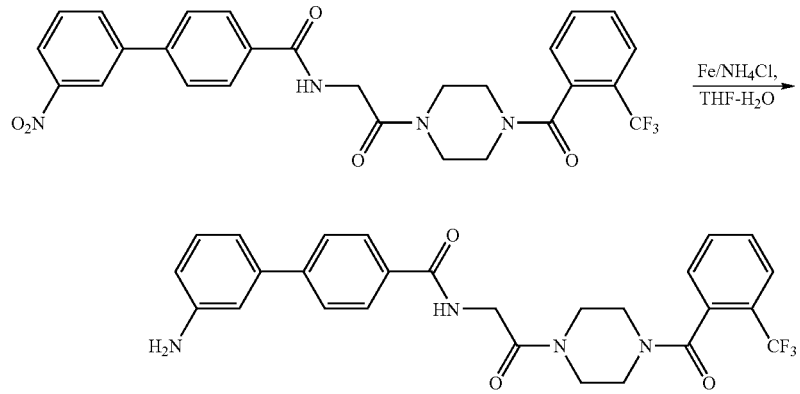

Ammonium chloride (74 mg, 1.4 mmol) was added to a stirred solution of 3'-nitro-biphenyl-4-carboxylic acid {2-oxo-2-[4-(2-trifluoromethyl-benzoyl)-piperazin-1-yl]-ethyl}-amide (prepared by the method as described above) (123 mg, 0.2 mmol) in a mixture of THF (6 mL) and H$_2$O (4 ml). Iron powder (77 mg) was then added and the resulting mixture at reflux temperature for 3 hrs. The mixture was filtered, and the filtrate was concentrated. The residue was dissolved in EtOAc, washed with 5% aqueous NaHCO$_3$ solution, followed by saturated brine solution. The organic layer was dried over Na$_2$SO$_4$ and concentrated in vacuo to afford 69 mg (49.3% yield) of 3'-Amino-biphenyl-4-carboxylic acid {2-oxo-2-[4-(2-trifluoromethyl-benzoyl)-piperazin-1-yl]-ethyl}-amide. LCMS Purity: 92.88%. $^1$H NMR (CDCl$_3$): δ 7.9 (d, 2H), 7.8-7.7 (bd, 1H), 7.7-7.6 (m, 4H), 7.6-7.55 (bs, 1H), 7.4-7.3 (d, 1H), 7.2 (d, 1H), 7.0 (d, 1H), 6.9 (t, 1H), 6.8 (d, 1H), 4.38-4.3 (m, 1H), 4.3-4.22 (m, 1H), 4.08-3.96 (bd, 2H), 3.94-3.86 (bs, 1H), 3.84-3.64 (m, 4H), 3.64-3.32 (m, 2H), 3.52-3.46 (d, 1H), 3.44-3.4 (t, 1H), 3.3-3.2 (bs, 2H).

56) Synthesis of 3-Methoxy-biphenyl-4-carboxylic acid {2-oxo-2-[4-(2-trifluoromethyl-benzoyl)-piperazin-1-yl]-ethyl}-amide

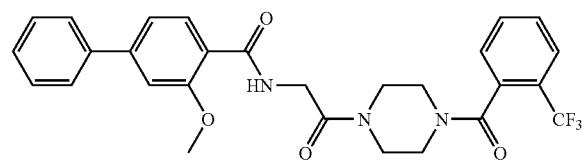

Methyl iodide (21 mg, 0.009 ml, 0.148 mmol) was added to a stirred solution of 3-hydroxy-biphenyl-4-carboxylic acid {2-oxo-2-[4-(2-trifluoromethyl-benzoyl)-piperazin-1-yl]-ethyl}-amide (prepared by the method as described above) (51 mg, 0.1 mmol) and K$_2$CO$_3$ (20 mg, 0.144 mmol) in DMF (3 mL) and the resulting mixture was stirred at 80° C. for 2 hrs. The mixture was filtered, the filtrate was diluted with cold water and filtered the solid precipitated out, dried to afford 41 mg (78.84% yield) of 3-methoxy-biphenyl-4-carboxylic acid {2-oxo-2-[4-(2-trifluoromethyl-benzoyl)-piperazin-1-yl]-ethyl}-amide. $^1$H NMR: (DMSO-d$_6$): δ 8.8-8.7 (bs, 1H), 8.04-7.98 (bs, 1H), 7.88-7.74 (dd, 4H), 7.72-7.64 (t, 1H), 7.58-7.46 (m, 3H), 7.46-7.34 (m, 3H), 4.32-4.18 (bs, 1H), 4.04 (s, 3H), 3.8-3.66 (bd, 2H), 3.66-3.54 (bt, 3H), 3.22-3.04 (bs, 1H).

57) Synthesis of 2',6'-Difluoro-biphenyl-4-carboxylic acid {2-oxo-2-[4-(2-trifluoromethyl-benzoyl)-piperazin-1-yl]-ethyl}-amide

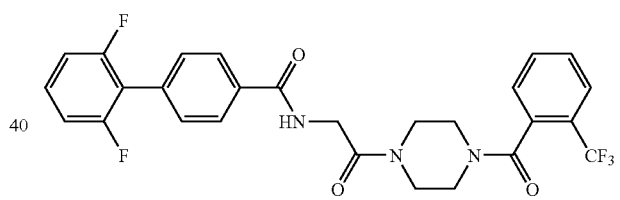

DIPEA (198.6 mg, 0.26 mL, 1.5 mmol) was added to a stirred solution of 2-amino-1-[4-(2-trifluoromethyl-benzoyl)-piperazin-1-yl]-ethanone hydrochloride salt (144.1 mg, 0.4 mmol) in DMF (4 mL). HOBT (50.7 mg, 0.37 mmol) and EDCI (163.6 mg, 0.85 mmol) were then added at room temperature. After 2 minutes, 2',6'-difluoro-biphenyl-4-carboxylic acid (80 mg, 0.34 mmol) (prepared by the method as described above) was added and the resulting mixture was stirred at room temperature overnight. Cold water was then added and the product was extracted with EtOAc and the organic layer was washed with brine. The organic phase was dried over Na$_2$SO$_4$ and concentrated under reduced pressure to get the residue. The obtained residue was purified by column chromatography (using silica gel of 60-120 mesh and 50% EtOAc in Hexane as eluent) to afford 65 mg (35.8% yield) of 2',6'-difluoro-biphenyl-4-carboxylic acid {2-oxo-2-[4-(2-trifluoromethyl-benzoyl)-piperazin-1-yl]-ethyl}-amide. LCMS Purity: 82.25%. $^1$H NMR (DMSO-d$_6$): δ 8.8-8.7 (t, 1H), 8.0 (d, 1H), 7.9-7.7 (m, 2H), 7.7-7.6 (m, 1H), 7.6-7.5 (m, 4H), 7.3-7.2 (m, 2H), 4.2 (dd, 2H), 3.8-3.7 (m, 2H), 3.7-3.5 (m, 3H), 3.2-3.1 (m, 2H).

58) Synthesis of N-{2-Oxo-2-[4-(2-trifluoromethyl-benzoyl)-piperazin-1-yl]-ethyl}-4-thiazol-5-yl-benzamide

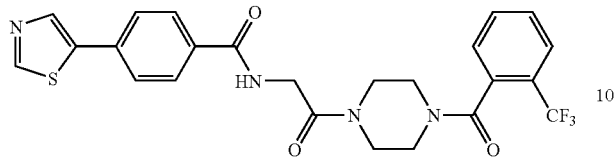

DIPEA (232 mg, 0.31 mL, 1.79 mmol) was added to a stirred solution of 2-amino-1-[4-(2-trifluoromethyl-benzoyl)-piperazin-1-yl]-ethanone hydrochloride salt (prepared by the method as described above) (190 mg, 0.54 mmol) in DMF (3 mL). HOBT (67 mg, 0.49 mmol) and EDCI (172 mg, 0.89 mmol) were then added at room temperature. After 2 minutes, 4-thiazol-5-yl-benzoic acid (100 mg, 0.49 mmol) (prepared by the method described above) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 70% EtOAc in Hexane as eluent) to afford 102 mg (45.33% yield) N-{2-Oxo-2-[4-(2-trifluoromethyl-benzoyl)-piperazin-1-yl]-ethyl}-4-thiazol-5-yl-benzamide. LCMS Purity: 97.53%. $^1$H NMR ($CDCl_3$): δ 8.8 (s, 1H), 8.16 (s, 1H), 7.92-7.84 (d, 2H), 7.78-7.72 (d, 1H), 7.7-7.52 (m, 4H), 7.38-7.3 (d, 2H), 4.36-4.3 (m, 1H), 4.28-4.2 (m, 1H), 4.1-4.0 (d, 2H), 3.98-3.88 (m, 1H), 3.8-3.64 (m, 2H), 3.64-3.5 (d, 2H), 3.44-3.18 (t, 1H), 3.3-3.21 (bs, 2H).

59) Synthesis of 2',5'-Difluoro-biphenyl-4-carboxylic acid {2-oxo-2-[4-(2-trifluoromethyl-benzoyl)-piperazin-1-yl]-ethyl}-amide

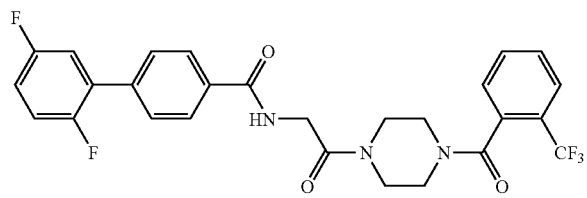

DIPEA (211 mg, 0.28 mL, 1.6 mmol) was added to a stirred solution of 2-amino-1-[4-(2-trifluoromethyl-benzoyl)-piperazin-1-yl]-ethanone hydrochloride salt (140.5 mg, 0.399 mmol) in DMF (3 mL). HOBT (53.9 mg, 0.39 mmol) and EDCI (139.2 mg, 0.72 mmol) were then added at room temperature. After 2 minutes, 2',5'-difluoro-biphenyl-4-carboxylic acid (85 mg, 0.36 mmol) (prepared by the method as described above) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 60% EtOAc in Hexane as eluent) to afford 38 mg (19.79% yield) of 2',5'-difluoro-biphenyl-4-carboxylic acid {2-oxo-2-[4-(2-trifluoromethyl-benzoyl)-piperazin-1-yl]-ethyl}-amide. LCMS Purity: 95.02%. $^1$H NMR (DMSO-$d_6$): δ 8.7 (s, 1H), 8.0 (d, 2H), 7.9-7.65 (m, 5H), 7.6-7.46 (m, 2H), 7.44-7.25 (m, 2H), 4.3-4.1 (d, 2H), 3.6-3.4 (m, 4H), 3.26-3.04 (m, 2H).

60) Synthesis of 2'-Methoxy-biphenyl-4-carboxylic acid {2-oxo-2-[4-(2-trifluoromethyl-benzoyl)-piperazin-1-yl]-ethyl}-amide

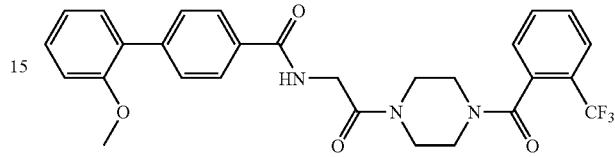

DIPEA (140 mg, 0.19 mL, 1.08 mmol) was added to a stirred solution of 2-amino-1-[4-(2-trifluoromethyl-benzoyl)-piperazin-1-yl]-ethanone hydrochloride salt (prepared by the method as described above) (119 mg, 0.38 mmol) in DMF (5 mL). HOBT (45 mg, 0.33 mmol) and EDCI (118 mg, 0.61 mmol) were then added at room temperature. After 2 minutes, 2'-Methoxy-biphenyl-4-carboxylic acid (70 mg, 0.30 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by preparative HPLC to afford 71 mg (44.1% yield) 2'-Methoxy-biphenyl-4-carboxylic acid {2-oxo-2-[4-(2-trifluoromethyl-benzoyl)-piperazin-1-yl]-ethyl}-amide. LCMS Purity: 98.92%. $^1$H NMR ($CDCl_3$): δ 7.94-7.84 (t, 1H), 7.8-7.72 (d, 1H), 7.7-7.56 (m, 4H), 7.5-7.44 (t, 1H), 7.4-7.3 (m, 3H), 7.1-7.0 (dd, 2H), 4.4-4.2 (m, 2H), 4.1-3.86 (m, 2H), 3.84-3.8 (s, 3H), 3.76-3.5 (m, 4H), 3.44-3.38 (t, 1H), 3.3-3.2 (bs, 2H).

61) Synthesis of N-{2-Oxo-2-[4-(2-trifluoromethyl-benzoyl)-piperazin-1-yl]-ethyl}-4-piperidin-1-yl-benzamide

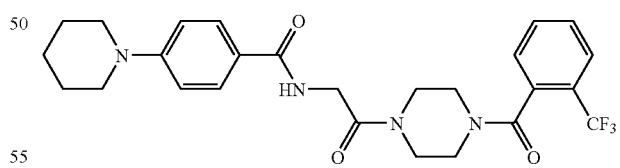

DIPEA (188.6 mg, 0.25 mL, 1.45 mmol) was added to a stirred solution of 2-amino-1-[4-(2-trifluoromethyl-benzoyl)-piperazin-1-yl]-ethanone hydrochloride salt (282.2 mg, 0.8 mmol) in DMF (4 mL). HOBT (108 mg, 0.8 mmol) and EDCI (279.7 mg, 1.45 mmol) were then added at room temperature. After 2 minutes, 4-piperidin-1-yl-benzoic acid (150 mg, 0.729 mmol) was added and the resulting mixture was stirred at room temperature overnight. Cold water was then added and the product was extracted with EtOAc and the organic layer was washed with brine. The organic phase was dried over Na₂SO₄ and concentrated under reduced pressure to get the residue. The obtained residue was purified by column chromatography (using silica gel of 60-120 mesh and 50% EtOAc in Hexane as eluent) to afford 80 mg (21.7% yield) N-{2-Oxo-2-[4-(2-trifluoromethyl-benzoyl)-piperazin-1-yl]-ethyl}-4-piperidin-1-yl-benzamide. LCMS Purity: 94.74%. $^1$H NMR (DMSO-d₆): δ 8.2 (s, 1H), 7.9-7.5 (m, 6H), 7.0-6.9 (d, 2H), 4.2-4.0 (d, 2H), 3.8-3.5 (m, 4H), 3.35-3.2 (m, 4H), 3.2-3.0 (m, 4H), 1.7-1.5 (s, 6H).

62) Synthesis of 4-Imidazol-1-yl-N-{2-oxo-2-[4-(2-trifluoromethyl-benzoyl)-piperazin-1-yl]-ethyl}-benzamide

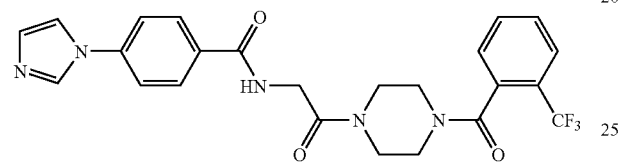

DIPEA (247.2 mg, 0.33 mL, 1.9 mmol) was added to a stirred solution of 2-amino-1-[4-(2-trifluoromethyl-benzoyl)-piperazin-1-yl]-ethanone hydrochloride salt (164.3 mg, 0.46 mmol) in DMF (2 mL). HOBT (63.1 mg, 0.46 mmol) and EDCI (179.2 mg, 0.93 mmol) were then added at room temperature. After 2 minutes, 4-imidazol-1-yl-benzoic acid (80 mg, 0.42 mmol) was added and the resulting mixture was stirred at room temperature overnight. Cold water was then added and the product was extracted with EtOAc and the organic layer was washed with brine. The organic phase was dried over Na₂SO₄ and concentrated under reduced pressure to get the residue. The obtained residue was purified by column chromatography (using silica gel of 60-120 mesh and 50% EtOAc in Hexane as eluent) to afford 69 mg (33.4% yield) 4-imidazol-1-yl-N-{2-oxo-2-[4-(2-trifluoromethyl-benzoyl)-piperazin-1-yl]-ethyl}-benzamide. LCMS Purity: 94.26%. $^1$H NMR (DMSO-d₆): δ 8.8-8.7 (s, 1H), 8.4 (s, 1H), 8.1-8.0 (d, 2H), 7.9-7.7 (m, 5H), 7.7-7.62 (m, 1H), 7.62-7.5 (t, 1H), 7.2-7.1 (s, 1H), 4.3-4.1 (d, 2H), 3.8-3.5 (m, 4H), 3.5-3.4 (m, 2H), 3.24-3.0 (m, 2H).

63) Synthesis of Biphenyl-4-carboxylic acid {2-[4-(2-bromo-5-hydroxy-benzoyl)-piperazin-1-yl]-2-oxo-ethyl}-amide

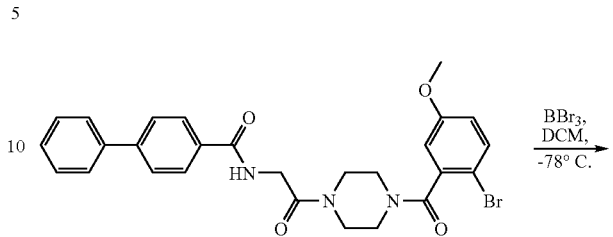

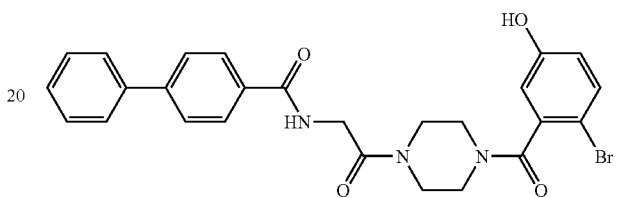

A solution of Biphenyl-4-carboxylic acid {2-[4-(2-bromo-5-methoxy-benzoyl)-piperazin-1-yl]-2-oxo-ethyl}-amide (prepared by the method as described above) (115 mg, 0.21 mmol) in DCM (5 ml) was cooled to −78° C. To the resulting mixture added BBr₃ (357 mg, 1.42 ml, 1.43 mmol) and stirred at same temperature for 4 hrs. The reaction mixture was brought to −30° C. and quenched with cold MeOH dropwise, concentrated the mixture under reduced pressure to get the residue. The obtained residue was purified by preparative HPLC to afford 33 mg (29.5% yield) Biphenyl-4-carboxylic acid {2-[4-(2-bromo-5-hydroxy-benzoyl)-piperazin-1-yl]-2-oxo-ethyl}-amide. LCMS Purity: 98.95%. $^1$H NMR (DMSO-d₆): δ 10.1 (s, 1H), 8.7-8.6 (bs, 1H), 8.0-7.9 (d, 2H), 7.8-7.7 (dd, 4H), 7.5-7.4 (m, 4H), 6.8-6.7 (t, 2H), 4.24-4.1 (dd, 2H), 3.74-3.44 (m, 6H), 3.24-3.1 (bd, 2H).

64) Synthesis of 2'-Hydroxy-biphenyl-4-carboxylic acid {2-oxo-2-[4-(2-trifluoromethyl-benzoyl)-piperazin-1-yl]-ethyl}-amide

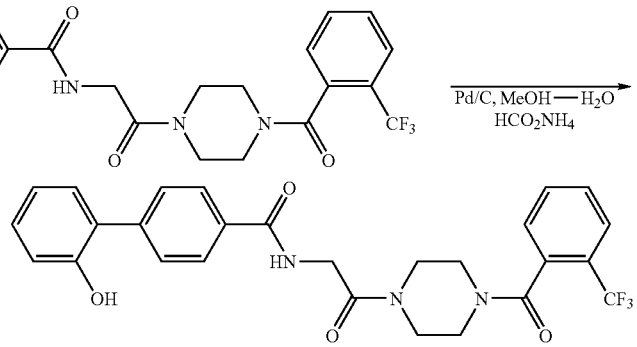

Ammonium formate (350 mg, 5.5 mmol) was added to a stirred solution of 2'-Benzyloxy-biphenyl-4-carboxylic acid {2-oxo-2-[4-(2-trifluoromethyl-benzoyl)-piperazin-1-yl]-ethyl}-amide (prepared by the method as described above) (156 mg, 0.26 mmol) in a mixture of MeOH (10 mL) and water (2 ml). 10% Pd/c (40 mg) was then added and the resulting mixture stirred at room temperature under an inert atmosphere. The reaction mixture was then stirred at reflux temperature for 3 hrs. The mixture was filtered over a bed of celite. The celite was washed with MeOH and the filtrate was concentrated. The residue was dissolved in EtOAc, washed with 5% aqueous NaOH solution, followed by saturated brine solution. The organic layer was dried over Na2SO4 and concentrated to get the residue. The residue was purified by preparative HPLC to afford 62 mg (47% yield) of 2'-Hydroxy-biphenyl-4-carboxylic acid {2-oxo-2-[4-(2-trifluoromethyl-benzoyl)-piperazin-1-yl]-ethyl}-amide. LCMS Purity: 98.83%. $^1$H NMR (DMSO-$d_6$): δ 9.6 (s, 1H), 8.64-8.5 (bs, 1H), 7.92-7.72 (m, 4H), 7.72-7.5 (m, 4H), 7.26-7.12 (d, 1H), 7.24-7.16 (t, 1H), 7.0-6.84 (m, 2H), 4.24-4.06 (bd, 2H), 3.82-3.52 (m, 4H), 3.52-3.42 (bs, 2H), 3.24-3.02 (bd, 2H).

65) Synthesis of 5-Methyl-1-phenyl-1H-pyrazole-4-carboxylic acid {2-oxo-2-[4-(2-trifluoromethyl-benzoyl)-piperazin-1-yl]-ethyl}-amide

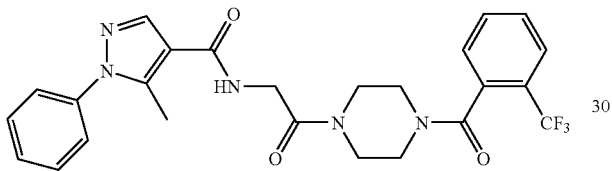

DIPEA (189 mg, 0.256 mL, 1.48 mmol) was added to a stirred solution of 2-amino-1-[4-(2-trifluoromethyl-benzoyl)-piperazin-1-yl]-ethanone hydrochloride salt (prepared by the method described above) (208 mg, 0.59 mmol) in DMF (2 mL). HOBT (80 mg, 0.59 mmol) and EDCI (114 mg, 0.59 mmol) were then added at room temperature. After 2 minutes, 5-Methyl-1-phenyl-1H-pyrazole-4-carboxylic acid (100 mg, 0.49 mmol) was added and the resulting mixture was stirred at room temperature for 4 hrs. Cold water was then added and the product was extracted with EtOAc and the organic layer was washed with brine. The organic phase was dried over Na$_2$SO$_4$ and concentrated under reduced pressure to afford 29 mg (11.74% yield) 5-Methyl-1-phenyl-1H-pyrazole-4-carboxylic acid {2-oxo-2-[4-(2-trifluoromethyl-benzoyl)-piperazin-1-yl]-ethyl}-amide. LCMS Purity: 94.32%. $^1$H NMR (DMSO-$d_6$): δ 8.24 (bs, 1H), 8.14 (s, 1H), 7.88-7.74 (m, 2H), 7.7-7.6 (m, 1H), 7.6-7.4 (m, 6H), 4.2-4.4 (d, 2H), 3.9-3.6 (m, 4H), 3.5-3.4 (m, 2H), 3.2-3.0 (m, 2H).

66) Synthesis of 1H-Indole-3-carboxylic acid {2-oxo-2-[4-(2-trifluoromethyl-benzoyl)-piperazin-1-yl]-ethyl}-amide

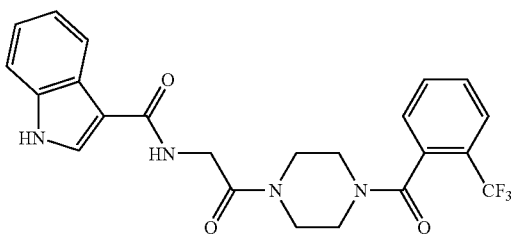

DIPEA (143 mg, 0.193 mL, 1.11 mmol) was added to a stirred solution of 2-amino-1-[4-(2-trifluoromethyl-benzoyl)-piperazin-1-yl]-ethanone hydrochloride salt (prepared by the method described above) (157 mg, 0.44 mmol) in DMF (2 mL). HOBT (60 mg, 0.44 mmol) and EDCI (85 mg, 0.44 mmol) were then added at room temperature. After 2 minutes, 1H-Indole-3-carboxylic acid (60 mg, 0.37 mmol) was added and the resulting mixture was stirred at room temperature for 4 hrs. Cold water was then added and the product was extracted with EtOAc and the organic layer was washed with brine. The organic phase was dried over Na$_2$SO$_4$ and concentrated under reduced pressure to the residue. The residue was purified by preparative HPLC to afford 21.3 mg (12.35% yield) of 1H-Indole-3-carboxylic acid {2-oxo-2-[4-(2-trifluoromethyl-benzoyl)-piperazin-1-yl]-ethyl}-amide. LCMS Purity: 95.81%. $^1$H NMR (CDCl$_3$): δ 9.1 (s, 1H), 8.1 (d, 1H), 7.9-7.5 (m, 4H), 7.4-7.1 (m, 4H), 4.4-4.2 (m, 2H), 4.1-3.8 (m, 2H), 3.8-3.4 (m, 4H), 3.4-3.1 (m, 3H).

67) Synthesis of 1H-Indazole-3-carboxylic acid {2-[4-(5-fluoro-2-trifluoromethyl-benzoyl)-piperazin-1-yl]-2-oxo-ethyl}-amide

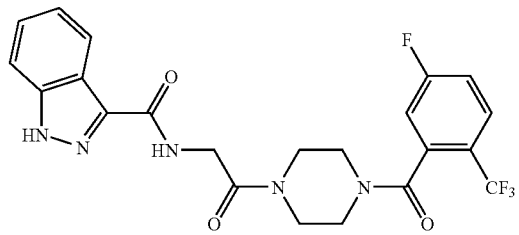

DIPEA (112 mg, 0.16 mL, 0.92 mmol) was added to a stirred solution of 2-amino-1-[4-(2-trifluoromethyl-benzoyl)-piperazin-1-yl]-ethanone hydrochloride salt (prepared by the method described above)(136 mg, 0.37 mmol) in DMF (2 mL). HOBT (49 mg, 0.37 mmol) and EDCI (71 mg, 0.37 mmol) were then added at room temperature. After 2 minutes, 1H-Indazole-3-carboxylic acid (50 mg, 0.3 mmol) was added and the resulting mixture was stirred at room temperature for 4 hrs. Cold water was then added and the product was extracted with EtOAc and the organic layer was washed with brine. The organic phase was dried over Na$_2$SO$_4$ and concentrated under reduced pressure to afford 62 mg (42.17% yield) 1H-Indazole-3-carboxylic acid {2-[4-(5-fluoro-2-trifluoromethyl-benzoyl)-piperazin-1-yl]-2-oxo-ethyl}-amide. LCMS Purity: 92.58%. $^1$H NMR (DMSO-$d_6$): δ 13.6 (s, 1H), 8.2 (m, 2H), 8.14 (m, 1H), 7.9 (m, 1H), 7.7-7.5 (m, 3H), 7.4 (t, 1H), 7.3 (t, 1H), 4.2 (d, 2H), 3.8-3.4 (m, 6H), 3.3-3.0 (m, 2H).

68) Synthesis of 1-phenyl-5-trifluoromethyl-1H-pyrazole-4-carboxylic acid {2-[4-(5-fluoro-2-trifluoromethyl-benzoyl)-piperazin-1-yl]-2-oxo-ethyl}-amide

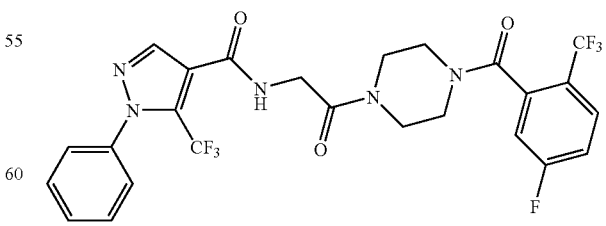

DIPEA (141 mg, 0.19 mL, 1.1 mmol) was added to a stirred solution of 1-phenyl-5-trifluoromethyl-1H-pyrazole-4-carboxylic acid (70 mg, 0.27 mmol) in DMF (5 mL). HOBT (40 mg, 0.29 mmol) and EDCI (131 mg, 0.68 mmol) were then added at room temperature. After 2 minutes, 2-amino-1-[4-

(5-fluoro-2-trifluoromethyl-benzoyl)-piperazin-1-yl]-ethanone hydrochloride salt (111 mg, 0.3 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using 60-120 silica gel and 70% EtOAC in hexane as eluent) to afford 43 mg (27.56% yield) of 1-phenyl-5-trifluoromethyl-1H-pyrazole-4-carboxylic acid {2-[4-(5-fluoro-2-trifluoromethyl-benzoyl)-piperazin-1-yl]-2-oxo-ethyl}-amide, LCMS Purity: 86.39%. $^1$H NMR (CDCl$_3$): δ 8.0 (s, 1H), 7.8 (t, 1H), 7.56-7.4 (m, 5H), 7.26 (s, 1H), 7.1 (d, 2H), 4.36-4.2 (m, 2H), 4.06-3.84 (m, 1H), 3.8-3.64 (m, 2H), 3.62-3.48 (m, 2H), 3.44 (t, 1H), 3.3-3.2 (m, 2H).

69) Synthesis of 5-(2-Fluoro-phenyl)-1H-pyrazole-3-carboxylic acid {2-[4-(5-fluoro-2-trifluoromethyl-benzoyl)-piperazin-1-yl]-2-oxo-ethyl}-amide

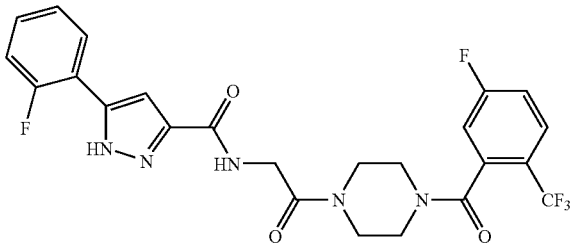

DIPEA (123 mg, 0.16 mL, 0.95 mmol) was added to a stirred solution of 5-(2-fluoro-phenyl)-1H-pyrazole-3-carboxylic acid (56 mg, 0.27 mmol) in DMF (2 mL). HOBT (39 mg, 0.28 mmol) and EDCI (55 mg, 0.28 mmol) were then added at room temperature. After 2 minutes, 2-amino-1-[4-(5-fluoro-2-trifluoromethyl-benzoyl)-piperazin-1-yl]-ethanone hydrochloride salt (100 mg, 0.27 mmol) was added and the resulting mixture was stirred at room temperature overnight. Cold water was then added and filtered the solid precipitate. The solid was purified by recrystallisation from a mixture of ethyl acetate and hexane to afford 65 mg (33.16% yield) of 5-(2-fluoro-phenyl)-1H-pyrazole-3-carboxylic acid {2-[4-(5-fluoro-2-trifluoromethyl-benzoyl)-piperazin-1-yl]-2-oxo-ethyl}-amide. LCMS Purity: 97.49%. $^1$H NMR (DMSO-d$_6$): δ 13.6 (s, 1H), 7.7 (m, 4H), 7.6 (m, 1H), 7.38 (m, 3H), 7.1 (m, 2H), 6.98 (m, 4H), 4.5 (m, 1H), 4.0 (m, 1H), 3.2 (m, 2H), 2.9 (m, 2H), 1.91 (m, 1H), 1.65 (m, 2H), 1.4 (m, 2H).

70) Synthesis of 5-(2-Fluoro-phenyl)-1H-pyrazole-3-carboxylic acid {2-oxo-2-[4-(2-trifluoromethyl-benzoyl)-piperazin-1-yl]-ethyl}-amide

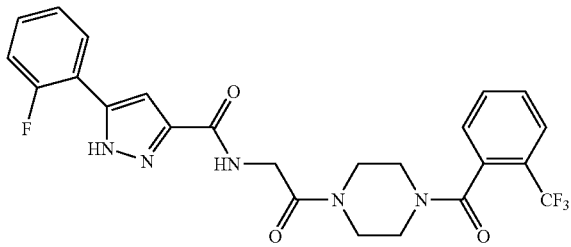

DIPEA (92 mg, 0.12 mL, 0.71 mmol) was added to a stirred solution of 5-(2-fluoro-phenyl)-1H-pyrazole-3-carboxylic acid (59 mg, 0.28 mmol) in DMF (2 mL). HOBT (40 mg, 0.29 mmol) and EDCI (57 mg, 0.29 mmol) were then added at room temperature. After 2 minutes, 2-amino-1-[4-(2-trifluoromethyl-benzoyl)-piperazin-1-yl]-ethanone (100 mg, 0.28 mmol) was added and the resulting mixture was stirred at room temperature overnight. Cold water was then added and filtered the solid precipitated to afford 131 mg (91.6% yield) of 5-(2-fluoro-phenyl)-1H-pyrazole-3-carboxylic acid {2-oxo-2-[4-(2-trifluoromethyl-benzoyl)-piperazin-1-yl]-ethyl}-amide. LCMS Purity: 95.28%. $^1$H NMR (DMSO-d$_6$): δ 13.8 (d, 1H), 8.0 (m, 1H), 7.6 (m, 3H), 7.2 (m, 4H), 7.1 (m, 1H), 4.1 (d, 2H), 3.5 (m, 4H), 3.35 (m, 2H), 3.0 (m, 2H).

71) Synthesis of 1-Phenyl-1H-pyrazole-4-carboxylic acid {2-[4-(5-fluoro-2-trifluoromethyl-benzoyl)-piperazin-1-yl]-2-oxo-ethyl}-amide

Step 1: Synthesis of 1-Phenyl-1H-pyrazole-4-carbaldehyde

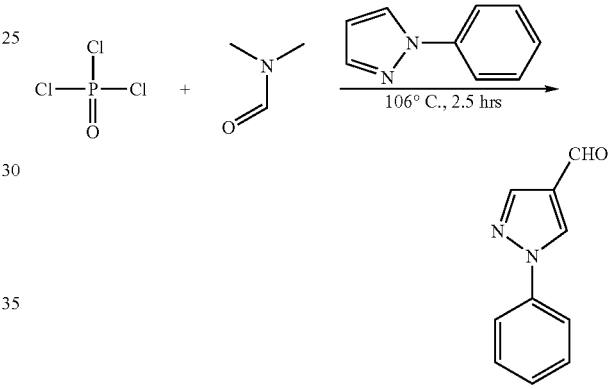

1-Phenyl-1H-pyrazole (250 mg, 1.7 mmol) was added to a cold (0-4° C.) solution of DMF (1.5 g, 1.6 mL, 9.7 mmol) and POCl$_3$ (1.86 g, 1.1 mL, 19.2 mmol) and stirring continued for 10 minutes. The resulting mixture was heated at 106° C. for 2.5 hrs. The reaction mixture was cooled and quenched with ice cold water, basified with 20% aqueous NaOH solution, filtered the solid precipitated to afford 330 mg (crude) of 1-Phenyl-1H-pyrazole-4-carbaldehyde. $^1$H NMR (CDCl$_3$): δ 10.0 (s, 1H), 8.45 (s, 1H), 8.2 (s, 1H), 7.75 (d, 2H), 7.55 (t, 2H), 7.45 (t, 1H).

Step 2: Synthesis of 1-Phenyl-1H-pyrazole-4-carboxylic acid

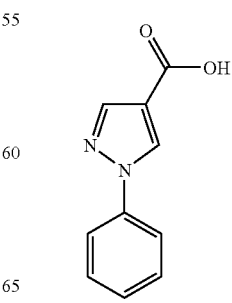

Sulphamic acid (253 mg, 2.6 mmol) in water (0.5 mL) was added at 0° C. to a mixture of phenyl-1H-pyrazole-4-carbaldehyde (0.5 g, 2.34 mmol) in acetone (3 mL). After 5 minutes sodium chlorite (315 mg, 3.5 mmol) was added and the resulting mixture was stirred at 0° C. for 30 minutes. Water was added and the solid obtained was isolated by filtration to afford 140 mg (85% yield) of 1-phenyl-1H-pyrazole-4-carboxylic acid.

Step 3: Synthesis of 1-Phenyl-1H-pyrazole-4-carboxylic acid {2-[4-(5-fluoro-2-trifluoromethyl-benzoyl)-piperazin-1-yl]-2-oxo-ethyl}-amide

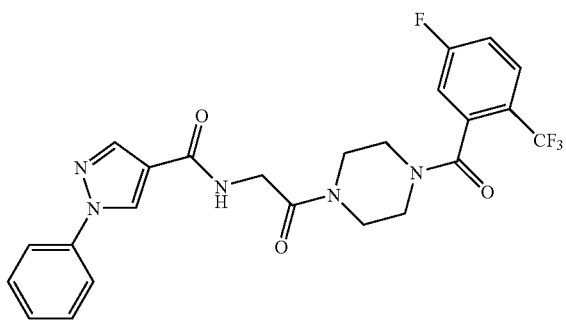

DIPEA (223 mg, 0.3 mL, 1.72 mmol) was added to a stirred solution of 1-phenyl-1H-pyrazole-4-carboxylic acid (65 mg, 0.34 mmol) in DMF (5 mL). HOBT (51 mg, 0.38 mmol) and EDCI (165 mg, 0.86 mmol) were then added at room temperature. After 2 minutes, 2-amino-1-[4-(5-fluoro-2-trifluoromethyl-benzoyl)-piperazin-1-yl]-ethanone hydrochloride salt (140 mg, 0.38 mmol) was added and the resulting mixture was stirred at room temperature overnight. Cold water was then added and filtered the solid precipitated out to afford 96 mg (53.3% yield) of 1-phenyl-1H-pyrazole-4-carboxylic acid {2-[4-(5-fluoro-2-trifluoromethyl-benzoyl)-piperazin-1-yl]-2-oxo-ethyl}-amide. LCMS Purity: 96.77%. $^1$H NMR (CDCl$_3$): δ 8.42 (d, 2H), 8.04 (s, 1H), 7.8-7.64 (m, 3H), 7.52-7.42 (t, 2H), 7.4-7.3 (t, 1H), 7.1 (d, 1H), 7.0-6.9 (bs, 1H), 4.34-4.18 (m, 2H), 4.04-3.84 (m, 1H), 3.8-3.5 (m, 4H), δ 3.44 (t, 1H), 3.3-3.2 (m, 2H).

72) Synthesis of Naphthalene-1-carboxylic acid {2-[4-(5-fluoro-2-trifluoromethyl-benzoyl)-piperazin-1-yl]-2-oxo-ethyl}-amide

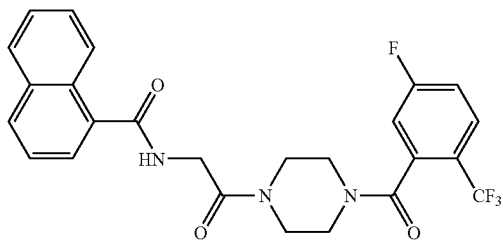

DIPEA (269 mg, 0.36 mL, 2.08 mmol) was added to a stirred solution of naphthalene-2-carboxylic acid (80 mg, 0.46 mmol) in DMF (2 mL). HOBT (69 mg, 0.51 mmol) and EDCI (177 mg, 0.92 mmol) were then added at room temperature. After 2 minutes, 2-amino-1-[4-(2-trifluoromethyl-benzoyl)-piperazin-1-yl]-ethanone hydrochloride salt (133 mg, 0.38 mmol) was added and the resulting mixture was stirred at room temperature overnight. Cold water was then added, extracted with EtOAc, the organic layer was washed with saturated sodium bicarbonate solution and brine. The organic phase was dried over Na$_2$SO$_4$ and concentrated under reduced pressure to get the residue. The residue obtained was purified by column chromatography using (silica gel of 60-120 mesh and 40% EtOAc in Hexane as eluent) to afford 70 mg (31% yield) of naphthalene-1-carboxylic acid {2-[4-(5-fluoro-2-trifluoromethyl-benzoyl)-piperazin-1-yl]-2-oxo-ethyl}-amide. LCMS Purity: 87.12%. $^1$H NMR (DMSO-d$_6$): δ 8.8-8.7 (t, 1H), 8.5-8.44 (s, 1H), 8.1-7.9 (m, 5H), 7.7-7.45 (m, 4H), 4.34-4.14 (m, 2H), 3.85-3.4 (m, 6H), 3.24-3.06 (m, 2H).

73) Synthesis of 1-Phenyl-1H-pyrazole-4-carboxylic acid {2-oxo-2-[4-(2-trifluoromethyl-benzoyl)-piperazin-1-yl]-ethyl}-amide

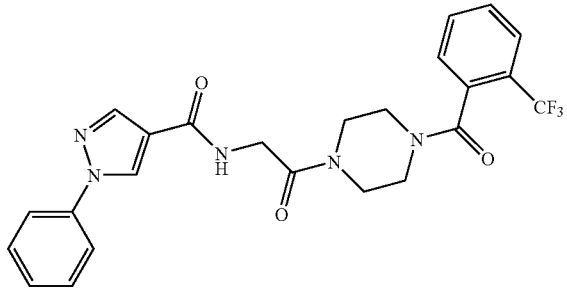

DIPEA (223 mg, 0.3 mL, 1.72 mmol) was added to a stirred solution of 1-phenyl-1H-pyrazole-4-carboxylic acid (65 mg, 0.34 mmol) in DMF (5 mL). HOBT (51 mg, 0.38 mmol) and EDCI (165 mg, 0.86 mmol) were then added at room temperature. After 2 minutes, 2-amino-1-[4-(2-trifluoromethyl-benzoyl)-piperazin-1-yl]-ethanone hydrochloride salt (133 mg, 0.38 mmol) was added and the resulting mixture was stirred at room temperature overnight. Cold water was then added and filtered the solid precipitated out to afford 41 mg (24.55% yield) of 1-phenyl-1H-pyrazole-4-carboxylic acid {2-oxo-2-[4-(2-trifluoromethyl-benzoyl)-piperazin-1-yl]-ethyl}-amide. LCMS Purity: 95.62%. $^1$H NMR (DMSO-d$_6$): δ 9.0 (s, 1H), 8.4 (s, 1H), 8.2 (s, 1H), 7.9-7.74 (m, 4H), 7.7 (t, 1H), 7.6 (t, 3H), 7.4 (t, 1H), 4.24 (d, 2H), 3.8 (s, 1H), 3.66 (s, 3H), δ 3.5 (s, 2H), 3.2 (d, 2H).

74) Synthesis of 1-Phenyl-1H-[1,2,3]triazole-4-carboxylic acid {2-[4-(5-fluoro-2-trifluoromethyl-benzoyl)-piperazin-1-yl]-2-oxo-ethyl}-amide

Step 1: Synthesis of 2-Diazo-3-oxo-propionic acid ethyl ester

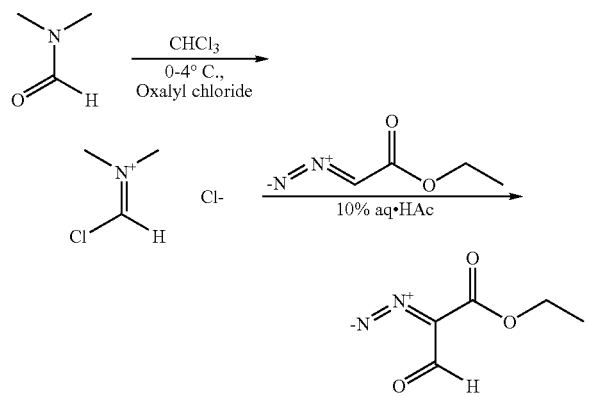

Oxalyl chloride (4.7 g, 3.1 mL, 37.0 mmol) was added to a cold (0-4° C.) solution of DMF (2.25 g, 2.4 mL, 30.8 mmol) in CHCl₃ (20 mL) and stirring was continued for 10 minutes. The reaction mixture was heated at 40° C. for 10 minutes and cooled to −10° C. Diazo-acetic acid ethyl ester (3.5 g, 3.5 mL, 30.6 mmol) was then added and stirred at room temperature for 1 hr. Reaction mixture was concentrated to get the residue. Ether was then added, filtered the solid precipitated and dissolved in 10% aq HAc (10 mL) and stirring was continued for 1 hr. The reaction mixture was extracted with ether, washed with saturated sodium bicarbonate solution and brine. The organic phase was dried over Na₂SO₄ and concentrated under reduced pressure to afford 590 mg (21% Yield) of 2-diazo-3-oxo-propionic acid ethyl ester. ¹H NMR (CDCl₃): δ 9.7 (s, 1H), 4.4 (q, 2H), 1.4 (t, 3H).

Step 2: Synthesis of 1-Phenyl-1H-[1,2,3]triazole-4-carboxylic acid ethyl ester

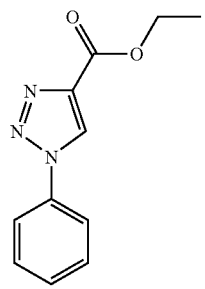

Aniline (143 mg, 1.5 mmol) was added to a solution of 2-diazo-3-oxo-propionic acid ethyl ester (200 mg, 1.4 mmol) and HAc (0.2 mL) in EtOH (0.5 mL) and stirring was at room temperature overnight. Reaction mixture was concentrated to get the residue. Cold water was then added, filtered the solid precipitated to afford 264 mg (87.41% Yield) of 1-phenyl-1H-[1,2,3]triazole-4-carboxylic acid ethyl ester. ¹H NMR (CDCl₃): δ 8.5 (s, 1H), 7.8 (d, 2H), 7.6-7.48 (m, 3H), 4.5 (q, 2H), 1.4 (t, 3H).

Step 3: Synthesis of 1-Phenyl-1H-[1,2,3]triazole-4-carboxylic acid

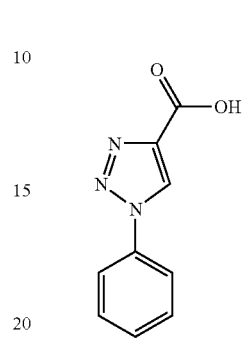

LiOH (80 mg, 1.9 mmol) was added to a stirred solution of 1-phenyl-1H-[1,2,3]triazole-4-carboxylic acid ethyl ester (130 mg, 0.6 mmol) in THF:H₂O (1:1, 4 mL), and the resulting mixture was stirred at room temperature for 45 min. The reaction mixture was concentrated under reduced pressure to get the residue. Cold water was then added and acidified it with 10% aqueous HCl, filtered the solid precipitated to afford 40 mg (35.4% yield) of 1-phenyl-1H-[1,2,3]triazole-4-carboxylic acid. ¹H NMR (DMSO-d₆): δ 13.4 (bs, 1H), 9.4 (s, 1H), 8.0 (d, 2H), 7.7 (t, 2H), 7.6 (t, 1H).

Step 4: Synthesis of 1-Phenyl-1H-[1,2,3]triazole-4-carboxylic acid {2-[4-(5-fluoro-2-trifluoromethyl-benzoyl)-piperazin-1-yl]-2-oxo-ethyl}-amide

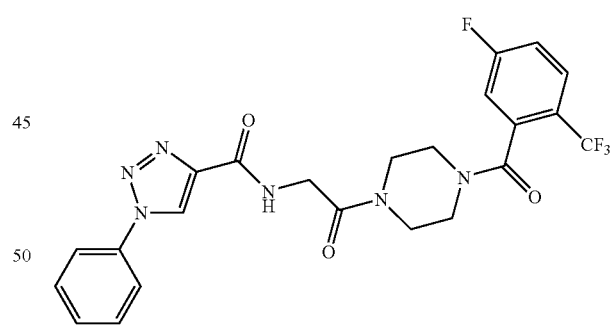

DIPEA (140 mg, 0.19 mL, 1.08 mmol) was added to a stirred solution of 1-phenyl-1H-[1,2,3]triazole-4-carboxylic acid (40 mg, 0.21 mmol) in DMF (5 mL). HOBT (32 mg, 0.23 mmol) and EDCI (102 mg, 0.53 mmol) were then added at room temperature. After 2 minutes, 2-amino-1-[4-(5-fluoro-2-trifluoromethyl-benzoyl)-piperazin-1-yl]-ethanone hydrochloride salt (90 mg, 0.24 mmol) was added and the resulting mixture was stirred at room temperature overnight. Cold water was then added and filtered the solid precipitated out to afford 88 mg (82.2% yield) of 1-phenyl-1H-[1,2,3]triazole-4-carboxylic acid {2-[4-(5-fluoro-2-trifluoromethyl-benzoyl)-piperazin-1-yl]-2-oxo-ethyl}-amide. LCMS Purity:

100%. ¹H NMR (DMSO-d6): δ 9.4 (s, 1H), 8.76 (t, 1H), 8.04 (m, 3H), 7.7-7.46 (m, 5H), 4.3 (d, 2H), 3.8-3.4 (m, 6H), 3.28 (d, 2H).

75) Synthesis of 1-Pyridin-2-yl-1H-[1,2,3]triazole-4-carboxylic acid {2-[4-(5-fluoro-2-trifluoromethyl-benzoyl)-piperazin-1-yl]-2-oxo-ethyl}-amide

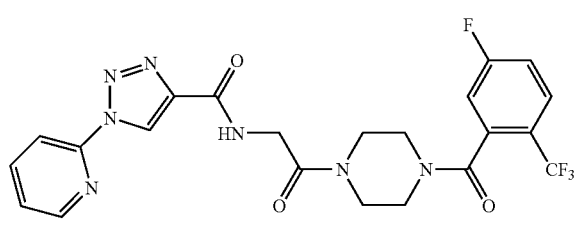

DIPEA (166 mg, 0.23 mL, 1.28 mmol) was added to a stirred solution of 1-Pyridin-2-yl-1H-[1,2,3]triazole-4-carboxylic acid (61 mg, 0.25 mmol)(prepared by the method as described above) in DMF (4 mL). HOBT (38 mg, 0.28 mmol) and EDCI (123 mg, 0.64 mmol) were then added at room temperature. After 2 minutes, 2-amino-1-[4-(5-fluoro-2-trifluoromethyl-benzoyl)-piperazin-1-yl]-ethanone hydrochloride salt (104 mg, 0.28 mmol) was added and the resulting mixture was stirred at room temperature overnight. Cold water was then added and filtered the solid precipitated out to afford 105 mg (80.7% yield) of 1-pyridin-2-yl-1H-[1,2,3]triazole-4-carboxylic acid {2-[4-(5-fluoro-2-trifluoromethyl-benzoyl)-piperazin-1-yl]-2-oxo-ethyl}-amide. LCMS Purity: 95.70%. ¹H NMR (DMSO-d6): δ 9.2 (s, 1H), 8.7 (m, 2H), 8.22 (d, 2H), 8.0 (t, 1H), 7.66-7.5 (m, 3H), 4.3-4.16 (dd, 2H), 3.84 (bs, 1H), 3.66-3.4 (m, 5H), 3.26 (d, 2H).

76) Synthesis of N-{2-[4-(5-Fluoro-2-trifluoromethyl-benzoyl)-piperazin-1-yl]-2-oxo-ethyl}-4-morpholin-4-yl-benzamide Step 1: Synthesis of 4-Morpholin-4-yl-benzoic acid methyl ester

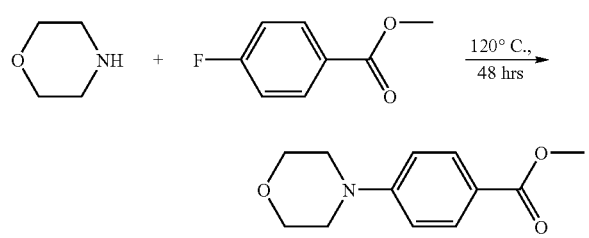

A mixture of morpholine (996 mg, 1 mL, 11.4 mmol) and 4-fluoro benzoic acid methyl ester (500 mg, 0.32 mmol) was stirred with heating at 120° C. for 48 hrs. Cold water then added, filtered the solid precipitated to afford 166 mg (23.15% yield) of 4-morpholin-4-yl-benzoic acid methyl ester. ¹H NMR (CDCl₃): δ 8.0 (d, 2H), 6.9 (d, 2H), 3.9 (m, 7H), 3.3 (t, 4H).

Step 2: Synthesis of 4-Morpholin-4-yl-benzoic acid

LiOH (92 mg, 0.22 mmol) was added to a stirred solution of 4-morpholin-4-yl-benzoic acid methyl ester (162 mg, 0.73 mmol) in THF:H₂O (1:1, 4 mL), and the resulting mixture was stirred at room temperature for 20 hrs. The reaction mixture was concentrated under reduced pressure to get the residue. Cold water was then added and acidified it with 10% aqueous HCl, filtered the solid precipitated to afford 130 mg (86% yield) of 4-morpholin-4-yl-benzoic acid. ¹H NMR (DMSO-d₆): δ 12.4 (s, 1H), 7.8 (d, 2H), 7.0 (d, 2H), 3.76 (t, 4H), 3.28 (t, 4H).

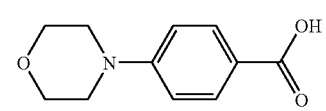

Step 3: Synthesis of N-{2-[4-(5-Fluoro-2-trifluoromethyl-benzoyl)-piperazin-1-yl]-2-oxo-ethyl}-4-morpholin-4-yl-benzamide

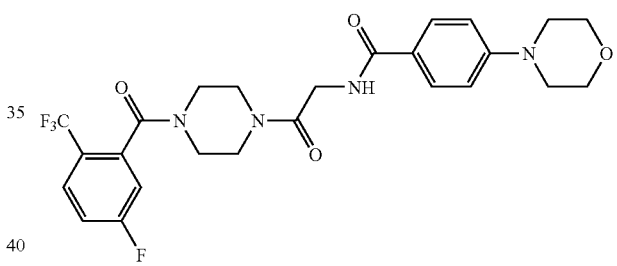

DIPEA (220 mg, 0.3 mL, 0.94 mmol) was added to a stirred solution of 4-morpholin-4-yl-benzoic acid (70 mg, 0.33 mmol) in DMF (5 mL). HOBT (50 mg, 0.37 mmol) and EDCI (142 mg, 0.74 mmol) were then added at room temperature. After 2 minutes, 2-amino-1-[4-(5-fluoro-2-trifluoromethyl-benzoyl)-piperazin-1-yl]-ethanone hydrochloride salt (137 mg, 0.37 mmol) was added and the resulting mixture was stirred at room temperature overnight. Cold water was then added and the product was extracted with EtOAc and the organic layer was washed with brine. The organic phase was dried over Na₂SO₄ and concentrated under reduced pressure to get the residue. The obtained residue was purified by column chromatography (using 60-120 silica gel and 20%-70% EtOAc in hexane as eluent) to afford 107 mg (60.8% yield) of N-{2-[4-(5-fluoro-2-trifluoromethyl-benzoyl)-piperazin-1-yl]-2-oxo-ethyl}-4-morpholin-4-yl-benzamide, LCMS Purity: 71.5%. ¹H NMR (DMSO-d₆): δ 8.4 (s, 1H), 8.0 (s, 1H), 7.82 (d, 2H), 7.64 (m, 2H), 7.04 (d, 2H), 4.2 (d, 2H), 3.8-3.46 (m, 10H), 3.3 (m, 6H).

77) Synthesis of N-{2-[4-(5-Fluoro-2-trifluorom-ethyl-benzoyl)-piperazin-1-yl]-2-oxo-ethyl}-4-(4-methyl-piperazin-1-yl)-benzamide Step 1: Synthesis of 4-(4-Methyl-piperazin-1-yl)-benzoic acid methyl ester

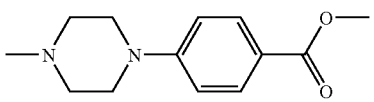

A mixture of 1-methyl-piperazine (1.3 g, 1.2 mmol) and 4-fluoro benzoic acid methyl ester (500 mg, 0.32 mmol) was stirred with heating at 120° C. for 20 hrs. Cold water then added, filtered the solid precipitated to afford 124 mg (16.4% yield) of 4-(4-methyl-piperazin-1-yl)-benzoic acid methyl ester. $^1$H NMR (CDCl$_3$): δ 8.0 (d, 2H), 6.9 (d, 2H), 3.9 (s, 3H), 3.4 (t, 4H), 2.6 (t, 4H), 2.4 (s, 3H).

Step 2: Synthesis of 4-(4-Methyl-piperazin-1-yl)-benzoic acid

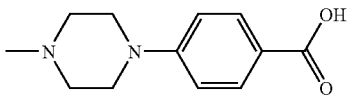

LiOH (67 mg, 1.6 mmol) was added to a stirred solution 4-(4-methyl-piperazin-1-yl)-benzoic acid methyl ester (124 mg, 0.73 mmol) in THF:H$_2$O (1:1, 4 mL), and the resulting mixture was stirred at room temperature overnight. The reaction mixture was concentrated under reduced pressure to get the residue. Cold water was then added and acidified it with 10% aqueous HCl and concentrated under reduced pressure to afford 116 mg (85.13% yield) of 4-(4-methyl-piperazin-1-yl)-benzoic acid. $^1$H NMR (DMSO-D$_2$O): δ 7.8 (d, 2H), 7.0 (d, 2H), 3.4 (s, 4H), 2.8 (s, 4H), 2.4 (s, 3H).

Step 3: Synthesis of N-{2-[4-(5-Fluoro-2-trifluorom-ethyl-benzoyl)-piperazin-1-yl]-2-oxo-ethyl}-4-(4-methyl-piperazin-1-yl)-benzamide

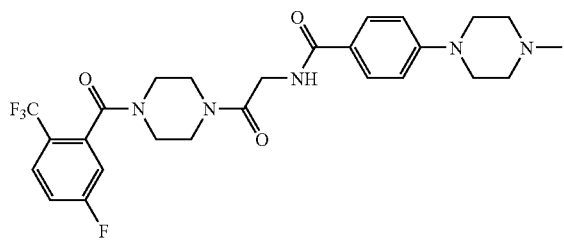

DIPEA (350 mg, 0.5 mL, 2.7 mmol) was added to a stirred solution of 4-(4-methyl-piperazin-1-yl)-benzoic acid hydrochloride salt (116 mg, 0.45 mmol) in DMF (5 mL). HOBT (67 mg, 0.5 mmol) and EDCI (216 mg, 1.12 mmol) were then added at room temperature. After 2 minutes, 2-amino-1-[4-(5-fluoro-2-trifluoromethyl-benzoyl)-piperazin-1-yl]-ethanone hydrochloride salt (184 mg, 0.5 mmol) was added and the resulting mixture was stirred at room temperature overnight. Cold water was then added and filtered the solid residue. The obtained residue was purified by preparative HPLC to afford 100 mg (41.3% yield) N-{2-[4-(5-fluoro-2-trifluoromethyl-benzoyl)-piperazin-1-yl]-2-oxo-ethyl}-4-(4-methyl-piperazin-1-yl)-benzamide. LCMS Purity: 88.3%. $^1$H NMR (DMSO-d$_6$): δ 10.4 (s, 1H), 8.4 (s, 1H), 8.0 (t, 1H), 7.86 (d, 2H), 7.64 (m, 2H), 7.1 (d, 2H), 4.2-3.96 (m, 4H), 3.66-3.4 (m, 8H), 3.24-3.0 (m, 6H), 2.9 (s, 3H).

78) Synthesis of N-Cyclopentyl-N'-{2-oxo-2-[4-(2-trifluoromethyl-benzoyl)-piperazin-1-yl]-ethyl}-terephthalamide

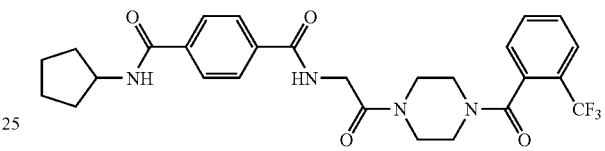

DIPEA (83.75 mg, 0.1 mL, 0.64 mmol) was added to a stirred solution of N-{2-oxo-2-[4-(2-trifluoromethyl-benzoyl)-piperazin-1-yl]-ethyl}-terephthalamic acid (100 mg, 0.21 mmol) in DMF (1 mL). HOBT (29.26 mg, 0.21 mmol) and EDCI (41.4 mg, 0.21 mmol) were then added at room temperature. After 2 minutes, cyclopentylamine (18.39 mg, 0.21 mmol) was added and the resulting mixture was stirred at room temperature overnight. Cold water was then added and the product was extracted with EtOAc and the organic layer was washed with 5% sodium bicarbonate solution followed by brine. The organic phase was dried over Na$_2$SO$_4$ and concentrated under reduced pressure to get the residue. The obtained residue was recrystallized from a mixture of EtOAc and ether to afford 38 mg (33% yield) of N-cyclopentyl-N'-{2-oxo-2-[4-(2-trifluoromethyl-benzoyl)-piperazin-1-yl]-ethyl}-terephthalamide. LCMS Purity: 91.36%. $^1$H NMR (CDO$_3$): δ 7.8-7.7 (m, 7H), 7.7-7.5 (m, 2H), 7.4-7.2 (m, 2H), 6.1 (d, 1H), 4.5-4.4 (q, 1H), 4.4-4.2 (m, 2H), 4.1-3.8 (m, 2H), 3.8-3.4 (m, 5H), 3.2 (m, 2H), 2.1 (m, 2H), 1.7 (m, 3H), 1.5 (m, 2H).

79) Synthesis of 4-Ethynyl-N-{2-[4-(5-fluoro-2-trifluoromethyl-benzoyl)-piperazin-1-yl]-2-oxo-ethyl}-benzamide Step 1: Synthesis of 4-Methyl-benzenesulfonyl azide

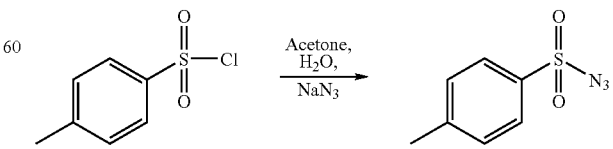

Sodium azide (2.7 g, 42 mmol) was added to a cold (0-4° C.) stirred solution of (4-methyl-benzenesulfonyl chloride (8 g, 42 mmol) in acetone:water (1:1, 240 mL) and continued stirring at 0° C. for 2 hr. Concentrated the reaction mixture to get the residue. The residue was extracted with diethyl ether and the organic phase was dried Na$_2$SO$_4$ and concentrated under reduced pressure to afford 7.3 g (88.2% yield) of 4-methyl-benzenesulfonyl azide.

Step 2: Synthesis of (1-diazo-2-oxo-propyl)-phosphonic acid dimethyl

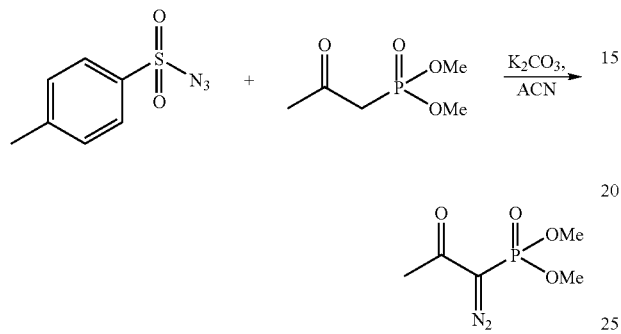

Potassium carbonate (1.3 g, 9.85 mmol) was added to a stirred solution of 4-methyl-benzenesulfonyl azide (1.95 g, 9.85 mmol) and (2-Oxo-propyl)-phosphonic acid dimethyl ester (1.32 g, 8.25 mmol) in acetonitrile (10 mL) and continued stirring at room temperature overnight. The reaction mixture was concentrated to get the residue. The residue obtained was diluted with DCM and organic phase was washed with 5% sodium bicarbonate and brine. The organic phase was dried over Na$_2$SO$_4$ and concentrated under reduced pressure to get the residue. The residue obtained was purified by column chromatography (using silica gel of 60-120 mesh and 70% EtOAc in Hexane as eluent) to afford 1.73 g (91.5% yield) (1-diazo-2-oxo-propyl)-phosphonic acid dimethyl).

Step 3: Synthesis of 4-Ethynyl-benzoic acid methyl ester

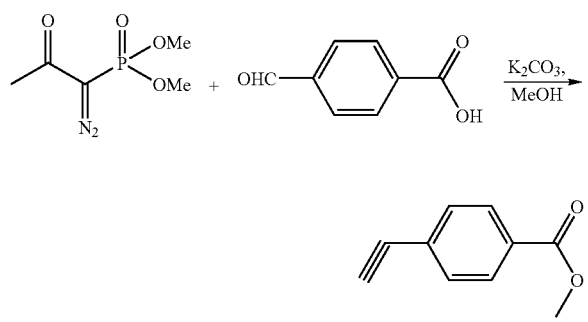

Potassium carbonate (316 mg, 2.28 mmol) was added to a stirred solution of (1-diazo-2-oxo-propyl)-phosphonic acid dimethyl (400 mg, 2.08 mmol) and 4-formyl-benzoic acid (341 mg, 2.08 mmol) in MeOH (20 mL) and continued stirring at room temperature overnight. The reaction mixture was filtered and concentrated to get the residue. The residue obtained was diluted with DCM and organic phase was washed with 5% sodium bicarbonate and brine. The organic phase was dried over Na$_2$SO$_4$ and concentrated under reduced pressure to afford 310 mg (79.4% yield) 4-ethynyl-benzoic acid methyl ester.

Step 4: Synthesis of 4-Ethynyl-benzoic Acid

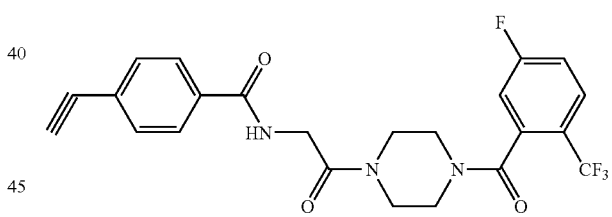

LiOH (95.97 mg, 2.2 mmol) was added to a stirred solution of 4-ethynyl-benzoic acid methyl ester (305 mg, 1.9 mmol) in MeOH:H$_2$O (1:1, 6 mL), and the resulting mixture was stirred at room temperature for 30 min. The reaction mixture was concentrated under reduced pressure to get the residue. Cold water was then added, acidified it with conc.HCl and extracted with EtOAc. The organic layer was washed with brine, dried over Na$_2$SO$_4$ and concentrated under reduced pressure to afford 226 mg (81.9% yield) of 4-ethynyl-benzoic acid.

Step 5: Synthesis of 4-Ethynyl-N-{2-[4-(5-fluoro-2-trifluoromethyl-benzoyl)-piperazin-1-yl]-2-oxo-ethyl}-benzamide

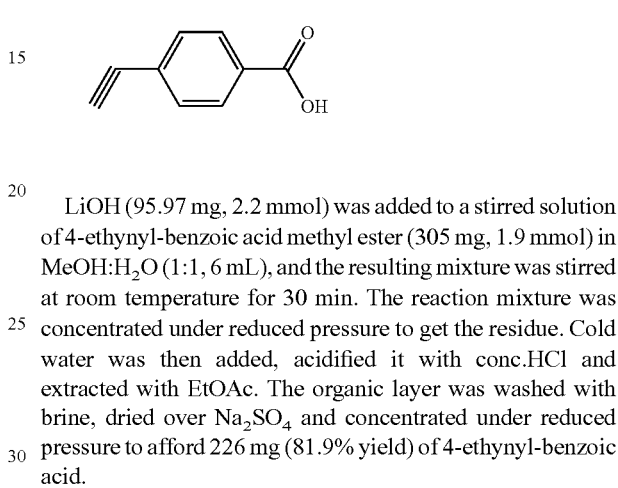

DIPEA (263.67 mg, 0.34 mL, 2.04 mmol) was added to a stirred solution of 4-Ethynyl-benzoic acid (100 mg, 0.68 mmol) in DMF (1.5 mL). HOBT (92 mg, 0.68 mmol) and EDCI (156.42 mg, 0.81 mmol) were then added at room temperature. After 2 minutes, 2-amino-1-[4-(5-fluoro-2-trifluoromethyl-benzoyl)-piperazin-1-yl]-ethanone (253 mg, 0.68 mmol) was added and the resulting mixture was stirred at room temperature overnight. Cold water was then added and the product was extracted with EtOAc and the organic layer was washed with 5% sodium bicarbonate solution followed by brine. The organic phase was dried over Na$_2$SO$_4$ and concentrated under reduced pressure to get the residue. The obtained residue was recrystallized from a mixture of EtOAc and ether to afford 130 mg (41.1% yield) of 4-Ethynyl-N-{2-[4-(5-fluoro-2-trifluoromethyl-benzoyl)-piperazin-1-yl]-2-oxo-ethyl}-benzamide. LCMS Purity: 87.29%. $^1$H NMR (DMSO-d$_6$): δ 8.7 (m, 1H), 8.0-7.8 (m, 3H), 7.6-7.4 (m, 4H), 4.4 (s, 1H), 4.2-4.1 (m, 2H), 3.8-3.4 (m, 3H), 3.2-3.0 (m, 2H).

80) Synthesis of 5-(2-Oxo-2,3-dihydro-benzooxazol-6-yl)-1H-pyrazole-3-carboxylic acid {2-[4-(5-fluoro-2-trifluoromethyl-benzoyl)-piperazin-1-yl]-2-oxo-ethyl}-amide

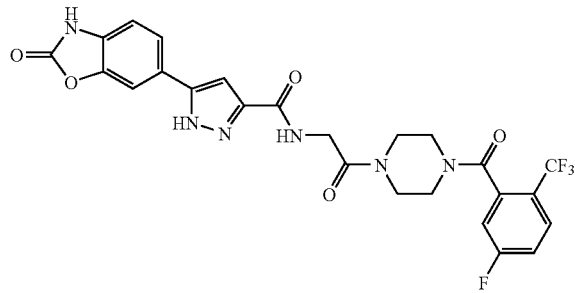

DIPEA (120 mg, 0.16 mL, 0.927 mmol) was added to a stirred solution of 5-(2-oxo-2,3-dihydro-benzooxazol-6-yl)-1H-pyrazole-3-carboxylic acid (65 mg, 0.26 mmol) in DMF (2.5 mL). HOBT (37.6 mg, 0.27 mmol) and EDCI (53.4 mg, 0.2783 mmol) were then added at room temperature. After 2 minutes, 2-amino-1-[4-(5-fluoro-2-trifluoromethyl-benzoyl)-piperazin-1-yl]-ethanone hydrochloride salt (98 mg, 0.265 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue recrystallized from EtOAc to afford 31 mg (21% yield) of 5-(2-Oxo-2,3-dihydro-benzooxazol-6-yl)-1H-pyrazole-3-carboxylic acid {2-[4-(5-fluoro-2-trifluoromethyl-benzoyl)-piperazin-1-yl]-2-oxo-ethyl}-amide. LCMS Purity: 80.27%. $^1$H NMR (DMSO-$d_6$): δ 13.7 (s, 1H), 11.8 (s, 1H), 8.0 (m, 1H), 7.9 (m, 1H), 7.7 (m, 1H), 7.5 (m, 3H), 7.06 (m, 2H), 4.1 (m, 2H), 3.4 (m, 6H), 3.1 (m, 2H).

81) Synthesis of 5-Phenyl-pyridine-2-carboxylic acid {2-[4-(5-fluoro-2-trifluoromethyl-benzoyl)-piperazin-1-yl]-2-oxo-ethyl}-amide

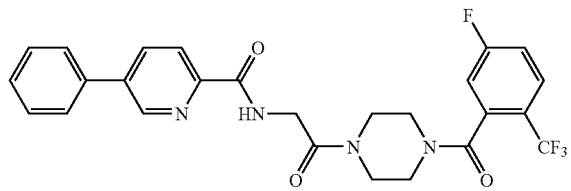

DIPEA (151 mg, 0.2 mL, 1.17 mmol) was added to a stirred solution of [(5-phenyl-pyridine-2-carbonyl)-amino]-acetic acid (100 mg, 0.39 mmol) in DMF (2 mL). HOBT (63 mg, 0.46 mmol) and EDCI (89 mg, 0.46 mmol) were then added at room temperature. After 2 minutes, (5-fluoro-2-trifluoromethyl-phenyl)-piperazin-1-yl-methanone hydrochloride salt (146 mg, 0.46 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to afford 78 mg (39% yield) of 5-phenyl-pyridine-2-carboxylic acid {2-[4-(5-fluoro-2-trifluoromethyl-benzoyl)-piperazin-1-yl]-2-oxo-ethyl}-amide. LCMS Purity: 95.81%. $^1$H NMR (DMSO-$d_6$): δ 9 (s, 1H), 8.8 (bt, 1H), 8.3 (d, 1H), 8.1 (m, 1H), 7.9 (m, 1H), 7.8 (d, 1H), 7.6-7.4 (m, 5H), 4.4-4.2 (dd, 2H), 3.8-3.4 (m, 6H), 3.3-3.1 (m, 2H).

82) Synthesis of 1H-Indole-2-carboxylic acid {2-oxo-2-[4-(2-trifluoromethyl-benzoyl)-piperazin-1-yl]-ethyl}-amide

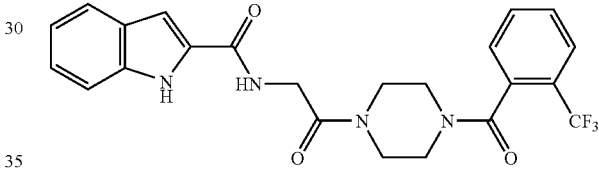

DIPEA (193 mg, 0.25 mL, 1.11 mmol) was added to a stirred solution of 1H-Indole-2-carboxylic acid (60 mg, 0.37 mmol) in DMF (2 mL). HOBT (60 mg, 0.44 mmol) and EDCI (85 mg, 0.44 mmol) were then added at room temperature. After 2 minutes, 2-amino-1-[4-(2-trifluoromethyl-benzoyl)-piperazin-1-yl]-ethanone hydrochloride salt (157 mg, 0.44 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to afford 112 mg (65.88% yield) of 1H-indole-2-carboxylic acid {2-oxo-2-[4-(2-trifluoromethyl-benzoyl)-piperazin-1-yl]-ethyl}-amide. LCMS Purity: 94.15%. $^1$H NMR (DMSO-$d_6$): δ 11.6 (s, 1H), 8.6 (s, 1H), 7.9-7.4 (m, 6H), 7.2 (m, 2H), 7.1-7.0 (m, 1H), 4.3-4.1 (m, 2H), 3.8-3.4 (m, 6H), 3.2-3.0 (m, 2H).

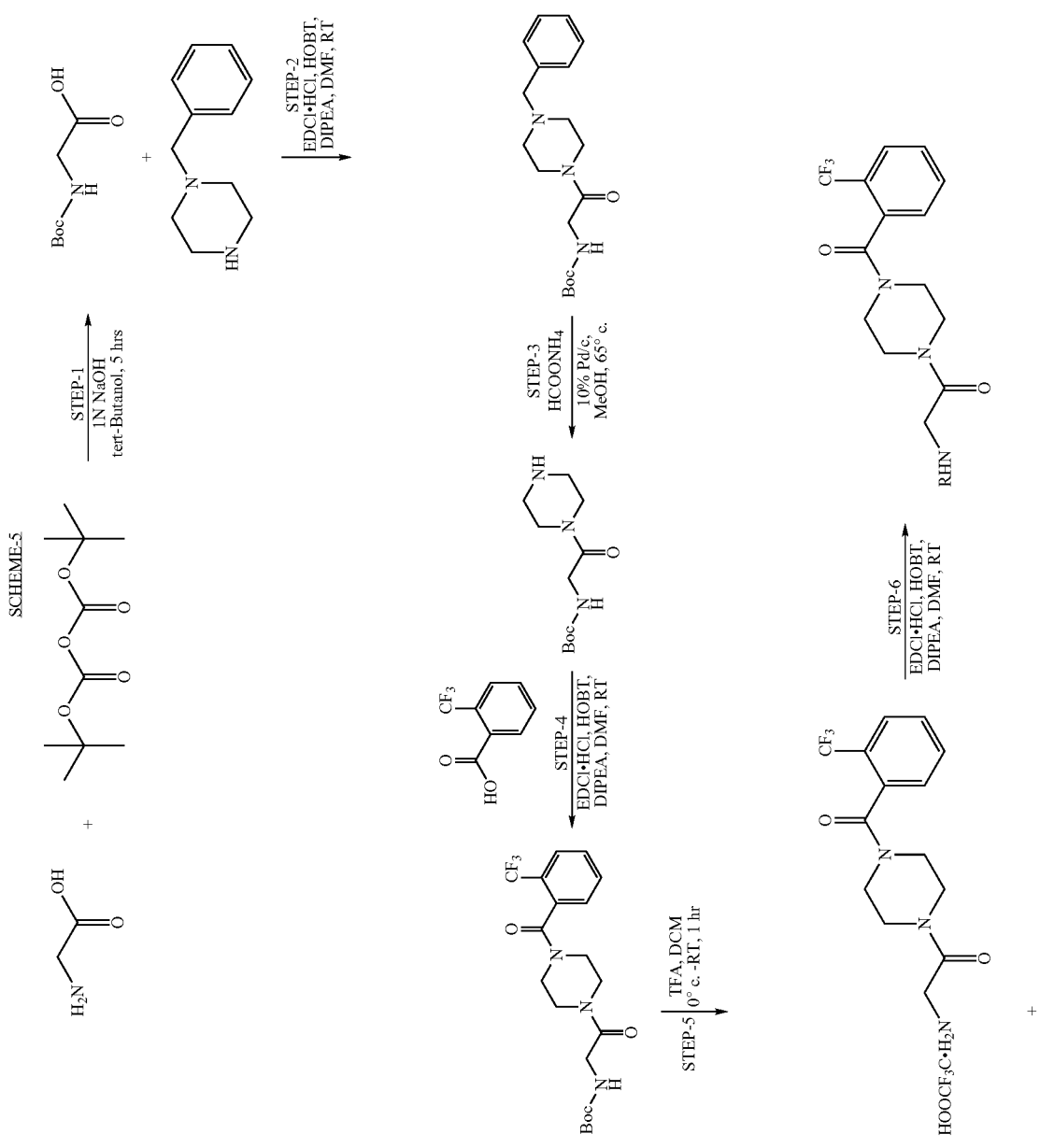

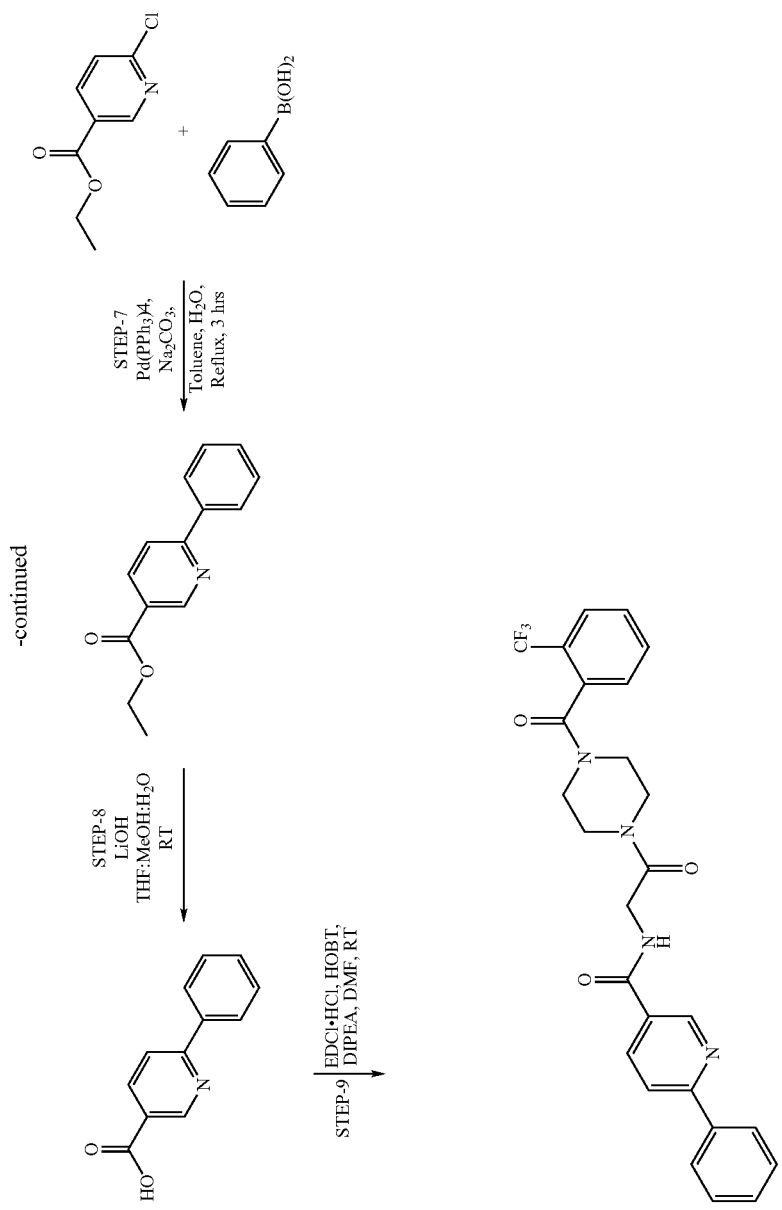

Step 1: Synthesis of tert-Butoxycarbonylamino-acetic acid

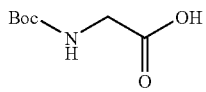

1N NaOH (660 mL, 27 g, 666.25 mmol) was added to a stirred solution of glycine (20 g, 266.5 mmol) in tert-butanol (180 mL). BOC-anhydride (67.34 ml, 293.14 mmole) was then added and the resulting mixture was stirred at room temperature for 5 hrs. The reaction mixture was acidified with dilute HCl and the resulting solid was filtered to afford 38 g (81.5% yield) of tert-butoxycarbonylamino-acetic acid. $^1$H NMR: (DMSO-$d_6$) δ 12.4 (s, 1H), 7.0 (t, 1H), 3.6 (d, 2H), 1.3 (s, 9H).

Step 2: Synthesis of [2-(4-Benzyl-piperazin-1-yl)-2-oxo-ethyl]-carbamic acid tert-butyl ester

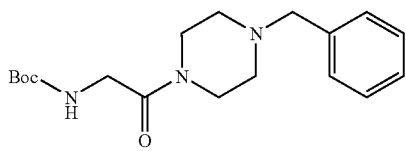

DIPEA (22.14 g, 171.3 mmol) was added to a stirred solution of tert-butoxycarbonylamino-acetic acid (10 g, 57.1 mmol) in DMF (40 mL). HOBT (9.25 g, 68.5 mmol) and EDCI.HCl (12.61 g, 68.5 mmol) were then added at room temperature. After 2 minutes N-benzylpiperazine (12.1 g, 68.5 mmol) was added, and the resulting mixture was stirred at room temperature overnight. Cold water was then added and the product was extracted with EtOAc and washed with brine. The organic phase was dried over $Na_2SO_4$ and concentrated under reduced pressure to afford 13.4 g (70.5% yield) of [2-(4-benzyl-piperazin-1-yl)-2-oxo-ethyl]-carbamic acid tert-butyl ester as white powder. $^1$H NMR (CDCl$_3$): δ 7.3 (m, 5H), 5.5 (bs, 1H), 4.0 (d, 2H), 3.7-3.6 (t, 2H), 2.5 (s, 2H), 3.4 (t, 2H), 2.4 (s, 4H), 1.3 (s, 9H).

Step 3: Synthesis of (2-oxo-2-piperazin-1-ethyl)-carbamic acid tert-butyl ester

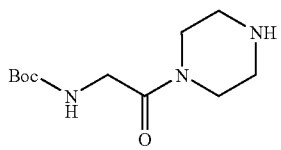

Ammonium formate (9.45 g, 149.9 mmol) was added to a stirred solution of [2-(4-benzyl-piperazin-1-yl)-2-oxo-ethyl]-carbamic acid tert-butyl ester (5.0 g, 14.99 mmol) in MeOH (50 mL). 10% Pd/c (1 g) was then added and the resulting mixture stirred at room temperature under an inert atmosphere. The reaction mixture was then stirred at reflux temperature for 3 hrs. The mixture was filtered over a bed of celite. The celite was washed with MeOH and the filtrate was concentrated. The residue was dissolved in EtOAc, washed with 5% aqueous NaOH solution, followed by saturated brine solution. The organic layer was dried over sodium sulphate and concentrated in vacuo to afford 3.1 g (86% yield) of (2-oxo-2-piperazin-1-ethyl)-carbamic acid tert-butyl ester.

Step 4: Synthesis of {2-Oxo-2-[4-(2-trifluoromethyl-benzoyl)-piperazin-1-yl]-ethyl}-carbamic acid tert-butyl ester

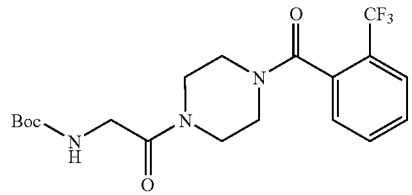

DIPEA (4.1 g, 31.55 mmol) was added to a stirred solution of (2-oxo-2-piperazin-1-ethyl)-carbamic acid tert-butyl ester (3.07 g, 12.62 mmol) in DMF (20 mL). HOBT (1.70 g, 12.62 mmol) and EDCI (2.42 g, 12.62 mmol) were then added at room temperature. After 2 minutes, 2-trifluoromethylbenzoic acid (2 g, 10.52 mmol) was added and the mixture stirred for a further 4 hrs. The reaction mixture was diluted with cold water and the product extracted with ethyl acetate. The organic layer was washed with saturated brine solution, dried over sodium sulphate and concentrated to afford 3.0 g (68.6% yield) of {2-Oxo-2-[4-(2-trifluoromethyl-benzoyl)-piperazin-1-yl]-ethyl}-carbamic acid tert-butyl ester product.

Step 5: Synthesis of 2-Amino-1-[4-(2-trifluoromethyl-benzoyl)-piperazin-1-yl]-ethanone TFA salt

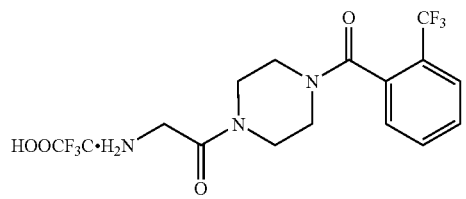

TFA (6 mL) was added to a chilled (0° C.) solution of {2-Oxo-2-[4-(2-trifluoromethyl-benzoyl)-piperazin-1-yl]-ethyl}-carbamic acid tert-butyl ester (3.0 g, 7.7 mmol) in DCM (30 mL) and stirring was maintained at this temperature for 2 hrs. The solvent was removed under reduced pressure and the resulting residue was washed with ether to afford 2.8 g (84.8% yield) of 2-amino-1-[4-(2-trifluoromethyl-benzoyl)-piperazin-1-yl]-ethanone TFA salt.

83) Synthesis of Biphenyl-4-sulfonicacid {2-oxo-2-[4-(2-trifluoromethyl-benzoyl)-piperazin-1-yl]-ethyl}-amide

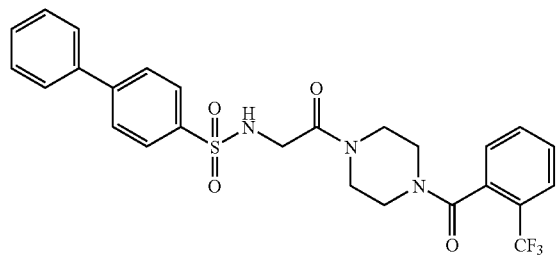

Et$_3$N (42 mg, 0.42 mmol) was added to a stirred solution of 2-amino-1[4-(2-trifluoromethyl-benzoyl)-piperazin-1-yl]- ethanone (80 mg, 0.19 mmol) in DCM (4 mL) at 0-5° C. 4-biphenylsulfonyl chloride (47 mg, 0.19 mmol) was then added and the mixture was stirred at 0-5° C. for 4 hrs. The reaction was then diluted with cold water and the product was extracted with DCM, washed with 5% NaHCO$_3$, 5% HCl, then saturated brine solution. The DCM layer was dried over sodium sulphate and concentrated. The residue was purified by column chromatography (using silica gel of 60-120 mesh and 60% EtOAc in hexane as eluent) to afford 33 mg (33.4% yield) of biphenyl-4-sulfonicacid {2-oxo-2-[4-(2-trifluoromethyl-benzoyl)-piperazin-1-yl]-ethyl}-amide. LC-MS purity: 90.35%. $^1$H-NMR (CDCl$_3$) δ 7.9 (m, 2H), 7.7 (d, 3H,), 7.6-7.5 (m 4H), 7.5-7.4 (m, 3H), 7.3 (m, 1H), 5.6 (s, 1H), 4.0-3.7 (m, 5H), 3.7-3.5 (m, 3H), 3.4-3.3 (m, 2H), 3.25-3.1 (m, 3H).

84) Synthesis of 5-(3-Trifluoromethyl-phenyl)-furan-2-carboxylic acid {2-oxo-2-[4-(2-trifluoromethyl-benzoyl)-piperazin-1-yl]-ethyl}-amide

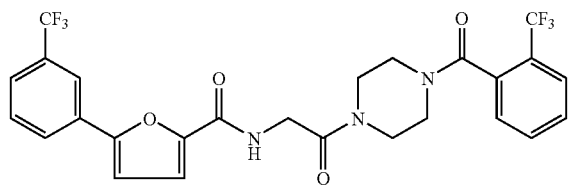

DIPEA (75 mg, 0.1 mL, 0.59 mmol) was added to a stirred solution of 2-amino-1-[4-(2-trifluoromethyl-benzoyl)-piperazin-1-yl]-ethanone TFA salt (100 mg, 0.23 mmol) in DMF (1 mL). HOBT (32 mg, 0.23 mmol) and EDCI (44 mg, 0.23 mmol) were then added at room temperature. After 2 minutes, 5-(3-trifluoromethyl-phenyl)-furan-2-carboxylic acid (50 mg, 0.20 mmol) was added and the resulting mixture was stirred at room temperature for 4 hrs. Cold water was then added and the product was extracted with EtOAc and the organic layer was washed with brine. The organic phase was dried over Na$_2$SO$_4$ and concentrated under reduced pressure to afford 40 mg (37% yield) of 5-(3-trifluoromethyl-phenyl)-furan-2-carboxylic acid {2-oxo-2-[4-(2-trifluoromethyl-benzoyl)-piperazin-1-yl]-ethyl}-amide. LCMS Purity: 86.88%. $^1$H NMR (DMSO-d$_6$): δ 8.8-8.7 (t, 1H), 8.3 (s, 1H), 8.2 (t, 1H), 7.9-7.6 (m, 5H), 7.6-7.5 (t, 1H), 7.4-7.3 (d, 1H), 7.3-7.2 (m, 1H), 4.3-4.1 (m, 2H), 3.8-3.4 (m, 6H), 3.2-3.1 (m, 2H).

85) Synthesis of N-{2-Oxo-2-[4-(2-trifluoromethyl-benzoyl)-piperazin-1-yl]-ethyl}-3-phenoxy-benzamide

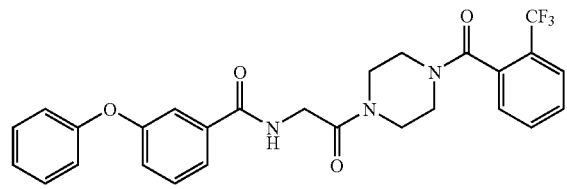

DIPEA (73 mg, 0.097 mL, 0.56 mmol) was added to a stirred solution of 2-amino-1-[4-(2-trifluoromethyl-benzoyl)-piperazin-1-yl]-ethanone TFA salt (96 mg, 0.22 mmol) in DMF (1 mL). HOBT (30 mg, 0.22 mmol) and EDCI.HCl (43 mg, 0.22 mmol) were then added at room temperature. After 2 minutes, 3-phenoxybenzoic acid (40 mg, 0.19 mmol) was added and the resulting mixture was stirred at room temperature for 4 hrs. Cold water was then added and the product was extracted with EtOAc and the organic layer was washed with brine. The organic phase was dried over Na$_2$SO$_4$ and concentrated under reduced pressure to afford 70 mg (72.5% yield) of N-{2-Oxo-2-[4-(2-trifluoromethyl-benzoyl)-piperazin-1-yl]-ethyl}-3-phenoxy-benzamide. LCMS Purity: 89.64%. $^1$H NMR (DMSO-d$_6$): δ 8.7-8.6 (t, 1H), 7.9-7.4 (m, 8H), 7.2 (m, 1H), 7.1-7.0 (d, 1H), 4.2-4.0 (m, 2H), 3.8-3.4 (m, 6H), 3.3-3.2 (m, 2H).

86) Synthesis of 4-Benzoyl-N-{2-oxo-2-[4-(2-trifluoromethyl-benzoyl)-piperazin-1-yl]-ethyl}-benzamide

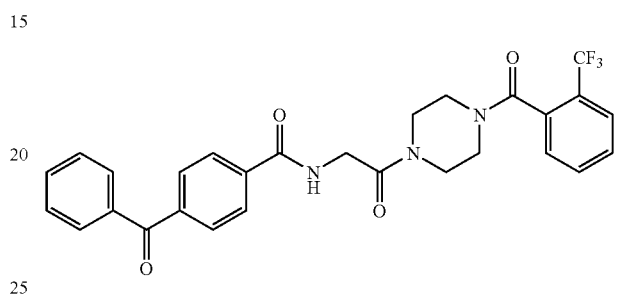

DIPEA (77 mg, 0.103 mL, 0.60 mmol) was added to a stirred solution of 2-amino-1-[4-(2-trifluoromethyl-benzoyl)-piperazin-1-yl]-ethanone TFA salt (102 mg, 0.29 mmol) in DMF (1 mL). HOBT (32 mg, 0.29 mmol) and EDCI.HCl (46 mg, 0.29 mmol) were then added at room temperature. After 2 minutes, 4-benzoylbenzoic acid (45 mg, 0.20 mmol) was added and the resulting mixture was stirred at room temperature for 4 hrs. Cold water was then added and the product was extracted with EtOAc and the organic layer was washed with brine. The organic phase was dried over Na$_2$SO$_4$ and concentrated under reduced pressure to afford 54 mg (51.9% yield) of 4-benzoyl-N-{2-oxo-2-[4-(2-trifluoromethyl-benzoyl)-piperazin-1-yl]-ethyl}-benzamide. LCMS Purity %: 91.57, HPLC Purity: 95.52%, $^1$H NMR (DMSO-d$_6$): δ 8.8 (t, 1H), 8.1-8.0 (d, 2H), 7.9-7.64 (m, 7H), 7.6 (t, 3H), 4.3-4.1 (m, 2H), 3.8-3.5 (m, 4H), 3.5-3.4 (m, 2H), 3.2-3.1 (m, 2H).

87) Synthesis of 4-Fluoro-N-{2-oxo-2-[4-(2-trifluoromethyl-benzoyl)-piperazin-1-yl]-ethyl}-benzamide

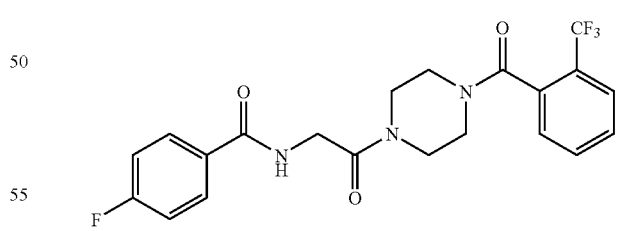

DIPEA (46.5 mg, 0.36 mmol) was added to a stirred solution of 2-amino-1-[4-(2-trifluoromethyl-benzoyl)-piperazin-1-yl]-ethanone TFA salt. (62 mg, 0.14 mmol) in DMF (1 mL). HOBT (19 mg, 0.14 mmol) and EDCI.HCl (28 mg, 0.14 mmol) were then added at room temperature. After 2 minutes, 4-fluorobenzoic acid (17 mg, 0.12 mmol) was added and the resulting mixture was stirred at room temperature for 4 hrs. Cold water (20 mL) was then added and the product was extracted with EtOAc and the organic layer was washed with brine. The organic phase was dried over Na$_2$SO$_4$ and concentrated under reduced pressure to afford 34 mg of 4-fluoro-N-{2-oxo-2-[4-(2-trifluoromethyl-benzoyl)-piperazin-1-yl]-ethyl}-benzamide LCMS Purity: 92.29%, HPLC Purity: 93.53%. NMR Values: $^1$H NMR (DMSO-d$_6$): δ 7.9-7.8 (2H, m), 7.8-7.7 (d, 1H), 7.6 (m, 2H), 7.4-7.3 (d, 1H), 7.3 (t, 2H), 4.3 (dd, 1H), 4.2 (dd, 2H), 4.0 (m, 2H), 3.8-3.6 (m, 2H), 3.6-3.5 (m, 2H), 3.4 (t, 1H), 3.3-3.2 (m, 2H).

88) Synthesis of 4-Nitro-N-{2-oxo-2-[4-(2-trifluoromethyl-benzoyl)-piperazin-1-yl]-ethyl}-benzamide

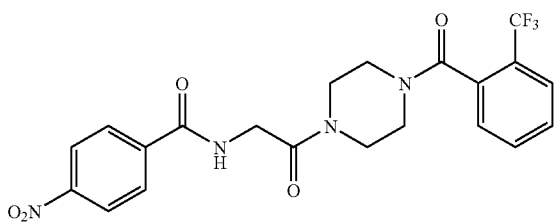

DIPEA (47 mg, 0.36 mmol) was added to a stirred solution of 2-amino-1-[4-(2-trifluoromethyl-benzoyl)-piperazin-1-yl]-ethanone TFA salt (62 mg, 0.14 mmol) in DMF (1 mL). HOBT (19 mg, 0.14 mmol) and EDCI.HCl (28 mg, 0.14 mmol) were then added at room temperature. After 2 minutes, 4-nitrobenzoic acid (20 mg, 0.12 mmol) was added and the resulting mixture was stirred at room temperature for 4 hrs. Cold water (20 mL) was then added and the product was extracted with EtOAc and the organic layer was washed with brine. The organic phase was dried over Na$_2$SO$_4$ and concentrated under reduced pressure to afford 40.7 mg (74% yield) of 4-nitro-N-{2-oxo-2-[4-(2-trifluoromethyl-benzoyl)-piperazin-1-yl]-ethyl}-benzamide. LCMS Purity: 88.6%, $^1$H NMR (CDCl$_3$): δ 8.3 (d, 2H), 8.0 (m, 2H), 7.8-7.7 (d, 1H), 7.6 (m, 2H), 7.4-7.3 (d, 2H), 4.4-4.3 (dd, 1H), 4.3-4.2 (dd, 2H), 4.1-3.9 (2m, H), 3.8-3.6 (dd, 2H), 3.6-3.5 (m, 2H), 3.4 (t, 1H), 3.3-3.2 (m, 2H).

89) Synthesis of N-{2-Oxo-2-[4-(2-trifluoromethyl-benzoyl)-piperazin-1-yl]-ethyl}-2-phenyl-acetamide

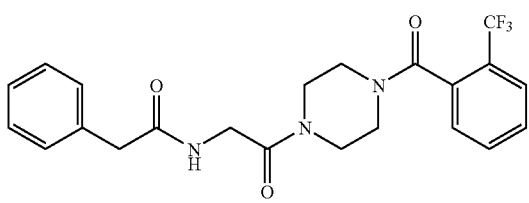

DIPEA (68 mg, 0.53 mmol) was added to a stirred solution of 2-amino-1-[4-(2-trifluoromethyl-benzoyl)-piperazin-1-yl]-ethanone TFA salt (76 mg, 0.18 mmol) in DMF (1 mL). HOBT (24 mg, 0.18 mmol) and EDCI.HCl (34 mg, 0.18 mmol) were then added at room temperature. After 2 minutes, phenyl acetic acid (20 mg, 0.15 mmol) was added and the resulting mixture was stirred at room temperature for 4 hrs. Cold water (20 mL) was then added and the product was extracted with EtOAc and the organic layer was washed with brine. The organic phase was dried over Na$_2$SO$_4$ and concentrated under reduced pressure. the resulting residue was purified by column chromatography (using silica gel 60-120 mesh and 1% methanol in chloroform as eluent) to afford 28 mg (43.7% yield) of N-{2-Oxo-2-[4-(2-trifluoromethyl-benzoyl)-piperazin-1-yl]-ethyl}-2-phenyl-acetamide. LCMS Purity: 94.1%, $^1$H NMR (CDCl$_3$): δ 7.8-7.7 (d, 1H). 7.6 (m, 2H), 7.4-7.2 (m, 5H), 6.5 (bd, 1H), 4.1 (m, 1H), 4.0 (m, 2H), 3.8 (m, 1H), 3.8-3.4 (m, 6H), 3.3 (t, 1H), 3.2-3.1 (m, 2H).

90) Synthesis of 4-Cyano-N-{2-oxo-2-[4-(2-trifluoromethyl-benzoyl)-piperazin-1-yl]-ethyl}-benzamide

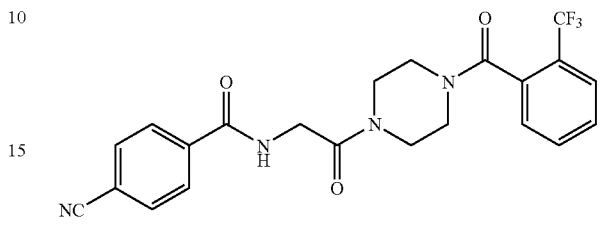

DIPEA (53 mg, 0.41 mmol) was added to a stirred solution of 2-amino-1-[4-(2-trifluoromethyl-benzoyl)-piperazin-1-yl]-ethanone TFA salt (69 mg, 0.16 mmol) in DMF (1 mL). HOBT (22 mg, 0.16 mmol) and EDCI.HCl (31 mg, 0.16 mmol) were then added at room temperature. After 2 minutes, 4-cyanobenzoic acid (20 mg, 0.14 mmol) was added and the resulting mixture was stirred at room temperature for 4 hrs. Cold water (20 mL) was then added and the product was extracted with EtOAc and the organic layer was washed with brine. The organic phase was dried over Na$_2$SO$_4$ and concentrated under reduced pressure to afford 30 mg (50% yield) of 4-cyano-N-{2-oxo-2-[4-(2-trifluoromethyl-benzoyl)-piperazin-1-yl]-ethyl}-benzamide. LCMS Purity: 96.9%, $^1$H NMR (CDCl$_3$): δ 7.9 (d, 2H), 7.8-7.7 (d, 3H), 7.6 (m, 2H), 7.4-7.3 (d, 2H), 4.2 (m, 2H), 4.4-4.2 (m, 2H), 4.0 (m, 2H), 3.8-3.4 (m, 5H), 3.4 (t, 1H), 3.2 (m, 2H).

91) Synthesis of N-{2-Oxo-2-[4-(2-trifluoromethyl-benzoyl)-piperazin-1-yl]-ethyl}-4-trifluoromethyl-benzamide

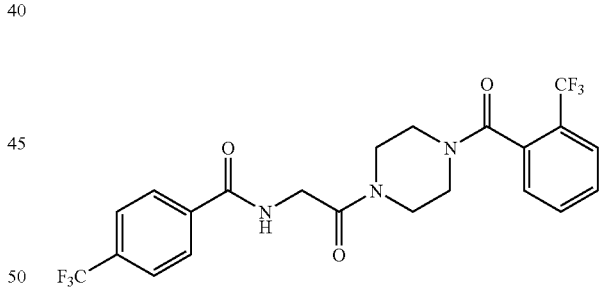

DIPEA (50 mg, 0.39 mmol) was added to a stirred solution of 2-amino-1-[4-(2-trifluoromethyl-benzoyl)-piperazin-1-yl]-ethanone TFA salt (68 mg, 0.16 mmol) in DMF (1 mL). HOBT (21 mg, 0.16 mmol) and EDCI.HCl (30 mg, 0.16 mmol) were then added at room temperature. After 2 minutes, 4-trifluoromethylbenzoic acid (25 mg, 0.13 mmol) was added and the resulting mixture was stirred at room temperature for 4 hrs. Cold water (20 mL) was then added and the product was extracted with EtOAc and the organic layer was washed with brine. The organic phase was dried over Na$_2$SO$_4$ and concentrated under reduced pressure. the resulting residue was purified by column chromatography (using silica gel 60-120 mesh and 1% methanol in chloroform as eluent) to afford 28 mg (50% yield) of N-{2-Oxo-2-[4-(2-trifluoromethyl-benzoyl)-piperazin-1-yl]-ethyl}-4-trifluoromethyl-benzamide. LCMS Purity: 92.7%, $^1$H NMR (CDCl$_3$): δ 8.0-7.9 (m, 2H), 7.8-7.7 (m, 3H), 7.6 (m, 2H), 7.4-7.3 (d, 1H), 4.4-4.3 (dd, 1H), 4.3-4.2 (dd, 1H), 4.0 (m, 2H), 3.8-3.5 (m, 4H), 3.4 (t, 1H), 3.3-3.2 (m, 2H).

Synthesis of N-{2-Oxo-2-[4-(2-trifluoromethyl-benzoyl)-piperazin-1-yl]-ethyl}-4-phenoxy-benzamide

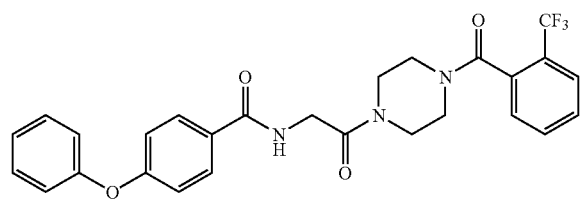

DIPEA (45 mg, 0.35 mmol) was added to a stirred solution of 2-amino-1-[4-(2-trifluoromethyl-benzoyl)-piperazin-1-yl]-ethanone TFA salt. (60 mg, 0.14 mmol) in DMF (1 mL). HOBT (19 mg, 0.14 mmol) and EDCI.HCl (27 mg, 0.14 mmol) were then added at room temperature. After 2 minutes, 4-phenoxybenzoic acid (25 mg, 0.12 mmol) was added the resulting mixture was stirred at room temperature for 4 hrs. Cold water (20 mL) was then added and the product was extracted with EtOAc and the organic layer was washed with brine. The organic phase was dried over $Na_2SO_4$ and concentrated under reduced pressure to afford 35 mg (58.3% yield) of N-{2-Oxo-2-[4-(2-trifluoromethyl-benzoyl)-piperazin-1-yl]-ethyl}-4-phenoxy-benzamide. LCMS Purity: 90.02%, HPLC Purity: 92.82%, $^1$H NMR (CDCl$_3$): δ 7.8 (dd, 2H), 7.8-7.7 (dd, 1H), 7.6 (m, 2H), 7.4-7.3 (m, 3H), 7.2-7.1 (t, 2H), 7.1-7.0 (m, 4H), 4.4-4.3 (dd, 1H), 4.3-4.2 (dd, 1H), 4.0 (m, 2H), 3.8-3.6 (m, 4H), 3.4 (t, 1H), 3.3-3.2 (m, 2H).

92) Synthesis of 5-(4-Benzyloxy-phenyl)-isoxazole-3-carboxylic acid {2-oxo-2-[4-(2-trifluoromethyl-benzoyl)-piperazin-1-yl]-ethyl}-amide

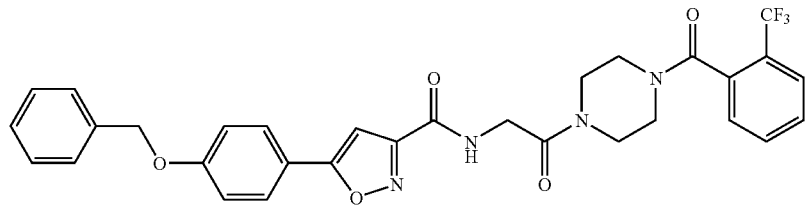

DIPEA (65.5 mg, 0.51 mmol) was added to a stirred solution of 2-amino-1-[4-(2-trifluoromethyl-benzoyl)-piperazin-1-yl]-ethanone TFA salt (87 mg, 0.20 mmol) in DMF (1 mL). HOBT (27 mg, 0.20 mmol) and EDCI.HCl (38 mg, 0.20 mmol) were then added at room temperature. After 2 minutes, 5-(4-benzyloxyphenyl)-isoxazole-3-carboxylic acid (50 mg, 0.17 mmol) was added and the resulting mixture was stirred at room temperature for 4 hrs. Cold water (20 mL) was then added and the product was extracted with EtOAc and the organic layer was washed with brine. The organic phase was dried over $Na_2SO_4$ and concentrated under reduced pressure. the resulting residue was purified by column chromatography (using silica gel 60-120 mesh and 2.5% methanol in chloroform as eluent) to afford 48 mg (48% yield) of 5-(4-benzyloxy-phenyl)-isoxazole-3-carboxylic acid {2-oxo-2-[4-(2-trifluoromethyl-benzoyl)-piperazin-1-yl]-ethyl}-amide. LCMS Purity: 83.69%, HPLC Purity: 99.66%, $^1$H NMR (DMSO-d$_6$): δ 8.6 (t, 1H), 8.0-7.8 (m, 3H), 7.8-7.7 (d, 1H), 7.7 (d, 1H), 7.6-7.5 (m, 1H), 7.4 (m, 4H), 7.3-7.2 (s, 1H), 7.2 (d, 2H), 5.0 (s, 2H), 4.3-4.2 (dd, 2H), 3.8-3.7 (m, 2H), 3.6 (m, 2H), 3.4 (m, 2H), 3.2-3.1 (m, 2H).

93) Synthesis of Biphenyl-4-carboxylic acid {2-oxo-2-[4-(2-trifluoromethyl-benzoyl)-piperazin-1-yl]-ethyl}-amide

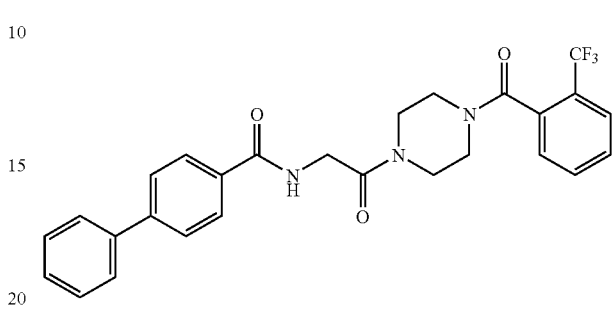

DIPEA (48 mg, 0.38 mmol) was added to a stirred solution of 2-amino-1-[4-(2-trifluoromethyl-benzoyl)-piperazin-1-yl]-ethanone TFA salt (87 mg, 0.20 mmol) in DMF (1 mL). HOBT (19 mg, 0.15 mmol) and EDCI.HCl (29 mg, 0.15 mmol) were then added at room temperature. After 2 minutes, biphenyl-4-carboxylic acid (25 mg, 0.13 mmol) was added and the resulting mixture was stirred at room temperature for 4 hrs. Cold water (20 mL) was then added and the product was extracted with EtOAc and the organic layer was washed with brine. The organic phase was dried over $Na_2SO_4$ and concentrated under reduced pressure to afford 26 mg (42% yield) of biphenyl-4-carboxylic acid {2-oxo-2-[4-(2-trifluoromethyl-benzoyl)-piperazin-1-yl]-ethyl}-amide. LCMS Purity: 94.87%, HPLC Purity: 97.28%, $^1$H NMR (DMSO-d$_6$): δ 8.6 (bs, 1H), 8.0-7.9 (d, 2H), 7.8-7.6 (m, 7H), 7.6-7.4 (m, 4H), 4.2 (d, 2H), 3.8-3.6 (m, 4H), 3.4 (m, 2H), 3.2-3.1 (m, 2H).

94) Synthesis of 5-(4-Hydroxy-phenyl)-isoxazole-3-carboxylic acid {2-oxo-2-[4-(2-trifluoromethyl-benzoyl)-piperazin-1-yl]-ethyl}-amide

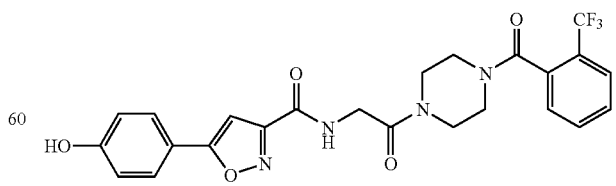

DIPEA (65 mg, 0.51 mmol) was added to a stirred solution of 2-amino-1-[4-(2-trifluoromethyl-benzoyl)-piperazin-1-yl]-ethanone TFA salt. (87 mg, 0.20 mmol) in DMF (1 mL).

HOBT (28 mg, 0.20 mmol) and EDCI.HCl (39 mg, 0.20 mmol) were then added at room temperature. After 2 minutes, 5-(4-hydroxyphenyl)-isoxazole-3-carboxylic acid (35 mg, 0.17 mmol) was added and the resulting mixture was stirred at room temperature for 4 hrs. Cold water (20 mL) was then added and the product was extracted with EtOAc and the organic layer was washed with brine. The organic phase was dried over $Na_2SO_4$ and concentrated under reduced pressure to afford 23 mg (26.7% yield) of 5-(4-hydroxy-phenyl)-isoxazole-3-carboxylic acid {2-oxo-2-[4-(2-trifluoromethyl-benzoyl)-piperazin-1-yl]-ethyl}-amide. LCMS Purity: 93.77%, HPLC Purity: 90.43%, $^1$H NMR (DMSO-$d_6$): δ 10.1-10.0 (s, 1H), 8.6-8.5 (s, 1H), 8.0-7.6 (m, 5H), 7.5 (bs, 1H), 7.1 (s, 1H), 6.8 (d, 2H), 4.2-4.1 (d, 2H) 3.8-3.7 (m, 2H), 3.6 (m, 2H), 3.4 (m, 2H), 3.2-3.1 (m, 2H).

95) Synthesis of 6-Hydroxy-N-{2-oxo-2-[4-(2-trifluoromethyl-benzoyl)-piperazin-1-yl]-ethyl}-nicotinamide

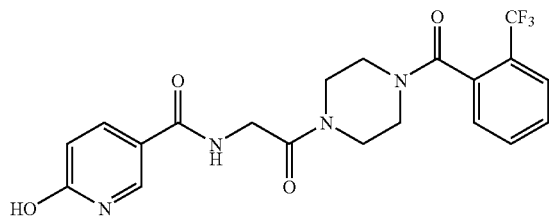

DIPEA (56 mg, 0.43 mmol) was added to a stirred solution of 2-amino-1-[4-(2-trifluoromethyl-benzoyl)-piperazin-1-yl]-ethanone TFA salt. (74 mg, 0.17 mmol) in DMF (1 mL). HOBT (23 mg, 0.17 mmol) and EDCI.HCl (33 mg, 0.17 mmol) were then added at room temperature. After 2 minutes, 6-hydroxy nicotinic acid (20 mg, 0.14 mmol) was added and the resulting mixture was stirred at room temperature for 4 hrs. Cold water (20 mL) was then added and the product was extracted with EtOAc and the organic layer was washed with brine. The organic phase was dried over $Na_2SO_4$ and concentrated under reduced pressure to afford 35 mg (56.5% yield) of 6-hydroxy-N-{2-oxo-2-[4-(2-trifluoromethyl-benzoyl)-piperazin-1-yl]-ethyl}-nicotinamide. LCMS Purity: 99.38%, HPLC Purity: 92.66%, $^1$H NMR (DMSO-$d_6$): δ 12 (s, 1H), 8.0 (t, 1H), 7.9-7.8 (m, 2H), 7.8-7.7 (d, 1H), 7.7-7.6 (t, 1H), 7.6-7.5 (m, 1H), 6.4-6.3 (dd, 1H), 4.2-4.0 (m, 2H), 3.8-3.7 (m, 2H), 3.6 (m, 2H), 3.4 (m, 2H), 3.2-3.1 (m, 2H).

96) Synthesis of 5-Nitro-furan-2-carboxylic acid {2-oxo-2-[4-(2-trifluoromethyl-benzoyl)-piperazin-1-yl]-ethyl}-amide

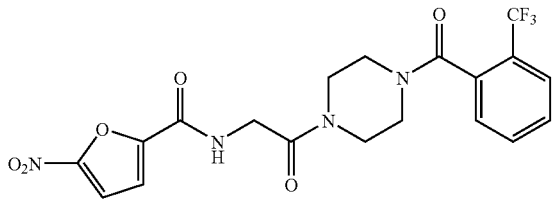

DIPEA (50 mg, 0.38 mmol) was added to a stirred solution of 2-amino-1-[4-(2-trifluoromethyl-benzoyl)-piperazin-1-yl]-ethanone TFA salt (66 mg, 0.15 mmol) in DMF (1 mL).

HOBT (21 mg, 0.15 mmol) and EDCI.HCl (29 mg, 0.15 mmol) were then added at room temperature. After 2 minutes, 5-nitro-furan-2-carboxylic acid (20 mg, 0.13 mmol) was added and the resulting mixture was stirred at room temperature for 4 hrs. Cold water (20 mL) was then added and the product was extracted with EtOAc and the organic layer was washed with brine. The organic phase was dried over $Na_2SO_4$ and concentrated under reduced pressure. The resulting residue was purified by column chromatography (using silica gel 60-120 mesh and 3% methanol in chloroform as eluent) to afford 29 mg (49.1% yield) of 5-Nitro-furan-2-carboxylic acid {2-oxo-2-[4-(2-trifluoromethyl-benzoyl)-piperazin-1-yl]-ethyl}-amide. LCMS Purity: 97.329%, HPLC Purity: 95.23%, $^1$H NMR (CDCl$_3$): δ 7.8-7.6 (d, 1H), 7.7-7.5 (m, 3H), 7.4-7.3 (m, 2H), 7.3 (m, 1H), 4.4-4.3 (t, 1H), 4.3-4.2 (t, 1H), 4.1-3.9 (m, 2H), 3.8-3.5 (m, 4H), 3.4 (t, 1H), 3.3-3.2 (m, 2H).

97) Synthesis of 4-(2,6-Difluoro-phenoxy)-N-{2-oxo-2-[4-(2-trifluoromethyl-benzoyl)-piperazin-1-yl]-ethyl}-benzamide

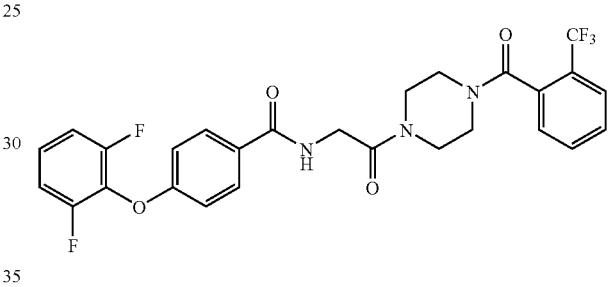

DIPEA (46 mg, 0.36 mmol) was added to a stirred solution of 2-amino-1-[4-(2-trifluoromethyl-benzoyl)-piperazin-1-yl]-ethanone TFA salt. (62 mg, 0.14 mmol) in DMF (1 mL). HOBT (19 mg, 0.14 mmol) and EDCI.HCl (28 mg, 0.14 mmol) were then added at room temperature. After 2 minutes, 4-(2,6-difluorophenoxy)benzoic acid (30 mg, 0.12 mmol) was added and the resulting mixture was stirred at room temperature for 4 hrs. Cold water (20 mL) was then added and the product was extracted with EtOAc and the organic layer was washed with brine. The organic phase was dried over $Na_2SO_4$ and concentrated under reduced pressure to afford 40 mg (60.6% yield) of 4-(2,6-difluoro-phenoxy)-N-{2-oxo-2-[4-(2-trifluoromethyl-benzoyl)-piperazin-1-yl]-ethyl}-benzamide. LCMS Purity: 94.3%, NMR Values: $^1$H NMR (CDCl$_3$): δ 7.9-7.7 (m, 3H). 7.7-7.5 (m, 2H), 7.4-7.3 (d, 1H), 7.2-7.1 (m, 2H), 7.1-6.9 (m, 4H), 4.3 (dd, 1H), 4.2 (dd, 1H), 4.0-3.5 (m, 6H), 3.4 (t, 1H), 3.2 (m, 2H).

98) Synthesis of 4-Amino-N-{2-oxo-2-[4-(2-trifluoromethyl-benzoyl)-piperazin-1-yl]-ethyl}-benzamide

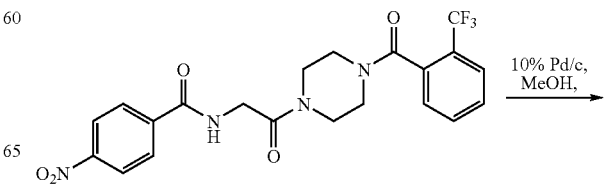

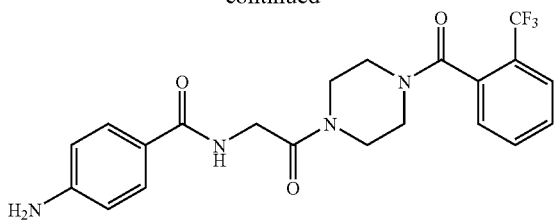

4-Nitro-N-{2-oxo-2-[4-(2-trifluoromethyl-benzoyl)-piperazin-1-yl]-ethyl}-benzamide (57 mg, 0.12 mmol) was dissolved in Methanol (1 mL). 10% Pd/C (10 mg) was added and the resulting mixture stirred for 4 hrs. The mixture was filtered over celite bed, and the filtrate was concentrated to afford 26 mg (49.1% yield) of 4-amino-N-{2-oxo-2-[4-(2-trifluoromethyl-benzoyl)-piperazin-1-yl]-ethyl}-benzamide. LCMS Purity: 97.4%, $^1$H NMR (CDCl$_3$): δ 7.8-7.5 (m, 5H), 7.4-7.3 (d, 1H), 7.1-7.0 (s, 1H), 6.7-6.6 (d, 2H), 4.3-4.1 (m, 2H), 4.0 (bs, 3H), 3.8-3.5 (m, 5H), 3.4 (t, 1H), 3.2 (m, 2H).

99) Synthesis of N-{2-Oxo-2-[4-(2-trifluoromethyl-benzoyl)-piperazin-1-yl]-ethyl}-6-phenyl-nicotinamide

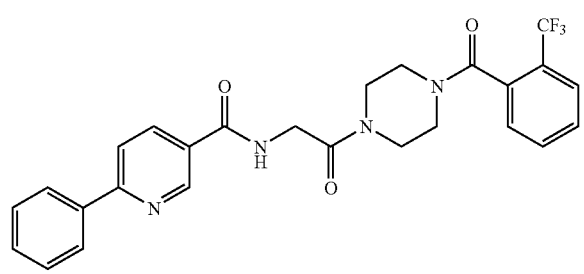

Step 1: Synthesis of 2-Amino-1-[4-(2-trifluoromethyl-benzoyl)-piperazin-1-yl]-ethanone TFA salt 2-Amino-1-[4-(2-trifluoromethyl-benzoyl)-piperazin-1-yl]-ethanone TFA salt was prepared as described above (Scheme 4).

Step 2: Synthesis of 6-Phenyl-nicotinic acid ethyl ester

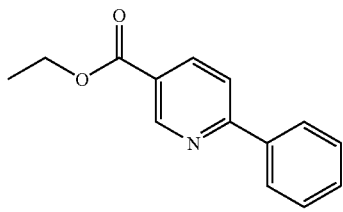

Na$_2$CO$_3$ (228 mg, 2.16 mmol) was added to a stirred solution of 6-chloro nicotinic acid ethyl ester (200 mg, 1.08 mmol) in toluene:H$_2$O (5:1, 6 mL). Pd (PPh$_3$)$_4$ (250 mg, 0.216 mmol) and phenylboronic acid (168 mg, 1.29 mmol) were then added and the reaction mixture was heated to reflux for 3 hrs. The reaction mixture was then diluted with water and the product was extracted with ethyl acetate. The organic layer was washed with saturated brine solution, dried over sodium sulphate and concentrated to afford 140 mg (64.4% yield) of 6-phenyl-nicotinic acid ethyl ester. LCMS Purity %: 98.2

Step 3: Synthesis of 6-Phenyl-nicotinic acid

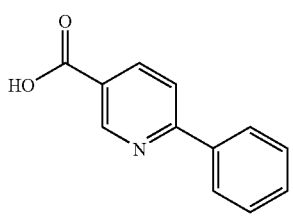

LiOH (38 mg, 0.93 mmol) was added to a stirred solution of 6-phenyl-nicotinic acid ethyl ester (140 mg, 0.62 mmol) in THF:MeOH:H$_2$O (3:1:1, 2.8 mL), and the resulting mixture was stirred at room temperature overnight. The methanol and THF were evaporated from the reaction mixture, which was then diluted with water (2 mL), acidified with citric acid solution and the product was extracted with EtOAc. The organic layer was washed with saturated brine solution, dried over Na$_2$SO$_4$ and concentrated in vacuo to afford 100 mg (81.9% yield) of 6-phenyl-nicotinic acid (100 mg). LCMS purity: 98.1%.

Step 4: Synthesis of N-{2-Oxo-2-[4-(2-trifluoromethyl-benzoyl)-piperazin-1-yl]-ethyl}-6-phenyl-nicotinamide

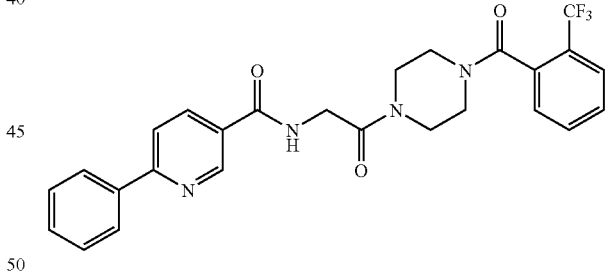

DIPEA (77 mg, 0.6 mmol) was added to a stirred solution of 2-amino-1-[4-(2-trifluoromethyl-benzoyl)-piperazin-1-yl]-ethanone TFA salt (103 mg, 0.24 mmol) in DMF (1 mL). HOBT (33 mg, 0.24 mmol) and EDCI.HCl (46 mg, 0.24 mmol) were then added at room temperature. After 2 minutes, 6-phenyl nicotinic acid (40 mg, 0.2 mmol) was added and the resulting mixture was stirred at room temperature for 4 hrs. Cold water was then added and the product was extracted with EtOAc and the organic layer was washed with brine. The organic phase was dried over Na$_2$SO$_4$ and concentrated under reduced pressure to afford 70 mg (70.7% yield) of N-{2-Oxo-2-[4-(2-trifluoromethyl-benzoyl)-piperazin-1-yl]-ethyl}-6-phenyl-nicotinamide. LCMS Purity: 92.6%, $^1$H NMR (DMSO-d$_6$): δ 9.1 (s, 1H), 8.7 (t, 1H), 8.3 (d, 1H), 8.2-8.1 (m, 3H), 7.9-7.7 (m, 3H), 7.7-7.6 (m, 1H), 7.6-7.4 (m, 4H), 4.2 (m, 2H), 3.4-3.2 (m, 8H).

100) Synthesis of Biphenyl-3-carboxylic acid {2-oxo-2-[4-(2-trifluoromethyl-benzoyl)-piperazin-1-yl]-ethyl}-amide

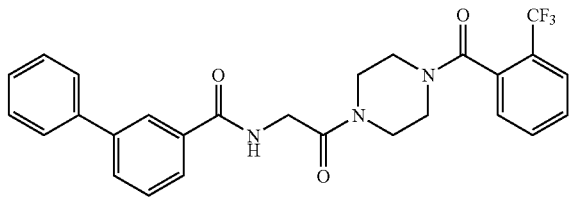

Synthesis of 2-Amino-1-[4-(2-trifluoromethyl-benzoyl)-piperazin-1-yl]-ethanone TFA salt 2-Amino-1-[4-(2-trifluoromethyl-benzoyl)-piperazin-1-yl]-ethanone TFA salt was prepared as described above (Scheme 4).

Synthesis of 3-Phenyl benzoic acid methyl ester

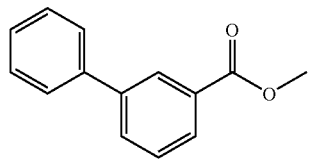

3-Phenyl benzoic acid methyl ester was prepared in a similar manner to that described above (Example 28) using different starting materials. 100 mg (62% yield), $^1$H NMR (DMSO-$d_6$): δ 8.2 (t, 1H), 7.9-7.8 (m, 2H), 7.7 (m, 2H), 7.7-7.6 (t, 1H), 7.5 (t, 2H), 7.4 (m, 1H), 4-3.9 (s, 3H).

Synthesis of 3-Phenyl benzoic acid

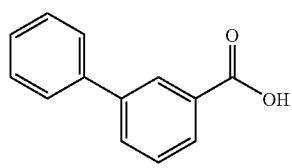

3-phenyl benzoic acid was prepared in a similar manner to that described above (Example 28) using different starting materials. 57 mg (58% yield).

Synthesis of Biphenyl-3-carboxylic acid {2-oxo-2-[4-(2-trifluoromethyl-benzoyl)-piperazin-1-yl]-ethyl}-amide

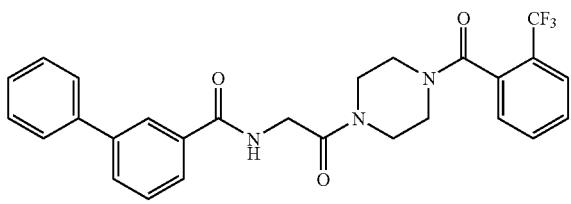

DIPEA (78 mg, 0.61 mmol) was added to a stirred solution of 2-amino-1-[4-(2-trifluoromethyl-benzoyl)-piperazin-1-yl]-ethanone TFA salt (104 mg, 0.24 mmol) in DMF (1 mL). HOBT (33 mg, 0.24 mmol) and EDCI.HCl (46 mg, 0.24 mmol) were then added at room temperature. After 2 minutes, 3-phenyl benzoic acid (40 mg, 0.20 mmol) was added and the resulting mixture was stirred at room temperature for 4 hrs. Cold water was then added and the product was extracted with EtOAc and the organic layer was washed with brine. The organic phase was dried over $Na_2SO_4$ and concentrated under reduced pressure to afford 70 mg (70% yield) of biphenyl-3-carboxylic acid {2-oxo-2-[4-(2-trifluoromethyl-benzoyl)-piperazin-1-yl]-ethyl}-amide. LCMS Purity: 95.7%, $^1$H NMR (DMSO-$d_6$): δ 8.8 (t, 1H), 8.2 (s, 1H), 7.9-7.8 (m, 3H), 7.8-7.6 (m, 4H), 7.6-7.4 (m, 4H), 7.4 (m, 1H), 4.2 (m, 2H), 3.8-3.6 (m, 4H), 3.5-3.4 (m, 2H), 3.2-3.0 (m, 2H).

101) Synthesis of 4-Phenyl-thiophene-2-carboxylic acid {2-oxo-2-[4-(2-trifluoromethyl-benzoyl)-piperazin-1-yl]-ethyl}-amide

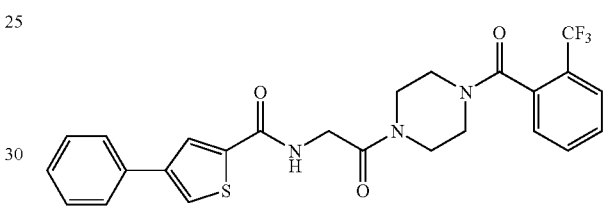

Synthesis of 2-Amino-1-[4-(2-trifluoromethyl-benzoyl)-piperazin-1-yl]-ethanone TFA salt 2-Amino-1-[4-(2-trifluoromethyl-benzoyl)-piperazin-1-yl]-ethanone TFA salt was prepared as described above (Scheme 4).

Synthesis of 4-Phenyl-thiophene-2-carboxaldehyde

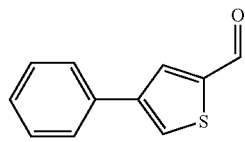

To a stirred solution of 4-bromothiophene-2-carboxaledehyde (200 mg, 1.05 mmol) in toluene:$H_2O$ (5:2) (7 mL), added $Na_2CO_3$ (222 mg, 2.09 mmol) followed by Pd(PPh$_3$)$_4$ (242 mg, 0.21 mmol) and phenylboronic acid (163 mg, 1.255 mmol) at room temperature. The reaction mixture was then heated to reflux for 3 hrs. The reaction mixture was diluted with water and extracted with ethyl acetate. The organic layer was washed with saturated brine solution, dried over sodium sulphate and concentrated. The resulting residue was purified by column chromatography (using silica gel 60-120 mesh and 3% ethylacetate in hexane as eluent) to afford 150 mg (76.5% yield) of 4-phenyl-thiophene-2-carboxaldehyde. $^1$H NMR (DMSO-$d_6$): δ 10.0 (s, 1H), 8.5 (d, 2H), 7.8 (d, 2H), 7.5 (t, 2H), 7.4-7.3 (m, 1H).

Synthesis of 4-Phenyl-thiophene-2-carboxylic acid

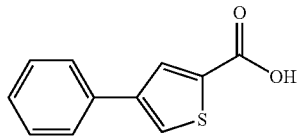

4-phenyl-thiophene-2-carboxaldehyde (150 mg, 0.80 mmol) was dissolved in acetone-water mixture (2:1) (3 mL) and cooled to 0° C. To this reaction mixture was added sulphamic acid (232 mg, 2.38 mmol) and sodium chlorite (288 mg, 3.18 mmol) dissolved in minimum amount of water. The resulting reaction mixture was allowed to stir at room temperature for half an hour. The reaction mixture was then diluted with water and extracted with ethyl acetate. The organic layer was washed with brine solution, dried over sodium sulphate and concentrated to afford 100 mg (62.5% yield) of 4-Phenyl-thiophene-2-carboxylic acid.

Synthesis of 4-Phenyl-thiophene-2-carboxylic acid {2-oxo-2-[4-(2-trifluoromethyl-benzoyl)-piperazin-1-yl]-ethyl}-amide

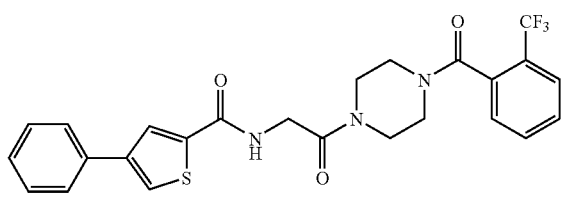

DIPEA (76 mg, 0.59 mmol) was added to a stirred solution of 2-amino-1-[4-(2-trifluoromethyl-benzoyl)-piperazin-1-yl]-ethanone TFA salt (100 mg, 0.24 mmol) in DMF (1 mL). HOBT (32 mg, 0.24 mmol) and EDCI.HCl (45 mg, 0.24 mmol) were then added at room temperature. After 2 minutes, 4-phenyl-thiophene-2-carboxylic acid (40 mg, 0.20 mmol) was added and the resulting mixture was stirred at room temperature for 4 hrs. Cold water was then added and the product was extracted with EtOAc and the organic layer was washed with brine. The organic phase was dried over Na$_2$SO$_4$ and concentrated under reduced pressure to afford 35 mg (35.7% yield) of 4-phenyl-thiophene-2-carboxylic acid {2-oxo-2-[4-(2-trifluoromethyl-benzoyl)-piperazin-1-yl]-ethyl}-amide. LCMS Purity %: 99.1%, $^1$H NMR (DMSO-$d_6$): δ 8.7 (t, 1H), 8.3 (s, 1H), 8.1 (s, 1H), 7.9-7.6 (m, 5H), 7.6-7.5 (m, 1H), 7.5-7.4 (t, 2H), 7.4-7.3 (m, 1H), 4.2 (m, 2H), 3.7-3.5 (m, 4H), 3.4 (m, 4H), 3.2-3.1 (m, 2H).

102) Synthesis of 5-Phenyl-pyridine-2-carboxylic acid {2-oxo-2-[4-(2-trifluoromethyl-benzoyl)-piperazin-1-yl]-ethyl}-amide

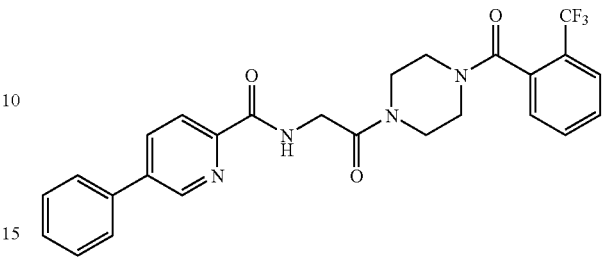

Synthesis of 2-Amino-1-[4-(2-trifluoromethyl-benzoyl)-piperazin-1-yl]-ethanone TFA salt 2-Amino-1-[4-(2-trifluoromethyl-benzoyl)-piperazin-1-yl]-ethanone TFA salt was prepared as described above (Scheme 4).

Synthesis of 5-Phenyl-pyridine-2-carbonitrile

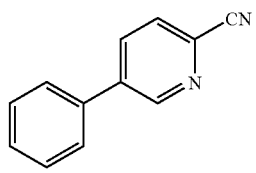

To a stirred solution of 5-chloro-2-cyanopyridine (300 mg, 2.17 mmol) in toluene: H$_2$O (7:3) (10 mL) was added Na$_2$CO$_3$ (459 mg, 4.33 mmol) followed by Pd(PPh$_3$)$_4$ (500 mg, 0.43 mmol) and phenylboronic acid (337 mg, 2.60 mmol) at room temperature. The resulting mixture was heated to reflux for 3 hrs. The reaction mixture was then diluted with water and extracted with ethyl acetate. The organic layer was washed with saturated brine solution, dried over sodium sulphate and concentrated. The resulting residue was purified by column chromatography (using silica gel 60-120 mesh and 4% ethylacetate in hexane as eluent) to afford 96 mg (24.6% yield) of 5-phenyl-pyridine-2-carbonitrile. LCMS Purity: 97.5%

Synthesis of 5-Phenyl-pyridine-2-carboxylic Acid

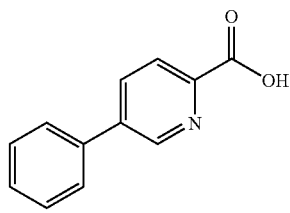

Water (1 mL) and NaOH (56 mg, 1.41 mmol) were added to a stirred solution of 5-phenyl-pyridine-2-carbonitrile (112 mg, 0.56 mmol) in ethanol at room temperature. The resulting mixture was heated at reflux temperature for 3 hours. The EtOH was evaporated, and the mixture was diluted with water (2 mL), acidified with citric acid solution and the product was extracted using EtOAc. The organic layer was washed with saturated brine solution, dried over Na₂SO₄ and concentrated under reduced pressure to afford 30 mg (27% yield) of 5-phenyl-pyridine-2-carboxylic acid.

Synthesis of 5-Phenyl-pyridine-2-carboxylic acid {2-oxo-2-[4-(2-trifluoromethyl-benzoyl)-piperazin-1-yl]-ethyl}-amide

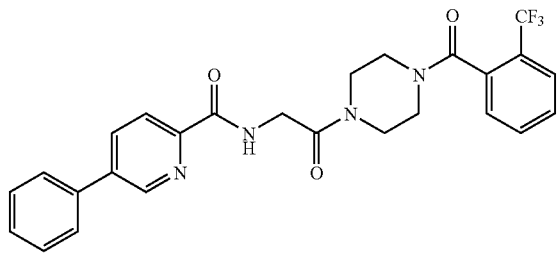

DIPEA (59 mg, 0.45 mmol) was added to a stirred solution of 2-amino-1-[4-(2-trifluoromethyl-benzoyl)-piperazin-1-yl]-ethanone TFA salt. (78 mg, 0.18 mmol) in DMF (1 mL). HOBT (24 mg, 0.18 mmol) and EDCI.HCl (29 mg, 0.15 mmol) were then added at room temperature. After 2 minutes, 5-phenyl-pyridine-2-carboxylic acid (30 mg, 0.15 mmol) was added and the resulting mixture was stirred at room temperature for 4 hrs. Cold water was then added and the product was extracted with EtOAc and the organic layer was washed with brine. The organic phase was dried over Na₂SO₄ and concentrated under reduced pressure to afford 55 mg (73.3% yield) of 5-phenyl-pyridine-2-carboxylic acid {2-oxo-2-[4-(2-trifluoromethyl-benzoyl)-piperazin-1-yl]-ethyl}-amide LCMS Purity %: 90.8%, ¹H NMR (DMSO-d₆): δ 9.0 (d, 1H), 8.9-8.8 (t, 1H), 8.3 (dd, 1H), 8.1 (m, 1H), 7.9-7.6 (m, 5H), 7.6-7.4 (m, 4H), 4.4-4.3 (d, 1H), 4.2 (d, 1H), 3.8-3.4 (m, 6H), 3.2-3.1 (m, 2H).

103) Synthesis of 1-Phenyl-piperidine-4-carboxylic acid {2-oxo-2-[4-(2-trifluoromethyl-benzoyl)-piperazin-1-yl]-ethyl}-amide

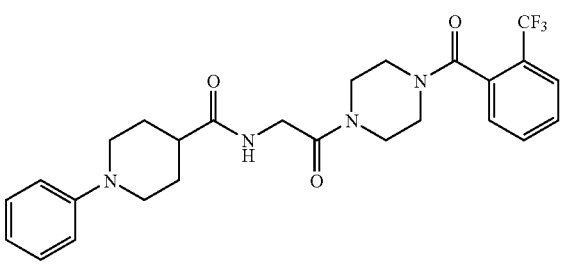

Synthesis of 2-Amino-1-[4-(2-trifluoromethyl-benzoyl)-piperazin-1-yl]-ethanone TFA Salt 2-Amino-1-[4-(2-trifluoromethyl-benzoyl)-piperazin-1-yl]-ethanone TFA salt was prepared as described above (Scheme 4).

Synthesis of 1-Phenyl-piperidine-4-carboxylic Acid Methyl Ester

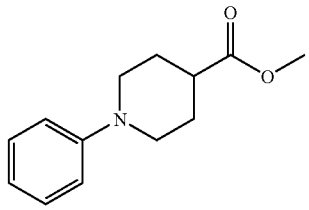

Step A

Cs₂CO₃ (1.8 g, 5.56 mmol) was added to a stirred solution of piperidine-4-carboxylic acid methyl ester HCl salt (200 mg, 1.11 mmol) in toluene (3 mL). The resulting mixture was stirred at room temperature and then used as is for the next step.

Step B

A mixture of toluene (3 mL), Pd(OAc)₂ (25 mg, 0.11 mmol) and BINAP (69 mg, 0.11 mmol) was purged with argon gas for 15 minutes, and then added in one portion to the solution prepared in Step A. The resulting mixture was sheated to reflux temperature overnight. The reaction mixture was diluted with water, and the product was extracted with ethyl acetate. The organic layer was washed with saturated brine solution, dried over sodium sulphate and concentrated. The resulting residue was purified by column chromatography using silica gel 60-120 mesh and 55% EtOAc in Hexane as eluent to afford 150 mg (61.5% yield) of 1-phenyl-piperidine-4-carboxylic acid methyl ester. LCMS Purity %: 94.0%

Synthesis of 1-Phenyl-piperidine-4-carboxylic Acid

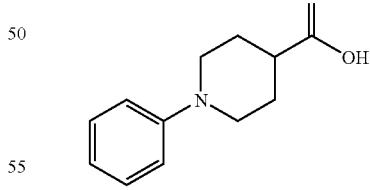

LiOH (43 mg, 1.03 mmol) was added to a stirred solution of 1-phenyl-piperidine-4-carboxylic acid methyl ester (150 mg, 0.68 mmol) in THF:MeOH:H₂O (3:1:1, 3.2 mL), and the resulting mixture was stirred at room temperature overnight. The MeOH and THF were evaporated and the residue was diluted with water (2 mL), acidified with citric acid solution and the product extracted with EtOAc. The organic layer was washed with saturated brine solution, dried over Na₂SO₄ and concentrated in vacuo to afford 94 mg (67.1% yield) of 1-Phenyl-piperidine-4-carboxylic acid. LCMS purity: 95.9%.

123

Synthesis of 1-Phenyl-piperidine-4-carboxylic acid {2-oxo-2-[4-(2-trifluoromethyl-benzoyl)-piperazin-1-yl]-ethyl}-amide

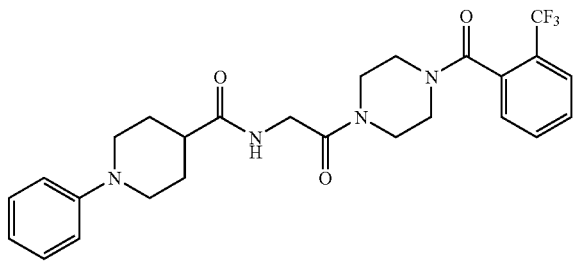

DIPEA (66 mg, 0.51 mmol) was added to a stirred solution of 2-amino-1-[4-(2-trifluoromethyl-benzoyl)-piperazin-1-yl]-ethanone TFA salt (125 mg, 0.29 mmol) in DMF (1.5 mL). HOBT (27 mg, 0.20 mmol) and EDCI.HCl (39 mg, 0.20 mmol) were then added at room temperature. After 2 minutes, 1-phenyl-piperidine-4-carboxylic acid (35 mg, 0.17 mmol) was added and the resulting mixture was stirred at room temperature for 4 hrs. Cold water was then added and the product was extracted with EtOAc and the organic layer was washed with brine. The organic phase was dried over $Na_2SO_4$ and concentrated under reduced pressure to afford 25 mg (29% yield) of 1-phenyl-piperidine-4-carboxylic acid {2-oxo-2-[4-(2-trifluoromethyl-benzoyl)-piperazin-1-yl]-ethyl}-amide. LCMS Purity %: 87.4%, $^1$H NMR (DMSO-$d_6$): δ 7.8-7.7 (m, 3H), 7.4-7.3 (d, 1H), 7.3-7.2 (t, 1H), 7.0-6.9 (d, 1H), 6.8 (t, 1H), 6.6 (m, 1H), 4.2-3.8 (m, 4H), 3.8-3.6 (m, 4H), 3.5 (m, 2H), 3.4-3.3 (t, 1H), 3.2 (m, 2H), 2.7 (m, 2H), 2.3 (m, 1H), 2.0-1.8 (m, 4H).

104) Synthesis of N-{2-Oxo-2-[4-(2-trifluoromethyl-benzoyl)-piperazin-1-yl]-ethyl}-terephthalamic Acid

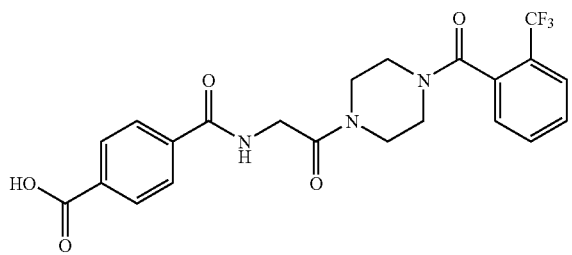

Step 1: Synthesis of 4-Formyl-N-{2-oxo-2-[4-(2-trifluoromethyl-benzoyl)-piperazin-1-yl]-ethyl}-benzamide

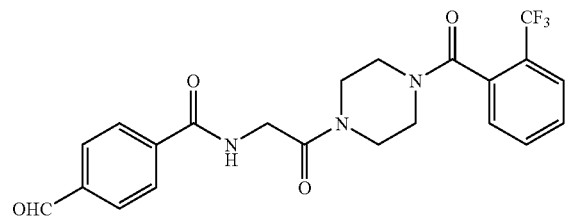

DIPEA (77 mg, 0.60 mmol) was added to a stirred solution of 2-amino-1-[4-(2-trifluoromethyl-benzoyl)-piperazin-1-yl]-ethanone TFA salt (103 mg, 0.24 mmol) in DMF (0.5 mL). HOBT (32 mg, 0.24 mmol) and EDCI.HCl (45 mg, 0.24 mmol) were then added at room temperature. After 2 minutes, 4-formyl benzoic acid (30 mg, 0.20 mmol) was added and the resulting mixture was stirred at room temperature for 4 hrs. Cold water was then added and the product was extracted with EtOAc and the organic layer was washed with brine. The organic phase was dried over $Na_2SO_4$ and concentrated under reduced pressure to afford 40 mg (45% yield) of 4-formyl-N-{2-oxo-2-[4-(2-trifluoromethyl-benzoyl)-piperazin-1-yl]-ethyl}-benzamide. LCMS Purity: 74.2%, Step 2: Synthesis of N-{2-Oxo-2-[4-(2-trifluoromethyl-benzoyl)-piperazin-1-yl]-ethyl}-terephthalamic acid

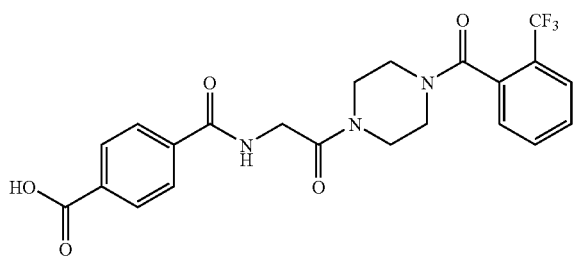

4-Formyl-N-{2-oxo-2-[4-(2-trifluoromethyl-benzoyl)-piperazin-1-yl]-ethyl}-benzamide (40 mg, 0.90 mmol) was dissolved in an acetone-water mixture (1:1, 0.9 mL) and cooled to 0° C. A mixture of sulphamic acid (26 mg, 0.27 mmol) and sodium chlorite (32 mg, 0.36 mmol) dissolved in minimum amount of water was then added. The resulting mixture was allowed to warm to room temperature and stirred for 30 minutes. 5 mL of water was then added, and the product was extracted with ethyl acetate. The organic layer was washed with brine solution, dried over sodium sulphate and concentrated to afford 25 mg (61% yield) of N-{2-Oxo-2-[4-(2-trifluoromethyl-benzoyl)-piperazin-1-yl]-ethyl}-terephthalamic acid. LCMS Purity: 95.8%, $^1$H NMR (DMSO-$d_6$): δ 13 (bs, 1H). 8.8 (m, 1H), 8.1-7.9 (m, 4H), 7.9-7.8 (m, 1H), 7.8-7.7 (m, 1H), 7.7 (m, 1H), 7.6-7.5 (m, 1H), 4.3-4.1 (m, 4H), 3.6-3.4 (m, 8H).

105) Synthesis of N-{2-Oxo-2-[4-(2-trifluoromethyl-benzoyl)-piperazin-1-yl]-ethyl}-terephthalamide

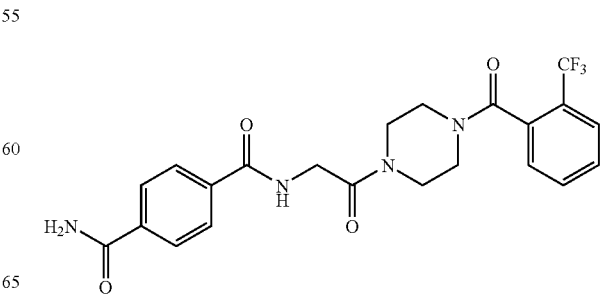

Step 1: Synthesis of Terephthalamic Acid Methyl Ester

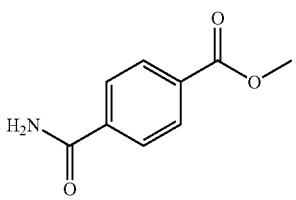

Terephthalic acid monomethyl ester (100 mg, 0.56 mmol) was dissolved in THF (1 mL) and cooled to −70° C. N-Methyl morpholino (67 mg, 0.67 mmol) was added, and, after five minutes, isobutyl chloroformate (83 mg, 0.61 mmol) was also at this temperature. The resulting mixture was stirred at −70° C. for 2 hours. The reaction was monitored by TLC (20% methanol in chloroform). After complete formation of anhydride, ammonia gas was bubbled through the reaction mixture at −70° C. for one hour. The resulting mixture was then stirred at room temperature for 2 hrs. Water (10 mL) was added, and the product was extracted with ethyl acetate. The organic layer was washed with brine solution, dried over sodium sulphate and concentrated to afford 35 mg (41.6% yield) of terephthalamic acid methyl ester. LCMS Purity: 96.9%

Step 2: Synthesis of Terephthalamic Acid

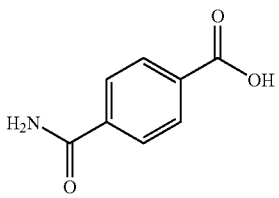

LiOH (26 mg, 0.6 mmol) was added to a stirred solution of terephthalamic acid methyl ester (73 mg, 0.41 mmol) in THF:MeOH:water mixture (3:1:1, 1 mL) and the resulting mixture was stirred at room temperature overnight. The THF and MeOH were then evaporated and the resulting residue was acidified to pH 2 using 10% citric acid solution. The product was extracted using EtOAc. The organic layer was washed with saturated brine solution, dried over $Na_2SO_4$ and concentrated under reduced pressure to afford 30 mg (53.6% yield) of terephthalamic acid. LCMS Purity: 92.2%.

Step 3: Synthesis of N-{2-Oxo-2-[4-(2-trifluoromethyl-benzoyl)-piperazin-1-yl]-ethyl}-terephthalamide

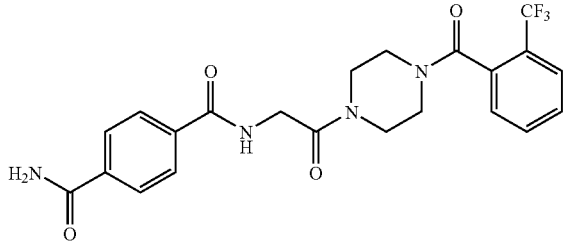

DIPEA (14.1 mg, 0.109 mmol) was added to a stirred solution of 2-amino-1-[4-(2-trifluoromethyl-benzoyl)-piperazin-1-yl]-ethanone TFA salt. (18 mg, 0.04 mmol) in DMF (1 mL). HOBT (6 mg, 0.04 mmol) and EDCl.HCl (8 mg, 0.04 mmol) were then added at room temperature. After 2 minutes, terephthalamic acid (6 mg, 0.04 mmol) was added and the resulting mixture was stirred at room temperature for 4 hrs. Cold water (20 mL) was then added and the product was extracted with EtOAc and the organic layer was washed with brine. The organic phase was dried over $Na_2SO_4$ and concentrated under reduced pressure. The resulting residue was purified by column chromatography (using silica gel 60-120 mesh and 3% methanol in chloroform as eluent) to afford 24 mg (59.5% yield) of N-{2-Oxo-2-[4-(2-trifluoromethyl-benzoyl)-piperazin-1-yl]-ethyl}-terephthalamide. LCMS Purity: 97.1%, $^1$H NMR (DMSO-$d_6$) δ 8.0-7.9 (s, 3H). 7.8-7.7 (d, 1H), 7.6 (m, 2H), 7.4-7.3 (d, 2H), 6.3-6.1 (bs, 1H), 5.8-5.6 (bs, 1H), 4.4-4.2 (m, 2H), 4.0-3.6 (m, 4H), 3.6-3.2 (m, 5H).

106) Synthesis of 4-(5-Cyano-pyridin-2-yloxy)-N-{2-oxo-2-[4-(2-trifluoromethyl-benzoyl)-piperazin-1-yl]-ethyl}-benzamide

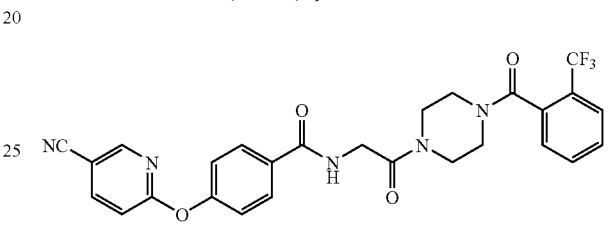

Step 1: Synthesis of 6-(4-Formyl-phenoxy)-nicotinonitrile

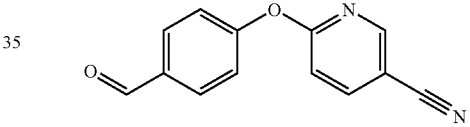

$K_2CO_3$ (450 mg, 3.27 mmol) and 6-chloronicotinonitrile (270 mg, 1.97 mmol) were added to 4-hydroxy-benzaldehyde (200 mg, 1.64 mmol) in DMF (2 mL) and the resulting mixture was heated to 70° C. for 3 hrs. The reaction mixture was then diluted with water and the resulting was filtered and dried to afford 310 mg (79.1% yield) of 6-(4-formyl-phenoxy)nicotinonitrile. LCMS Purity: 97.3%.

Step 2: Synthesis of 4-(5-Cyano-pyridin-2-yloxy)-benzoic Acid

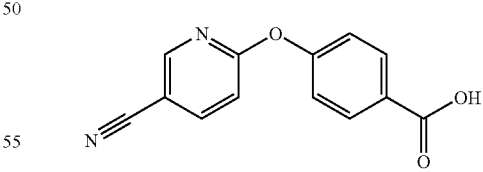

6-(4-formyl-phenoxy)-nicotinonitrile (310 mg, 1.38 mmol) was dissolved in acetone-water mixture (3.5:3) (6.5 mL) and cooled to 0° C. Sulphamic acid (403 mg, 4.15 mmol) and sodium chlorite (499 mg, 5.52 mmol) dissolved in minimum amount of water were added and the resulting mixture was stirred at room temperature for half an hour. The reaction mixture was then diluted with water and extracted with ethyl acetate. The organic layer was washed with brine solution, dried over sodium sulphate and concentrated to afford 288 mg 4-(5-cyano-pyridin-2-yloxy)-benzoic acid, (85.2% yield). LCMS Purity: 83.2%,

Step 3: Synthesis of 4-(5-Cyano-pyridin-2-yloxy)-N-{2-oxo-2-[4-(2-trifluoromethyl-benzoyl)-piperazin-1-yl]-ethyl}-benzamide

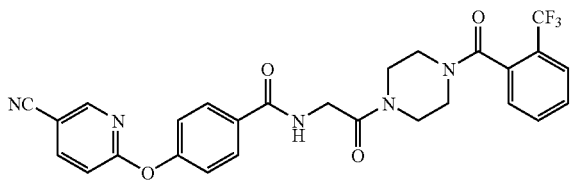

DIPEA (43 mg, 0.34 mmol) was added to a stirred solution of 2-amino-1-[4-(2-trifluoromethyl-benzoyl)-piperazin-1-yl]-ethanone TFA salt. (58 mg, 0.13 mmol) in DMF (1 mL). HOBT (18 mg, 0.13 mmol) and EDCI.HCl (26 mg, 0.13 mmol) were then added at room temperature. After 2 minutes, 4-(5-cyano-pyridin-2-yloxy)benzoic acid (30 mg, 0.11 mmol) was added and the resulting mixture was stirred at room temperature for 4 hrs. Cold water was then added and the product was extracted with EtOAc and the organic layer was washed with brine. The organic phase was dried over $Na_2SO_4$ and concentrated under reduced pressure to afford 34.4 mg (57.3% yield) of 4-(5-cyano-pyridin-2-yloxy)-N-{2-oxo-2-[4-(2-trifluoromethyl-benzoyl)-piperazin-1-yl]-ethyl}-benzamide. LCMS Purity: 85.6%, $^1$H NMR ($CDCl_3$): δ 8.5 (ds, 1H), 8.0-7.9 (s, 3H), 7.8-7.5 (m, 4H), 7.5-7.4 (m, 1H), 7.0 (m, 2H), 4.5-3.5 (m, 8H), 3.5-3.0 (m, 3H).

107) Synthesis of Biphenyl-4-carboxylic acid {2-[4-(2-amino-benzoyl)-piperazin-1-yl]-2-oxo-ethyl}-amide

Step 1: Synthesis of [2-(4-{2-[(Biphenyl-4-carbonyl)-amino]-acetyl}-piperazine-1-carbonyl)-phenyl]-carbamic Acid tert-butyl ester

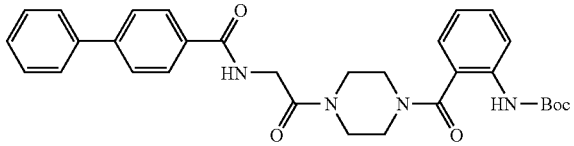

DIPEA (194.78 mg, 0.26 mL, 0.15 mmol) was added to a stirred solution of 2-tert-butoxycarbonylamino-benzoic acid (79.47 mg, 0.33 mmol) in DMF (3 mL). HOBT (49.7 mg, 0.36 mmol) and EDCI (160.5 mg, 0.83 mmol) were then added at room temperature. After 2 minutes, Biphenyl-4-carboxylic acid (2-oxo-2-piperazin-1-yl-ethyl)-amide (130 mg, 0.4 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silicagel of 60-120 mesh and 60% EtOAc in Hexane as eluent) to afford 90 mg (49.5% yield) [2-(4-{2-[(Biphenyl-4-carbonyl)-amino]-acetyl}-piperazine-1-carbonyl)-phenyl]-carbamic acid tert-butyl ester

Step 2: Synthesis of Biphenyl-4-carboxylic acid {2-[4-(2-amino-benzoyl)-piperazin-1-yl]-2-oxo-ethyl}-amide

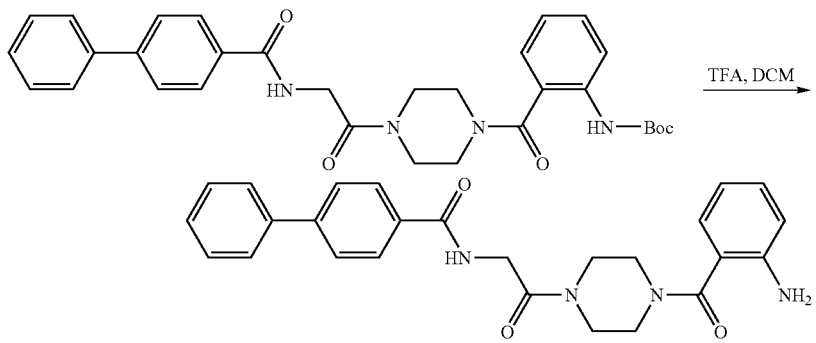

Trifluoroacetic acid (0.6 mL) was added to a stirred cold (0-5° C.) solution of [2-(4-{2-[(Biphenyl-4-carbonyl)-amino]-acetyl}-piperazine-1-carbonyl)-phenyl]-carbamic acid tert-butyl ester (90 mg, 0.165 mmol) in DCM (4 mL). Stirring was continued at same temperature for 4 hr. The mixture was quenched with DIPEA (1.1 ml) and cold water was then added and the product was extracted with DCM and the organic layer was washed with brine. The organic phase was dried over $Na_2SO_4$ and concentrated under reduced pressure to get the residue. The obtained residue was purified by column chromatography (using neutral alumina and 100% EtOAc as eluent) to afford 30 mg (40.8% yield) of biphenyl-4-carboxylic acid {2-[4-(2-amino-benzoyl)-piperazin-1-yl]-2-oxo-ethyl}-amide. LCMS Purity: 98.48%. $^1$H NMR ($CDCl_3$): δ 7.9 (d, 2H), 7.68 (d, 2H), 7.62 (d, 2H), 7.5-7.4 (t, 3H), 7.4 (m, 1H), 7.3 (s, 1H), 7.2 (d, 1H), 7.08 (dd, 1H), 6.8-6.7 (m, 2H), 4.4 (s, 1H), 4.3 (d, 2H), 3.7 (d, 6H), 3.56 (t, 2H), 3.3 (s, 1H).

108) Synthesis of Biphenyl-4-carboxylic acid {2-[4-(3,5-dichloro-benzoyl)-piperazin-1-yl]-2-oxo-ethyl}-amide

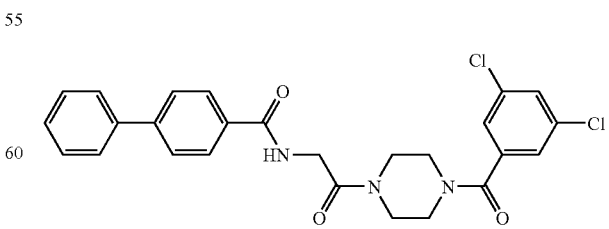

DIPEA (149.8 mg, 0.2 mL, 1.15 mmol) was added to a stirred solution of 3,5-dichloro-benzoic acid (49.2 mg, 0.25 mmol) in DMF (3 mL). HOBT (38.2 mg, 0.28 mmol) and EDCI (123 mg, 0.34 mmol) were then added at room temperature. After 2 minutes, Biphenyl-4-carboxylic acid (2-oxo-2-piperazin-1-yl-ethyl)-amide (100 mg, 0.30 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 60% EtOAc in Hexane as eluent) to afford 42 mg (32.8% yield) of biphenyl-4-carboxylic acid {2-[4-(3,5-dichloro-benzoyl)-piperazin-1-yl]-2-oxo-ethyl}-amide. LCMS Purity: 98.36%. $^1$H NMR (DMSO-$d_6$): δ 8.7-8.62 (t, 1H), 8.0-7.94 (d, 2H), 7.84-7.7 (m, 5H), 7.58-7.46 (m, 4H), 7.44-7.36 (m, 1H), 4.26-4.1 (bs, 2H), 3.74-3.46 (bs, 7H), 3.42-3.34 (m, 1H).

109) Synthesis of Biphenyl-4-carboxylic acid {2-[4-(2-fluoro-6-trifluoromethyl-benzoyl)-piperazin-1-yl]-2-oxo-ethyl}-amide

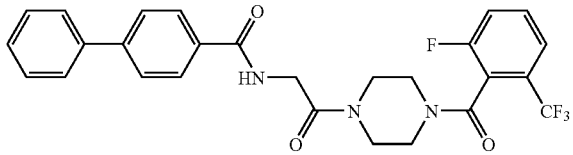

DIPEA (118 mg, 0.16 mL, 0.92 mmol) was added to a stirred solution of 2-fluoro-6-trifluoromethyl-benzoic acid (48 mg, 0.23 mmol) in DMF (2 mL). HOBT (46 mg, 0.35 mmol) and EDCI (100 mg, 0.57 mmol) were then added at room temperature. After 2 minutes, Biphenyl-4-carboxylic acid (2-oxo-2-piperazin-1-yl-ethyl)-amide (75 mg, 0.23 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using basic alumina and 10% MeOH in $CHCl_3$ as eluent) to afford 60 mg (50.8% yield) of biphenyl-4-carboxylic acid {2-[4-(2-fluoro-6-trifluoromethyl-benzoyl)-piperazin-1-yl]-2-oxo-ethyl}-amide. LCMS Purity: 96.5%. $^1$H NMR (CDCl$_3$): δ 7.9 (m, 2H), 7.6 (m, 6H), 7.4 (m, 4H), 4.3 (m, 2H), 3.8 (m, 3H), 3.8 (m, 3H), 3.6-(m, 2H), 3.5 (m, 1H) 3.3 (m, 2H).

110) Synthesis of Biphenyl-4-carboxylic acid {2-[4-(2-bromo-5-nitro-benzoyl)-piperazin-1-yl]-2-oxo-ethyl}-amide

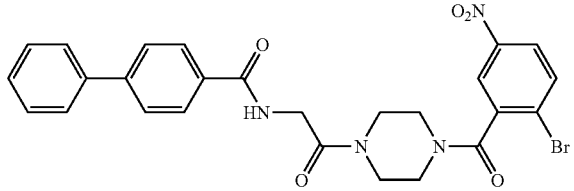

DIPEA (230 mg, 0.33 mL, 1.8 mmol) was added to a stirred solution of 2-bromo-5-nitro-benzoic acid (114 mg, 0.46 mmol) in DMF (2 mL). HOBT (93 mg, 0.69 mmol) and EDCI (220 mg, 1.15 mmol) were then added at room temperature. After 2 minutes, Biphenyl-4-carboxylic acid (2-oxo-2-piperazin-1-yl-ethyl)-amide (150 mg, 0.46 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using basic alumina and 10% MeOH in $CHCl_3$ as eluent) to afford 100 mg (39.5% yield) of biphenyl-4-carboxylic acid {2-[4-(2-bromo-5-nitro-benzoyl)-piperazin-1-yl]-2-oxo-ethyl}-amide. LCMS Purity: 96.4%. $^1$H NMR (CDCl$_3$): δ 8.4 (bs, 1H), 8.2 (m, 2H), 7.9 (d, 2H), 7.6 (m, 5H), 7.5 (m, 3H), 7.4 (m, 1H), 6.0 (d, 1H), 4.4 (m, 2H), 4.0 (m, 2H), 3.8 (m, 3H), 3.6 (m, 3H), 3.5-(m, 2H).

111) Synthesis of Biphenyl-4-carboxylic acid {2-[4-(2,6-dichloro-benzoyl)-piperazin-1-yl]-2-oxo-ethyl}-amide

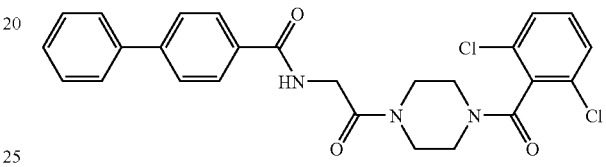

DIPEA (159.8 mg, 0.21 mL, 1.2 mmol) was added to a stirred solution of 2,6-dichloro-benzoic acid (59 mg, 0.3 mmol) in DMF (3 mL). HOBT (45.9 mg, 0.34 mmol) and EDCI (130.4 mg, 0.68 mmol) were then added at room temperature. After 2 minutes, Biphenyl-4-carboxylic acid (2-oxo-2-piperazin-1-yl-ethyl)-amide (120 mg, 0.37 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 60% EtOAc in Hexane as eluent) to afford 25 mg (16.3% yield) of biphenyl-4-carboxylic acid {2-[4-(2,6-dichloro-benzoyl)-piperazin-1-yl]-2-oxo-ethyl}-amide. LCMS Purity: 86.98%. $^1$H NMR (CDCl$_3$): δ 7.96-7.86 (d, 2H), 7.72-7.56 (dd, 4H), 7.5-7.34 (m, 6H), 7.32-7.2 (m, 2H), 4.4-4.24 (dd, 2H), 4.0-3.8 (bs, 2H), 3.8-3.6 (m, 3H), 3.6-3.5 (t, 1H), 3.4-3.24 (q, 2H).

112) Synthesis of Synthesis of Biphenyl-4-carboxylic acid {2-[4-(2,6-difluoro-benzoyl)-piperazin-1-yl]-2-oxo-ethyl}-amide

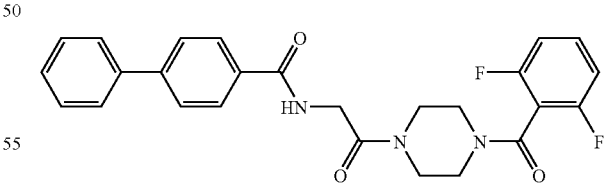

DIPEA (179.7 mg, 0.24 mL, 1.39 mmol) was added to a stirred solution of 2,6-difluoro-benzoic acid (48.8 mg, 0.30 mmol) in DMF (3 mL). HOBT (45.9 mg, 0.34 mmol) and EDCI (148.1 mg, 0.77 mmol) were then added at room temperature. After 2 minutes, Biphenyl-4-carboxylic acid (2-oxo-2-piperazin-1-yl-ethyl)-amide (120 mg, 0.37 mmol) was added and the resulting mixture was stirred at room temperature overnight. Cold water was then added and the product was extracted with EtOAc and the organic layer was washed with brine. The organic phase was dried over $Na_2SO_4$

113) Synthesis of Biphenyl-4-carboxylic acid {2-[4-(2-chloro-pyridine-4-carbonyl)-piperazin-1-yl]-2-oxo-ethyl}-amide

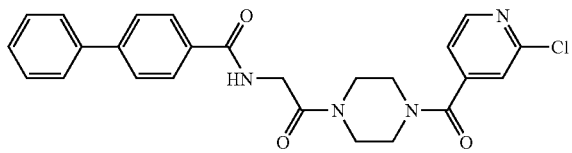

DIPEA (179.7 mg, 0.24 mL, 1.39 mmol) was added to a stirred solution of 6-chloro-pyridine-4-carboxylic acid (48.6 mg, 0.37 mmol) in DMF (3 mL). HOBT (45.9 mg, 0.34 mmol) and EDCI (148.1 mg, 0.77 mmol) were then added at room temperature. After 2 minutes, Biphenyl-4-carboxylic acid (2-oxo-2-piperazin-1-yl-ethyl)-amide (120 mg, 0.37 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 80% EtOAc in Hexane as eluent) to afford 70 mg (49.2% yield) of biphenyl-4-carboxylic acid {2-[4-(2-chloro-pyridine-4-carbonyl)-piperazin-1-yl]-2-oxo-ethyl}-amide. LCMS Purity: 99.47, $^1$H NMR (DMSO-$d_6$-$D_2O$): δ 8.5 (s, 1H), 7.96-7.86 (d, 2H), 7.8-7.64 (m, 4H), 7.6-7.34 (m, 5H), 4.2-4.06 (dd, 2H), 3.72-3.42 (m, 6H), 3.38-3.2 (m, 2H).

114) Synthesis of Biphenyl-4-carboxylic acid {2-[4-(6-chloro-pyridine-3-carbonyl)-piperazin-1-yl]-2-oxo-ethyl}-amide

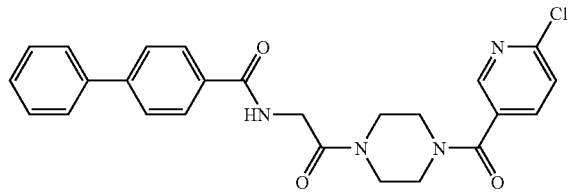

DIPEA (179.7 mg, 0.24 mL, 1.39 mmol) was added to a stirred solution of 6-chloro-pyridine-3-carboxylic acid (48.6 mg, 0.37 mmol) in DMF (3 mL). HOBT (45.9 mg, 0.34 mmol) and EDCI (148.1 mg, 0.77 mmol) were then added at room temperature. After 2 minutes, Biphenyl-4-carboxylic acid (2-oxo-2-piperazin-1-yl-ethyl)-amide (120 mg, 0.37 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 90% EtOAc in Hexane as eluent) to afford 58 mg (40.8% yield) of biphenyl-4-carboxylic acid {2-[4-(6-chloro-pyridine-3-carbonyl)-piperazin-1-yl]-2-oxo-ethyl}-amide. LCMS Purity: 95.92, $^1$H NMR (DMSO-$d_6$): δ 8.7-8.6 (t, 1H), 8.5 (d, 1H), 8.0-7.9 (m, 3H), 7.84-7.7 (q, 4H), 7.68-7.6 (d, 1H), 7.54-7.46 (t, 2H), 7.46-7.36 (m, 1H), 4.2 (bs, 2H), 3.8-3.4 (m, 8H).

115) Synthesis of Biphenyl-4-carboxylic acid {2-[4-(2-chloro-pyridine-3-carbonyl)-piperazin-1-yl]-2-oxo-ethyl}-amide

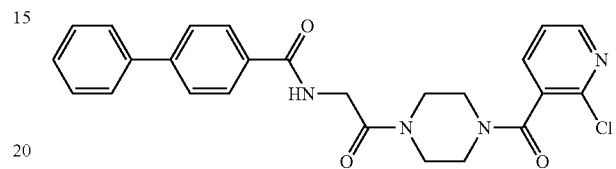

DIPEA (179.7 mg, 0.24 mL, 1.39 mmol) was added to a stirred solution of 2-chloro-pyridine-3-carboxylic acid (48.6 mg, 0.37 mmol) in DMF (3 mL). HOBT (45.9 mg, 0.34 mmol) and EDCI (148.1 mg, 0.77 mmol) were then added at room temperature. After 2 minutes, Biphenyl-4-carboxylic acid (2-oxo-2-piperazin-1-yl-ethyl)-amide (120 mg, 0.37 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 90% EtOAc in Hexane as eluent) to afford 65 mg (45.7% yield) of biphenyl-4-carboxylic acid {2-[4-(2-chloro-pyridine-3-carbonyl)-piperazin-1-yl]-2-oxo-ethyl}-amide. LCMS Purity: 99.71, $^1$H NMR (DMSO-$d_6$): δ 8.7-8.6 (t, 1H), 8.5 (d, 1H), 8.0-7.9 (d, 3H), 7.84-7.7 (q, 4H), 7.6-7.46 (m, 3H), 7.44-7.36 (m, 1H), 4.26-4.3 (m, 2H), 3.8-3.58 (m, 4H), 3.58-3.46 (m, 2H), 3.28-3.12 (m, 2H).

116) Synthesis of Biphenyl-4-carboxylic acid {2-[4-(5-amino-2-bromo-benzoyl)-piperazin-1-yl]-2-oxo-ethyl}-amide

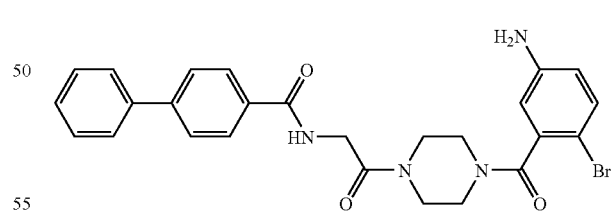

10% Pd/C (60 mg) was added to a stirred solution of biphenyl-4-carboxylic acid {2-[4-(2-bromo-5-nitro-benzoyl)-piperazin-1-yl]-2-oxo-ethyl}-amide (120 mg, 2.4 mmol) in methanol (10 mL) and the mixture was stirred under an atmosphere of hydrogen with pressure overnight. The mixture was then filtered over celite and the filtrate concentrated to afford 46 mg (40.7%) of biphenyl-4-carboxylic acid {2-[4-(5-amino-2-bromo-benzoyl)-piperazin-1-yl]-2-oxo-ethyl}-amide. LCMS: 95.6%, $^1$H NMR (CDCl$_3$): δ 7.9 (m, 2H), 7.6 (m, 4H), 7.4 (m, 4H), 6.8 (m, 2H), 4.2 (m, 2H), 4.0 (m, 11H), 3.6 (m, 3H).

(Continuation from previous page:)

and concentrated under reduced pressure to get the residue. The obtained residue was purified by column chromatography (using silica gel of 60-120 mesh and 60% EtOAc in Hexane as eluent) to afford 55 mg (38.4% yield) of biphenyl-4-carboxylic acid {2-[4-(2,6-difluoro-benzoyl)-piperazin-1-yl]-2-oxo-ethyl}-amide. LCMS Purity: 99.12%. $^1$H NMR (DMSO-$d_6$): δ 8.7-8.6 (t, 1H), 8.0-7.94 (d, 2H), 7.82-7.7 (q, 4H), 7.62-7.54 (m, 1H), 7.54-7.38 (m, 3H), 7.3-7.2 (t, 2H), 4.2 (dd, 2H), 3.8-3.4 (m, 8H).

117) Synthesis of 3'-Dimethylamino-biphenyl-4-carboxylic acid {2-oxo-2-[4-(2-trifluoromethyl-benzoyl)-piperazin-1-yl]-ethyl}-amide

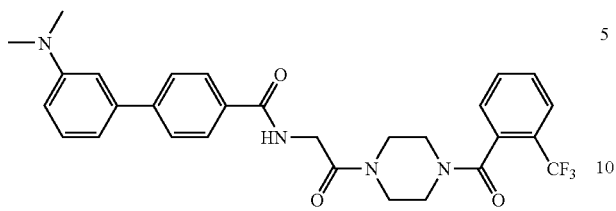

DIPEA (120 mg, 0.16 mL, 0.927 mmol) was added to a stirred solution of 5-(2-oxo-2,3-dihydro-benzooxazol-6-yl)-1H-pyrazole-3-carboxylic acid (65 mg, 0.26 mmol) in DMF (2.5 mL). HOBT (37.6 mg, 0.27 mmol) and EDCI (53.4 mg, 0.2783 mmol) were then added at room temperature. After 2 minutes, 2-amino-1-[4-(5-fluoro-2-trifluoromethyl-benzoyl)-piperazin-1-yl]-148 ethanone hydrochloride salt (98 mg, 0.265 mmol) was added and the resulting mixture was stirred at room temperature overnight. Cold water was then added and the product was extracted with EtOAc and the organic layer was washed with 10% HCl solution, saturated bicarbonate solution followed by brine. The organic phase was dried over $Na_2SO_4$ and concentrated under reduced pressure to get the residue. The obtained residue was purified by column chromatography (using neutral alumina and 60% EtOAc in hexane as eluent) to afford 92 mg (51.6% yield) of 3'-dimethylamino-biphenyl-4-carboxylic acid {2-oxo-2-[4-(2-trifluoromethyl-benzoyl)-piperazin-1-yl]-ethyl}-amide. LCMS Purity: 95.15%. $^1$H NMR (DMSO-$d_6$): δ 8.7-8.6 (d, 1H), 8.0-7.9 (d, 2H), 7.9-7.74 (m, 4H), 7.74-7.65 (m, 1H), 7.6-7.54 (t, 1H), 7.3 (t, 1H), 7.0 (m, 2H), 6.8 (dd, 1H), 4.3-4.1 (d, 2H), 3.8-3.5 (m, 4H), δ 3.5-3.4 (m, 2H), 3.3-3.1 (m, 2H), 3.0 (s, 6H).

118) Synthesis of Biphenyl-4-carboxylic acid methyl-{2-oxo-2-[4-(2-trifluoromethyl-benzoyl)-piperazin-1-yl]-ethyl}-amide

Step 1: Synthesis of [(Biphenyl-4-carbonyl)-methyl-amino]-acetic Acid Methyl Ester

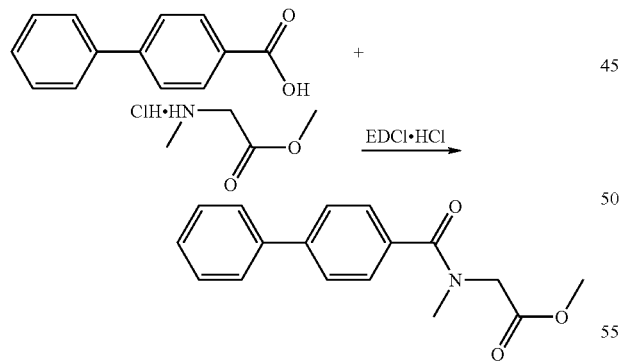

DIPEA (880 mg, 1.2 mL, 6.8 mmol) was added to a stirred solution of biphenyl-4-carboxylic acid (300 mg, 1.5 mmol) in DMF (5 mL). HOBT (224 mg, 1.66 mmol) and EDCI (725 mg, 3.7 mmol) were then added at room temperature. After 2 minutes methylamino-acetic acid methyl ester hydrochloride salt (253 mg, 1.8 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using silica gel of 60-120 mesh and 20% EtOAc in hexane as eluent) filtered the solid precipitated out to afford 330 mg (76.96% yield) of [(biphenyl-4-carbonyl)-methyl-amino]-acetic acid methyl ester.

Step 2: Synthesis of [(Biphenyl-4-carbonyl)-methyl-amino]-acetic Acid

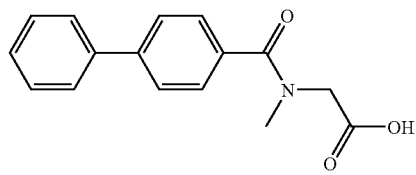

LiOH (293 mg, 6.9 mmol) was added to a stirred solution of [(biphenyl-4-carbonyl)-methyl-amino]-acetic acid methyl ester (330 mg, 1.1 mmol) in THF:MeOH:$H_2O$ (2:2:1, 10 mL), and the resulting mixture was stirred at room temperature for 4 hrs. The reaction mixture was concentrated under reduced pressure to get the residue. Cold water was then added and acidified it with 10% aqueous HCl, filtered the solid precipitated to afford 250 mg (79.7% yield) of [(biphenyl-4-carbonyl)-methyl-amino]-acetic acid.

Step 3: Synthesis of Biphenyl-4-carboxylic acid methyl-{2-oxo-2-[4-(2-trifluoromethyl-benzoyl)-piperazin-1-yl]-ethyl}-amide

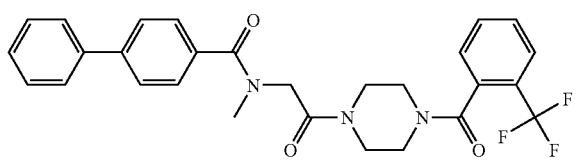

DIPEA (216 mg, 0.3 mL, 1.6 mmol) was added to a stirred solution of [(biphenyl-4-carbonyl)-methyl-amino]-acetic acid (100 mg, 0.37 mmol) in DMF (3 mL). HOBT (55.2 mg, 0.4 mmol) and EDCI (178 mg, 0.92 mmol) were then added at room temperature. After 2 minutes piperazin-1-yl-(2-trifluoromethyl-phenyl)-methanone hydrochloride salt (131 mg, 0.44 mmol) was added and the resulting mixture was stirred at room temperature overnight. Cold water was then added and filtered the solid precipitated out to afford 135 mg (71.3% yield) of biphenyl-4-carboxylic acid methyl-{2-oxo-2-[4-(2-trifluoromethyl-benzoyl)-piperazin-1-yl]-ethyl}-amide. LCMS Purity: 96.56%. $^1$H NMR (DMSO-$d_6$): δ 7.9-7.6 (m, 7H), 7.6-7.45 (q, 4H), δ 7.45-7.3 (q, 2H), 4.5-4.2 (m, 2H), 4.15 (s, 1H), 3.8-3.5 (m, 4H), 3.5-3.4 (m, 2H), 3.25-3.1 (m, 2H), 3.0 (s, 3H).

119) Synthesis of Biphenyl-4-carboxylic acid {2-[4-(2-bromo-5-methoxy-benzoyl)-3-methyl-piperazin-1-yl]-2-oxo-ethyl}-amide

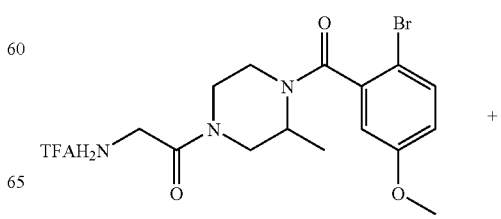

-continued

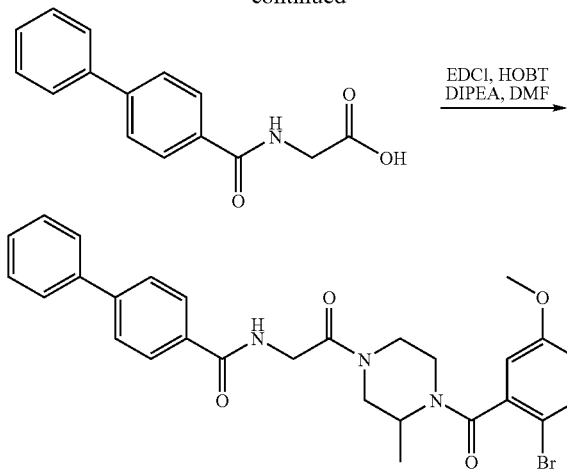

DIPEA (362 mg, 0.48 mL, 2.8 mmol) was added to a stirred solution of [(Biphenyl-4-carbonyl)-amino]-acetic acid (262 mg, 1.03 mmol) in DMF (3 mL). HOBT (151.6 mg, 1.12 mmol) and EDCI (214 mg, 1.12 mmol) were then added at room temperature. After 2 minutes, 2-Amino-1-[4-(2-bromo-5-methoxy-benzoyl)-3-methyl-piperazin-1-yl]-ethanone trifluoroacetic acid salt (400 mg, 0.93 mmol) (prepared by the method described above) was added and the resulting mixture was stirred at room temperature overnight. Cold water was then added and filtered the solid precipitated to 480 mg (93.3% yield) of biphenyl-4-carboxylic acid {2-[4-(2-bromo-5-methoxy-benzoyl)-3-methyl-piperazin-1-yl]-2-oxo-ethyl}-amide. LCMS Purity: 98.8%. $^1$H NMR (DMSO-d6): δ 8.5 (m, 1H), 8.0 (d, 2H), 7.8-7.7 (m, 4H), 7.6-7.4 (m, 4H), 7.0 (m, 2H), 4.75 (s, 1H), 4.4 (m, 1H), 4.2 (m, 2H), 3.8 (d, 4H), 3.2 (m, 2H), 1.4-1.1 (m, 4H).

120) Synthesis of Biphenyl-4-carboxylic acid {2-oxo-2-[4-(2,4,5-trifluoro-benzoyl)-piperazin-1-yl]-ethyl}-amide

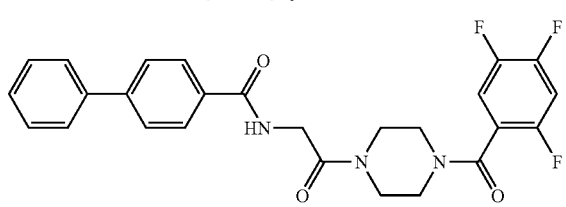

DIPEA (149.8 mg, 0.2 mL, 1.15 mmol) was added to a stirred solution of 3,4,5-trifluoro-benzoic acid (45.3 mg, 0.25 mmol) in DMF (3 mL). HOBT (38.2 mg, 0.28 mmol) and EDCI (123 mg, 0.34 mmol) were then added at room temperature. After 2 minutes, Biphenyl-4-carboxylic acid (2-oxo-2-piperazin-1-yl-ethyl)-amide (100 mg, 0.30 mmol) was added and the resulting mixture was stirred at room temperature overnight. Cold water was then added and the product was extracted with EtOAc and the organic layer was washed with brine. The organic phase was dried over Na$_2$SO$_4$ and concentrated under reduced pressure to get the residue. The obtained residue was purified by column chromatography (using silica gel of 60-120 mesh and 50% EtOAc in Hexane as eluent) to afford 45 mg (36.2% yield) of biphenyl-4-carboxylic acid {2-oxo-2-[4-(2,4,5-trifluoro-benzoyl)-piperazin-1-yl]-ethyl}-amide. LCMS Purity: 92.11%. $^1$H NMR (DMSO-d$_6$): δ 7.97-7.9 (d, 2H), 7.74-7.6 (q, 4H), 7.52-7.44 (t, 2H), 7.44-7.36 (m, 1H), 7.36-7.28 (m, 1H), 7.02-6.92 (m, 1H), 4.4-4.26 (dd, 2H), 3.98-3.82 (m, 3H), 3.78-3.72 (t, 1H), 3.68-3.62 (t, 1H), 3.58-3.52 (m, 1H), 3.48-3.38 (m, 2H).

121) Synthesis of Biphenyl-4-carboxylic acid {2-[4-(6-bromo-pyridine-2-carbonyl)-piperazin-1-yl]-2-oxo-ethyl}-amide

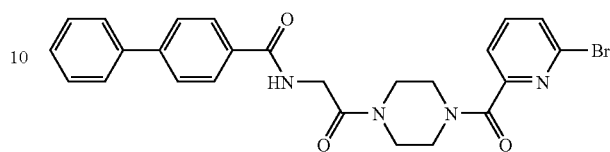

DIPEA (149.8 mg, 0.2 mL, 1.15 mmol) was added to a stirred solution of 6-bromo-pyridine-2-carboxylic acid (52.03 mg, 0.25 mmol) in DMF (3 mL). HOBT (38.2 mg, 0.28 mmol) and EDCI (123 mg, 0.34 mmol) were then added at room temperature. After 2 minutes, Biphenyl-4-carboxylic acid (2-oxo-2-piperazin-1-yl-ethyl)-amide (100 mg, 0.30 mmol) was added and the resulting mixture was stirred at room temperature overnight. Cold water was then added and the product was extracted with EtOAc and the organic layer was washed with brine. The organic phase was dried over Na$_2$SO$_4$ and concentrated under reduced pressure to get the residue. The obtained residue was purified by column chromatography (using silica gel of 60-120 mesh and 80% EtOAc in Hexane as eluent) to afford 32 mg (24.6% yield) of biphenyl-4-carboxylic acid {2-[4-(6-bromo-pyridine-2-carbonyl)-piperazin-1-yl]-2-oxo-ethyl}-amide. LCMS Purity: 93.11%. $^1$H NMR (CDCl$_3$): δ 8.0-7.9 (d, 2H), 7.8-7.66 (m, 4H), 7.66-7.58 (m, 7H), 7.52-7.46 (t, 2H), 7.44-7.38 (m, 1H), 7.38-7.32 (m, 1H), 4.4-4.3 (dd, 2H), 3.92-3.74 (m, 6H), 3.7-3.6 (m, 2H).

122) Synthesis of Biphenyl-4-carboxylic acid {2-[4-(2-chloro-5-fluoro-benzoyl)-piperazin-1-yl]-2-oxo-ethyl}-amide

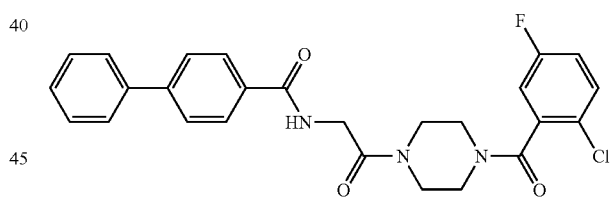

DIPEA (149.8 mg, 0.2 mL, 1.15 mmol) was added to a stirred solution of 2-chloro-5-fluoro-benzoic acid (44.9 mg, 0.25 mmol) in DMF (3 mL). HOBT (38.2 mg, 0.28 mmol) and EDCI (123 mg, 0.34 mmol) were then added at room temperature. After 2 minutes, Biphenyl-4-carboxylic acid (2-oxo-2-piperazin-1-yl-ethyl)-amide (100 mg, 0.30 mmol) was added and the resulting mixture was stirred at room temperature overnight. Cold water was then added and the product was extracted with EtOAc and the organic layer was washed with brine. The organic phase was dried over Na$_2$SO$_4$ and concentrated under reduced pressure to get the residue. The obtained residue was purified by column chromatography (using silica gel of 60-120 mesh and 60% EtOAc in Hexane as eluent) to afford 35 mg (28.3% yield) of biphenyl-4-carboxylic acid {2-[4-(2-chloro-5-fluoro-benzoyl)-piperazin-1-yl]-2-oxo-ethyl}-amide. LCMS Purity: 98.32%. $^1$H NMR (DMSO-d$_6$): δ 8.7-8.6 (t, 1H), 8.02-7.92 (d, 2H), 7.84-7.7 (q, 4H), 7.68-7.58 (m, 1H), 7.54-7.28 (m, 5H), 4.3-4.1 (dd, 2H), 3.8-3.44 (m, 6H), 3.26-3.12 (m, 2H).

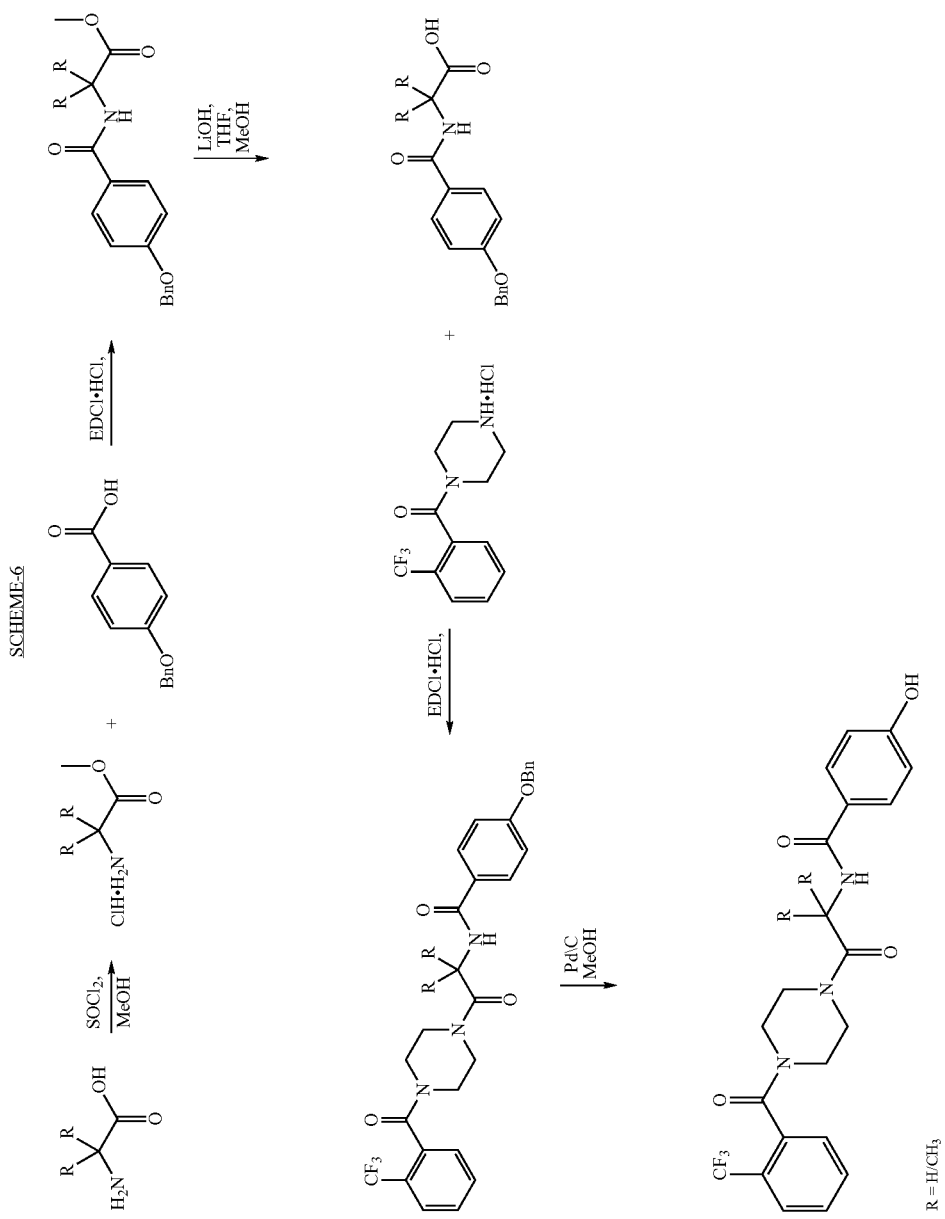

Step 1: Synthesis of 2-Amino-2-methyl-propionic Acid Methyl Ester

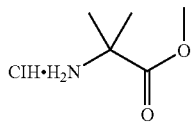

To a stirred solution of 2-amino-2-methyl-propionic acid (1 gm, 9.6 mol) in MeOH (20 ml) cooled in ice bath, thionyl-chloride (1.38 gm, 0.85 ml, 11.63 mol) was added drop wise slowly and left at room temperature overnight. The reaction mass was concentrated to get the residue which was washed with hexane twice to afford 2-amino-2-methyl-propionic acid methyl ester hydrochloride salt 1.43 gm (96.62%). $^1$H NMR (DMSO-d$_6$): δ 8.9 (s, 2H), 8.6 (s, 1H), 3.8 (s, 3H), 1.55 (s, 6H), 1.5 (s, 3H).

Step 2: Synthesis of 2-(4-Benzyloxy-benzoylamino)-2-methyl-propionic Acid Methyl Ester

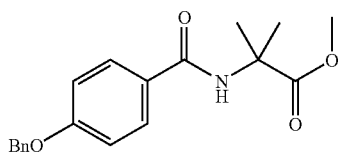

DIPEA (407 mg, 0.28 mL, 3.15 mmol) was added to a stirred solution of 4-benzyloxy-benzoic acid (200 mg, 0.87 mmol)(prepared by the method as described above) in DMF (2 mL). HOBT (142 mg, 1.05 mmol) and EDCI (201 mg, 1.05 mmol) were then added at room temperature. After 2 minutes, 2-amino-2-methyl-propionic acid methyl ester (161 mg, 1.05 mmol) was added and the resulting mixture was stirred at room temperature overnight. Cold water was then added and filtered the solid precipitated out to afford 200 mg (70% yield) of 2-(4-benzyloxy-benzoylamino)-2-methyl-propionic acid methyl ester. LCMS Purity: 93%.

Step 3: Synthesis of 2-(4-Benzyloxy-benzoylamino)-2-methyl-propionic Acid

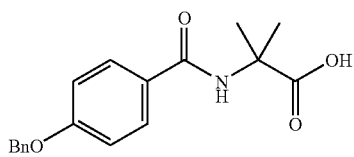

LiOH (38.5 mg, 0.9 mmol) was added to a stirred solution of 2-(4-benzyloxy-benzoylamino)-2-methyl-propionic acid methyl ester (200 mg, 0.6 mmol) in THF:MeOH:H$_2$O (3:1:1, 3.5 mL), and the resulting mixture was stirred at room temperature for 4 hrs. The reaction mixture was concentrated under reduced pressure to get the residue. Cold water was then added, acidified it with aqueous citric acid solution and extracted with EtOAc. The organic phase was dried over Na$_2$SO$_4$ and concentrated under reduced pressure to afford 170 mg (90% yield) of 2-(4-benzyloxy-benzoylamino)-2-methyl-propionic acid.

Step 4

123) Synthesis of 4-Benzyloxy-N-{1,1-dimethyl-2-oxo-2-[4-(2-trifluoromethyl-benzoyl)-piperazin-1-yl]-ethyl}-benzamide

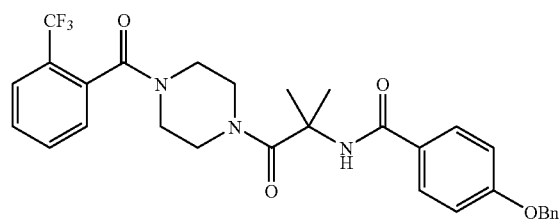

DIPEA (284 mg, 0.19 mL, 1.62 mmol) was added to a stirred solution of 2-(4-benzyloxy-benzoylamino)-2-methyl-propionic acid (170 mg, 0.54 mmol) in DMF (2 mL). HOBT (88 mg, 0.65 mmol) and EDCI (125 mg, 0.65 mmol) were then added at room temperature. After 2 minutes, piperazin-1-yl-(2-trifluoromethyl-phenyl)-methanone hydrochloride salt (192 mg, 0.65 mmol) was added and the resulting mixture was stirred at room temperature overnight. Cold water was then added and filtered the solid precipitated out to afford 150 mg (50% yield) of 4-benzyloxy-N-{1,1-dimethyl-2-oxo-2-[4-(2-trifluoromethyl-benzoyl)-piperazin-1-yl]-ethyl}-benzamide. LCMS Purity: 93.29%. $^1$H NMR (DMSO-d$_6$): δ 8.4 (bs, 1H), 7.6-7.8 (m, 5H), 7.4 (m, 6H), 7.0-7.1 (d, 2H), 5.2 (m, 2H), 3.5 (m, 5H), 3.0 (m, 3H), 1.4 (s, 6H).

124) Synthesis of N-{1,1-Dimethyl-2-oxo-2-[4-(2-trifluoromethyl-benzoyl)-piperazin-1-yl]-ethyl}-4-hydroxy-benzamide

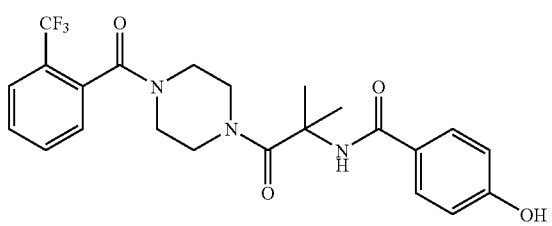

Pd/c (20 mg) was added to a stirred solution of 4-benzyloxy-N-{1,1-dimethyl-2-oxo-2-[4-(2-trifluoromethyl-benzoyl)-piperazin-1-yl]-ethyl}-benzamide (70 mg, 0.12 mmol) in a mixture methanol (2 mL) and ethyl acetate (5 ml) and stirring was continued at room temperature under hydrogen atmosphere for 2 hrs. The mixture was filtered over a bed of celite. The celite was washed with methanol and the filtrate was concentrated under reduced pressure to afford 50 mg (86.2% yield) of N-{1,1-dimethyl-2-oxo-2-[4-(2-trifluoromethyl-benzoyl)-piperazin-1-yl]-ethyl}-4-hydroxy-benzamide. LCMS Purity: 95.26%. $^1$H NMR (DMSO): δ 8.2-8.3 (bs, 1H), 7.5-7.9 (m, 6H), 7.4 (d, 2H), 6.8 (d, 2H), 3.5 (m, 6H), 3 (m, 2H), 1.4 (s, 6H).

125) Synthesis of 4-Benzyloxy-N-{1-methyl-2-oxo-2-[4-(2-trifluoromethyl-benzoyl)-piperazin-1-yl]-ethyl}-benzamide

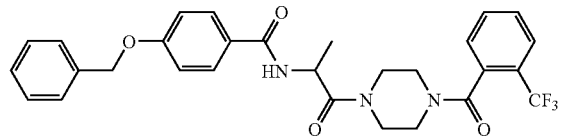

DIPEA (131 mg, 0.17 mL, 0.76 mmol) was added to a stirred solution of 4-Benzyloxy-benzoic acid (58 mg, 0.25 mmol) in DMF (2 mL). HOBT (41 mg, 0.3 mmol) and EDCI (58 mg, 0.3 mmol) were then added at room temperature. After 2 minutes, 2-amino-1-[4-(2-trifluoromethyl-benzoyl)-piperazin-1-yl]-propan-1-one (85 mg, 0.25 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to get the residue. The obtained residue was purified by column chromatography (using 60-120 silica gel and 10% MeOH in $CHCl_3$ as eluent) to afford 65 mg (47% yield) of 4-benzyloxy-N-{1-methyl-2-oxo-2-[4-(2-trifluoromethyl-benzoyl)-piperazin-1-yl]-ethyl}-benzamide. LCMS Purity: 95%. $^1$H NMR ($CDCl_3$): δ 7.76 (m, 3H), 7.6 (m, 2H), 7.4-7.3 (m, 5H), 7.1 (d, 1H), 7.0 (d, 2H), 5.22 (s, 2H), 4.2 (d, 1H), 3.82 (m, 2H), 3.7-3.4.(m, 6H), 2.0 (m, 1H), 1.4 (dd, 3H).

126) Synthesis of 4-Hydroxy-N-{1-methyl-2-oxo-2-[4-(2-trifluoromethyl-benzoyl)-piperazin-1-yl]-ethyl}-benzamide

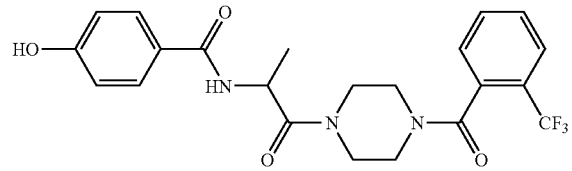

Ammonium formate (49 mg, 0.77 mmol) was added to a stirred solution of 4-benzyloxy-N-{1-methyl-2-oxo-2-[4-(2-trifluoromethyl-benzoyl)-piperazin-1-yl]-ethyl}-benzamide (42 mg, 0.07 mmol) in MeOH (10 mL). 10% Pd/c (10 mg) was then added and the resulting mixture stirred at room temperature under an inert atmosphere. The reaction mixture was then stirred at reflux temperature for 2 hrs. The mixture was filtered over a bed of celite. The celite was washed with MeOH and the filtrate was concentrated. The residue was dissolved in EtOAc, washed with water, followed by saturated brine solution. The organic layer was dried over sodium sulphate and concentrated in vacuo to afford 28 mg (82% yield) of 4-hydroxy-N-{1-methyl-2-oxo-2-[4-(2-trifluoromethyl-benzoyl)-piperazin-1-yl]-ethyl}-benzamide. LCMS Purity: 95%. $^1$H NMR (DMSO-$d_6$): δ 7.76 (d, 1H), 7.60 (m, 4H), 7.36 (t, 1H), 7.26 (t, 1H), 6.8 (d, 2H), 5.2 (m, 1H), 4.2 (m, 1H), 3.9-3.4 (m, 8H), 1.4 (dd, 3H).

SCHEME-7

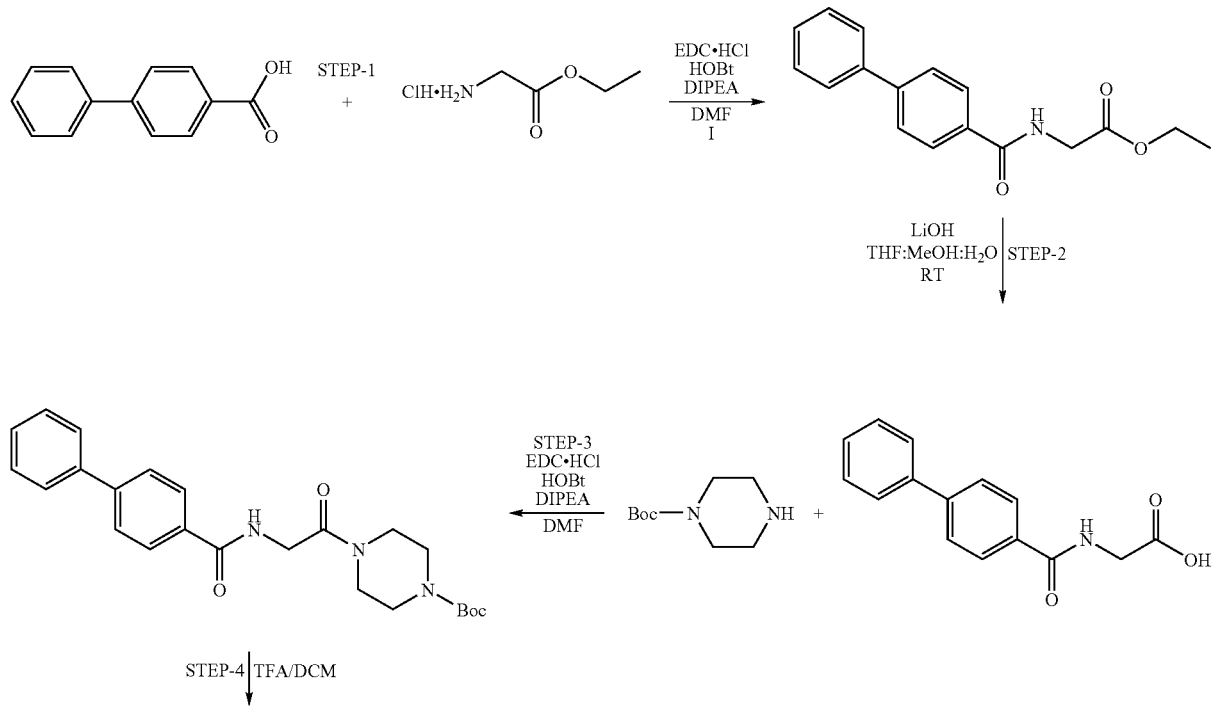

-continued

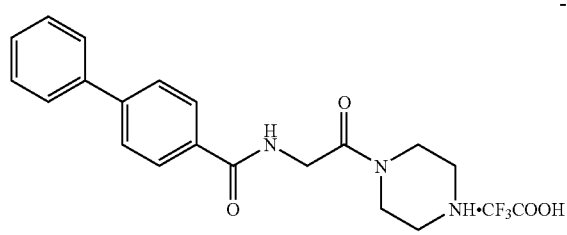 STEP-5 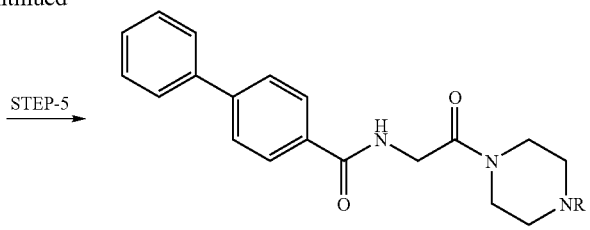

Step 1: Synthesis of [(Biphenyl-4-carbonyl)-amino]-acetic acid ethyl ester

Step 3: Synthesis of 4-{2-[(Biphenyl-4-carbonyl)-amino]-acetyl}-piperazine-1-carboxylicacid tert-butyl ester

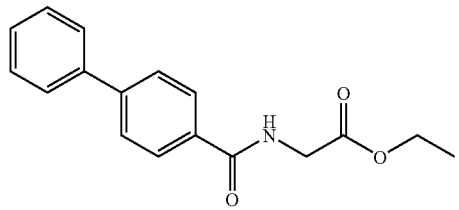

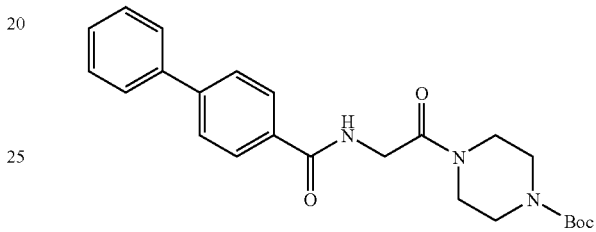

DIPEA (7.825 g, 60.54 mmol) was added to a stirred solution of biphenyl-4-carboxylic acid (4 g, 20.18 mmol) in DMF (40 mL). HOBT (3.27 g, 24.22 mmol) and EDCI.HCl (3.87 mg, 24.22 mmol) were then added at room temperature. After 2 minutes, glycine ethyl ester hydrochloride (3.381 g, 24.22 mmol) was added and the resulting mixture was stirred overnight. The reaction mixture was diluted with cold water and the product was extracted with ethyl acetate. The ethyl acetate layer was washed with saturated brine solution, dried over sodium sulphate and concentrated under reduced pressure to afford 5 g (87.4% yield) of [(biphenyl-4-carbonyl)-amino]-acetic acid ethyl ester. LC-MS purity: 93.4%

Step 2: Synthesis of [(Biphenyl-4-carbonyl)-amino]-acetic acid

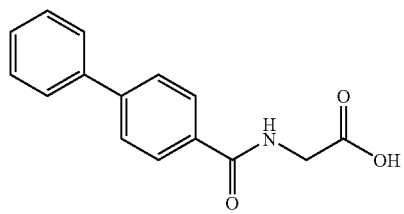

LiOH (1.111 g, 26.47 mmol) was added to a stirred solution of [(biphenyl-4-carbonyl)-amino]-acetic acid ethyl ester (5 g, 17.65 mmol) in THF:MeOH:H$_2$O (3:1:1, 95 mL), and the resulting mixture was stirred at room temperature overnight. The MeOH and THF were evaporated, and the residue was diluted with water (2 mL), acidified with citric acid solution and extracted with EtOAc. The organic layer was washed with saturated brine solution, dried over Na$_2$SO$_4$ and concentrated in vacuo to obtain afford 3.892 g (86.3% yield) of [(biphenyl-4-carbonyl)-amino]-acetic acid. LCMS purity: 96.4%.

DIPEA (2.928 g, 22.66 mmol) was added to a stirred solution of [(biphenyl-4-carbonyl)-amino]-acetic acid (2.892 g, 11.33 mmol) in DMF (30 mL). HOBT (1.835 g, 13.59 mmol) and EDCI.HCl (2.532 g, 13.59 mmol) were then added at room temperature. After 2 minutes, N-Boc-piperazine (3.381 g, 24.22 mmol) was added and the resulting mixture was stirred overnight. The reaction mixture was diluted with cold water and the product was extracted with ethyl acetate. The ethyl acetate layer was washed with saturated brine solution, dried over sodium sulphate and concentrated in vacuo to afford 1.7 g (37.5% yield) of 4-{2-[(biphenyl-4-carbonyl)-amino]-acetyl}-piperazine-1-carboxylicacid tert-butyl ester. LC-MS purity: 82.06%

Step 4: Synthesis of Biphenyl-4-carboxylic acid (2-oxo-2-piperazin-1-yl-ethyl)-amide TFA salt TFA (3.6 mL) was added to a stirred solution of 4-{2-[(biphenyl-4-carbonyl)-amino]-acetyl}-piperazine-1-carboxylicacid tert-butyl ester (1.7 g, 4.01 mmol) in DCM (18 mL) at 0-4° C. and the resulting mixture was stirred at this temperature for 3 hrs. The reaction mixture was concentrated to afford 1.67 g (94.8% yield) of biphenyl-4-carboxylic acid (2-oxo-2-piperazin-1-yl-ethyl)-amide TFA salt. LC-MS purity: 85.4%,

127) Synthesis of Biphenyl-4-carboxylicacid {2-[4-(2,5-dichloro-benzoyl)-piperazin-1-yl]-2-oxo-ethyl}-amide

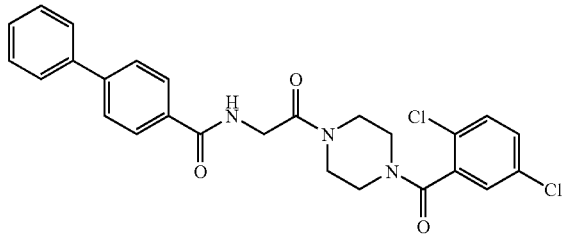

DIPEA (110 mg, 0.85 mmol) was added to a stirred solution of biphenyl-4-carboxylic acid (2-oxo-2-piperazin-1-yl-ethyl)-amide TFA salt (100 mg, 0.22 mmol) in DMF (3 mL). HOBT (28.3 mg, 0.2 mmol) and EDCI.HCl (91.25 mg, 0.47 mmol) were then added. After 2 minutes 2,5-dichlorobenzoic acid (36.4 mg, 0.19 mmol) was added and the resulting mixture was stirred overnight. The reaction mixture was diluted with cold water and the product was precipitated and isolated by filtration to afford crude product, which was purified by preparative HPLC (Column: Zorbax-XDB-9.4×250 mm, 5 μm, mobile phase: A-0.1% Trifluoroacetic acid, B-Acetonitrile, Flow: 7 ml/min). The product obtained was extracted with ethyl acetate and the ethyl acetate layer was washed with NaHCO$_3$ solution, saturated brine solution, dried over sodium sulphate and concentrated to afford 30 mg (26.5% yield) of biphenyl-4-carboxylicacid {2-[4-(2,5-dichloro-benzoyl)-piperazin-1-yl]-2-oxo-ethyl}-amide. LC-MS purity: 99.5%, $^1$H NMR: (DMSO) δ 8.6 (t, 1H), 8.0 (d, 2H), 7.7 (q, 4H), 7.5 (m, 5H), 7.4 (t, 1H), 4.25-4.1 (m, 2H), 3.8-3.6 (m, 4H), 3.5-3.4 (m, 2H), 3.25 (m, 2H).

128) Synthesis of Biphenyl-4-carboxylicacid {2-[4-(2-fluoro-benzoyl)-piperazin-1-yl]-2-oxo-ethyl}-amide

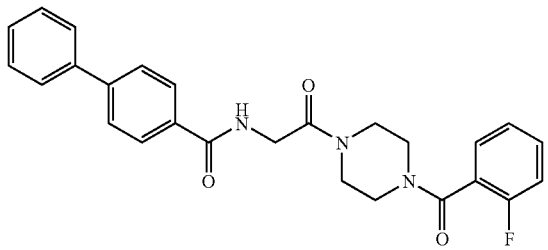

DIPEA (77.35 mg, 0.598 mmol) was added to a stirred solution of biphenyl-4-carboxylicacid (2-oxo-2-piperazin-1-yl-ethyl)-amide TFA salt (70 mg, 0.16 mmol) in DMF (2 mL). HOBT (19.8 mg, 0.15 mmol) and EDCI.HCl (63.74 mg, 0.33 mmol) were then added. After 2 minutes 2-fluorobenzoic acid (18.6 mg, 0.133 mmol) was added and the resulting mixture was stirred overnight. The reaction mixture was diluted with cold water and the product was precipitated and isolated by filtration to afford crude product, which was purified by column chromotography (using silica gel of 160-120 mesh and 50% EtOAc in hexane as eluent) to afford 25 mg (41.4% yield) of Biphenyl-4-carboxylicacid {2-[4-(2-fluoro-benzoyl)-piperazin-1-yl]-2-oxo-ethyl}-amide. LC-MS purity: 94.8%, $^1$H NMR: (CDCl$_3$) δ 7.9 (d, 2H), 7.6 (dd, 4H), 7.4 (m, 4H), 7.2 (s, 1H), 7.1 (t, 1H), 4.4 (dd, 2H), 3.8 (t, 2H), 3.6 (t, 4H), 3.4 (s, 2H).

129) Synthesis of Biphenyl-4-carboxylicacid {2-[4-(2,4-dimethyl-benzoyl)-piperazin-1-yl]-2-oxo-ethyl}-amide

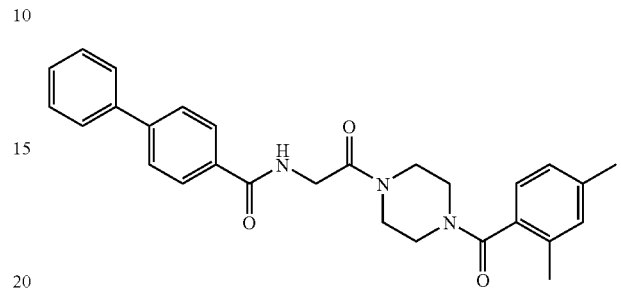

DIPEA (77.35 mg, 0.60 mmol) was added to a stirred solution of biphenyl-4-carboxylicacid (2-oxo-2-piperazin-1-yl-ethyl)-amide TFA salt (70 mg, 0.16 mmol) in DMF (2 mL). HOBT (19.8 mg, 0.14 mmol) and EDCI.HCl (63.74 mg, 0.33 mmol) were then added. After 2 minutes 2,4-dimethylbenzoic acid (20 mg, 0.13 mmol) was added and the resulting mixture was stirred overnight. The reaction mixture was diluted with cold water and the product was precipitated and filtered to afford 50 mg (82.4% yield) of biphenyl-4-carboxylicacid {2-[4-(2,4-dimethyl-benzoyl)-piperazin-1-yl]-2-oxo-ethyl}-amide. LC-MS purity: 95.3%, $^1$H NMR: (CDCl$_3$) δ 7.9 (d, 2H), 7.6 (dd, 4H), 7.5 (t, 2H), 7.35 (t, 1H), 7.3 (s, 1H), 7.0 (s, 3H), 4.4-4.2 (d, 2H), 3.9-

130) Synthesis of Biphenyl-4-carboxylicacid {2-[4-(4-fluoro-benzoyl)-piperazin-1-yl]-2-oxo-ethyl}-amide

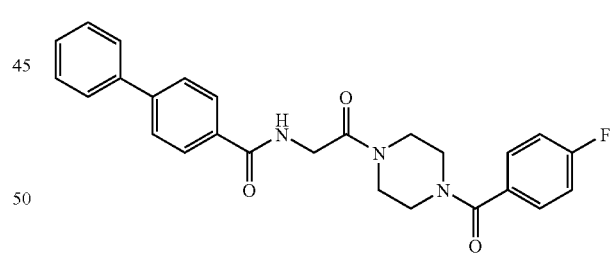

DIPEA (77.35 mg, 0.60 mmol) was added to a stirred solution of biphenyl-4-carboxylicacid (2-oxo-2-piperazin-1-yl-ethyl)-amide TFA salt (70 mg, 0.16 mmol) in DMF (2 mL). HOBT (19.8 mg, 0.14 mmol) and EDCI.HCl (63.74 mg, 0.33 mmol) were then added. After 2 minutes 4-fluorobenzoic acid (18.6 mg, 0.133 mmol) was added and the resulting mixture was stirred overnight. The reaction mixture was diluted with cold water and the product was precipitated and filtered to afford 28 mg (46.7% yield) of biphenyl-4-carboxylicacid {2-[4-(4-fluoro-benzoyl)-piperazin-1-yl]-2-oxo-ethyl}-amide. LC-MS purity: 94.8%, $^1$H NMR Values: (CDCl$_3$) δ 7.9 (d, 2H), 7.7-7.6 (q, 4H), 7.5-7.4 (m, 5H), 7.3 (t, 1H), 7.2-7.1 (t, 2H), 4.4 (d, 2H), 4.0-3.5 (d, 8H).

131) Synthesis of Biphenyl-4-carboxylicacid {2-[4-benzoyl-piperazin-1-yl]-2-oxo-ethyl}-amide

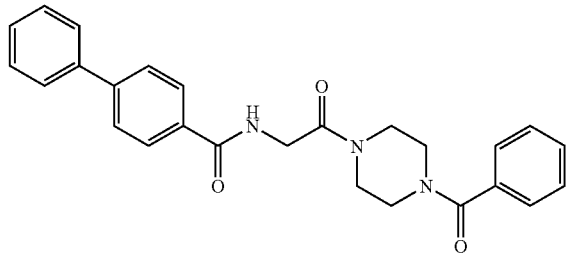

DIPEA (77.35 mg, 0.60 mmol) was added to a stirred solution of biphenyl-4-carboxylicacid (2-oxo-2-piperazin-1-yl-ethyl)-amide TFA salt (70 mg, 0.16 mmol) in DMF (2 mL). HOBT (19.8 mg, 0.14 mmol) and EDCI.HCl (63.74 mg, 0.33 mmol) were then added. After 2 minutes benzoic acid (16.35 mg, 0.13 mmol) was added and the resulting mixture was stirred overnight. The reaction mixture was diluted with cold water and the product was precipitated and filtered to afford 40 mg (67.2% yield) of biphenyl-4-carboxylicacid {2-[4-benzoyl-piperazin-1-yl]-2-oxo-ethyl}-amide. LC-MS purity: 92.6%, $^1$H NMR Values: (CDCl$_3$) δ 7.9 (d, 2H), 7.7 (d, 2H), 7.6 (d, 2H), 7.5-7.4 (m, 8H), 7.3 (s, 1H), 4.4 (s, 2H), 3.8 (s, 4H), 3.6 (s, 4H).

132) Synthesis of Biphenyl-4-carboxylicacid {2-[4-(2-trifluoromethyl-benzyl)-piperazin-1-yl]-2-oxo-ethyl}-amide

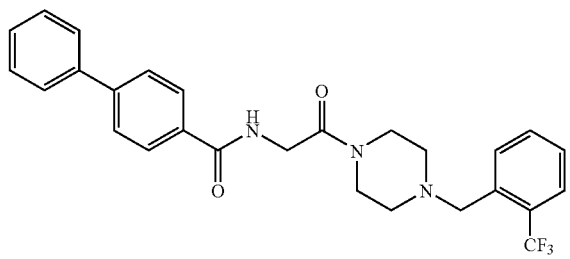

Step 1: Synthesis of 2-Trifluoromethyl benzyl bromide

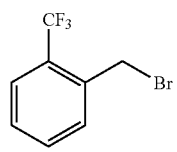

A solution of 2-trifluoromethyl benzyl alcohol (1 g, 5.67 mmol) in aqueous HBr (6 mL) was stirred at 50° C. for 4 hrs. The reaction mixture was diluted with cold water and the product extracted with ethyl acetate. The organic layer was washed with saturated brine solution, dried over sodium sulphate and concentrated to afford 780 mg of 2-trifluoromethylbenzyl bromide.

Step 2: Synthesis of Biphenyl-4-carboxylicacid {2-[4-(2-trifluoromethyl-benzyl)-piperazin-1-yl]-2-oxo-ethyl}-amide

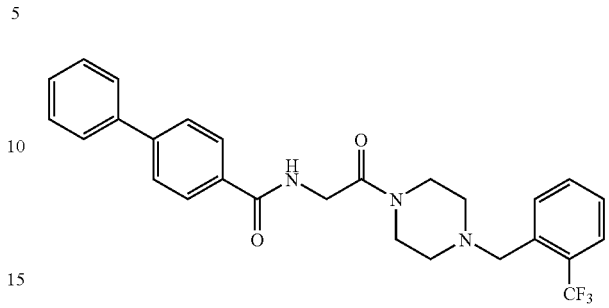

K$_2$CO$_3$ (50.5 mg, 0.37 mmol) was added to a stirred solution of biphenyl-4-carboxylicacid (2-oxo-2-piperazin-1-yl-ethyl)-amide TFA salt (80 mg, 0.18 mmol) in DMF (3 mL). 2-Trifluoromethyl benzyl bromide (52.2 mg, 0.22 mmol) was then added, and the resulting mixture was heated to 90° C. overnight. The product was extracted with ethyl acetate and the ethyl acetate layer was washed with saturated brine solution, dried over sodium sulphate and concentrated to afford 48 mg (45.7% yield) of biphenyl-4-carboxylicacid {2-[4-(2-trifluoromethyl-benzyl)-piperazin-1-yl]-2-oxo-ethyl}-amide. LC-MS purity: 94.3%, $^1$H NMR: (CDCl$_3$) δ 7.9 (d, 2H), 7.8-7.7 (d, 1H), 7.7-7.6 (m, 5H), 7.55 (m, 1H), 7.5 (m, 2H), 7.4 (m, 3H), 4.3 (d, 2H), 3.7 (s, 4H), 3.5 (t, 2H), 2.5 (q, 4H).

133) Synthesis of Biphenyl-4-carboxylicacid {2-[4-(3-methyl-thiophene-2-carbonyl)-piperazin-1-yl]-2-oxo-ethyl}-amide

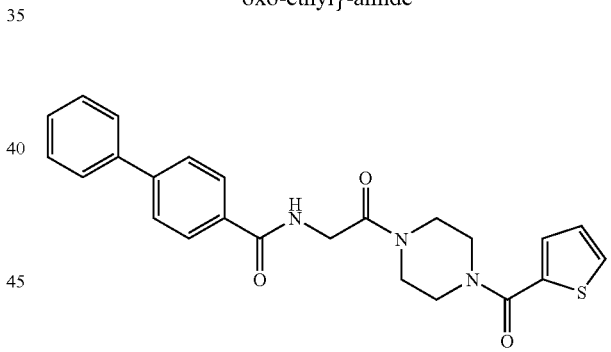

DIPEA (110.8 mg, 0.147 mL, 0.85 mmol) was added to a stirred solution of biphenyl-4-carboxylic acid (2-oxo-2-piperazin-1-yl-ethyl)-amide TFA salt (100 mg, 0.22 mmol) in DMF (3 mL). HOBT (28.3 mg, 0.2 mmol) and EDCI.HCl (91.25 mg, 0.47 mmol) were then added. After 2 minutes 3-methyl-thiophene-2-carboxylic acid (27 mg, 0.19 mmol) was added and the resulting mixture was stirred overnight. The reaction mixture was diluted with cold water. The product was extracted with ethyl acetate and the ethyl acetate layer was washed with NaHCO$_3$ solution, saturated brine solution, dried over sodium sulphate and concentrated under reduced pressure to afford 62 mg (72.9% yield) of biphenyl-4-carboxylicacid {2-[4-(3-methyl-thiophene-2-carbonyl)-piperazin-1-yl]-2-oxo-ethyl}-amide. LC-MS purity: 90.22%, HPLC Purity: 92.38%, $^1$H NMR: (CDCl$_3$) δ 7.9 (d, 2H), 7.75-7.6 (m, 4H), 7.5 (m, 2H), 7.4 (m, 1H), 7.3-7.4 (m, 2H), 6.9 (d, 1H), 4.3 (d, 2H), 3.7 (m, 6H), 3.5 (m, 2H), 2.4 (s, 3H).

134) Synthesis of Biphenyl-4-carboxylicacid {2-[4-(2-methyl-benzoyl)-piperazin-1-yl]-2-oxo-ethyl}-amide

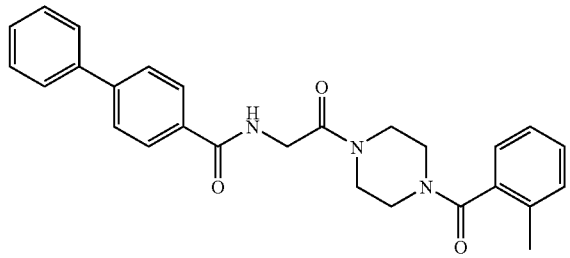

DIPEA (152 mg, 0.66 mmol) was added to a stirred solution of biphenyl-4-carboxylic acid (2-oxo-2-piperazin-1-yl-ethyl)-amide TFA salt (116 mg, 0.26 mmol) in DMF (1 mL). HOBT (36 mg, 0.26 mmol) and EDCI.HCl (50 mg, 0.26 mmol) were then added. After 2 minutes 2-methylbenzoic acid (30 mg, 0.22 mmol) was added and the resulting mixture was stirred overnight. The reaction mixture was diluted with cold water. The product was extracted with ethyl acetate and the ethyl acetate layer was washed with NaHCO$_3$ solution, saturated brine solution, dried over sodium sulphate and concentrated under reduced pressure. The residue was washed with diethyl ether to afford 62 mg (72.9% yield) of biphenyl-4-carboxylicacid {2-[4-(2-methyl-benzoyl)-piperazin-1-yl]-2-oxo-ethyl}-amide as a pale yellow solid. LC-MS purity: 94.42%, HPLC Purity: 92.84%. $^1$H NMR: (DMSO) δ 8.7-8.6 (bs, 1H), 8.0 (d, 2H) 7.8 (m, 4H), 7.6-7.2 (m, 7H), 4.1-4.3 (dd, 2H), 3.8-3.4 (m, 6H), 3.2 (m, 2H), 2.2 (s, 3H).

135) Synthesis of Biphenyl-4-carboxylic acid {2-[4-(2-bromo-5-methoxy-benzoyl)-piperazin-1-yl]-2-oxo-ethyl}-amide

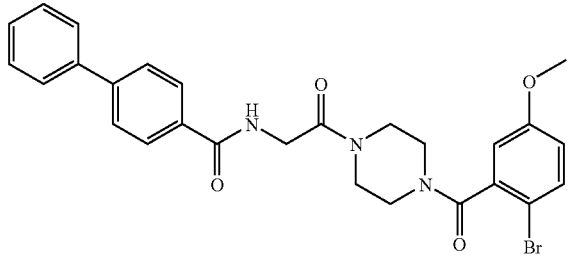

DIPEA (66 mg, 0.51 mmol) was added to a stirred solution of biphenyl-4-carboxylicacid (2-oxo-2-piperazin-1-yl-ethyl)-amide TFA salt (90 mg, 0.21 mmol) in DMF (2 mL). HOBT (28 mg, 0.21 mmol) and EDCI.HCl (40 mg, 0.21 mmol) were then added. After 2 minutes 2-bromo-5-methoxy benzoic acid (40 mg, 0.17 mmol) was added and the resulting mixture was stirred overnight. The reaction mixture was diluted with cold water. The product was extracted with ethyl acetate and the ethyl acetate layer was washed with NaHCO$_3$ solution, saturated brine solution, dried over sodium sulphate and concentrated under reduced pressure to afford crude product, which was purified by column chromatography (using silica gel of 160-120 mesh and 2.5% MeOH in chloroform as eluent) to afford 31 mg (34% yield) of biphenyl-4-carboxylic acid {2-[4-(2-bromo-5-methoxy-benzoyl)-piperazin-1-yl]-2-oxo-ethyl}-amide as a white solid. LC-MS purity: 98.31%, HPLC Purity: 97.73%. $^1$H NMR: (DMSO) δ 8.7-8.6 (b s, 1H), 8.0 (m, 2H), 7.8 (m, 4H), 7.6-7.4 (m, 4H), 7.0 (m, 2H), 4.2 (m, 2H), 3.8 (s, 3H), 3.4-3.7 (m, 6H), 3.2-3.1 (m, 2H).

136) Synthesis of Biphenyl-4-carboxylic acid {2-[4-(2-bromo-benzoyl)-piperazin-1-yl]-2-oxo-ethyl}-amide

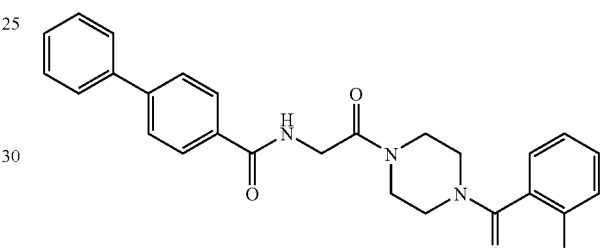

DIPEA (144 mg, 1.11 mmol) was added to a stirred solution of biphenyl-4-carboxylicacid (2-oxo-2-piperazin-1-yl-ethyl)-amide TFA salt (120 mg, 0.37 mmol) in DMF (5 mL). HOBT (60 mg, 0.45 mmol) and EDCI.HCl (178 mg, 0.93 mmol) were then added. After 2 minutes 2-bromobenzoic acid (89 mg, 0.45 mmol) was added and the resulting mixture was stirred overnight. The reaction mixture was diluted with cold water and the product was precipitated and filtered. Purification by column chromatography using silica gel 60-120 mesh and 80% EtOAc in hexane as eluent afforded 105 mg (56% yield) of biphenyl-4-carboxylic acid {2-[4-(2-bromo-benzoyl)-piperazin-1-yl]-2-oxo-ethyl}-amide. LC-MS purity: 96.78%, HPLC Purity: 97.31%. $^1$H NMR: (DMSO) δ 8.7 (t, 1H), 8.0 (d, 2H), 7.8 (m, 5H), 7.5 (m, 6H), 4.2 (dd, 2H), 3.6 (m, 6H), 3.2 (m, 2H).

SCHEME-8

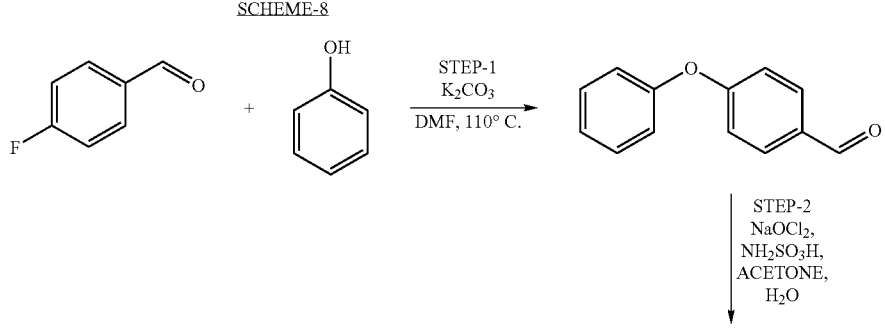

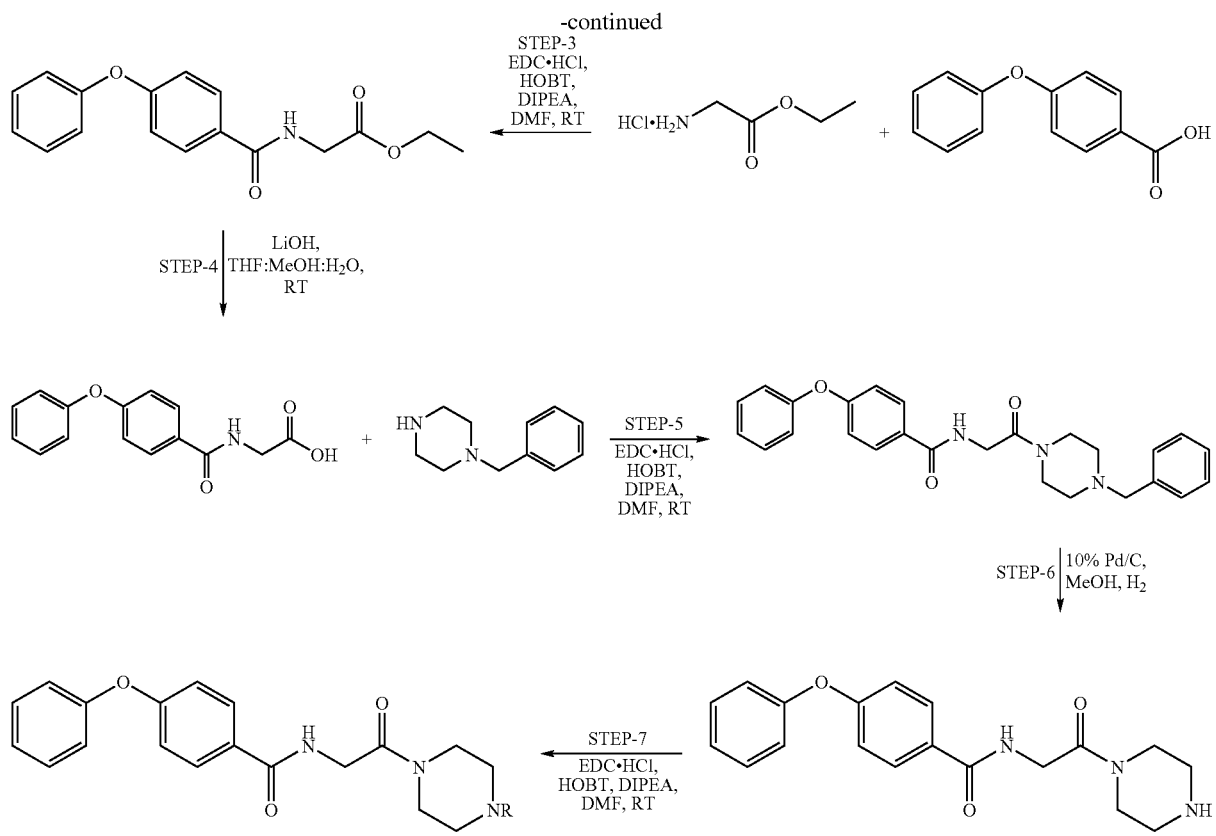

Step 1: Synthesis of 4-Phenoxy benzaldehyde

To a stirred solution of 4-fluorobenzaldehyde (5 g, 40.28 mmol) and phenol (3.8 g, 44.42 mmol) in DMF (50 mL) was added $K_2CO_3$ (11.13 g, 80.57 mmol) and the resulting mixture was stirred at 110° C. overnight. The mixture was filtered, the filtrate was diluted with cold water and the product was extracted with EtOAc. The organic layer was washed with 5% aqueous NaOH solution, saturated brine solution and dried over sodium sulphate. The organic layer was then concentrated under reduced pressure to afford 7.7 g (96.5% yield) of 4-phenoxy benzaldehyde as a pale brown oil. $^1H$ NMR: ($CDCl_3$) δ 9.9 (s, 1H), 7.8 (d, 2H), 7.4 (t, 2H), 7.2 (t, 1H), 7.0 (t, 4H).

Step 2: Synthesis of 4-Phenoxy benzoic acid

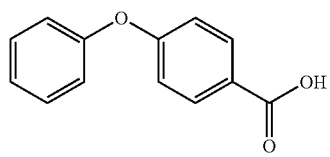

Sulfamic acid (7.35 g, 75.7 mmol) in water (5 mL) was added to a stirred solution of 4-phenoxy benzaldehyde (5 g, 25.23 mmol) in acetone (25 mL) at 4° C. Sodium chlorite (9.13 g, 100.9 mmol) in water (5 mL) was then added slowly resulting in formation of a yellow solid with effervescence. The mixture was stirred at the same temperature for 30 minutes. The reaction mixture was then diluted with cold water and the product extracted with ethyl acetate. The organic layer was washed with saturated brine solution, dried over sodium sulphate and concentrated under reduced pressure to afford 4 g (74% yield) of 4-phenoxy benzoic acid. $^1H$ NMR (DMSO): δ 7.98-7.92 (d, 2H), 7.5-7.44 (t, 2H), 7.28-7.2 (t, 1H), 7.16-7.1 (d, 2H), 7.06-7.0 (d, 2H).

Step 3: Synthesis of (4-Phenoxy-benzoylamino)-acetic acid ethyl ester

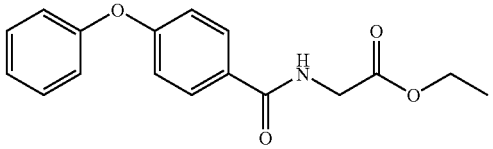

DIPEA (12.1 g, 16.2 mL, 93.6 mmol) was added to a stirred solution of 4-phenoxy benzoic acid (4.011 g, 18.73 mmol) in DMF (40 mL). HOBT (2.78 g, 20.57 mmol) and EDCI.HCl (9 g, 47 mmol) were then added. After 2 minutes, glycine ethyl ester hydrochloride (3.14 g, 22.5 mmol) was added and the mixture was stirred at room temperature overnight. The reaction mixture was diluted with cold water and the product extracted with ethyl acetate. The organic layer was washed with saturated brine solution, dried over sodium sulphate and concentrated under reduced pressure to afford 5.73 g of (4-phenoxy-benzoylamino)-acetic acid ethyl ester as a white powder. $^1H$ NMR (DMSO): δ 8.85 (t, 1H), 7.85 (d, 2H), 7.4 (t, 2H), 7.2 (t, 1H), 7.0 (m, 4H), 4.1 (q, 2H), 3.9 (d, 2H), 1.2 (t, 3H).

Step 4: Synthesis of (4-Phenoxy-benzoylamino)-acetic acid

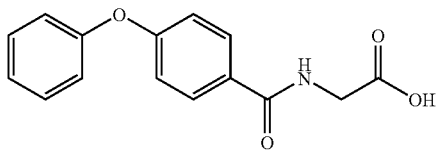

LiOH (4.81 g, 114.63 mmol) was added to a stirred solution of (4-phenoxy-benzylamino)-acetic acid ethyl ester (5.72 g, 19.12 mmol) in THF:MeOH:H$_2$O (3:1:1, 75 mL), and the resulting mixture was stirred at room temperature for 5 hrs. The MeOH and THF were evaporated, and the residue was acidified with cold 20% aqueous HCl. The resulting precipitate was filtered, washed with water and dried to afford 4.74 g (91.41% yield) of (4-phenoxy-benzoylamino)-acetic acid. $^1$H NMR (DMSO): δ 7.8 (d, 2H,), 7.75 (t, 1H), 7.4 (t, 2H), 7.15 (t, 1H), 7.05 (d, 2H), 7.0 (d, 2H).

Step 5: Synthesis of N-[2-(4-Benzyl-piperazin-1-yl)-2-oxo-ethyl]-4-phenoxy-benzamide

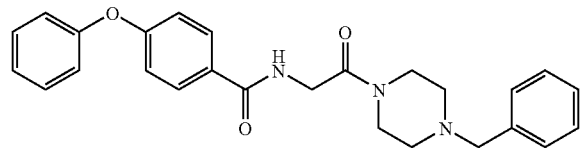

DIPEA (1.07 g, 1.432 mL, 8.28 mmol) was added to a stirred solution of 4-Phenoxy-benzoylamino)-acetic acid (0.5 g, 1.84 mmol) in DMF (6 mL). HOBT (0.273 g, 2.02 mmol) and EDCI.HCl (0.881 g, 4.6 mmol) were then added at room temperature. After 2 minutes, N-Benzyl piperazine (0.389 g, 2.2 mmol) was added and the resulting mixture was stirred at room temperature overnight. The reaction mixture was then diluted with cold water and the resulting precipitate was filtered. The solid was washed with water, then hexane and dried to afford 0.49 g (79% yield) of N-[2-(4-benzyl-piperazin-1-yl)-2-oxo-ethyl]-4-phenoxy-benzamide as a solid. $^1$H NMR (CDCl$_3$): δ 7.8 (d, 2H), 7.42-7.3 (m, 7H), 7.22 (m, 1H), 7.1-7.0 (m, 4H), 4.2 (d, 2H), 3.7 (t, 2H), 3.55 (s, 2H), 3.46 (t, 2H), 2.5 (s, 4H).

Step 6: Synthesis of N-(2-Oxo-2-piperazin-1-yl-ethyl)-4-phenoxy-benzamide

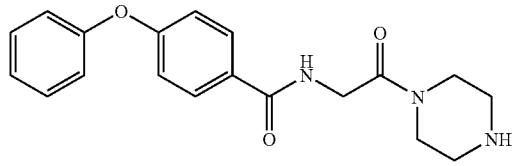

Under an inert atmosphere, 10% Pd/C (111 mg) was added to a stirred solution of N-[2-(4-benzyl-piperazin-1-yl)-2-oxo-ethyl]-4-phenoxy-benzamide (490 mg, 1.14 mmol) in MeOH (90 mL). Hydrogen gas was then passed into the reaction mixture by means of a hydrogen filled bladder and the mixture was stirred at room temperature overnight. The mixture was filtered over celite and the celite was washed with MeOH. The filtrate was collected and concentrated under reduced pressure to afford 390 mg (quantitative yield) of N-(2-Oxo-2-piperazin-1-yl-ethyl)-4-phenoxy-benzamide as a solid. LC-MS purity: 88.65, $^1$H NMR (CDCl$_3$): δ 7.8 (d, 2H), 7.38 (m, 2H), 7.26 (bs, 1H), 7.18 (tt, 1H), 7.08-7.0 (m, 4H), 4.24 (d, 2H), 3.66 (t, 2H), 3.5 (s, 1H), 3.44 (t, 2H), 2.9 (q, 4H), 2.5-2.6 (m, 1H).

137) Synthesis of N-{2-[4-(2-Bromo-5-methoxy-benzoyl)-piperazin-1-yl]-2-oxo-ethyl}-4-phenoxy-benzamide

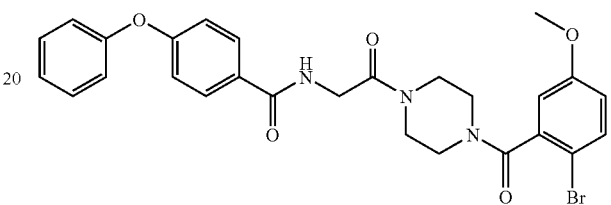

Step 7

DIPEA (85.5 mg, 0.114 mL, 0.66 mmol) was added to a stirred solution of N-(2-Oxo-2-piperazin-1-yl-ethyl)-4-phenoxy-benzamide (60 mg, 0.176 mmol) in DMF (2 mL). HOBT (21.89 mg, 0.16 mmol) and EDCI.HCl (70.5 mg, 0.36 mmol) were then added at room temperature. After 2 minutes, 2-Bromo-5-methoxy benzoic acid (33.9 mg, 0.15 mmol) was added and the resulting mixture was stirred at room temperature overnight. The reaction mixture was then diluted with cold water, and the resulting precipitate was filtered, washed with water then hexane and dried to afford 70 mg (86.5% yield) of N-{2-[4-(2-Bromo-5-methoxy-benzoyl)-piperazin-1-yl]-2-oxo-ethyl}-4-phenoxy-benzamide as a pale yellow solid. LCMS Purity: 95.76%, HPLC Purity: 96.07%. $^1$H NMR (CDCl$_3$): δ 8.5 (bs, 1H), 7.9 (d, 2H), 7.5 (m, 1H), 7.4 (m, 2H), 7.2 (m, 1H), 6.9 (m, 5H), 4.2 (m, 2H), 3.8 (s, 3H), 3.5 (m, 6H), 3.2 (m, 2H), 2.1 (s, 1H), 2.0 (m, 1H), 1.3 (s, 3H), 0.8 (m, 1H).

138) Synthesis of N-{2-[4-(3-Methyl-thiophene-2-carbonyl)-piperazin-1-yl]-2-oxo-ethyl}-4-phenoxy-benzamide

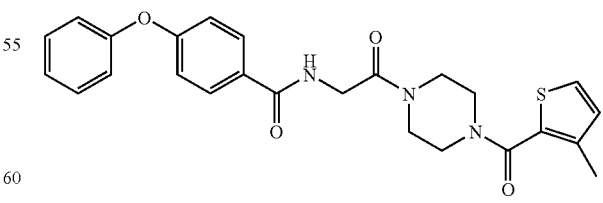

DIPEA (85.5 mg, 0.114 mL, 0.66 mmol) was added to a stirred solution of N-(2-Oxo-2-piperazin-1-yl-ethyl)-4-phenoxy-benzamide (60 mg, 0.176 mmol) in DMF (3 mL). HOBT (21.89 mg, 0.16 mmol) and EDCI.HCl (70.5 mg, 0.36 mmol) were then added at room temperature. After 2 minutes, 3-methyl-thiophene-2-carboxylic acid (20.9 mg, 0.15 mmol) was added and the resulting mixture was stirred at room temperature overnight. The reaction mixture was then diluted with cold water, and the resulting precipitate was filtered, washed with water then hexane and dried to afford 52 mg (76.5% yield) of N-{2-[4-(3-methyl-thiophene-2-carbonyl)-piperazin-1-yl]-2-oxo-ethyl}-4-phenoxy-benzamide as a pale brown solid. LCMS Purity: 98.86%, HPLC Purity: 98.50%. $^1$H NMR (CDCl$_3$): δ 7.8 (d, 2H), 7.4 (m, 2H), 7.3 (d, 1H), 7.2 (s, 1H), 7.1 (t, 1H), 7.0 (m, 4H), 6.85 (d, 1H), 4.3 (dd, 2H), 3.7 (m, 6H), 3.5 (t, 2H), 2.2 (s, 3H).

139) Synthesis of N-{2-[4-(Furan-2-carbonyl)-piperazin-1-yl]-2-oxo-ethyl}-4-phenoxy-benzamide DIPEA (0.091 mL, 0.53 mmol) was added drop wise to furan-2-carboxylic acid (23 mg, 0.21 mmol) in DMF (5 mL). EDCI (84 mg, 0.44 mmol) and HOBT (28 mg, 0.21 mmol) were added consecutively and, after 10 mins, N-(2-Oxo-2-piperazin-1-yl-ethyl)-4-phenoxy-benzamide (60 mg, 0.18 mmol) was added and the resulting mixture was stirred at room temperature overnight. Water was then added, and the resulting solid was filtered under reduced pressure to afford N-{2-[4-(furan-2-carbonyl)-piperazin-1-yl]-2-oxo-ethyl}-4-phenoxy-benzamide in 65% yield. LC-MS purity: 92%, $^1$H NMR (DMSO-D6): δ 8.5 (t, 1H), 8 (t, 3H), 7.4 (t, 2H), 7.2 (t, 1H), 7 (m, 4H), 6.6 (s, 1H), 4.2 (d, 2H), 3.6 (m, 8H).

140) Synthesis of N-{2-[4-(2-Methyl-benzoyl)-piperazin-1-yl]-2-oxo-ethyl}-4-phenoxy-benzamide DIPEA (0.091 mL, 0.53 mmol) was added drop wise to 2-Methyl benzoic acid (23 mg, 0.2123 mmol) in DMF (5 mL). EDCI (84 mg, 0.44 mmol) and HOBT (28 mg, 0.21 mmol) were added consecutively and, after 10 mins, N-(2-Oxo-2-piperazin-1-yl-ethyl)-4-phenoxy-benzamide (60 mg, 0.18 mmol) was added and the resulting mixture was stirred at room temperature overnight. Water was then added, and the resulting solid was filtered under reduced pressure. The residue was dissolved in methylene chloride and filtered to afford N-{2-[4-(2-Methyl-benzoyl)-piperazin-1-yl]-2-oxo-ethyl}-4-phenoxy-benzamide in 36% yield. LC-MS purity: 98%, 1H NMR (DMSO-D6): δ 8.5 (d, 1H), 7.9 (d, 2H), 7.4 (t, 2H), 7.2 (m, 5H), 7.1 (q, 4H), 4.2 (2d, 2H), 3.6 (m, 4H), 3.4 (m, 2H), 3.2 (m, 2H), 2.2 (s, 3H).

141) Synthesis of N-{2-[4-(2-Fluoro-benzoyl)-piperazin-1-yl]-2-oxo-ethyl}-4-phenoxy-benzamide Step 1: Synthesis of N-(2-Oxo-2-piperazin-1-yl-ethyl)-4-phenoxy-benzamide hydrochloride

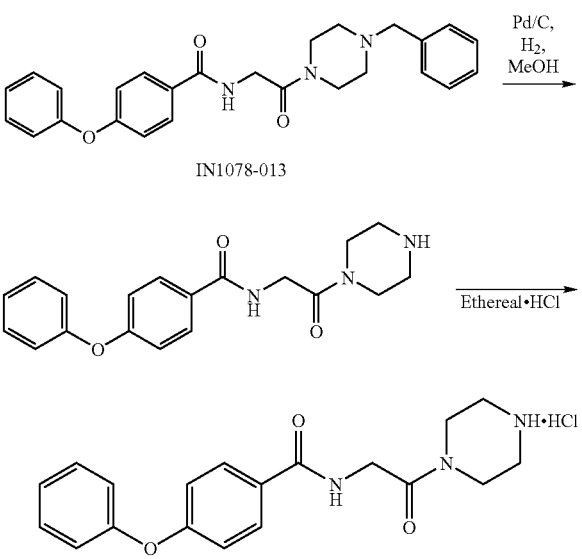

IN1078-013

Pd/C (500 mg in 1 mL of water) was added to N-[2-(4-benzyl-piperazin-1-yl)-2-oxo-ethyl]-4-phenoxy-benzamide (2.08 g, 4.85 mmol) in MeOH (100 mL). The resulting reaction mixture was stirred at room temperature overnight under an atmosphere of hydrogen. Additional Pd/C (500 mg in 1 mL of water) was then added and the mixture was stirred under a hydrogen atmosphere for a further 24 hours. The reaction mixture was then filtered through a bed of celite under reduced pressure. Methanol was removed and ethereal HCl was added to the residue and the mixture stirred for 10 minutes. The resulting off-white solid was washed with ether (3×15 mL) to afford N-(2-Oxo-2-piperazin-1-yl-ethyl)-4-phenoxy-benzamide hydrochloride in 76% yield.

Step 2: Synthesis of 2-Fluoro-benzoic acid

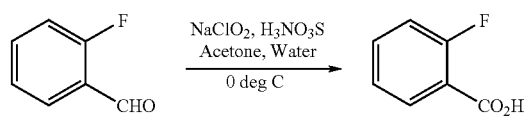

Sodium chlorite (1.45 g, 16.11 mmol) in 2 mL water was added at 0° C. to 2-fluoro-benzaldehyde (0.5 g, 4.03 mmol) in 5 mL acetone. After 5 minutes, sulphamic acid (1.17 gm, 12.086 mmol) was added and the resulting mixture was stirred at 0° C. for 20 minutes. Water was then added, and the resulting precipitate was filtered under reduced pressure. The aqueous layer was extracted with EtOAc and washed with brine. The organic phase was dried over Na$_2$SO$_4$ and concentrated under reduced pressure to afford 2-fluorobenzoic acid in 86% yield.

Step 3: Synthesis of N-{2-[4-(2-Fluoro-benzoyl)-piperazin-1-yl]-2-oxo-ethyl}-4-phenoxy-benzamide

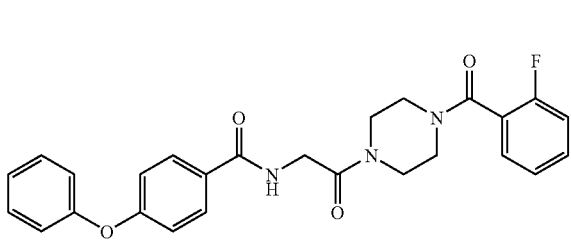

DIPEA (0.106 mL, 0.62 mmol) was added drop wise to 2-fluorobenzoic acid (34 mg, 0.25 mmol) in DMF (5 mL). EDCI (98 mg, 0.51 mmol) and HOBT (33 mg, 0.25 mmol) were added consecutively and, after 10 mins, N-(2-Oxo-2-piperazin-1-yl-ethyl)-4-phenoxy-benzamide hydrochloride (77 mg, 0.25 mmol) was added and the resulting mixture was stirred at room temperature overnight. Water was then added, and the product was extracted with EtOAc. The organic layer was washed with brine, dried over Na$_2$SO$_4$ and concentrated under reduced pressure to afford the crude product. Purification using column chromatography (silica gel of mesh size of 60-120 using 70:30 EtOAc:hexane as eluent) afforded N-{2-[4-(2-fluoro-benzoyl)-piperazin-1-yl]-2-oxo-ethyl}-4-phenoxy-benzamide in 42% yield. LC-MS purity: 97%, $^1$H NMR (DMSO-D$_6$): δ 8.5 (t, 1H), 7.9 (d, 2H), 7.5 (m, 4H), 7.3 (m, 2H), 7.2 (t, 1H), 7.1 (m, 4H), 4.2 (dd, 2H), 3.6 (m, 4H), 3.5 (m, 2H), 3.2 (m, 2H).

142) Synthesis of N-[2-(4-Benzyl-piperazin-1-yl)-2-oxo-ethyl]-4-phenoxy-benzamide

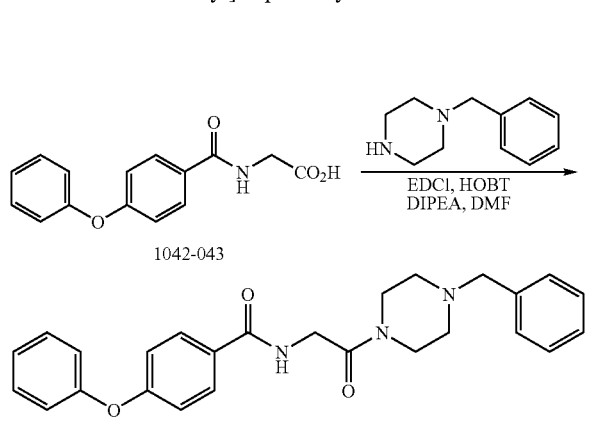

DIPEA (0.114 mL, 0.66 mmol) was added drop wise to (4-phenoxy-benzoylamino)-acetic acid (60 mg, 0.22 mmol) in DMF (5 mL). EDCI (106 mg, 0.55 mmol) and HOBT (35 mg, 0.27 mmol) were then added, and after 10 mins, 1-Benzyl-piperazine (46 mg, 0.27 mmol) was added. The resulting mixture was stirred at room temperature overnight. Water was added, and the resulting solid was isolated by filtration under reduced pressure to afford N-[2-(4-benzyl-piperazin-1-yl)-2-oxo-ethyl]-4-phenoxy-benzamide in 58% yield. LC-MS purity: 99%, $^1$H NMR (DMSO-D6): δ 8.5 (t, 1H), 7.9 (d, 2H), 7.5 (t, 2H), 7.3 (m, 7H), 7.1 (m, 4H), 4.1 (d, 2H), 3.6 (s, 2H), 3.5 (m, 4H), 2.4 (m, 4H).

143) Synthesis of N-{2-[4-(4-Fluoro-benzoyl)-piperazin-1-yl]-2-oxo-ethyl}-4-phenoxy-benzamide

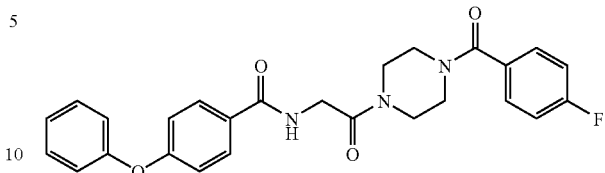

DIPEA (0.138 mL, 0.80 mmol) was added drop wise to 4-fluorobenzoic acid (44 mg, 0.32 mmol) in DMF (5 mL). EDCI (127 mg, 0.67 mmol) and HOBT (43 mg, 0.32 mmol) were added consecutively and, after 10 mins, N-(2-oxo-2-piperazin-1-yl-ethyl)-4-phenoxy-benzamide hydrochloride (100 mg, 0.27 mmol) was added and the resulting mixture was stirred at room temperature overnight. Water was then added, and the product was extracted with EtOAc. The organic layer was washed with brine, dried over Na$_2$SO$_4$ and concentrated under reduced pressure to afford the crude product. Purification using column chromatography (silica gel of mesh size of 60-120 using 70:30 EtOAc:hexane as eluent) afforded N-{2-[4-(4-fluoro-benzoyl)-piperazin-1-yl]-2-oxo-ethyl}-4-phenoxy-benzamide in 49% yield. LC-MS purity: 97%, $^1$H NMR (CDCl$_3$): δ 7.8 (d, 2H), 7.4 (m, 4H), 7.2 (m, 4H), 7.1 (m, 4H), 4.3 (s, 2H), 3.6 (m, 8H).

144) Synthesis of N-{2-Oxo-2-[4-(2-trifluoromethyl-benzyl)-piperazin-1-yl]-ethyl}-4-phenoxy-benzamide

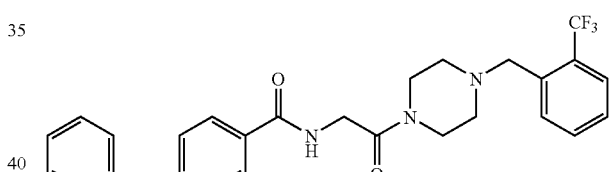

Step 1

N-(2-Oxo-2-piperazin-1-yl-ethyl)-4-phenoxy-benzamide hydrochloride was prepared as described above.

Step 2: Synthesis of 1-Bromomethyl-2-trifluoromethyl-benzene

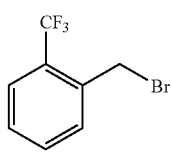

A mixture of (2-trifluoromethyl-phenyl)-methanol (100 mg, 0.57 mmol) and HBr (0.6 mL) was stirred at 0° C. for 2 hours then at 60° C. for 3 hours. Water was then added, and the product extracted with EtOAc. The organic layer was washed with brine, dried over Na$_2$SO$_4$ and concentrated under reduced pressure to afford 1-bromomethyl-2-trifluoromethyl-benzene in 55% yield.

Step 3: Synthesis of N-{2-Oxo-2-[4-(2-trifluoromethyl-benzyl)-piperazin-1-yl]-ethyl}-4-phenoxy-benzamide

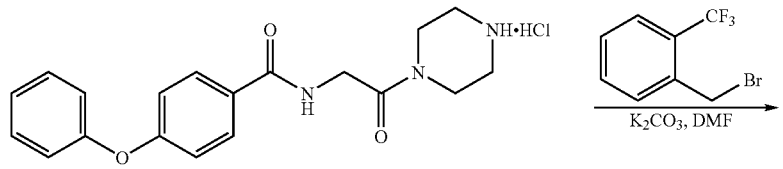

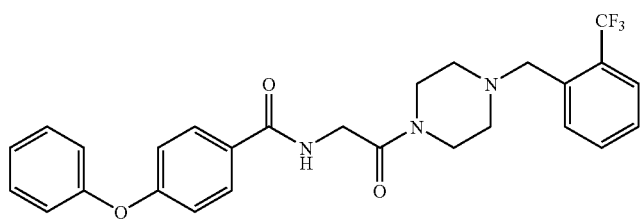

K₂CO₃ (130 mg, 0.95 mmol) was added to N-(2-Oxo-2-piperazin-1-yl-ethyl)-4-phenoxy-benzamide hydrochloride (141 mg, 0.38 mmol) in 5 mL of DMF. After 10 minutes atr room temperature, 1-Bromomethyl-2-trifluoromethyl-benzene (75 mg, 0.32 mmol) was added and the resulting mixture was stirred at 60° C. for 4 hours. Water was then added, and the product was extracted with EtOAc. The organic layer was washed with brine, dried over sodium sulphate and concentrated. Purification by column chromatography (60-120 mesh silica gel using 6:4 EtOAc and Hexane as the eluent) afforded N-{2-Oxo-2-[4-(2-trifluoromethyl-benzyl)-piperazin-1-yl]-ethyl}-4-phenoxy-benzamide in 39% yield. LC-MS purity: 86%. ¹H NMR (DMSO-D6): δ 8.5 (t, 1H), 7.9 (d, 2H), 7.8 (d, 1H), 7.7 (q, 2H), 7.4 (m, 3H), 7.2 (t, 1H), 7.1 (m, 2H), 7 (m, 2H), 4.1 (d, 2H), 3.7 (s, 2H), 3.5 (m, 4H), 2.4 (m, 4H).

145) Synthesis of N-{2-[4-(2,4-Dimethyl-benzoyl)-piperazin-1-yl]-2-oxo-ethyl}-4-phenoxy-benzamide

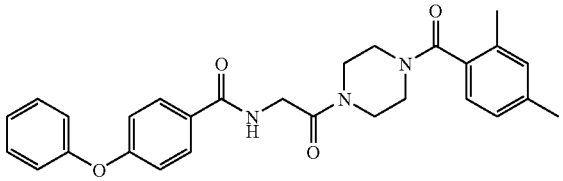

Step 1

N-(2-Oxo-2-piperazin-1-yl-ethyl)-4-phenoxy-benzamide hydrochloride was prepared as described above.

Step 2: Synthesis of N-{2-[4-(2,4-Dimethyl-benzoyl)-piperazin-1-yl]-2-oxo-ethyl}-4-phenoxy-benzamide

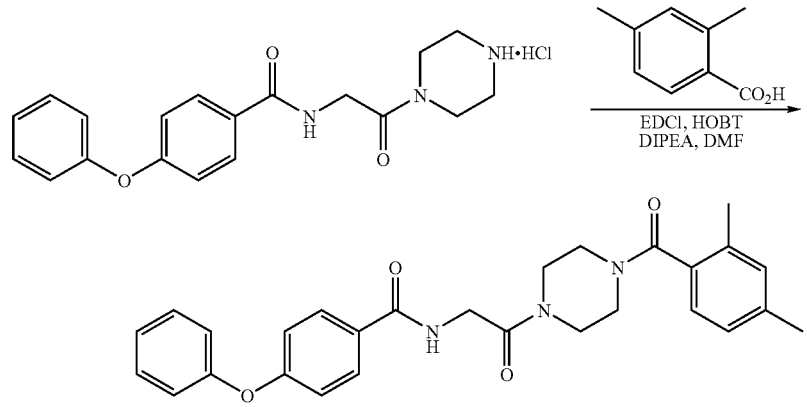

DIPEA (0.138 mL, 0.80 mmol) was added drop wise to 2,4-Dimethylbenzoic acid (48 mg, 0.32 mmol) in DMF (5 mL). EDCI (127 mg, 0.67 mmol) and HOBT (43 mg, 0.32 mmol) were added consecutively. After 10 mins, N-(2-Oxo-2-piperazin-1-yl-ethyl)-4-phenoxy-benzamide hydrochloride (100 mg, 0.27 mmol) was added and the resulting mixture was stirred at room temperature overnight. Water was then added, and the product was extracted with EtOAc. The organic layer was washed with brine, dried over $Na_2SO_4$ and concentrated under reduced pressure to afford the crude product. Purification using column chromatography (silica gel of mesh size of 60-120 using 60:40 EtOAc:hexane as eluent) afforded N-{2-[4-(2,4-dimethyl-benzoyl)-piperazin-1-yl]-2-oxo-ethyl}-4-phenoxy-benzamide in 56% yield. LC-MS purity: 98%, $^1$H NMR (DMSO-D6): δ 8.5 (t, 1H), 7.9 (d, 2H), 7.4 (t, 2H), 7.2 (t, 1H), 7.1 (m, 7H), 4.1 (d, 2H), 3.6 (m, 4H), 3.4 (m, 2H), 3.2 (m, 2H), 2.3 (s, 3H), 2.2 (s, 3H).

146) Synthesis of N-[2-(4-Benzoyl-piperazin-1-yl)-2-oxo-ethyl]-4-phenoxy-benzamide

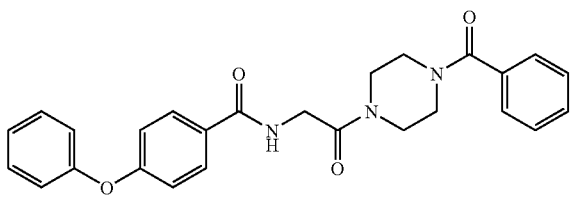

Step 1

N-(2-Oxo-2-piperazin-1-yl-ethyl)-4-phenoxy-benzamide hydrochloride was prepared as described above.

Step 2: Synthesis of N-[2-(4-Benzoyl-piperazin-1-yl)-2-oxo-ethyl]-4-phenoxy-benzamide

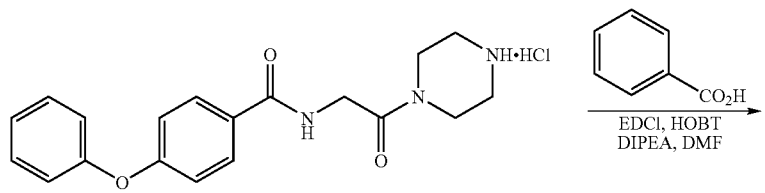

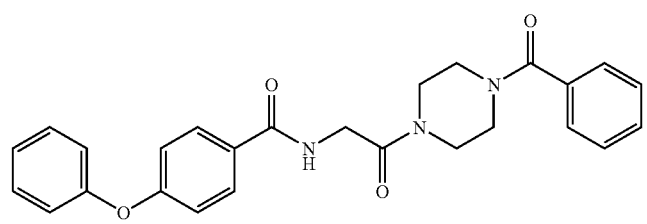

DIPEA (0.138 mL, 0.80 mmol) was added drop wise to benzoic acid (39 mg, 0.32 mmol) in DMF (5 mL). EDCI (127 mg, 0.67 mmol) and HOBT (43 mg, 0.32 mmol) were added consecutively. After 10 mins, N-(2-Oxo-2-piperazin-1-yl-ethyl)-4-phenoxy-benzamide hydrochloride (100 mg, 0.27 mmol) was added and the resulting mixture was stirred at room temperature overnight. Water was then added, and the product was extracted with EtOAc. The organic layer was washed with brine, dried over $Na_2SO_4$ and concentrated under reduced pressure to afford the crude product. Purification using column chromatography (silica gel of mesh size of 60-120 using 70:30 EtOAc:hexane as eluent) afforded N-[2-(4-benzoyl-piperazin-1-yl)-2-oxo-ethyl]-4-phenoxy-benzamide in 57% yield. LC-MS purity: 99%, $^1$H NMR (DMSO-D6): δ 8.6 (t, 1H), 7.9 (d, 2H), 7.5 (m, 7H), 7.2 (t, 1H), 7.1 (m, 4H), 4.2 (d, 2H), 3.6 (m, 8H).

147) Synthesis of N-[2-(4-Benzenesulfonyl-piperazin-1-yl)-2-oxo-ethyl]-4-phenoxy-benzamide

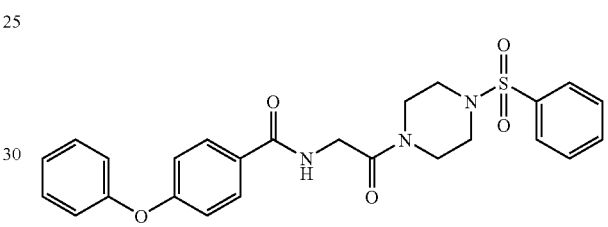

Step 1

N-(2-Oxo-2-piperazin-1-yl-ethyl)-4-phenoxy-benzamide hydrochloride was prepared as described above.

Step 2: Synthesis of N-[2-(4-Benzenesulfonyl-piperazin-1-yl)-2-oxo-ethyl]-4-phenoxy-benzamide

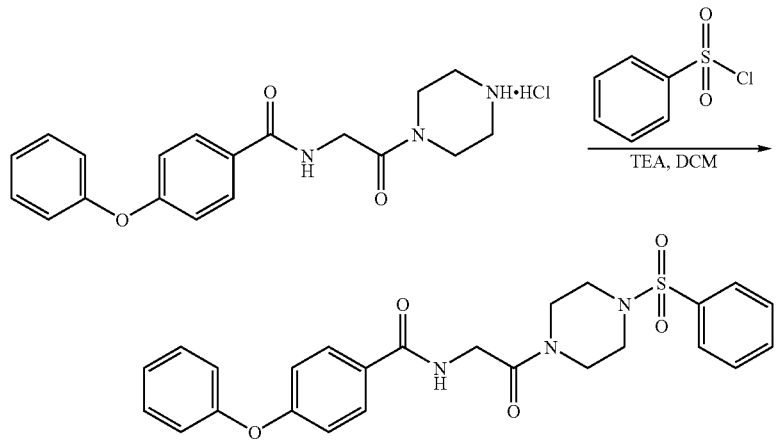

TEA (0.074 mL, 0.53 mmol) was added dropwise to a chilled (0° C.) mixture of N-(2-Oxo-2-piperazin-1-yl-ethyl)-4-phenoxy-benzamide hydrochloride (100 mg, 0.27 mmol) in DCM (5 mL). After 5 minutes, benzenesulfonyl chloride (0.032 mL, 0.26 mmol) was added and the resulting mixture was stirred at room temperature for 5 hours. DCM was added, followed by the addition of iced water. The product was washed with brine, dried over $Na_2SO_4$ and concentrated under reduced pressure. The crude product was purified by column chromatography (using silica gel of mesh size of 60-120 and 70:30 EtOAc:hexane as eluent) to afford N-[2-(4-benzenesulfonyl-piperazin-1-yl)-2-oxo-ethyl]-4-phenoxy-benzamide in 47% yield. LC-MS purity: 98%, $^1$H NMR (DMSO-D6): δ 8.5 (t, 1H), 7.9 (d, 2H), 7.8 (m, 3H), 7.6 (m, 2H), 7.4 (t, 2H), 7.2 (t, 1H), 7.1 (d, 2H), 7 (d, 2H), 4.1 (d, 2H), 3.6 (m, 4H), 2.9 (m, 4H).

Synthesis of N-{2-[4-(2,4-Dichloro-benzoyl)-piperazin-1-yl]-2-oxo-ethyl}-4-phenoxy-benzamide

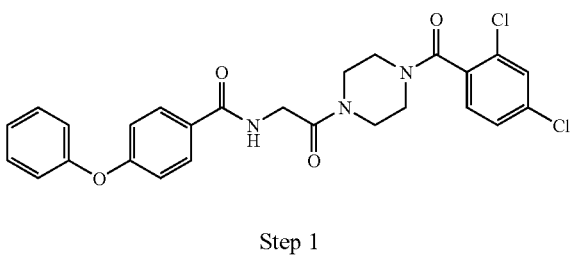

Step 1

N-(2-Oxo-2-piperazin-1-yl-ethyl)-4-phenoxy-benzamide hydrochloride was prepared as described above.

Step 2: Synthesis of N-{2-[4-(2,4-Dichloro-benzoyl)-piperazin-1-yl]-2-oxo-ethyl}-4-phenoxy-benzamide

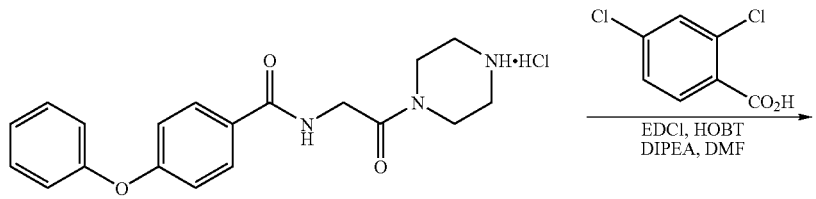

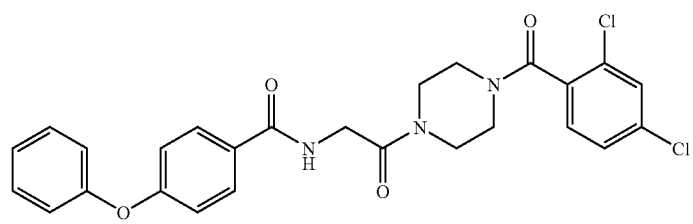

DIPEA (0.11 mL, 0.64 mmol) was added drop wise to 2,4-dichlorobenzoic acid (48 mg, 0.26 mmol) in DMF (5 mL). EDCI (102 mg, 0.53 mmol) and HOBT (34 mg, 0.26 mmol) were added consecutively. After 10 mins, N-(2-Oxo-2-piperazin-1-yl-ethyl)-4-phenoxy-benzamide hydrochloride (80 mg, 0.21 mmol) was added and the resulting mixture was stirred at room temperature overnight. Water was then added, and the product was extracted with EtOAc. The organic layer was washed with brine, dried over Na₂SO₄ and concentrated under reduced pressure to afford the crude product. Purification using column chromatography (silica gel of mesh size of 60-120 using 60:40 EtOAc:hexane as eluent) afforded N-{2-[4-(2,4-Dichloro-benzoyl)-piperazin-1-yl]-2-oxo-ethyl}-4-phenoxy-benzamide: in 64% yield. LC-MS purity: 97%, ¹H NMR (DMSO-D6): δ 8.5 (t, 1H), 7.9 (d, 2H), 7.7 (s, 1H), 7.5 (m, 4H), 7.2 (t, 1H), 7.1 (m, 4H), 4.2 (dd, 2H), 3.6 (m, 4H), 3.5 (m, 2H), 3.2 (m, 2H).

148) Synthesis of N-{2-[4-(2,5-Dichloro-benzoyl)-piperazin-1-yl]-2-oxo-ethyl}-4-phenoxy-benzamide

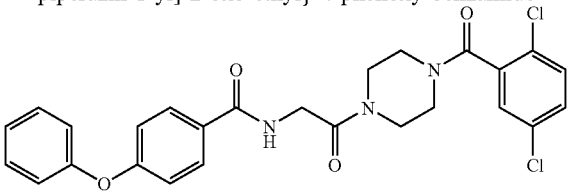

Step 1

N-(2-Oxo-2-piperazin-1-yl-ethyl)-4-phenoxy-benzamide hydrochloride was prepared as described above.

Step 2: Synthesis of N-{2-[4-(2,5-Dichloro-benzoyl)-piperazin-1-yl]-2-oxo-ethyl}-4-phenoxy-benzamide

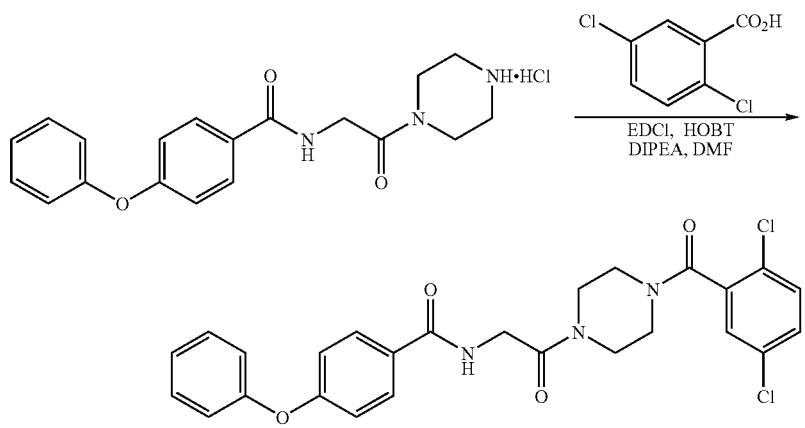

DIPEA (0.11 mL, 0.64 mmol) was added drop wise to 2,5-dichlorobenzoic acid (48 mg, 0.26 mmol) in DMF (5 mL). EDCI (102 mg, 0.53 mmol) and HOBT (34 mg, 0.26 mmol) were added consecutively. After 10 mins, N-(2-Oxo-2-piperazin-1-yl-ethyl)-4-phenoxy-benzamide hydrochloride (80 mg, 0.21 mmol) was added and the resulting mixture was stirred at room temperature overnight. Water was then added, and the product was extracted with EtOAc. The organic layer was washed with brine, dried over Na₂SO₄ and concentrated under reduced pressure to afford the crude product. Purification using column chromatography (silica gel of mesh size of 60-120 using 60:40 EtOAc:Hexane as eluent) afforded N-{2-[4-(2,5-Dichloro-benzoyl)-piperazin-1-yl]-2-oxo-ethyl}-4-phenoxy-benzamide in 55% yield LC-MS purity: 99%, ¹H NMR (DMSO-D6): δ 8.5 (t, 1H), 7.9 (d, 2H), 7.6 (t, 3H), 7.5 (t, 2H), 7.2 (t, 1H), 7.1 (m, 4H), 4.2 (d, 2H), 3.5 (m, 6H), 3.3 (m, 2H).

SCHEME-9

Step-1-A
Step-1-B

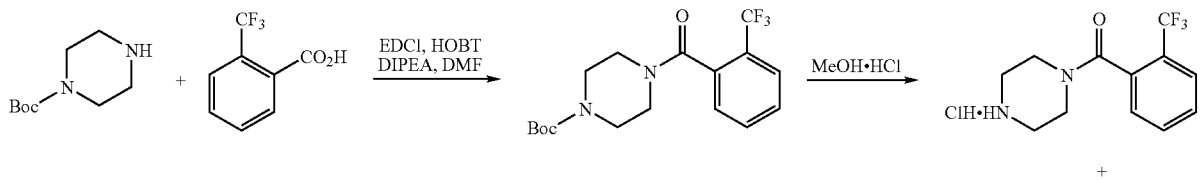

-continued

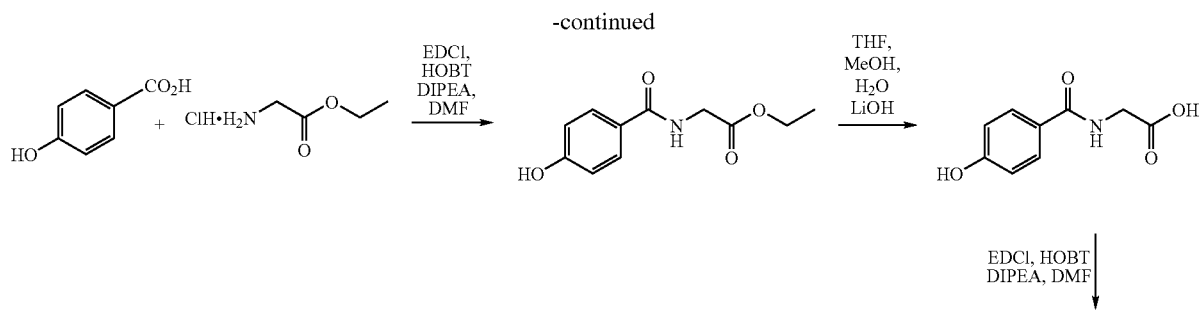

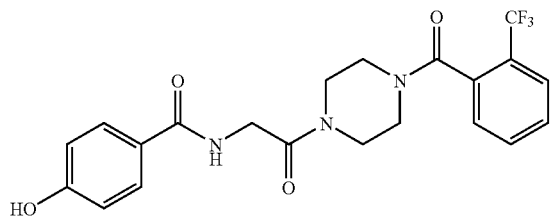

Step-2-A
Step-2-B

Step 1A: Synthesis of 4-(2-trifluoromethyl-benzoyl)-piperazine-1-carboxylic acid tert-butyl ester

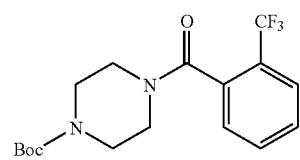

DIPEA (5.7 g, 44.30 mmol) was added drop wise to 2-trifluoromethyl benzoic acid (3.36 g, 17.72 mmol) in DMF (25 mL). EDCI (7.07 gm, 36.91 mmol) and HOBT (2.39 g, 17.72 mmol) were added consecutively and, after 15 minutes, N-Boc piperazine (2.75 g, 14.77 mmoles). The resulting mixture was stirred at room temperature overnight. Water was then added, and the product was extracted with EtOAc. The organic layer was washed with brine, dried over Na₂SO₄ and concentrated under reduced pressure to afford the crude product. Purification using column chromatography (silica gel of mesh size of 60-120 using 30:70 EtOAc:hexane as eluent) afforded 4-(2-trifluoromethyl-benzoyl)-piperazine-1-carboxylic acid tert-butyl ester in 39% yield.

Step 1B: Synthesis of piperazin-1-yl-(2-trifluoromethyl-phenyl)-methanone

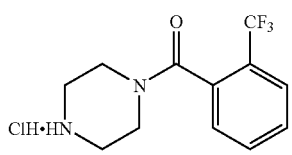

A mixture of 4-(2-trifluoromethyl-benzoyl)-piperazine-1-carboxylic acid tert-butyl ester (2.1 g, 5.87 mmol) and MeOH.HCl (15 mL) was stirred for 30 minutes at 0° C. The reaction mixture was allowed to warm to room temperature and stirred for a further 2 hrs. To complete the reaction HCl gas was then purged into the mixture (NaCl+H₂SO₄) at 0° C. for 1 hr. The methanol was then evaporated. Toluene (2×20 mL) was added and evaporated. The resultant sticky mass was recrystallized from hexane to afford 1.57 g (91% yield) of piperazin-1-yl-(2-trifluoromethyl-phenyl)-methanone.

Step 2A: Synthesis of (4-Hydroxy-benzoyl amino)-acetic Acid Ethyl Ester

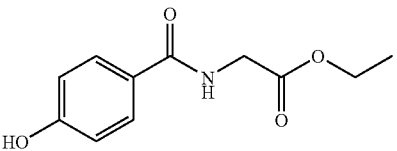

DIPEA (1.4 g, 10.86 mmol) was added drop wise to 4-hydroxy benzoic acid (500 mg, 3.62 mmol) in DMF (10 mL). EDCI (1.7 g, 9.05 mmol) and HOBT (586 mg, 4.34 mmol) were added consecutively and, after 15 minutes, glycine ethyl ester HCl (603 mg, 4.344 mmol) was added. The resulting mixture was stirred at room temperature overnight. Water was then added, and the product was extracted with EtOAc. The organic layer was washed with brine, dried over Na₂SO₄ and concentrated under reduced pressure to afford (4-hydroxy-benzoyl amino)-acetic acid ethyl ester in 91% yield.

169

Step 2B: Synthesis of 4-Hydroxy-benzoyl amino)-acetic Acid

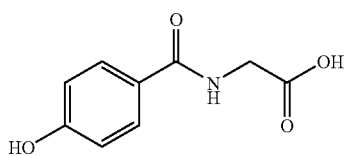

LiOH (556 mg in 2.5 mL water) was added to (4-hydroxy-benzoyl amino)-acetic acid ethyl ester (740 mg, 3.32 mmol) in a THF MeOH mixture and the resulting mixture stirred at room temperature overnight. The THF and MeOH were evaporated under reduced pressure and the resulting residue was acidified to pH 2 using 10% citric acid solution. The product was extracted with EtOAc. The organic layer was washed with brine, dried over $Na_2SO_4$ and concentrated under reduced pressure to afford 4-hydroxy-benzoyl amino)-acetic acid in 72% yield. LC-MS purity: 100%

170

149) Synthesis of 4-Hydroxy-N-[2-Oxo-2-trifluoromethyl-benzoyl)-piperazine-1-yl]-ethyl]-benzamide

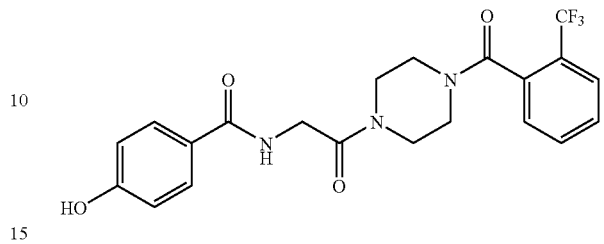

DIPEA (397 mg, 3.08 mmol) was added drop wise to 4-(hydroxybenzoyl amino)-acetic acid (200 mg, 1.03 mmol) in DMF (6 mL). EDCI (294 mg, 1.54 mmol) and HOBT (166 mg, 1.23 mmol) were added consecutively and, after 15 mins, piperazin-1-yl-(2-trifluoromethyl-phenyl)-methanone (390 mg, 1.33 mmoles) was added. The resulting mixture was stirred at room temperature overnight. Water was then added, and the product was extracted with EtOAc. The organic layer was washed with brine, dried over $Na_2SO_4$ and concentrated under reduced pressure to afford the crude product. Purification using column chromatography (silica gel of mesh size of 60-120 using 70:30 EtOAc:hexane as eluent) afforded 4-hydroxy-N-[2-Oxo-2-trifluoromethyl-benzoyl)-piperazine-1-yl]-ethyl]-benzamide in 65% yield. LC-MS purity: 93%, $^1$H NMR (DMSO-$D_6$): δ 10 (s, 1H), 8.3 (d, 1H), 7.8 (m, 5H), 7.5 (t, 1H), 6.8 (d, 2H), 4.1 (d, 2H), 3.6 (m, 5H), 3.1 (m, 3H).

SCHEME-10

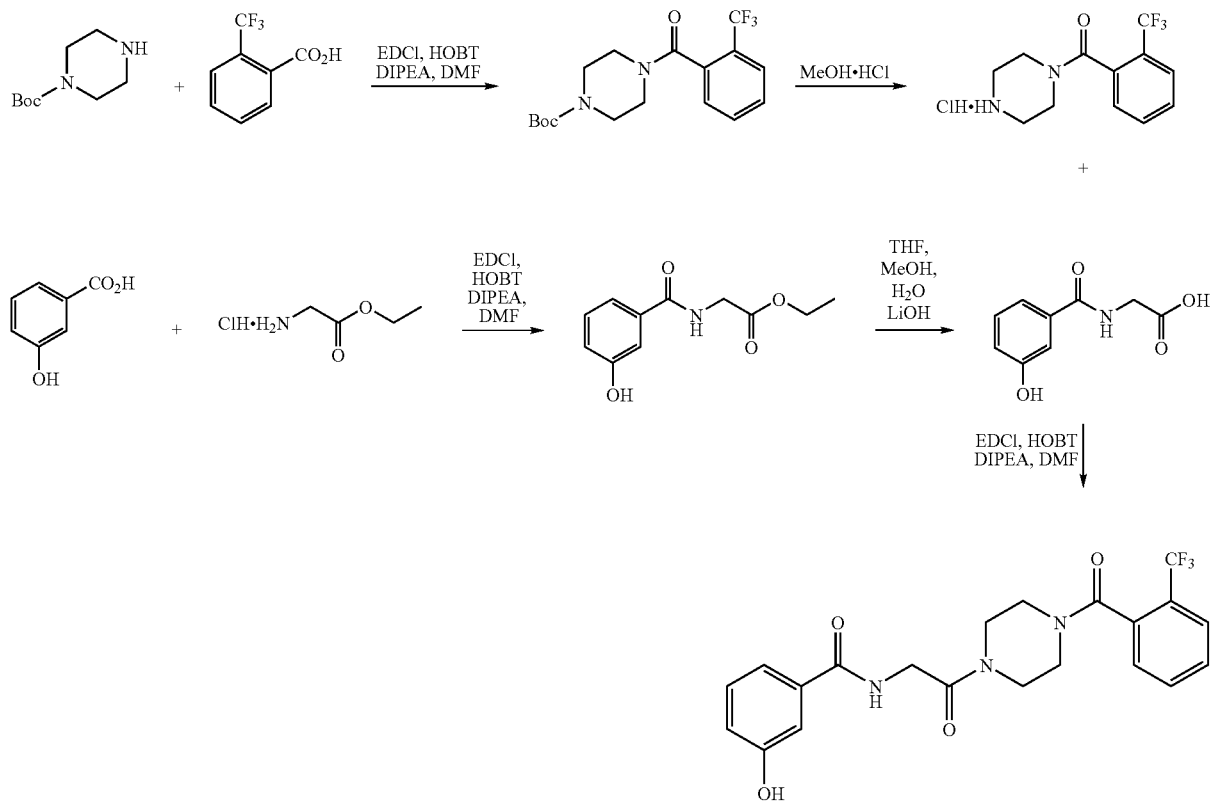

Step 1A: Synthesis of 4-(2-trifluoromethyl-benzoyl)-piperazine-1-carboxylic acid tert-butyl ester

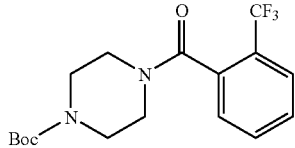

4-(2-trifluoromethyl-benzoyl)-piperazine-1-carboxylic acid tert-butyl ester was prepared as described above (Scheme 9).

Step 1B: Synthesis of piperazin-1-yl-(2-trifluoromethyl-phenyl)-methanone

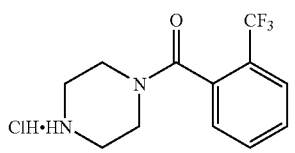

Piperazin-1-yl-(2-trifluoromethyl-phenyl)-methanone was prepared as described above (Scheme 9).

Step 2A: Synthesis of (3-Hydroxy-benzoyl amino)-acetic acid ethyl ester

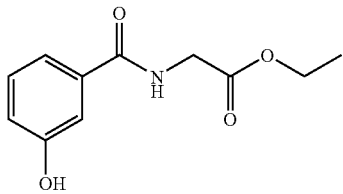

DIPEA (375 µL, 2.17 mmol) was added drop wise to 3-hydroxy benzoic acid (100 mg, 0.72 mmol) in DMF (4 mL). EDCI (208 mg, 1.09 mmol) and HOBT (117 mg, 0.87 mmol) were added consecutively and after 15 mins, glycine ethyl ester HCl (120 mg, 0.87 mmoles) was added. The resulting mixture was stirred at room temperature overnight. Water was then added, and the product was extracted with EtOAc. The organic layer was washed with brine, dried over $Na_2SO_4$ and concentrated under reduced pressure to afford (3-Hydroxy-benzoyl amino)-acetic acid ethyl ester in quantitative yield.

Step 2B: Synthesis of (3-Hydroxy-benzoyl amino)-acetic acid

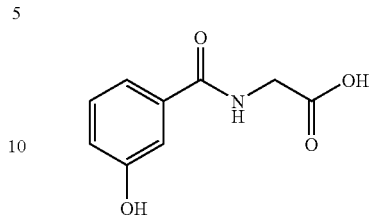

LiOH (75 mg in 2 mL water) was added to (3-hydroxy-benzoyl amino)-acetic acid ethyl ester (100 mg, 0.45 mmol) in a mixture of THF and MeOH mixture. This was followed by the addition of to the reaction mixture. The resulting mixture was stirred at room temperature overnight. The THF and MeOH were then evaporated under reduced pressure and the resulting residue was acidified to pH 2 using 10% citric acid solution. The product was extracted with EtOAc. The organic layer was washed with brine, dried over $Na_2SO_4$ and concentrated under reduced pressure to afford (3-hydroxy-benzoyl amino)-acetic acid in 89% yield. $^1$H NMR (DMSO-$D_6$): δ 12.4 (s, 1H), 9.6 (s, 1H), 8.7 (t, 1H), 7.2 (d, 3H), 6.9 (m, 1H), 4.0 (d, 2H).

Step 2C

150) Synthesis of 3-Hydroxy-N-[2-Oxo-2-trifluoromethyl-benzoyl)-piperazine-1-yl]-ethyl]-benzamide

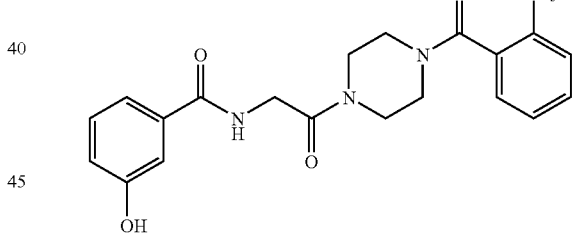

DIPEA (0.7692 g, 3 mmol) was added dropwise to (3-hydroxy-benzoyl amino)-acetic acid (50 mg, 0.26 mmol) in DMF (4 mL). EDCI (122 mg, 0.64 mmol) and HOBT (41 mg, 0.31 mmol) were added consecutively and after 10 mins, piperazin-1-yl-(2-trifluoromethyl-phenyl)-methanone (90 mg, 0.31 mmol) was added and was allowed to stir at room temperature overnight. The resulting mixture was stirred at room temperature overnight. Water was then added, and the product was extracted with EtOAc. The organic layer was washed with brine, dried over $Na_2SO_4$ and concentrated under reduced pressure to afford the crude product. Purification using column chromatography (silica gel of mesh size of 60-120 using 90:10 EtOAc:hexane as eluent) afforded 3-hydroxy-N-[2-Oxo-2-trifluoromethyl-benzoyl)-piperazine-1-yl]-ethyl]-benzamide in 39% yield. LC-MS purity: 98%, $H^1$—NMR (DMSO-$D_6$): δ 9.6 (s, 1H), 8.4 (d, 1H), 7.8 (dd, 2H), 7.7 (d, 1H), 7.6 (t, 1H), 7.2 (d, 3H), 6.9 (d, 1H), 4.1 (dd, 2H), 3.6 (m, 4H), 3.4 (s, 2H), 3.2 (d, 2H).

SCHEME-11

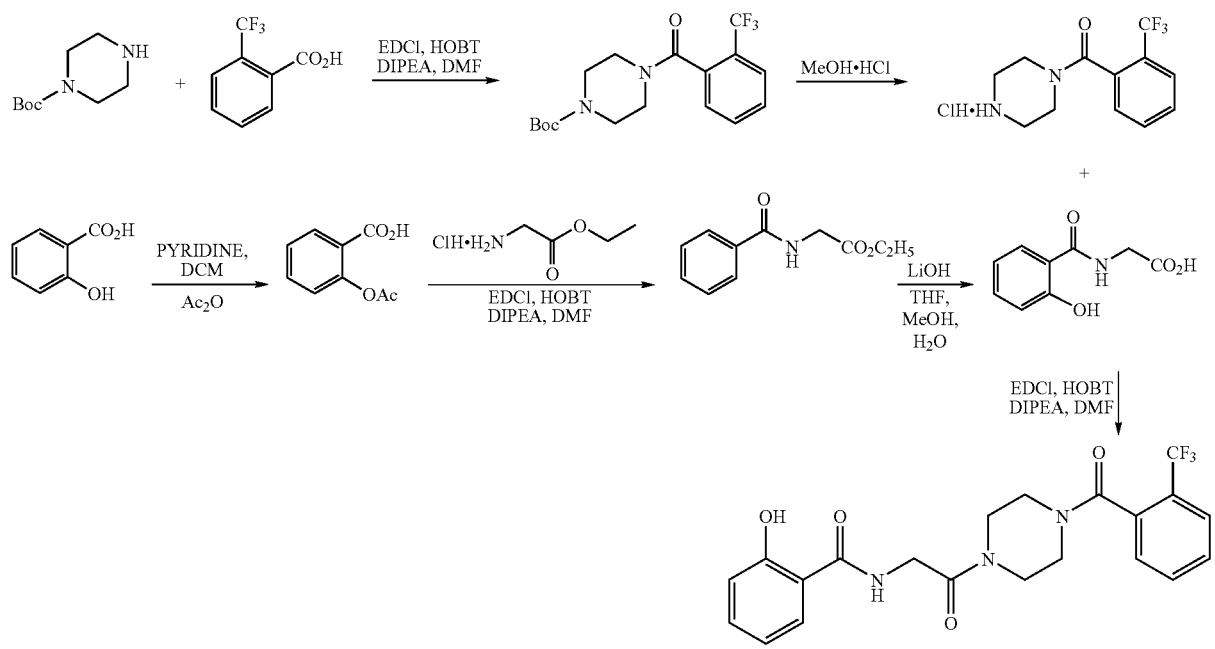

Step 1A: Synthesis of 4-(2-trifluoromethyl-benzoyl)-piperazine-1-carboxylic acid tert-butyl ester

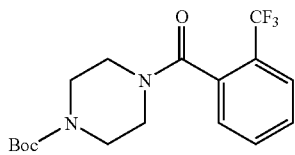

4-(2-trifluoromethyl-benzoyl)-piperazine-1-carboxylic acid tert-butyl ester was prepared as described above (Scheme 9).

Step 1B: Synthesis of piperazin-1-yl-(2-trifluoromethyl-phenyl)-methanone

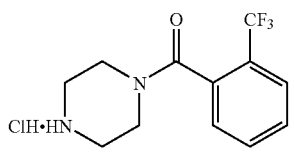

Piperazin-1-yl-(2-trifluoromethyl-phenyl)-methanone was prepared as described above (Scheme 9).

Step 2A: Synthesis of 2-Acetoxy-benzoic acid

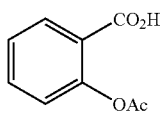

Pyridine (64 μl, 0.80 mmol) was added to an ice cooled mixture of salicylic acid (10 mg, 0.72 mmol) and methylene chloride (10 mL). After 5 minutes, acetic anhydride (10 μl, 1.09 mmoles) was added. The resulting mixture was stirred at room temperature for 4 hrs. The product was extracted with methylene chloride and water. The organic layer was washed with brine, dried over $Na_2SO_4$ and concentrated under reduced pressure to afford 2-acetoxybenzoic acid in 76% yield.

Step 2B: Synthesis of (2-Acetoxy-benzoyl amino)-acetic acid ethyl ester

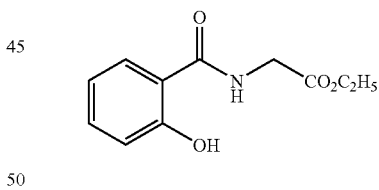

DIPEA (0.288 mL, 1.67 mmol) was added dropwise to 2-acetoxy benzoic acid (100 mg, 0.56 mmol) in DMF (5 mL). EDCI (266 mg, 1.39 mmol) and HOBT (90 mg, 0.67 mmol) were added consecutively and after 10 mins, glycine ethyl ester. HCl (92 mg, 0.67 mmoles) was added. The resulting mixture was stirred at room temperature overnight. Water was then added, and the product was extracted with EtOAc. The organic layer was washed with brine, dried over $Na_2SO_4$ and concentrated under reduced pressure to afford (2-Acetoxy-benzoyl amino)-acetic acid ethyl ester in 97% yield. $^1H$ NMR (DMSO-$D_6$): δ 12.2 (s, 1H), 9.2 (t, 1H), 7.9 (dd, 1H), 7.4 (dt, 1H), 6.9 (d, 2H), 4.2 (q, 2H), 4.1 (d, 2H), 3.8 (d, 1H), 1.3 (t, 3H).

Step 2C: Synthesis of (2-Hydroxybenzoyl amino)-acetic acid

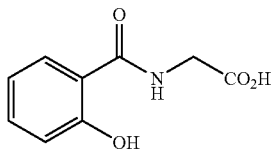

LiOH in water (82 mg in 2 mL of water) was added dropwise to (2-hydroxy-benzoyl amino)-acetic acid ethyl ester (110 mg, 0.49 mmol) in a mixture of THF and MeOH. The THF and MeOH were evaporated under reduced pressure and the residue was acidified using 10% citric acid solution. The product was extracted with EtOAc. The organic layer was washed with brine, dried over $Na_2SO_4$ and concentrated under reduced pressure to afford (2-hydroxybenzoyl amino)-acetic acid in 93% yield. $^1$H NMR (DMSO-$D_6$): δ 12.8 (s, 1H), 12.2 (s, 1H), 9.2 (t, 1H), 7.9 (d, 1H), 7.5 (dt, 1H), 7.0 (d, 2H), 4.0 (d, 2H).

151) Synthesis of 2-Hydroxy-N-[2-Oxo-2-[4-(2-trifluoromethyl-benzoyl)-piperazine-1-yl]-ethyl]-benzamide

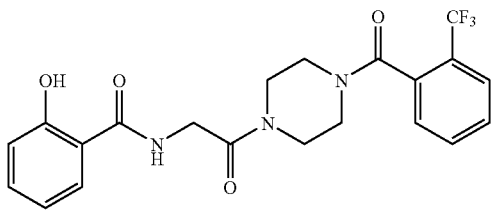

DIPEA (0.239 mL, 1.39 mmol) was added drop wise to (2-hydroxy-benzoyl amino)-acetic acid (90 mg, 0.46 mmol) in DMF (7 mL). EDCI (221 mg, 1.15 mmol) and HOBT (74 mg, 0.55 mmol) were added consecutively and after 5 minutes, piperazin-1-yl-(2-trifluoromethyl-phenyl)-methanone (162 mg, 0.55 mmol) was added. The resulting mixture was stirred at room temperature overnight. Water was then added, and the product was extracted with EtOAc. The organic layer was washed with brine, dried over $Na_2SO_4$ and concentrated under reduced pressure to afford the crude product. Purification using column chromatography (silica gel of mesh size of 60-120 using 70:30 EtOAc:hexane as eluent) afforded 2-hydroxy-N-[2-Oxo-2-[4-(2-trifluoromethyl-benzoyl)-piperazine-1-yl]-ethyl]-benzamide in 25% yield. LC-MS purity: 97%, $^1$H NMR (DMSO-$D_6$): δ 12.0 (s, 1H), 9.1 (t, 1H), 7.9 (m, 3H), 7.7 (d, 1H), 7.6 (m, 1H), 7.4 (t, 1H), 6.9 (t, 2H), 4.2 (dd, 2H), 3.6 (m, 4H), 3.4 (m, 2H), 3.2 (m, 2H).

152) Synthesis of 5-Phenyl-furan-2-carboxylic acid {2-oxo-2-[4-(2-trifluoromethyl-benzoyl)-piperazin-1-yl]-ethyl}-amide

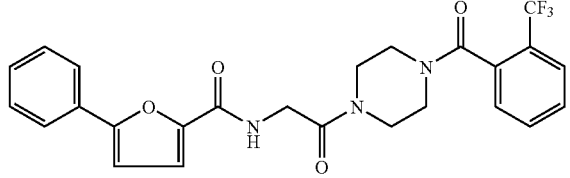

DIPEA (82 mg, 0.109 mL, 0.64 mmol) was added to a stirred solution of 2-amino-1-[4-(2-trifluoromethyl-benzoyl)-piperazin-1-yl]-ethanone TFA salt, (109 mg, 0.26 mmol) in DMF (1 mL). HOBT (34 mg, 0.26 mmol) and EDCI.HCl (49 mg, 0.26 mmol) were added at room temperature. After 2 minutes 5-phenyl furoic acid (40 mg, 0.21 mmol) was added. The resulting mixture was stirred at room temperature overnight. Water was then added, and the product was extracted with EtOAc. The organic layer was washed with brine, dried over $Na_2SO_4$ and concentrated under reduced pressure to afford 45 mg (40% yield) of 5-phenyl-furan-2-carboxylic acid {2-oxo-2-[4-(2-trifluoromethyl-benzoyl)-piperazin-1-yl]-ethyl}-amide. LCMS Purity %: 84.97, HPLC Purity: 92.51%, $^1$H NMR (DMSO-$d_6$): δ 8.6 (t, 1H), 8.0-7.9 (d, 2H) 7.9-7.6 (m, 3H), 7.6-7.5 (bt, 1H), 7.5 (t, 2H), 7.4-7.3 (m, 1H), 7.2 (m, 1H), 7.1 (d, 1H), 4.2-4.1 (m, 2H), 3.8-3.5 (m, 4H), 3.4 (m, 2H), 3.2-3.1 (m, 2H).

153) Synthesis of 5-(3-Trifluoromethyl-phenyl)-furan-2-carboxylic acid {2-oxo-2-[4-(2-trifluoromethyl-benzoyl)-piperazin-1-yl]-ethyl}-amide

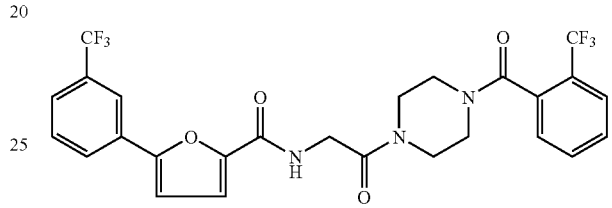

DIPEA (75 mg, 0.1 mL, 0.59 mmol) was added to a stirred solution of 2-amino-1-[4-(2-trifluoromethyl-benzoyl)-piperazin-1-yl]-ethanone TFA salt (100 mg, 0.23 mmol) in DMF (1 mL). HOBT (32 mg, 0.23 mmol) and EDCI.HCl (44 mg, 0.23 mmol) were then added at room temperature. After 2 minutes, 5-(3-trifluoromethyl-phenyl)-furan-2-carboxylic acid (50 mg, 0.20 mmol) was added. The resulting mixture was stirred at room temperature for four hours. Water was then added, and the product was extracted with EtOAc. The organic layer was washed with brine, dried over $Na_2SO_4$ and concentrated under reduced pressure to afford 40 mg (37% yield) of 5-(3-trifluoromethyl-phenyl)-furan-2-carboxylic acid {2-oxo-2-[4-(2-trifluoromethyl-benzoyl)-piperazin-1-yl]-ethyl}-amide. LCMS Purity %: 86.88, HPLC 92.52%, $^1$H NMR (DMSO-$d_6$): δ 8.8-8.7 (bt, 1H), 8.3 (s, 1H), 8.2 (bt, 1H), 7.9-7.6 (m, 5H), 7.6-7.5 (bt, 1H), 7.4-7.3 (d, 1H), 7.3-7.2 (m, 1H), 4.3-4.1 (m, 2H), 3.8-3.4 (m, 6H), 3.2-3.1 (m, 2H).

154) Synthesis of N-{2-Oxo-2-[4-(2-trifluoromethyl-benzoyl)-piperazin-1-yl]-ethyl}-3-phenoxy-benzamide

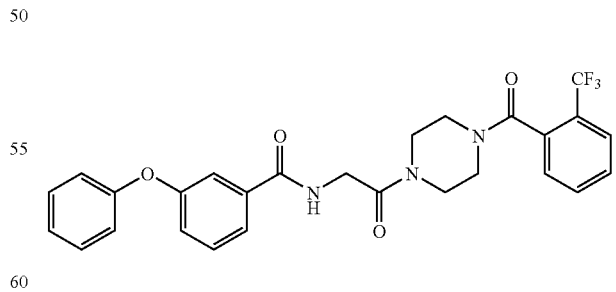

DIPEA (73 mg, 0.097 mL, 0.56 mmol) was added to a stirred solution of 2-amino-1-[4-(2-trifluoromethyl-benzoyl)-piperazin-1-yl]-ethanone TFA salt (96 mg, 0.22 mmol) in DMF (1 mL). HOBT (30 mg, 0.22 mmol) and EDCI.HCl (43 mg, 0.22 mmol) were added at room temperature. After 2 minutes, 3-phenoxy-benzoic acid (40 mg, 0.19 mmol) was added. The resulting mixture was stirred at room temperature for four hours. Water was then added, and the product was extracted with EtOAc. The organic layer was washed with brine, dried over Na₂SO₄ and concentrated under reduced pressure to afford 70 mg (72.5% yield) of LCMS Purity %: 89.64, HPLC Purity %: 91.62, ¹H NMR (DMSO-d₆): δ 8.7-8.6 (bt, 1H), 7.9-7.4 (m, 8H), 7.2 (m, 1H), 7.1-7.0 (d, 1H), 4.2-4.0 (m, 2H), 3.8-3.4 (m, 6H), 3.2-3 (m, 2H).

155) Synthesis of 4-Benzoyl-N-{2-oxo-2-[4-(2-trifluoromethyl-benzoyl)-piperazin-1-yl]-ethyl}-benzamide

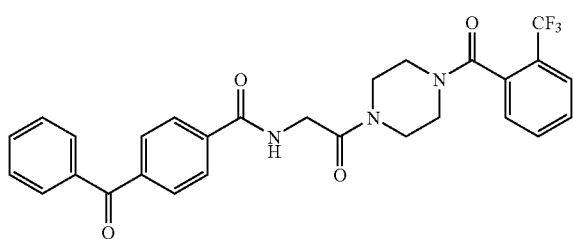

DIPEA (77 mg, 0.103 mL, 0.60 mmol) was added to a stirred solution of 2-Amino-1-[4-(2-trifluoromethyl-benzoyl)-piperazin-1-yl]-ethanone TFA salt (102 mg, 0.29 mmol) in DMF (1 mL). HOBT (32 mg, 0.238 mmol) and EDCI.HCl (46 mg, 0.238 mmol) were at room temperature. After 2 minutes, 4-benzoyl-benzoic acid (45 mg, 0.20 mmol) was added. The resulting mixture was stirred at room temperature for four hours. Water was then added, and the product was extracted with EtOAc. The organic layer was washed with brine, dried over Na₂SO₄ and concentrated under reduced pressure to afford 54 mg (51.86% yield) of 4-benzoyl-N-{2-oxo-2-[4-(2-trifluoromethyl-benzoyl)-piperazin-1-yl]-ethyl}-benzamide. LCMS Purity %: 91.57, HPLC Purity %: 95.52, ¹H NMR (DMSO-d₆): δ 8.8 (bt, 1H), 8.1-8.0 (d, 2H), 7.9-7.7 (m, 7H), 7.6 (t, 3H), 4.3-4.1 (m, 2H), 3.8-3.5 (m, 4H), 3.5-3.4 (m, 2H), 3.2-3.1 (m, 2H).

156) Synthesis of 4-Fluoro-N-{2-oxo-2-[4-(2-trifluoromethyl-benzoyl)-piperazin-1-yl]-ethyl}-benzamide

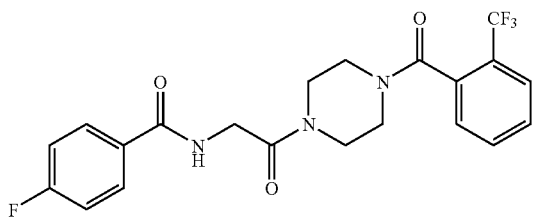

DIPEA (46.5 mg, 0.36 mmol) was added to a stirred solution of 2-amino-1-[4-(2-trifluoromethyl-benzoyl)-piperazin-1-yl]-ethanone-TFA salt (62 mg, 0.14 mmol) in DMF (0.5 mL). HOBT (19 mg, 0.14 mmol) and EDCI.HCl (28 mg, 0.14 mmol) were added at room temperature. After 2 minutes, 4-fluorobenzoic acid, (17 mg, 0.12 mmol) was added. The resulting mixture was stirred at room temperature for four hours. Water was then added, and the product was extracted with EtOAc. The organic layer was washed with brine, dried over Na₂SO₄ and concentrated under reduced pressure to afford 35 mg (67% yield) of 4-fluoro-N-{2-oxo-2-[4-(2-trifluoromethyl-benzoyl)-piperazin-1-yl]-ethyl}-benzamide. LCMS Purity: 92.29%, HPLC Purity: 93.53%.

157) Synthesis of 4-Nitro-N-{2-oxo-2-[4-(2-trifluoromethyl-benzoyl)-piperazin-1-yl]-ethyl}-benzamide

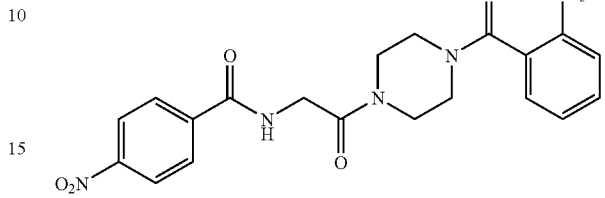

DIPEA (47 mg, 0.36 mmol) was added to a stirred solution of 2-amino-1-[4-(2-trifluoromethyl-benzoyl)-piperazin-1-yl]-ethanone-TFA salt (62 mg, 0.14 mmol) in DMF (0.5 mL). HOBT (19 mg, 0.14 mmol) and EDCI.HCl (28 mg, 0.14 mmol) were added at room temperature. After 2 minutes, 4-nitro benzoic acid (20 mg, 0.12 mmol) was added. The resulting mixture was stirred at room temperature for four hours. Water was then added, and the product was extracted with EtOAc. The organic layer was washed with brine, dried over Na₂SO₄ and concentrated under reduced pressure to afford 40.7 mg (74% yield) of 4-Nitro-N-{2-oxo-2-[4-(2-trifluoromethyl-benzoyl)-piperazin-1-yl]-ethyl}-benzamide. LCMS Purity: 88.67%, HPLC Purity: 92.93%, ¹H NMR (CDCl₃): δ 8.3 (d, 2H), 8.0 (m, 2H), 7.8-7.7 (d, 1H), 7.6 (m, 2H), 7.4-7.3 (d, 2H), 4.4-4.3 (dd, 1H), 4.3-4.2 (dd, 2H), 4.1-3.9 (m, H), 3.8-3.7 (m, 2H), 3.6 (m, 2H), 3.4 (bt, 1H), 3.2 (m, 2H).

158) Synthesis of 5-Nitro-furan-2-carboxylic acid {2-oxo-2-[4-(2-trifluoromethyl-benzoyl)-piperazin-1-yl]-ethyl}-amide

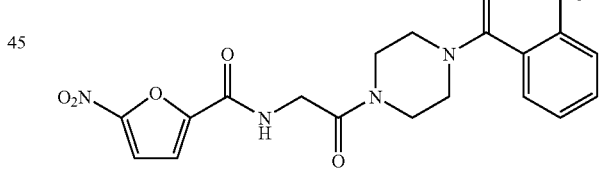

DIPEA (50 mg, 0.38 mmol) was added to a stirred solution of 2-amino-1-[4-(2-trifluoromethyl-benzoyl)-piperazin-1-yl]-ethanone-TFA salt (66 mg, 0.15 mmol) in DMF (1 mL). HOBT (21 mg, 0.15 mmol) and EDCI.HCl (29 mg, 0.15 mmol) were added at room temperature. After 2 minutes, 5-nitro-furan-2-carboxylic acid (20 mg, 0.13 mmol) was added. The resulting mixture was stirred at room temperature for four hours. Water was then added, and the product was extracted with EtOAc. The organic layer was washed with brine, dried over Na₂SO₄ and concentrated under reduced pressure. Purification by column chromatography (using silica gel of mesh size of 60-120 and 3% methanol in chloroform as the eluent) afforded 28 mg (49.12% yield) of 5-nitro-furan-2-carboxylic acid {2-oxo-2-[4-(2-trifluoromethyl-benzoyl)-piperazin-1-yl]-ethyl}-amide. LCMS Purity: 97.329%, HPLC Purity %: 95.234, ¹H NMR (CDCl₃): δ

7.8-7.7 (d, 1H), 7.7-7.5 (m, 3H), 7.4-7.3 (m, 2H), 4.4-4.3 (t, 1H), 4.2 (bt, 1H), 4.1-3.8 (m, 2H), 3.8-3.5 (m, 4H), 3.4 (bt, 1H), 3.3-3.2 (m, 2H).

159) Synthesis of 1-Phenyl-piperidine-4-carboxylic acid {2-oxo-2-[4-(2-trifluoromethyl-benzoyl)-piperazin-1-yl]-ethyl}-amide

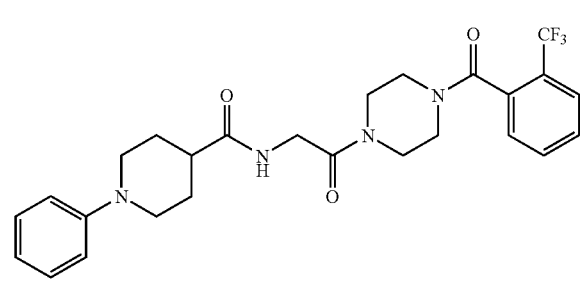

Step 1: Synthesis of
1-Phenyl-piperidine-4-carboxylic acid methyl ester

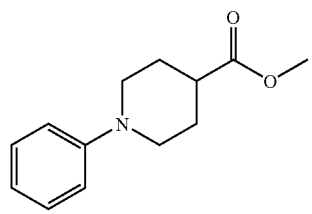

Step 1A

Cs$_2$CO$_3$ (1.8 g, 5.57 mmol) was added to a stirred solution of piperidine-4-carboxylic acid methyl ester HCl salt (200 mg, 1.113 mmol) in toluene (6 mL) under an atmosphere of argon. The resulting mixture was stirred at room temperature for 15 minutes.

Step 1B

A solution of toluene (1 mL), Pd (OAc)$_2$ (25 mg, 0.11 mmol) and BINAP (69 mg, 0.11 mmol) in toluene (1 mL) was stirred under an atmosphere of argon for 15 minutes. This mixture was then added in one portion to the solution prepared in Step 1A and the resulting mixture was heated to reflux temperature overnight. The mixture was diluted with water and the product was extracted with EtOAc. The organic layer was washed with brine, dried over Na$_2$SO$_4$ and concentrated under reduced pressure. Purification by column chromatography (using silica gel of mesh size of 60-120 and 55% EtOAc in hexane as the eluent) afforded 150 mg (61.5% yield). LCMS Purity %: 94.07.

Step 2: Synthesis of
1-Phenyl-piperidine-4-carboxylic acid

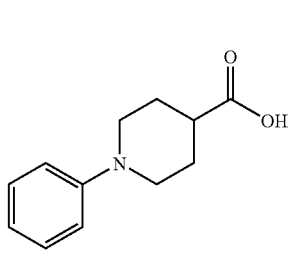

LiOH (43 mg, 1.03 mmol) was added at room temperature to a stirred solution of 1-phenyl-piperidine-4-carboxylic acid methyl ester (150 mg, 0.68 mmol) in THF:MeOH:H$_2$O (3:1:1, 3.2 mL). The resulting mixture was stirred at room temperature overnight. The MeOH and THF were evaporated and the residue was diluted with water (2 mL), acidified with citric acid solution and extracted with EtOAc. The organic layer was washed with saturated brine, dried over Na$_2$SO$_4$ and concentrated under reduced pressure to afford 94 mg (67.14% yield) of 1-phenyl-piperidine-4-carboxylic acid. LCMS purity: 95.98%.

Step 3: Synthesis of 1-Phenyl-piperidine-4-carboxylic acid {2-oxo-2-[4-(2-trifluoromethyl-benzoyl)-piperazin-1-yl]-ethyl}-amide DIPEA (66 mg, 0.088 mL, 0.51 mmol) was added to a stirred solution of 2-Amino-1-[4-(2-trifluoromethyl-benzoyl)-piperazin-1-yl]-ethanone TFA salt (125 mg, 0.29 mmol) in DMF (1.5 mL). HOBT (27 mg, 0.20 mmol) and EDCI.HCl (39 mg, 0.20 mmol) were added at room temperature. After 2 minutes 1-phenyl-piperidine-4-carboxylic acid (35 mg, 0.17 mmol) was added. The resulting mixture was stirred at room temperature for four hours. Water was then added, and the product was extracted with EtOAc. The organic layer was washed with brine, dried over Na$_2$SO$_4$ and concentrated under reduced pressure to afford 25 mg (29% yield) of 1-phenyl-piperidine-4-carboxylic acid {2-oxo-2-[4-(2-trifluoromethyl-benzoyl)-piperazin-1-yl]-ethyl}-amide. LCMS Purity %: 87.42, HPLC Purity: 88.83%, $^1$H NMR (DMSO-d$_6$): δ 7.8-7.5 (m, 3H), 7.4-7.3 (d, 1H), 7.3-7.2 (t, 1H), 7.0-6.9 (d, 1H), 6.8 (t, 1H), 6.6 (m, 1H), 4.2-3.7 (m, 4H), 3.8-3.6 (m, 4H), 3.5 (m, 2H), 3.4-3.3 (bt, 1H), 3.2 (m, 2H), 2.7 (m, 2H), 2.3 (m, 1H), 2.0-1.8 (m, 4H).

SCHEME-12

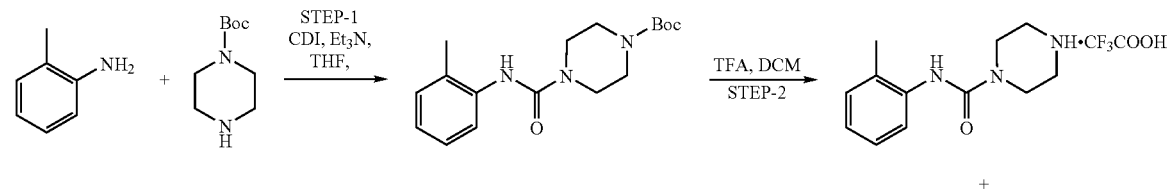

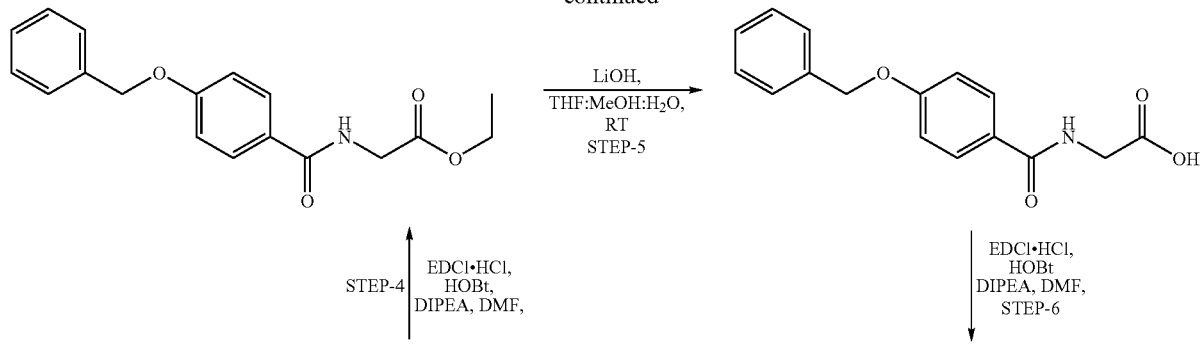

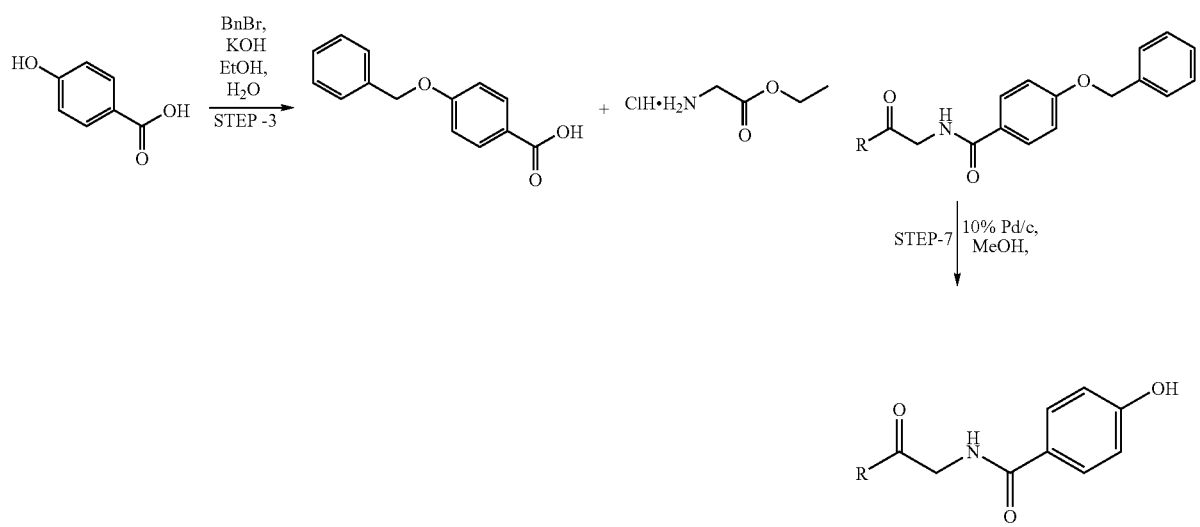

Step 1: Synthesis of 4-O-Tolylcarbamoyl-piperazine-1-carboxylic acid tert-butyl ester

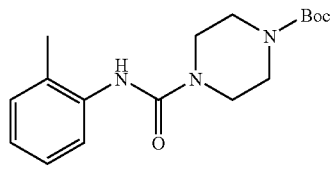

Et₃N (0.47 g, 0.644 mL, 4.66 mmol), carbonyldiimidazole (1.5 g, 9.32 mmol) were added to a stirred solution of O-toluedine (0.5 g, 4.66 mmol) in THF (5 mL) and the resulting mixture was stirred at reflux temperature for one hour. N-Boc-piperazine (0.87 g, 4.66 mmol) was added and the mixture stirred at reflux temperature for 2 hrs. Ethyl acetate was added and the resultant was washed with 5% aqueous HCl solution, followed by saturated NaHCO₃ solution, water and saturated brine solution. The organic layer was dried over sodium sulphate and concentrated in vacuo to afford 1.3 g (87.25% yield) of 4-O-tolylcarbamoyl-piperazine-1-carboxylic acid tert-butyl ester. LCMS Purity %: 95.61, ¹H NMR (CDCl₃): δ 7.6-7.5 (d, 1H), 7.2-7.1 (m, 2H), 7.0 (t, 1H), 6.2 (s, 1H), 3.4 (s, 8H), 2.2 (s, 3H), 1.4 (s, 9H).

Step 2: Synthesis of piperazine-1-carboxylic acid o-tolylamide TFA salt

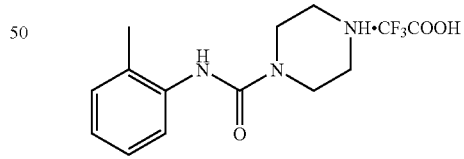

A stirred solution of 4-O-tolylcarbamoyl-piperazine-1-carboxylic acid tert-butyl ester (0.5 g, 1.56 mmol) in methylene chloride (5 mL) was cooled to 0° C. TFA (1 mL) was added and the mixture was stirred at 0° C. for 2 hrs. The solvent was removed under reduced pressure and the residue was washed with ether to afford 0.5 g (96% yield) of piperazine-1-carboxylic acid o-tolylamide TFA salt. ¹H NMR (CDCl₃): δ 8.8 (bs, 2H), 8.2 (s, 1H), 7.2-7.0 (m, 4H), 3.6 (bt, 4H), 3.2 (bt, 4H), 2.2 (s, 3H).

Step 3: Synthesis of 4-Benzyloxy benzoic acid

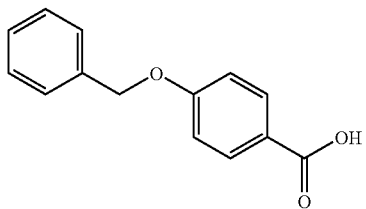

KOH (6.16 g, 109.78 mmol) and benzyl bromide (9.42 g, 55.08 mmol) were added to a stirred solution of 4-hydroxy benzoic acid (6.9 g, 49.96 mmol) in EtOH:$H_2O$ (9:1, 176 mL) and the resulting mixture was heated to reflux for 20 hrs. 20% KOH solution (60 mL) was then added the mixture maintained at reflux for 4 hours. The reaction mixture was diluted with water (200 mL) and acidified with 20% HCl. The resulting white precipitate was filtered and washed with water followed by hexane to afford 7.1 g (62.2% yield) of 4-benzyloxy benzoic acid. $^1$H NMR (DMSO-$d_6$): δ 12.6 (s, 1H), 7.9 (d, 2H), 7.4 (m, 5H), 7.1 (d, 2H), 5.2 (s, 2H).

Step 4: Synthesis of (4-Benzyloxy-benzoylamino)-acetic acid ethyl ester

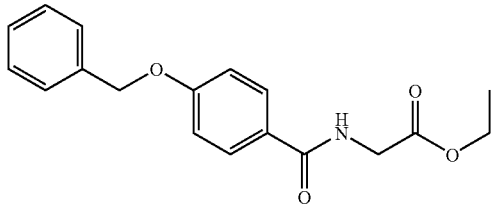

DIPEA (5.12 g, 6.85 mL, 0.59 mmol) was added to a stirred solution of 4-benzyloxy benzoic acid (2 g, 8.7 mmol) in DMF (18 mL). HOBT (1.3 g, 9.5 mmol) and EDCI.HCl (4.2 g, 21.7 mmol) were added at room temperature. After 2 minutes glycine ethyl ester HCl (1.47 g, 10.5 mmol) was added to the reaction mixture. The resulting mixture was stirred at room temperature overnight. Water was then added, and the product was extracted with EtOAc. The organic layer was washed with brine, dried over $Na_2SO_4$ and concentrated under reduced pressure to afford the crude product. Purification using column chromatography (silica gel of mesh size of 60-120 using 40% EtOAc in Hexane as eluent) afforded 2.47 g (90.1% yield) of (4-Benzyloxy-benzoylamino)-acetic acid ethyl ester. LCMS Purity %: 98.6, $^1$H NMR (DMSO): δ 8.9 (t, 1H), 7.8 (d, 2H), 7.5 (m, 5H), 7.2 (d, 2H), 5.4 (s, 2H), 4.2 (q, 2H), 4.0 (d, 2H), 0.8 (t, 3H).

Step 5: Synthesis of (4-Benzyloxy-benzoylamino)-acetic Acid

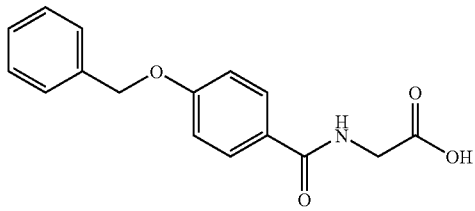

LiOH (1.32 g, 31.5 mmol) was added to a stirred solution of (4-benzyloxy-benzoylamino)-acetic acid ethyl ester (2.47 g, 7.8 mmol) in THF:MeOH:$H_2O$ (2:2:1, 50 mL). The resulting mixture was stirred at room temperature overnight. The MeOH and THF were evaporated and the residue was diluted with water (20 mL) and acidified with 10% HCl solution. The resulting precipitate was washed with water followed by hexane and dried to afford 2.03 g (90.6 yield) of (4-benzyloxy-benzoylamino)-acetic acid. $^1$H NMR: (DMSO) δ 7.9 (d, 2H), 7.8 (s, 1H), 7.5 (m, 5H), 7.1 (d, 2H), 5.2 (s, 2H), 3.6 (d, 2H).

Step 6

160) Synthesis of 4-[2-(4-Benzyloxy-benzoylamino)-acetyl]-piperazine-1-carboxylic acid o-tolylamide

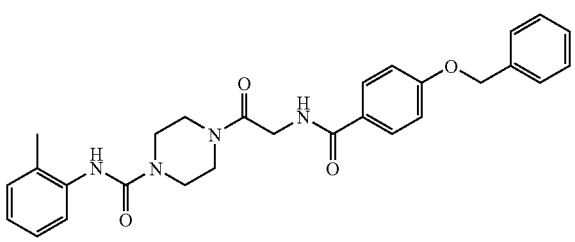

DIPEA (136 mg, 0.182 mL, 1.05 mmol) was added to a stirred solution of (4-Benzyloxy-benzoylamino)-acetic acid (100 mg, 0.35 mmol) in DMF (1 mL). HOBT (57 mg, 0.42 mmol) and EDCI.HCl (83 mg, 0.42 mmol) were added at room temperature. After 2 minutes piperazine-1-carboxylic acid O-tolylamide TFA salt (140 mg, 0.42 mmol) was added. The reaction mixture was diluted with cold water and the resulting precipitate was filtered under reduced pressure to afford 87 mg (50.8% yield) of 4-[2-(4-benzyloxy-benzoylamino)-acetyl]-piperazine-1-carboxylic acid o-tolylamide. LCMS Purity %: 89.31, HPLC Purity %: 91.55, $^1$H NMR (DMSO-$d_6$): δ 8.5-8.4 (bt, 1H), 8.2-8.1 (s, 1H), 7.9-7.8 (d, 2H), 7.4 (m, 5H), 7.2-7.0 (m, 6H) 5.2 (s, 2H), 4.2-4.1 (d, 2H), 3.5 (m, 8H), 2.2 (s, 3H).

Step 7

161) Synthesis of 4-[2-(4-Hydroxy-benzoylamino)-acetyl]-piperazine-1-carboxylic acid o-tolylamide

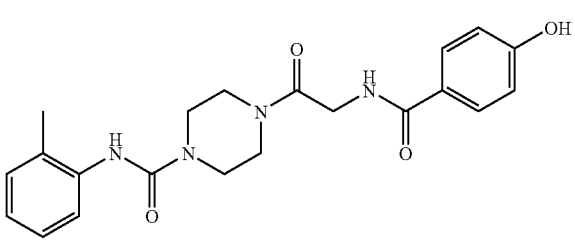

10% Pd/c (13 mg) was added to a stirred solution of 4-[2-(4-benzyloxy-benzoylamino)-acetyl]-piperazine-1-carboxylic acid O-tolylamide (60 mg, 0.12 mmol) in EtOAc:MeOH (1:1, 2 mL) and the resulting mixture was stirred under an atmosphere of hydrogen overnight. The mixture was filtered over celite and the celite was washed with MeOH. The filtrate and the washings were then concentrated under reduced pressure to afford 31.2 mg (51.6% yield) of 4-[2-(4-hydroxy-benzoylamino)-acetyl]-piperazine-1-carboxylic acid o-tolylamide. LCMS Purity %: 94.22, HPLC Purity %: 90.75, $^1$H NMR (DMSO-$d_6$): δ 10.2-10 (bs, 1H), 8.4-8.3 (t, 1H), 8.2-8.1

(s, 1H), 7.8-7.7 (d, 2H), 7.2-7.0 (m, 4H) 6.8 (d, 2H), 4.2-4.1 (d, 2H), 3.6-3.4 (m, 8H), 2.2 (s, 3H).

162) Synthesis of 4-Benzyloxy-N-{2-oxo-2-[4-(2-trifluoromethyl-benzoyl)-piperazin-1-yl]-ethyl}-benzamide

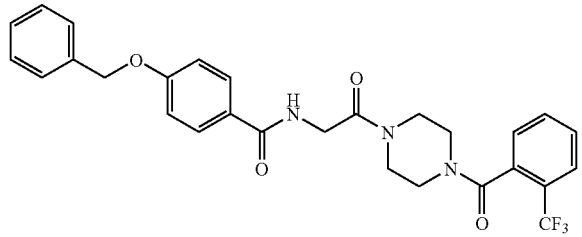

DIPEA (98 mg, 0.76 mmol) was added to a stirred solution of (4-benzyloxy-benzoylamino]-acetic acid (50 mg, 0.17 mmol) in DMF (3 mL). HOBT (25.8 mg, 0.19 mmol) and EDCI.HCl (83 mg, 0.43 mmol) were added at room temperature. After 2 minutes, piperazine-1-yl-(2-trifluoromethyl-phenyl)-methanone hydrochloride (61.5 mg, 0.21 mmol). The resulting mixture was stirred at room temperature overnight. The mixture was diluted with cold water and the resulting precipitate was filtered, washed with hexane and dried to afford 93 mg (99% yield) of 4-benzyloxy-N-{2-oxo-2-[4-(2-trifluoromethyl-benzoyl)-piperazin-1-yl]-ethyl}-benzamide. LC-MS purity: 87%, $^1$H NMR (DMSO): δ 8.5 (s, 1H,), 7.8 (m, 5H), 7.5 (s, 1H), 7.4 (m, 4H), 7.1 (d, 2H), 5.2 (s, 2H), 4.2 (d, 2H), 3.7 (m, 4H), 3.5 (s, 2H), 3.4 (s, 2H), 3.3 (s, 2H).

163) Synthesis of 4-Benzyloxy-N-{2-oxo-2-[4-(2-trifluoromethyl-benzoyl)-piperazin-1-yl]-ethyl}-benzamide

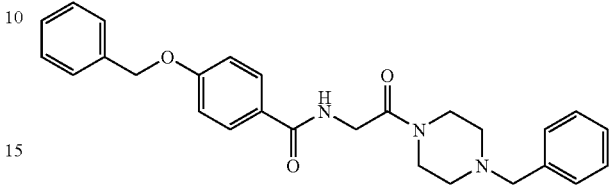

DIPEA (102 mg, 0.79 mmol) was added to a stirred solution of (4-benzyloxy-benzoylamino]-acetic acid (50 mg, 0.18 mmol) in DMF (2 mL). HOBT (26 mg, 0.19 mmol) and EDCI.HCl (84 mg, 0.44 mmol) were added at room temperature. After 2 minutes 1-benzylpiperazine (37 mg, 0.21 mmol) was added. The resulting mixture was stirred at room temperature overnight. The mixture was diluted with cold water and the resulting precipitate was filtered, washed with hexane and dried to afford 65 mg (83.5% yield) of 4-benzyloxy-N-{2-oxo-2-[4-(2-trifluoromethyl-benzoyl)-piperazin-1-yl]-ethyl}-benzamide. LC-MS purity: 79.1%, $^1$H NMR (CDCl$_3$) δ 7.7 (d, 2H,), 7.4 (m 9H), 7.2 (s, 2H), 7.0 (d, 2H), 5.4 (t, 1H), 5.2 (s, 2H), 4.2 (d, 2H), 3.7 (t, 2H), 3.6 (s, 2H), 3.4 (t, 2H), 2.8 (s, 4H).

SCHEME-13

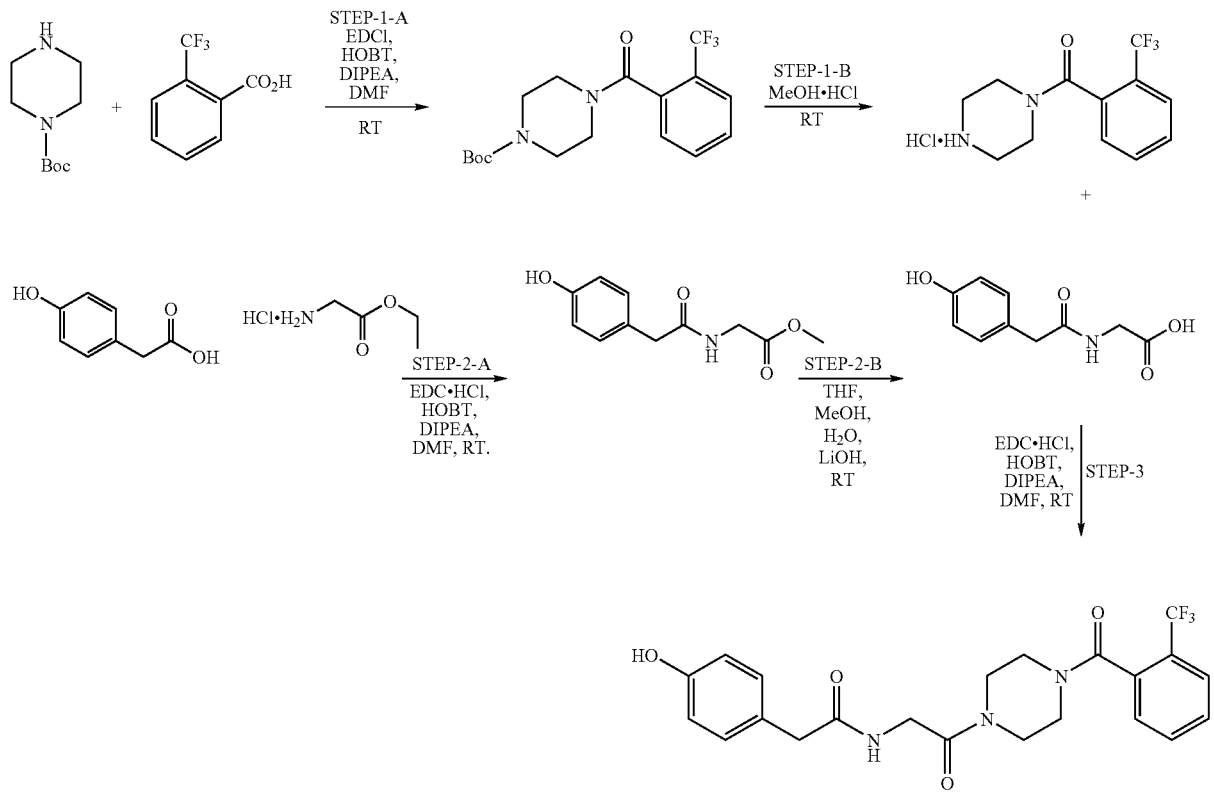

164) Synthesis of 2-(4-Hydroxy-phenyl) N-{2-oxo-2-[4-(2-trifluoromethyl-benzoyl)-piperazin-1-yl]-ethyl}-acetamide

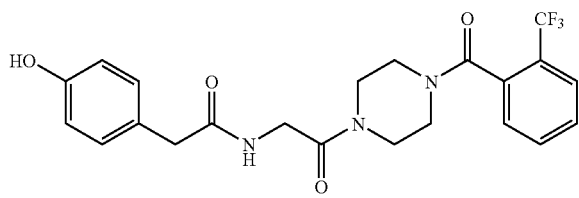

Step 1A: Synthesis of 4-(2-trifluoromethyl-benzoyl)-piperazine-1-carboxylic acid tert-butyl ester

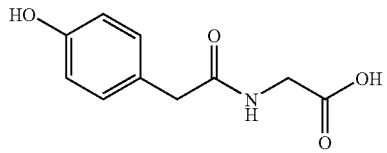

4-(2-trifluoromethyl-benzoyl)-piperazine-1-carboxylic acid tert-butyl ester was prepared as described above (Scheme 9).

Step 1B: Synthesis of piperazin-1-yl-(2-trifluoromethyl-phenyl)-methanone

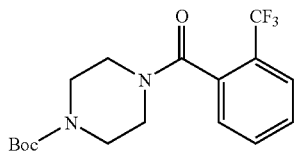

Piperazin-1-yl-(2-trifluoromethyl-phenyl)-methanone was prepared as described above (Scheme 9).

Step 2A: Synthesis of [2-(4-Hydroxy-phenyl)-acetyl amino]-acetic acid ethyl ester

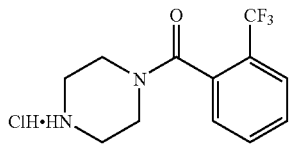

DIPEA (441 mg, 0.6 ml, 3.41 mmol) was added to a stirred solution of 4-hydroxyphenyl acetic acid (104 mg, 0.68 mmol) in DMF (4 mL). HOBT (101 mg, 0.748 mmol) and EDCI.HCl (245 mg, 1.28 mmol) were added at room temperature. After 2 minutes glycine ethyl ester hydrochloride (114.5 mg, 0.82 mmol) was added. The resulting mixture was stirred at room temperature for 24 hours. Water was then added, and the product was extracted with EtOAc. The organic layer was washed with brine, dried over $Na_2SO_4$ and concentrated under reduced pressure to afford 172 mg of [2-(4-hydroxy-phenyl)-acetyl amino]-acetic acid ethyl ester). LC-MS purity: 81.298%, HPLC purity 93.36%. $^1$H NMR ($CDCl_3$): δ 7.1 (d, 2H), 6.8 (d, 2H), 6.0 (bs, 1H), 4.15 (q, 2H), 4.0 (d, 2H), 3.5 (s, 2H), 1.2 (t, 3H).

Step 2B: Synthesis of [2-(4-Hydroxy-phenyl)-acetyl amino]-acetic acid

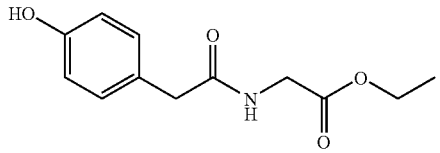

LiOH (52.1 mg, 2.17 mmol) was added to a stirred solution of 4-hydroxyphenyl acetic acid ethyl ester (172 mg, 0.73 mmol) in $THF:MeOH:H_2O$ (3:1:1, 5 mL) and the resulting mixture was stirred at room temperature for five hours. The MeOH and THF were then evaporated and the residue was diluted with water (2 mL), acidified with 20% aq HCl and extracted with EtOAc. The organic layer was washed with saturated brine solution, dried over $Na_2SO_4$ and concentrated under reduced pressure to afford 55 mg (38.5% yield) of [2-(4-hydroxy-phenyl)-acetyl amino]-acetic acid as a pale white solid. LCMS purity: 99.07%.

Step 3: Synthesis of 2-(4-Hydroxy-phenyl) N-{2-oxo-2-[4-(2-trifluoromethyl-benzoyl)-piperazin-1-yl]-ethyl}-acetamide

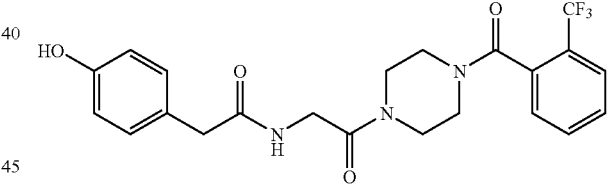

DIPEA (0.407 g, 0.545 mL, 3.15 mmol) was added to a stirred solution of [2-(4-Hydroxy-phenyl)-acetyl amino]-acetic acid (55 mg, 0.26 mmol) in DMF (5 mL). HOBT (39 mg, 2.8 mmol) and EDCI.HCl (110 mg, 0.57 mmol) were added at room temperature. After 2 minutes, piperazine-1-yl-(2-trifluoromethyl-phenyl)-methanone hydrochloride (85.2 mg, 0.29 mmol) was added. The resulting mixture was stirred at room temperature overnight. Water was then added, and the product was extracted with EtOAc. The organic layer was washed with brine, dried over $Na_2SO_4$ and concentrated under reduced pressure to afford the crude product. Purification by preparative HPLC (Column: Zorbax-XDB-9.4×250 mm, 5 µm, mobile phase: A, 0.1% Trifluoroacetic acid, B-Acetonitrile, Flow: 7 ml/min) afforded 68 mg (45% yield) of 2-(4-hydroxy-phenyl) N-{2-oxo-2-[4-(2-trifluoromethyl-benzoyl)-piperazin-1-yl]-ethyl}-acetamide as a white crystalline solid. LC-MS purity: 94.32%, HPLC purity: 98.38%. $^1$H NMR (DMSO): δ 9.4 (s, 1H,), 8.0 (t, 1H), 7.9-7.7 (m, 2H), 7.65 (t, 1H), 7.5 (d, 1H), 7.0 (d, 2H), 6.6 (d, 2H), 4.04-3.9 (d, 2H), 3.7-3.5 (m, 4H), 3.25 (m, 4H), 3.0 (m, 2H).

SCHEME-14
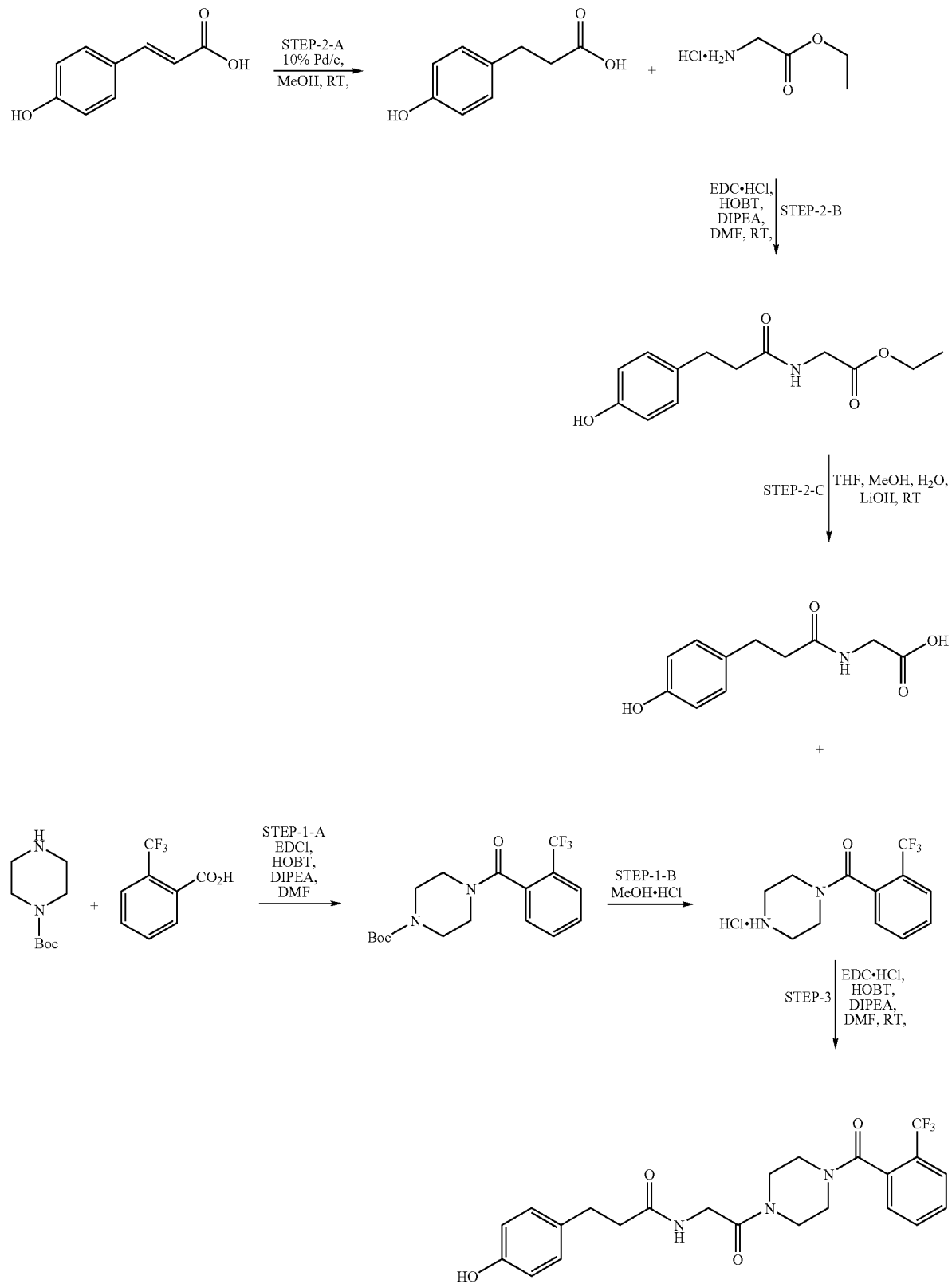

Step 1A 4-(2-trifluoromethyl-benzoyl)-piperazine-1-carboxylic acid tert-butyl ester was prepared as described above (Scheme 9).

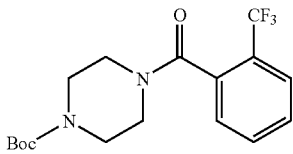

Step 1B: Synthesis of piperazin-1-yl-(2-trifluoromethyl-phenyl)-methanone

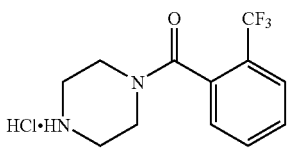

Piperazin-1-yl-(2-trifluoromethyl-phenyl)-methanone was prepared as described above (Scheme 9).

Step 2A: Synthesis of 3-[4-Hydroxy phenyl]propionic acid

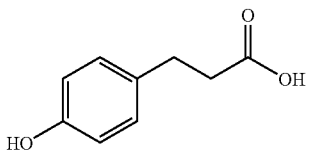

10% Pd/C (60 mg) was added to a stirred solution of 4-hydroxycinnamic acid (325 mg, 1.98 mmol) in MeOH (15 mL) under an inert atmosphere. Hydrogen gas was then passed through the reaction mixture by means of a hydrogen filled bladder and the mixture was stirred at room temperature for 2 hrs. The reaction mixture was filtered over celite and the celite was washed with MeOH. The filtrate was collected and concentrated under reduced pressure to afford 310 mg (94.5% yield) of 3-[4-hydroxy phenyl]propionic acid as a white solid. $^1$H NMR (DMSO): δ 7.0 (d, 2H), 6.6 (d, 2H), 2.35 (t, 2H), 2.25 (t, 2H), LC-MS purity: 96.55%.

Step 2B: Synthesis of [3-(4-Hydroxy-phenyl) propionylamino]-acetic acid ethyl ester

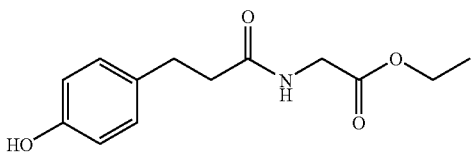

DIPEA (390 mg, 0.52 mL, 3.02 mmol) was added to a stirred solution of 3-[4-hydroxy phenyl]propionic acid (100 mg, 0.60 mmol) in DMF (10 mL). HOBT (90 mg, 0.67 mmol) and EDCI.HCl (290 mg, 1.51 mmol) were added at room temperature. After 2 minutes glycine ethyl ester hydrochloride (100 mg, 0.72 mmol) was added. The resulting mixture was stirred at room temperature for 48 hours. Water was then added, and the product was extracted with EtOAc. The organic layer was washed with brine, dried over Na$_2$SO$_4$ and concentrated under reduced pressure to afford 196 mg of [3-(4-hydroxy-phenyl) propionylamino]-acetic acid ethyl ester. $^1$H NMR (CDCL$_3$): δ 7 (d, 2H), 6.65 (d, 2H), 6.0 (bs, 1H), 4.15 (q, 2H), 4.0 (d, 2H), 3.5 (s, 2H), 2.8 (t, 2H), 2.45 (t, 2H), 1.2 (t, 3H), LC-MS purity: 68.23%.

Step 2C: Synthesis of [3-(4-Hydroxy-phenyl) propionylamino]-acetic acid

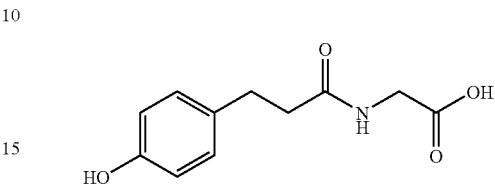

LiOH (56 mg, 2.33 mmol) was added at room temperature to a stirred solution of [3-(4-hydroxy-phenyl) propionylamino]-acetic acid ethyl ester (151 mg, 0.6 mmol) in THF:MeOH:H$_2$O (3:1:1, 5 mL). The resulting mixture was stirred at room temperature for five hours. The MeOH and THF were then evaporated and the residue was diluted with water (2 mL), acidified with 20% aqueous HCl and extracted with EtOAc. The organic layer was washed with saturated brine solution, dried over Na$_2$SO$_4$ and concentrated under reduced pressure to afford 120 mg (89.55% yield) of [3-(4-hydroxy-phenyl) propionylamino]-acetic acid as a pale white solid (120 mg). LCMS purity: 90.42%.

Step 3

165) Synthesis of 3-(4-Hydroxy-phenyl) N-{2-oxo-2-[4-(2-trifluoromethyl-benzoyl)-piperazin-1-yl]-ethyl}-propionamide

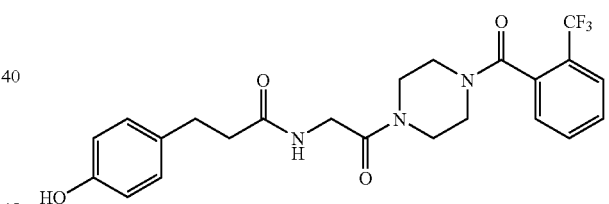

DIPEA (145 mg, 0.194 mL, 1.12 mmol) was added to a stirred solution of [3-(4-hydroxy-phenyl)propionylamino]-acetic acid (50 mg, 0.22 mmol) in DMF (4 mL). HOBT (33.3 mg, 0.25 mmol) and EDCI.HCl (107 mg, 0.56 mmol) were added at room temperature. After 2 minutes piperazine-1-yl-(2-trifluoromethyl-phenyl)-methanone hydrochloride (72.6 mg, 0.25 mmol) was added. The resulting mixture was stirred at room temperature for 24 hours. Water was then added, and the product was extracted with EtOAc. The organic layer was washed with brine, dried over Na$_2$SO$_4$ and concentrated under reduced pressure to afford the crude product. Purification by preparative HPLC (column: Zorbax-Eclipse-XDB-C18-9.4×250 mm, 5 µm, mobile phase: A-0.1% Trifluoroacetic acid, B-Acetonitrile, Flow: 7 ml/min) afforded 60 mg (58.25% yield) of 3-(4-Hydroxy-phenyl) N-{2-oxo-2-[4-(2-trifluoromethyl-benzoyl)-piperazin-1-yl]-ethyl}-propionamide as a pale white crystalline solid (60 mg). LC-MS purity: 91.16%, HPLC purity: 98.8%. $^1$H NMR (DMSO): δ 9.2 (s, 1H,), 8.0 (t, 1H), 7.92-7.8 (m, 2H), 7.7 (t, 1H), 7.56 (d, 1H), 7.0 (d, 2H), 6.66 (d, 2H), 4.08-3.94 (d, 2H), 3.84-3.68 (m, 2H), 3.66-3.5 (bs, 4H), 3.2-3.1 (bd, 2H), 2.7 (bs, 2H), 2.4 (t, 2H).

SCHEME-15

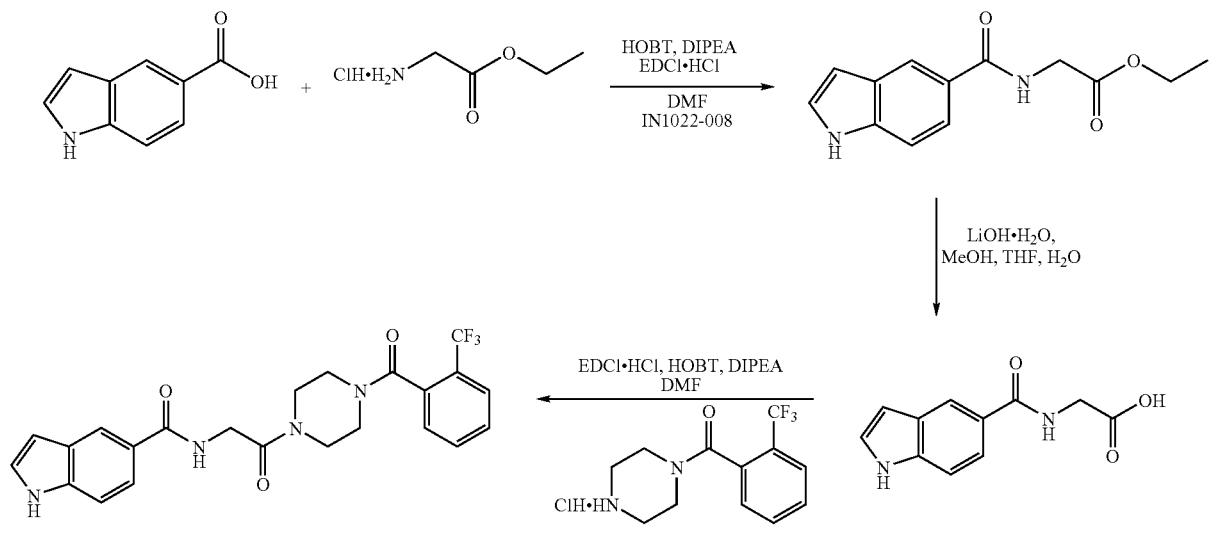

166) Synthesis of 1H-Indole-5-carboxylic acid {2-oxo-2-[4-(2-trifluoromethyl-benzoyl)-piperazine-1-yl]-ethyl}-amide

Step 1: Synthesis of 1H-Indole-5-carbonyl)-amino]-acetic acid ethyl ester

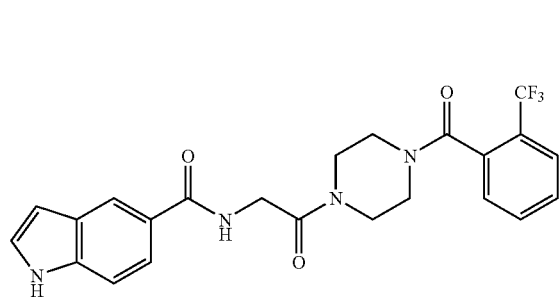

DIPEA (0.24 mL, 1.86 mmol) was added to a stirred solution of 1H-Indole-5-carboxylic acid (100 mg, 0.62 mmol) in DMF (2 mL). HOBT (100 mg, 0.74 mmol), and EDCI.HCl (142 mg, 0.74 mmol) were then added, followed by the addition of ethyl glycine ester hydrochloride (87 mg, 0.62 mmol) at room temperature. The resulting mixture was stirred at room temperature overnight. The mixture was diluted with water and the resulting precipitate was filtered to afford 1H-Indole-5-carbonyl)-amino]-acetic acid ethyl ester in 78 5 yield. LC-MS purity: 95%

Step 2: Synthesis of [(1H-Indole-5-carbonyl)-amino]-acetic acid

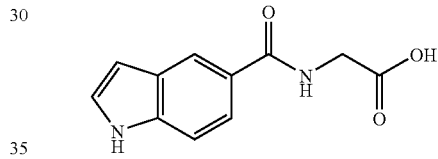

LiOH.H$_2$O (82 mg, 1.95 mmol) was added to a solution of 1H-Indole-5-carboxylic acid ethyl ester (120 mg, 0.49 mmol) in a mixture of MeOH (5 mL), THF (2.5 mL) and H$_2$O (2.5 mL). The resulting mixture was stirred for 3 hrs at room temperature. The MeOH and THF were evaporated and the resulting residue was diluted with water (2 mL), acidified with citric acid and extracted with EtOAc. The organic layer was washed with brine solution, dried over Na$_2$SO$_4$ and concentrated under reduced pressure to afford [(1H-Indole-5-carbonyl)-amino]-acetic acid in 75% yield. LC-MS purity: 88%

Step 3: Synthesis of 1H-Indole-5-carboxylic acid {2-oxo-2-[4-(2-trifluoromethyl-benzoyl)-piperazine-1-yl]-ethyl}-amide DIPEA (0.111 mL, 0.64 mmol) was added to a stirred solution of [(1H-Indole-5-carbonyl)-amino]-acetic acid (40 mg, 0.18 mmol) in DMF (1.0 mL). HOBT (29 mg, 0.22 mmol) and EDCI.HCl (42 mg, 0.22 mmol) were added, followed by the addition of piperazine-1-yl-(2-trifluoromethyl-phenyl)-methanone hydrochloride (59 mg, 0.20 mmol) at room temperature. The resulting mixture was stirred at room temperature overnight. The mixture was then diluted with water and the resulting precipitate was filtered to afford 1H-Indole-5-carboxylic acid {2-oxo-2-[4-(2-trifluoromethyl-benzoyl)-piperazine-1-yl]-ethyl}-amide in 45% yield. LC-MS purity: 91%, $^1$H NMR (CDCl$_3$): δ 8.48 (s, 1H), 8.18 (s, 1H), 7.78-7.54 (m, 4H), 7.42-7.30 (m, 2H), 7.28 (s, 1H), 6.62 (s, 1H), 4.40-4.20 (m, 2H), 4.18-3.82 (m, 2H), 3.78-3.52 (m, 4H), 3.24 (s, 2H).

SCHEME-16

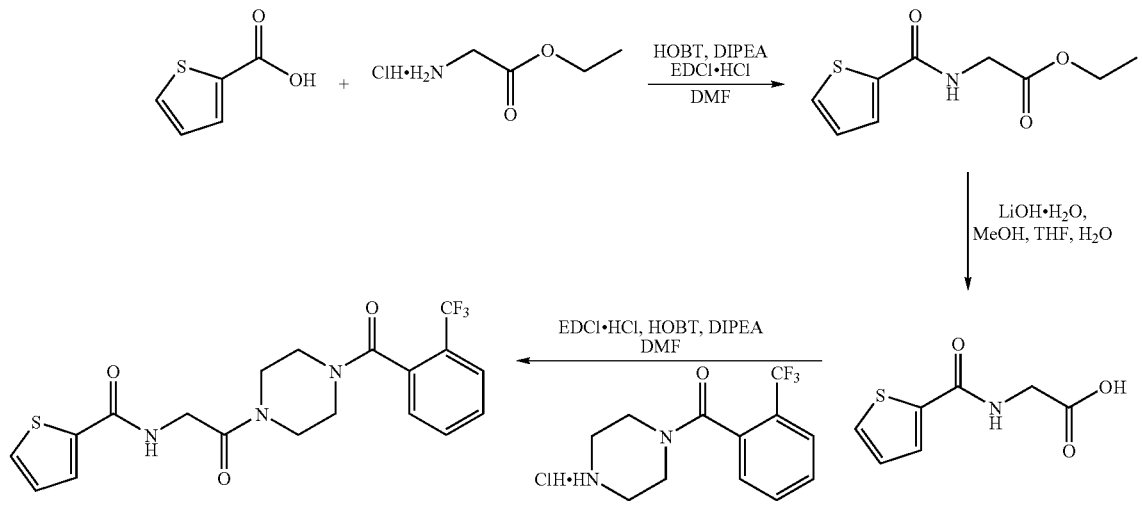

167) Synthesis of Thiophene-2-carboxylic acid {2-oxo-2-[4-(2-trifluoromethyl-benzoyl)-piperazine-1-yl]-ethyl}-amide Step 1: Synthesis of [(Thiophene-2-carbonyl)-amino]-acetic acid ethyl ester

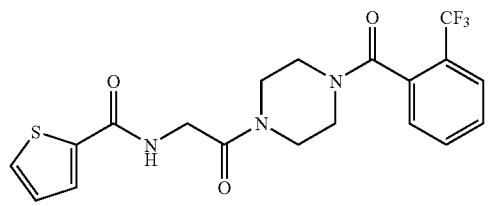

DIPEA (0.472 mL, 2.73 mmol) was added to a stirred solution of thiophene-2-carboxylic acid (100 mg, 0.78 mmol) in DMF (1 mL). HOBT (126 mg, 0.94 mmol) and EDCI.HCl (179 mg, 0.94 mmol) were added, followed by the addition of ethyl glycine ester hydrochloride (119 mg, 0.86 mmol) at room temperature. The reaction mixture was stirred at room temperature overnight. The mixture was then diluted with water and the product extracted with EtOAc. The organic layer was washed with brine solution, dried over $Na_2SO_4$ and concentrated under reduced pressure to afford [(thiophene-2-carbonyl)-amino]-acetic acid ethyl ester in 84% yield, LC-MS purity: 97%

Step 2: Synthesis of [(Thiophene-2-carbonyl)-amino]-acetic acid

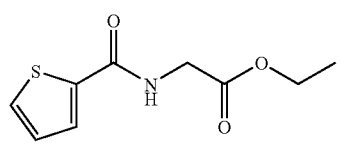

LiOH.$H_2$O (110 mg, 2.63 mmol) was added to a solution of [(thiophene-2-carbonyl)-amino]-acetic acid ethyl ester (140 mg, 0.66 mmol) in a mixture of MeOH (5 mL), THF (2.5 mL) and $H_2O$ (2.5 mL). The resulting mixture was stirred for 3 hrs at room temperature. The MeOH and THF were evaporated and the resulting residue was diluted with water (2 mL), acidified with citric acid and extracted with EtOAc. The organic layer was washed with brine solution, dried over $Na_2SO_4$ and concentrated under reduced pressure to afford [(thiophene-2-carbonyl)-amino]-acetic acid in 70% yield. LC-MS purity: 92%.

Step 3: Synthesis of Thiophene-2-carboxylic acid {2-oxo-2-[4-(2-trifluoromethyl-benzoyl)-piperazine-1-yl]-ethyl}-amide DIPEA (0.130 mL, 0.76 mmol) was added to a stirred solution of [(thiophene-2-carbonyl)-amino]-acetic acid (40 mg, 0.22 mmol) in DMF (1 mL). HOBT (35 mg, 0.26 mmol) and EDCI.HCl (49 mg, 0.26 mmol) were added, followed by the addition of piperazine-1-yl-(2-trifluoromethyl-phenyl)-methanone hydrochloride (70 mg, 0.24 mmol) at room temperature. The reaction mixture was stirred at room temperature overnight. Water was then added, and the product was extracted with EtOAc. The organic layer was washed with brine, dried over $Na_2SO_4$ and concentrated under reduced pressure to afford thiophene-2-carboxylic acid {2-oxo-2-[4-(2-trifluoromethyl-benzoyl)-piperazine-1-yl]-ethyl}-amide in 54% yield. LC-MS purity: 98% $^1$H NMR (CDCL$_3$): δ 7.78-7.44 (m, 5H), 7.34 (t, 1H), 7.10 (d, 2H), 4.40-4.18 (m, 2H), 4.08-3.82 (m, 2H), 3.80-3.50 (m, 4H).

SCHEME-17

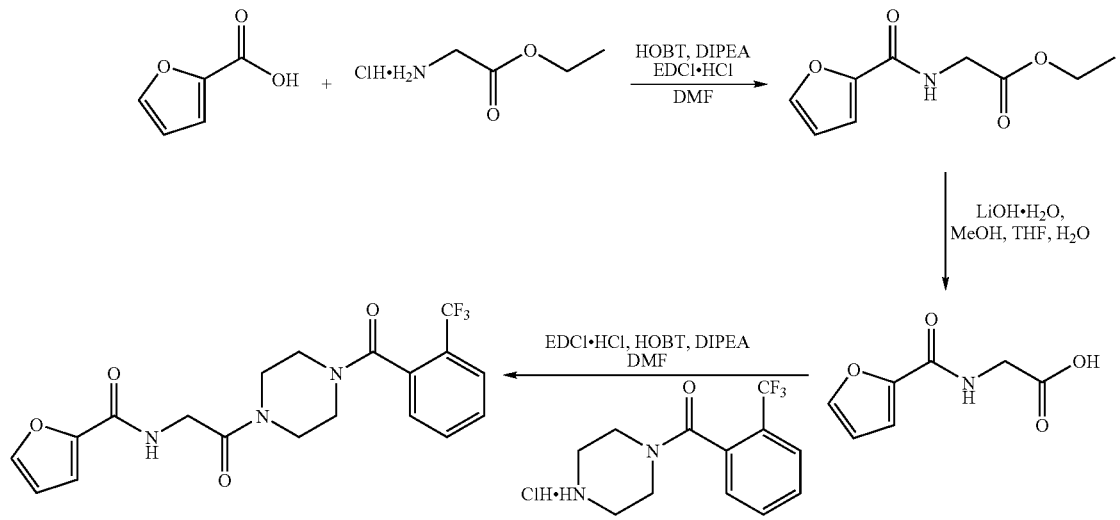

168) Synthesis of Furan-2-carboxylic acid {2-oxo-2-[4-(2-trifluoromethyl-benzoyl)-piperazine-1-yl]-ethyl}-amide Step 2: Synthesis of [(Furan-2-carbonyl)-amino]-acetic acid

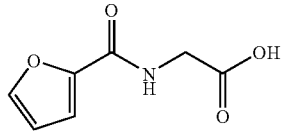

LiOH.H$_2$O (102 mg) was added to a solution of furan-2-carboxylic acid ethyl ester (120 mg, 0.62 mmol) in a mixture of MeOH (5 mL), THF (2 mL) and H$_2$O (2 mL). The resulting mixture was stirred for 3 hrs at room temperature. The MeOH and THF were evaporated and the resulting residue was diluted with water (2 mL), acidified with citric acid and extracted with EtOAc. The organic layer was washed with brine solution, dried over Na$_2$SO$_4$ and concentrated under reduced pressure to afford [(furan-2-carbonyl)-amino]-acetic acid in 36% yield. LC-MS purity: 98%

Step 3: Synthesis of Furan-2-carboxylic acid {2-oxo-2-[4-(2-trifluoromethyl-benzoyl)-piperazine-1-yl]-ethyl}-amide

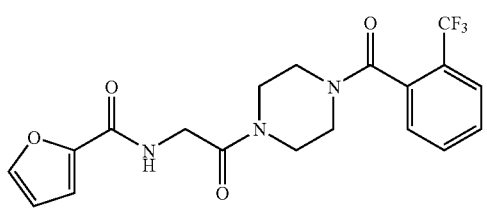

Step 1: Synthesis of (Furan-2-carbonyl)-amino]-acetic acid ethyl ester

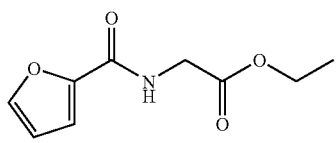

DIPEA (0.463 mL, 2.68 mmol) was added to a stirred solution of furan-2-carboxylic acid (100 mg, 0.89 mmol) in DMF (2 mL). HOBT (144 mg, 1.07 mmol), EDCI.HCl (205 mg, 1.07 mmol) were added, followed by the addition of ethyl glycine ester hydrochloride (124 mg, 0.98 mmol) at room temperature. The resulting mixture was stirred at room temperature overnight. The mixture was diluted with cold water and the resulting precipitate was filtered, washed with hexane and dried to afford (furan-2-carbonyl)-amino]-acetic acid ethyl ester in 77% yield. LC-MS purity: 61%

DIPEA (0.143 mL, 0.83 mmol) was added to a stirred solution of [(furan-2-carbonyl)-amino]-acetic acid (40 mg, 0.24 mmol) in DMF (1 mL). HOBT (38 mg, 0.28 mmol), EDCI.HCl (54 mg, 0.28 mmol) were added, followed by the addition of piperazine-1-yl-(2-trifluoromethyl-phenyl)-methanone hydrochloride (0.2602 mmol) at room temperature. The resulting mixture was stirred at room temperature overnight. Water was then added, and the product was extracted with EtOAc. The organic layer was washed with brine, dried over Na$_2$SO$_4$ and concentrated under reduced pressure to afford the crude product. Purification using column chromatography (using silica gel, 60-120 A° and 10% methanol in chloroform as the eluent) afforded furan-2-carboxylic acid {2-oxo-2-[4-(2-trifluoromethyl-benzoyl)-piperazine-1-yl]-ethyl}-amide in 33% yield. LC-MS purity: 83%, $^1$H NMR (CDCl$_3$): δ 7.74 (d, 1H), 7.60 (m, 2H), 7.56 (d, 2H), 7.48 (s, 1H), 7.12 (t, 1H), 6.50 (q, 1H), 4.30 (m, 2H), 4.08-3.82 (m, 2H), 3.78-3.64 (m, 2H), 3.62-3.48 (m, 2H), 3.22 (m, 2H).

SCHEME-18

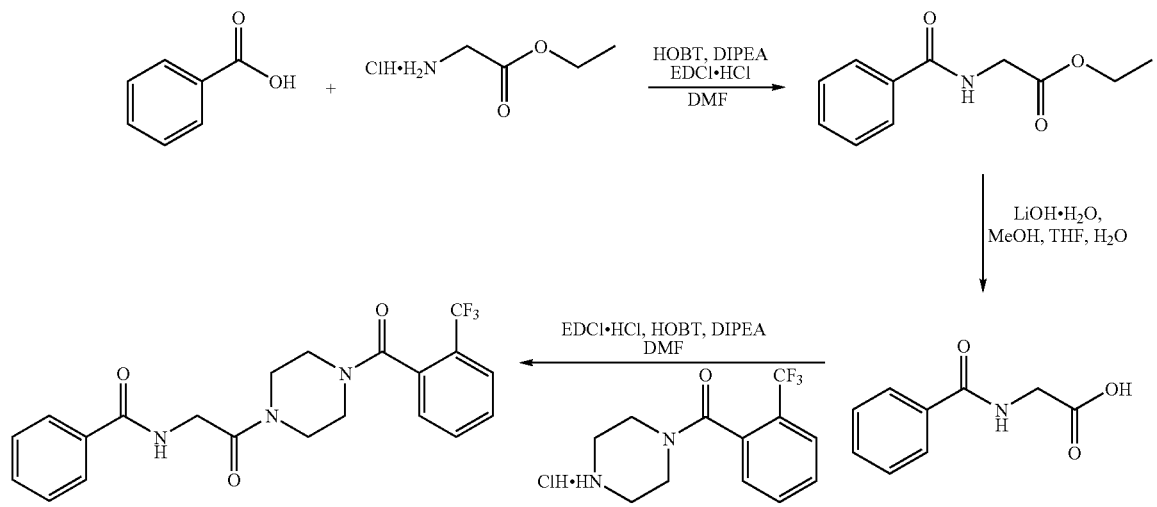

169) Synthesis of N-{2-Oxo-2-[4-(2-trifluoromethyl-benzoyl)-piperazine-1-yl]-ethyl}benzamide

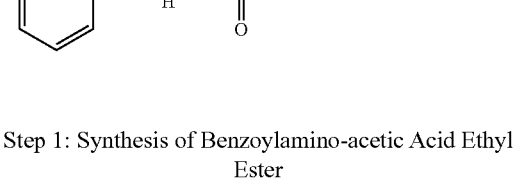

Step 1: Synthesis of Benzoylamino-acetic Acid Ethyl Ester

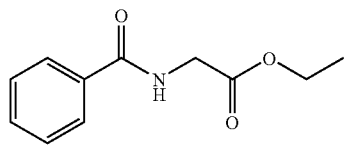

DIPEA (0.425 mL, 2.46 mmol) was added to a stirred solution of benzoic acid (100 mg, 0.82 mmol) in DMF (2 mL). HOBT (132 mg, 0.98 mmol) and EDCI.HCl (188 mg, 0.98) were then added, followed by the addition of ethyl glycine ester hydrochloride (0.82 mmol) at room temperature. The resulting mixture was stirred at room temperature overnight. Water was then added, and the product was extracted with EtOAc. The organic layer was washed with brine, dried over $Na_2SO_4$ and concentrated under reduced pressure to afford the crude product. Purification using column chromatography (using silica gel, 60-120 A° and 20% methanol in chloroform as the eluent) afforded Benzoylamino-acetic acid ethyl ester in 53% yield, LC-MS purity: 98%

Step 2: Synthesis of Benzoylamino-acetic Acid

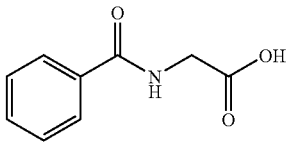

LiOH.$H_2O$ (73 mg, 1.74 mmol) was added to a solution of benzoylamino-acetic acid ethyl ester (90 mg, 0.43 mmol) in a mixture of MeOH (5 mL), THF (2 mL) and $H_2O$ (2 mL). The resulting mixture was stirred for 3 hrs at room temperature. The MeOH and THF were evaporated and the resulting residue was diluted with water (2 mL), acidified with citric acid and extracted with EtOAc. The organic layer was washed with brine solution, dried over $Na_2SO_4$ and concentrated under reduced pressure to afford benzoylamino-acetic acid in 77% yield. LC-MS purity: 92%

Step 3: Synthesis of N-{2-Oxo-2-[4-(2-trifluoromethyl-benzoyl)-piperazine-1-yl]-ethyl}Benzamide DIPEA (0.169 mL, 0.98 mmol) was added to a stirred solution of benzoylamino-acetic acid (50 mg, 0.28 mmol) in DMF (1 mL). HOBT (45 mg, 0.34 mmol) and EDCI.HCl (64 mg, 0.34 mmol) were added followed by the addition of piperazine-1-yl-(2-trifluoromethyl-phenyl)-methanone hydrochloride (0.31 mmol) at room temperature. The resulting mixture was stirred at room temperature overnight. Water was then added, and the product was extracted with EtOAc. The organic layer was washed with brine, dried over $Na_2SO_4$ and concentrated under reduced pressure to afford the crude product. Purification using column chromatography (using silica gel, 60-120 A° and 10% methanol in chloroform as the eluent) afforded N-{2-Oxo-2-[4-(2-trifluoromethyl-benzoyl)-piperazine-1-yl]-ethyl}benzamide in 30% yield, LC- MS purity: 95%, ¹H NMR (CDCl₃): δ 7.84 (d, 2H), 7.76 (d, 1H), 7.66-7.56 (m, 2H), 7.54-7.42 (m, 3H), 7.34 (d, 2H), 7.24 (t, 1H), 4.36-4.20 (m, 2H), 4.02-3.84 (m, 2H), 3.78-3.50 (m, 4H), 3.26 (m, 2H).

170) Synthesis of Biphenyl-4-carboxylicacid {2-[4-(2-methoxy-benzoyl)-piperazin-1-yl]-2-oxo-ethyl}-amide

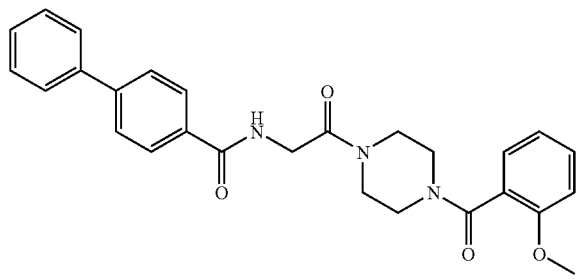

DIPEA (149.8 mg, 1.16 mmol) was added at room temperature to a stirred solution of 2-methoxy-benzoic acid (39.2 mg, 0.26 mmol) in DMF (3 mL), HOBt (38.2 mg, 0.28 mmol) and EDCI.HCl (123 mg, 0.64 mmol). After 2 minutes biphenyl-4-carboxylic acid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 60 mg (93.0% yield) of biphenyl-4-carboxylicacid {2-[4-(2-methoxy-benzoyl)-piperazin-1-yl]-2-oxo-ethyl}-amide. LC-MS purity: 92.98%, HPLC Purity: 98.70%. ¹H NMR: (CDCl₃) δ 7.94 (d, 2H), 7.7-7.6 (q, 4H), 7.52-7.44 (t, 2H), 7.44-7.4 (m, 1H), 7.4-7.3 (m, 2H), 7.1-7.0 (t, 1H), 7.0-6.92 (dd, 1H), 4.4-4.24 (dd, 2H), 4.0 (s, 1H), 3.88 (d, 3H), 3.8 (s, 2H), 3.7-3.58 (m, 2H), 3.5-3.24 (m, 3H).

171) Synthesis of Biphenyl-4-carboxylicacid {2-[4-(2-fluoro-5-trifluoromethyl-benzoyl)-piperazin-1-yl]-2-oxo-ethyl}-amide

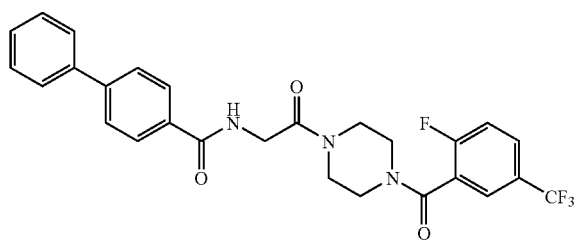

DIPEA (149.8 mg, 1.16 mmol) was added to a stirred solution of 2-fluoro-5-trifluoromethyl-benzoic acid (53.6 mg, 0.26 mmol) in DMF (3 mL), HOBt (38.2 mg, 0.28 mmol) and EDCI.HCl (123 mg, 0.64 mmol) at room temperature. After 2 minutes Biphenyl-4-carboxylicacid (2-oxo-2-piperazin-1-yl-ethyl)-amide (100 mg, 0.309 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 56 mg (42.3% yield) of biphenyl-4-carboxylicacid {2-[4-(2-fluoro-5-trifluoromethyl-benzoyl)-piperazin-1-yl]-2-oxo-ethyl}-amide. LC-MS purity: 99.19%, HPLC Purity: 98.21%. ¹H NMR: (DMSO) δ 8.7 (t, 1H), 8.0-7.9 (d, 4H), 7.84-7.7 (q, 4H), 7.6 (t, 1H), 7.5 (t, 2H), 7.4 (t, 1H), 4.2 (dd, 2H), 3.8-3.6 (d, 4H), 3.6-3.4 (s, 2H), 3.3 (s, 2H).

172) Synthesis of Biphenyl-4-carboxylic acid {2-[4-(2-cyclopropylmethoxy-benzoyl)-piperazin-1-yl]-2-oxo-ethyl}-amide

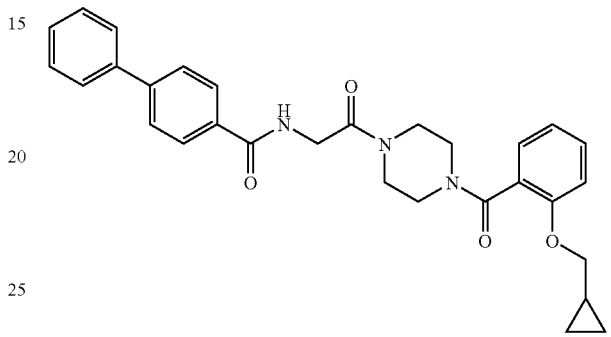

DIPEA (149.8 mg, 1.16 mmol) was added to the stirred solution of 2-Cyclopropylmethoxy-benzoic acid (59.4 mg, 0.31 mmol) in DMF (3 mL), HOBt (45.9 mg, 0.34 mmol) and EDCI.HCl (148.1 mg, 0.77 mmol) at room temperature. After 2 minutes biphenyl-4-carboxylicacid (2-oxo-2-piperazin-1-yl-ethyl)-amide (120 mg, 0.37 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 40 mg (26.0% yield) of biphenyl-4-carboxylic acid {2-[4-(2-cyclopropylmethoxy-benzoyl)-piperazin-1-yl]-2-oxo-ethyl}-amide, LC-MS purity: 92.64%. ¹H NMR: (DMSO) δ 8.64 (t, 1H), 7.96 (d, 2H), 7.8-7.7 (q, 3H), 7.54-7.46 (t, 2H), 7.44-7.32 (m, 2H), 7.2 (d, 1H), 7.1-6.94 (m, 2H), 4.2 (d, 2H), 3.9 (d, 1H), 3.7-3.4 (m, 6H), 3.25-3.0 (m, 2H), 1.2 (s, 2H), 0.6 (d, 2H), 0.3 (s, 2H).

173) Synthesis of Biphenyl-4-carboxylicacid {2-[4-(2-acetyl-benzoyl)-piperazin-1-yl]-2-oxo-ethyl}-amide

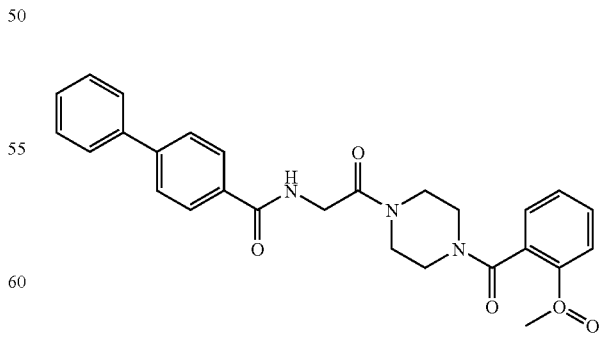

DIPEA (179.8 mg, 1.39 mmol) was added to the stirred solution of 2-acetyl-benzoic acid (50.75 mg, 0.31 mmol) in DMF (3 mL), HOBt (45.95 mg, 0.34 mmol) and EDCI.HCl (148.14 mg, 0.77 mmol) at room temperature. After 2 minutes biphenyl-4-carboxylicacid (2-oxo-2-piperazin-1-yl-ethyl)-amide (120 mg, 0.37 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 30 mg (20.6% yield) of biphenyl-4-carboxylicacid {2-[4-(2-acetyl-benzoyl)-piperazin-1-yl]-2-oxo-ethyl}-amide, LC-MS purity: 95.52%, $^1$H NMR: (DMSO) δ 8.64 (s, 1H), 8.0 (dd, 3H), 7.84-7.72 (q, 4H), 7.7-7.64 (t, 1H), 7.6 (t, 1H), 7.5 (t, 2H), 7.44-7.32 (m, 2H), 4.26-4.1 (dd, 2H), 3.76-3.62 (d, 4H), 3.46 (s, 2H), 3.3 (d, 2H), 2.6 (s, 3H).

174) Synthesis of Biphenyl-4-carboxylicacid {2-[4-benzene sulfonyl-piperazin-1-yl]-2-oxo-ethyl}-amide

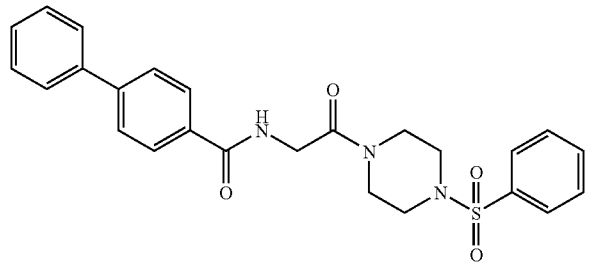

TEA (62.57 mg, 062 mmol) followed by benzenesulphonyl chloride (54.6 mg, 0.31 mmol) were added at to 0° C. to biphenyl-4-carboxylicacid (2-oxo-2-piperazin-1-yl-ethyl)-amide (100 mg, 0.31 mmol) in DCM (4 mL). The resulting mixture was stirred at room temperature overnight. Cold water was then added and the product extracted with DCM. The organic layer was separated, washed with 10% HCl solution, saturated NaHCO$_3$ solution and brine, dried over sodium sulphate and concentrated. The resulting residue was purified by column chromatography (using 60-120 mesh silica gel and 30% EtOAc in hexane as eluent) to afford 45 mg (31.4% yield) of biphenyl-4-carboxylicacid {2-[4-benzene sulfonyl-piperazin-1-yl]-2-oxo-ethyl}-amide, LC-MS purity: 98.75%, $^1$H NMR: (DMSO) δ 8.76 (t, 1H), 7.92 (d, 2H), 7.8-7.6 (m, 9H), 7.54-7.44 (t, 2H), 7.44-7.36 (t, 1H), 4.1 (d, 2H), 3.6 (s, 4H), 3.0-2.86 (d, 4H).

175) Synthesis of Biphenyl-4-carboxylicacid {2-[4-(2,5-bis-trifluoromethyl-benzoyl)-piperazin-1-yl]-2-oxo-ethyl}-amide

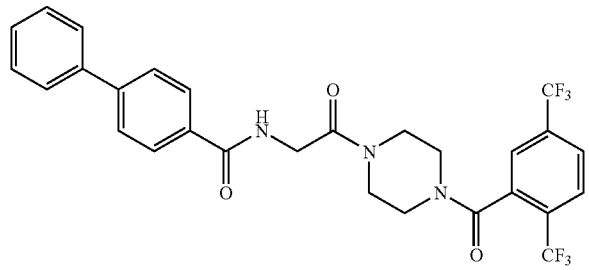

DIPEA (149.8 mg, 1.15 mmol) was added to a stirred solution of 2,5-bis-trifluoromethyl-benzoic acid (66.5 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 75 mg (51.6% yield) of biphenyl-4-carboxylicacid {2-[4-(2,5-bis-trifluoromethyl-benzoyl)-piperazin-1-yl]-2-oxo-ethyl}-amide, LC-MS purity: 95.51%, $^1$H NMR: (DMSO) δ 8.65 (t, 1H), 8.1 (t, 3H), 8.0 (d, 2H), 7.83-7.7 (q, 4H), 7.5 (t, 2H), 7.42 (t, 1H), 4.2 (d, 2H), 3.8-3.42 (d, 6H), 3.2 (m, 2H).

176) Synthesis of Biphenyl-4-carboxylicacid {2-[4-(2-chloro-5-trifluoromethyl-benzoyl)-piperazin-1-yl]-2-oxo-ethyl}-amide

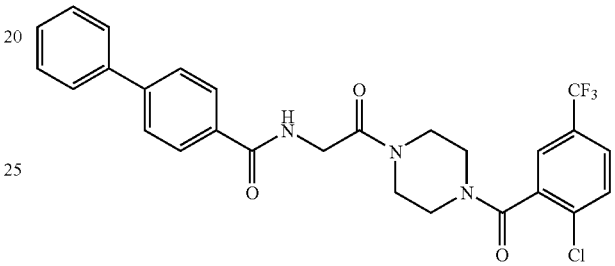

DIPEA (149.8 mg, 1.15 mmol) was added to a stirred solution of 2-chloro-5-trifluoromethyl-benzoic acid (57.8 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 63 mg (42.1% yield) of biphenyl-4-carboxylicacid {2-[4-(2-chloro-5-trifluoromethyl-benzoyl)-piperazin-1-yl]-2-oxo-ethyl}-amide, LC-MS purity: 97.5%, $^1$H NMR: (DMSO) δ 8.7 (s, 1H), 8.0-7.9 (t, 3H), 7.9-7.7 (m, 6H), 7.54-7.38 (m, 3H), 4.2 (dd, 2H), 3.8-3.6 (m, 4H), 3.6-3.4 (m, 2H), 3.2 (d, 2H).

177) Synthesis of Biphenyl-4-carboxylicacid {2-[4-(5-fluoro-2-trifluoromethyl-benzoyl)-piperazin-1-yl]-2-oxo-ethyl}-amide

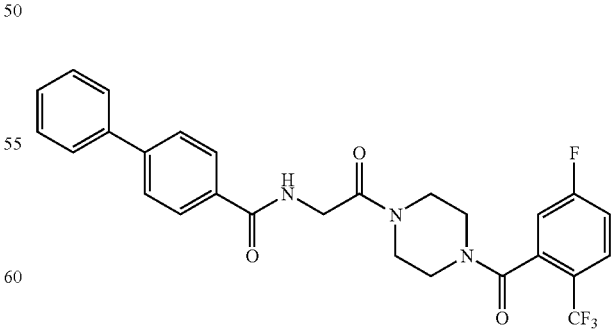

DIPEA (149.8 mg, 1.15 mmol) was added to a stirred solution of 5-fluoro-2-trifluoromethyl-benzoic acid (53.6 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 58 mg (43.8% yield) of biphenyl-4-carboxylicacid {2-[4-(5-fluoro-2-trifluoromethyl-benzoyl)-piperazin-1-yl]-2-oxo-ethyl}-amide, LC-MS purity: 98.5%, $^1$H NMR: (DMSO) δ 8.7 (s, 1H), 8.0-7.9 (d, 3H), 7.84-7.7 (q, 4H), 7.6-7.4 (m, 5H), 4.2 (d, 2H), 3.8-3.4 (m, 6H), 3.24-3.06 (m, 2H).

178) Synthesis of Biphenyl-4-carboxylicacid {2-[4-(2-hydroxy-benzoyl)-piperazin-1-yl]-2-oxo-ethyl}-amide

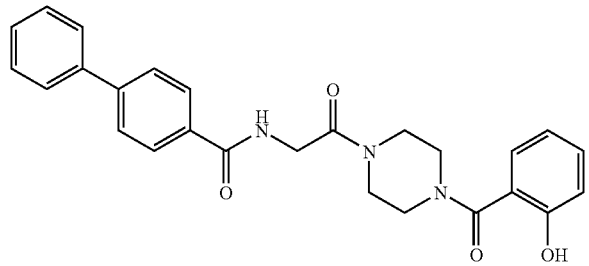

DIPEA (149.8 mg, 1.15 mmol) was added to a stirred solution of 2-hydroxy-benzoic acid (35.5 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 60% EtOAc in hexane as eluent). Further purification by preparative HPLC afforded 58 mg (50.9% yield) of biphenyl-4-carboxylicacid {2-[4-(2-hydroxy-benzoyl)-piperazin-1-yl]-2-oxo-ethyl}-amide, LC-MS purity: 93.06%, $^1$H NMR: (DMSO) δ 8.6 (t, 1H), 8.0-7.92 (d, 2H), 7.84-7.7 (q, 4H), 7.56-7.46 (t, 2H), 7.44-7.38 (t, 1H), 7.3-7.2 (t, 1H), 7.2-7.12 (d, 1H), 6.94-6.8 (m, 2H), 4.2 (s, 2H), 3.7-3.5 (s, 5H), 3.3-3.1 (s, 3H).

179) Synthesis of Biphenyl-4-carboxylicacid {2-[4-(4-trifluoromethyl-benzoyl)-piperazin-1-yl]-2-oxo-ethyl}-amide

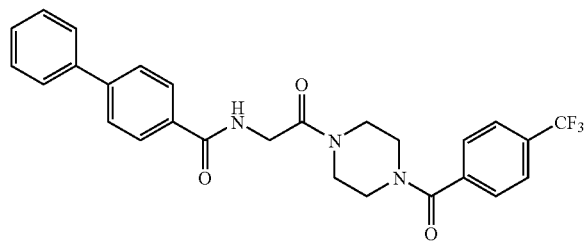

DIPEA (149.8 mg, 1.15 mmol) was added to a stirred solution of 4-trifluoromethyl-benzoic acid (48.9 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 60% EtOAc in hexane as eluent) to afford 33 mg (25.9% yield) of biphenyl-4-carboxylicacid {2-[4-(4-trifluoromethyl-benzoyl)-piperazin-1-yl]-2-oxo-ethyl}-amide, LC-MS purity: 98.96%, $^1$H NMR: (DMSO) δ 8.65 (t, 1H), 8.0 (d, 2H), 7.9-7.7 (m, 6H), 7.7-7.64 (d, 2H), 7.56-7.46 (t, 2H), 7.46-7.38 (t, 1H) 4.2 (s, 3H), 3.6 (d, 7H).

180) Synthesis of Biphenyl-4-carboxylicacid {2-oxo-2-[4-(4-trifluoromethyl-pyridine-3-carbonyl)-piperazin-1-yl]-ethyl}-amide

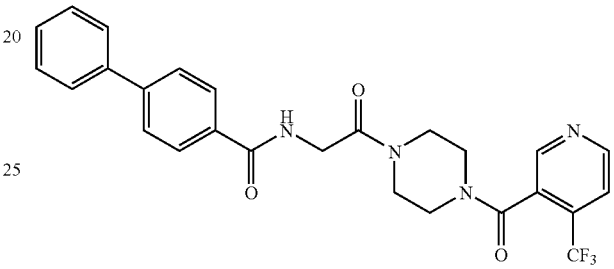

DIPEA (149.8 mg, 1.15 mmol) was added to a stirred solution of 4-trifluoromethyl-nicotinic acid (49.2 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 80% EtOAc in hexane as eluent) to afford 48 mg (47.6% yield) of biphenyl-4-carboxylicacid {2-oxo-2-[4-(4-trifluoromethyl-pyridine-3-carbonyl)-piperazin-1-yl]-ethyl}-amide, LC-MS purity: 94.74%, $^1$H NMR: (DMSO) δ 9.0-8.84 (d, 2H), 8.7-8.6 (t, 1H), 8.0 (d, 2H), 7.9 (d, 1H), 7.84-7.7 (q, 4H), 7.6-7.4 (m, 3H) 4.2 (d, 2H), 3.8-3.6 (d, 4H), 3.3-3.2 (s, 4H).

181) Synthesis of Biphenyl-4-carboxylicacid {2-oxo-2-[4-(pyrazine-2-carbonyl)-piperazin-1-yl]-ethyl}-amide

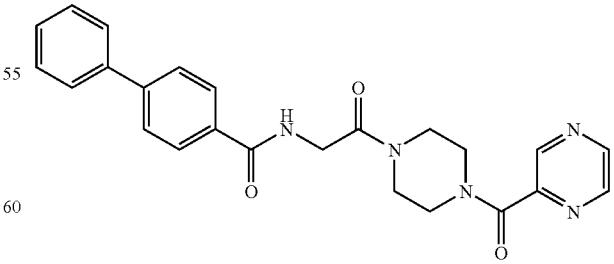

DIPEA (149.8 mg, 1.15 mmol) was added to a stirred solution of pyrazine-2-carboxylic acid (31.9 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 90% EtOAc in hexane as eluent) to afford 43 mg (38.9% yield) of biphenyl-4-carboxylicacid {2-oxo-2-[4-(pyrazine-2-carbonyl)-piperazin-1-yl]-ethyl}-amide, LC-MS purity: 86.93%, $^1$H NMR: (DMSO) δ 8.9 (s, 1H), 8.8 (s, 1H), 8.7 (q, 2H), 8.0 (d, 2H), 7.8-7.7 (q, 4H), 7.5 (t, 2H), 7.4 (t, 1H), 4.2 (dd, 2H), 3.8 (s, 1H), 3.7 (d, 3H), 3.6-3.5 (m, 4H).

182) Synthesis of Biphenyl-4-carboxylicacid {2-oxo-2-[4-(3,4,5-trifluoro-benzoyl)-piperazin-1-yl]-ethyl}-amide

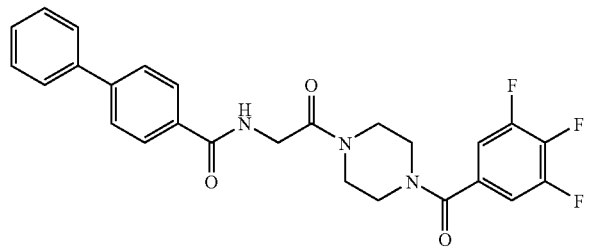

DIPEA (149.8 mg, 1.15 mmol) was added to a stirred solution of 3,4,5-trifluoro-benzoic acid (45.3 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 60% EtOAc in hexane as eluent) to afford 32 mg (25.8% yield) of biphenyl-4-carboxylicacid {2-oxo-2-[4-(3,4,5-trifluoro-benzoyl)-piperazin-1-yl]-ethyl}-amide, LC-MS purity: 98.04%, $^1$H NMR: (DMSO) δ 8.76-8.6 (bs, 1H), 8.08-7.92 (m, 2H), 7.88-7.72 (m, 4H), 7.6-7.4 (m, 4H), 4.2 (s, 2H), 3.6 (s, 5H), 3.2 (m, 3H).

183) Synthesis of Biphenyl-4-carboxylicacid {2-oxo-2-[4-(2-trifluoromethoxy-benzoyl)-piperazin-1-yl]-ethyl}-amide

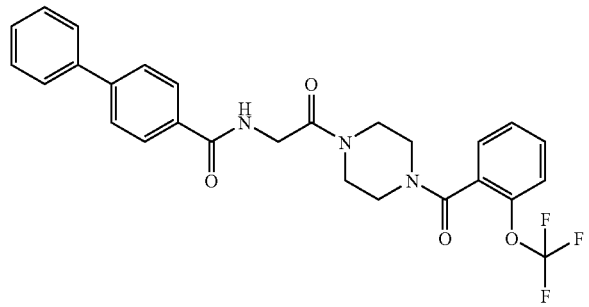

DIPEA (149.8 mg, 1.15 mmol) was added to a stirred solution of 2-trifluoromethoxy-benzoic acid (53.09 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 45 mg (34.1% yield) of biphenyl-4-carboxylicacid {2-oxo-2-[4-(2-trifluoromethoxy-benzoyl)-piperazin-1-yl]-ethyl}-amide, LC-MS purity: 99.18%, $^1$H NMR: (DMSO) δ 8.7 (s, 1H), 8.0 (s, 2H), 7.8 (s, 4H), 7.4 (s, 7H), 4.2 (d, 2H), 3.8-3.4 (m, 6H), 3.2 (m, 2H).

184) Synthesis of Biphenyl-4-carboxylicacid {2-[4-(2-chloro-4-fluoro-benzoyl)-piperazin-1-yl]-2-oxo-ethyl}-amide

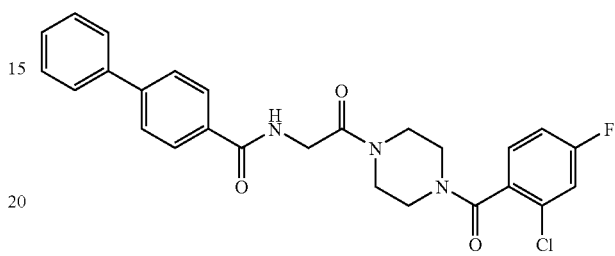

DIPEA (149.8 mg, 1.15 mmol) was added to a stirred solution of 2-chloro-4-fluoro-benzoic acid (44.9 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 26 mg (21.0% yield) of biphenyl-4-carboxylicacid {2-[4-(2-chloro-4-fluoro-benzoyl)-piperazin-1-yl]-2-oxo-ethyl}-amide, LC-MS purity: 99.27%, $^1$H NMR: (CDCl$_3$) δ 7.94 (d, 2H), 7.74-7.6 (q, 4H), 7.54-7.46 (t, 2H), 7.44-7.38 (t, 1H), 7.38-7.3 (m, 2H), 7.24-7.2 (m, 1H), 7.16-7.06 (tt, 1H), 4.4-4.26 (td, 2H), 4.1-3.84 (m, 2H), 3.78-3.6 (m, 3H), 3.54-3.24 (m, 3H).

185) Synthesis of Biphenyl-4-carboxylicacid {2-[4-(2-chloro-benzoyl)-piperazin-1-yl]-2-oxo-ethyl}-amide

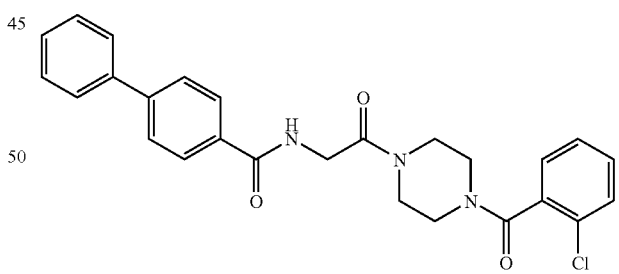

DIPEA (149.8 mg, 1.15 mmol) was added to a stirred solution of 2-chloro-benzoic acid (40.3 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 60% EtOAc in hexane as eluent) to afford 46 mg (38.6% yield) of biphenyl-4-carboxylicacid {2-[4-(2-chloro-benzoyl)-piperazin-1-yl]-2-oxo-ethyl}-amide, LC-MS purity: 99.47%, $^1$H NMR: (DMSO) δ

8.7-8.6 (bs, 1H), 8.02-7.92 (d, 2H), 7.84-7.7 (q, 4H), 7.6-7.38 (m, 7H), 4.24 (d, 1H), 4.18 (d, 1H), 3.8-3.6 (m, 4H), 3.56-3.46 (m, 2H), 3.26-3.12 (m, 2H).

186) Synthesis of Biphenyl-4-carboxylicacid {2-[4-(2-chloro-pyridine-3-carbonyl)-piperazin-1-yl]-2-oxo-ethyl}-amide

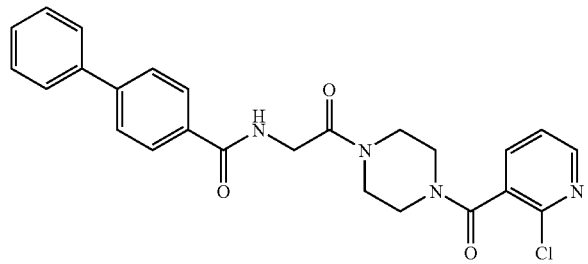

DIPEA (149.8 mg, 1.15 mmol) was added to a stirred solution of 2-chloro-nicotinic acid (40.5 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 90% EtOAc in hexane as eluent) to afford 39 mg (32.8% yield) of biphenyl-4-carboxylicacid {2-[4-(2-chloro-pyridine-3-carbonyl)-piperazin-1-yl]-2-oxo-ethyl}-amide, LC-MS purity: 89.81%, $^1$H NMR: (DMSO) δ 8.74-8.62 (bs, 1H), 8.56-8.46 (bs, 1H), 8.06-7.92 (d, 3H), 7.84-7.7 (q, 4H), 7.6-7.38 (m, 4H), 4.28-4.12 (d, 2H), 3.78-3.46 (bt, 6H), 3.28-3.18 (bs, 2H).

187) Synthesis of Biphenyl-4-carboxylicacid {2-[4-(4-chloro-2,5-difluoro-benzoyl)-piperazin-1-yl]-2-oxo-ethyl}-amide

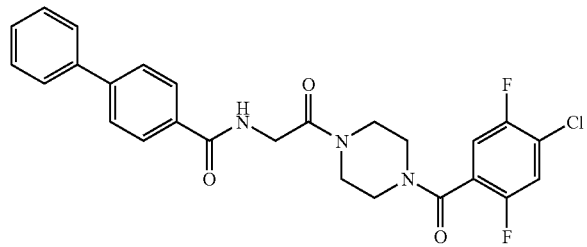

DIPEA (149.8 mg, 1.15 mmol) was added to a stirred solution of 4-chloro-2,5-difluoro-benzoic acid (49.6 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 65 mg (50.7% yield) of biphenyl-4-carboxylicacid {2-[4-(4-chloro-2,5-difluoro-benzoyl)-piperazin-1-yl]-2-oxo-ethyl}-amide, LC-MS purity: 99.40%, $^1$H NMR: (DMSO) δ 8.7-8.6 (s, 1H), 8.04-7.92 (d, 2H), 7.88-7.7 (q, 5H), 7.7-7.6 (s, 1H), 7.58-7.46 (d, 2H), 7.46-7.38 (d, 1H), 4.3-4.12 (d, 2H), 3.8-3.58 (d, 5H), 3.56-3.44 (s, 3H).

188) Synthesis of Biphenyl-4-carboxylicacid {2-[4-(2-bromo-5-fluoro-benzoyl)-piperazin-1-yl]-2-oxo-ethyl}-amide

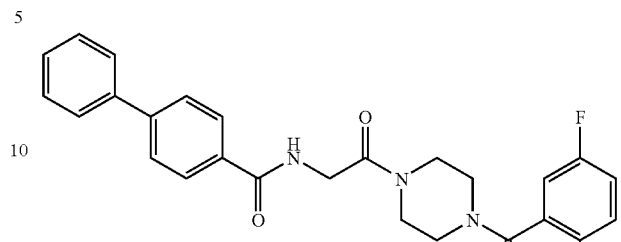

DIPEA (149.8 mg, 1.15 mmol) was added to a stirred solution of 2-bromo-5-fluoro-benzoic acid (56.4 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.32 mmol) was added and the resulting mixture was stirred at room temperature overnight. Cold water was then added, and the resulting precipitate was filtered. The residue was purified by column chromatography (using 60-120 mesh silica gel and 60% EtOAc in hexane as eluent) to afford 60 mg (44.6% yield) of biphenyl-4-carboxylicacid {2-[4-(2-bromo-5-fluoro-benzoyl)-piperazin-1-yl]-2-oxo-ethyl}-amide, LC-MS purity: 98.34%, $^1$H NMR: (CDCl$_3$) δ 7.96-7.88 (d, 2H), 7.72-7.64 (d, 2H), 7.64-7.54 (m, 3H), 7.52-7.43 (t, 2H), 7.43-7.35 (m, 1H), 7.35-7.28 (m, 1H), 7.08-6.98 (m, 2H), 4.4-4.24 (d, 2H), 4.07-3.85 (m, 2H), 3.8-3.7 (m, 2H), 3.66-3.58 (m, 1H), 3.52-3.42 (m, 1H), 3.42-3.33 (m, 1H), 3.33-3.2 (m, 1H).

189) Synthesis of Biphenyl-4-carboxylicacid {2-[4-(2,5-difluoro-benzoyl)-piperazin-1-yl]-2-oxo-ethyl}-amide

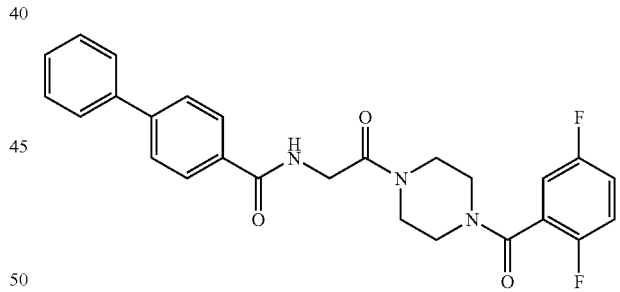

DIPEA (149.8 mg, 1.15 mmol) was added to a stirred solution of 2,5-difluoro-benzoic acid (40.7 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 56 mg (46.9% yield) of biphenyl-4-carboxylicacid {2-[4-(2,5-difluoro-benzoyl)-piperazin-1-yl]-2-oxo-ethyl}-amide, LC-MS purity: 97.42%, $^1$H NMR: (CDCl$_3$) δ 7.98-7.88 (d, 2H), 7.74-7.58 (dd, 4H), 7.54-7.34 (m, 3H), 7.2-7.08 (s, 3H), 4.4-4.26 (d, 2H), 3.94-3.78 (m, 3H), 3.76-3.56 (d, 3H), 3.54-3.38 (d, 3H).

190) Synthesis of Biphenyl-4-carboxylicacid {2-[4-(2,4-dichloro-5-fluoro-benzoyl)-piperazin-1-yl]-2-oxo-ethyl}-amide

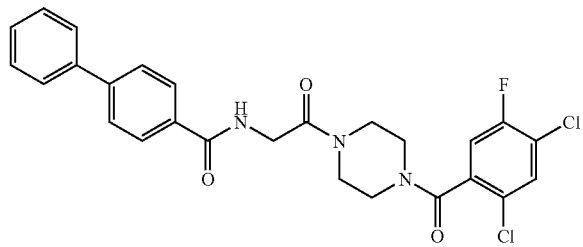

DIPEA (149.8 mg, 1.15 mmol) was added to a stirred solution of 2,4-dichloro-5-fluoro-benzoic acid (53.8 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 50% EtOAc in hexane as eluent) to afford 45 mg (33.9% yield) of biphenyl-4-carboxylicacid {2-[4-(2,4-dichloro-5-fluoro-benzoyl)-piperazin-1-yl]-2-oxo-ethyl}-amide, LC-MS purity: 98.74%, $^1$H NMR: (DMSO) δ 8.7-8.62 (t, 1H), 8.02-7.92 (d, 3H), 7.82-7.7 (q, 4H), 7.7-7.64 (q, 1H), 7.52-7.45 (t, 2H), 7.45-7.36 (m, 1H), 4.26-4.12 (dd, 2H), 3.76-3.56 (m, 4H), 3.54-3.44 (m, 2H), 3.28-3.14 (m, 2H).

191) Synthesis of Biphenyl-4-carboxylicacid {2-[4-(3-fluoro-5-trifluoromethyl-benzoyl)-piperazin-1-yl]-2-oxo-ethyl}-amide

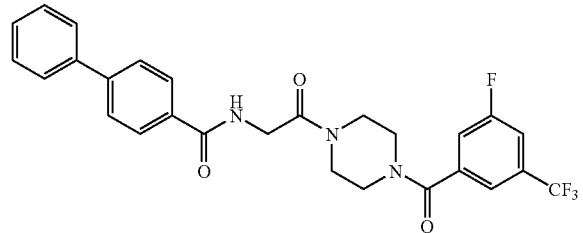

DIPEA (149.8 mg, 1.15 mmol) was added to a stirred solution of 3-fluoro-5-trifluoromethyl-benzoic acid (53.6 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 60% EtOAc in hexane as eluent) to afford 60 mg (45.3% yield) of biphenyl-4-carboxylicacid {2-[4-(3-fluoro-5-trifluoromethyl-benzoyl)-piperazin-1-yl]-2-oxo-ethyl}-amide, LC-MS purity: 99.64%, $^1$H NMR: (DMSO) δ 8.7-8.62 (t, 1H), 8.02-7.94 (d, 2H), 7.86-7.66 (m, 7H), 7.54-7.46 (m, 2H), 7.44-7.38 (m, 1H), 4.26-4.12 (bs, 2H), 3.74-3.44 (m, 6H), 3.42-3.34 (m, 2H).

192) Synthesis of Biphenyl-4-carboxylicacid {2-oxo-2-[4-(2,3,6-trifluoro-benzoyl)-piperazin-1-yl]-ethyl}-amide

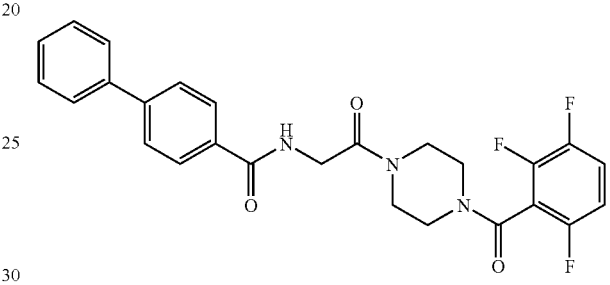

DIPEA (149.8 mg, 1.15 mmol) was added to a stirred solution of 2,3,6-trifluoro-benzoic acid (45.3 mg, 0.26 mmol) in DMF (3 mL), HOBt (38.2 mg, 0.28 mmol) and EDCI.HCl (123.4 mg, 0.64 mmol) at room temperature. After 2 minutes biphenyl-4-carboxylicacid (2-oxo-2-piperazin-1-yl-ethyl)-amide (100 mg, 0.31 mmol) was added and the resulting mixture was stirred at room temperature overnight. Cold water was then added, and the resulting precipitate was filtered. The residue was purified by column chromatography (using 60-120 mesh silica gel and 60% EtOAc in hexane as eluent) to afford 45 mg (36.2% yield) of biphenyl-4-carboxylicacid {2-oxo-2-[4-(2,3,6-trifluoro-benzoyl)-piperazin-1-yl]-ethyl}-amide, LC-MS purity: 92.11%, $^1$H NMR: (DMSO) δ 7.97-7.9 (d, 2H), 7.74-7.6 (q, 4H), 7.52-7.44 (t, 2H), 7.44-7.36 (m, 1H), 7.36-7.28 (m, 1H), 7.02-6.92 (m, 1H), 4.4-4.26 (dd, 2H), 3.98-3.82 (m, 3H), 3.78-3.72 (t, 1H), 3.68-3.62 (t, 1H), 3.58-3.52 (m, 1H), 3.48-3.38 (m, 2H).

193) Synthesis of 5-Phenyl-[1,3,4]oxadiazole-2-carboxylic acid {2-oxo-2-[4-(2-trifluoromethyl-benzoyl)-piperazin-1-yl]-ethyl}-amide

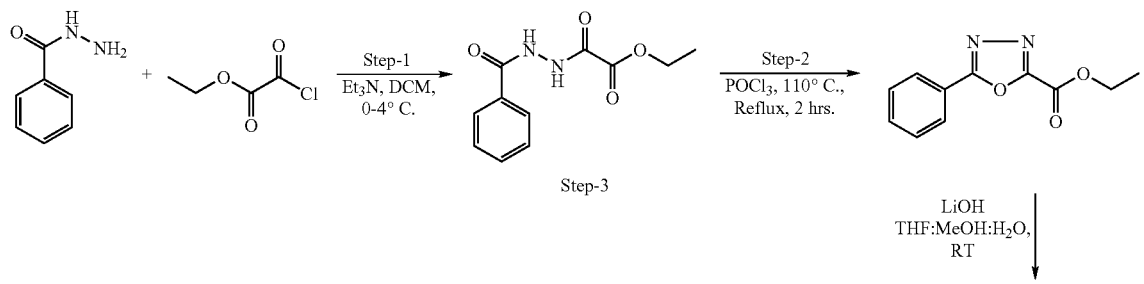

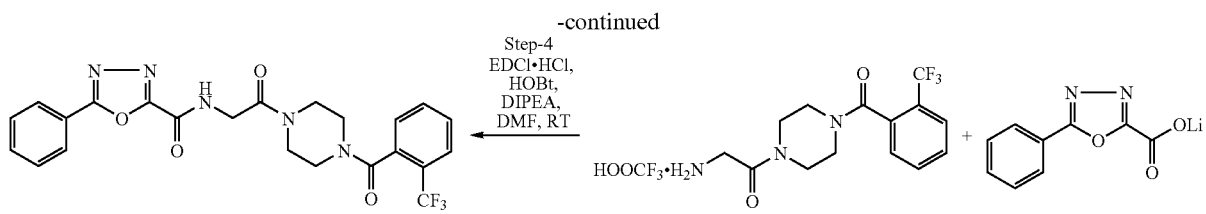

Step 1: Synthesis of (N'-Benzoyl-hydrazino)-oxo-acetic acid ethyl ester

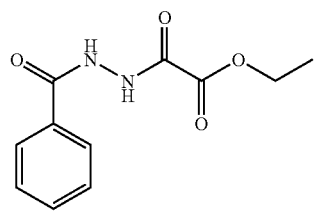

Triethylamine (771.5 mg, 1.058 mL, 7.62 mmol) was added to a stirred, ice cold solution of benzoic acid hydrazide (1.038 g, 7.62 mmol) in DCM (20 mL). Ethyl chloro oxo acetate (1.033 g, 0.845 mL, 7.62 mmol) was then added dropwise with vigorous stirring, After 1 hour, water was added. The organic layer was separated, washed with brine solution, dried over sodium sulphate and concentrated under reduced pressure to afford 1.6 g (89.4% yield) of (N'-benzoyl-hydrazino)-oxo-acetic acid ethyl ester as a white solid. LCMS purity: 93.04%

Step 2: Synthesis of 5-Phenyl-[1,3,4]oxadiazole-2-carboxylic acid ethyl ester

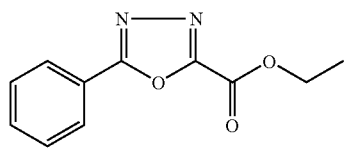

A solution of (N'-benzoyl-hydrazino)-oxo-acetic acid ethyl ester (508 mg, 2.15 mmol) in POCl$_3$ (4 mL) was heated to reflux for 3 hrs. The reaction mixture was then concentrated under reduced pressure to remove POCl$_3$ and the resulting residue was dissolved in ethyl acetate. Subsequently, the ethyl acetate layer was washed with water and brine solution, dried over sodium sulphate and concentrated under reduced pressure to afford 450 mg (96.2% yield) of 5-phenyl[1,3,4]oxa-diazole-2-carboxylic acid ethyl ester as off white solid. LCMS purity: 93.86%

Step 3: Synthesis of 5-Phenyl-[1,3,4]oxadiazole-2-carboxylic acid Lithium salt

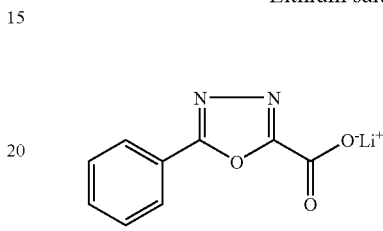

LiOH (25 mg, 0.60 mmol) was added at room temperature to a stirred solution of 5-phenyl-[1,3,4]oxadiazole-2-carboxylic acid ethyl ester (60 mg, 0.275 mmol) in THF:MeOH:H$_2$O (3:1:1, 5 mL) and the resulting mixture stirred for 1 hr. Removal of the volatiles by evaporation under reduced pressure afforded 5-phenyl-[1,3,4]oxadiazole-2-carboxylic acid lithium salt, which was used for the next step without further purification.

Step 4: Synthesis of 5-Phenyl-[1,3,4]oxadiazole-2-carboxylic acid {2-oxo-2-[4-(2-trifluoromethyl-benzoyl)-piperazin-1-yl]-ethyl}-amide

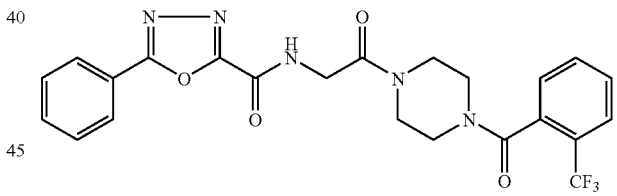

DIPEA (106 mg, 0.142 mL, 0.82 mmol) followed by HOBT (40.8 mg, 0.30 mmol), EDCI.HCl (131.8 mg, 0.69 mmol) and 2-amino-1-[4-(2-trifluoromethyl-benzoyl)-piperazin-1-yl]-ethanone TFA salt (129 mg, 0.3 mmol) were added sequentially to a stirred solution of 5-phenyl-[1,3,4]oxadiazole-2-carboxylic acid lithium salt (52 mg, 0.27 mmol) in DMF (5 mL). The resulting mixture was maintained at room temperature for 6 hrs. Cold water was added and the product was extracted with ethyl acetate. The organic layer was washed with saturated brine solution, dried over sodium sulphate and concentrated. The crude residue was purified by column chromatography (using 60-120 mesh silica gel and 50% EtOAc in hexane as eluent) to afford 30 mg (22.4% yield) of 5-phenyl-[1,3,4]oxadiazole-2-carboxylic acid {2-oxo-2-[4-(2-trifluoromethyl-benzoyl)-piperazin-1-yl]-ethyl}-amide as a white solid, LCMS purity: 87.99%, $^1$H NMR: (DMSO) δ 9.2 (t, 1H), 8.1 (d, 2H), 7.9-7.72 (dd, 2H), 7.72-7.6 (m, 3H), 7.6-7.5 (t, 1H), 4.3-4.1 (dd, 2H), 3.8-3.5 (m, 4H), 3.3-3.0 (m, 4H).

194) Synthesis of 4-Phenyl-pyrazole-1-carboxylic acid {2-oxo-2-[4-(2-trifluoromethyl-benzoyl)-piperazin-1-yl]-ethyl}-amide Step 1: Synthesis of 4-Iodo-1-trityl-1H-pyrazole

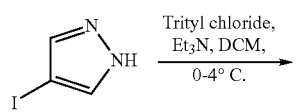

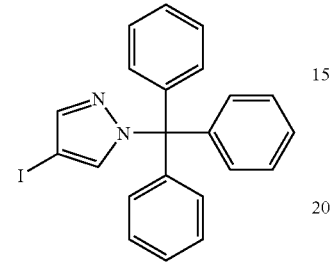

Trityl chloride (885 mg, 3.2 mmol) was added to a stirred cold (0-5° C.) solution of 4-iodo pyrazole (513 mg, 2.6 mmol) and triethylamine (401 mg, 0.55 mL, 0.4 mmol) in DCM (10 mL). Stirring was continued at room temperature overnight. Cold water was then added and the product was extracted with DCM and the organic layer was washed with sat. sodium bicarbonate solution followed by brine. The organic phase was dried over $Na_2SO_4$ and concentrated under reduced pressure to get the residue. The obtained residue was purified by column chromatography (using neutral alumina and 2% EtOAc in Hexane as eluent) to afford 300 mg (26% yield) of 4-iodo-1-trityl-1H-pyrazole.

Step 2: Synthesis of 4-Phenyl-1-trityl-1H-pyrazole

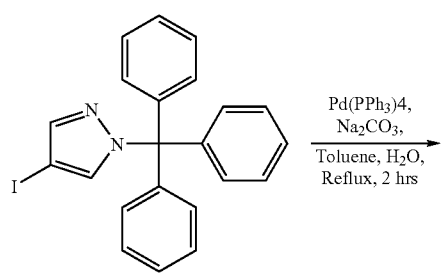

$Na_2CO_3$ (146 mg, 1.37 mmol) was added to a stirred solution of 4-iodo-1-trityl-1H-pyrazole (300 mg, 0.69 mmol) in toluene: $H_2O$ (5:1, 11.5 mL). Pd $(PPh_3)_4$ (80 mg, 0.07 mmol) and phenylboronic acid (126 mg, 1.03 mmol) were then added and the reaction mixture was heated to reflux for 2 hrs. The reaction mixture was then diluted with water and the product was extracted with ethyl acetate. The organic layer was washed with saturated brine solution, dried over sodium sulphate and concentrated to get the residue. The residue obtained was purified by column chromatography (using silica gel of 60-120 mesh and 5% EtOAc in Hexane as eluent) afford 120 mg (48.38% yield) of 4-phenyl-1-trityl-1H-pyrazole. $^1H$ NMR ($CDCl_3$): δ 7.96-7.94 (s, 1H), 7.64-7.6 (s, 1H), 7.46-7.4 (d, 2H), 7.36-7.0 (m, 1H), 7.24-7.16 (m, 7H).

Step 3: Synthesis of 4-Phenyl-1H-pyrazole hydrochloride salt

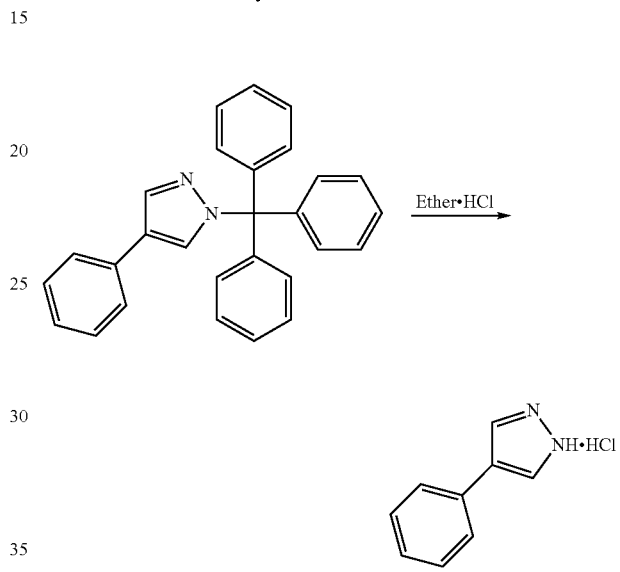

A solution of 4-phenyl-1-trityl-1H-pyrazole (120 mg, 0.33 mmol) in Ether.HCl (10 mL) was stirred for 1 hr. The reaction mixture was then concentrated under reduced pressure to afford the residue. The residue obtained was washed with hexane to afford 44 mg (93.61%) of 4-phenyl-1H-pyrazole hydrochloride salt. $^1H$ NMR (DMSO-$d_6$): δ 8.1-8.08 (s, 2H), 7.64 (d, 2H), 7.38 (t, 2H), 7.22 (t, 1H).

Step 4: Synthesis of 4-Phenyl-pyrazole-1-carboxylic acid {2-oxo-2-[4-(2-trifluoromethyl-benzoyl)-piperazin-1-yl]-ethyl}-amide

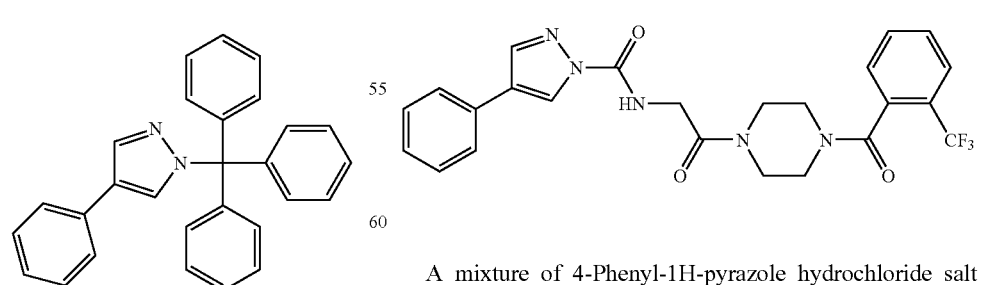

A mixture of 4-Phenyl-1H-pyrazole hydrochloride salt (prepared by the method described above)(44 mg, 0.3 mmol), DIPEA (88 mg, 0.119 ml, 0.685 mmol) and DCM (2 ml) was added to a stirred solution of triphosgene (36 mg, 0.12 mmol) in DCM (1 mL) at room temperature. After 30 minutes, to the above solution, a mixture of 2-amino-1-[4-(2-trifluoromethyl-benzoyl)-piperazin-1-yl]-ethanone hydrochloride salt (prepared by the method described above)(108 mg, 0.3 mmol), DIPEA (88 mg, 0.119 ml, 0.685 mmol) and DCM (2 ml) was added and the resulting mixture was stirred at room temperature for 30 minutes. Cold water was then added and the product was extracted with EtOAc and the organic layer was washed with brine. The organic phase was dried over Na$_2$SO$_4$ and concentrated under reduced pressure to get the residue. The obtained residue was purified by column chromatography (using silica gel of 60-120 mesh and 30-70% EtOAc in Hexane as eluent) to afford 48.8 mg (32.97% yield) 4-Phenyl-pyrazole-1-carboxylic acid {2-oxo-2-[4-(2-trifluoromethyl-benzoyl)-piperazin-1-yl]-ethyl}-amide. LCMS Purity: 97.25%. $^1$H NMR (CDCl$_3$): δ 8.48-8.4 (d, 1H), 8.04-7.98 (bs, 1H), 7.96-7.92 (s, 1H), 7.8-7.74 (d, 1H), 7.7-7.58 (m, 2H), 7.56-7.5 (d, 2H), 7.44-7.1 (m, 4H), 4.38-4.3 (d, 2H), 4.28-4.2 (t, 1H), 4.1-4.0 (bs, 1H), 3.82-3.66 (m, 2H), 3.64-3.5 (m, 2H), 3.46-3.38 (t, 1H),), 3.32-3.2 (s, 2H).

195) Synthesis of 4-Phenyl-pyrazole-1-carboxylic acid {2-[4-(5-fluoro-2-trifluoromethyl-benzoyl)-piperazin-1-yl]-2-oxo-ethyl}-amide

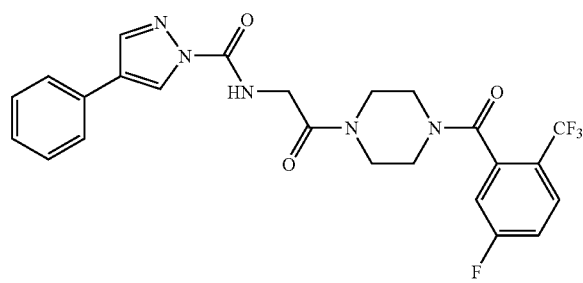

A mixture of 4-phenyl-1H-pyrazole hydrochloride salt (prepared by the method as described above)(45 mg, 0.2 mmol), DIPEA (80.5 mg, 0.11 ml, 0.625 mmol) and DCM (1 ml) was added to a stirred solution of triphosgene (40 mg, 0.1 mmol) in DCM (5 mL) at room temperature. After 30 minutes, to the above solution, a mixture of 2-amino-1-[4-(5-fluoro-2-trifluoromethyl-benzoyl)-piperazin-1-yl]-ethanone hydrochloride salt (prepared by the method as described above)(100 mg, 0.27 mmol), DIPEA (80.5 mg, 0.11 ml, 0.625 mmol) and DCM (1 ml) was added and the resulting mixture was stirred at room temperature for 30 minutes. Cold water was then added and the product was extracted with EtOAc and the organic layer was washed with 10% HCl solution, saturated sodium bicarbonate solution and brine. The organic phase was dried over Na$_2$SO$_4$ and concentrated under reduced pressure to get the residue. The obtained residue was purified by column chromatography (using silica gel of 60-120 mesh and 50% EtOAc in Hexane as eluent) to afford 57 mg (45.6% yield) 4-phenyl-pyrazole-1-carboxylic acid {2-[4-(5-fluoro-2-trifluoromethyl-benzoyl)-piperazin-1-yl]-2-oxo-ethyl}-amide. LCMS Purity: 96.83%. $^1$H NMR (CDCl$_3$): δ 8.5 (d, 1H), 8.02 (s, 1H), 7.94 (s, 1H), 7.8 (m, 1H), 7.56 (d, 2H), 7.44 (t, 2H), 7.14 (d, 2H), 7.1 (d, 1H), 4.38-4.2 (m, 2H), 4.08-3.8 (m, 1H), 3.8-3.6 (m, 4H), 3.46-3.36 (s, 1H), 3.34-3.18 (s, 2H).

196) Synthesis of 4-(2-Fluoro-phenyl)-pyrazole-1-carboxylic acid {2-[4-(5-fluoro-2-trifluoromethyl-benzoyl)-piperazin-1-yl]-2-oxo-ethyl}-amide

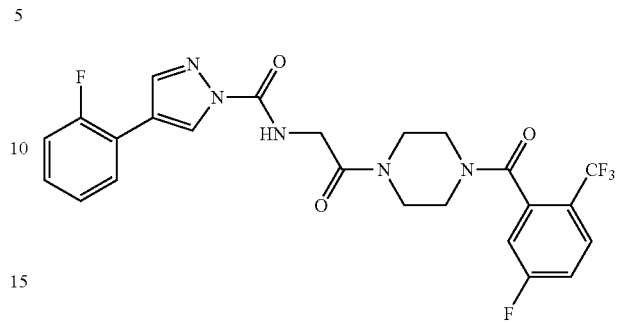

A mixture of 4-(2-fluoro-phenyl)-1H-pyrazolehydrochloride salt (prepared by the method described above) (50 mg, 0.25 mmol), DIPEA (85 mg, 0.115 ml, 0.66 mmol) and DCM (1.5 ml) was added to a stirred solution of triphosgene (30 mg, 0.1 mmol) in DCM (2.5 mL) at room temperature. After 30 minutes, to the above solution, a mixture of 2-amino-1-[4-(5-fluoro-2-trifluoromethyl-benzoyl)-piperazin-1-yl]-ethanone hydrochloride salt (prepared by the method described above) (102 mg, 0.27 mmol), DIPEA (85 mg, 0.115 ml, 0.66 mmol) and DCM (1.5 ml) was added and the resulting mixture was stirred at room temperature for 1 hr. Cold water was then added and the product was extracted with DCM and the organic layer was washed with 10% HCl solution, saturated sodium bicarbonate solution and brine. The organic phase was dried over Na$_2$SO$_4$ and concentrated under reduced pressure to get the residue. The obtained residue was purified by column chromatography (using silica gel of 60-120 mesh and 50% EtOAc in Hexane as eluent) to afford 59 mg (45% yield) 4-(2-fluoro-phenyl)-pyrazole-1-carboxylic acid {2-[4-(5-fluoro-2-trifluoromethyl-benzoyl)-piperazin-1-yl]-2-oxo-ethyl}-amide. LCMS Purity: 95.23%. $^1$H NMR (CDCl$_3$): δ 8.6 (t, 1H), 8.0 (m, 2H), 7.8 (m, 1H), 7.6 (t, 1H), 7.3 (m, 1H), 7.2-7.0 (m, 3H), 4.36-4.2 (m, 2H), 4.1-3.8 (m, 1H), 3.8-3.46 (m, 4H), 3.6 (t, 1H), 3.3-3.2 (m, 2H).

197) Synthesis of 5-Phenyl-1H-pyrrole-2-carboxylic acid {2-oxo-2-[4-(2-trifluoromethyl-benzoyl)-piperazin-1-yl]-ethyl}-amide Step 1: Synthesis of 5-Bromo-1H-pyrrole-2-carboxylic acid ethyl ester

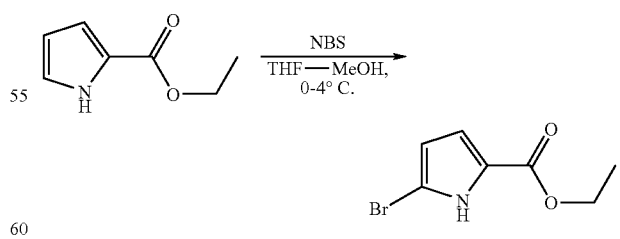

NBS (0.15 mg, 0.83 mmol) was added to a stirred cold (0-5° C.) solution of 1H-pyrrole-2-carboxylic acid ethyl ester (200 mg, 1.44 mmol) in THF: MeOH (2:1, 24 mL). Stirring was continued at same temperature for 2 hrs. Solvent was removed under vacuum to get the residue. The residue obtained was purified by column chromatography (using silica gel of 200-430 mesh and 10% Ether in Hexane as eluent) to afford 100 mg (31.95% yield) of 5-bromo-1H-pyrrole-2-carboxylic acid ethyl ester. ¹H NMR (CDCl₃): δ 9.4 (bs, 1H), 6.8 (s, 1H), 6.2 (s, 1H), 4.4-4.2 (q, 2H), 1.4 (t, 3H).

Step 2: Synthesis of
5-Phenyl-1H-pyrrole-2-carboxylic acid ethyl ester

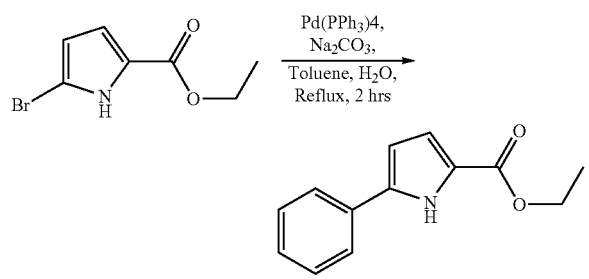

Na₂CO₃ (97.5 mg, 0.92 mmol) was added to a stirred solution of 5-bromo-1H-pyrrole-2-carboxylic acid ethyl ester (100 mg, 0.46 mmol) in toluene: H₂O (5:1, 11 mL). Pd (PPh₃)₄ (53 mg, 0.046 mmol) and phenylboronic acid (84.3 mg, 0.7 mmol) were then added and the reaction mixture was heated to reflux for 2 hrs. The reaction mixture was then diluted with water and the product was extracted with ethyl acetate. The organic layer was washed with saturated brine solution, dried over sodium sulphate and concentrated to get the residue. The residue obtained was purified by column chromatography (using silica gel of 60-120 mesh and 5% EtOAc in Hexane as eluent) afford 67 mg (67.95% yield) of 5-phenyl-1H-pyrrole-2-carboxylic acid ethyl ester. ¹H NMR (CDCl₃): δ 9.4 (s, 1H), 7.64 (d, 2H), 7.48 (t, 2H), 7.36 (d, 11H), 7.0 (s, 1H), 6.58 (s, 1H), 4.4 (q, 2H), 1.4 (t, 3H).

Step 3: Synthesis of
5-Phenyl-1H-pyrrole-2-carboxylic acid

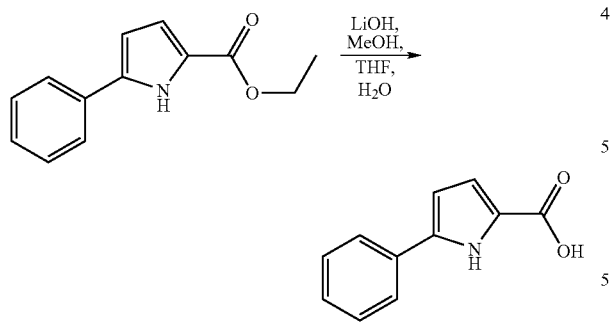

LiOH (27.5 mg, 0.65 mmol) was added to a stirred solution of 5-phenyl-1H-pyrrole-2-carboxylic acid ethyl ester (67 mg, 0.31 mmol) in THF:MeOH:H₂O (3:1:1, 3 mL), and the resulting mixture was stirred at room temperature for 2 hrs. The reaction mixture was concentrated under reduced pressure to get the residue. Cold water was then added and acidified it with 10% aqueous HCl, filtered the solid precipitated to afford 37 mg (63.79% yield) of 5-Phenyl-1H-pyrrole-2-carboxylic acid. LCMS Purity: 92.24%.

Step 4: Synthesis of 5-Phenyl-1H-pyrrole-2-carboxylic acid {2-oxo-2-[4-(2-trifluoromethyl-benzoyl)-piperazin-1-yl]-ethyl}-amide

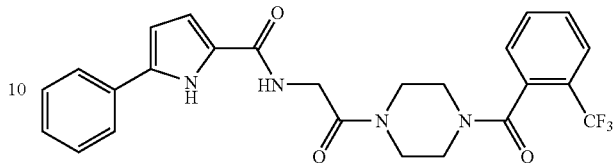

DIPEA (102 mg, 0.14 mL, 0.79 mmol) was added to a stirred solution of 5-phenyl-1H-pyrrole-2-carboxylic acid (37 mg, 0.19 mmol) in DMF (4 mL). HOBT (30 mg, 0.22 mmol) and EDCI (57 mg, 0.29 mmol) were then added at room temperature. After 2 minutes, 2-amino-1-[4-(2-trifluoromethyl-benzoyl)-piperazin-1-yl]-ethanone hydrochloride salt (prepared by the method as described above) (83.6 mg, 0.23 mmol) was added and the resulting mixture was stirred at room temperature overnight. Cold water was then added and filtered the solid precipitated to afford 69 mg (72% yield) of 5-phenyl-1H-pyrrole-2-carboxylic acid {2-oxo-2-[4-(2-trifluoromethyl-benzoyl)-piperazin-1-yl]-ethyl}-amide. LCMS Purity: 89.78%. ¹H NMR (DMSO-d₆): δ 11.7 (s, 1H), 8.2-8.1 (bs, 1H), 7.9-7.7 (s, 4H), 7.7-7.6 (s, 1H), 7.6-7.5 (s, 1H), 7.45-7.3 (t, 2H), 7.3-7.2 (t, 1H), 6.9-6.8 (s, 1H), 6.6-6.5 (s, 1H), 4.28-4.04 (d, 2H), 3.84-3.5 (bs, 4H), 3.5-3.4 (s, 2H), 3.2-3.0 (d, 2H).

198) Synthesis of 4-Phenyl-1H-pyrrole-2-carboxylic acid {2-oxo-2-[4-(2-trifluoromethyl-benzoyl)-piperazin-1-yl]-ethyl}-amide Step 1: Synthesis of (3-Dimethylamino-2-phenyl-allylidene)-dimethyl-ammonium perchlorate

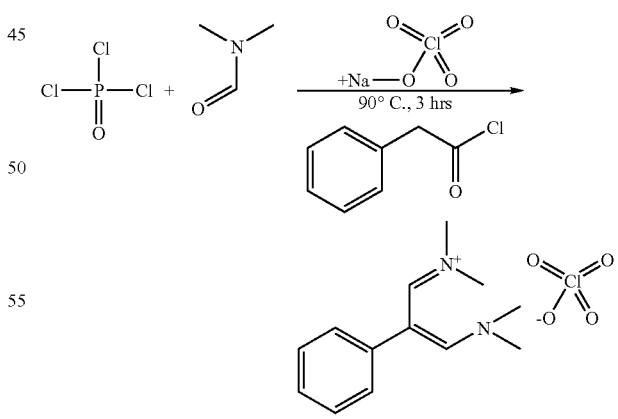

A mixture of DMF (1.485 g, 0.9 mL, 9.7 mmol), POCl₃ (1.407 g, 1.5 mL, 19.2 mmol) phenacyl chloride (0.5 g, 3.2 mmol) was heated at 90° C. for 3 hrs. The reaction mixture was cooled and quenched with sodium perchlorate (514 mg, 4.2 mmol) in H₂O (20 mL), filtered the solid precipitated to afford 500 mg (51.07% Yield) of (3-dimethylamino-2-phenyl-allylidene)-dimethyl-ammonium; perchlorate. $^1$H NMR (DMSO-$d_6$): δ 7.74 (s, 2H), 7.48 (s, 3H), 7.34 (s, 2H), 3.26 (s, 6H), 2.44 (s, 6H).

Step 2: Synthesis of
4-Phenyl-1H-pyrrole-2-carboxylic acid ethyl ester

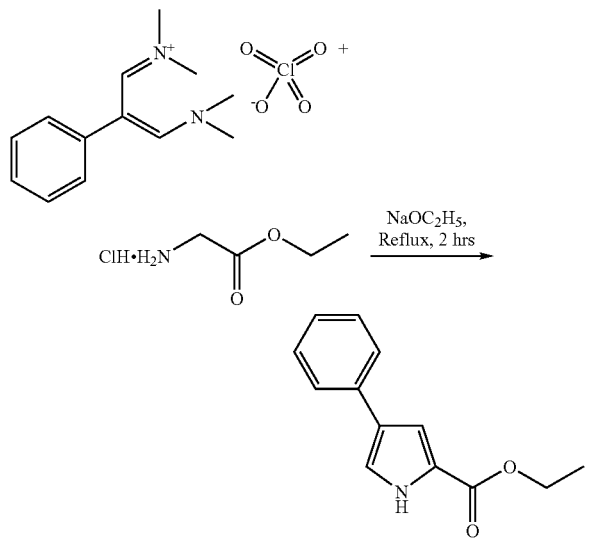

Sodium metal (119 mg, 5.1 mmol) was added to EtOH (15 mL) and stirred for 30 minutes. Glycine ethyl esater hydrochloride (345 mg, 2.47 mmol) and (3-dimethylamino-2-phenyl-allylidene)-dimethyl-ammonium; perchlorate (500 mg, 1.65 mmol) was then added. The resulting mixture was stirred and heated to reflux for 2 hrs. Evaporated the reaction mixture to get the residue. The residue was diluted with cold water and extracted with EtOAc. The organic layer was washed with brine, dried over Na$_2$SO$_4$ and concentrated under reduced pressure to get the residue. The residue obtained was purified by column chromatography (using silicagel of 60-120 mesh and 10% EtOAc in Hexane as eluent) to afford 113 mg (31.83% yield) of 4-phenyl-1H-pyrrole-2-carboxylic acid ethyl ester. LCMS Purity: 98.96%. $^1$H NMR (CDCl$_3$): δ 9.2 (bs, 1H), 7.58 (d, 2H), 7.42 (t, 2H), 7.26 (m, 3H), 4.4 (q, 2H), 1.4 (t, 3H).

Step 3: Synthesis of
4-Phenyl-1H-pyrrole-2-carboxylic acid

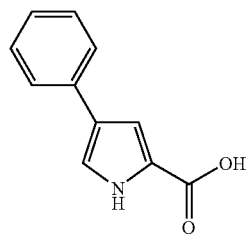

LiOH (180 mg, 4.3 mmol) was added to a stirred solution of 4-phenyl-1H-pyrrole-2-carboxylic acid ethyl ester (143 mg, 0.66 mmol) in THF:MeOH:H$_2$O (3:1:1, 5 mL), and the resulting mixture was stirred at room temperature for 8 hrs. The reaction mixture was concentrated under reduced pressure to get the residue. Cold water was then added and acidified it with concentrated HCl, filtered the solid precipitated to afford 103 mg (83.06% yield) of 4-Phenyl-1H-pyrrole-2-carboxylic acid.

Step 4: Synthesis of 4-Phenyl-1H-pyrrole-2-carboxylic acid {2-oxo-2-[4-(2-trifluoromethyl-benzoyl)-piperazin-1-yl]-ethyl}-amide

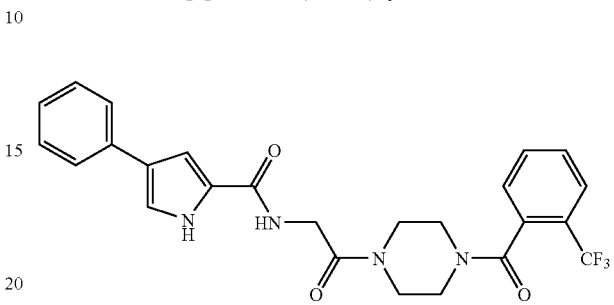

DIPEA (155 mg, 0.2 mL, 1.19 mmol) was added to a stirred solution of 4-Phenyl-1H-pyrrole-2-carboxylic acid (50 mg, 0.26 mmol) in DMF (4 mL). HOBT (40 mg, 0.29 mmol) and EDCI (153 mg, 0.79 mmol) were then added at room temperature. After 2 minutes, 2-amino-1-[4-(2-trifluoromethyl-benzoyl)-piperazin-1-yl]-ethanone hydrochloride salt (prepared by the method as described above) (103 mg, 0.29 mmol) was added and the resulting mixture was stirred at room temperature for 4 hrs. Cold water was then added and filtered the solid precipitated to afford 113 mg (87.59% yield) of 4-phenyl-1H-pyrrole-2-carboxylic acid {2-oxo-2-[4-(2-trifluoromethyl-benzoyl)-piperazin-1-yl]-ethyl}-amide. LCMS Purity: 92.52%. $^1$H NMR (DMSO-$d_6$): δ 11.6 (s, 1H), 8.2-8.1 (bs, 1H), 7.9-7.72 (m, 2H), 7.7-7.64 (t, 1H), 7.6-7.5 (d, 3H), 7.38-7.28 (t, 3H), 7.24-7.1 (m, 2H), 4.2-4.04 (bd, 2H), 3.82-3.56 (m, 4H), 3.5-3.4 (bs, 2H), 3.2-3.1 (bd, 2H).

199) Synthesis of 1-Phenyl-1H-pyrazole-3-carboxylic acid {2-oxo-2-[4-(2-trifluoromethyl-benzoyl)-piperazin-1-yl]-ethyl}-amide Step 1: Synthesis of
1-Phenyl-1H-pyrazole-3-carboxylic acid

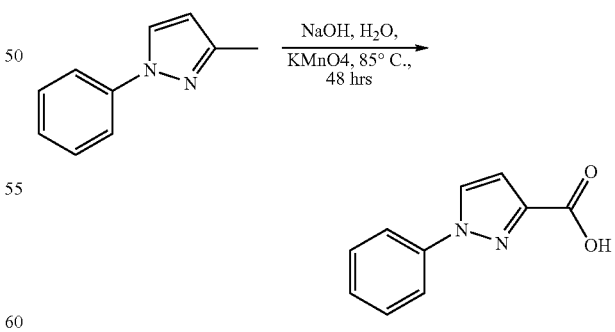

KMnO$_4$ (1.2 g, 7.6 mmol) was added portionwise to a stirred solution of 3-Methyl-1-phenyl-1H-pyrazole (100 mg, 0.63 mmol) and NaOH (504 mg, 12.6 mmol) in H$_2$O (4 mL). The resulting mixture was heated to 85° C. for 48 hrs. The reaction mixture was filtered, filtrate was acidified with 30% aqueous HCl solution, extracted the aqueous layer with EtOAc. The organic phase was dried over Na$_2$SO$_4$ and concentrated under reduced pressure to get the residue. The obtained residue was purified by washing with hexane to afford 53 mg (44.53% yield) of 1-phenyl-1H-pyrazole-3-carboxylic acid. $^1$H NMR (DMSO-d$_6$): δ 8.6 (d, 1H), 7.9 (d, 2H), 7.6-7.5 (t, 2H), 7.4 (t, 1H), 6.96 (d, 1H).

Step 2: Synthesis of 1-Phenyl-1H-pyrazole-3-carboxylic acid {2-oxo-2-[4-(2-trifluoromethyl-benzoyl)-piperazin-1-yl]-ethyl}-amide

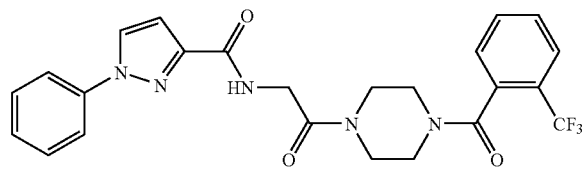

DIPEA (130 mg, 0.17 mL, 1.0 mmol) was added to a stirred solution of 1-phenyl-1H-pyrazole-3-carboxylic acid (47 mg, 0.25 mmol) in DMF (5 mL). HOBT (37 mg, 0.27 mmol) and EDCI (120 mg, 0.62 mmol) were then added at room temperature. After 2 minutes, 2-amino-1-[4-(2-trifluoromethyl-benzoyl)-piperazin-1-yl]-ethanone hydrochloride salt (prepared by the method as described above) (97 mg, 0.27 mmol) was added and the resulting mixture was stirred at room temperature overnight. Cold water was then added and the product was extracted with EtOAc and the organic layer was washed with brine. The organic phase was dried over Na$_2$SO$_4$ and concentrated under reduced pressure to get the residue. The obtained residue was purified by column chromatography (using silica gel of 60-120 mesh and 70% EtOAc in Hexane as eluent) to afford 37 mg (30.5% yield) of 1-phenyl-1H-pyrazole-3-carboxylic acid {2-oxo-2-[4-(2-trifluoromethyl-benzoyl)-piperazin-1-yl]-ethyl}-amide. LCMS Purity: 96.28%. $^1$H NMR (CDCl$_3$): δ 7.9 (d, 2H), 7.7 (d, 3H), 7.68-7.54 (m, 2H), 7.44 (t, 2H), 7.32 (d, 2H), 6.8 (d, 1H), 4.42-4.2 (m, 2H), 4.1-3.86 (m, 2H), 3.82-3.4 (m, 4H), 3.2 (s, 2H).

SCHEME-19

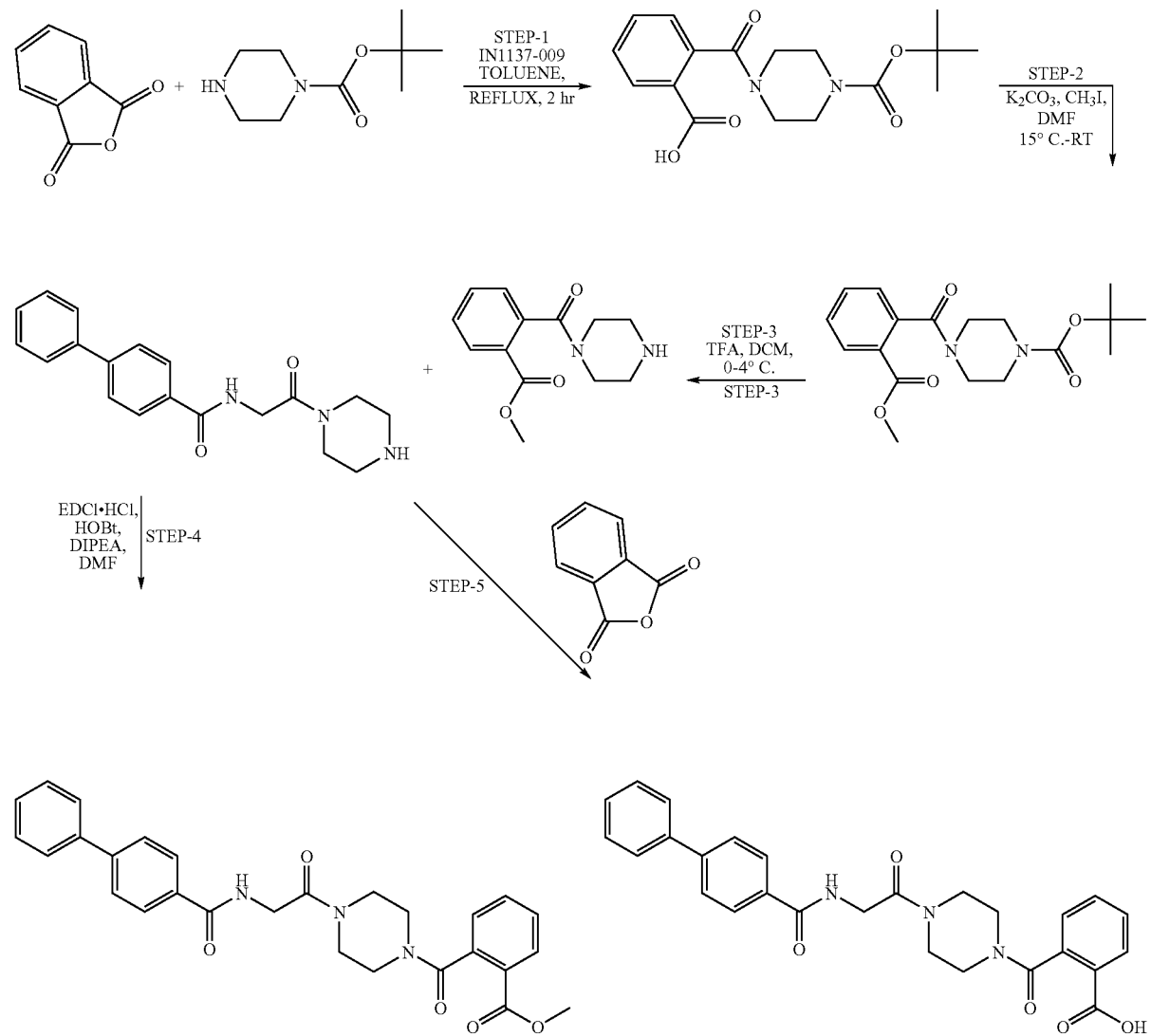

Step 1: Synthesis of 4-(2-Carboxy-benzoyl)-piperazine-1-carboxylic acid tert-butyl ester

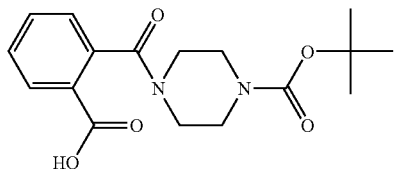

A mixture of piperazine-1-carboxylic acid tert-butyl ester (167 mg, 0.90 mmol) and pthalic anhydride (160 mg, 1.08 mmol) in toluene (20 mL) were heated to reflux for 2 hours. The reaction mixture was concentrated under reduced pressure to afford 4-(2-carboxy-benzoyl)-piperazine-1-carboxylic acid tert-butyl ester.

Step 2: Synthesis of 4-(2-Methoxycarbonyl-benzoyl)-piperazine-1-carboxylic acid tert-butyl ester

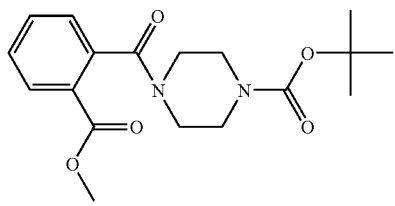

$K_2CO_3$ (383 mg, 2.8 mmol) and $CH_3I$ (236 mg, 1.66 mmol) were added, with vigorous stirring, to a solution of 4-(2-carboxy-benzoyl)-piperazine-1-carboxylic acid tert-butyl ester (371 mg, 1.1 mmol) in DMF (5 mL) and the resulting mixture was stirred at room temperature for 2 hours. The mixture was then diluted with cold water and the product extracted with ethyl acetate. The organic layer was washed with saturated brine solution, dried over sodium sulphate and concentrated under reduced pressure to afford 390 mg of 4-(2-methoxycarbonyl-benzoyl)-piperazine-1-carboxylic acid tert-butyl ester as a yellow oil. LC-MS purity: 92.15%.

Step 3: Synthesis of 2-(piperazine-1-carbonyl)-benzoic acid methyl ester

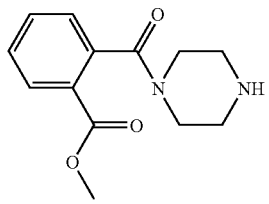

TFA (1.2 mL) was added to a stirred solution of 4-(2-Methoxycarbonyl-benzoyl)-piperazine-1-carboxylic acid tert-butyl ester (200 mg, 0.58 mmol) in DCM (5 mL) at 0° C. The resulting mixture was stirred at the same temperature for 2 hours. DIPEA (1.5 mL) was added to the cold reaction mixture and the mixture was concentrated under reduced pressure to afford 2-(piperazine-1-carbonyl)-benzoic acid methyl ester.

Step 4

200) Synthesis of 2-(4-{2-[(Biphenyl-4-carbonyl)-amino]-acetyl}-piperazine-1-carbonyl)-benzoic acid methylester

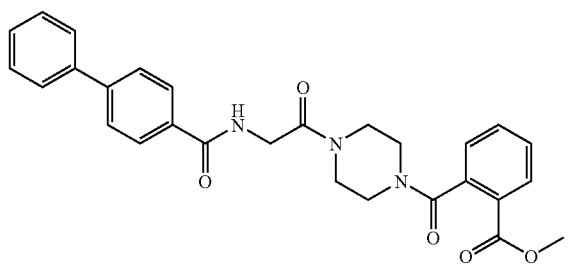

DIPEA (233 mg, 1.80 mmol) was added to a stirred solution of [(biphenyl-4-carbonyl)-amino]-acetic acid (161 mg, 0.63 mmol) in DMF (5 mL), HOBt (85.6 mg, 0.63 mmol) and EDCI.HCl (276 mg, 1.44 mmol) at room temperature. After 2 minutes 2-(piperazine-1-carbonyl)-benzoic acid methyl ester (143 mg, 0.58 mmol) was and the resulting mixture was stirred at room temperature overnight. The mixture was then diluted with cold water and the product extracted with ethyl acetate. The organic layer was separated, washed with 10% HCl solution, $NaHCO_3$ solution, and brine, dried over sodium sulphate and concentrated to afford 106 mg (37.9% yield) of 2-(4-{2-[(biphenyl-4-carbonyl)-amino]-acetyl}-piperazine-1-carbonyl)-benzoic acid methylester, LC-MS purity: 98.96%, $^1$H NMR: (DMSO) δ 8.6 (bs, 1H), 7.9 (d, 3H), 7.8-7.6 (m, 5H), 7.54 (t, 1H), 7.54-7.46 (t, 2H), 7.44-7.36 (t, 2H), 4.1 (d, 1H), 3.8 (s, 3H), 3.6 (d, 4H), 3.4 (bs, 2H), 3.1 (bd, 2H).

Step 5

201) Synthesis of 2-(4-{2-[(Biphenyl-4-carbonyl)-amino]-acetyl}-piperazine-1-carbonyl)-benzoic acid

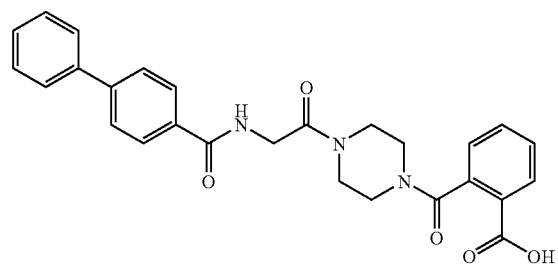

Biphenyl-4-carboxylic acid (2-oxo-2-piperazin-1-yl-ethyl)-amide (150 mg, 0.46 mmol) and phthalic anhydride (69 mg, 0.46 mmol) in toluene (20 mL) were heated to reflux for 2 hours. The reaction mixture was then concentrated under reduced pressure. The resulting residue was purified by Preparative TLC (using silicagel 60$F_{254}$ coated glass plate (20×20 cm, 1 mm (thickness) as the stationary phase with the mobile phase being 10% MeOH in Chloroform) to afford 106 mg (48.5% yield) of 2-(4-{2-[(biphenyl-4-carbonyl)-amino]-acetyl}-piperazine-1-carbonyl)-benzoic acid, LC-MS purity: 86.97%, ¹H NMR: (DMSO) δ 8.6 (t, 1H), 7.9 (d, 2H), 7.85-7.7 (m, 4H), 7.5 (t, 2H), 7.4 (t, 1H), 7.3-7.2 (bs, 2H), 7.0 (bs, 1H), 4.25-4.05 (m, 2H), 3.75-3.4 (m, 6H), 3.1-3.0 (bs, 2H).

202) Synthesis of 5-(3-Hydroxy-phenyl)-isoxazole-3-carboxylic acid {2-oxo-2-[4-(2-trifluoromethyl-benzoyl)-piperazin-1-yl]-ethyl}-amide

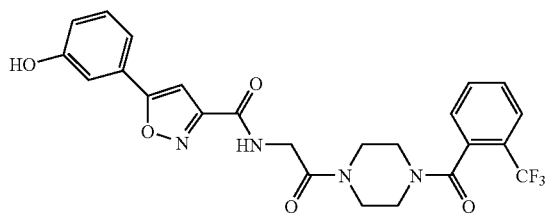

10% Pd/c (40 mg) was added to a stirred solution of 5-(3-benzyloxy-phenyl)-isoxazole-3-carboxylic acid {2-oxo-2-[4-(2-trifluoromethyl-benzoyl)-piperazin-1-yl]-ethyl}-amide (74 mg, 0.12 mmol) (prepared by the method as described above) in MeOH (30 mL) and stirred under hydrogen atmosphere. The reaction mixture was then stirred for 6 hrs. The mixture was filtered over a bed of celite. The celite was washed with MeOH and the filtrate was concentrated under reduced pressure to afford 26 mg (41.9% yield) of 5-(3-hydroxy-phenyl)-isoxazole-3-carboxylic acid {2-oxo-2-[4-(2-trifluoromethyl-benzoyl)-piperazin-1-yl]-ethyl}-amide. LCMS Purity: 99.07%. ¹H NMR (CD₃OD): δ 7.64 (m, 4H), 7.5 (d, 1H), 7.32 (m, 1H), 7.24 (s, 1H), 6.98 (m, 2H), 4.26 (m, 2H), 3.7 (m, 4H), 3.5 (m, 2H), 3.38 (m, 1H), 3.24 (m, 1H).

203) Synthesis of 5-(2-Hydroxy-phenyl)-isoxazole-3-carboxylic acid {2-oxo-2-[4-(2-trifluoromethyl-benzoyl)-piperazin-1-yl]-ethyl}-amide

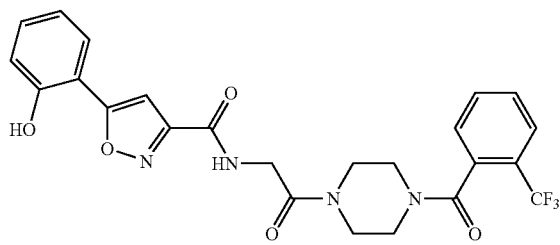

10% Pd/c (20 mg) was added to a stirred solution of 5-(2-benzyloxy-phenyl)-isoxazole-3-carboxylic acid {2-oxo-2-[4-(2-trifluoromethyl-benzoyl)-piperazin-1-yl]-ethyl}-amide (90 mg, 0.15 mmol) (prepared by the method as described above) in MeOH (50 mL) and stirred under hydrogen atmosphere. The reaction mixture was then stirred for 6 hrs. The mixture was filtered over a bed of celite. The celite was washed with MeOH and the filtrate was concentrated under reduced pressure to afford 47.3 mg (62% yield) of 5-(2-hydroxy-phenyl)-isoxazole-3-carboxylic acid {2-oxo-2-[4-(2-trifluoromethyl-benzoyl)-piperazin-1-yl]-ethyl}-amide. LCMS Purity: 91.92%. ¹H NMR (DMSO): δ 9.95 (s, 1H), 8.7 (s, 1H), 7.5 (m, 4H), 7.2 (m, 3H), 6.9 (m, 1H), 4.2 (m, 2H), 3.6 (m, 4H), 3.4 (m, 2H), 3.1 (m, 2H).

204) Synthesis of 5-(2-Fluoro-phenyl)-isoxazole-3-carboxylic acid {2-[4-(5-fluoro-2-trifluoromethyl-benzoyl)-piperazin-1-yl]-2-oxo-ethyl}-amide

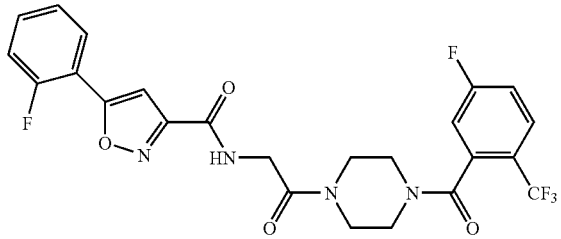

DIPEA (219 mg, 0.29 mL, 1.68 mmol) was added to a stirred solution of 5-(2-fluoro-phenyl)-isoxazole-3-carboxylic acid (100 mg, 0.48 mmol) in DMF (2 mL). HOBT (68.5 mg, 0.5 mmol) and EDCI (97.2 mg, 0.5 mmol) were then added at room temperature. After 2 minutes, 2-amino-1-[4-(5-fluoro-2-trifluoromethyl-benzoyl)-piperazin-1-yl]-ethanone hydrochloride salt (100 mg, 0.48 mmol) was added and the resulting mixture was stirred at room temperature overnight. Cold water was then added and filtered the solid precipitated. The obtained solid was purified by column chromatography (using silica gel of 60-120 mesh and 50% EtOAc in hexane as eluent) to afford 82 mg (32.5% yield) of 5-(2-fluoro-phenyl)-isoxazole-3-carboxylic acid {2-[4-(5-fluoro-2-trifluoromethyl-benzoyl)-piperazin-1-yl]-2-oxo-ethyl}-amide. LCMS Purity: 98.05%. ¹H NMR (DMSO-d₆): δ 8.8 (t, 1H), 7.9 (m, 2H), 7.4 (m, 5H), 7.2 (d, 1H), 7.2 (d, 1H), 4.2 (m, 2H), 3.9 (m, 1H), 3.5 (m, 3H), 3.4 (m, 1H), 3.1 (m, 2H).

SCHEME-20

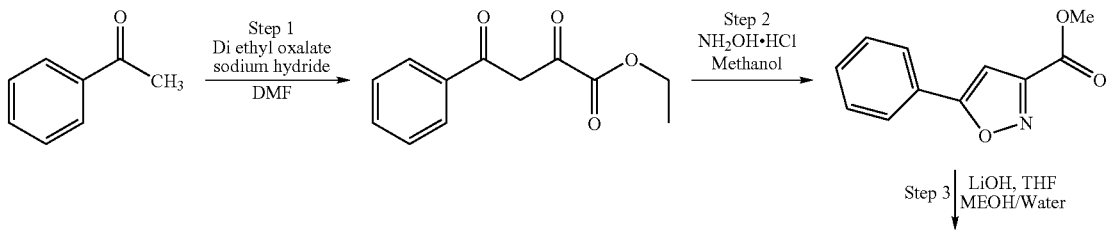

-continued

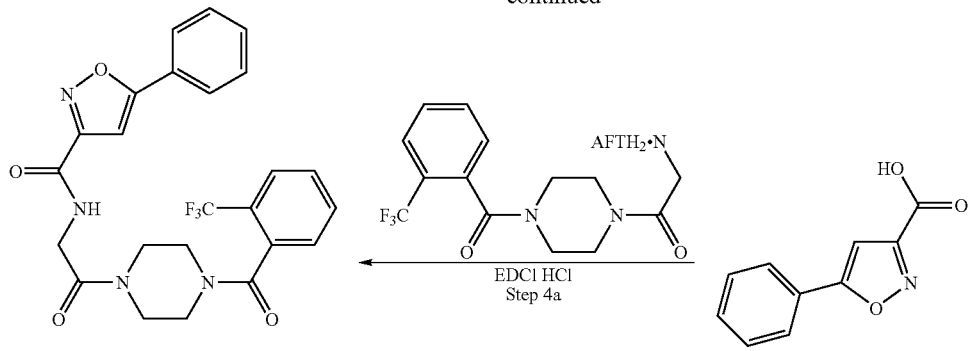

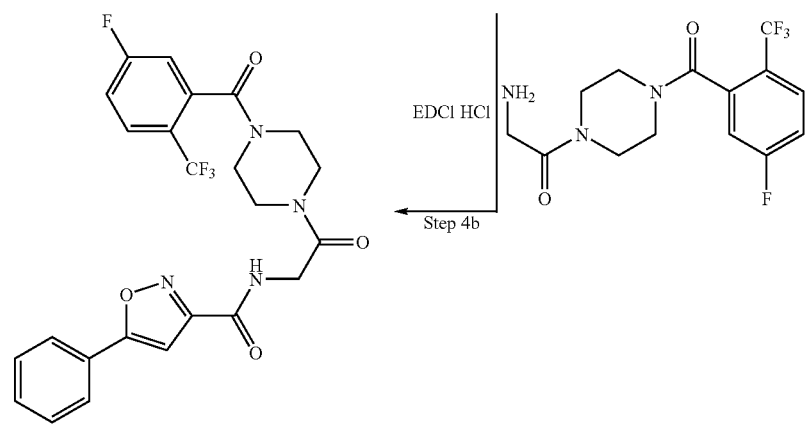

Step 1: Synthesis of 2,4-Dioxo-4-phenyl-butyric acid ethyl ester

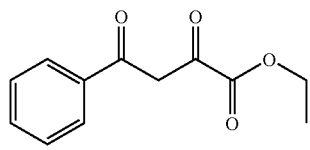

Diethyl oxalate (7.23 g, 49.47 mmol) was added to a stirred solution of 1-phenyl-ethanone (5.0 g, 41.6 mmol) in DMF (40 mL) at room temperature. The reaction mixture was cooled to 0° C. and sodium hydride (60% dispersion in oil, 2.0 g, 83.3 mmol) was added. The resulting mixture was maintained at 0° C. for 30 minutes, stirred for a further hour at room temperature and then slowly heated to 50° C. and stirred for a further 30 minutes. Chilled water was then added, the mixture was acidified with 2.4 N HCl and the resulting precipitate was filtered to afford 2,4-dioxo-4-phenyl-butyric acid ethyl ester in 42.6% yield. LC-MS purity: 85.2%.

Step 2: Synthesis of 5-Phenyl-isoxazole-3-carboxylic Acid Methyl Ester

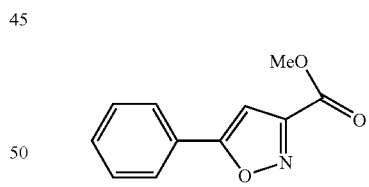

$NH_2$—OH. HCl (3.65 g, 52.6 mmol) was added to a solution of 2,4-dioxo-4-phenyl-butyric acid ethyl ester (3.86 g, 17.54 mmol) in methanol (78 mL). The resulting reaction mixture was heated to reflux overnight. The methanol was then evaporated and the residue extracted with $CHCl_3$, dried over $Na_2SO_4$ and evaporated under reduced pressure. The crude product was purified by column chromatography using silica gel (60-120 mesh) and 4% ethyl acetate in hexane as the eluant to afford the 5-phenyl-isoxazole-3-carboxylic acid methyl ester as a solid in 78.6% yield. LC-MS purity: 97.58%.

Step 3: Synthesis of 5-Phenyl-isoxazole-3-carboxylic Acid

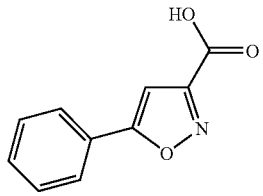

LiOH.H$_2$O (870 mg, 20.73 mmol) was added to a solution of 5-phenyl-isoxazole-3-carboxylic acid methyl ester (2.8 g, 13.79 mmol) in a mixture of methanol (10 mL), THF (10 mL) and H$_2$O (10 mL). The resulting reaction mixture was stirred for two and half hours at room temperature. The volatiles were then removed and the residue was diluted with water, washed with diethyl ether, acidified with con. HCl and extracted with ethyl acetate. The organic layer was washed with brine solution, dried over Na$_2$SO$_4$ and concentrated under reduced pressure to afford 5-phenyl-isoxazole-3-carboxylic acid in 84.6% yield. LC-MS purity: 96.4%.

Step 4a

205) Synthesis of 5-Phenyl-isoxazole-3-carboxylic acid {2-oxo-2-[4-(2-trifluoromethyl-benzoyl)-piperazin-1-yl]-ethyl}-amide

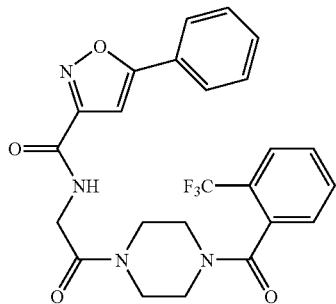

HOBt (44.6 mg, 0.33 mmol) and DIPEA (136.7 mg, 1.06 mmol) were added to a stirred solution of 5-phenyl-isoxazole-3-carboxylic acid (50 mg, 0.27 mmol) in DMF (1.0 mL). The reaction mixture was then cooled to 10° C. and EDCI.HCl (63.3 mg, 0.33 mmol) was added, followed by the addition 2-amino-1-[4-(2-trifluoromethyl-benzoyl)-piperazin-1-yl]-ethanone (as TFA salt) (113.5 mg, 0.27 mmol). Then resulting mixture was stirred at room temperature overnight. The reaction mixture was then diluted with water and the product extracted with ethyl acetate. The organic layer was washed with brine solution, dried over Na$_2$SO$_4$ and concentrated. The crude product thus obtained was purified by column chromatography using neutral alumina as stationary phase and 100% ethyl acetate as the eluent to afford 5-phenyl-isoxazole-3-carboxylic acid {2-oxo-2-[4-(2-trifluoromethyl-benzoyl)-piperazin-1-yl]-ethyl}-amide as a solid in 20.3% yield. LC-MS purity: 98.075%, $^1$H NMR (DMSO-D$_6$): δ 8.6 (s, 1H), 7.9 (m, 2H), 7.7 (m, 2H), 7.65 (m, 1H), 7.5 (m, 3H), 7.4 (s, 1H), 4.1 (m, 2H), 3.6 (m, 4H), 3.4 (m, 2H), 3.1 (m, 2H).

206) Synthesis of 5-Phenyl-isoxazole-3-carboxylic acid {2-[4-(5-fluoro-2-trifluoromethyl-benzoyl)-piperazin-1-yl]-2-oxo-ethyl}-amide

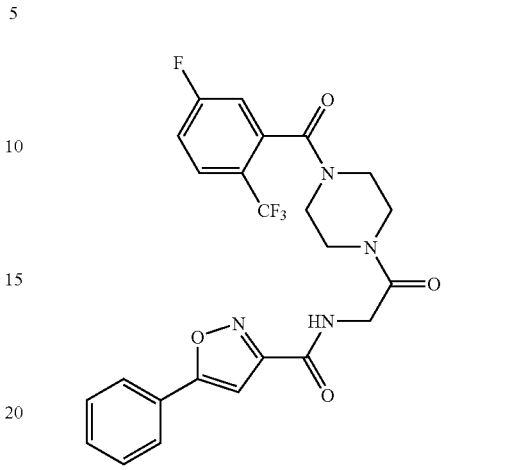

Steps 1-3: 5-Phenyl-isoxazole-3-carboxylic acid was prepared as described above (Scheme 19)

Step 4b

HOBt (38 mg, 0.28 mmol) and DIPEA (145 mg, 1.12 mmol) were added to a stirred solution of 5-phenyl-isoxazole-3-carboxylic acid (43 mg, 0.22 mmol) in DMF (1.0 mL). Then reaction mass was cooled to 10° C. and EDCI.HCl (54 mg, 0.28 mmol) and 2-amino-1-[4-(5-fluoro-2-trifluoromethyl-benzoyl)-piperazin-1-yl]-ethanone (as TFA salt) (100 mg, 0.22 mmol) were added. Then resulting mixture was stirred at the room temperature overnight. The mixture was then diluted with water and the product extracted with ethyl acetate. The organic layer was washed with brine solution, dried over Na$_2$SO$_4$, evaporated and purified by column chromatography using silica gel (60-120 mesh) and 50% ethyl acetate in hexane as the eluant to afford 5-phenyl-isoxazole-3-carboxylic acid {2-[4-(5-fluoro-2-trifluoromethyl-benzoyl)-piperazin-1-yl]-2-oxo-ethyl}-amide as a solid in 49.1% yield. LC-MS purity: 95.66%, $^1$H NMR (DMSO-D6): δ 8.7 (t, 1H), 7.94 (m, 3H), 7.56 (m, 5H), 7.4 (s, 1H), 4.15 (m, 2H), 3.75 (m, 1H), 3.6 (m, 3H), 3.45 (m, 2H), 3.2 (m, 2H), 3.1 (m, 1H).

207) Synthesis of 5-(3-Hydroxy-phenyl)-1H-pyrazole-3-carboxylic acid {2-oxo-2-[4-(2-trifluoromethyl-benzoyl)-piperazin-1-yl]-ethyl}-amide

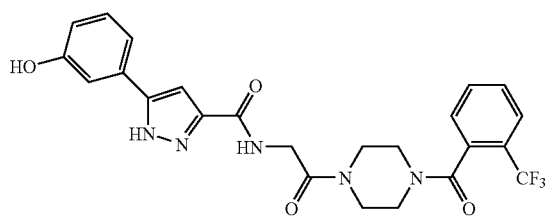

10% Pd/c (30 mg) was added to a stirred solution of 5-(3-benzyloxy-phenyl)-1H-pyrazole-3-carboxylic acid {2-oxo- 2-[4-(2-trifluoromethyl-benzoyl)-piperazin-1-yl]-ethyl}-amide (120.3 mg, 0.2 mmol) in a mixture of MeOH (15 mL) and DCM (10 mL) and stirred under hydrogen atmosphere. The reaction mixture was then stirred overnight at room temperature. The mixture was filtered over a bed of celite. The celite was washed with MeOH and the filtrate was concentrated under reduced pressure. The crude was recrystallized from a mixture of ethyl acetate and methanol to afford 23.9 mg (23.7% yield) of 5-(3-Hydroxy-phenyl)-1H-pyrazole-3-carboxylic acid {2-oxo-2-[4-(2-trifluoromethyl-benzoyl)-piperazin-1-yl]-ethyl}-amide. LCMS Purity: 98.15%. $^1$H NMR (DMSO-$d_6$): δ 13.6 (s, 1H), 9.6 (s, 1H), 8.6 (d, 1H), 8.1 (s, 1H), 7.6 (m, 3H), 7.5 (m, 1H), 7.1 (m, 3H), 7.0 (s, 1H), 6.7 (d, 1H), 4.1 (d, 2H), 3.6 (m, 2H), 3.5 (m, 2H), 3.4 (m, 2H), 3.1 (m, 2H).

208) Synthesis of 5-(2-Hydroxy-phenyl)-1H-pyrazole-3-carboxylic acid {2-[4-(5-fluoro-2-trifluoromethyl-benzoyl)-piperazin-1-yl]-2-oxo-ethyl}-amide

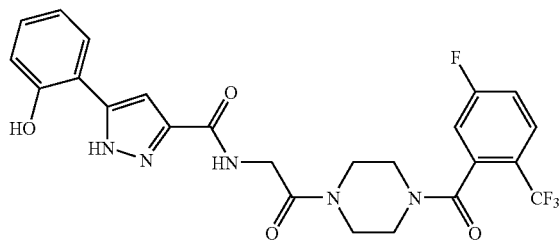

10% Pd/c (25 mg) was added to a stirred solution of 5-(2-benzyloxy-phenyl)-1H-pyrazole-3-carboxylic acid {2-[4-(5-fluoro-2-trifluoromethyl-benzoyl)-piperazin-1-yl]-2-oxo-ethyl}-amide (94 mg, 0.15 mmol) in a mixture of MeOH (60 mL) and THF (10 mL) and stirred under hydrogen atmosphere. The reaction mixture was then stirred for 1 hrs at room temperature. The mixture was filtered over a bed of celite. The celite was washed with MeOH and the filtrate was concentrated under reduced pressure. The crude was washed with ethyl acetate, filtered and dried to afford 36 mg (45% yield) of 5-(2-hydroxy-phenyl)-1H-pyrazole-3-carboxylic acid {2-[4-(5-fluoro-2-trifluoromethyl-benzoyl)-piperazin-1-yl]-2-oxo-ethyl}-amide. LCMS Purity: 94.89%. $^1$H NMR (DMSO-$d_6$): δ 13.2 (s, 1H), 10.4 (s, 1H), 7.9 (m, 2H), 7.5 (m, 2H), 6.9 (m, 3H), 4.1 (d, 2H), 3.4 (m, 6H), 3.1 (m, 2H).

209) Synthesis of 5-(2-Amino-phenyl)-1H-pyrazole-3-carboxylic acid {2-oxo-2-[4-(2-trifluoromethyl-benzoyl)-piperazin-1-yl]-ethyl}-amide

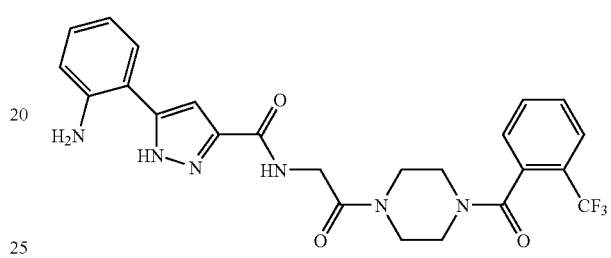

10% Pd/c (30 mg) was added to a stirred solution of 5-(2-Nitro-phenyl)-1H-pyrazole-3-carboxylic acid {2-oxo-2-[4-(2-trifluoromethyl-benzoyl)-piperazin-1-yl]-ethyl}-amide (160 mg, 0.3 mmol) in mixture of MeOH (60 mL) and THF (10 mL) and stirred under hydrogen atmosphere. The reaction mixture was then stirred for 1.5 hrs at room temperature. The mixture was filtered over a bed of celite. The celite was washed with MeOH and the filtrate was concentrated under reduced pressure. The crude was washed with ethyl acetate, filtered and dried to afford 40.3 mg (27% yield) of 5-(2-Amino-phenyl)-1H-pyrazole-3-carboxylic acid {2-oxo-2-[4-(2-trifluoromethyl-benzoyl)-piperazin-1-yl]-ethyl}-amide. LCMS Purity: 97.73%. $^1$H NMR (DMSO-$d_6$): δ 13.6 (s, 1H), 8.6 (m, 1H), 7.6 (m, 4H), 7.5 (m, 1H), 7.4 (d, 1H), 7.3 (s, 1H), 7.0 (s, 1H), 6.5 (m, 4H), 6.2 (m, 2H), 5.1 (m, 1H), 4.2 (m, 3H), 3.6 (m, 4H), 3.4 (m, 2H), 3.2 (m, 2H).

SCHEME-21

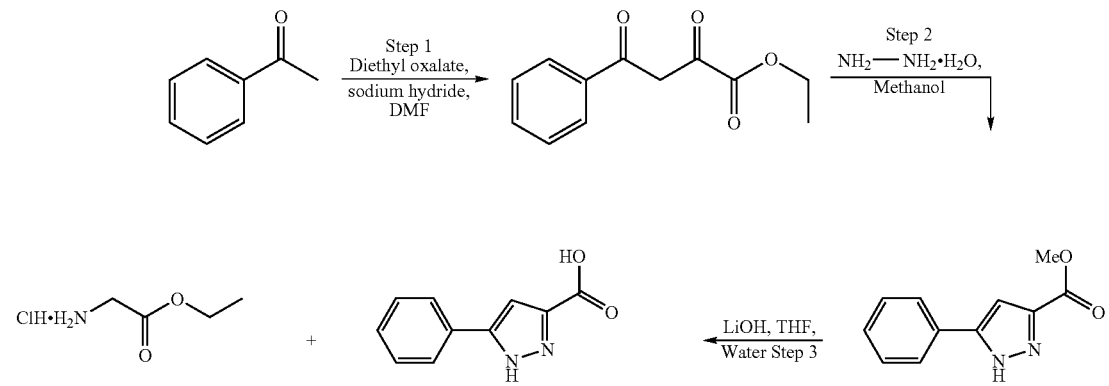

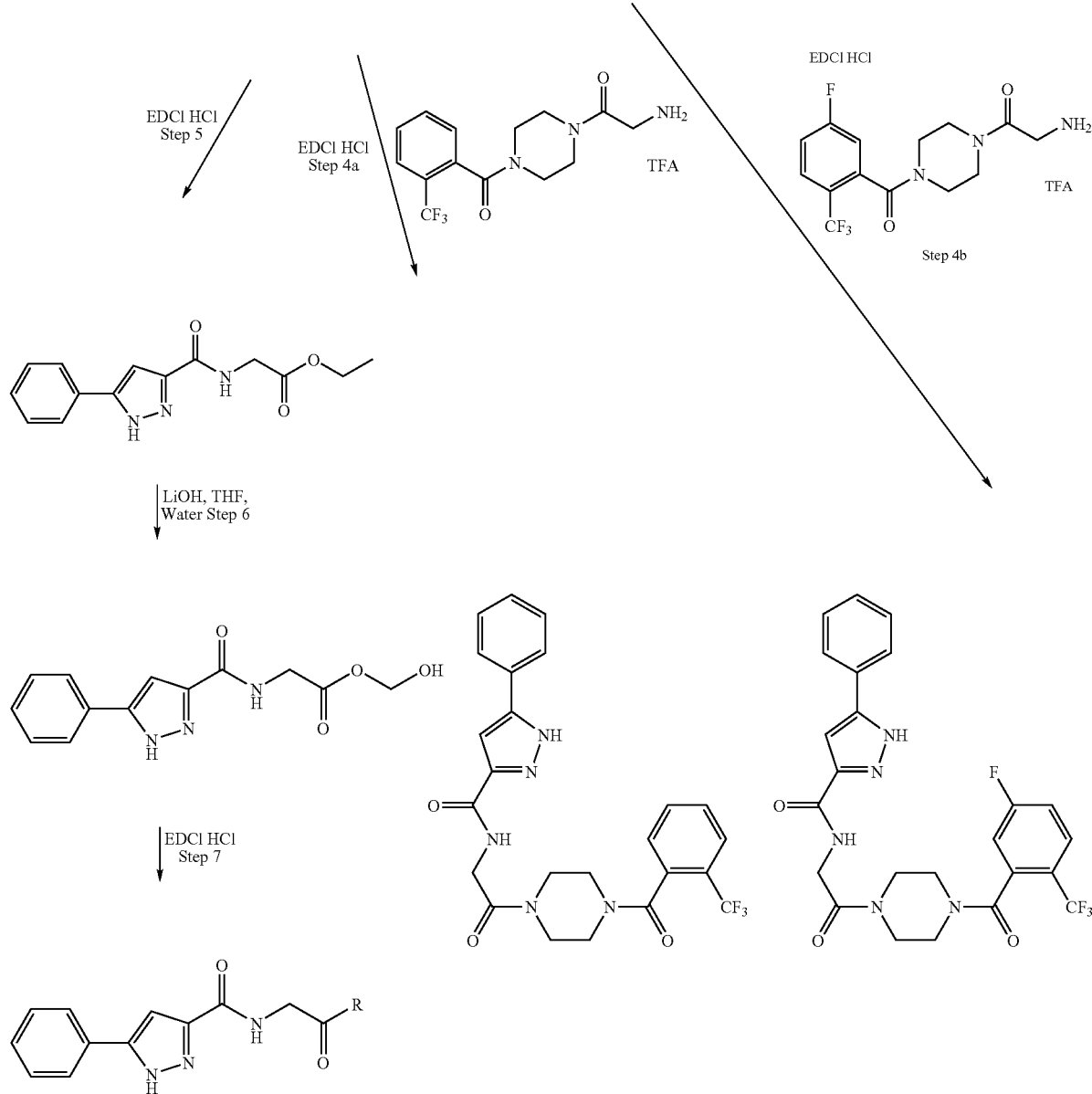

210) Synthesis of 5-(2-Hydroxy-phenyl)-1H-pyrazole-3-carboxylic acid {2-oxo-2-[4-(2-trifluoromethyl-benzoyl)-piperazin-1-yl]-ethyl}-amide

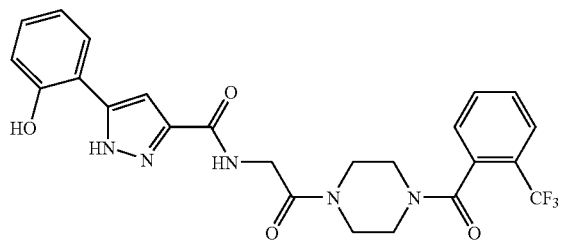

10% Pd/c (20 mg) was added to a stirred solution of 5-(2-Benzyloxy-phenyl)-1H-pyrazole-3-carboxylic acid {2-oxo-2-[4-(2-trifluoromethyl-benzoyl)-piperazin-1-yl]-ethyl}-amide (103 mg, 0.17 mmol))(prepared by the method as described above) in MeOH (50 mL) and stirred under hydrogen atmosphere. The reaction mixture was then stirred for 6 hrs. The mixture was filtered over a bed of celite. The celite was washed with MeOH and the filtrate was concentrated under reduced pressure to afford 35.8 mg (41.3% yield) of 5-(2-Hydroxy-phenyl)-1H-pyrazole-3-carboxylic acid {2-oxo-2-[4-(2-trifluoromethyl-benzoyl)-piperazin-1-yl]-ethyl}-amide. LCMS Purity: 93.92%. $^1$H NMR (DMSO): δ 13.1 (s, 1H), 10.3 (s, 1H), 8.2 (s, 1H), 7.74 (m, 2H), 7.62 (m, 2H), 7.52 (m, 1H), 7.16 (m, 1H), 7.04 (s, 1H), 6.96 (m, 1H), 6.86 (m, 1H), 4.1 (m, 2H), 3.55 (m, 4H), 3.4 (m, 2H), 3.2 (m, 2H).

211) Synthesis of 5-Benzo[1,3]dioxol-5-yl-1H-pyrazole-3-carboxylic acid {2-oxo-2-[4-(2-trifluoromethyl-benzoyl)-piperazin-1-yl]-ethyl}-amide

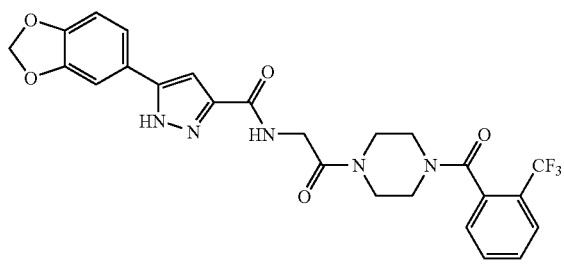

DIPEA (77 mg, 0.1 mL, 0.59 mmol) was added to a stirred solution of 5-benzo[1,3]dioxol-5-yl-1H-pyrazole-3-carboxylic acid (60 mg, 0.17 mmol))(prepared by the method as described above) in DMF (2 mL). HOBT (24 mg, 0.17 mmol) and EDCI (34.3 mg, 0.17 mmol) were then added at room temperature. After 2 minutes, 2-amino-1-[4-(2-trifluoromethyl-benzoyl)-piperazin-1-yl]-ethanone hydrochloride salt (60 mg, 0.17 mmol) was added and the resulting mixture was stirred at room temperature overnight. Cold water was then added and the product was extracted with EtOAc and the organic layer was washed with brine. The organic phase was dried over $Na_2SO_4$ and concentrated under reduced pressure to afford 86 mg (95% yield) of 5-benzo[1,3]dioxol-5-yl-1H-pyrazole-3-carboxylic acid {2-oxo-2-[4-(2-trifluoromethyl-benzoyl)-piperazin-1-yl]-ethyl}-amide. LCMS Purity: 95.365%. $^1$H NMR (DMSO-$d_6$): δ 13.6 (s, 1H), 8.0 (s, 1H), 7.7 (m, 2H), 7.6 (m, 1H), 7.5 (m, 1H), 7.3 (m, 2H), 7.0 (m, 2H), 6.0 (s, 2H), 4.1 (m, 2H), 3.7 (m, 2H), 3.54 (m, 2H), 3.4 (m, 2H), 3.1 (m, 2H).

212) Synthesis of 5-(2-Hydroxy-phenyl)-1H-pyrazole-3-carboxylic acid {2-[4-(2-bromo-5-fluoro-benzoyl)-piperazin-1-yl]-2-oxo-ethyl}-amide

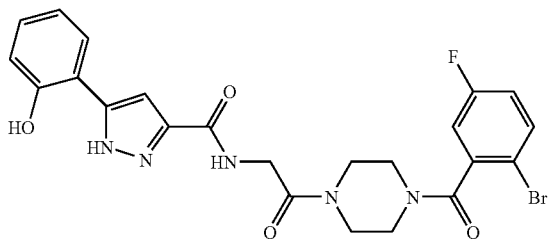

DIPEA (100 mg, 0.13 mL, 0.7 mmol) was added to a stirred solution of (2-Bromo-5-fluoro-phenyl)-piperazin-1-yl-methanone; hydrochloride salt (prepared by the method as described above)(68 mg, 0.21 mmol) in DMF (4 mL). HOBT (31 mg, 0.23 mmol) and EDCI (91 mg, 0.47 mmol) were then added at room temperature. After 2 minutes, {[5-(2-Hydroxy-phenyl)-1H-pyrazole-3-carbonyl]-amino}-acetic acid (50 mg, 0.19 mmol) was added and the resulting mixture was stirred at room temperature for 4 hrs. Cold water was then added and the product was extracted with EtOAc and the organic layer was washed with brine. The organic phase was dried over $Na_2SO_4$ and concentrated under reduced pressure to afford 68.5 mg (68.5% yield) 5-(2-Hydroxy-phenyl)-1H-pyrazole-3-carboxylic acid {2-[4-(2-bromo-5-fluoro-benzoyl)-piperazin-1-yl]-2-oxo-ethyl}-amide. LCMS Purity: 95.24%. $^1$H NMR (DMSO-$d_6$): δ 13.4-13.2 (bs, 1H), 10.4-10.2 (bs, 1H), 8.2-8.0 (bs, 1H), 7.8-7.64 (m, 2H), 7.46-7.34 (bs, 1H), 7.34-7.2 (t, 2H), 7.02-6.84 (m, 4H), 4.26-4.1 (bd, 2H), 3.76-3.46 (bt, 6H), 3.24-3.1 (bd, 2H).

213) Synthesis of 5-(2-Hydroxy-phenyl)-1H-pyrazole-3-carboxylic acid {2-[4-(2,5-dichloro-benzoyl)-piperazin-1-yl]-2-oxo-ethyl}-amide

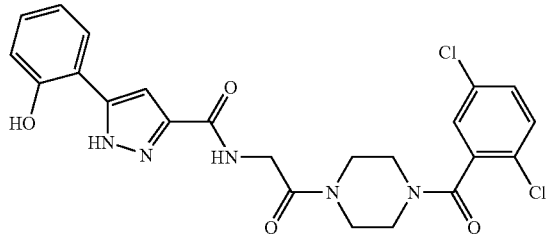

DIPEA (170.4 mg, 0.23 mL, 1.3 mmol) was added drop wise to 5-(2-Hydroxy-phenyl)-1H-pyrazole-3-carboxylic acid (prepared by the method as described above) (60 mg, 0.29 mmol) in DMF (2 mL). EDCI (140.4 mg, 0.73 mmol) and HOBT (43.6 mg, 0.32 mmol) were then added. After 2 minutes, 2-Amino-1-[4-(2,5-dichloro-benzoyl)-piperazin-1-yl]-ethanone in its HCl salt form (113.9 mg, 0.32 mmol) was added. The resulting mixture was stirred at room temperature overnight. Cold water was then added and the product was extracted with EtOAc and the organic layer was washed with brine. The organic phase was dried over $Na_2SO_4$ and concentrated under reduced pressure to get the residue purified by column chromatography (using silica gel of 60-120 mesh and 10% MeOH in $CHCl_3$ as eluent) to afford 28 mg (20% yield) of 5-(2-hydroxy-phenyl)-1H-pyrazole-3-carboxylic acid {2-[4-(2,5-dichloro-benzoyl)-piperazin-1-yl]-2-oxo-ethyl}-amide. LCMS Purity: 97.07%. $^1$H NMR (DMSO-$d_6$): δ 13.3 (s, 1H), 10.3 (s, 1H), 8.0 (t, 1H), 7.8-7.4 (m, 4H), 7.28-7.1 (t, 1H), 7.1-7.05 (s, 1H), 7.02-6.8 (m, 2H), 4.3-4.1 (d, 2H), 3.8-3.6 (m, 4H), 3.55-3.42 (s, 2H), 3.3-3.1 (m, 3H).

214) Synthesis of 5-(2-Methoxy-phenyl)-1H-pyrazole-3-carboxylic acid {2-[4-(5-fluoro-2-trifluoromethyl-benzoyl)-piperazin-1-yl]-2-oxo-ethyl}-amide

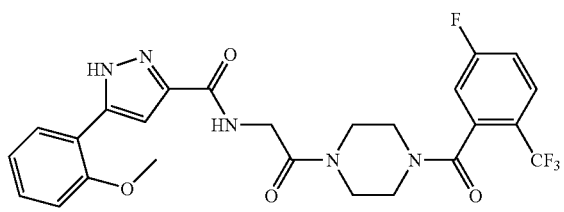

DIPEA (166 mg, 0.22 mL, 1.28 mmol) was added to a stirred solution of 5-(2-methoxy-phenyl)-1H-pyrazole-3-carboxylic acid (70 mg, 0.32 mmol) in DMF (2 mL). HOBT (55 mg, 0.4 mmol) and EDCI (77 mg, 0.4 mmol) were then added at room temperature. After 2 minutes, 2-amino-1-[4-(2-trifluoromethyl-5-fluoro-benzoyl)-piperazin-1-yl]-ethanone hydrochloride salt (119 mg, 0.32 mmol) was added and the resulting mixture was stirred at room temperature overnight. Cold water was then added and filtered the solid precipitated out to afford 70 mg (40.9% yield) of 5-(2-methoxy-phenyl)-1H-pyrazole-3-carboxylic acid {2-[4-(5-fluoro-2-trifluoromethyl-benzoyl)-piperazin-1-yl]-2-oxo-ethyl}-amide. LCMS Purity: 94.72%. $^1$H NMR (DMSO-$d_6$): δ 13.45 (s, 1H), 8.0 (m, 1H), 7.88 (m, 1H), 7.7 (d, 1H), 7.46 (m, 2H), 7.4 (m, 1H), 7.1 (d, 1H), 7.0 (m, 2H), 4.32 (d, 2H), 3.86 (s, 3H), 3.64 (m, 1H), 3.5 (m, 3H), 3.4 (m, 1H), 3.1 (m, 3H).

215) Synthesis of 5-(2-Trifluoromethyl-phenyl)-1H-pyrazole-3-carboxylic acid {2-[4-(5-fluoro-2-trifluoromethyl-benzoyl)-piperazin-1-yl]-2-oxo-ethyl}-amide

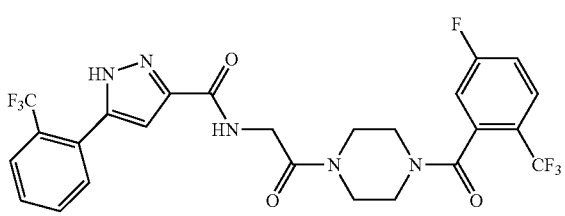

DIPEA (124 mg, 0.16 mL, 0.95 mmol) was added to a stirred solution of 5-(2-trifluoromethyl-phenyl)-1H-pyrazole-3-carboxylic acid (70 mg, 0.27 mmol) in DMF (2 mL). HOBT (43 mg, 0.31 mmol) and EDCI (60 mg, 0.31 mmol) were then added at room temperature. After 2 minutes, 2-amino-1-[4-(5-fluoro-2-trifluoromethyl-benzoyl)-piperazin-1-yl]-ethanone hydrochloride salt (101 mg, 0.27 mmol) was added and the resulting mixture was stirred at room temperature overnight. Cold water was then added, filtered the solid precipitate. The solid was purified by dissolving in DCM and washed with 1.2N HCl. The organic phase was dried over Na$_2$SO$_4$ and concentrated under reduced pressure to afford 57 mg (36.77% yield) of 5-(2-trifluoromethyl-phenyl)-1H-pyrazole-3-carboxylic acid {2-[4-(5-fluoro-2-trifluoromethyl-benzoyl)-piperazin-1-yl]-2-oxo-ethyl}-amide. LCMS Purity: 93.30%. $^1$H NMR (DMSO-$d_6$): δ 13.6 (s, 1H), 8.1 (m, 1H), 7.9 (m, 2H), 7.5 (m, 21H), 7.5 (m, 6H), 6.79 (s, 1H), 4.1 (d, 2H), 3.5 (m, 7H), 3.0 (m, 3H).

216) Synthesis of 5-(2-Trifluoromethyl-phenyl)-1H-pyrazole-3-carboxylic acid {2-oxo-2-[4-(2-trifluoromethyl-benzoyl)-piperazin-1-yl]-ethyl}-amide

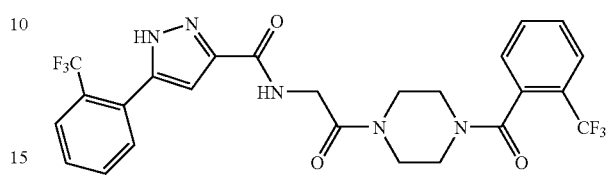

DIPEA (137 mg, 0.18 mL, 1.06 mmol) was added to a stirred solution of {[5-(2-trifluoromethyl-phenyl)-1H-pyrazole-3-carbonyl]-amino}-acetic acid (95 mg, 0.30 mmol) in DMF (2 mL). HOBT (47 mg, 0.34 mmol) and EDCI (67 mg, 0.34 mmol) were then added at room temperature. After 2 minutes, piperazin-1-yl-(2-trifluoromethyl-phenyl)-methanone hydrochloride salt (90 mg, 0.30 mmol) was added and the resulting mixture was stirred at room temperature overnight. Cold water was then added and filtered the solid precipitated out to afford 115 mg (68.45% yield) of 5-(2-trifluoromethyl-phenyl)-1H-pyrazole-3-carboxylic acid {2-oxo-2-[4-(2-trifluoromethyl-benzoyl)-piperazin-1-yl]-ethyl}-amide. LCMS Purity: 93.52%. $^1$H NMR (DMSO-$d_6$): δ 13.6 (m, 1H), 8.2 (m, 1H), 7.7 (m, 4H), 7.6 (m, 3H), 7.5 (m, 1H), 6.7 (m, 1H), 4.2 (d, 2H), 3.7 (m, 1H), 3.5 (m, 3H), 3.4 (m, 2H), 3.0 (m, 2H).

217) Synthesis of 5-(2-Methoxy-phenyl)-1H-pyrazole-3-carboxylic acid {2-oxo-2-[4-(2-trifluoromethyl-benzoyl)-piperazin-1-yl]-ethyl}-amide

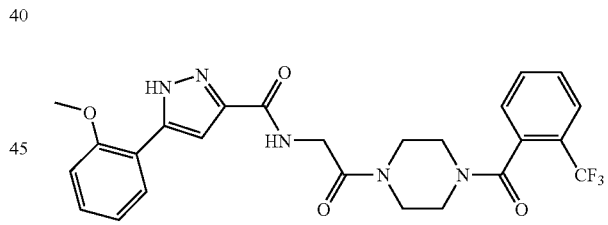

DIPEA (99 mg, 0.13 mL, 0.76 mmol) was added to a stirred solution of {[5-(2-methoxy-phenyl)-1H-pyrazole-3-carbonyl]-amino}-acetic acid (60 mg, 0.21 mmol) in DMF (2 mL). HOBT (34 mg, 0.25 mmol) and EDCI (49 mg, 0.25 mmol) were then added at room temperature. After 2 minutes, piperazin-1-yl-(2-trifluoromethyl-phenyl)-methanone hydrochloride salt (64.3 mg, 0.21 mmol) was added and the resulting mixture was stirred at room temperature overnight. Cold water was then added and filtered the solid precipitated to afford 40 mg (35.7% yield) of 5-(2-methoxy-phenyl)-1H-pyrazole-3-carboxylic acid {2-oxo-2-[4-(2-trifluoromethyl-benzoyl)-piperazin-1-yl]-ethyl}-amide. LCMS Purity: 97.45%. $^1$H NMR (DMSO-$d_6$): δ 13.5 (s, 1H), 8.0 (m, 1H), 7.62 (m, 4H), 7.5 (m, 1H), 7.3 (m, 1H), 7.16 (m, 1H), 7.01 (m, 2H), 4.1 (d, 2H), 3.84 (s, 3H), 3.6 (m, 2H), 3.56 (m, 2H), 3.36 (m, 2H), 3.1 (m, 2H).

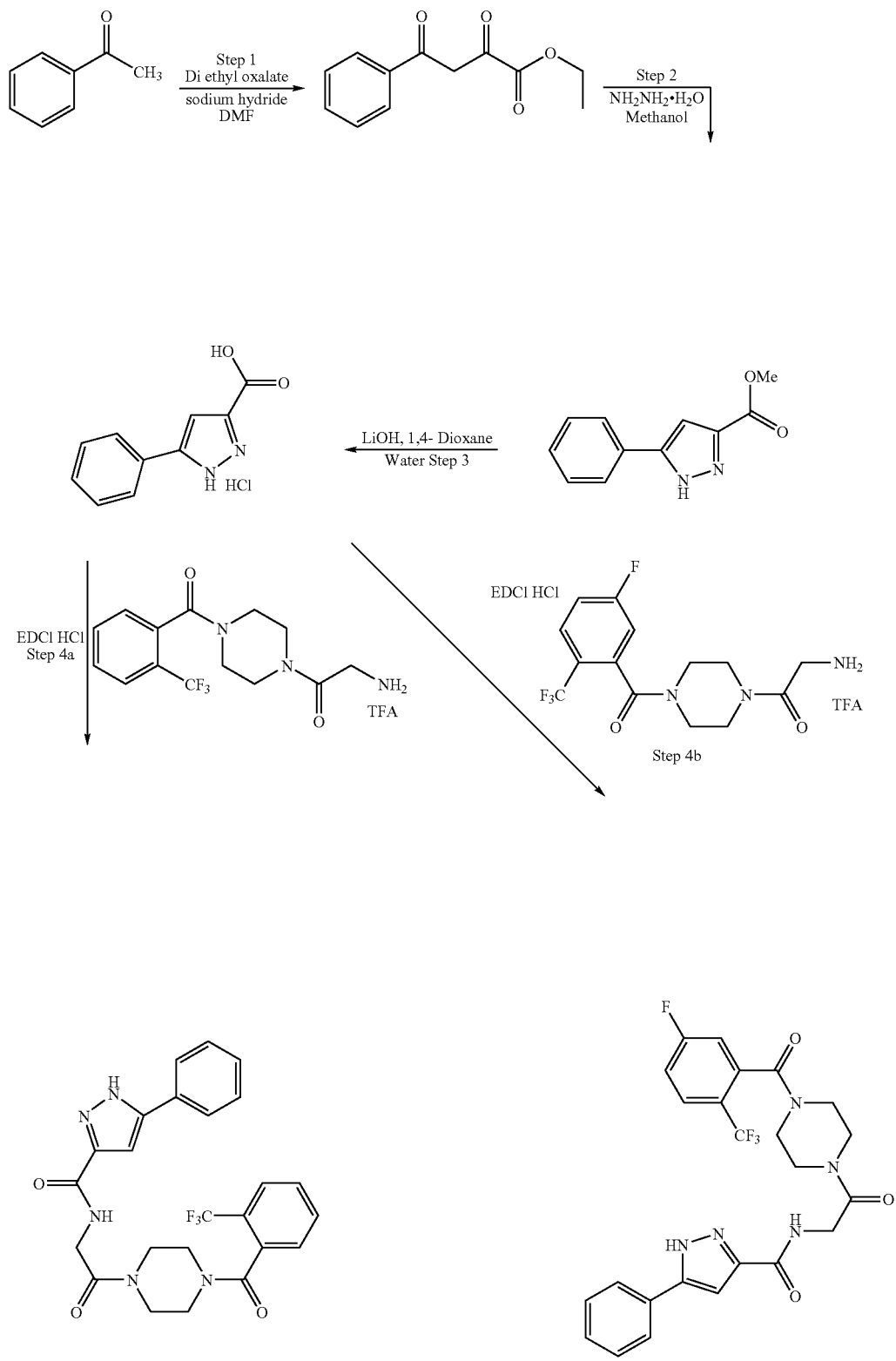

Step 1: Synthesis of 2,4-Dioxo-4-phenyl-butyric acid ethyl ester

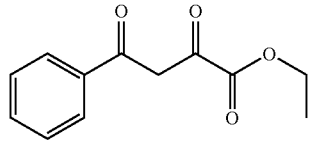

2,4-Dioxo-4-phenyl-butyric acid ethyl ester was prepared as described above (Scheme 20).

Step 2: Synthesis of 5-Phenyl-1H-pyrazole-3-carboxylic Acid Methyl Ester

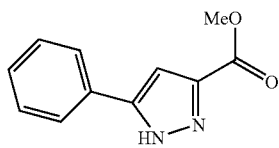

NH$_2$—NH$_2$—H$_2$O (1.0 g, 20 mmol) was added to a solution of 2,4-dioxo-4-phenyl-butyric acid ethyl ester (1.94 g, 8.81 mmol) in methanol (17 mL). The resulting reaction mixture was heated to reflux for two and half hours. The methanol was evaporated and the resulting solid was heated with 2.5% ethyl acetate in hexane to afford 5-phenyl-1H-pyrazole-3-carboxylic acid methyl ester as a solid in 77.3% yield. LC-MS purity: 93.345%.

Step 3: Synthesis of 5-Phenyl-1H-pyrazole-3-carboxylic Acid Hydrochloride

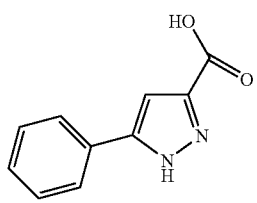

LiOH.H$_2$O (232 mg, 5.54 mmol) was added to a solution of 5-phenyl-1H-pyrazole-3-carboxylic acid methyl ester (375 mg, 1.85 mmol) in a mixture of 1,4-dioxane (5 mL) and H$_2$O (5 mL). The resulting mixture was stirred overnight at ambient temperature. The mixture was then diluted with water, washed with ethyl acetate, acidified with con. HCl and extracted with ethyl acetate. The organic layer was washed with brine solution, dried over Na$_2$SO$_4$ and concentrated under reduced pressure to afford 5-phenyl-1H-pyrazole-3-carboxylic acid hydrochloride in 30% yield. LC-MS purity: 95.85%.

Step 4a

218) Synthesis of 5-Phenyl-1H-pyrazole-3-carboxylic acid {2-oxo-2-[4-(2-trifluoromethyl-benzoyl)-piperazin-1-yl]-ethyl}-amide

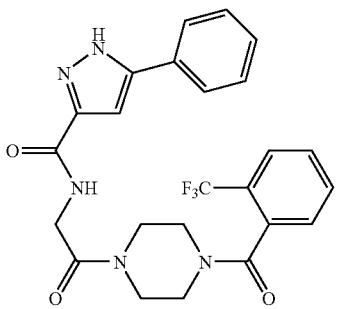

HOBt (45 mg, 0.33 mmol) and DIPEA (137.5 mg, 1.06 mmol) were added to a stirred solution of 5-phenyl-1H-pyrazole-3-carboxylic acid hydrochloride (50 mg, 0.22 mmol) in DMF (1.0 mL). The reaction mass was cooled to 10° C. and EDCI.HCl (64 mg, 0.33 mmol) was added, followed by the addition of 2-amino-1-[4-(2-trifluoromethyl-benzoyl)-piperazin-1-yl]-ethanone (as TFA salt) (125 mg, 0.29 mmol). The resulting mixture was stirred at room temperature overnight. The mixture was then diluted with water and the resulting precipitate was filtered and dried in vacuo to afford 5-phenyl-1H-pyrazole-3-carboxylic acid {2-oxo-2-[4-(2-trifluoromethyl-benzoyl)-piperazin-1-yl]-ethyl}-amide as a solid product in 62% yield, LC-MS purity: 99.127%, $^1$H NMR (DMSO): δ 13.6 (s, 1H), 8.1 (s, 1H), 7.7 (m, 5H), 7.4 (m, 4H), 7.1 (s, 1H), 4.1 (m, 2H), 3.6 (m, 4H), 3.4 (m, 2H), 3.2 (m, 2H).

219) Synthesis of 5-Phenyl-1H-pyrazole-3-carboxylic acid {2-[4-(5-fluoro-2-trifluoromethyl-benzoyl)-piperazin-1-yl]-2-oxo-ethyl}-amide

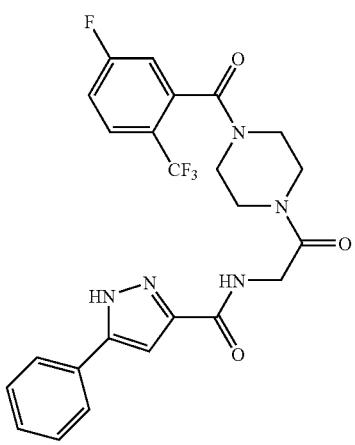

Steps 1-3: 5-Phenyl-1H-pyrazole-3-carboxylic acid hydrochloride was prepared as described above (Scheme 22)

Step 4b

HOBt (38 mg, 0.28 mmol) and DIPEA (145 mg, 1.12 mmol) were added to a stirred solution of 5-phenyl-1H-pyrazole-3-carboxylic acid hydrochloride (51 mg, 0.22 mmol) in DMF (1.0 mL). The reaction mass was cooled to 10° C., and EDCI.HCl (54 mg, 0.28 mmol) was added, followed by the addition of 2-amino-1-[4-(5-fluoro-2-trifluoromethyl-benzoyl)-piperazin-1-yl]-ethanone (100 mg, 0.22 mmol). The resulting mixture was stirred at room temperature overnight. The mixture was then diluted with water and the resulting precipitate was filtered and dried under reduced pressure to afford 5-phenyl-1H-pyrazole-3-carboxylic acid {2-[4-(5-fluoro-2-trifluoromethyl-benzoyl)-piperazin-1-yl]-2-oxo-ethyl}-amide as a solid in 26.8% yield, LC-MS purity: 96.054%, $^1$H NMR (DMSO): δ 8.1 (s, 1H), 7.95 (s, 1H), 7.8 (d, 2H), 7.56 (m, 2H), 7.5 (t, 2H), 7.4 (m, 1H), 7.1 (s, 1H) 4.2 (m, 2H), 3.75 (m, 1H), 3.6 (m, 4H), 3.5 (m, 2H), 3.2 (m, 2H), 3.1 (s, 1H).

Bromo-5-methoxy-benzoyl)-piperazin-1-yl]-2-oxo-ethyl}-carbamic acid tert-butyl ester in 97% yield. LC-MS purity: 97.79%

Step 2: Synthesis of 2-amino-1-[4-(2-bromo-5-methoxy-benzoyl)-piperazin-1-yl]-ethanone hydrochloride Saturated HCl in 1,4-dioxane (1.0 ml) was added to a stirred solution of {2-[4-(2-bromo-5-methoxy-benzoyl)-piperazin-1-yl]-2-oxo-ethyl}-carbamic acid tert-butyl ester (375 mg, 0.82 mmol) in 1,4-dioxane (1.0 mL) at room temperature and the resulting mixture was stirred for 15 minutes. The mixture was then concentrated and the product obtained was

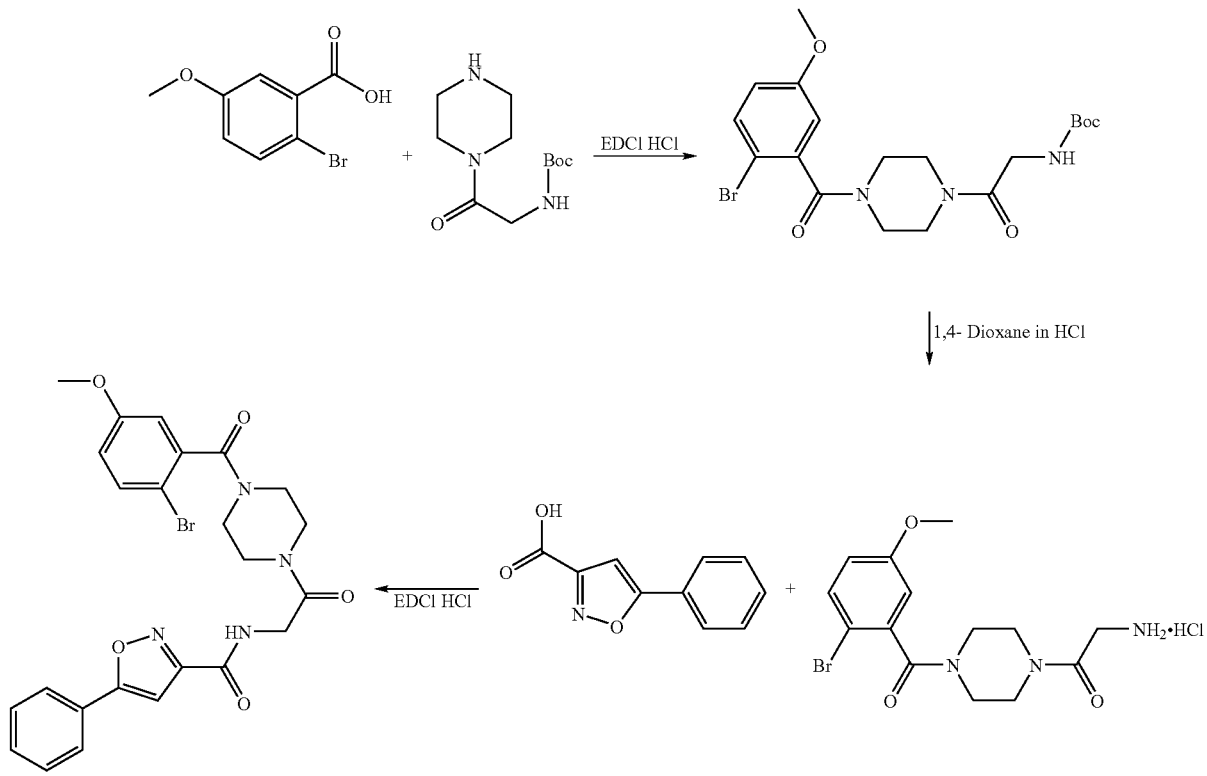

SCHEME-23

Step 1: Synthesis of {2-[4-(2-bromo-5-methoxy-benzoyl)-piperazin-1-yl]-2-oxo-ethyl}-carbamic acid tert-butyl ester HOBt (125 mg, 0.93 mmol) and DIPEA (287 mg, 2.2 mmol) were added to a stirred solution of 2-bromo-5-methoxy-benzoic acid (171 mg, 0.74 mmol) in DMF (2.5 mL). The mixture was then cooled to 10° C. and EDCI.HCl (178 mg, 0.93 mmol) followed by (2-oxo-2-piperazin-1-yl-ethyl)-carbamic acid tert-butyl ester (200 mg, 0.82 mmol) were added. The reaction mixture was then stirred at room temperature overnight. Water was added, and the product was extracted with ethyl acetate. The organic layer was washed with brine solution, dried over Na$_2$SO$_4$ and concentrated. Purification using column chromatography (silica gel (60-120 mesh) and 50% ethyl acetate in hexane as the eluent) afforded {2-[4-(2- washed with diethyl ether to afford 2-amino-1-[4-(2-bromo-5-methoxy-benzoyl)-piperazin-1-yl]-ethanone hydrochloride in 87.8% yield. LC-MS purity: 83.28%

Step 2A

5-Phenyl-isoxazole-3-carboxylic acid was prepared as described above (Scheme 20)

Step 3

220) Synthesis of 5-phenyl-isoxazole-3-carboxylic acid {2-[4-(2-bromo-5-methoxy-benzoyl)-piperazin-1-yl]-2-oxo-ethyl}-amide HOBt (21.5 mg, 0.16 mmol) and DIPEA (66 mg, 0.51 mmol) were added to a stirred solution of 5-phenyl-isoxazole-3-carboxylic acid (24 mg, 0.13 mmol) in DMF (1.0 mL). The mixture was then cooled to 10° C. and EDCl.HCl (30.5 mg, 0.16 mmol) followed by 2-amino-1-[4-(2-bromo-5-methoxy-benzoyl)-piperazin-1-yl]-ethanone hydrochloride (50 mg, 0.13 mmol) were added. The reaction mixture was then stirred at room temperature overnight. Water was added, and the resulting precipitate was isolated by filtration under reduced pressure and dried to afford 5-phenyl-isoxazole-3-carboxylic acid {2-[4-(2-bromo-5-methoxy-benzoyl)-piperazin-1-yl]-2-oxo-ethyl}-amide as a solid in 53.8% yield. LC-MS purity: 92.97%, $^1$H-NMR (DMSO): δ 8.7 (t, 1H), 8.0 (m, 2H), 7.58 (m, 4H), 7.41 (s, 1H), 7.0 (m, 2H), 4.2 (m, 2H), 3.78 (s, 3H), 3.5 (m, 6H), 3.2 (m, 2H).

was then cooled to 10° C. and EDCl.HCl (178 mg, 0.93 mmol) followed by (2-oxo-2-piperazin-1-yl-ethyl)-carbamic acid tert-butyl ester (200 mg, 0.82 mmol) were added. The reaction mixture was then stirred at room temperature overnight. Water was added, and the product was extracted with ethyl acetate. The organic layer was washed with brine solution, dried over $Na_2SO_4$ and concentrated. Purification using column chromatography (silica gel (60-120 mesh) using 30% ethyl acetate in hexane as the eluent) afforded {2-[4-(2,5-dichloro-benzoyl)-piperazin-1-yl]-2-oxo-ethyl}-carbamic acid tert-butyl ester as a solid in 91.2% yield. LC-MS purity: 99.48%.

SCHEME-24

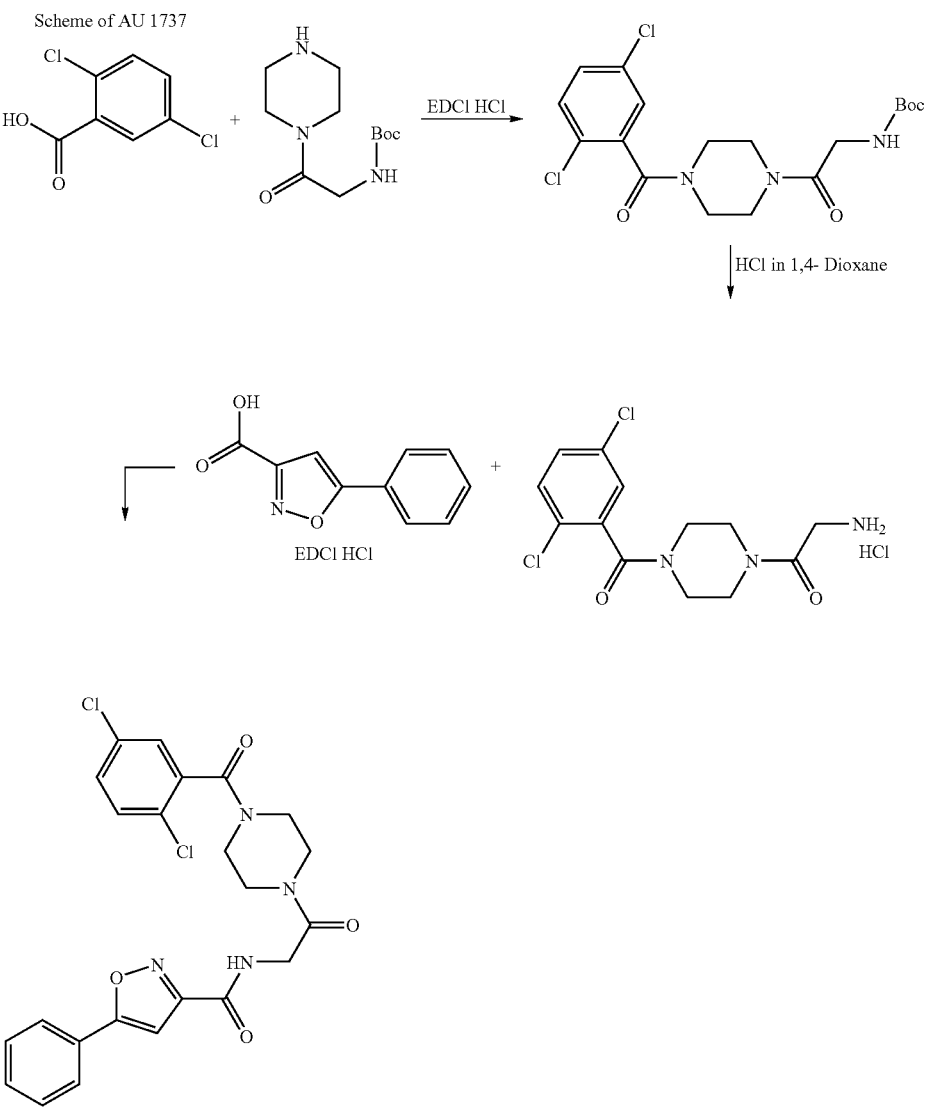

Step 1: Synthesis of {2-[4-(2,5-dichloro-benzoyl)-piperazin-1-yl]-2-oxo-ethyl}-carbamic acid tert-butyl ester HOBt (125 mg, 0.93 mmol) and DIPEA (207 mg, 2.2 mmol) were added to a stirred solution of 2,5-dichloro-benzoic acid (141 mg, 0.74 mmol) in DMF (2.5 mL). The mixture Step 2: Synthesis of 2-amino-1-[4-(2,5-dichloro-benzoyl)-piperazin-1-yl]-ethanone hydrochloride Saturated HCl in 1,4-dioxane (1.0 mL) was added to a stirred solution of {2-[4-(2,5-dichloro-benzoyl)-piperazin-1-yl]-2-oxo-ethyl}-carbamic acid tert-butyl ester (280 mg, 0.67 mmol) in 1,4-dioxane (1.0 mL) at ambient temperature. The mixture was stirred at room temperature for 15 minutes then concentrated. The resulting solid was washed with diethyl ether to afford 2-amino-1-[4-(2,5-dichloro-benzoyl)-piperazin-1-yl]-ethanone hydrochloride as a solid in 78.9% yield. LC-MS purity: 94.019%

Step 2A

5-Phenyl-isoxazole-3-carboxylic acid was prepared as described above (Scheme 20)

Step 3

221) Synthesis of 5-Phenyl-isoxazole-3-carboxylic acid {2-[4-(2,5-dichloro-benzoyl)-piperazin-1-yl]-2-oxo-ethyl}-amide HOBt (24 mg, 0.18 mmol) and DIPEA (74 mg, 0.57 mmol) were added to a stirred solution of 5-phenyl-isoxazole-3-carboxylic acid (27 mg, 0.14 mmol) in DMF (1.0 mL). The mixture was then cooled to 10° C. and EDCI.HCl (34 mg, 0.18 mmol) followed by 2-amino-1-[4-(2,5-dichloro-benzoyl)-piperazin-1-yl]-ethanone hydrochloride (50 mg, 0.15 mmol) were added. The reaction mixture was then stirred at room temperature overnight. Water was added, and the resulting precipitate was isolated by filtration under reduced pressure and dried in vacuo to afford 5-phenyl-isoxazole-3-carboxylic acid {2-[4-(2,5-dichloro-benzoyl)-piperazin-1-yl]-2-oxo-ethyl}-amide as a solid 53.39% yield. LC-MS purity: 92.758%. $^1$H-NMR (DMSO): δ 8.78 (t, 1H), 8.0 (m, 2H), 7.6 (m, 6H), 7.47 (s, 1H), 4.2 (m, 2H), 3.8 (m, 1H), 3.7 (m, 2H), 3.56 (m, 2H), 3.2 (m, 3H).

Step 1

5-Phenyl-1H-pyrazole-3-carboxylic acid hydrochloride was prepared as described above (Scheme 22).

Step 2

2-Amino-1-[4-(2-bromo-5-methoxy-benzoyl)-piperazin-1-yl]-ethanone hydrochloride was prepared as described above (Scheme 23).

Step 3

222) Synthesis of 5-phenyl-1H-pyrazole-3-carboxylic acid {2-[4-(2-bromo-5-methoxy-benzoyl)-piperazin-1-yl]-2-oxo-ethyl}-amide HOBt (22 mg, 0.16 mmol) and DIPEA (66 mg, 0.51 mmol) were added to a stirred solution of 5-phenyl-1H-pyrazole-3-carboxylic acid hydrochloride (29 mg, 0.13 mmol) in DMF (1.0 mL). The mixture was then cooled to 10° C. and EDCI.HCl (30.5 mg, 0.16 mmol) followed by 2-amino-1-[4-(2-bromo-5-methoxy-benzoyl)-piperazin-1-yl]-ethanone hydrochloride (50 mg, 0.13 mmol) were added. The reaction mixture was then stirred at room temperature overnight. Water was added, and the resulting precipitate was isolated by filtration. The crude product was washed with hexane and diethyl ether to afford 5-phenyl-1H-pyrazole-3-carboxylic acid {2-[4-(2-bromo-5-methoxy-benzoyl)-piperazin-1-yl]-2-oxo-ethyl}-amide as a solid in 59% yield. LC-MS purity: 89.83%, $^1$H-NMR (DMSO): δ 8.62 (s, 1H), 8.08 (t, 1H), 7.8 (d, 2H), 7.58 (m, 1H), 7.5 (m, 2H), 7.4 (m, 1H), 7.1 (s, 1H), 7.0 (m, 2H), 4.2 (m, 2H), 3.8 (s, 3H), 3.75 (m, 2H), 3.6 (m, 2H), 3.55 (m, 2H), 3.2 (m, 2H).

SCHEME-25

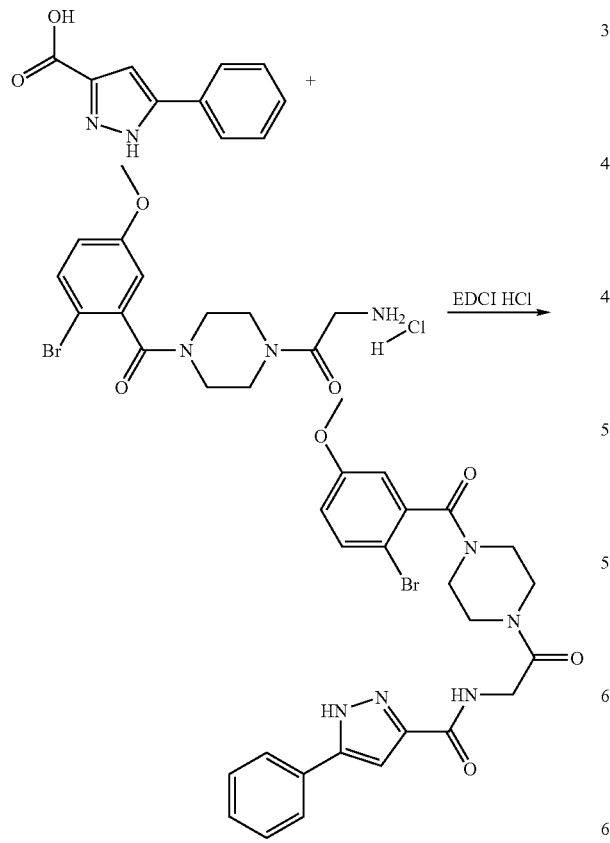

SCHEME-26

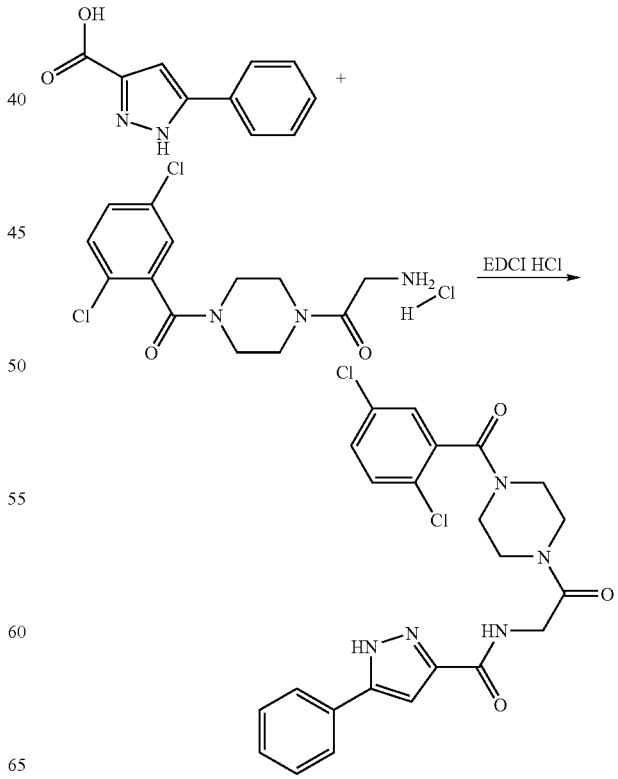

Step 1

5-Phenyl-1H-pyrazole-3-carboxylic acid hydrochloride was prepared as described above (Scheme 22).

Step 2

Synthesis of 2-Amino-1-[4-(2,5-dichloro-benzoyl)-piperazin-1-yl]-ethanone hydrochloride was prepared as described above (Scheme 24).

Step 3

223) Synthesis of 5-Phenyl-1H-pyrazole-3-carboxylic acid {2-[4-(2,5-dichloro-benzoyl)-piperazin-1-yl]-2-oxo-ethyl}-amide HOBt (24 mg, 0.18 mmol) and DIPEA (74 mg, 0.57 mmol) were added to a stirred solution of 5-phenyl-1H-pyrazole-3-carboxylic acid; hydrochloride (32 mg, 0.14 mmol) in DMF (1.0 mL). The mixture was then cooled to 10° C. and EDCI.HCl (34 mg, 0.18 mmol), followed by 2-amino-1-[4-(2,5-dichloro-benzoyl)-piperazin-1-yl]-ethanone hydrochloride (50 mg, 0.14 mmol) were added. The reaction mixture was then stirred at room temperature overnight. Water was added, and the resulting precipitate was isolated by filtration and dried under reduced pressure to afford 5-phenyl-1H-pyrazole-3-carboxylic acid {2-[4-(2,5-dichloro-benzoyl)-piperazin-1-yl]-2-oxo-ethyl}-amide as a solid in 89.47% Yield. LC-MS purity: 92.226%. $^1$H-NMR (DMSO): δ 8.6 (s, 1H), 8.1 (t, 1H), 7.8 (m, 2H), 7.6 (m, 3H), 7.45 (m, 4H), 7.1 (s, 1H), 3.9 (m, 2H), 3.4 (m, 6H), 3.2 (m, 2H).

221) Synthesis of 2-[(Biphenyl-4-ylmethyl)-amino]-1-[4-(5-fluoro-2-trifluoromethyl-benzoyl)-piperazin-1-yl]-ethanone

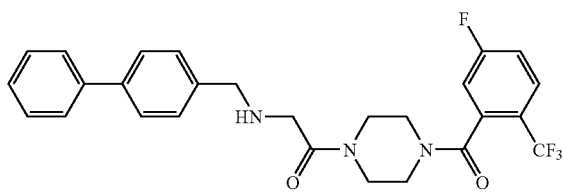

To a stirred suspension of LiOH.H$_2$O (48.5 mg, 1.15 mmol), 4A° molecular sieves (130 mg) in DMF (4 mL), was added 2-amino-1-[4-(2-trifluoromethyl-benzoyl)-piperazin-1-yl]-ethanone hydrochloride salt (214 mg, 0.57 mmol) and 4-phenyl benzyl bromide (130 mg, 0.52 mmol) and the resulting mixture was stirred at room temperature overnight. The mixture was filtered, cold water was then added, the product was extracted with EtOAc and the organic layer was washed with brine. The organic phase was dried over Na$_2$SO$_4$ and concentrated under reduced pressure. The residue obtained was purified by preparative HPLC to afford 50 mg (19.01% yield) 2-[(biphenyl-4-ylmethyl)-amino]-1-[4-(5-fluoro-2-trifluoromethyl-benzoyl)-piperazin-1-yl]-ethanone. LCMS Purity: 95.88%. $^1$H NMR (DMSO-d$_6$): δ 7.9 (q, 1H), 7.7-7.6 (m, 4H), 7.58-7.3 (m, 7H), 3.8-3.7 (d, 2H), 3.7-3.6 (m, 1H), 3.6-3.5 (m, 3H), 3.5-3.4 (m, 3H), 3.2-3.0 (m, 2H).

222) Synthesis of 1-[4-(5-Fluoro-2-trifluoromethyl-benzoyl)-piperazin-1-yl]-2-[(5-phenyl-isoxazol-3-ylmethyl)-amino]-ethanone

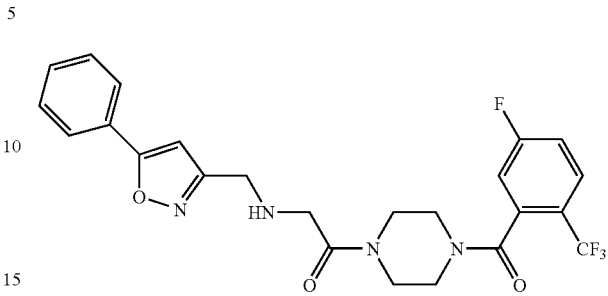

K$_2$CO$_3$ (121 mg, 0.87 mmol) was added to a stirred solution of methanesulfonic acid 5-phenyl-isoxazol-3-ylmethyl ester (120 mg, 0.43 mmol) and 2-amino-1-[4-(5-fluoro-2-trifluoromethyl-benzoyl)-piperazin-1-yl]-ethanone hydrochloride salt (162 mg, 0.43 mmol) in DMF (2 mL). The resulting mixture was heated at 40° C. for 1 hr. Cold water was then added and the resulting precipitate was isolated by filtration. The crude solid was purified by preparative HPLC [(Column-AV/SP/C$_{18}$-25/003, mobile phase-0.1% TFA in water (A)/acetonitrile (B), flow: 6 mL/min, gradient: (Time): (% B)-0:20; 2:20; 10:70)] to afford 38 mg (17.64% yield) of 1-[4-(5-fluoro-2-trifluoromethyl-benzoyl)-piperazin-1-yl]-2-[(5-phenyl-isoxazol-3-ylmethyl)-amino]-ethanone. LCMS Purity: 91.95%. $^1$H NMR (CDCl$_3$): δ 7.94-7.64 (m, 3H), 7.56-7.4 (m, 3H), 7.2 (m, 1H), 7.3 (d, 1H), 6.64-6.48 (d, 1H), 4.0-3.9 (d, 2H), 3.9-3.8 (m, 1H), 3.76-3.56 (m, 2H), 3.56-3.4 (m, 4H), 3.56-3.26 (bs, 1H), 3.2 (d, 2H), 2.49-2.29 (bs, 1H).

223) Synthesis of 2-[(5-Phenyl-isoxazol-3-ylmethyl)-amino]-1-[4-(2-trifluoromethyl-benzoyl)-piperazin-1-yl]-ethanone

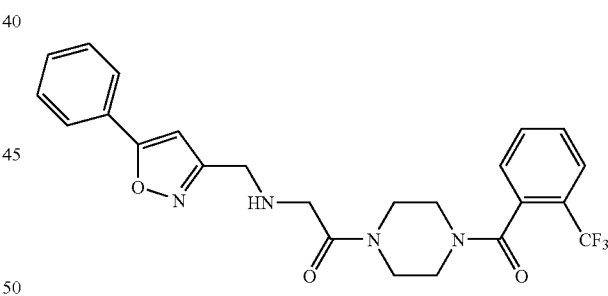

K$_2$CO$_3$ (201 mg, 1.46 mmol) was added to a stirred solution of methanesulfonic acid 5-phenyl-isoxazol-3-ylmethyl ester (200 mg, 0.73 mmol) and 2-amino-1-[4-(2-trifluoromethyl-benzoyl)-piperazin-1-yl]-ethanone hydrochloride salt (257 mg, 0.73 mmol) in DMF (4 mL). The resulting mixture was heated at 40° C. for 1 hr. Cold water was then added and the resulting precipitate was isolated by filtration. The crude solid was purified by column chromatography using (silica gel of 60-120 mesh and 2% MeOH in CHCl$_3$ as eluent) to afford 32 mg (9.2% yield) of 2-[(5-phenyl-isoxazol-3-ylmethyl)-amino]-1-[4-(2-trifluoromethyl-benzoyl)-piperazin-1-yl]-ethanone. LCMS Purity: 96.53%. $^1$H NMR (DMSO-d$_6$): δ 9.85 (s, 2H), 7.96-7.82 (m, 3H), 7.82-7.74 (t, 1H), 7.3 (d, 1H), 6.64-6.48 (d, 1H), 4.0-3.9 (d, 2H), 3.9-3.8 (m, 1H), 3.76-3.56 (m, 2H), 3.56-3.4 (m, 4H), 3.56-3.26 (bs, 1H), 3.2 (d, 2H), 2.49-2.29 (bs, 1H).

SCHEME-27
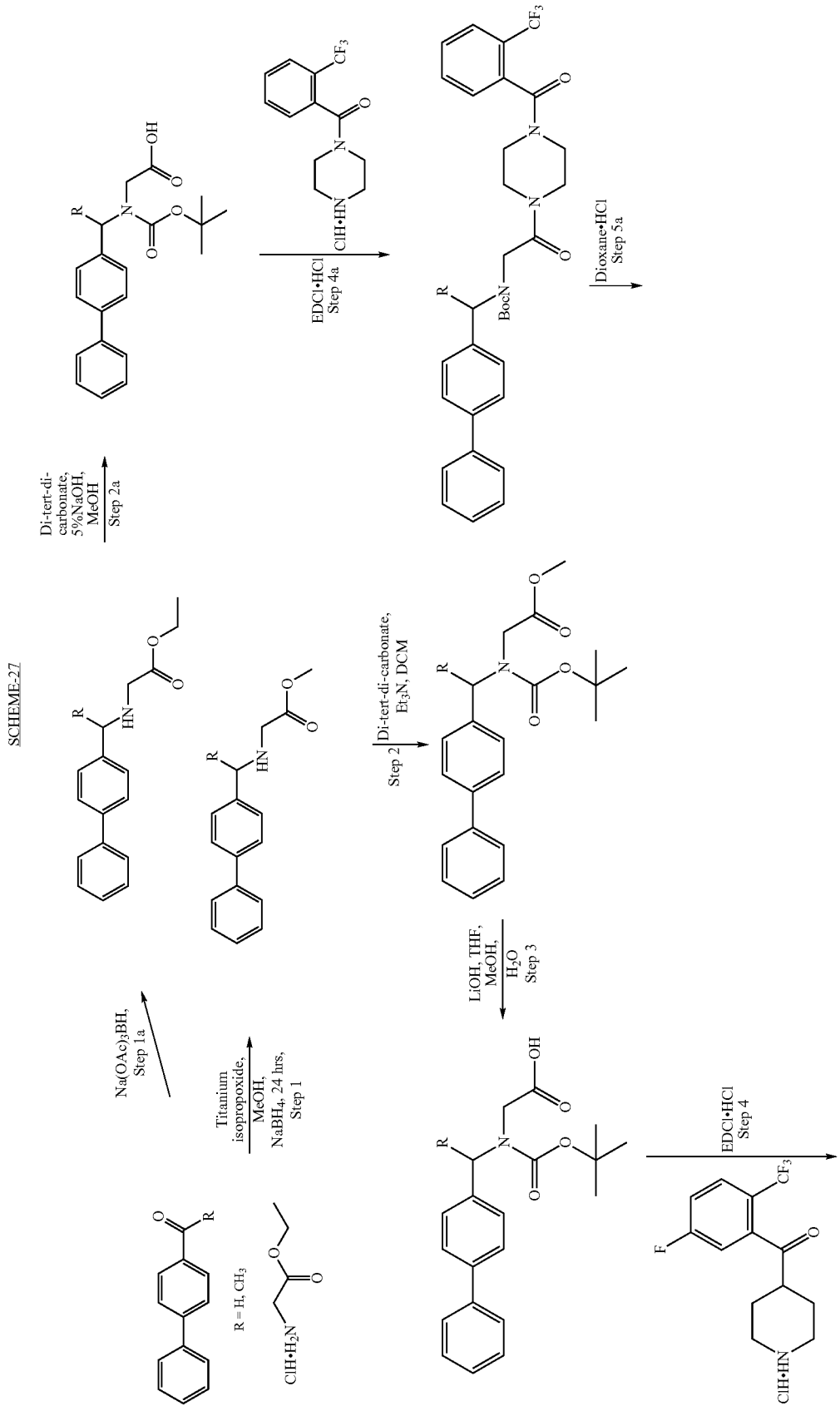

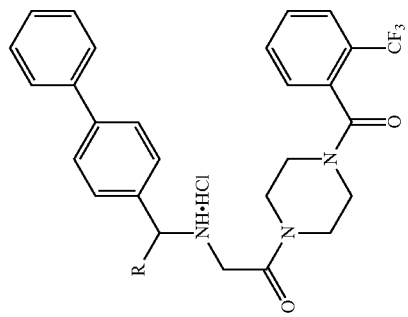
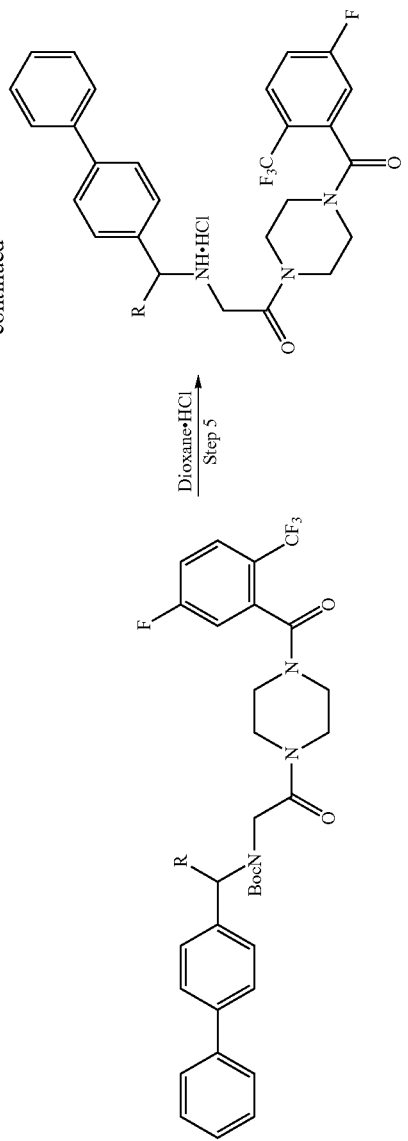

Step 1: Synthesis of (1-Biphenyl-4-yl-ethylamino)-acetic acid methyl ester

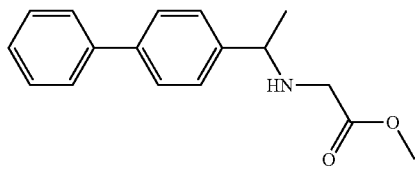

Titanium isopropoxide (4.4 g, 4.6 mL, and 15.5 mmol) was added to a stirred solution of 4-acetyl-biphenyl (1 g, 5.1 mmol) and glycine ethyl ester hydrochloride (2.2 g, 16.0 mmol) in MeOH (20 mL) and stirring continued at room temperature overnight. NaBH$_4$ (800 mg, 20 mmol) was added in portion wise and the resulting mixture was stirred at room temperature for 10 hrs. The above mixture was quenched with 2N aqueous NH$_3$ solution, filtered the solid precipitated. The filtrate was extracted with EtOAc, the organic layer was dried over Na$_2$SO$_4$ and concentrated under reduced pressure. The resulting residue was purified by column chromatography (using neutral alumina and 20% EtOAc in hexane as eluent) to afford 297 mg (21.67% yield) of (1-biphenyl-4-yl-ethylamino)-acetic acid methyl ester. $^1$H NMR (CDCl$_3$): δ 7.64 (t, 4H), 7.5-7.3 (m, 5H), 3.9-3.8 (q, 2H), 3.7 (s, 3H), 3.4 (d, 2H), 1.5 (d, 3H).

Step 2: Synthesis of [(1-Biphenyl-4-yl-ethyl)-tert-butoxycarbonyl-amino]-acetic acid methyl ester

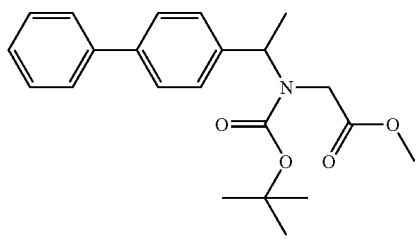

Di-tert-butyl dicarbonate (500 mg, 2.3 mmole) was added to a cold (0-4° C.) solution of (1-biphenyl-4-yl-ethylamino)-acetic acid methyl ester. (295 mg, 1.1 mmole) and triethyl amine (360 mg, 0.5 mL, 3.5 mole) in DCM (5 mL) and stirring was continued at room temperature overnight. Cold water was then added and extracted with DCM. The organic phase was dried over Na$_2$SO$_4$ and concentrated under reduced pressure. The resulting residue was purified by column chromatography (using neutral alumina and 10% EtOAc in hexane as eluent) to afford 290 mg (72.5% yield) of [(1-biphenyl-4-yl-ethyl)-tert-butoxycarbonyl-amino]-acetic acid methyl ester. $^1$H NMR (CDCl$_3$): δ 7.6-7.5 (m, 4H), 7.5-7.3 (m, 5H), 3.8 (d, 1H), 3.7 (s, 3H), 3.6-3.4 (t, 1H), 1.8-1.6 (s, 9H), 1.5 (d, 3H).

Step 3: Synthesis of [(1-Biphenyl-4-yl-ethyl)-tert-butoxycarbonyl-amino]-acetic acid

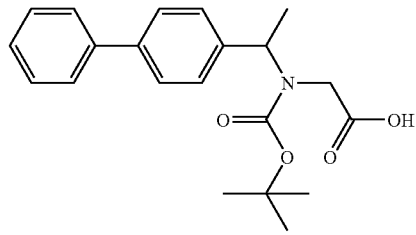

LiOH (140 mg, 3.3 mmol) was added to a stirred solution of [(1-biphenyl-4-yl-ethyl)-tert-butoxycarbonyl-amino]-acetic acid methyl ester (202 mg, 0.54 mmol) in THF:MeOH:H$_2$O (3:1:1, 10 mL), and the resulting mixture was stirred at room temperature for 12 hrs. The reaction mixture was concentrated under reduced pressure. Cold water was then added, the product was acidified with aqueous citric acid solution and then extracted with EtOAc. The organic phase was dried over Na$_2$SO$_4$ and concentrated under reduced pressure to afford 190 mg (97.9% yield) of [(1-biphenyl-4-yl-ethyl)-tert-butoxycarbonyl-amino]-acetic acid.

Step 4: Synthesis of (1-Biphenyl-4-yl-ethyl)-{2-[4-(5-fluoro-2-trifluoromethyl-benzoyl)-piperazin-1-yl]-2-oxo-ethyl}-carbamic acid tert-butyl ester

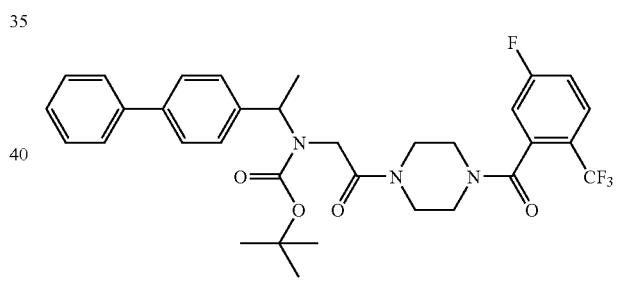

DIPEA (182 mg, 0.24 mL, 1.4 mmol) was added to a stirred solution of [(1-biphenyl-4-yl-ethyl)-tert-butoxycarbonyl-amino]-acetic acid (100 mg, 0.28 mmol) in DMF (5 mL). HOBT (42 mg, 0.31 mmol) and EDCI (135 mg, 0.7 mmol) were then added at room temperature. After 2 minutes, (5-Fluoro-2-trifluoromethyl-phenyl)-piperazin-1-yl-methanone hydrochloride salt (105 mg, 0.3 mmol) was added and the resulting mixture was stirred at room temperature overnight. Cold water was then added and the product was extracted with EtOAc and the organic layer was washed with brine. The organic phase was dried over Na$_2$SO$_4$ and concentrated under reduced pressure. The resulting residue was purified by column chromatography (using 60-120 silica gel and 30-50% EtOAc in hexane as eluent) to afford 43 mg (27.56% yield) of (1-biphenyl-4-yl-ethyl)-{2-[4-(5-fluoro-2-trifluoromethyl-benzoyl)-piperazin-1-yl]-2-oxo-ethyl}-carbamic acid tert-butyl ester, LCMS Purity: 96.02%. $^1$H NMR (CDCl$_3$): δ 7.78 (t 1H), 7.64-7.5 (s, 4H), 7.5-7.3 (m, 5H), 7.24 (d, 1H), 7.04 (m, 1H), 5.8-5.2 (bd, 2H), 4.0 (s, 1H), 3.8 (s, 3H), 3.6-3.2 (m, 5H), 3.1 (s, 3H), 1.5 (s, 9H).

Step 5

224) Synthesis of 2-(1-Biphenyl-4-yl-ethylamino)-1-[4-(5-fluoro-2-trifluoromethyl-benzoyl)-piperazin-1-yl]-ethanone.hydrochloride

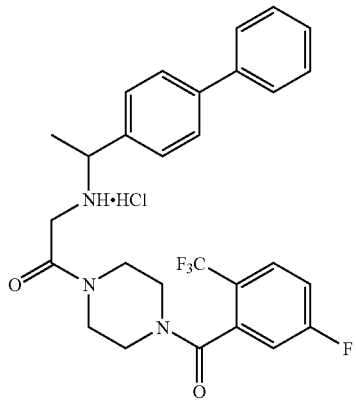

A solution of (1-biphenyl-4-yl-ethyl)-{2-[4-(5-fluoro-2-trifluoromethyl-benzoyl)-piperazin-1-yl]-2-oxo-ethyl}-carbamic acid tert-butyl ester (140 mg, 0.23 mmol in dioxane.HCl (10 ml) was stirred at room temperature for 1 hr. The reaction mixture was concentrated to get the residue. The residue was washed with hexane to afford 98 mg (78.4% Yield) of 2-(1-Biphenyl-4-yl-ethylamino)-1-[4-(5-fluoro-2-trifluoromethyl-benzoyl)-piperazin-1-yl]-ethanone hydrochloride. LCMS Purity: 93.9%. $^1$H NMR (CDCl$_3$): δ 9.6 (d, 3H), 8.0 (t, 1H), 7.8-7.6 (m, 6H), 7.6-7.36 (m, 5H), 4.5 (t, 1H), 4.2-3.6 (m, 2H), 3.6-3.4 (m, 5H), 3.2-3.0 (m, 3H), 1.6 (t, 3H).

225) Synthesis of 2-[(Biphenyl-4-ylmethyl)-amino]-1-[4-(2-trifluoromethyl-benzoyl)-piperazin-1-yl]-ethanone

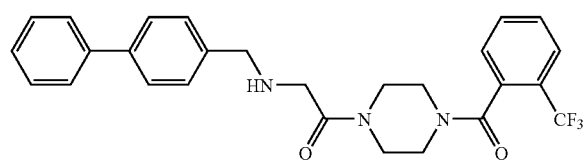

A solution of biphenyl-4-yl-methyl-{2-oxo-2-[4-(2-trifluoromethyl-benzoyl)-piperazin-1-yl]-ethyl}-carbamic acid tert-butyl ester (95 mg, 0.16 mmol) (prepared by the method as described above) in dioxan.HCl (5 ml) was stirred at 0° C. for 20 min. The reaction mixture was concentrated to get the residue. The residue was washed with ether, basified with saturated sodium bicarbonate solution and the product was extracted with EtOAc. The resulting residue was purified by preparative HPLC to afford 25 mg (32%) of 2-[(biphenyl-4-ylmethyl)-amino]-1-[4-(2-trifluoromethyl-benzoyl)-piperazin-1-yl]-ethanone. LCMS Purity: 97.5%. $^1$H NMR (CDCl$_3$): δ 7.74 (d, 1H), 7.6 (m, 6H), 7.44 (m, 4H), 7.36 (m, 2H), 3.9 (m, 4H), 3.7 (m, 3H), 3.5 (m, 3H), 3.42 (s, 1H), 3.2 (t, 1H), 3.2 (m, 2H).

226) Synthesis of 1-[4-(5-Fluoro-2-trifluoromethyl-benzoyl)-piperazin-1-yl]-2-[(1-phenyl-1H-pyrazol-4-ylmethyl)-amino]-ethanone

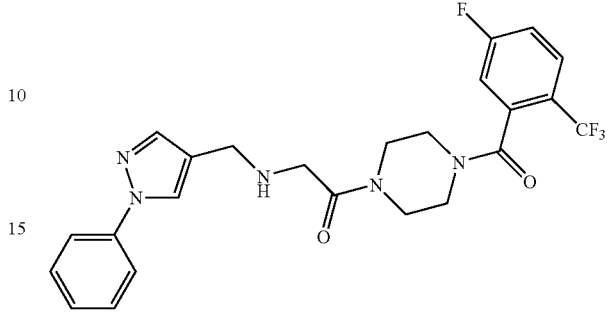

A mixture of sodium cyano borohydride (100 mg, 1.6 mmol) and zinc chloride (100 mg, 0.73 mmol) was added in portions to a cold solution of 1-phenyl-1H-pyrazole-4-carbaldehyde (60 mg, 0.35 mmol) and 2-amino-1-[4-(5-fluoro-2-trifluoromethyl-benzoyl)-piperazin-1-yl]-ethanone hydrochloride salt (142 mg, 0.38 mmol) in methanol (10 ml) and stirring was continued at room temperature overnight. The reaction mixture was concentrated under reduced pressure to get the residue. The residue was quenched with saturated aqueous sodium bicarbonate solution and extracted with EtOAc. The organic phase was dried over Na$_2$SO$_4$ and concentrated under reduced pressure to get the residue. The obtained residue was purified by preparative HPLC [(Column-AU/SP/C$_{18}$-28/006, mobile phase-0.1% TFA in water (A)/acetonitrile (B), flow: 6 mL/minute, gradient: (% B)-0: 20; 2:30; 8:70)]) to afford 32 mg (18.8% yield) of 1-[4-(5-fluoro-2-trifluoromethyl-benzoyl)-piperazin-1-yl]-2-[(1-phenyl-1H-pyrazol-4-ylmethyl)-amino]-ethanone. LCMS Purity: 98.11%. $^1$H NMR (DMSO-d$_6$): δ 9.2 (s, 2H), 8.6 (d, 1H), 8.0-7.76 (m, 4H), 7.62 (m, 2H), 7.4 (t, 1H), 4.2-4.0 (d, 4H), 3.8 (s, 1H), 3.66-3.44 (m, 4H), 3.3 (d, 3H).

227) Synthesis of 1-[4-(5-Fluoro-2-trifluoromethyl-benzoyl)-piperazin-1-yl]-2-(4-thiophen-3-yl-benzylamino)-ethanone

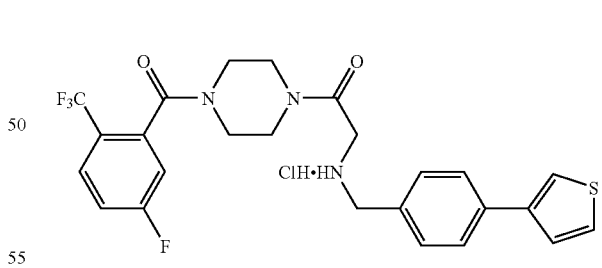

To a solution of 1-[4-(5-fluoro-2-trifluoromethyl-benzoyl)-piperazin-1-yl]-2-(4-thiophen-3-yl-benzylamino)-ethanone (50 mg, 0.09 mmol) in ethereal.HCl (5 ml) was stirred at room temperature for 1 hr. The reaction mixture was then concentrated and the resulting residue was washed with ether to afford 36 mg (67.2%) of 1-[4-(5-fluoro-2-trifluoromethyl-benzoyl)-piperazin-1-yl]-2-(4-thiophen-3-yl-benzylamino)-ethanone hydrochloride salt. LCMS Purity: 96.34%. $^1$H NMR (DMSO-d$_6$): δ 9.2 (s, 1H), 8.0-7.9 (m, 2H), 7.85-7.74 (m, 2H), 7.7-7.5 (m, 6H), 4.2-4.0 (m, 4H), 3.8-3.4 (m, 5H), 3.3-3.0 (m, 3H).

Enzyme Activity

Rat liver microsomes that have been induced to overexpress SCD-1 have been used as a source of SCD-1 activity. Tritiated stearoyl CoA labeled at position 9 and 10 is used as the substrate in the in vitro assay. SCD-1 activity is measured by detecting tritiated water released upon desaturation of the substrate. Desaturation by SCD-1 (a delta 9 desaturase) results in release of tritiated water which is measured in a scintillation counter.

The compounds of the present invention typically show greater than 50% inhibition of SCD1 enzyme at 10 mM concentration.

The entire disclosures of all applications, patents and publications, cited above and below, are hereby incorporated by reference.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects.

What is claimed is:

1. A compound of formula (I):

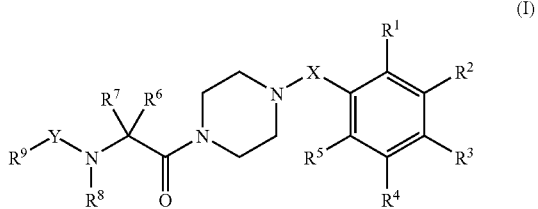

(I)

wherein $R^1$ is halogenated alkyl;

$R^2$, $R^3$, $R^4$ and $R^5$ are each independently hydrogen, halogen, hydroxy, cyano, nitro, amino, alkylamino, dialkylamino, carboxyl, alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, cycloalkyloxy, cycloalkylalkyloxy, arylalkyloxy, heteroarylalkyloxy, alkylthio, arylthio, alkylsulfinyl, alkylsulfonyl, alkoxycarbonyl, aryloxycarbonyl or heteroaryloxycarbonyl;

$R^6$ and $R^7$ are each independently hydrogen, hydroxyl, cyano, alkyl, alkenyl, alkynyl, aryl, arylalkyl, heteroaryl, heteroarylalkyl, heterocycle or heterocyclealkyl;

$R^8$ is hydrogen, alkyl, alkenyl, alkynyl, aryl, arylalkyl, heteroaryl, heteroarylalkyl, heterocycle or heterocyclealkyl;

$R^9$ is hydrogen, alkyl, alkenyl, alkynyl, aryl, arylalkyl, heteroaryl, heteroarylalkyl, heterocycle or heterocyclealkyl;

X is —C(O)—, —C(O)—O—, —S(O)$_2$—, —S(O)—, or —C(O)NR$^{10}$—, where R$^{10}$ is hydrogen, alkyl, alkenyl, alkynyl, cycloalkyl, cycloalkylalkyl, aryl, arylalkyl, heteroaryl, heteroarylalkyl, heterocycle or heterocyclealkyl;

Y is —C(O)—, —S(O)$_2$—, or —S(O)—;

wherein, when present, any aryl, heteroaryl, or heterocycle group may optionally be substituted by halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl, arylalkyl-C(O)—, —C(O)O-alkyl, benzodioxol, benzo[d]oxazol-2(3H)-one, cycloalkyl-NH—C(O)—, and combinations thereof;

or pharmaceutically acceptable salts thereof;

with the proviso that said compound is not 4-chloro-N-[2-oxo-[4-[[2-(trifluoromethyl)phenyl]sulfonyl]-1-piperazinyl]ethyl]benzamide or a pharmaceutically acceptable salt thereof.

2. The compound of claim 1, wherein $R^1$ is $CF_3$ and $R^2$, $R^3$, $R^4$ and $R^5$ are each independently hydrogen or halogen.

3. The compound of claim 1, wherein $R^9$ is aryl, heteroaryl, heterocycle or arylalkyl, each of which may be optionally substituted.

4. The compound of claim 3, wherein $R^9$ is phenyl, furanyl, isoxazolyl, pyridinyl, thienyl, indolyl, oxadiazolyl, pyrazolyl, piperidinyl, benzyl or phenethyl, each of which may be optionally substituted.

5. The compound of claim 3, wherein $R^9$ is aryl, heteroaryl, heterocycle or arylalkyl each of which may be optionally substituted by hydroxyl, halogen, nitro, cyano, amino, carboxyl, amido, optionally substituted alkyl, optionally substituted arylalkyloxy, optionally substituted heteroaryloxy, optionally substituted arylamino, optionally substituted arylsulfinyl, optionally substituted arylsulfonyl, optionally substituted aryloxy, optionally substituted aryl, optionally substituted acyl and combinations thereof.

6. The compound of claim 5, wherein $R^9$ is aryl, heteroaryl, heterocycle or arylalkyl, each of which may be optionally substituted by hydroxyl, halogen, nitro, cyano, amino, carboxyl, amido, —CF$_3$, —OCH$_2$C$_6$H$_5$, —O—C$_5$H$_3$N(CN), —NHC$_6$H$_5$, —S(O)—C$_6$H$_5$, —S(O)$_2$—C$_6$H$_5$, —OC$_6$H$_5$, —OC$_6$H$_4$(OH), —OC$_6$H$_3$F$_2$, —C$_6$H$_5$, —C$_6$H$_4$(CF$_3$), —C$_6$H$_4$(OH), —C$_6$H$_4$—O—CH$_2$C$_6$H$_5$, —C(O)C$_6$H$_5$, 2-oxo-2,3-dihydrobenzooxazol, benzo[1,3]dioxol, cyclopentylamide, —C$_6$H$_3$(F)$_2$, —C$_6$H$_4$F, —C$_6$H$_4$—N(CH$_3$)$_2$, —C$_6$H$_4$(OCH$_3$), —C(O)CH$_2$CH$_2$C$_6$H$_5$, —CH$_2$CH$_2$CH$_2$C$_6$H$_5$, —OC(O)CH$_3$, —C(O)NHCH$_3$, N(C$_6$H$_4$)(CH$_3$), —C$_5$H$_3$N(OH), —C$_6$H$_4$(NH$_2$), —CCH, —C$_3$H$_4$N$_2$, —C$_7$H$_6$N$_2$, —C$_8$H$_7$N, —OCH$_3$, —CH$_3$, —C$_3$H$_2$NO(CH$_3$), —C$_2$HON$_2$(CH$_3$), —C$_4$H$_9$N$_2$(CH$_3$), —C$_3$H$_3$N$_2$(CH$_3$), —C$_4$H$_9$ON, —C$_{10}$H$_8$, —C$_2$H$_2$N$_2$O, —C$_6$H$_5$, —O(CH$_2$)$_2$C$_6$H$_5$, —(CH$_2$)$_3$C$_6$H$_5$, —C$_5$H$_{11}$N, —C$_5$—H$_5$N, —C$_4$H$_4$N, —C$_3$H$_3$SN, —C$_4$H$_4$S, and combinations thereof.

7. The compound of claim 1, wherein X is —C(O)—.

8. The compound of claim 1, wherein Y is —C(O)— or —S(O)$_2$—.

9. A compound of claim 1, selected from:
4-Benzenesulfinyl-N-{2-oxo-2-[4-(2-trifluoromethyl-benzoyl)-piperazin-1-yl]-ethyl}-benzamide,
N-{2-Oxo-2-[4-(2-trifluoromethyl-benzoyl)-piperazin-1-yl]-ethyl}-4-phenylamino-benzamide,
4-(4-Hydroxy-phenoxy)-N-{2-oxo-2-[4-(2-trifluoromethyl-benzoyl)-piperazin-1-yl]-ethyl}-benzamide, 4-Benzenesulfonyl-N-{2-oxo-2-[4-(2-trifluoromethyl-benzoyl)-piperazin-1-yl]-ethyl}-benzamide,
Biphenyl-4-sulfonic acid {2-oxo-2-[4-(2-trifluoromethyl-benzoyl)-piperazin-1-yl]-ethyl}-amide,
5-(3-Trifluoromethyl-phenyl)-furan-2-carboxylic acid {2-oxo-2-[4-(2-trifluoromethyl-benzoyl)-piperazin-1-yl]-ethyl}-amide,
N-{2-Oxo-2-[4-(2-trifluoromethyl-benzoyl)-piperazin-1-yl]-ethyl}-3-phenoxy-benzamide,
4-Benzoyl-N-{2-oxo-2-[4-(2-trifluoromethyl-benzoyl)-piperazin-1-yl]-ethyl}-benzamide,
4-Fluoro-N-{2-oxo-2-[4-(2-trifluoromethyl-benzoyl)-piperazin-1-yl]-ethyl}-benzamide,
4-Nitro-N-{2-oxo-2-[4-(2-trifluoromethyl-benzoyl)-piperazin-1-yl]-ethyl}-benzamide,
N-{2-oxo-2-[4-(2-trifluoromethyl-benzoyl)-piperazin-1-yl]-ethyl}-2-phenyl-acetamide,
4-Cyano-N-{2-oxo-2-[4-(2-trifluoromethyl-benzoyl)-piperazin-1-yl]-ethyl}-benzamide,
N-{2-Oxo-2-[4-(2-trifluoromethyl-benzoyl)-piperazin-1-yl]-ethyl}-4-trifluoromethyl-benzamide,
N-{2-Oxo-2-[4-(2-trifluoromethyl-benzoyl)-piperazin-1-yl]-ethyl}-4-phenoxy-benzamide,
5-(4-Benzyloxy-phenyl)-isoxazole-3-carboxylic acid {2-oxo-2-[4-(2-trifluoromethyl-benzoyl)-piperazin-1-yl]-ethyl}-amide,
Biphenyl-4-carboxylic acid {2-oxo-2-[4-(2-trifluoromethyl-benzoyl)-piperazin-1-yl]-ethyl}-amide,
5-(4-Hydroxy-phenyl)-isoxazole-3-carboxylic acid {2-oxo-2-[4-(2-trifluoromethyl-benzoyl)-piperazin-1-yl]-ethyl}-amide,
6-Hydroxy-N-{2-oxo-2-[4-(2-trifluoromethyl-benzoyl)-piperazin-1-yl]-ethyl}-nicotinamide,
5-Nitro-furan-2-carboxylic acid {2-oxo-2-[4-(2-trifluoromethyl-benzoyl)-piperazin-1-yl]-ethyl}-amide,
4-(2,6-Difluoro-phenoxy)-N-{2-oxo-2-[4-(2-trifluoromethyl-benzoyl)-piperazin-1-yl]-ethyl}-benzamide,
4-Amino-N-{2-oxo-2-[4-(2-trifluoromethyl-benzoyl)-piperazin-1-yl]-ethyl}-benzamide,
N-{2-Oxo-2-[4-(2-trifluoromethyl-benzoyl)-piperazin-1-yl]-ethyl}-6-phenyl-nicotinamide,
Biphenyl-3-carboxylic acid {2-oxo-2-[4-(2-trifluoromethyl-benzoyl)-piperazin-1-yl]-ethyl}-amide,
4-Phenyl-thiophene-2-carboxylic acid {2-oxo-2-[4-(2-trifluoromethyl-benzoyl)-piperazin-1-yl]-ethyl}-amide,
5-Phenyl-pyridine-2-carboxylic acid {2-oxo-2-[4-(2-trifluoromethyl-benzoyl)-piperazin-1-yl]-ethyl}-amide,
1-Phenyl-piperidine-4-carboxylic acid {2-oxo-2-[4-(2-trifluoromethyl-benzoyl)-piperazin-1-yl]-ethyl}-amide,
N-{2-oxo-2-[4-(2-trifluoromethyl-benzoyl)-piperazin-1-yl]-ethyl}-terephthalamic acid,
N-{2-Oxo-2-[4-(2-trifluoromethyl-benzoyl)-piperazin-1-yl]-ethyl}-terephthalamide,
4-(5-Cyano-pyridin-2-yloxy)-N-{2-oxo-2-[4-(2-trifluoromethyl-benzoyl)-piperazin-1-yl]-ethyl}-benzamide,
4-Hydroxy-N-{2-oxo-2-[4-(2-trifluoromethyl-benzoyl)-piperazin-1-yl]-ethyl}-benzamide,
3-Hydroxy-N-{2-oxo-2-[4-(2-trifluoromethyl-benzoyl)-piperazin-1-yl]-ethyl}-benzamide,
2-Hydroxy-N-{2-oxo-2-[4-(2-trifluoromethyl-benzoyl)-piperazin-1-yl]-ethyl}-benzamide,
5-Phenyl-furan-2-carboxylic acid {2-oxo-2-[4-(2-trifluoromethyl-benzoyl)-piperazin-1-yl]-ethyl}-amide,
5-(3-Trifluoromethyl-phenyl)-furan-2-carboxylic acid {2-oxo-2-[4-(2-trifluoromethyl-benzoyl)-piperazin-1-yl]-ethyl}-amide,
N-{2-oxo-2-[4-(2-trifluoromethyl-benzoyl)-piperazin-1-yl]-ethyl}-3-phenoxy-benzamide,
4-Benzoyl-N-{2-oxo-2-[4-(2-trifluoromethyl-benzoyl)-piperazin-1-yl]-ethyl}-benzamide,
4-Fluoro-N-{2-oxo-2-[4-(2-trifluoromethyl-benzoyl)-piperazin-1-yl]-ethyl}-benzamide,
4-Nitro-N-{2-oxo-2-[4-(2-trifluoromethyl-benzoyl)-piperazin-1-yl]-ethyl}-benzamide,
5-Nitro-furan-2-carboxylic acid {2-oxo-2-[4-(2-trifluoromethyl-benzoyl)-piperazin-1-yl]-ethyl}-amide,
1-Phenyl-piperidine-4-carboxylic acid {2-oxo-2-[4-(2-trifluoromethyl-benzoyl)-piperazin-1-yl]-ethyl}-amide,
4-Benzyloxy-N-{2-oxo-2-[4-(2-trifluoromethyl-benzoyl)-piperazin-1-yl]-ethyl}-benzamide,
2-(4-Hydroxy-phenyl) N-{2-oxo-2-[4-(2-trifluoromethyl-benzoyl)-piperazin-1-yl]-ethyl}-acetamide,
3-(4-Hydroxy-phenyl) N-{2-oxo-2-[4-(2-trifluoromethyl-benzoyl)-piperazin-1-yl]-ethyl}-propionamide,
1H-Indole-5-carboxylic acid {2-oxo-2-[4-(2-trifluoromethyl-benzoyl)-piperazine-1-yl]-ethyl}-amide,
Thiophene-2-carboxylic acid {2-oxo-2-[4-(2-trifluoromethyl-benzoyl)-piperazine-1-yl]-ethyl}-amide,
Furan-2-carboxylic acid {2-oxo-2-[4-(2-trifluoromethyl-benzoyl)-piperazine-1-yl]-ethyl}-amide, and
N-{2-Oxo-2-[4-(2-trifluoromethyl-benzoyl)-piperazine-1-yl]-ethyl}benzamide,
or pharmaceutically acceptable salts thereof;
wherein if the compound exhibits chirality it can be in the form of a mixture of enantiomers such as a racemate or a mixture of diastereomers, or can be in the form of a single enantiomer or a single diastereomer.

10. A compound of claim 1, selected from:
5-Phenyl-[1,3,4]oxadiazole-2-carboxylic acid {2-oxo-2-[4-(2-trifluoromethyl-benzoyl)-piperazin-1-yl]-ethyl}-amide,
5-Phenyl-isoxazole-3-carboxylic acid {2-oxo-2-[4-(2-trifluoromethyl-benzoyl)-piperazin-1-yl]-ethyl}-amide,
5-Phenyl-isoxazole-3-carboxylic acid {2-[4-(5-fluoro-2-trifluoromethyl-benzoyl)-piperazin-1-yl]-2-oxo-ethyl}-amide,
5-Phenyl-1H-pyrazole-3-carboxylic acid {2-oxo-2-[4-(2-trifluoromethyl-benzoyl)-piperazin-1-yl]-ethyl}-amide, and
5-Phenyl-1H-pyrazole-3-carboxylic acid {2-[4-(5-fluoro-2-trifluoromethyl-benzoyl)-piperazin-1-yl]-2-oxo-ethyl}-amide,
or pharmaceutically acceptable salts thereof;
wherein if the compound exhibits chirality it can be in the form of a mixture of enantiomers such as a racemate or a mixture of diastereomers, or can be in the form of a single enantiomer or a single diastereomer.

11. A compound of claim 1, selected from:
5-(3-Hydroxy-phenyl)-1H-pyrazole-3-carboxylic acid {2-oxo-2-[4-(2-trifluoromethyl-benzoyl)-piperazin-1-yl]-ethyl}-amide,
5-(2-Hydroxy-phenyl)-1H-pyrazole-3-carboxylic acid {2-[4-(5-fluoro-2-trifluoromethyl-benzoyl)-piperazin-1-yl]-2-oxo-ethyl}-amide,
5-(2-Amino-phenyl)-1H-pyrazole-3-carboxylic acid {2-oxo-2-[4-(2-trifluoromethyl-benzoyl)-piperazin-1-yl]-ethyl}-amide,
5-Phenyl-pyridine-2-carboxylic acid {2-[4-(5-fluoro-2-trifluoromethyl-benzoyl)-piperazin-1-yl]-2-oxo-ethyl}-amide,
1H-Indole-2-carboxylic acid {2-oxo-2-[4-(2-trifluoromethyl-benzoyl)-piperazin-1-yl]-ethyl}-amide, 4-Phenyl-pyrazole-1-carboxylic acid {2-oxo-2-[4-(2-trifluoromethyl-benzoyl)-piperazin-1-yl]-ethyl}-amide,
4-Phenyl-pyrazole-1-carboxylic acid {2-[4-(5-fluoro-2-trifluoromethyl-benzoyl)-piperazin-1-yl]-2-oxo-ethyl}-amide,
4-(2-Fluoro-phenyl)-pyrazole-1-carboxylic acid {2-[4-(5-fluoro-2-trifluoromethyl-benzoyl)-piperazin-1-yl]-2-oxo-ethyl}-amide,
5-Phenyl-1H-pyrrole-2-carboxylic acid {2-oxo-2-[4-(2-trifluoromethyl-benzoyl)-piperazin-1-yl]-ethyl}-amide,
4-Phenyl-1H-pyrrole-2-carboxylic acid {2-oxo-2-[4-(2-trifluoromethyl-benzoyl)-piperazin-1-yl]-ethyl}-amide,
1-Phenyl-1H-pyrazole-3-carboxylic acid {2-oxo-2-[4-(2-trifluoromethyl-benzoyl)-piperazin-1-yl]-ethyl}-amide,
3'-Dimethylamino-biphenyl-4-carboxylic acid {2-oxo-2-[4-(2-trifluoromethyl-benzoyl)-piperazin-1-yl]-ethyl}-amide,
Biphenyl-4-carboxylic acid methyl-{2-oxo-2-[4-(2-trifluoromethyl-benzoyl)-piperazin-1-yl]-ethyl}-amide,
5-(3-Hydroxy-phenyl)-isoxazole-3-carboxylic acid {2-oxo-2-[4-(2-trifluoromethyl-benzoyl)-piperazin-1-yl]-ethyl}-amide,
5-(2-Hydroxy-phenyl)-isoxazole-3-carboxylic acid {2-oxo-2-[4-(2-trifluoromethyl-benzoyl)-piperazin-1-yl]-ethyl}-amide,
5-(2-Fluoro-phenyl)-isoxazole-3-carboxylic acid {2-[4-(5-fluoro-2-trifluoromethyl-benzoyl)-piperazin-1-yl]-2-oxo-ethyl}-amide,
5-(2-Hydroxy-phenyl)-1H-pyrazole-3-carboxylic acid {2-oxo-2-[4-(2-trifluoromethyl-benzoyl)-piperazin-1-yl]-ethyl}-amide,
5-Benzo[1,3]dioxol-5-yl-1H-pyrazole-3-carboxylic acid {2-oxo-2-[4-(2-trifluoromethyl-benzoyl)-piperazin-1-yl]-ethyl}-amide,
5-(2-Methoxy-phenyl)-1H-pyrazole-3-carboxylic acid {2-[4-(5-fluoro-2-trifluoromethyl-benzoyl)-piperazin-1-yl]-2-oxo-ethyl}-amide,
5-(2-Trifluoromethyl-phenyl)-1H-pyrazole-3-carboxylic acid {2-[4-(5-fluoro-2-trifluoromethyl-benzoyl)-piperazin-1-yl]-2-oxo-ethyl}-amide,
5-(2-Trifluoromethyl-phenyl)-1H-pyrazole-3-carboxylic acid {2-oxo-2-[4-(2-trifluoromethyl-benzoyl)-piperazin-1-yl]-ethyl}-amide,
5-(2-Methoxy-phenyl)-1H-pyrazole-3-carboxylic acid {2-oxo-2-[4-(2-trifluoromethyl-benzoyl)-piperazin-1-yl]-ethyl}-amide,
1-(3-Phenyl-propionyl)-piperidine-4-carboxylic acid {2-oxo-2-[4-(2-trifluoromethyl-benzoyl)-piperazin-1-yl]-ethyl}-amide,
1-(3-Phenyl-propyl)-piperidine-4-carboxylic acid {2-oxo-2-[4-(2-trifluoromethyl-benzoyl)-piperazin-1-yl]-ethyl}-amide,
Pyrazine-2-carboxylic acid {2-oxo-2-[4-(2-trifluoromethyl-benzoyl)-piperazin-1-yl]-ethyl}-amide,
N-{2-oxo-2-[4-(2-trifluoromethyl-benzoyl)-piperazin-1-yl]-ethyl}-4-thiophen-3-yl-benzamide,
Dibenzofuran-2-carboxylic acid {2-oxo-2-[4-(2-trifluoromethyl-benzoyl)-piperazin-1-yl]-ethyl}-amide,
4-(1-Methyl-1H-pyrazol-4-yl)-N-{2-oxo-2-[4-(2-trifluoromethyl-benzoyl)-piperazin-1-yl]-ethyl}-benzamide,
N-{2-Oxo-2-[4-(2-trifluoromethyl-benzoyl)-piperazin-1-yl]-ethyl}-4-pyrimidin-5-yl-benzamide,
N-{2-Oxo-2-[4-(2-trifluoromethyl-benzoyl)-piperazin-1-yl]-ethyl}-4-pyrimidin-2-yl-benzamide,
N-{2-Oxo-2-[4-(2-trifluoromethyl-benzoyl)-piperazin-1-yl]-ethyl}-4-pyrazin-2-yl-benzamide,
9H-Fluorene-2-carboxylic acid {2-oxo-2-[4-(2-trifluoromethyl-benzoyl)-piperazin-1-yl]-ethyl}-amide,
4-[1,2,4]Oxadiazol-3-yl-N-{2-oxo-2-[4-(2-trifluoromethyl-benzoyl)-piperazin-1-yl]-ethyl}-benzamide,
1-Oxy-5-phenyl-pyridine-2-carboxylic acid {2-oxo-2-[4-(2-trifluoromethyl-benzoyl)-piperazin-1-yl]-ethyl}-amide,
5-Hydroxy-pyrazine-2-carboxylic acid {2-oxo-2-[4-(2-trifluoromethyl-benzoyl)-piperazin-1-yl]-ethyl}-amide,
N-{2-oxo-2-[4-(2-trifluoromethyl-benzoyl)-piperazin-1-yl]-ethyl}-4-pyridin-2-yl-benzamide,
2'-Fluoro-biphenyl-4-carboxylic acid {2-oxo-2-[4-(2-trifluoromethyl-benzoyl)-piperazin-1-yl]-ethyl}-amide,
5-Methyl-isoxazole-3-carboxylic acid {2-oxo-2-[4-(2-trifluoromethyl-benzoyl)-piperazin-1-yl]-ethyl}-amide,
2,4-Difluoro-biphenyl-4-carboxylic acid {2-oxo-2-[4-(2-trifluoromethyl-benzoyl)-piperazin-1-yl]-ethyl}-amide,
5-Phenyl-pyrazine-2-carboxylic acid {2-oxo-2-[4-(2-trifluoromethyl-benzoyl)-piperazin-1-yl]-ethyl}-amide,
6-Phenyl-pyridazine-3-carboxylic acid {2-oxo-2-[4-(2-trifluoromethyl-benzoyl)-piperazin-1-yl]-ethyl}-amide,
2-Phenyl-thiazole-5-carboxylic acid {2-oxo-2-[4-(2-trifluoromethyl-benzoyl)-piperazin-1-yl]-ethyl}-amide,
4-Methyl-N-{2-oxo-2-[4-(2-trifluoromethyl-benzoyl)-piperazin-1-yl]-ethyl}-benzamide,
N-{2-Oxo-2-[4-(2-trifluoromethyl-benzoyl)-piperazin-1-yl]-ethyl}-isophthalamic acid methyl ester,
4-[1,3,4]Oxadiazol-2-yl-N-{2-oxo-2-[4-(2-trifluoromethyl-benzoyl)-piperazin-1-yl]-ethyl}-benzamide,
N-Methyl-N'-{2-oxo-2-[4-(2-trifluoromethyl-benzoyl)-piperazin-1-yl]-ethyl}-terephthalamide,
N-Methyl-N'-{2-oxo-2-[4-(2-trifluoromethyl-benzoyl)-piperazin-1-yl]-ethyl}-isophthalamide,
4-(5-Methyl-[1,3,4]oxadiazol-2-yl)-N-{2-oxo-2-[4-(2-trifluoromethyl-benzoyl)-piperazin-1-yl]-ethyl}-benzamide,
4-[1,3,4]Oxadiazol-2-yl-N-{2-oxo-2-[4-(2-trifluoromethyl-benzoyl)-piperazin-1-yl]-ethyl}-benzamide,
4-(2-Oxo-2H-pyridin-1-yl)-N-{2-oxo-2-[4-(2-trifluoromethyl-benzoyl)-piperazin-1-yl]-ethyl}-benzamide,
6-Benzyloxy-N-{2-oxo-2-[4-(2-trifluoromethyl-benzoyl)-piperazin-1-yl]-ethyl}-nicotinamide,
3-Hydroxy-biphenyl-4-carboxylic acid {2-oxo-2-[4-(2-trifluoromethyl-benzoyl)-piperazin-1-yl]-ethyl}-amide,
2',3'-Difluoro-biphenyl-4-carboxylic acid {2-oxo-2-[4-(2-trifluoromethyl-benzoyl)-piperazin-1-yl]-ethyl}-amide
6-Hydroxy-N-{2-oxo-2-[4-(2-trifluoromethyl-benzoyl)-piperazin-1-yl]-ethyl}-nicotinamide,
3'-Amino-biphenyl-4-carboxylic acid {2-oxo-2-[4-(2-trifluoromethyl-benzoyl)-piperazin-1-yl]-ethyl}-amide,
3-Methoxy-biphenyl-4-carboxylic acid {2-oxo-2-[4-(2-trifluoromethyl-benzoyl)-piperazin-1-yl]-ethyl}-amide,
2',6'-Difluoro-biphenyl-4-carboxylic acid {2-oxo-2-[4-(2-trifluoromethyl-benzoyl)-piperazin-1-yl]-ethyl}-amide,
N-{2-Oxo-2-[4-(2-trifluoromethyl-benzoyl)-piperazin-1-yl]-ethyl}-4-thiazol-5-yl-benzamide,
2',5'-Difluoro-biphenyl-4-carboxylic acid {2-oxo-2-[4-(2-trifluoromethyl-benzoyl)-piperazin-1-yl]-ethyl}-amide, 2'-Methoxy-biphenyl-4-carboxylic acid {2-oxo-2-[4-(2-trifluoromethyl-benzoyl)-piperazin-1-yl]-ethyl}-amide,
N-{2-oxo-2-[4-(2-trifluoromethyl-benzoyl)-piperazin-1-yl]-ethyl}-4-piperidin-1-yl-benzamide,
4-Imidazol-1-yl-N-{2-oxo-2-[4-(2-trifluoromethyl-benzoyl)-piperazin-1-yl]-ethyl}-benzamide,
2'-Hydroxy-biphenyl-4-carboxylic acid {2-oxo-2-[4-(2-trifluoromethyl-benzoyl)-piperazin-1-yl]-ethyl}-amide,
5-Methyl-1-phenyl-1H-pyrazole-4-carboxylic acid {2-oxo-2-[4-(2-trifluoromethyl-benzoyl)-piperazin-1-yl]-ethyl}-amide,
1H-Indole-3-carboxylic acid {2-oxo-2-[4-(2-trifluoromethyl-benzoyl)-piperazin-1-yl]-ethyl}-amide,
1H-Indazole-3-carboxylic acid {2-[4-(5-fluoro-2-trifluoromethyl-benzoyl)-piperazin-1-yl]-2-oxo-ethyl}-amide,
1-phenyl-5-trifluoromethyl-1H-pyrazole-4-carboxylic acid {2-[4-(5-fluoro-2-trifluoromethyl-benzoyl)-piperazin-1-yl]-2-oxo-ethyl}-amide,
5-(2-Fluoro-phenyl)-1H-pyrazole-3-carboxylic acid {2-[4-(5-fluoro-2-trifluoromethyl-benzoyl)-piperazin-1-yl]-2-oxo-ethyl}-amide,
5-(2-Fluoro-phenyl)-1H-pyrazole-3-carboxylic acid {2-oxo-2-[4-(2-trifluoromethyl-benzoyl)-piperazin-1-yl]-ethyl}-amide,
1-Phenyl-1H-pyrazole-4-carboxylic acid {2-[4-(5-fluoro-2-trifluoromethyl-benzoyl)-piperazin-1-yl]-2-oxo-ethyl}-amide,
Naphthalene-1-carboxylic acid {2-[4-(5-fluoro-2-trifluoromethyl-benzoyl)-piperazin-1-yl]-2-oxo-ethyl}-amide,
1-Phenyl-1H-pyrazole-4-carboxylic acid {2-oxo-2-[4-(2-trifluoromethyl-benzoyl)-piperazin-1-yl]-ethyl}-amide,
1-Phenyl-1H-[1,2,3]triazole-4-carboxylic acid {2-[4-(5-fluoro-2-trifluoromethyl-benzoyl)-piperazin-1-yl]-2-oxo-ethyl}-amide,
1-Pyridin-2-yl-1H-[1,2,3]triazole-4-carboxylic acid {2-[4-(5-fluoro-2-trifluoromethyl-benzoyl)-piperazin-1-yl]-2-oxo-ethyl}-amide,
N-{2-[4-(5-Fluoro-2-trifluoromethyl-benzoyl)-piperazin-1-yl]-2-oxo-ethyl}-4-morpholin-4-yl-benzamide,
N-{2-[4-(5-Fluoro-2-trifluoromethyl-benzoyl)-piperazin-1-yl]-2-oxo-ethyl}-4-(4-methyl-piperazin-1-yl)-benzamide,
N-Cyclopentyl-N'-{2-oxo-2-[4-(2-trifluoromethyl-benzoyl)-piperazin-1-yl]-ethyl}-terephthalamide,
4-Ethynyl-N-{2-[4-(5-fluoro-2-trifluoromethyl-benzoyl)-piperazin-1-yl]-2-oxo-ethyl}-benzamide,
5-(2-oxo-2,3-dihydro-benzooxazol-6-yl)-1H-pyrazole-3-carboxylic acid {2-[4-(5-fluoro-2-trifluoromethyl-benzoyl)-piperazin-1-yl]-2-oxo-ethyl}-amide,
4-Benzyloxy-N-{1,1-dimethyl-2-oxo-2-[4-(2-trifluoromethyl-benzoyl)-piperazin-1-yl]-ethyl}-benzamide,
N-{1,1-Dimethyl-2-oxo-2-[4-(2-trifluoromethyl-benzoyl)-piperazin-1-yl]-ethyl}-4-hydroxy-benzamide,
4-Benzyloxy-N-{1-methyl-2-oxo-2-[4-(2-trifluoromethyl-benzoyl)-piperazin-1-yl]-ethyl}-benzamide,
4-Hydroxy-N-{1-methyl-2-oxo-2-[4-(2-trifluoromethyl-benzoyl)-piperazin-1-yl]-ethyl}-benzamide,
N-{2-[4-(5-Fluoro-2-trifluoromethyl-benzoyl)-piperazin-1-yl]-2-oxo-ethyl}-4-phenylamino-benzamide,
4-(Methyl-phenyl-amino)-N-{2-oxo-2-[4-(2-trifluoromethyl-benzoyl)-piperazin-1-yl]-ethyl}-benzamide,
5-Phenylamino-pyridine-2-carboxylic acid {2-[4-(5-fluoro-2-trifluoromethyl-benzoyl)-piperazin-1-yl]-2-oxo-ethyl}-amide,
5-Phenylamino-pyridine-2-carboxylic acid {2-oxo-2-[4-(2-trifluoromethyl-benzoyl)-piperazin-1-yl]-ethyl}-amide,
N-{2-Oxo-2-[4-(2-trifluoromethyl-benzoyl)-piperazin-1-yl]-ethyl}-6-phenylamino-nicotinamide,
Biphenyl-4-carboxylic acid {2-[4-(2-fluoro-6-trifluoromethyl-benzoyl)-piperazin-1-yl]-2-oxo-ethyl}-amide,
or pharmaceutically acceptable salts thereof;
wherein if the compound exhibits chirality it can be in the form of a mixture of enantiomers such as a racemate or a mixture of diastereomers, or can be in the form of a single enantiomer or a single diastereomer.

12. A pharmaceutical composition comprising a compound of claim 1 and a pharmaceutically acceptable carrier.

13. A compound of formula (II):

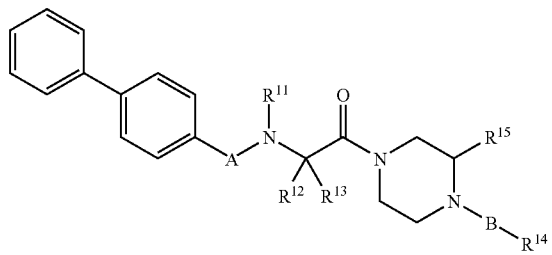

wherein
$R^{11}$ is hydrogen, alkyl, alkenyl, alkynyl, aryl, arylalkyl, heteroaryl, heteroarylalkyl, heterocycle or heterocyclealkyl;
$R^{12}$ and $R^{13}$ are each independently hydrogen, hydroxyl, cyano, alkyl, alkenyl, alkynyl, aryl, arylalkyl, heteroaryl, heteroarylalkyl, heterocycle or heterocyclealkyl;
$R^{15}$ is hydrogen or alkyl;
A is —C(O)—, —S(O)$_2$—, or —S(O)—;
B is a bond, —C(O)—, —C(O)—O—, —S(O)$_2$—, —S(O)—, or —C(O)NR$^{15}$—, where $R^{15}$ is hydrogen, alkyl, alkenyl, alkynyl, cycloalkyl, cycloalkylalkyl, aryl, arylalkyl, heteroaryl, heteroarylalkyl, heterocycle or heterocyclealkyl;
$R^{14}$ is aryl, arylalkyl, heteroaryl, heteroarylalkyl, heterocycle or heterocyclealkyl;
wherein, when present, any aryl, heteroaryl, or heterocycle group may optionally be substituted by halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl and combinations thereof;
or pharmaceutically acceptable salts thereof;
with the proviso that when B is a bond, $R^{14}$ is arylalkyl; and said compound is not
N-[2-[4-(2-furanylcarbonyl)-1-piperazinyl]-2-oxoethyl]-[1,1'-biphenyl]-4-carboxamide, N-[2oxo-2-[4-(2-thienylcarbonyl)-1-piperazinyl]ethyl]-[1,1'-biphenyl]-4-carboxamide, or N-[1-methyl-2-oxo-2-[4-(phenylmethyl)-1-piperazinyl]ethyl]-[1,1'-biphenyl]-4-carboxamide, N-[2-[4-[(4-cyanophenyl)methyl]-1-piperazinyl]-2-oxoethyl]-[1,1'-biphenyl]-4-carboxamide, 2-[([1,1'-biphenyl]-4-ylmethyl)amino]3-phenyl-1-[4-(phenylmethyl)-1-piperazinyl]-1-propanone, or a pharmaceutically acceptable salt thereof.

14. A compound of claim 13, wherein B is a bond, —C(O)— or —S(O)$_2$—.

15. A compound of claim 13, wherein A is —C(O)—.

16. A compound of claim 13, wherein $R^{14}$ is aryl, heteroaryl or arylalkyl, each of which may be optionally substituted.

17. A compound of claim 16, wherein $R^{14}$ is phenyl, thienyl, pyridinyl, pyrazinyl or benzyl, each of which may be optionally substituted.

18. A compound of claim 16, wherein $R^{14}$ is aryl, heteroaryl or arylalkyl each of which may be optionally substituted by halogen, alkyl, halogenated alkyl, alkoxy, acyl, cycloalkylalkyloxy, hydroxyl, carboxyl, alkoxycarbonyl and combinations thereof.

19. A compound of claim 13, selected from:

Biphenyl-4-carboxylicacid {2-[4-(2,5-dichloro-benzoyl)-piperazin-1-yl]-2-oxo-ethyl}-amide, Biphenyl-4-carboxylicacid {2-[4-(2-fluoro-benzoyl)-piperazin-1-yl]-2-oxo-ethyl}-amide, Biphenyl-4-carboxylicacid {2-[4-(2,4-dimethyl-benzoyl)-piperazin-1-yl]-2-oxo-ethyl}-amide, Biphenyl-4-carboxylicacid {2-[4-(4-fluoro-benzoyl)-piperazin-1-yl]-2-oxo-ethyl}-amide, Biphenyl-4-carboxylicacid {2-[4-benzoyl-piperazin-1-yl]-2-oxo-ethyl}-amide, Biphenyl-4-carboxylicacid {2-[4-(2-trifluoromethyl-benzyl)-piperazin-1-yl]-2-oxo-ethyl}-amide, Biphenyl-4-carboxylicacid {2-[4-(3-methyl-thiophene-2-carbonyl)-piperazin-1-yl]-2-oxo-ethyl}-amide, Biphenyl-4-carboxylicacid {2-[4-(2-methyl-benzoyl)-piperazin-1-yl]-2-oxo-ethyl}-amide, Biphenyl-4-carboxylic acid {2-[4-(2-bromo-5-methoxy-benzoyl)-piperazin-1-yl]-2-oxo-ethyl}-amide, and Biphenyl-4-carboxylic acid {2-[4-(2-bromo-benzoyl)-piperazin-1-yl]-2-oxo-ethyl}-amide, or pharmaceutically acceptable salts thereof;

wherein if the compound exhibits chirality it can be in the form of a mixture of enantiomers such as a racemate or a mixture of diastereomers, or can be in the form of a single enantiomer or a single diastereomer.

20. A compound of claim 13, selected from:

Biphenyl-4-carboxylicacid {2-[4-(2-methoxy-benzoyl)-piperazin-1-yl]-2-oxo-ethyl}-amide, Biphenyl-4-carboxylicacid {2-[4-(2-fluoro-5-trifluoromethyl-benzoyl)-piperazin-1-yl]-2-oxo-ethyl}-amide, Biphenyl-4-carboxylic acid {2-[4-(2-cyclopropylmethoxy-benzoyl)-piperazin-1-yl]-2-oxo-ethyl}-amide, Biphenyl-4-carboxylicacid {2-[4-(2-acetyl-benzoyl)-piperazin-1-yl]-2-oxo-ethyl}-amide, Biphenyl-4-carboxylicacid {2-[4-benzene sulfonyl-piperazin-1-yl]-2-oxo-ethyl}-amide, Biphenyl-4-carboxylicacid {2-[4-(2,5-bis-trifluoromethyl-benzoyl)-piperazin-1-yl]-2-oxo-ethyl}-amide, Biphenyl-4-carboxylicacid {2-[4-(2-chloro-5-trifluoromethyl-benzoyl)-piperazin-1-yl]-2-oxo-ethyl}-amide, Biphenyl-4-carboxylicacid {2-[4-(5-fluoro-2-trifluoromethyl-benzoyl)-piperazin-1-yl]-2-oxo-ethyl}-amide, Biphenyl-4-carboxylicacid {2-[4-(2-hydroxy-benzoyl)-piperazin-1-yl]-2-oxo-ethyl}-amide, Biphenyl-4-carboxylicacid {2-[4-(4-trifluoromethyl-benzoyl)-piperazin-1-yl]-2-oxo-ethyl}-amide, Biphenyl-4-carboxylicacid {2-oxo-2-[4-(4-trifluoromethyl-pyridine-3-carbonyl)-piperazin-1-yl]-ethyl}-amide, Biphenyl-4-carboxylicacid {2-oxo-2-[4-(pyrazine-2-carbonyl)-piperazin-1-yl]-ethyl}-amide, Biphenyl-4-carboxylicacid {2-oxo-2-[4-(3,4,5-trifluoro-benzoyl)-piperazin-1-yl]-ethyl}-amide, Biphenyl-4-carboxylicacid {2-oxo-2-[4-(2-trifluoromethoxy-benzoyl)-piperazin-1-yl]-ethyl}-amide, Biphenyl-4-carboxylicacid {2-[4-(2-chloro-4-fluoro-benzoyl)-piperazin-1-yl]-2-oxo-ethyl}-amide, Biphenyl-4-carboxylicacid {2-[4-(2-chloro-benzoyl)-piperazin-1-yl]-2-oxo-ethyl}-amide, Biphenyl-4-carboxylicacid {2-[4-(2-chloro-pyridine-3-carbonyl)-piperazin-1-yl]-2-oxo-ethyl}-amide, Biphenyl-4-carboxylicacid {2-[4-(4-chloro-2,5-difluoro-benzoyl)-piperazin-1-yl]-2-oxo-ethyl}-amide, Biphenyl-4-carboxylicacid {2-[4-(2-bromo-5-fluoro-benzoyl)-piperazin-1-yl]-2-oxo-ethyl}-amide, Biphenyl-4-carboxylicacid {2-[4-(2,5-difluoro-benzoyl)-piperazin-1-yl]-2-oxo-ethyl}-amide, Biphenyl-4-carboxylic acid {2-[4-(2,4-dichloro-5-fluoro-benzoyl)-piperazin-1-yl]-2-oxo-ethyl}-amide, Biphenyl-4-carboxylicacid {2-[4-(3-fluoro-5-trifluoromethyl-benzoyl)-piperazin-1-yl]-2-oxo-ethyl}-amide, Biphenyl-4-carboxylicacid {2-oxo-2-[4-(2, 3 ,6-trifluoro-benzoyl)-piperazin-1-yl]-1-ethyl}-amide, 2-(4-{2-[(Biphenyl-4-carbonyl)-amino]-acetyl}-piperazine-1-carbonyl)-benzoic acid methylester, and 2-(4-{2-[(Biphenyl-4-carbonyl)-amino]-acetyl}-piperazine-1-carbonyl)-benzoic acid, or pharmaceutically acceptable salts thereof;

wherein if the compound exhibits chirality it can be in the form of a mixture of enantiomers such as a racemate or a mixture of diastereomers, or can be in the form of a single enantiomer or a single diastereomer;

N-{2-[4-(2-Chloro-5-trifluoromethyl-benzoyl)-piperazin-1-yl]-2-oxo-ethyl}-4-phenylamino-benzamide, N-{2-[4-(3,5-Dichloro-benzoyl)-piperazin-1-yl]-2-oxo-ethyl}-4-phenylamino-benzamide, or pharmaceutically acceptable salts thereof;

wherein if the compound exhibits chirality it can be in the form of a mixture of enantiomers such as a racemate or a mixture of diastereomers, or can be in the form of a single enantiomer or a single diastereomer.

21. A compound of claim 13, selected from:

Biphenyl-4-carboxylic acid {2-oxo-2-[4-(2,4,5-trifluoro-benzoyl)-piperazin-1-yl]-ethyl}-amide, Biphenyl-4-carboxylic acid {2-[4-(6-bromo-pyridine-2-carbonyl)-piperazin-1-yl]-2-oxo-ethyl}-amide, Biphenyl-4-carboxylic acid {2-[4-(2-chloro-5-fluoro-benzoyl)-piperazin-1-yl]-2-oxo-ethyl}-amide, Biphenyl-4-carboxylic acid {2-[4-(3,5-dichloro-benzoyl)-piperazin-1-yl]-2-oxo-ethyl}-amide, Biphenyl-4-carboxylic acid {2-[4-(2-amino-benzoyl)-piperazin-1-yl]-2-oxo-ethyl}-amide, Biphenyl-4-carboxylic acid {2-[4-(2-bromo-5-nitro-benzoyl)-piperazin-1-yl]-2-oxo-ethyl}-amide, Biphenyl-4-carboxylic acid {2-[4-(2,6-dichloro-benzoyl)-piperazin-1-yl]-2-oxo-ethyl}-amide, Biphenyl-4-carboxylic acid {2-[4-(2,6-difluoro-benzoyl)-piperazin-1-yl]-2-oxo-ethyl}-amide, Biphenyl-4-carboxylic acid {2-[4-(2-chloro-pyridine-4-carbonyl)-piperazin-1-yl]-2-oxo-ethyl}-amide,
Biphenyl-4-carboxylic acid {2-[4-(6-chloro-pyridine-3-carbonyl)-piperazin-1-yl]-2-oxo-ethyl}-amide,
Biphenyl-4-carboxylic acid {2-[4-(2-chloro-pyridine-3-carbonyl)-piperazin-1-yl]-2-oxo-ethyl}-amide,
Biphenyl-4-carboxylic acid {2-[4-(5-amino-2-bromo-benzoyl)-piperazin-1-yl]-2-oxo-ethyl}-amide,
Biphenyl-4-carboxylic acid {2-[4-(2-bromo-5-hydroxy-benzoyl)-piperazin-1-yl]-2-oxo-ethyl}-amide,
Biphenyl-4-carboxylic acid {2-[4-(2-bromo-5-methoxy-benzoyl)-3-methyl-piperazin-1-yl]-2-oxo-ethyl}-amide, or pharmaceutically acceptable salts thereof;
wherein if the compound exhibits chirality it can be in the form of a mixture of enantiomers such as a racemate or a mixture of diastereomers, or can be in the form of a single enantiomer or a single diastereomer.

22. A pharmaceutical composition comprising a compound of claim 13 and a pharmaceutically acceptable carrier.

23. A compound of formula (III):

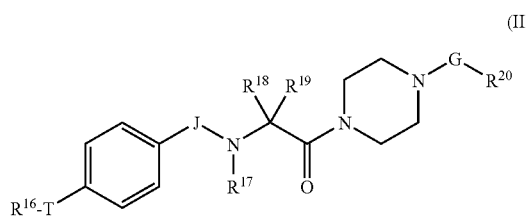

(III)

wherein
$R^{16}$ is hydrogen, aryl, arylalkyl, heteroaryl, heteroarylalkyl, heterocycle or heterocyclealkyl;
$R^{17}$ is hydrogen, alkyl, alkenyl, alkynyl, aryl, arylalkyl, heteroaryl, heteroarylalkyl, heterocycle or heterocyclealkyl;
$R^{18}$ and $R^{19}$ are each independently hydrogen, hydroxyl, cyano, alkyl, alkenyl, alkynyl, aryl, arylalkyl, heteroaryl, heteroarylalkyl, heterocycle or heterocyclealkyl;
$R^{20}$ is aryl, arylalkyl, heteroaryl, heteroarylalkyl, heterocycle or heterocyclealkyl;
J is —C(O)—, —S(O)$_2$—, or —S(O)—;
G is a bond, —C(O)—, —C(O)—O—, —S(O)$_2$—, —S(O)—, or —C(O)NR$^{21}$—, where $R^{21}$ is hydrogen, alkyl, alkenyl, alkynyl, cycloalkyl, cycloalkylalkyl, aryl, arylalkyl, heteroaryl, heteroarylalkyl, heterocycle or heterocyclealkyl;
T is —O—, —S—, —NH—, —C(O)—, —S(O)— or —S(O)$_2$—;
wherein, when present, any aryl, heteroaryl, or heterocycle group may optionally be substituted by halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl and combinations thereof;

or pharmaceutically acceptable salts thereof;
with the proviso that when J is —C(O)—, $R^{17}$-$R^{19}$ are hydrogen and G is a bond, then $R^{20}$ is not thienylmethyl, thiazolylmethyl, pyridinyl, thiazolylmethyl, pyrrolidinylethyl or pyridinylmethyl;
and said compound is not
N-[2-[4-(2-furanylcarbonyl)-1-piperazinyl]2-oxoethyl]-4-phenoxy-benzamide,
N-[2-[4-[(3,5-dimethyl-4-isoxazolyl)sulfonyl]-1-piperazinyl]-2-oxoethyl]-4-phenoxy-benzamide,
N-[(3,5-dimethyl-4-isoxazolyl)methoxy]-N-methyl-N-[2-oxo-2-[4-(phenylmethyl)-1-piperazinyl]ethyl]-benzamide,
$N^2$-oxo-2-[4-(2-thienylsulfonyl)-1-piperazinyl]ethyl]-4-phenoxy-benzamide,
N-[2-oxo-2-[4-(2-thienylcarbonyl)-1-piperazinyl]ethyl]-4-phenoxy-benzamide, or
N-methyl-N-[2-[4-[(3-methylphenyl)methyl]-1-piperazinyl]-2-oxoethyl]-4-(1-pyrrolidinylsulfonyl)-benzamide,
N-[2-[4-(4-acetylphenyl)-1-piperazinyl]-2-oxoethyl]-4-phenoxy-benzamide,
N-[2-[4-(4-methoxyphenyl)-1-piperazinyl]-2-oxoethyl]-4-phenoxy-benzamide,
or a pharmaceutically acceptable salt thereof.

24. A compound of claim 23, wherein G is a bond, —S(O)$_2$—, —C(O)—NR$^{21}$— or —C(O)—.

25. A compound of claim 23, wherein J is —C(O)—.

26. A compound of claim 23, wherein T is —O—.

27. A compound of claim 23, wherein $R^{16}$ is hydrogen or arylalkyl or aryl, both of which may be optionally substituted.

28. A compound of claim 27, wherein $R^{16}$ is hydrogen or phenyl or benzyl, both of which may be optionally substituted.

29. A compound of claim 23, wherein $R^{20}$ is aryl, arylalkyl, or heteroaryl, each of which may be optionally substituted.

30. A compound of claim 29, wherein $R^{20}$ is phenyl, benzyl, thienyl or furanyl, each of which may be optionally substituted.

31. A compound of claim 29, wherein $R^{20}$ is phenyl, benzyl, thienyl or furanyl, each of which may be optionally substituted by halogen, alkyl, halogenated alkyl, alkoxy and combinations thereof.

32. A compound of claim 23, selected from:
4-Benzyloxy-N-[2-oxo-2-(4-phenylacetyl-piperazin-1-yl)-ethyl]-benzamide,
4-Hydroxy-N-[2-oxo-2-(4-phenylacetyl-piperazin-1-yl)-ethyl]-benzamide,
4-Benzyloxy-N-{2-[4-(3-methyl-thiophene-2-carbonyl)-piperazin-1-yl]-2-oxo-ethyl}-benzamide,
4-Hydroxy-N-{2-[4-(3-methyl-thiophene-2-carbonyl)-piperazin-1-yl]-2-oxo-ethyl}-benzamide,
4-Benzyloxy-N-{2-[4-(2-bromo-5-methoxy-benzoyl)-piperazin-1-yl]-2-oxo-ethyl}-benzamide,
4-Hydroxy-N-{2-[4-(3-methoxy-benzoyl)-piperazin-1-yl]-2-oxo-ethyl}-benzamide,
N-{2-[4-(2-Bromo-5-methoxy-benzoyl)-piperazin-1-yl]-2-oxo-ethyl}-4-phenoxy-benzamide,
N-{2-[4-(3-Methyl-thiophene-2-carbonyl)-piperazin-1-yl]-2-oxo-ethyl}-4-phenoxy-benzamide,
N-{2-[4-(Furan-2-carbonyl)-piperazin-1-yl]-2-oxo-ethyl}-4-phenoxy-benzamide,
N-{2-[4-(2-Methyl-benzoyl)-piperazin-1-yl]-2-oxo-ethyl}-4-phenoxy-benzamide,
N-{2-[4-(2-Fluoro-benzoyl)-piperazin-1-yl]-2-oxo-ethyl}-4-phenoxy-benzamide, N-[2-(4-Benzyl-piperazin-1-yl)-2-oxo-ethyl]-4-phenoxy-benzamide, N-{2-[4-(4-Fluoro-benzoyl)-piperazin-1-yl]-2-oxo-ethyl}-4-phenoxy-benzamide, N-{2-Oxo-2-[4-(2-trifluoromethyl-benzyl)-piperazin-1-yl]-ethyl}-4-phenoxy-benzamide, N-{2-[4-(2,4-Dimethyl-benzoyl)-piperazin-1-yl]-2-oxo-ethyl}-4-phenoxy-benzamide, N-[2-(4-Benzoyl-piperazin-1-yl)-2-oxo-ethyl]-4-phenoxy-benzamide, N-[2-(4-Benzenesulfonyl-piperazin-1-yl)-2-oxo-ethyl]-4-phenoxy-benzamide, N-{2-[4-(2,4-Dichloro-benzoyl)-piperazin-1-yl]-2-oxo-ethyl}-4-phenoxy-benzamide, N-{2-[4-(2,5-Dichloro-benzoyl)-piperazin-1-yl]-2-oxo-ethyl}-4-phenoxy-benzamide, 4-[2-(4-Benzyloxy-benzoylamino)-acetyl]-piperazine-1-carboxylic acid o-tolylamide, 4-[2-(4-Hydroxy-benzoylamino)-acetyl]-piperazine-1-carboxylic acid o-tolylamide, and 4-Benzyloxy-N-{2-oxo-2-[4-(2-trifluoromethyl-benzoyl)-piperazin-1-yl]-ethyl}-benzamide, or pharmaceutically acceptable salts thereof;

wherein if the compound exhibits chirality it can be in the form of a mixture of enantiomers such as a racemate or a mixture of diastereomers, or can be in the form of a single enantiomer or a single diastereomer.

33. A compound of claim 23, selected from:

N-{2-[4-(2,4-Dichloro-benzoyl)-piperazin-1-yl]-2-oxo-ethyl}-4-phenylamino-benzamide, $R^{24}$ is halogen or alkoxy;

$R^{22}$, $R^{23}$ and $R^{25}$ are each independently hydrogen, halogen, hydroxy, cyano, nitro, amino, alkylamino, dialkylamino, carboxyl, alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, cycloalkyloxy, cycloalkylalkyloxy, arylalkyloxy, heteroarylalkyloxy, alkylthio, arylthio, alkylsulfinyl, alkylsulfonyl, alkoxycarbonyl, aryloxycarbonyl or heteroaryloxycarbonyl;

$R^{26}$ and $R^{27}$ are each independently hydrogen, hydroxyl, cyano, alkyl, alkenyl, alkynyl, aryl, arylalkyl, heteroaryl, heteroarylalkyl, heterocycle or heterocyclealkyl;

$R^{28}$ is hydrogen, alkyl, alkenyl, alkynyl, aryl, arylalkyl, heteroaryl, heteroarylalkyl, heterocycle or heterocyclealkyl;

$R^{29}$ is aryl, arylalkyl, heteroaryl, heteroarylalkyl, heterocycle or heterocyclealkyl;

D is —C(O)—, —C(O)—O—, —S(O)$_2$—, —S(O)—, or —C(O)NR$^{30}$—, where $R^{30}$ is hydrogen, alkyl, alkenyl, alkynyl, cycloalkyl, cycloalkylalkyl, aryl, arylalkyl, heteroaryl, heteroarylalkyl, heterocycle or heterocyclealkyl;

M is —C(O)—, —S(O)$_2$, or —S(O)—;

wherein, when present, any aryl, heteroaryl, or heterocycle group may optionally be substituted by halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl and combinations thereof;

or pharmaceutically acceptable salts thereof;

with the proviso that said compound is not

N-[2-[4-[(2,5-difluorophenyl)sulfonyl]1-piperazinyl]2-oxo ethyl]-3-fluoro-benzamide, N-[2-[4-[(2,5-difluorophenyl)sulfonyl]1-piperazinyl]2-oxoethyl]-3,4-dimethoxy-benzamide, N-[2-[4-(2-bromo-5-methoxybenzoyl)-1-piperazinyl]-2-oxoethyl]-4-methoxy-2-quinolinecarboxamide, N-[2-[4-(2,5-dibromophenyl)sulfonyl]-1-piperazinyl]-2-oxoethyl]-4-methoxy-2-quinolinecarboxamide, or a pharmaceutically acceptable salt thereof.

34. A pharmaceutical composition comprising a compound of claim 23 and a pharmaceutically acceptable carrier.

35. A compound of formula (IV):

(IV)

wherein $R^{21}$ is halogen.

36. A compound of claim 35, wherein $R^{21}$ is halogen and $R^{24}$ is halogen.

37. A compound of claim 35, wherein $R^{21}$ is halogen and $R^{24}$ is alkoxy.

38. A compound according to claim 35, wherein $R^{21}$ is halogen, $R^{24}$ is halogen or alkoxy and $R^{22}$, $R^{23}$ and $R^{25}$ are each hydrogen.

39. A compound according to claim 38, wherein $R^{26}$, $R^{27}$ and $R^{28}$ are hydrogen.

40. A compound according to claim 35, wherein $R^{29}$ is optionally substituted heteroaryl.

41. A compound according to claim 40, wherein $R^{29}$ is isoxazolyl or pyrazolyl, each of which may be optionally substituted.

42. A compound according to claim 35, wherein D is —C(O)— and M is —C(O).

43. A compound of claim 35, selected from:

5-Phenyl-isoxazole-3-carboxylic acid {2-[4-(2-bromo-5-methoxy-benzoyl)-piperazin-1-yl]-2-oxo-ethyl}-amide, 5-Phenyl-isoxazole-3-carboxylic acid {2-[4-(2,5-dichloro-benzoyl)-piperazin-1-yl]-2-oxo-ethyl}-amide, 5-Phenyl-1H-pyrazole-3-carboxylic acid {2-[4-(2-bromo-5-methoxy-benzoyl)-piperazin-1-yl]-2-oxo-ethyl}-amide, and 5-Phenyl-1H-pyrazole-3-carboxylic acid {2-[4-(2,5-dichloro-benzoyl)-piperazin-1-yl]-2-oxo-ethyl}-amide, or pharmaceutically acceptable salts thereof;

wherein if the compound exhibits chirality it can be in the form of a mixture of enantiomers such as a racemate or a mixture of diastereomers, or can be in the form of a single enantiomer or a single diastereomer.

44. A compound of claim 35, selected from:
5-(2-Hydroxy-phenyl)-1H-pyrazole-3-carboxylic acid {2-[4-(2-bromo-5-fluoro-benzoyl)-piperazin-1-yl]-2-oxo-ethyl}-amide,
5-(2-Hydroxy-phenyl)-1H-pyrazole-3-carboxylic acid {2-[4-(2,5-dichloro-benzoyl)-piperazin-1-yl]-2-oxo-ethyl}-amide,
N-{2-[4-(2,5-Dichloro-benzoyl)-piperazin-1-yl]-2-oxo-ethyl}-4-phenylamino-benzamide,
N-{2-[4-(2-Bromo-5-methoxy-benzoyl)-piperazin-1-yl]-2-oxo-ethyl}-4-phenylamino-benzamide,
N-{2-[4-(2,5-Difluoro-benzoyl)-piperazin-1-yl]-2-oxo-ethyl}-4-phenylamino-benzamide,
N-{2-[4-(2-Bromo-5-fluoro-benzoyl)-piperazin-1-yl]-2-oxo-ethyl}-4-phenylamino-benzamide,
or pharmaceutically acceptable salts thereof;
wherein if the compound exhibits chirality it can be in the form of a mixture of enantiomers such as a racemate or a mixture of diastereomers, or can be in the form of a single enantiomer or a single diastereomer.

45. A pharmaceutical composition comprising a compound of claim 35 and a pharmaceutically acceptable carrier.

46. A compound of formula (V):

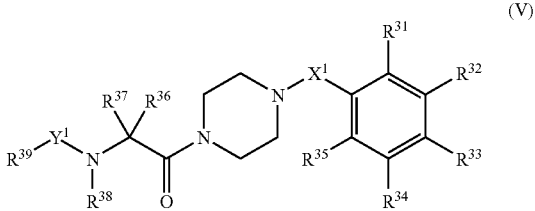

(V)

Wherein
$R^{31}$ is halogenated alkyl;
$R^{32}$, $R^{33}$, $R^{34}$ and $R^{35}$ are each independently hydrogen or halogen;
$R^{36}$ and $R^{37}$ are each independently hydrogen or alkyl;
$R^{38}$ is hydrogen or alkyl;
$R^{39}$ is aryl, arylalkyl, heteroaryl, heteroarylalkyl, heterocycle or heterocyclealkyl;
$X^1$ is —C(O)—, —S(O)$_2$—, or —S(O)—;
$Y^1$ is —C($R^{40}$)($R^{41}$)—, where $R^{40}$ and $R^{41}$ are each independently hydrogen or alkyl;
wherein, when present, any aryl, heteroaryl, or heterocycle group may optionally be substituted by halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl and combinations thereof;
or pharmaceutically acceptable salts thereof.

47. The compound of claim 46, wherein $R^{31}$ is $CF_3$.

48. The compound of claim 46, wherein $Y^1$ is —CH$_2$— or —CH(alkyl)-.

49. The compound of claim 46, wherein $R^{39}$ is aryl or heteroaryl, each of which may be optionally substituted.

50. The compound of claim 49, wherein $R^{39}$ is aryl or heteroaryl, each of which may be optionally substituted by aryl, heteroaryl and combinations thereof.

51. The compound of claim 46, wherein $X^1$ is —C(O)—.

52. A compound of claim 46, selected from:
2-[(Biphenyl-4-ylmethyl)-amino]-1-[4-(5-fluoro-2-trifluoromethyl-benzoyl)-piperazin-1-yl]-ethanone,
1-[4-(5-Fluoro-2-trifluoromethyl-benzoyl)-piperazin-1-yl]-2-[(5-phenyl-isoxazol-3-ylmethyl)-amino]-ethanone,
2-[(5-Phenyl-isoxazol-3-ylmethyl)-amino]-1-[4-(2-trifluoromethyl-benzoyl)-piperazin-1-yl]-ethanone,
2-(1-Biphenyl-4-yl-ethylamino)-1-[4-(5-fluoro-2-trifluoromethyl-benzoyl)-piperazin-1-yl]-ethanone.hydrochloride,
2-[(Biphenyl-4-ylmethyl)-amino]-1-[4-(2-trifluoromethyl-benzoyl)-piperazin-1-yl]-ethanone,
1-[4-(5-Fluoro-2-trifluoromethyl-benzoyl)-piperazin-1-yl]-2-[(1-phenyl-1H-pyrazol-4-ylmethyl)-amino]-ethanone,
1-[4-(5-Fluoro-2-trifluoromethyl-benzoyl)-piperazin-1-yl]-2-(4-thiophen-3-yl-benzylamino)-ethanone,
or pharmaceutically acceptable salts thereof;
wherein if the compound exhibits chirality it can be in the form of a mixture of enantiomers such as a racemate or a mixture of diastereomers, or can be in the form of a single enantiomer or a single diastereomer.

53. A pharmaceutical composition comprising a compound of claim 46 and a pharmaceutically acceptable carrier.

* * * * *